United States Patent
Kotschy et al.

(10) Patent No.: US 9,670,227 B2
(45) Date of Patent: Jun. 6, 2017

(54) THIENOPYRIMIDINE DERIVATIVES, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LIMITED, Winnersh (GB)

(72) Inventors: András Kotschy, Törökbálint (HU); Zoltán Szlávik, Budapest (HU); Márton Csékei, Dunakeszi (HU); Attila Paczal, Budapest (HU); Zoltán Szabó, Budapest (HU); Szabolcs Sipos, Budapest (HU); Gábor Radics, Erd (HU); Ágnes Proszenyák, Molnári (HU); Balázs Bálint, Fót (HU); Alain Bruno, Paris (FR); Olivier Geneste, Rueil-Malmaison (FR); James Edward Paul Davidson, Great Shelford (GB); James Brooke Murray, Linton (GB); I-Jen Chen, Cambridge (GB); Françoise Perron-Sierra, Paris (FR)

(73) Assignees: LES LABORATOIRES SERVIER, Suresnes (FR); VERNALIS (R&D) LTD, Winnersh (GB)

( * ) Notice: Subject to any disclaimer, the term of this patent is extended or adjusted under 35 U.S.C. 154(b) by 84 days.

(21) Appl. No.: 14/576,683

(22) Filed: Dec. 19, 2014

(65) Prior Publication Data
US 2015/0175623 A1    Jun. 25, 2015

(30) Foreign Application Priority Data
Dec. 23, 2013   (FR) .................................... 13 63500

(51) Int. Cl.
| | | |
|---|---|---|
| C07D 239/00 | (2006.01) | |
| C07D 333/00 | (2006.01) | |
| C07D 495/04 | (2006.01) | |
| A61K 31/519 | (2006.01) | |
| A61K 31/5377 | (2006.01) | |
| A61K 31/538 | (2006.01) | |
| A61K 31/55 | (2006.01) | |
| A61K 45/06 | (2006.01) | |
| A61N 5/10 | (2006.01) | |

(52) U.S. Cl.
CPC .......... *C07D 495/04* (2013.01); *A61K 31/519* (2013.01); *A61K 31/538* (2013.01); *A61K 31/5377* (2013.01); *A61K 31/55* (2013.01); *A61K 45/06* (2013.01); *A61N 5/10* (2013.01)

(58) Field of Classification Search
CPC ... C07D 239/00; C07D 333/00; C07D 495/04
See application file for complete search history.

(56) References Cited

U.S. PATENT DOCUMENTS

2010/0261736 A1   10/2010  Lampe

FOREIGN PATENT DOCUMENTS

| CA | 2 861 160 | 1/2013 |
|---|---|---|
| WO | 2005/067546 | 7/2005 |
| WO | 2006/004656 | 1/2006 |
| WO | 2008/155017 | 12/2008 |
| WO | 2010/054285 | 5/2010 |
| WO | WO 2013/072694 | 5/2013 |
| WO | WO 2013/110890 | 8/2013 |

OTHER PUBLICATIONS

Coumar, et al., Journal of Medicinal Chemistry, vol. 53, p. 4980-4988, Jun. 15, 2010.
Preliminary Search Report for FR1363500 of Jun. 23, 2014.

*Primary Examiner* — Bruck Kifle
(74) *Attorney, Agent, or Firm* — Hueschen and Sage

(57) ABSTRACT

Compounds of formula (I):

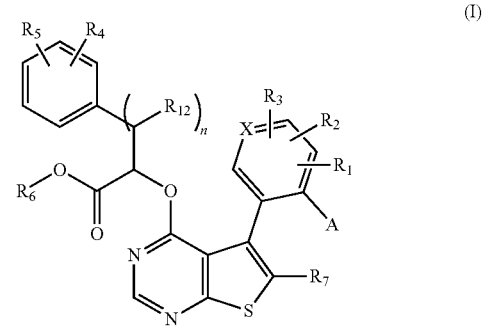

wherein $R_1$, $R_2$, $R_3$, $R_4$, $R_5$, $R_6$, $R_7$, $R_{12}$, X, A and n are as defined in the description.
Medicinal products containing the same which are useful in treating pathologies involving a deficit in apoptosis, such as cancer, auto-immune diseases, and diseases of the immune system.

40 Claims, No Drawings

THIENOPYRIMIDINE DERIVATIVES, A PROCESS FOR THEIR PREPARATION AND PHARMACEUTICAL COMPOSITIONS CONTAINING THEM

The present invention relates to new thienopyrimidine derivatives, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in auto-immune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colon cancer, breast cancer, small-cell lung cancer, non-small-cell lung cancer, bladder cancer, ovarian cancer, prostate cancer, chronic lymphoid leukaemia, lymphoma, myeloma, acute myeloid leukemia, pancreatic cancer, etc. Overexpression of the anti-apoptotic proteins of the Bcl-2 family is involved in tumorigenesis, in resistance to chemotherapy and in the clinical prognosis of patients affected by cancer. Notably, Mcl-1, an anti-apoptotic Bcl-2 family member, is overexpressed in various types of cancer (Beroukhim R. et al., Nature 2010, 899-905). There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer and of immune and auto-immune diseases.

The present invention relates more especially to compounds of formula (I):

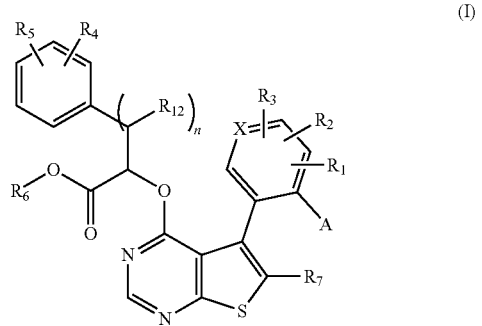

(I)

wherein:
A represents a linear or branched $(C_1$-$C_6)$alkyl group, a linear or branched $(C_2$-$C_6)$alkenyl group, a linear or branched $(C_2$-$C_6)$alkynyl group, a linear or branched $(C_1$-$C_6)$alkoxy group, —S—$(C_1$-$C_6)$alkyl group, a linear or branched $(C_1$-$C_6)$polyhaloalkyl, a hydroxy group, a cyano, —$NR_{10}R_{10}'$, -$Cy_6$ or an halogen atom,
$R_1$, $R_2$, $R_3$, $R_4$ and $R_5$ independently of one another represent a hydrogen atom, a halogen atom, a linear or branched $(C_1$-$C_6)$alkyl group, a linear or branched $(C_2$-$C_6)$alkenyl group, a linear or branched $(C_2$-$C_6)$alkynyl group, a linear or branched $(C_1$-$C_6)$polyhaloalkyl, a hydroxy group, a linear or branched $(C_1$-$C_6)$alkoxy group, —S—$(C_1$-$C_6)$alkyl group, a cyano, a nitro group, -alkyl$(C_0$-$C_6)$—$NR_8R_8'$, —O-$Cy_1$, -alkyl$(C_0$-$C_6)$-$Cy_1$, -alkenyl$(C_2$-$C_6)$-$Cy_1$, -alkynyl$(C_2$-$C_6)$-$Cy_1$, —O-alkyl$(C_1$-$C_6)$—$R_9$, —C(O)—$OR_8$, —O—C(O)—$R_8$, —C(O)—$NR_8R_8'$, —$NR_8$—C(O)—$R_8'$, —$NR_8$—C(O)—$OR_8'$, -alkyl$(C_1$-$C_6)$—$NR_8$—C(O)—$R_8'$, —$SO_2$—$NR_8R_8'$, —$SO_2$-alkyl$(C_1$-$C_6)$,
or the substituents of one of the pairs ($R_1$, $R_2$), ($R_2$, $R_3$), ($R_1$, $R_3$), ($R_4$, $R_5$) when grafted onto two adjacent carbon atoms, form together with the carbon atoms carrying them an aromatic or non-aromatic ring composed of from 5 to 7 ring members, which may contain from one to 3 heteroatoms selected from oxygen, sulphur and nitrogen, it being understood that resulting ring may be substituted by a group selected from a linear or branched $(C_1$-$C_6)$alkyl group, —$NR_{10}R_{10}'$, -alkyl$(C_0$-$C_6)$-$Cy_1$ or an oxo,
X represents a carbon or a nitrogen atom,
$R_6$ represents a hydrogen, a linear or branched $(C_1$-$C_8)$ alkyl group, an aryl, an heteroaryl group, an arylalkyl $(C_1$-$C_6)$ group, an heteroarylalkyl$(C_1$-$C_6)$ group,
$R_7$ represents a linear or branched $(C_1$-$C_6)$alkyl group, a linear or branched $(C_2$-$C_6)$alkenyl group, a linear or branched $(C_2$-$C_6)$alkynyl group, -$Cy_3$, -alkyl$(C_1$-$C_6)$-$Cy_3$, -alkenyl$(C_2$-$C_6)$-$Cy_3$, -alkynyl$(C_2$-$C_6)$-$Cy_3$, —$Cy_3$-$Cy_4$, -alkynyl$(C_2$-$C_6)$—O-$Cy_3$, -$Cy_3$-alkyl$(C_0$-$C_6)$—O-alkyl$(C_0$-$C_6)$-$Cy_4$, an halogen atom, a cyano, —C(O)—$R_{11}$, —C(O)—$NR_{11}R_{11}'$,
$R_8$ and $R_8'$ independently of one another represent a hydrogen atom, a linear or branched $(C_1$-$C_6)$alkyl group, or -alkyl$(C_0$-$C_6)$-$Cy_1$,
or ($R_8$, $R_8'$) form together with the nitrogen atom carrying them an aromatic or non-aromatic ring composed of from 5 to 7 ring members, which may contain in addition to the nitrogen atom from one to 3 heteroatoms selected from oxygen, sulphur and nitrogen, it being understood that the nitrogen in question may be substituted by a group representing a hydrogen atom, or a linear or branched $(C_1$-$C_6)$alkyl group and it being understood that one or more of the carbon atoms of the possible substituents, may be deuterated,
$R_9$ represents -$Cy_1$, -$Cy_1$-alkyl$(C_0$-$C_6)$-$Cy_2$, -$Cy_1$-alkyl $(C_0$-$C_6)$—O-alkyl$(C_0$-$C_6)$-$Cy_2$, -$Cy_1$-alkyl$(C_0$-$C_6)$—$NR_8$-alkyl$(C_0$-$C_6)$-$Cy_2$, -$Cy_1$-$Cy_2$-O-alkyl$(C_0$-$C_6)$—$Cy_5$, —C(O)—$NR_8R_8'$, —$NR_8R_8'$, —$OR_8$, —$NR_8$—C(O)—$R_8'$, —O-alkyl$(C_1$-$C_6)$—$OR_8$, —$SO_2$—$R_8$, —C(O)—$OR_8$, —NH—C(O)—NH—$R_8$,
$R_{10}$, $R_{10}'$, $R_{11}$ and $R_{11}'$ independently of one another represent a hydrogen atom or an optionally substituted linear or branched $(C_1$-$C_6)$alkyl group,
$R_{12}$ represents a hydrogen or a hydroxy group,
$Cy_1$, $Cy_2$, $Cy_3$, $Cy_4$, $Cy_5$ and $Cy_6$ independently of one another, represent a cycloalkyl group, a heterocycloalkyl group, an aryl or an heteroaryl group,
n is an integer equal to 0 or 1, it being understood that:
"aryl" means a phenyl, naphthyl, biphenyl, indanyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched ($C_1$-$C_6$)alkyl, optionally substituted linear or branched ($C_2$-$C_6$) alkenyl group, optionally substituted linear or branched ($C_2$-$C_6$)alkynyl group, optionally substituted linear or branched ($C_1$-$C_6$)alkoxy, optionally substituted ($C_1$-$C_6$) alkyl-S—, hydroxy, oxo (or N-oxide where appropriate), nitro, cyano, —C(O)—OR', —O—C(O)—R', —C(O)—NR'R", —NR'R", —C(=NR')—OR", linear or branched ($C_1$-$C_6$)polyhaloalkyl, trifluoromethoxy, or halogen, it being understood that R' and R" independently of one another represent a hydrogen atom or an optionally substituted linear or branched ($C_1$-$C_6$)alkyl group, and it being understood that one or more of the carbon atoms of the preceding possible substituents, may be deuterated, their enantiomers, diastereoisomers and atropoisomers, and addition salts thereof with a pharmaceutically acceptable acid or base.

In another embodiment, the invention relates to compounds of formula (I-a):

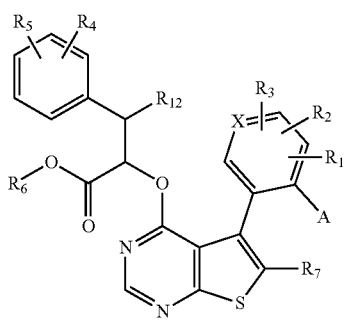

(I-a)

wherein:
A represents a linear or branched ($C_1$-$C_6$)alkyl group or an halogen atom,
$R_1$, $R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$) alkynyl group, a linear or branched ($C_1$-$C_6$)polyhaloalkyl, a hydroxy group, a linear or branched ($C_1$-$C_6$) alkoxy group, —S—($C_1$-$C_6$)alkyl group, a cyano, a nitro group, -alkyl($C_0$-$C_6$)—$NR_8R_8$', —O-$Cy_1$, -alkyl($C_0$-$C_6$)-$Cy_1$, -alkenyl($C_2$-$C_6$)—$Cy_1$, -alkynyl($C_2$-$C_6$)-$Cy_1$, —O-alkyl($C_1$-$C_6$)—$R_9$, —C(O)—$OR_8$, —O—C(O)—$R_8$, —C(O)—$NR_8R_8$', —$NR_8$—C(O)—$R_8$', —$NR_8$—C(O)—$OR_8$', -alkyl($C_1$-$C_6$)—$NR_8$—C(O)—$R_8$', —$SO_2$—$NR_8R_8$', —$SO_2$-alkyl($C_1$-$C_6$),
or the substituents of one of the pairs ($R_1$, $R_2$), ($R_2$, $R_3$), ($R_1$, $R_3$), ($R_4$, $R_5$) when grafted onto two adjacent carbon atoms, form together with the carbon atoms carrying them an aromatic or non-aromatic ring composed of from 5 to 7 ring members, which may contain from one to 3 heteroatoms selected from oxygen, sulphur and nitrogen, it being understood that resulting ring may be substituted by a group selected from a linear or branched ($C_1$-$C_6$)alkyl group, —$NR_{10}R_{10}$', -alkyl($C_0$-$C_6$)-$Cy_1$ or an oxo,
X represents a carbon or a nitrogen atom,
$R_6$ represents a hydrogen, a linear or branched ($C_1$-$C_6$) alkyl group, an aryl, an heteroaryl group, an arylalkyl ($C_1$-$C_6$) group, an heteroarylalkyl($C_1$-$C_6$) group,
$R_7$ represents a linear or branched ($C_1$-$C_6$)alkyl group, a linear or branched ($C_2$-$C_6$)alkenyl group, a linear or branched ($C_2$-$C_6$)alkynyl group, -$Cy_3$, -alkyl($C_1$-$C_6$)-$Cy_3$, -alkenyl($C_2$-$C_6$)-$Cy_3$, -alkynyl($C_2$-$C_6$)-$Cy_3$, —$Cy_3$-$Cy_4$, -$Cy_3$-alkyl($C_0$-$C_6$)—O-alkyl($C_0$-$C_6$)-$Cy_4$, an halogen atom, a cyano, —C(O)—$R_{11}$, —C(O)—$NR_{11}R_{11}$',
$R_8$ and $R_8$' independently of one another represent a hydrogen atom, a linear or branched ($C_1$-$C_6$)alkyl group, or -alkyl($C_0$-$C_6$)-$Cy_1$,
or ($R_8$, $R_8$') form together with the nitrogen atom carrying them an aromatic or non-aromatic ring composed of from 5 to 7 ring members, which may contain in addition to the nitrogen atom from one to 3 heteroatoms selected from oxygen, sulphur and nitrogen, it being understood that the nitrogen in question may be substituted by a group representing a hydrogen atom, a linear or branched ($C_1$-$C_6$)alkyl group,
$R_9$ represents -$Cy_1$, -$Cy_1$-alkyl($C_0$-$C_6$)-$Cy_2$, -$Cy_1$-alkyl ($C_0$-$C_6$)—O-alkyl($C_0$-$C_6$)-$Cy_2$, -$Cy_1$-alkyl($C_0$-$C_6$)—$NR_8$-alkyl($C_0$-$C_6$)-$Cy_2$, —C(O)—$NR_8R_8$', —$NR_8R_8$', —$NR_8$—C(O)$R_8$', —$OR_8$, O-alkyl($C_1$-$C_6$)—$OR_8$, —$SO_2$—$R_8$, —C(O)—$OR_8$, —NH—C(O)—NH—$R_8$,
$R_{10}$, $R_{10}$', $R_{11}$ and $R_{11}$' independently of one another represent a hydrogen atom or an optionally substituted linear or branched ($C_1$-$C_6$)alkyl group,
$R_{12}$ represents a hydrogen or a hydroxy group,
$Cy_1$, $Cy_2$, $Cy_3$ and $Cy_4$, independently of one another, represent a cycloalkyl group, a heterocycloalkyl group, an aryl or an heteroaryl group,
it being understood that:
"aryl" means a phenyl, naphthyl, biphenyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems,
it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched ($C_1$-$C_6$)alkyl, optionally substituted linear or branched ($C_2$-$C_6$) alkenyl group, optionally substituted linear or branched ($C_2$-$C_6$)alkynyl group, optionally substituted linear or branched ($C_1$-$C_6$)alkoxy, optionally substituted ($C_1$-$C_6$)alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched ($C_1$-$C_6$)polyhaloalkyl, trifluoromethoxy, or halogen, it being understood that R' and R" independently of one another represent a hydrogen atom or an optionally substituted linear or branched ($C_1$-$C_6$)alkyl group, their enantiomers, diastereoisomers and atropoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Advantageously, at least one of the groups selected from $R_1$, $R_2$ and $R_3$ does not represent a hydrogen atom.

More especially, compounds of formula (I) to which preference is given are compounds wherein n is an integer equal to 1.

In another embodiment of the invention, an advantageous possibility consists of compounds of formula (I-b):

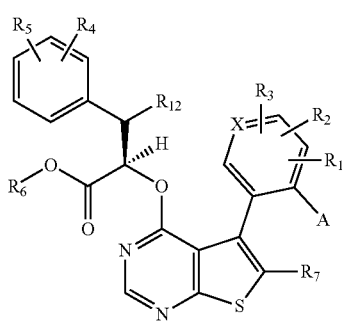

(I-b)

wherein A, $R_1$, $R_2$, $R_3$, $R_4$, $R_5$, $R_6$, $R_7$, $R_{12}$ and X are as defined for formula (I).

In the preferred compounds of the invention, A represents a linear or branched ($C_1$-$C_6$)alkyl group or a halogen atom. More preferably, A represents a methyl group, an ethyl group, a bromine atom or a chlorine atom.

Atropisomers are stereoisomers arising because of hindered rotation about a single bond, where energy differences due to steric strain or other contributors create a barrier to rotation that is high enough to allow for isolation of individual conformers. For compounds according to the invention, atropisomers are as follows:

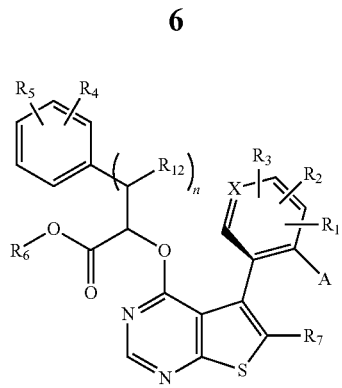

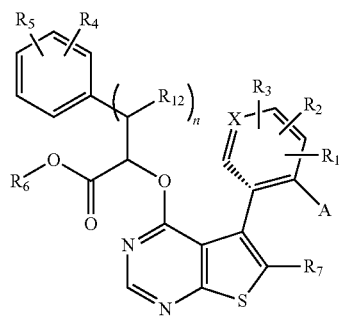

Preferred atropisomer is (5$S_a$) when X represents a carbon atom. Preferred atropisomer is (5$R_a$) when X represents a nitrogen atom.

Preferably, X represents a carbon atom.

Advantageously, $R_{12}$ represents a hydrogen atom.

In some preferred embodiment of the invention,

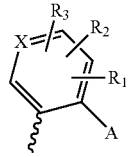

represents

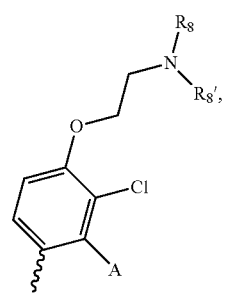

wherein A, $R_8$ and $R_8$' are as defined for formula (I).

In the preferred compounds of the invention,

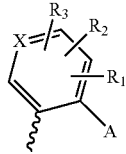

represents

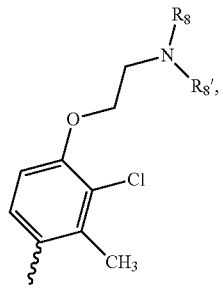

wherein $R_8$ and $R_8'$ are as defined for formula (I).

In another embodiment of the invention, $R_4$ represents an optionally substituted linear or branched ($C_1$-$C_6$)alkoxy group or a —O-alkyl($C_1$-$C_6$)—$R_9$ group. Advantageously, $R_4$ represents a 2,2,2-trifluoroethoxy group, a methoxy group, a 2-methoxyethoxy group or a —O-alkyl($C_1$-$C_6$)—$R_9$ group.

$R_5$ preferably represents a hydrogen atom.

In the preferred compounds of the invention,

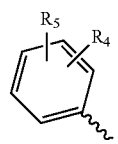

represents

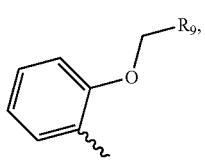

wherein $R_9$ is as defined for formula (I).

In another embodiment of the invention, an advantageous possibility consists of compounds of formula (I-c):

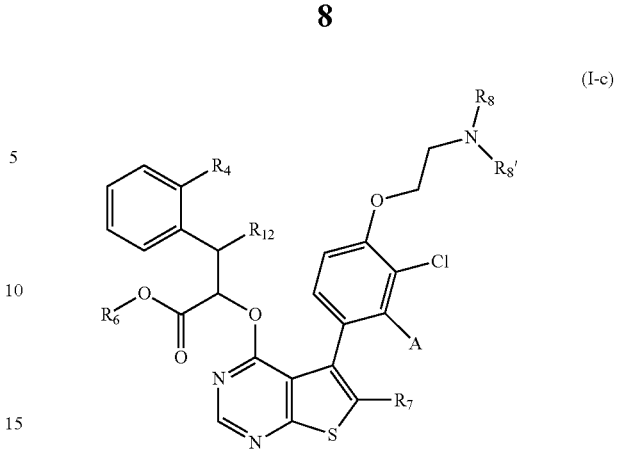

(I-c)

wherein $R_4$, $R_6$, $R_7$, $R_8$, $R_8'$, $R_{12}$ and A are as defined for formula (I).

Preferably, $R_6$ represents a hydrogen, an optionally substituted linear or branched ($C_1$-$C_8$)alkyl group, or an heteroarylalkyl($C_1$-$C_6$) group. Preferred $R_6$ groups are as follows: hydrogen; methyl; ethyl; 2-methoxyethyl; 2,2,2-trifluoroethyl; tert-butylcarbonyloxymethyl; (5-methyl-2-oxo-1,3-dioxol-4-yl)methyl; 2-(dimethylamino)-2-oxoethyl; 2-(2-methoxyethoxy)ethyl. Even more preferably, $R_6$ represents hydrogen.

In the preferred compounds of the invention, $R_7$ represents a linear or branched ($C_1$-$C_6$)alkyl group, a linear or branched ($C_2$-$C_6$)alkenyl group, a linear or branched ($C_2$-$C_6$)alkynyl group, an aryl or an heteroaryl group. Advantageously, $R_7$ represents a linear or branched ($C_2$-$C_6$)alkynyl group, an aryl or an heteroaryl group. More preferably, $R_7$ represents a prop-1-yn-1-yl group, a but-1-yn-1-yl group, a phenyl group or a furan-2-yl group. In a more preferred embodiment, $R_7$ represents a 4-(benzyloxy)phenyl group, a 4-(pyridin-4-ylmethoxy)phenyl group, a 4-phenylbut-1-yn-1-yl group, a 4-fluorophenyl group or a 5-fluorofuran-2-yl group. Even more preferentially, $R_7$ represents a 4-fluorophenyl group.

In the preferred compounds of the invention, $R_8$ and $R_8'$ independently of one another represent a linear or branched ($C_1$-$C_6$)alkyl group, or ($R_8$, $R_8'$) form together with the nitrogen atom carrying them a non-aromatic ring composed of from 5 to 7 ring members, which may contain in addition to the nitrogen atom from one to 3 heteroatoms selected from oxygen, sulphur and nitrogen, it being understood that the nitrogen in question may be substituted by a group representing a hydrogen atom, a linear or branched ($C_1$-$C_6$) alkyl group. More preferably, $R_8$ and $R_8'$ represent a methyl group, or ($R_8$, $R_8'$) form together a 4-methyl-piperazinyl group or a 4-ethyl-piperazinyl group. In a more preferred embodiment, ($R_8$, $R_8'$) form together a 4-methyl-piperazinyl group. In another preferred embodiment, $R_8$ and $R_8'$ represent a methyl group.

Advantageously, $R_9$ represents -$Cy_1$, -$Cy_1$-alkyl($C_0$-$C_6$)—O-alkyl($C_0$-$C_6$)-$Cy_2$ or -$Cy_1$-alkyl($C_0$-$C_6$)-$Cy_2$. More particularly, $R_9$ represents -$Cy_1$, -$Cy_1$-O—$CH_2$-$Cy_2$, or -$Cy_1$-$Cy_2$.

$Cy_1$ preferably represents a heteroaryl group, particularly, a pyrimidinyl group, a pyrazolyl group, a triazolyl group, a pyrazinyl group or a pyridinyl group. More preferably, $Cy_1$ represents a pyrimidin-4-yl group, a pyrazol-5-yl group, a triazol-5-yl group, a pyrazin-2-yl group or a pyridin-4-yl group. In the preferred compounds of the invention, $Cy_1$ represents a pyrimidin-4-yl group.

In another embodiment of the invention, Cy$_1$ represents a heteroaryl group which is substituted by an optionally substituted linear or branched (C$_1$-C$_6$)alkyl group, an optionally substituted linear or branched (C$_1$-C$_6$)alkoxy group, a —NR'R" group, or a linear or branched (C$_1$-C$_6$) polyhaloalkyl group, it being understood that R' and R" independently of one another represent a hydrogen atom or an optionally substituted linear or branched (C$_1$-C$_6$)alkyl group.

Cy$_2$ preferably represents a phenyl group, a pyridinyl group, a pyrazolyl group, a morpholinyl group, a furanyl group or a cyclopropyl group. More preferably, Cy$_2$ represents a phenyl group, a pyridin-2-yl group, a pyridin-3-yl group, a pyridin-4-yl group, a pyrazol-1-yl group, a morpholin-4-yl group, a furan-2-yl group or a cyclopropyl group. In the preferred compounds of the invention, Cy$_2$ represents a phenyl group.

Other compounds of the invention to which preference is given are those wherein R$_9$ represents -Cy$_1$-Cy$_2$ in which Cy$_1$ represents a pyrimidinyl group and Cy$_2$ represents a phenyl group, a pyridinyl group, a pyrazolyl group, a morpholinyl group, a furanyl group, or a cyclopropyl group. Even more preferentially, R$_9$ represents

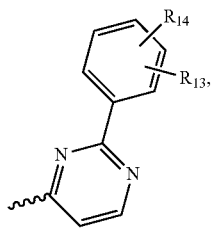

in which R$_{13}$ and R$_{14}$ independently of one another represent a hydrogen, an optionally substituted linear or branched (C$_1$-C$_6$)alkyl, optionally substituted linear or branched (C$_1$-C$_6$)alkoxy, hydroxy, linear or branched (C$_1$-C$_6$)polyhaloalkyl, or halogen atom. Preferred R$_{13}$ and R$_{14}$ groups are as follows: hydrogen; methyl; ethyl; methoxy; ethoxy; isopropoxy; methoxyethoxy; fluoro; hydroxy; trifluoromethyl. Advantageously, R$_{14}$ represents hydrogen and R$_{13}$ is located at ortho position of the phenyl group.

Among the preferred compounds of the invention there may be mentioned:

(2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-methoxyphenyl)propanoic acid, (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(2-methoxyethoxy)phenyl] propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(2,2,2-trifluoro ethoxy) phenyl]propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(pyrazin-2-ylmethoxy) phenyl]propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(1-methyl-1H-pyrazol-5-yl)methoxy]phenyl}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(propan-2-yl)-1H-pyrazol-5-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(propan-2-yl)-1H-pyrazol-5-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(trifluoromethyl) pyridin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-ethoxypyrimidin-4-yl) methoxy]phenyl}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(propan-2-yloxy) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(pyridin-2-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyethyl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[2-(cyclopropylmethoxy) pyrimidin-4-yl]methoxy}phenyl)propanoic acid, (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(5-fluorofuran-2-yl) thieno[2,3-d]pyrimidin-4-yl]oxy}propanoic acid, (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid, (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(5-fluorofuran-2-yl) thieno[2,3-d]pyrimidin-4-yl]oxy}propanoic acid, ethyl (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[1-(propan-2-yl)-1H-pyrazol-5-yl]methoxy}phenyl)propanoate, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-cyclopropyl pyrimidin-4-yl)methoxy]phenyl}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(furan-2-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-propylpyrimidin-4-yl) methoxy]phenyl}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2,2,2-trifluoroethyl)-1H-pyrazol-5-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2, 3-d]pyrimidin-4-yl]oxy}-3-(2-{[1-(2,2,2-trifluoro ethyl)-1H-pyrazol-5-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(thiophen-2-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(morpholin-4-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(pyridin-4-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-ethoxypyrimidin-4-yl)methoxy]phenyl}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyethoxy) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(2-methoxyethyl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(1H-pyrazol-1-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-methoxypyridin-4-yl)methoxy]phenyl}propanoic acid, (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methylpyridin-4-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl) pyrimidin-4-yl]methoxy}phenyl)propanoic acid, (2R)-3-{2-[(1-butyl-1H-1,2,3-triazol-5-yl)methoxy]phenyl}-2-{[(5S$_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-methylpyridin-3-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(morpholin-4-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2,2,2-trifluoro ethoxy) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[(2-methoxyethyl) amino]pyrimidin-4-yl}methoxy)phenyl]propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methylphenyl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[1-(2,2,2-trifluoroethyl)-1H-pyrazol-5-yl]methoxy}phenyl)propanoic acid, (2R)-2-{[(5S$_a$)-5-{3-chloro-4-[2-(dimethylamino)ethoxy]-2-methylphenyl}-6-(5-fluorofuran-2-yl)thieno[2,3-d]pyrimidin-4-yl]oxy}-3-(2-{[2-(morpholin-4-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(morpholin-4-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-ethoxyphenyl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-methylpyridin-4-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3,3,3-trifluoro propoxy) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(3-methylpyridin-4-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(methoxymethyl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(3-methylpyridin-4-yl) pyrimidin-4-yl]methoxy}phenyl)propanoic acid, (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(4-methylpyridin-3-yl) pyrimidin-4-yl]methoxy}phenyl)propanoic acid, (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-methoxyphenyl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(2,2,2-trifluoro ethoxy) pyrimidin-4-yl]methoxy}phenyl)propanoic acid, ethyl (2R)-2-{[(5S$_a$)-5-{3-chloro-2-methyl-4-[2-(4-methylpiperazin-1-yl)ethoxy] phenyl}-6-(4-fluorophenyl)thieno [2,3-d]pyrimidin-4-yl]oxy}-3-(2-{[2-(2,2,2-trifluoroethoxy)pyrimidin-4-yl]methoxy}phenyl)propanoate, ethyl (2R)-2-{[(5S$_a$)-5-{3-chloro-2-methyl-4-[2-(4-methylpiperazin-1-yl)ethoxy] phenyl}-6-(4-fluorophenyl)thieno [2,3-d]pyrimidin-4-yl]oxy}-3-(2-{[2-(2-methoxy phenyl) pyrimidin-4-yl]methoxy}phenyl)propanoate, 2,2,2-trifluoroethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoate, propan-2-yl (2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate, 2-methoxyethyl (2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate, ethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(pyridin-3-yl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(ethoxymethyl) pyrimidin-4-yl]methoxy}phenyl)propanoic acid, (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-fluorophenyl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-methoxy pyrimidin-4-yl)methoxy]phenyl}propanoic acid, (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(prop-1-yn-1-yl) thieno[2,3-d]pyrimidin-4-yl]oxy}propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-hydroxyphenyl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(propan-2-yloxy)phenyl]pyrimidin-4-yl}methoxy)phenyl]propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(2-methoxy ethoxy)phenyl]pyrimidin-4-yl}methoxy)phenyl]propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-ethylphenyl) pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[4-methoxy-2-(trifluoromethyl)phenyl]pyrimidin-4-yl}methoxy)phenyl]propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2,5-dimethyl pyridin-4-yl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(5-methoxy-2-methyl-pyridin-4-yl)pyrimidin-4-yl]methoxy}phenyl)propanoic acid, (2R)-2-{[(5S$_a$)-5-{3-chloro-2-ethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, (2R)-2-{[(5S$_a$)-5-{2-bromo-3-chloro-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, (2R)-2-{[(5S$_a$)-5-{2,3-dichloro-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl) pyrimidin-4-yl]methoxy}phenyl)propanoic acid, (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d] pyrimidin-4-yl]oxy}propanoic acid, (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoic acid, (2R)-2-[(6-[4-(benzyloxy)phenyl]-(5S$_a$)-5-{3-chloro-2-methyl-4-[2-(4-methyl piperazin-1-yl)ethoxy]phenyl}thieno[2,3-d]pyrimidin-4-yl)oxy]-3-(2-{[2-(2-methoxyphenyl)pyrimidin-4-yl]methoxy}phenyl)propanoic acid, (2R)-2-[((5S$_a$)-5-{3-chloro-2-methyl-4-[2-(4-methylpiperazin-1-yl)ethoxy]phenyl}-6-[4-(pyridin-4-ylmethoxy)phenyl]thieno[2,3-d]pyrimidin-4-yl)oxy]-3-(2-{[2-(2-methoxyphenyl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy]phenyl}-6-(4-phenylbut-1-yn-1-yl)thieno[2,3-d]pyrimidin-4-yl]oxy}-3-(2-{[2-(2-methoxy phenyl)pyrimidin-4-yl]methoxy}phenyl)propanoic acid, methyl (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-methoxy phenyl)pyrimidin-4-yl]methoxy}phenyl)propanoate, ethyl (2R)-2-{[(5S$_a$)-5-{3-chloro-4-[2-(4-ethylpiperazin-1-yl)ethoxy]-2-methyl phenyl}-6-(4-fluorophenyl)thieno[2,3-d]pyrimidin-4-yl]oxy}-3-(2-{[2-(2-fluoro phenyl)pyrimidin-4-yl]methoxy}phenyl)propanoate, ethyl (2R)-3-{2-[(1-tert-butyl-1H-pyrazol-5-yl)methoxy] phenyl}-2-{[5(5S$_a$)-{3-chloro-4-[2-(dimethylamino)ethoxy]-2-methylphenyl}-6-(4-fluorophenyl) thieno[2,3-d]pyrimidin-4-yl]oxy}propanoate, {[(2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-methoxy phenyl)pyrimidin-4-yl]methoxy}phenyl)propanoyl]oxy}methyl 2,2-dimethylpropanoate, (5-methyl-2-oxo-1,3-dioxol-4-yl)methyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate, 2-(dimethylamino)-2-oxoethyl (2R)-2-{[(5S$_a$)-5-{3-chloro-2-methyl-4-[2-(4-methyl piperazin-1-yl)ethoxy]phenyl}-6-(4-fluorophenyl)thieno[2,3-d]pyrimidin-4-yl] oxy}-3-(2-{[2-(2-methoxyphenyl)pyrimidin-4-yl]methoxy}phenyl)propanoate, 2-(2-methoxyethoxy)ethyl (2R)-2-{[(5S$_a$)-5-{3-chloro-2-methyl-4-[2-(4-methyl piperazin-1-yl)ethoxy]phenyl}-6-(4-fluorophenyl)thieno[2,3-d]pyrimidin-4-yl] oxy}-3-(2-{[2-(2-methoxyphenyl)pyrimidin-4-yl]methoxy}phenyl)propanoate.

The invention relates also to a process for the preparation of compounds of formula (I), which process is characterised in that there is used as starting material the compound of formula (II-a):

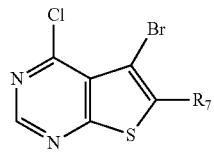
(II-a)

wherein R$_7$ is as defined for formula (I),
which compound of formula (II-a) is subjected to coupling with a compound of formula (III):

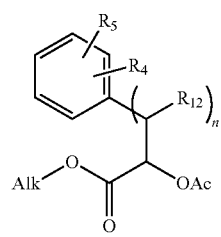
(III)

wherein R$_4$, R$_5$, R$_{12}$ and n are as defined for formula (I), and Alk represents a linear or branched (C$_1$-C$_6$)alkyl group, to yield the compound of formula (IV):

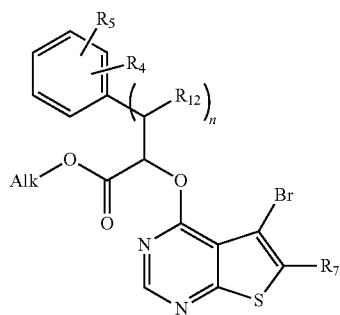
(IV)

wherein R$_4$, R$_5$, R$_7$, R$_{12}$ and n are as defined for formula (I) and Alk is as defined before,
compound of formula (IV) which is further subjected to coupling with compound of formula (V):

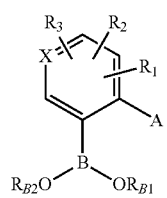
(V)

wherein R$_1$, R$_2$, R$_3$, X and A are as defined for formula (I), and R$_{B1}$ and R$_{B2}$ represent a hydrogen, a linear or branched (C$_1$-C$_6$) alkyl group, or R$_{B1}$ and R$_{B2}$ form with the oxygen carrying them an optionally methylated ring, to yield the compound of formula (VI):

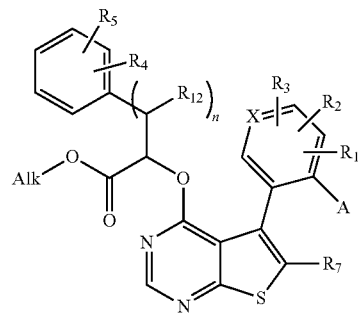
(VI)

wherein R$_1$, R$_2$, R$_3$, R$_4$, R$_5$, R$_7$, R$_{12}$, X, A and n are as defined for formula (I) and Alk is as defined before,
the Alk-O—C(O)— ester function of which compound of formula (VI) is hydrolysed to yield the carboxylic acid, which may optionally be optionally be reacted with an alcohol of formula R$_6$OH wherein R$_6$ is as defined in formula (I),
to yield the compound of formula (I), which may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

In an other embodiment of the invention, compounds of formula (I) may be obtained using an alternative process, which process is characterised in that there is used as starting material the compound of formula (II-b):

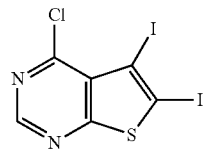
(II-b)

which compound of formula (II-b) is converted into compound of formula (II-c):

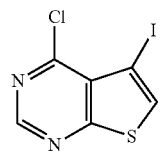
(II-c)

which compound of formula (II-c) is subjected to coupling with a compound of formula (V):

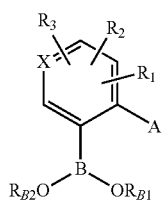

(V)

wherein $R_1$, $R_2$, $R_3$, X and A are as defined for formula (I), and $R_{B1}$ and $R_{B2}$ represent a hydrogen, a linear or branched ($C_1$-$C_6$) alkyl group, or $R_{B1}$ and $R_{B2}$ form with the oxygen carrying them an optionally methylated ring, to yield the compound of formula (VII):

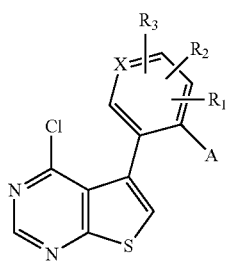

(VII)

wherein $R_1$, $R_2$, $R_3$, A and X are as defined in formula (I), which compound of formula (VII) is further subjected to the action of $I_2$ in the presence of lithium diisopropylamide (strong base) to yield compound of formula (VIII):

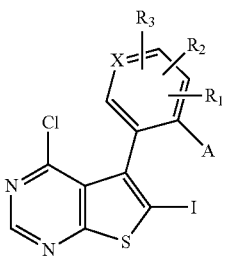

(VIII)

wherein $R_1$, $R_2$, $R_3$, A and X are as defined in formula (I), which compound of formula (VIII) is further subjected to coupling with a compound of formula (IX):

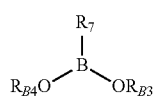

(IX)

wherein $R_7$ is as defined for formula (I), and $R_{B3}$ and $R_{B4}$ represent a hydrogen, a linear or branched ($C_1$-$C_6$)alkyl group, or $R_{B3}$ and $R_{B4}$ form with the oxygen carrying them an optionally methylated ring, to yield compound of formula (X):

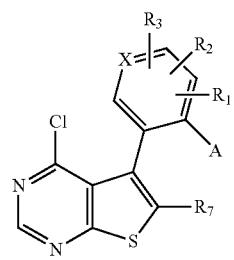

(X)

wherein $R_1$, $R_2$, $R_3$, A, X and $R_7$ are as defined in formula (I), which compound of formula (X) is further subjected to coupling with a compound of formula (III):

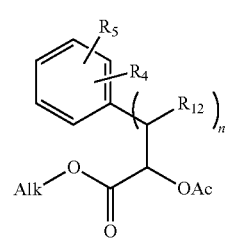

(III)

wherein $R_4$, $R_5$, $R_{12}$ and n are as defined for formula (I), and Alk represents a linear or branched ($C_1$-$C_6$)alkyl group, to yield the compound of formula (VI):

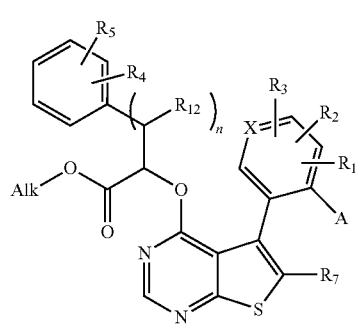

(VI)

wherein $R_1$, $R_2$, $R_3$, $R_4$, $R_5$, $R_7$, $R_{12}$, X, A and n are as defined for formula (I) and Alk is as defined before, the ester function of which compound of formula (VI) is hydrolysed to yield the carboxylic acid, which may optionally be optionally reacted with an alcohol of formula $R_6$OH wherein $R_6$ is as defined in formula (I), to yield the compound of formula (I), which may be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II-a), (II-b), (III), (V), (IX) and the alcohol R₆OH are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers and of immune and auto-immune diseases.

More especially, the compounds according to the invention will be useful in the treatment of chemo- or radio-resistant cancers.

Among the cancer treatments envisaged there may be mentioned, without implying any limitation, treatment of cancers of the bladder, brain, breast and uterus, chronic lymphoid leukaemias, cancer of the colon, œsophagus and liver, lymphoblastic leukaemias, acute myeloid leukaemias, lymphomas, melanomas, malignant haemopathies, myelomas, ovarian cancer, non-small-cell lung cancer, prostate cancer, pancreatic cancer and small-cell lung cancer.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formula (I) with an anticancer agent selected from genotoxic agents, mitotic poisons, anti-metabolites, proteasome inhibitors, kinase inhibitors and antibodies, and also to pharmaceutical compositions comprising that type of combination and their use in the manufacture of medicaments for use in the treatment of cancer.

Advantageously, the present invention relates to the combination of a compound of formula (I) with an EGFR inhibitor, and also to pharmaceutical compositions comprising that type of combination.

In another embodiment, the present invention relates to the combination of a compound of formula (I) with a mTOR/PI3K inhibitor, and also to pharmaceutical compositions comprising that type of combination.

In a preferred embodiment, the present invention relates to the combination of a compound of formula (I) with a MEK inhibitor, and also to pharmaceutical compositions comprising that type of combination.

Preferably, the present invention relates to the combination of a compound of formula (I) with a HER2 inhibitor, and also to pharmaceutical compositions comprising that type of combination.

Advantageously, the present invention relates to the combination of a compound of formula (I) with a RAF inhibitor, and also to pharmaceutical compositions comprising that type of combination.

In another embodiment, the present invention relates to the combination of a compound of formula (I) with a EGFR/HER2 inhibitor, and also to pharmaceutical compositions comprising that type of combination.

In a preferred embodiment, the present invention relates to the combination of a compound of formula (I) with a taxane, and also to pharmaceutical compositions comprising that type of combination.

In another embodiment, the present invention relates to the combination of a compound of formula (I) with a proteasome inhibitor, an immunomodulator or an alkylating agent, and also to pharmaceutical compositions comprising that type of combination.

The combination of a compound of formula (I) with an anticancer agent may be administered simultaneously or sequentially. The administration route is preferably the oral route, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The compounds of the invention may also be used in combination with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn. 2000, 13, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol. 2001, 74(4):257-75), the protein Z derivative from the domain B of staphylococcal protein A, thioredoxin A or any protein with a repeated domain such as an "ankyrin repeat" (Kohl et al., PNAS 2003, 100(4), 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention but do not limit it in any way.

General Procedures

All reagents obtained from commercial sources were used without further purification. Anhydrous solvents were obtained from commercial sources and used without further drying.

Flash chromatography was performed on ISCO Combi-Flash Rf 200i with pre-packed silica-gel cartridges (RediSep®$R_f$ Gold High Performance).

Thin layer chromatography was conducted with 5×10 cm plates coated with Merck Type 60 F254 silica-gel.

Microwave heating was performed in an Anton Parr MonoWave or CEM Discover® instrument.

Preparative HPLC purifications were performed on an Armen Spot Liquid Chromatography system with a Gemini-NX® 10 μM C18, 250 mm×50 mm i.d. column running at a flow rate of 118 mL min$^{-1}$ with UV diode array detection (210-400 nm) using 25 mM aqueous $NH_4HCO_3$ solution and MeCN as eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF/$H_2O$ (1:1) with 5 μL loop injection. LCMS analyses were performed on two instruments, one of which was operated with basic, and the other with acidic eluents.

Basic LCMS: Gemini-NX, 3 μm, C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 μm, 50 mm×4.6 mm i.d. column at 40° C., at a flow rate of 1 mL min$^{-1}$ using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-$d_6$ or CDCl$_3$ as solvent. $^1$H NMR data is in the form of delta values, given in part per million (ppm), using the residual peak of the solvent (2.50 ppm for DMSO-$d_6$ and 7.26 ppm for CDCl$_3$) as internal standard. Splitting patterns are designated as: s (singlet), d (doublet), t (triplet), q (quartet), quint (quintet), m (multiplet), br s (broad singlet), dd (doublet of doublets), td (triplet of doublets), dt (doublet of triplets), ddd (doublet of doublet of doublets).

Combination gas chromatography and low resolution mass spectrometry were performed on Agilent 6850 gas chromatograph and Agilent 5975C mass spectrometer using 15 m×0.25 mm column with 0.25 μm HP-5MS coating and helium as carrier gas. Ion source: EI$^+$, 70 eV, 230° C., quadrupole: 150° C., interface: 300° C.

HRMS were determined on a Shimadzu IT-TOF, ion source temperature 200° C., ESI +/-, ionization voltage: (+-)4.5 kV. Mass resolution min. 10000.

Elementary analyses were performed on a Thermo Flash EA 1112 Elemental Analyzer.

LIST OF ABBREVIATIONS

| Abbreviation | Name |
| --- | --- |
| 2-Me-THF | 2-methyl-tetrahydrofurane |
| Ac | acetyl |
| Ad | adamantyl |
| AIBN | 2-[(1-cyano-1-methyl-ethyl)azo]-2-methyl-propanenitrile |
| AtaPhos | bis(di-tert-butyl(4-dimethylaminophenyl)phosphine)dichloropalladium(II) |
| CuTC | copper(I) thiophene-2-carboxylate |
| DAST | diethylaminosulfur trifluoride |
| dba | dibenzylideneacetone |
| DCM | methylene chloride |
| Dess-Martin periodinane | 1,1,1-tris(acetyloxy)-1,1-dihydro-1,2-benziodoxol-3-(1H)-one |
| DIPA | diisopropylamine |
| DIPEA | diisopropylethylamine |
| DME | 1,2-dimethoxyethane |
| DMF | dimethylformamide |
| dppf | 1,1'-bis(diphenylphosphino)ferrocene |
| eq. | equivalent |
| Et | ethyl |
| HMDS | hexamethyldisilazane |
| $^i$Pr | isopropyl |
| LDA | lithium diisopropylamide |
| Me | methyl |
| MeCN | acetonitrile |
| NBS | N-bromosuccinimide |
| $^n$Bu | n-butyl |
| NCS | N-chlorosuccinimide |
| Ph | phenyl |
| PyBOP | benzotriazol-1-yloxy(tripyrrolidin-1-yl)phosphonium hexafluorophosphate |
| rt | room temperature |
| Selectfluor | 1-chloromethyl-4-fluoro-1,4-diazoniabicyclo[2.2.2]octane bis(tetrafluoroborate) |
| SPhos | 2-dicyclohexylphosphino-2',6'-dimethoxybiphenyl |
| TBAF | tetrabutyl ammonium fluoride |
| TBAOH | tetrabutyl ammonium hydroxyde |
| $^t$Bu | tert-butyl |
| tBuXPhos | 2-di(tert-butylphosphino)-2',4',6'-triisopropylbiphenyl |
| TEA | triethylamine |
| TFA | trifluoroacetic acid |
| THF | tetrahydrofurane |
| TIPSCl | triisopropylsilyl chloride |

Preparation 1a:
5-Bromo-4-chloro-6-iodo-thieno[2,3-d]pyrimidine

Step A: 6-Iodo-3H-thieno[2,3-d]pyrimidin-4-one

A 2 L round bottomed flask equipped with mechanical stirrer, thermometer and reflux condenser was charged with the solution of 433 mL acetic acid, 13 mL sulfuric acid and 87 mL water. 69.3 g 3H-thieno[2,3-d]pyrimidin-4-one (0.46 mol), 51.9 g periodic acid (0.23 mol) and 104 g iodine (0.41 mol) were added to the stirred solution heated to 60° C. for 1 h. The resulting suspension was cooled to room temperature, filtered off, washed with a mixture of acetic acid and water (5:1) and then with diethyl ether. The resulting beige crystalline solid was air dried.

$^1$H NMR (500 MHz, DMSO-$d_6$): 12.57 (brs, 1H), 8.09 (s, 1H), 7.65 (s, 1H).

Step B: 4-Chloro-6-iodo-thieno[2,3-d]pyrimidine

A 1 L round bottomed flask equipped with mechanical stirrer, thermometer, reflux condenser and a CaCl$_2$-tube was charged with 113 mL phosphorous oxychloride and 35 mL N,N-dimethylaniline (0.29 mol). 75.54 g 6-iodo-3H-thieno[2,3-d]pyrimidin-4-one (0.27 mol) was added to the mixture in portions during 5 minutes. The reaction mixture was stirred at 105° C. for 1 hour. The resulting suspension was cooled to 10° C., filtered and washed with hexane. The crude product was added to ice water and stirred for 10 minutes, filtered off, washed with cold water, diethyl ether and air dried. Beige crystalline solid was obtained.

$^1$H NMR (400 MHz, DMSO-d$_6$): 8.89 (s, 1H), 7.98 (s, 1H).

Step C: 5-Bromo-4-chloro-6-iodo-thieno[2,3-d]pyrimidine

A 2 L round bottomed flask equipped with mechanical stirrer, thermometer and a bubbler was charged with 600 mL acetonitrile. 84.9 g 4-chloro-6-iodo-thieno[2,3-d]pyrimidine (0.29 mol), 50.9 g NBS (0.29 mol) and 8.5 mL tetrafluoroboric acid diethyl ether complex were added. The reaction mixture was stirred at room temperature for 16 hours. Further 22.9 g (0.12 mol) NBS was added to the mixture in three portions. After cooling the suspension to 0° C. and stirring for further 1 hour the precipitate was filtered off, washed with acetonitrile and air dried. The product was obtained as beige crystalline solid.

$^1$H NMR (500 MHz, DMSO-d$_6$): 8.88 (s, 1H).

Preparation 1b:
4-Chloro-5,6-diiodo-thieno[2,3-d]pyrimidine

Step A: 5,6-Diiodo-3H-thieno[2,3-d]pyrimidin-4-one

To a well stirred slurry of 61.3 g 3H-thieno[2,3-d]pyrimidin-4-one (396 mmol), 92.4 g periodic acid (405 mmol), 1 L acetic acid, 200 mL water and 6 mL cc. sulfuric acid was added 203 g iodine (799 mmol). The reaction mixture was heated to 110° C. and stirred for 3 hours. The suspension was cooled to room temperature then 940 mL diethyl ether was added and stirred further at 10° C. for 30 minutes. The precipitate was filtered off washed with a 2:1 mixture of diethyl ether and ethanol (100 mL), finally with diethyl ether (3×250 mL) and air dried to give the product as a tan powder.

Step B: 4-Chloro-5,6-diiodo-thieno[2,3-d]pyrimidine

To a well stirred slurry of 180 g 5,6-diiodo-3H-thieno[2,3-d]pyrimidin-4-one (445 mmol) in 2.5 L phosphorous oxychloride was added 64 mL N,N-dimethylaniline. The reaction mixture was heated to 105° C. and stirred for 1.5 hours. The resulting suspension was cooled to room temperature and 1.5 L hexane was added and it was stirred further for 20 minutes. The precipitate was filtered off, washed with hexane (3×500 ml) and water (3×100 mL) then air dried to give the product as a grey crystalline solid.

$^1$H NMR (400 MHz, DMSO-d$_6$): 8.88 (s, 1H).

Preparation 1c:
4-Chloro-5-iodo-thieno[2,3-d]pyrimidine 52.8 g 4-chloro-5,6-diiodo-thieno[2,3-d]pyrimidine (Preparation 1b) (125 mmol) was dissolved in 400 mL abs. THF and cooled to 0° C. 100 ml $^t$BuMgCl (200 mmol, 2 M in diethyl ether) was added over 15 minutes. 50 mL water was added then the solution was decanted and concentrated under reduced pressure. The crude product was sonicated in a mixture of acetonitrile and water (3:1) and then collected by filtration.

$^1$H NMR (400 MHz, DMSO-d$_6$): 8.95 (s, 1H), 8.45 (s, 1H).

Preparation 1d:
4-Chloro-6-ethyl-5-iodo-thieno[2,3-d]pyrimidine

Step A: 6-Ethyl-3H-thieno[2,3-d]pyrimidin-4-one

The mixture of 701 g 2-amino-5-ethyl-thiophene-3-carboxylic acid ethyl ester (3.52 mol) and 2200 mL formamide was heated to 200° C. and the lower boiling point solvents were distilled off. After 2 hours further 250 mL formamide was added and the mixture was stirred at the same temperature for another hour then at room temperature for 16 hours. The resulting mixture was poured into 7.5 L water and the precipitate was filtered off, washed with 1.5 L toluene and 3 L water then air dried to give the product as a brown crystalline solid.

Step B: 6-Ethyl-5-iodo-3H-thieno[2,3-d]pyrimidin-4-one

The mixture of 301 g 6-ethyl-3H-thieno[2,3-d]pyrimidin-4-one, 847 g iodine, 1040 g silver sulfate and 1.7 L ethanol was stirred at room temperature for 3 days. The resulting precipitate was filtered off and washed with ethanol (3×400 ml). The product was eluted from the filter cake with the following procedure: the filter cake was stirred with 800 mL N,N-dimethylformamide at 50° C. for 1 hour then the suspension was filtered. This sequence was repeated 6 times. The combined organic layer was evaporated to dryness to give the product as a tan crystalline solid.

Step C: 4-Chloro-6-ethyl-5-iodo-thieno[2,3-d]pyrimidine

The mixture of stirred 880 ml phosphorous oxychloride and 102 mL N,N-dimethylaniline was heated to 95° C. and 220 g 6-ethyl-5-iodo-thieno[2,3-d]pyrimidin-4-one (0.719 mol) was added quickly at the same temperature and then stirred for further 15 minutes. The reaction mixture was cooled to 80° C. and poured on a stirred mixture of water (1 L), crushed ice (2 kg) and DCM (700 ml). The resulting mixture was stirred for further 30 minutes while the temperature was kept below 20° C. The phases were separated, the inorganic layer was extracted with DCM (100 ml) and the organic layer was washed with water (100 ml). The combined organic layer was dried with MgSO$_4$ and concentrated under reduced pressure to give the product as a tan crystalline solid.

$^1$H NMR (400 MHz, DMSO-d$_6$): 8.79 (s, 1H), 3.02 (q, 2H), 1.39 (t, 3H).

Preparation 1e:
6-Bromo-4-chloro-5-iodo-thieno[2,3-d]pyrimidine

Step A: 6-Bromo-3H-thieno[2,3-d]pyrimidin-4-one

The mixture of 60.1 g 3H-thieno[2,3-d]pyrimidin-4-one (0.395 mol), 605 mL acetic acid and 24 mL bromine (0.468 mol) was stirred at room temperature for 16 hours. The reaction mixture was monitored by LCMS. Further bromine was added in three portions (12 mL, 5 mL, 10 mL) until the conversion exceeded 95%. The precipitate was filtered off, washed with acetic acid (3×50 mL), diethyl ether (3×100 mL) and then air dried to give the product as a tan powder.

Step B: 6-Bromo-5-iodo-3H-thieno[2,3-d]pyrimidin-4-one

1 L cc. sulfuric acid was cooled with ice-water bath and 72.0 g potassium iodide (0.434 mol) was added in portions during 15 minutes and then 32.4 g sodium periodate (0.151 mol) during a 10 minutes period. The resulting mixture was stirred at room temperature for 30 minutes then 80.0 g 6-bromo-3H-thieno[2,3-d]pyrimidin-4-one (0.346 mol) was added to the mixture in portions in 30 minutes while the internal temperature was kept between −21° C. and −19° C. The reaction mixture was stirred at −20° C. for 1.5 hours. Ice (3 kg) was added to the suspension then the precipitate was filtered off, washed with water (3×500 mL), finally with diethyl ether (3×200 mL) and air dried to give the product as a tan crystalline solid.

Step C: 6-Bromo-4-chloro-5-iodo-thieno[2,3-d]pyrimidine

To a well stirred slurry of 116 g 6-bromo-5-iodo-3H-thieno[2,3-d]pyrimidin-4-one (0.324 mol) in 910 mL phosphorous oxychloride 41 mL N,N-dimethylaniline was added. The stirred reaction mixture was heated to 100° C. for 1.5 hours. The resulting suspension was cooled to room temperature, hexane (1100 mL) was added and it was stirred for further 20 minutes. The precipitate was filtered off, washed with hexane (3×500 mL), water (3×100 mL) and diisopropyl ether (2×200 mL), finally air dried to give the Preparation 1e as a green shaded powder.

$^1$H NMR (400 MHz, DMSO-$d_6$): 8.95 (s, 1H)

Preparation 2a: 5-Bromo-4-chloro-6-(4-fluorophenyl)thieno[2,3-d]pyrimidine 75.08 g 5-bromo-4-chloro-6-iodo-thieno[2,3-d]pyrimidine (Preparation 1a) (200 mmol), 53.63 g 2-(4-fluorophenyl)-4,4,5,5-tetramethyl-1,3,2-dioxaborolane (240 mmol), 130 g cesium carbonate (400 mmol), 2.245 g Pd(OAc)$_2$ (10 mmol) and 8.50 g $^t$BuX-Phos (20 mmol) were placed in a 2 L flask. 600 mL THF and 200 mL water were added, and then stirred overnight at 70° C. under argon atmosphere. THF was evaporated, and then the product was collected by filtration. Crude product was sonicated in 250 mL acetonitrile and filtered again. Then Preparation 2a was crystallized from EtOH/THF (2:1).

$^1$H NMR (400 MHz, DMSO-$d_6$): 9.02 (s, 1H), 7.80-7.77 (m, 2H), 7.47-7.43 (m, 2H).

Preparation 2b: 5-Bromo-4-chloro-6-(5-fluoro-2-furyl)thieno[2,3-d]pyrimidine 112.6 g (300 mmol) 5-bromo-4-chloro-6-iodo-thieno[2,3-d]pyrimidine (Preparation 1a), 254.4 g (1200 mmol) 2-(5-fluoro-2-furyl)-4,4,5,5-tetramethyl-1,3,2-dioxaborolane, 195.5 g (600 mmol) cesium carbonate, 3.36 g (15 mmol) Pd(OAc)$_2$, 12.74 g (30 mmol) $^t$BuX-Phos were placed in a 2 L flask. 1000 mL THF and 400 mL water were added, and then stirred overnight at 70° C. under argon atmosphere. THF was evaporated, and then the product was collected by filtration. Crude product was dissolved in THF, and then celite was added and the volatiles were evaporated under reduced pressure. The solid residue was purified by flash chromatography on silica gel using heptane/EtOAc as eluents.

$^1$H NMR (400 MHz, DMSO-$d_6$): 8.95 (s, 1H), 7.55 (t, 1H), 6.23 (dd, 1H).

Preparation 2c: 5-Bromo-4-chloro-6-(2-furyl)thieno[2,3-d]pyrimidine 112.6 g 5-bromo-4-chloro-6-iodo-thieno[2,3-d]pyrimidine (Preparation 1a) (300 mmol), 93.14 g 2-(2-furyl)-4,4,5,5-tetramethyl-1,3,2-dioxaborolane (480 mmol), 215.0 g cesium carbonate (660 mmol), 3.367 g Pd(OAc)$_2$ (15 mmol) and 12.74 g $^t$BuX-Phos (20 mmol) were placed in a 2 L flask. 1000 mL THF and 300 mL water were added, and then stirred for 7 hours at 70° C. under argon atmosphere. THF was evaporated, and then the product was collected by filtration. Crude product was sonicated in 250 mL acetonitrile and filtered again. Then Preparation 2c was crystallized from EtOH/THF (2:1).

$^1$H NMR (400 MHz, DMSO-$d_6$): 8.96 (s, 1H), 8.05 (dd, 1H), 7.59 (dd, 1H), 6.86 (dd, 1H).

Preparation 2d: 5-Bromo-4-chloro-6-(5-chloro-2-furyl)thieno[2,3-d]pyrimidine 33.29 g 5-bromo-4-chloro-6-(2-furyl)thieno[2,3-d]pyrimidine (Preparation 2c) (105.7 mmol) and 16.90 g NCS (126.6 mmol) were placed in a 1 L flask. 400 mL THF and 20 mL TFA were added, and the stirred for 2 hours at room temperature. Reaction mixture was washed with saturated NaHCO$_3$. The organic phas was dried over MgSO$_4$, filtered and concentrated to give Preparation 2d.

$^1$H NMR (400 MHz, CDCl$_3$): 8.84 (s, 1H), 7.52 (d, 1H), 6.45 (d, 1H).

Preparation 2e: 5-Bromo-4-chloro-6-(4-fluoro-3-methoxy-phenyl)thieno[2,3-d] pyrimidine 15.01 g 5-bromo-4-chloro-6-iodo-thieno[2,3-d]pyrimidine (Preparation 1a) (40 mmol), 12.10 g 2-(4-fluoro-3-methoxy-phenyl)-4,4,5,5-tetramethyl-1,3,2-dioxaborolane (44 mmol), 32.58 g cesium carbonate (100 mmol), 1.463 g Pd(dppf)Cl$_2$ (2 mmol) were placed in an 1 L flask. 150 mL THF and 150 mL water were added, and then stirred overnight at 70° C. under argon atmosphere. To the reaction mixture brine was added and the pH was set to 6 with 2 M HCl, and then extracted with DCM. The volatiles from the organic phase were evaporated under reduced pressure and the crude product was purified by flash chromatography on silica gel using heptane/DCM as eluents.

$^1$H NMR (400 MHz, DMSO-$d_6$): 8.94 (s, 1H), 7.42 (dd, 1H), 7.36 (dd, 1H), 7.24-7.20 (m, 1H), 3.90 (s, 3H).

Preparation 2f: 4-Chloro-5-iodo-6-(prop-1-ynyl)-thieno[2,3-d]pyrimidine 42.24 g 4-chloro-5,6-diiodo-thieno[2,3-d]pyrimidine (Preparation 1b) (100 mmol), 3.509 g Pd(PPh$_3$)$_2$Cl (5 mmol) and 1.904 g CuI (10 mmol) were dissolved in 400 mL DIPA, then propyne was bubbled through the reaction mixture, which was stirred for 6 hours at room temperature. After full conversion the volatiles were evaporated under reduced pressure and the crude product was purified by flash chromatography on silica gel using heptane EtOAc as eluents.

$^1$H NMR (400 MHz, DMSO-$d_6$): 8.92 (s, 1H), 2.25 (s, 3H).

Preparation 2g: 5-Bromo-4-chloro-6-(3,4-difluoro-phenyl)thieno[2,3-d]pyrimidine 9.39 g 5-bromo-4-chloro-6-iodo-thieno[2,3-d]pyrimidine (Preparation 1a) (25 mmol), 9.00 g 2-(3,4-difluorophenyl)-4,4,5,5-tetramethyl-1,3,2-dioxaborolane (37.5 mmol), 16.29 g cesium carbonate (50 mmol), 912 mg Pd(dppf)Cl$_2$ (1.25 mmol) were placed in a 250 mL flask. 100 mL THF and 50 mL water were added, and then stirred for 2 hours at 70° C. under argon atmosphere. THF was evaporated, and then it was extracted with EtOAc. The organic layer was dried over Na$_2$SO$_4$, filtered and concentrated under reduced pressure. The crude product was purified via flash chromatography using DCM and MeOH as eluents.

$^1$H NMR (400 MHz, DMSO-$d_6$): 9.06 (s, 1H), 7.91 (m, 1H), 7.71 (m, 1H), 7.60 (m, 1H).

Preparation 2h: 5-Bromo-4-chloro-6-(2,3-difluoro-phenyl)thieno[2,3-d]pyrimidine 9.39 g 5-bromo-4-chloro-6-iodo-thieno[2,3-d]pyrimidine (Preparation 1a) (25 mmol), 9.00 g 2-(2,3-difluorophenyl)-4,4,5,5-tetramethyl-1,3,2-dioxaborolane (37.5 mmol), 16.29 g cesium carbonate (50 mmol), 912 mg Pd(dppf)Cl$_2$ (1.25 mmol) were placed in a 250 mL flask. 100 mL THF and 50 mL water were added, and then stirred for 2 hours at 70° C. under argon atmosphere. THF was evaporated, and then it was extracted with EtOAc. The organic layer was dried over Na$_2$SO$_4$, filtered and concentrated under reduced pressure. The crude product was purified via flash chromatography using DCM and MeOH as eluents to obtain Preparation 2h.

HRMS calculated for C$_{12}$H$_4$BrClF$_2$N$_2$S: 359.8935. found: 360.9013 (M+H).

Preparation 2i: 5-Bromo-4-chloro-6-[4-(methoxymethoxy)phenyl]thieno[2,3-d] pyrimidine 15.904 g (42.4 mmol) 5-bromo-4-chloro-6-iodo-thieno[2,3-d]pyrimidine (Preparation 1a), 16.784 g (63.5 mmol) 2-(4-methoxymethoxy-phenyl)-4,4,5,5-tetramethyl-[1,3,2]dioxaborolane, 1.798 g (4.2 mmol) $^t$BuXPhos, 473 mg (2.1 mmol) Pd(OAc)$_2$ and 41.365 g (127 mmol) Cs$_2$CO$_3$ were dissolved in 200 mL THF and 200 mL H$_2$O. The mixture was stirred at 70° C. under N$_2$ until no further conversion was observed. It was diluted with brine, the pH was set to 7 with 2 M HCl, and then it was extracted with DCM. The combined organic layers were dried over Na$_2$SO$_4$, filtered and concentrated under reduced pressure. The crude product was purified via flash chromatography using heptane and EtOAc as eluents to obtain Preparation 2i.

MS: (M+H)=385.0, 387.0.

Unless otherwise specified, most of the compounds of Preparation 3aa to 3br were obtained using General Procedures 3A, 3B or 3C described below.

General Procedure 3A:
Step A:

1.0 eq. ethyl (2R)-2-acetoxy-3-(2-hydroxyphenyl)propanoate (Preparation 3aa-(R)), 2.0 eq. of the appropriate alcohol and 2.0 eq. triphenylphosphine were dissolved in dry toluene (0.2 M for the phenol), then 2.0 eq. di-tert-butyl azodicarboxylate was added. The mixture was stirred at 50° C. under nitrogen. After reaching an appropriate conversion the volatiles were removed under reduced pressure, the crude intermediate was purified via flash chromatography using heptane/EtOAc as eluents.

Step B:

The obtained intermediate was dissolved in ethanol (0.5 M for the Step A product) then sodium ethoxide solution (1.0 M in ethanol) was added (2-5 mol %). The resulting mixture was stirred at room temperature. Additional sodium ethoxide solution was added if conversion was not complete. The mixture was concentrated to half of its volume, then water and brine was added, and it was extracted with ethyl acetate. The combined organics were dried over Na$_2$SO$_4$, filtered and evaporated under reduced pressure then it was purified via flash chromatography using heptane/EtOAc as eluents or other solvents, if indicated.

General Procedure 3B:
(Tetrahedron Lett. 1994, 35, 5205-5208.)
Step A:

To a stirred mixture of 1.0 eq. of the appropriate carbaldehyde and 1.25 eq. ethyl chloroacetate in THF (1.0 M for the carbaldehyde) at −78° C. 1.25 eq. sodium bis(trimethylsilyl-amide) solution (1.0 M in THF) was added dropwise. After addition temperature was allowed to reach room temperature. When the reaction reached an appropriate conversion to the oxirane the mixture was quenched with saturated NH$_4$Cl, the layers were separated, the aqueous layer was extracted with Et$_2$O, the combined organics were dried over Na$_2$SO$_4$ filtered and concentrated.

Step B:

The crude oxirane was dissolved in THF or EtOAc (1.0 M) and transferred to a hydrogenating vessel, 5 mol % of Pd(OH)$_2$ was added and the mixture was hydrogenated at 3-4.5 bars of hydrogen pressure. In case of a low conversion glacial acetic acid and Pd(OH)$_2$ were added to the mixture and hydrogenation was continued. When the appropriate reduction occurred, the mixture was filtered through a pad of celite, the filtrate was concentrated under reduced pressure and purified via flash chromatography using heptane/EtOAc as eluents (or other solvents, if indicated).

General Procedure 3C:
Step A:

To a stirred mixture of water/tert-butanol (1:1, 0.2 M for the cinnamate derivative), 1.0 eq. methane sulfonamide, 1 g/mmol AD-mix-α and 1.0 eq. cinnamate derivative were added at room temperature. The mixture was stirred at room temperature until no further conversion was observed, and then the mixture was cooled to 0-5° C. and 2.5 eq. sodium metabisulfite was added in small portions, then stirring was continued for 30 minutes at room temperature. The mixture was diluted with water and extracted with ethyl acetate. The combined organic layers were dried over Na$_2$SO$_4$, filtered and evaporated under reduced pressure. The residue was purified via flash chromatography using DCM/methanol as eluents to obtain the appropriate dihydroxy compound.

Step B:

The solution of the dihydroxy compound in dichloromethane/trifluoroacetic anhydride (4:1, 0.25 M) was stirred at room temperature for 1 hour. The mixture was concentrated under reduced pressure, and the residue was dissolved in methanol (~0.25 M), 5 mol % Pd/C (10 m/m %) was added, and then it was stirred overnight at room temperature under atmospheric hydrogen pressure. The reaction mixture was filtered through a pad of celite and purified via flash chromatography using hexane chloroform as eluents or other solvents, if indicated.

Preparation 3aa-(rac): Ethyl 2-acetoxy-3-(2-hydroxyphenyl)propanoate

Step A: [2-(Bromomethyl)phenyl]acetate 60.07 g 2-methylphenyl acetate (400 mmol) and 106.8 g NBS (600 mmol) were placed in a 1 L flask. 500 mL cyclohexane was added, and then with intensive stirring 3.284 g AIBN (20 mmol) was added over 30 min. The mixture was stirred at 80° C. until no further conversion was observed, then cooled to room temperature. The precipitate was filtered off and washed with cyclohexane. The mother liquor was concentrated under reduced pressure, and the crude product was used in Step B without further purification.

Step B: Ethyl 2-acetoxy-3-(2-hydroxyphenyl)propanoate 23.10 g anhydrous LiCl (545 mmol) and 65.36 g anhydrous ZnCl$_2$ (479.6 mmol) were placed in a 2 L flask, then dried at 160° C. under 0.1 Hgmm for 1 hour. After cooling to room temperature under argon atmosphere, 26.49 g magnesium turnings (1090 mmol) and 1 L dry pre-cooled (0° C.) THF were added. The resulting mixture was immersed into an ice-bath, and then stirred for 30 min.

100 g [2-(bromomethyl)phenyl]acetate—crude product from Step A—(~436 mmol) was dissolved in 120 mL dry THF and was added to the precooled inorganics over 15 min. After addition of the reagent the resulting mixture was stirred for 45 min while keeping the temperature between 0-5° C. To the mixture 64.82 mL ethyl 2-oxoacetate (654 mmol, 50% in toluene) was added over 5 mins and the resulting mixture was stirred for another 15 mins.

From the mixture the remaining inorganics were removed by filtration, and then 500 mL MeOH was added to the filtrate. This mixture was stirred until the intramolecular acetyl group migration from the phenolic oxygen to the alkyl oxygen was completed. To the mixture 30 mL acetic acid was added then the volatiles were evaporated under reduced pressure. To the residue 350 mL water was added and it was extracted with EtOAc. The combined organic layers were washed with saturated NaHCO$_3$ and with brine, and then dried over MgSO$_4$, filtered and evaporated under reduced pressure. To the residue 100 mL hexane was added and it was stirred for 30 mins at 0° C. The formed white crystals were collected by filtration and washed with hexane yielding Preparation 3aa-(rac).

$^1$H NMR (500 MHz, DMSO-d$_6$) δ 9.53 (s, 1H), 7.06 (t, 1H), 7.04 (d, 1H), 6.79 (d, 1H), 6.71 (t, 1H), 5.10 (dd, 1H), 4.05 (q, 2H), 3.06 (dd, 1H), 2.94 (dd, 1H), 2.00 (s, 3H), 1.09 (t, 3H).

Preparation 3aa-(S): Ethyl (2S)-2-acetoxy-3-(2-hydroxyphenyl)propanoate and

Preparation 3aa-(R): Ethyl (2R)-2-acetoxy-3-(2-hydroxyphenyl)propanoate

Enantiomers of Preparation 3aa-(rac) were separated via chiral chromatography. Column: OD; Eluents: heptane/EtOH; the enantiomer eluting earlier was collected as Preparation 3aa-(S) with 99.8% ee and the enantiomer eluting later was collected as Preparation 3aa-(R) with 99.9% ee.

Preparation 3ab-(R): Ethyl (2R)-2-hydroxy-3-(2-tetrahydropyran-2-yloxyphenyl)propanoate Step A: Ethyl (2R)-2-acetoxy-3-(2-tetrahydropyran-2-yloxyphenyl)propanoate 103.3 g ethyl (2R)-2-acetoxy-3-(2-hydroxyphenyl)propanoate (Preparation 3aa-(R)) (409 mmol) was dissolved in 280 mL 3,4-dihydro-2H-pyran. 300 mg para-toluenesulfonic acid monohydrate was added and the mixture was stirred until no further conversion was observed. Then it was diluted with 1 L ethyl acetate, washed with 200 mL saturated NaHCO$_3$ solution, then with 200 mL water. Combined organic layers were dried over Na$_2$SO$_4$, filtered and concentrated. Then it was purified via flash chromatography using heptane/EtOAc.

Step B: Ethyl (2R)-2-hydroxy-3-(2-tetrahydropyran-2-yloxyphenyl)propanoate 137.57 g ethyl (2R)-2-acetoxy-3-(2-tetrahydropyran-2-yloxyphenyl)propanoate (409 mmol) was dissolved in 600 mL ethanol, then 20 mL sodium ethoxide solution (1.0 M in ethanol) was added and it was stirred until no further conversion was observed. The mixture was concentrated to half of its volume, then 300 mL water and 300 mL brine was added, and it was extracted with ethyl acetate. The combined organics were dried over sodium sulfate, filtered and concentrated. The enantiopurity of the starting material was conserved.

$^1$H NMR (500 MHz, DMSO-d$_6$, 1:1 mixture of diastereomers) δ 7.16 (t, 1H), 7.13 (d, 1H), 7.04 (d, 1H), 6.87 (t, 1H), 5.51/5.47 (m, 1H), 4.27 (m, 1H), 4.04/4.02 (q, 2H), 3.73/3.56 (m, 2H), 3.06/3.04/2.74/2.71 (dd, 2H), 1.95/1.64 (m, 2H), 1.79 (m, 2H), 1.65/1.50 (m, 2H), 1.12/1.10 (t, 3H).

Preparation 3ab-(S): Ethyl (2S)-2-hydroxy-3-(2-tetrahydropyran-2-yloxyphenyl)propanoate Step A: Ethyl (2S)-2-acetoxy-3-(2-tetrahydropyran-2-yloxyphenyl)propanoate 103.3 g ethyl (2S)-2-acetoxy-3-(2-hydroxyphenyl)propanoate (Preparation 3aa-(S)) (409 mmol) was dissolved in 280 mL 3,4-dihydro-2H-pyran. 300 mg para-toluenesulfonic acid monohydrate was added and the mixture was stirred until no further conversion was observed. Then it was diluted with 1 L ethyl acetate, washed with 200 mL saturated NaHCO$_3$ solution, then with 200 mL water. Combined organic layers were dried over Na$_2$SO$_4$, filtered and concentrated. Then it was purified via flash chromatography using heptane/EtOAc.

Step B: Ethyl (2S)-2-hydroxy-3-(2-tetrahydropyran-2-yloxyphenyl)propanoate 137.57 g ethyl (2S)-2-acetoxy-3-(2-tetrahydropyran-2-yloxyphenyl)propanoate (409 mmol) was dissolved in 600 mL ethanol, then 20 mL sodium ethoxide solution (1.0 M in ethanol) was added and it was stirred until no further conversion was observed. The mixture was concentrated to half of its volume, then 300 mL water and 300 mL brine was added, and it was extracted with ethyl acetate. The combined organics were dried over sodium sulfate, filtered and concentrated. The enantiopurity of the starting material was conserved.

HRMS calculated for C$_{16}$H$_{22}$O$_5$: 294.1467. found: 317.1349 and 317.1343 (M+Na).

Preparation 3ac: Ethyl (2R)-2-hydroxy-3-[2-(pyrazin-2-ylmethoxy)phenyl]propanoate Using General Procedure 3A and pyrazin-2-ylmethanol as the appropriate alcohol Preparation 3ac was obtained. The product was purified by column chromatography using DCM/methanol.

$^1$H NMR (400 MHz, DMSO-d$_6$,) δ 8.88 (s, 1H), 8.64 (dd, 2H), 7.22-7.16 (m, 2H), 7.06 (d, 1H), 6.89 (t, 1H), 5.46 (d, 1H), 5.27 (dd, 2H), 4.29 (dq, 1H), 4.00 (q, 2H), 3.09 (dd, 1H), 2.79 (dd, 1H), 1.08 (t, 3H).

Preparation 3ad: Ethyl (2R)-2-hydroxy-3-(2-methoxyphenyl)propanoate and

Preparation 3bi: Ethyl (2S)-2-hydroxy-3-(2-methoxyphenyl)propanoate

Using General Procedure 3B and 2-methoxy-benzaldehyde as the appropriate carbaldehyde the lactic ester was obtained in racemic form.

$^1$H NMR (400 MHz, CDCl$_3$) δ 7.23 (dt, 1H), 7.12 (dd, 1H), 6.89-6.84 (m, 2H), 5.26 (dd, 1H), 4.14 (dq, 2H), 3.24 (dd, 1H), 3.03 (dd, 1H), 2.04 (s, 3H), 1.19 (t, 3H).

Enantiomers were separated via chiral chromatography; Column: AD, Eluent: 2-PrOH; the enantiomer eluting earlier was collected as Preparation 3ad with 99.8% ee and the enantiomer eluting earlier was collected as Preparation 3bi with 97.8% ee.

Preparation 3ae: Ethyl (2R)-2-hydroxy-3-[2-[(4-methoxyphenyl)methoxy]phenyl] propanoate Using General Procedure 3A and (4-methoxyphenyl)methanol as the appropriate alcohol Preparation 3ae was obtained.

$^1$H NMR (400 MHz, CDCl$_3$) δ 7.38 (d, 2H), 7.21 (dt, 1H), 7.15 (dd, 1H), 6.92-6.88 (m, 4H), 5.29 (dd, 1H), 5.05 (d, 1H), 5.01 (d, 1H), 4.12 (dq, 2H), 3.31 (dd, 1H), 3.04 (dd, 1H), 2.02 (s, 3H), 1.16 (t, 3H).

Preparation 3af: Ethyl (2R)-2-hydroxy-3-[2-[[(2S)-tetrahydrofuran-2-yl]methoxy] phenyl]propanoate and

Preparation 3bj: Ethyl (2R)-2-hydroxy-3-[2-[[(2R)-tetrahydrofuran-2-yl]methoxy] phenyl]propanoate Using General Procedure 3A and tetrahydrofuran-2-yl-methanol as the appropriate alcohol diastereoisomer mixture of the lactic esters were obtained. Diastereoisomers were separated by chiral chromatography. Column: IC, Eluents: heptane/EtOH; the diastereoisomer eluting earlier was collected as Preparation 3af with 99.6% de.
$^1$H NMR (400 MHz, CDCl$_3$) δ 7.26-7.24 (m, 2H), 6.92 (dt, 1H), 6.87 (d, 1H), 4.46-4.41 (m, 1H), 4.35-4.29 (m, 1H), 4.20 (dq, 2H), 4.04 (dd, 1H), 3.99-3.93 (m, 2H), 3.88-3.82 (m, 1H), 3.32 (d, 1H), 3.17 (dd, 1H), 3.00 (dd, 1H), 2.14-2.05 (m, 1H), 2.03-1.90 (m, 2H), 1.85-1.76 (m, 1H), 1.25 (t, 3H).

The diastereoisomer eluting later was collected as Preparation 3bj with 99.5% de.
$^1$H NMR (400 MHz, CDCl$_3$) δ 7.23-7.15 (m, 2H), 6.91 (dt, 1H), 6.86 (d, 1H), 4.48-4.44 (m, 1H), 4.33-4.27 (m, 1H), 4.18 (dq, 2H), 4.06-3.97 (m, 3H), 3.87-3.82 (m, 1H), 3.35 (d, 1H), 3.18 (dd, 1H), 3.00 (dd, 1H), 2.14-2.05 (m, 1H), 2.04-1.92 (m, 2H), 1.90-1.82 (m, 1H), 1.24 (t, 3H).

Preparation 3ag: Methyl (2R)-2-hydroxy-3-phenyl-propanoate 1.66 g (2R)-2-hydroxy-3-phenyl-propanoic acid (10 mmol) was dissolved in 30 mL dry methanol and stirred at in presence of catalytic amount of concentrated sulfuric acid until no further conversion was observed. Reaction mixture was concentrated under reduced pressure, to the residue 50 mL EtOAc was added and washed with saturated NaHCO$_3$ and with brine. Organic phase was dried over MgSO$_4$, filtered and evaporated under reduced pressure to yield Preparation 3ag.
$^1$H NMR (400 MHz, CDCl$_3$) δ 7.33-7.21 (m, 5H), 4.46 (q, 1H), 3.78 (s, 3H), 3.14 (dd, 1H), 2.98 (dd, 1H), 2.77 (d, 1H).

Preparation 3ah: Ethyl (2R)-2-hydroxy-3-[2-[(2-methoxypyrimidin-4-yl)methoxy] phenyl]propanoate Using General Procedure 3A and (2-methoxypyrimidin-4-yl)methanol as the appropriate alcohol Preparation 3ah was obtained.
$^1$H NMR (400 MHz, CDCl$_3$) δ 8.64 (d, 1H), 7.29 (d, 1H), 7.21-7.17 (m, 2H), 6.98 (d, 1H), 6.89 (dt, 1H), 5.52 (d, 1H), 5.17 (d, 1H), 5.13 (d, 1H), 4.34-4.30 (m, 1H), 4.04 (dq, 2H), 3.92 (s, 3H), 3.11 (dd, 1H), 2.83 (dd, 1H), 1.10 (t, 3H).

Preparation 3ai: Methyl (2R)-2-hydroxy-3-[2-(trifluoromethoxy)phenyl]propanoate Using General Procedure 3C and methyl (2E)-3-[2-(trifluoromethoxy)phenyl]prop-2-enoate as the appropriate cinnamic acid derivative Preparation 3ai was obtained with 99.4% ee.
H NMR (400 MHz, CDCl$_3$) δ 7.41-7.33 (m, 1H), 7.34-7.16 (m, 3H), 4.46 (ddd, 1H), 3.80 (s, 3H), 3.22 (dd, 1H), 3.03 (dd, 1H), 2.75 (d, 1H).

Preparation 3aj: Methyl (2R)-3-[2-(difluoromethoxy)phenyl]-2-hydroxy-propanoate Using General Procedure 3C and methyl (2E)-3-[2-(difluoromethoxy)phenyl]prop-2-enoate as the appropriate cinnamic acid derivative Preparation 3aj was obtained with 99.9% ee.
$^1$H NMR (500 MHz, CDCl$_3$) δ 7.31 (dd, 1H), 7.29-7.24 (m, 1H), 7.21-7.15 (m, 1H), 7.11 (d, 1H), 6.53 (t, 1H), 4.46 (dd, 1H), 3.80 (s, 3H), 3.21 (dd, 1H), 3.03 (dd, 1H), 2.68 (br s, 1H).

Preparation 3ak: Methyl (2R)-3-(3-fluorophenyl)-2-hydroxy-propanoate

Using General Procedure 3C and methyl (2E)-3-(3-fluorophenyl)prop-2-enoate as the appropriate cinnamic acid derivative Preparation 3ak was obtained with 98.6% ee.
$^1$H NMR (500 MHz, CDCl$_3$) δ 7.27-7.24 (m, 1H), 7.00 (d, 1H), 6.97-6.92 (m, 2H), 4.46 (dd, 1H), 3.79 (s, 3H), 3.13 (dd, 1H), 2.96 (dd, 1H), 2.64 (br s, 1H).

Preparation 3al: Methyl (2R)-2-hydroxy-3-(3-methoxyphenyl)propanoate

Using General Procedure 3C and methyl (2E)-3-(3-methoxyphenyl)prop-2-enoate as the appropriate cinnamic acid derivative Preparation 3al was obtained with 97.3% ee.
$^1$H NMR (500 MHz, CDCl$_3$) δ 7.23 (t, 1H), 6.83-6.77 (m, 3H), 4.48 (dd, 1H), 3.81 (s, 3H), 3.80 (s, 3H), 3.12 (dd, 1H), 2.96 (dd, 1H), 2.33 (br s, 1H).

Preparation 3am: Methyl (2R)-3-(2,3-difluorophenyl)-2-hydroxy-propanoate

Using General Procedure 3C and methyl (2E)-3-(2,3-difluorophenyl)prop-2-enoate as the appropriate cinnamic acid derivative Preparation 3am was obtained with 96.9% ee.
$^1$H NMR (500 MHz, CDCl$_3$) δ 7.19-6.93 (m, 3H), 4.48 (dd, 1H), 3.82 (s, 3H), 3.20 (dd, 1H), 3.06 (dd, 1H), 2.73 (br s, 1H).

Preparation 3an: Methyl (2R)-2-hydroxy-3-[2-(trifluoromethyl)phenyl]propanoate Using General Procedure 3C and methyl (2E)-3-[2-(trifluoromethyl)phenyl]prop-2-enoate as the appropriate cinnamic acid derivative Preparation 3an was obtained with 99.6% ee.
$^1$H NMR (500 MHz, CDCl$_3$) δ 7.67 (d, 1H), 7.53-7.47 (m, 2H), 7.37 (t, 1H), 4.43 (dd, 1H), 3.81 (s, 3H), 3.40 (dd, 1H), 3.01 (dd, 1H), 2.70 (br s, 1H).

Preparation 3ao: Methyl (2R)-2-hydroxy-3-(o-tolyl)propanoate

Using General Procedure 3C and methyl (2E)-3-(o-tolyl)prop-2-enoate as the appropriate cinnamic acid derivative Preparation 3ao was obtained with 99.3% ee.
$^1$H NMR (500 MHz, CDCl$_3$) δ 7.20-7.14 (m, 4H), 4.44 (dd, 1H), 3.80 (s, 3H), 3.18 (dd, 1H), 2.95 (dd, 1H), 2.59 (br s, 1H), 2.37 (s, 3H).

Preparation 3ap: Methyl (2R)-2-hydroxy-3-(m-tolyl)propanoate

Using General Procedure 3C and methyl (2E)-3-(m-tolyl)prop-2-enoate as the appropriate cinnamic acid derivative Preparation 3ap was obtained with 96.7% ee.

$^1$H NMR (500 MHz, CDCl$_3$) δ 7.20 (t, 1H), 7.07 (d, 1H), 7.05 (s, 1H), 7.02 (d, 1H), 4.46 (dd, 1H), 3.79 (s, 3H), 3.11 (dd, 1H), 2.94 (dd, 1H), 2.54 (br s, 1H), 2.35 (s, 3H).

Preparation 3aq: Ethyl (2R)-3-(3-fluoro-2-methoxy-phenyl)-2-hydroxy-propanoate

Using General Procedure 3C and ethyl (2E)-3-(3-fluoro-2-methoxy-phenyl)prop-2-enoate as the appropriate cinnamic acid derivative Preparation 3aq was obtained with 99.9% ee.

$^1$H NMR (400 MHz, CDCl$_3$) δ 7.04-6.03 (m, 3H), 4.44 (q, 1H), 4.23 (dq, 2H), 3.96 (d, 3H), 3.17 (dd, 1H), 3.02 (dd, 1H), 1.27 (t, 3H).

Preparation 3ar: Ethyl (2R)-3-(5-fluoro-2-methoxy-phenyl)-2-hydroxy-propanoate

Using General Procedure 3C and ethyl (2E)-3-(5-fluoro-2-methoxy-phenyl)prop-2-enoate as the appropriate cinnamic acid derivative Preparation 3ar was obtained with 99.9% ee.

$^1$H NMR (400 MHz, CDCl$_3$) δ 6.95-6.90 (m, 2H), 6.81-6.78 (m, 1H), 4.47 (q, 1H), 4.22 (dq, 2H), 3.83 (s, 3H), 3.14 (dd, 1H), 2.97 (dd, 1H), 1.28 (t, 3H).

Preparation 3as: Ethyl (2R)-3-(4-fluoro-2-methoxy-phenyl)-2-hydroxy-propanoate

Using General Procedure 3C and ethyl (2E)-3-(4-fluoro-2-methoxy-phenyl)prop-2-enoate as the appropriate cinnamic acid derivative Preparation 3as was obtained with 99.9% ee.

$^1$H NMR (500 MHz, CDCl$_3$) δ 7.10 (t, 1H), 6.61-6.57 (m, 2H), 4.42 (q, 1H), 4.19 (dq, 2H), 3.82 (s, 3H), 3.07 (dd, 1H), 2.96 (dd, 1H), 2.80 (d, 1H), 1.25 (t, 3H).

Preparation 3at: Ethyl (2R)-2-hydroxy-3-(2-methoxy-5-methyl-phenyl)propanoate

Using General Procedure 3C and ethyl (2E)-3-(2-methoxy-5-methyl-phenyl)prop-2-enoate as the appropriate cinnamic acid derivative Preparation 3at was obtained with 99.9% ee.

$^1$H NMR (400 MHz, CDCl$_3$) δ 7.04 (dd, 1H), 6.99 (d, 1H), 6.78 (d, 1H), 4.47 (dd, 1H), 4.21 (dq, 2H), 3.79 (s, 3H), 3.14 (dd, 1H), 2.98 (dd, 1H), 2.28 (s, 3H), 1.27 (t, 3H).

Preparation 3au: Ethyl (2R)-2-hydroxy-3-(2-methoxy-3-methyl-phenyl)propanoate

Using General Procedure 3C and ethyl (2E)-3-(2-methoxy-3-methyl-phenyl)prop-2-enoate as the appropriate cinnamic acid derivative Preparation 3au was obtained with 99.8% ee.

$^1$H NMR (500 MHz, CDCl$_3$) δ 7.10-7.03 (m, 2H), 6.97 (t, 1H), 4.45 (q, 1H), 4.21 (dq, 2H), 3.26 (s, 3H), 3.16 (dd, 1H), 3.01 (d, 1H), 2.31 (s, 3H), 1.25 (t, 3H).

Preparation 3av: Ethyl (2R)-3-[2-(tert-butoxycarbonylamino)phenyl]-2-hydroxy-propanoate Using General Procedure 3C and ethyl (2E)-3-[2-(tert-butoxycarbonylamino)phenyl]prop-2-enoate as the appropriate cinnamic acid derivative Preparation 3av was obtained with 99.8% ee.

$^1$H NMR (500 MHz, CDCl$_3$) δ 7.92 (br s, 1H), 7.75 (d, 1H), 7.24 (t, 1H), 7.10 (d, 1H), 7.01 (t, 1H), 4.51 (q, 1H), 4.27 (q, 2H), 3.34 (br s, 1H), 3.25 (dd, 1H), 3.01 (dd, 1H), 1.52 (s, 9H), 1.35 (t, 3H).

Preparation 3aw: Ethyl (2R)-3-[2-[(tert-butoxycarbonylamino)methyl]phenyl]-2-hydroxy-propanoate Using General Procedure 3C and ethyl (2E)-3-[2-[(tert-butoxycarbonylamino)methyl] phenyl]prop-2-enoate as the appropriate cinnamic acid derivative Preparation 3aw was obtained with 98.8% ee.

$^1$H NMR (500 MHz, CDCl$_3$) δ 7.34 (m, 1H), 5.63 (br s, 1H), 4.44-4.35 (m, 3H), 4.26 (q, 2H), 3.21 (dd, 1H), 3.10 (dd, 1H), 1.45 (s, 9H), 1.32 (t, 3H).

Preparation 3ax: Ethyl (2S)-2-hydroxy-3-[2-(2,2,2-trifluoroethylsulfanyl)phenyl] propanoate and Preparation 3ay: Ethyl (2R)-2-hydroxy-3-[2-(2,2,2-trifluoroethylsulfanyl)phenyl] propanoate Step A: 1-Methyl-2-(2,2,2-trifluoroethylsulfanyl)benzene To a solution of 2.357 mL 2-methylbenzenethiol (20 mmol) in 30 mL dry DMF, 8.292 g potassium carbonate (40 mmol) was added. After 5 min stirring 3.168 mL 2,2,2-trifluoroethyl trifluoromethanesulfonate (28 mmol) was added over 5 mins. The resulting mixture was stirred until no further conversion was observed. Brine was added and the mixture was extracted with ethyl acetate. The combined organic layers were dried over MgSO$_4$, filtered and evaporated under reduced pressure. The residue was purified via flash chromatography using heptane/EtOAc as eluents.

$^1$H NMR (400 MHz, CDCl$_3$) δ 7.48 (dd, 1H), 7.24-7.13 (m, 3H), 3.40 (q, 2H), 2.48 (s, 3H).

Step B: 1-(Bromomethyl)-2-(2,2,2-trifluoroethylsulfanyl)benzene 3.100 g 1-methyl-2-(2,2,2-trifluoroethylsulfanyl)benzene (15 mmol) and 4.005 g NBS (22.50 mmol) were placed in a 25 mL flask. 10 mL CCl$_4$ was added, and then 49.2 mg AIBN was added over 5 mins. Mixture was stirred at 80° C. overnight, then cooled to room temperature; the precipitate was filtered off and washed with hexane. The mother liquor was concentrated, and used in the next step without further purification.

Step C: Ethyl (2R)-2-hydroxy-3-[2-(2,2,2-trifluoroethylsulfanyl)phenyl]propanoate 632 mg anhydrous LiCl (14.90 mmol) and 1.787 g anhydrous ZnCl$_2$ (13.11 mmol) were placed in a 250 mL flask, then dried at 160° C. under 0.1 Hgmm for 1 hour. After cooling to room temperature under argon atmosphere 725 mg magnesium turnings (29.81 mmol) and 80 mL dry, pre-cooled (0° C.) THF were added. The resulting mixture was immersed into an ice-bath, and then 3.400 g 1-(bromomethyl)-2-(2,2,2-trifluoroethylsulfanyl)benzene (~11.92 mmol, from Step B) dissolved in 20 mL dry THF and was added to the pre-cooled inorganics over 10 min. The reaction mixture was stirred for 45 min between 0-5° C. To the prepared zinc organic compound 3.546 mL ethyl 2-oxoacetate (3.652 mmol, 50% in toluene) was added over 5 min and further was stirred for 15 min. From the mixture the remained inorganics were removed by filtration, and after addition of saturated NH$_4$Cl the mixture was extracted with ethyl acetate. The combined organic phase was dried over Mg$_2$SO$_4$, filtered and evaporated under reduced pressure.

The residue was purified via flash chromatography using heptane/ethyl acetate as eluents giving the appropriate lactic ester in racemic form.

$^1$H NMR (400 MHz, CDCl$_3$) δ 7.59 (dd, 1H), 7.33-7.23 (m, 3H), 4.48-4.43 (m, 1H), 4.29-4.22 (m, 2H), 3.46-3.39 (m, 3H), 3.21 (dd, 1H), 2.78 (d, 1H), 1.29 (t, 1H).

Enantiomers were separated via chiral chromatography. Column: AS-V, Eluents: heptane/2-PrOH; the enantiomer eluting earlier was collected as Preparation 3ax with 99.6% ee and the enantiomer eluting later was collected as Preparation 3ay with 99.5% ee.

Preparation 3az: Ethyl (2S)-3-(2-fluorophenyl)-2-hydroxy-propanoate and

Preparation 3ba: Ethyl (2R)-3-(2-fluorophenyl)-2-hydroxy-propanoate

Using General Procedure 3B and 2-fluorobenzaldehyde as the appropriate carbaldehyde lactic ester was obtained in racemic form.

$^1$H NMR (400 MHz, DMSO) δ 7.34-7.22 (m, 2H), 7.16-7.07 (m, 2H), 5.60 (d, 1H), 4.23 (dd, 1H), 4.05 (q, 2H), 2.99 (dd, 1H), 2.86 (dd, 1H), 1.12 (t, 3H).

Enantiomers were separated via chiral chromatography. Column: AS-V, Eluents: heptane/2-BuOH; the enantiomer eluting earlier was collected as Preparation 3az with 99.8% ee and the enantiomer eluting later was collected as Preparation 3ba with 99.4% ee.

Preparation 3bb: Ethyl 3-(benzofuran-7-yl)-2-hydroxy-propanoate

Using General Procedure 3B and benzofuran-7-carbaldehyde as the appropriate carbaldehyde Preparation 3bb was obtained. Upon reduction the saturation of the furan moiety was also observed, thus hydrogenolysis was stopped at the point, when the desired product was present with the highest concentration in the mixture. The product was purified via flash chromatography using DCM/EtOAc as eluents.

$^1$H NMR (500 MHz, DMSO) δ 7.98 (d, 1H), 7.51 (m, 1H), 7.16 (m, 2H), 6.94 (d, 1H), 5.63 (d, 1H), 4.40 (dd, 1H), 4.02 (q, 2H), 3.25 (dd, 1H), 3.09 (dd, 1H), 1.07 (t, 3H).

Preparation 3bc: Ethyl 3-(benzofuran-4-yl)-2-hydroxy-propanoate

Using General Procedure 3B and benzofuran-4-carbaldehyde as the appropriate carbaldehyde Preparation 3bc was obtained.

$^1$H NMR (400 MHz, CDCl$_3$) δ 7.62 (d, 1H), 7.41 (d, 1H), 7.23 (t, 1H), 7.10 (d, 1H), 6.85 (dd, 1H), 4.53 (dd, 1H), 4.24-4.12 (m, 2H), 3.37 (dd, 1H), 3.21 (dd, 1H), 2.80 (bs, 1H), 1.24 (t, 3H).

Preparation 3bd: Ethyl (2R)-3-(2,3-dihydrobenzofuran-7-yl)-2-hydroxy-propanoate and Preparation 3be: Ethyl (2S)-3-(2,3-dihydrobenzofuran-7-yl)-2-hydroxy-propanoate Using General Procedure 3B and benzofuran-7-carbaldehyde as the appropriate carbaldehyde and applying longer reaction time in Step B, the partially saturated lactic ester was obtained as the main product in racemic form, which was purified via flash chromatography using DCM/EtOAc as eluents.

$^1$H NMR (500 MHz, DMSO) δ 7.07 (m, 1H), 6.92 (m, 1H), 6.72 (t, 1H), 5.49 (d, 1H), 4.50 (m, 2H), 4.23 (m, 1H), 4.04 (q, 2H), 3.15 (t, 2H), 2.88 (dd, 1H), 2.71 (dd, 1H), 1.12 (t, 3H).

Enantiomers were separated via chiral chromatography. Column: OJ-H, Eluents: heptane/1-PrOH; the enantiomer eluting earlier was collected as Preparation 3bd with 99.6% ee and the enantiomer eluting later was collected as Preparation 3be with 92.4% ee.

Preparation 3bf: Ethyl (2R)-3-[4-fluoro-2-(methoxymethoxy)phenyl]-2-hydroxy-propanoate Step A: 4-Fluoro-2-(methoxymethoxy)benzaldehyde To a solution of 1.242 g 4-fluoro-2-hydroxy-benzaldehyde (8.86 mmol) in 10 mL dry acetone 2.444 g K$_2$CO$_3$ (17.7 mmol) and 1.01 mL chloromethyl-methyl-ether (13.3 mmol) were added and stirred at room temperature until no further conversion was observed. The mixture was diluted with ethyl acetate and it was extracted with water and with brine. The organic phase was dried over Na$_2$SO$_4$, filtered and concentrated under reduced pressure giving 4-fluoro-2-(methoxymethoxy)benzaldehyde.

$^1$H NMR (400 MHz, CDCl$_3$) δ 10.39 (s, 1H), 7.87 (dd, 1H), 6.96 (dd, 1H), 6.78 (dt, 1H), 5.29 (s, 2H), 3.53 (s, 3H).

Step B: Ethyl (2R)-3-[4-fluoro-2-(methoxymethoxy)phenyl]-2-hydroxy-propanoate

Using General Procedure 3B and 4-Fluoro-2-(methoxymethoxy)benzaldehyde as the appropriate carbaldehyde the desired lactic ester was obtained in racemic form. Enantiomers were separated via chiral chromatography. Column: AS-V, Eluents: heptane/EtOH; the enantiomer eluting later was collected as Preparation 3bf with 96.6% ee.

$^1$H NMR (500 MHz, DMSO) δ 7.16 (dd, 1H), 6.90 (dd, 1H), 6.73 (m, 1H), 5.52 (brs, 1H), 5.24 (s, 2H), 4.22 (brm, 1H), 4.03 (q, 2H), 3.40 (s, 3H), 2.94 (dd, 1H), 2.77 (dd, 1H), 1.10 (t, 3H).

Preparation 3bg: Ethyl (2R)-3-(1,3-benzodioxol-4-yl)-2-hydroxy-propanoate and

Preparation 3bh: Ethyl (2S)-3-(1,3-benzodioxol-4-yl)-2-hydroxy-propanoate (*Tetrahedron Lett.* 1994, 35, 5205-5208.)

1,3-Benzodioxole-4-carbaldehyde was reacted according to General method B with the exception, that in Step A after the formation of the oxirane the aqueous workup was completely omitted and the solution was directly carried further to in Step B resulting the title compound in racemic form.

$^1$H NMR (500 MHz, DMSO) δ 6.78 (dd, 1H), 6.74 (t, 1H), 6.71 (dd, 1H), 5.96 (d, 2H), 5.59 (d, 1H), 4.25 (m, 1H), 4.05 (q, 2H), 2.91 (dd, 1H), 2.76 (dd, 1H), 1.13 (t, 3H).

Enantiomers were separated via chiral chromatography. Column: AS-V, Eluents: heptane/1-BuOH; the enantiomer eluting earlier was collected as Preparation 3bg with 99.4% ee and the enantiomer eluting later was collected as Preparation 3bh with 99.8% ee.

Preparation 3bk: Ethyl (2R)-2-hydroxy-3-[2-[2-(4-methylpiperazin-1-yl)ethoxy] phenyl]propanoate and Preparation 3bo: Ethyl (2S)-2-hydroxy-3-[2-[2-(4-methylpiperazin-1-yl)ethoxy] phenyl]propanoate Using General Procedure 3A starting from ethyl 2-acetoxy-3-(2-hydroxyphenyl)propanoate (Preparation 3aa-(rac)) and 2-(4-methylpiperazin-1-yl)ethanol as the appropriate alcohol the lactic ester was obtained in racemic form.

$^1$H NMR (500 MHz, DMSO-$d_6$) δ 7.17 (m, 1H), 7.10 (dm, 1H), 6.94 (dm, 1H), 6.83 (m, 1H), 5.4 (d, 1H), 4.28 (m, 1H), 4.06 (t, 2H), 4.02 (m, 2H), 2.97 (dd, 1H), 2.71 (dd, 1H), 2.69 (t, 2H), 2.49 (brs, 4H), 2.30 (brs, 4H), 2.13 (s, 3H), 1.11 (t, 3H).

Enantiomers were separated via chiral chromatography. Column: OD, Eluents: heptane/1-PrOH; the enantiomer eluting earlier was collected as Preparation 3bk with 99.8% ee and the enantiomer eluting later was collected as Preparation 3bo with 99.6% ee.

Preparation 3bl: Ethyl (2R)-2-hydroxy-3-[2-(2,2,2-trifluoroethoxy)phenyl]propanoate Step A: Ethyl (2R)-2-hydroxy-3-(2-hydroxyphenyl)propanoate To a solution of 13.633 g ethyl (2R)-2-acetoxy-3-(2-hydroxyphenyl)propanoate (Preparation 3aa-(R)) (54 mmol) in 200 mL dry ethanol 30 mL sodium ethoxide (1.0 M) solution was added and stirred at room temperature. If needed, the addition of the sodium ethoxide solution was repeated until the cleavage of the acetyl group was complete. The mixture was diluted with 600 mL water and it was extracted with ethyl acetate. The combined organic layers were dried over Na$_2$SO$_4$ filtered and evaporated under reduced pressure. The obtained material was used in the next step without purification.

Step B: Ethyl (2R)-2-hydroxy-3-[2-(2,2,2-trifluoroethoxy)phenyl]propanoate

To a solution of 9.18 g ethyl (2R)-2-hydroxy-3-(2-hydroxyphenyl)propanoate (43.7 mmol) in 130 mL dry DMF, 6.040 g potassium carbonate (43.7 mmol) was added. After 5 mins stirring 7.7 mL 2,2,2-trifluoroethyl trifluoromethanesulfonate (48 mmol) was added over 5 mins. The resulting mixture was stirred until no further conversion was observed. The reaction mixture was extracted with brine/EtOAc. The combined organic layers were dried over Na$_2$SO$_4$, filtered and evaporated under reduced pressure. The product was purified via flash chromatography using heptane/EtOAc as eluents.

$^1$H NMR (500 MHz, DMSO-$d_6$) δ 7.23 (t, 1H), 7.18 (d, 1H), 7.06 (d, 1H), 6.95 (t, 1H), 5.50 (d, 1H), 4.75 (q, 2H), 4.22 (m, 1H), 4.02 (q, 2H), 3.00 (dd, 1H), 2.76 (dd, 1H), 1.09 (t, 3H).

Preparation 3bm: Ethyl (2S)-2-hydroxy-3-[2-[[(2R)-tetrahydrofuran-2-yl]methoxy] phenyl]propanoate Using General Procedure 3A starting from ethyl (2S)-2-acetoxy-3-(2-hydroxyphenyl)propanoate (Preparation 3aa-(S)) and [(2R)-tetrahydrofuran-2-yl]methanol as the appropriate alcohol Preparation 3bm was obtained.

$^1$H NMR (400 MHz, CDCl$_3$) δ 7.26-7.24 (m, 2H), 6.92 (dt, 1H), 6.87 (d, 1H), 4.46-4.41 (m, 1H), 4.35-4.29 (m, 1H), 4.20 (dq, 2H), 4.04 (dd, 1H), 3.99-3.93 (m, 2H), 3.88-3.82 (m, 1H), 3.32 (d, 1H), 3.17 (dd, 1H), 3.00 (dd, 1H), 2.14-2.05 (m, 1H), 2.03-1.90 (m, 2H), 1.85-1.76 (m, 1H), 1.25 (t, 3H).

Preparation 3bn: Ethyl (2R)-2-hydroxy-3-[2-(2-pyridylmethoxy)phenyl]propanoate

Using General Procedure 3A and 2-pyridylmethanol as the appropriate alcohol Preparation 3bn was obtained.

$^1$H NMR (500 MHz, DMSO-$d_6$) δ 8.58 (dm, 1H), 7.85 (td, 1H), 7.59 (d, 1H), 7.35 (ddd, 1H), 7.19 (td, 1H), 7.17 (dd, 1H), 7.01 (d, 1H), 6.88 (td, 1H), 5.52 (d, 1H), 5.21 (d, 1H), 5.17 (d, 1H), 4.32 (m, 1H), 4.02 (m, 2H), 3.09 (dd, 1H), 2.83 (dd, 1H), 1.09 (t, 3H).

Preparation 3bp: Ethyl (2R)-2-hydroxy-3-[2-[[2-(2,2,2-trifluoroethyl)pyrazol-5-yl] methoxy]phenyl] propanoate 10.1 g (40 mmol) Preparation 3aa-(R), 10.8 g (60 mmol) Preparation 9du and 15.7 g PPh$_3$ (60 mmol) were dissolved in 120 mL dry toluene, then 13.8 g (60 mmol) ditertbutyl azodicarboxylate was added. The mixture was stirred at 50° C. under N$_2$ until no further conversion was observed. Volatiles were evaporated under reduced pressure. Residue was purified via flash chromatography using EtOAc and MeOH as eluents. The obtained intermediate was dissolved in 50 mL dioxane-water 1:1 and 4.0 g LiOH×H$_2$O was added. The mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents. 688 mg from this intermediate was dissolved in 10 mL EtOH and 0.3 mL cc. H$_2$SO$_4$ was added. Mixture was stirred at 70° C. until no further conversion was observed. Then it was diluted with brine, neutralized with cc. NaHCO$_3$ solution, extracted with dichloromethane. The combined organic phases were dried over Na$_2$SO$_4$, filtered and concentrated under reduced pressure and purified via flash chromatography using heptane and EtOAc as eluents to obtain Preparation 3bp.

MS: (M+H)$^+$=373.2.

Preparation 3bq: Ethyl (2R)-3-[2-[[2-(2-fluorophenyl)pyrimidin-4-yl]methoxy] phenyl]-2-hydroxypropanoate 3.98 g (15.8 mmol) ethyl (2R)-2-hydroxy-3-(2-hydroxyphenyl)propanoate, 4.84 g (23.7 mmol) Preparation 9 eq and 6.22 g (23.7 mmol) PPh$_3$ were dissolved in 17 mL abs. toluene and 10.8 mL 40% (23.7 mmol) DEAD (in toluene) was added dropwise. The mixture was stirred at 50° C. under N$_2$ until no further conversion was observed. Volatiles were evaporated under reduced pressure. Residue was purified via flash chromatography using EtOAc and MeOH as eluents. MS: (M+H)$^+$=369.0. Then it was dissolved in 50 mL EtOH, and 4 mL cc. H$_2$SO$_4$ was added. The mixture was stirred at 50° C. under N$_2$ until no further conversion was observed. Mixture was neutralized with cc. NaHCO$_3$ solution and extracted with DCM. The combined organic phases were dried over Na$_2$SO$_4$, filtered and concentrated under reduced pressure and purified via flash chromatography using heptane and EtOAc as eluents to obtain Preparation 3bq.

MS: (M+H)$^+$=397.0.

Preparation 3br: (2R)-2-Hydroxy-3-[2-[[2-(2-methoxyphenyl)pyrimidin-4-yl] methoxy]phenyl] propanoic acid 37.84 g (150 mmol) ethyl (2R)-2-acetoxy-3-(2-hydroxyphenyl)propanoate (Preparation 3aa-(R)), 48.65 g (225 mmol) [2-(2-methoxyphenyl)pyrimidin-4-yl]methanol (Preparation 9bp) and 59.01 g (225 mmol) triphenyl phosphine were dissolved in 160 mL abs. toluene, then 102.47 mL (225 mmol) diethylazodicarboxylate was added. The mixture was stirred at 50° C. under nitrogen until no further conversion was observed. The volatiles were evaporated under reduced pressure. Then 400 mL $Et_2O$ was added, the mixture was sonicated and filtered (to remove $PPh_3$). $Et_2O$ was removed in vacuo. Residue was dissolved in 130 mL THF, then 30 g NaOH in 130 mL $H_2O$ was added. The mixture was stirred at room temperature until no further conversion was observed. Then it was acidified with 2 M HCl, THF was removed in vacou. 300 mL dichloromethane was added, and the precipitate was filtered, washed with cold $H_2O$ and DCM dried in vacuo to obtain Preparation 3br.

$^1$H-NMR (400 MHz, DMSO-$d_6$): 8.88 (d, 1H), 7.80 (d, 1H), 7.55 (dd, 1H), 7.49-7.44 (m, 1H), 7.26 (dd, 1H), 7.17-7.11 (m, 2H), 7.06 (t, 1H), 6.98 (d, 1H), 6.88 (t, 1H), 5.22 (s, 2H), 3.81 (dd, 1H), 3.77 (s, 3H), 3.73 (dd, 1H), 2.44 (dd, 1H).

Preparation 3bs: Ethyl (2R)-2-hydroxy-3-[2-[[2-(2-methoxyphenyl)pyrimidin-4-yl] methoxy]phenyl] propanoate 51.7 g (136 mmol) Preparation 3br was dissolved in 520 mL EtOH, then 20 mL cc. $H_2SO_4$ was added. The mixture was stirred at 60° C. until no further conversion was observed. Then it was diluted with water, neutralized with cc $NaHCO_3$ solution and extracted with dichloromethane. The combined organic phases were dried over $Na_2SO_4$, filtered and concentrated under reduced pressure and purified via flash chromatography using EtOAc and MeOH as eluents to obtain Preparation 3bs.

HRMS calculated for $C_{23}H_{24}N_2O_5$: 408.1685. found: 409.1757 (M+H).

Preparation 4a: Ethyl (2R)-2-[5-bromo-6-(4-fluorophenyl)thieno[2,3-d]pyrimidin-4-yl]oxy-3-(2-tetrahydropyran-2-yloxyphenyl)propanoate 48.45 g 5-bromo-4-chloro-6-(4-fluorophenyl)thieno[2,3-d]pyrimidine (Preparation 2a) (141 mmol), 45.63 g ethyl (2R)-2-hydroxy-3-(2-tetrahydropyran-2-yloxyphenyl)propanoate (Preparation 3ab-(R)) (155 mmol) and 137.8 g $Cs_2CO_3$ (423 mmol) were placed in a 2 L flask. 1.4 L tert-butanol was added and the mixture was stirred at 70° C. under $N_2$ until no further conversion was observed. Approximately 1 L solvent was evaporated under reduced pressure, then it was diluted with water, the pH was set to 8 with 2 M HCl, and then it was extracted with DCM. The combined organic layers were dried over $Na_2SO_4$, filtered and concentrated under reduced pressure. The crude product was purified via flash chromatography using heptane and EtOAc as eluents to obtain Preparation 4a as a mixture of diastereoisomers.

$^1$H NMR (500 MHz, DMSO-$d_6$): 8.67/8.66 (s, 1H), 7.75 (m, 2H), 7.43 (dm, 1H), 7.41 (m, 2H), 7.19 (m, 1H), 7.08/7.06 (dm, 1H), 6.89 (m, 1H), 5.87/5.70 (dd, 1H), 5.60/5.55 (m, 1H), 4.23-4.08 (m, 2H), 3.80-3.48 (m, 2H), 3.52/3.49 (dd, 1H), 3.19/3.17 (dd, 1H), 2.09-1.49 (m, 6H), 1.15/1.10 (t, 3H).

HRMS calculated for $C_{28}H_{26}BrFN_2O_5S$: 600.0730. found: 601.0809601.0798 (M+H).

Preparation 4b: Ethyl (2R)-2-[5-bromo-6-(4-fluorophenyl)thieno[2,3-d]pyrimidin-4-yl]oxy-3-[2-(pyrazin-2-ylmethoxy)phenyl]propanoate 1.718 g 5-bromo-4-chloro-6-(4-fluorophenyl)thieno[2,3-d]pyrimidine (Preparation 2a) (5.00 mmol), 1.512 g ethyl (2R)-2-hydroxy-3-[2-(pyrazin-2-ylmethoxy)phenyl]propanoate (Preparation 3ac) (5.00 mmol) and 5.700 g $Cs_2CO_3$ (17.5 mmol) were placed in a 50 mL flask. 15 mL tert-butanol was added and the mixture was stirred at 70° C. under $N_2$ until no further conversion was observed. The reaction mixture was diluted with water, the pH was set between 6-7 with 2 M HCl, and then it was extracted with DCM. The combined organic layers were dried over $Na_2SO_4$, filtered and concentrated under reduced pressure. The crude product was purified via flash chromatography using heptane and EtOAc as eluents to obtain Preparation 4b.

MS: (M+H)$^+$=609.0.

Preparation 4c: Ethyl (2R)-2-[5-bromo-6-(5-fluoro-2-furyl)thieno[2,3-d]pyrimidin-4-yl]oxy-3-(2-tetrahydropyran-2-yloxyphenyl)propanoate 50.03 g 5-bromo-4-chloro-6-(5-fluoro-2-furyl)thieno[2,3-d]pyrimidine (Preparation 2b) (150 mmol), 44.15 g ethyl (2R)-2-hydroxy-3-(2-tetrahydropyran-2-yloxyphenyl)propanoate (Preparation 3ab-(R)) (150 mmol) and 146.6 g $Cs_2CO_3$ (450 mmol) were placed in a 2 L flask. 1.5 L tert-butanol was added and the mixture was stirred at 70° C. under $N_2$ until no further conversion was observed. Approximately 1 L solvent was evaporated, then it was diluted with DCM and water, the pH was set to 8 with 2 M HCl, and then it was extracted with DCM. The combined organic layers were dried over $Na_2SO_4$, filtered and concentrated under reduced pressure. The crude product was purified via flash chromatography using heptane and EtOAc as eluents to obtain Preparation 4c as a mixture of diastereoisomers.

$^1$H NMR (500 MHz, DMSO-$d_6$): 8.63/8.62 (s, 1H), 7.44 (dm, 1H), 7.42 (m, 1H), 7.19 (tm, 1H), 7.07 (d, 1H), 6.90 (t, 1H), 6.17 (m, 1H), 5.80/5.68 (dd, 1H), 5.61/5.55 (t, 1H), 4.14 (m, 2H), 3.78-3.40 (m, 2H), 3.51 (m, 1H), 3.18 (m, 1H), 2.00 (m, 1H), 1.82 (m, 2H), 1.68-1.37 (m, 2H), 1.66 (m, 1H), 1.14/1.11 (t, 3H).

HRMS calculated for $C_{26}H_{24}BrFN_2O_6S$: 590.0522. found: 591.0599 (M+H).

Preparation 4d: Ethyl (2R)-2-[5-bromo-6-(2-furyl)thieno[2,3-d]pyrimidin-4-yl]oxy-3-(2-tetrahydropyran-2-yloxyphenyl)propanoate 36.87 g 5-bromo-4-chloro-6-(2-furyl)thieno[2,3-d]pyrimidine (Preparation 2c) (117 mmol), 37.83 g ethyl (2R)-2-hydroxy-3-(2-tetrahydropyran-2-yloxyphenyl)propanoate (Preparation 3ab-(R)) (129 mmol) and 98.00 g $Cs_2CO_3$ (300 mmol) were placed in a 1 L flask. 400 mL tert-butanol was added and the mixture was stirred at 50° C. under $N_2$ until no further conversion was observed. The reaction mixture was diluted with DCM and brine, and then it was extracted with DCM. The combined organic layers were dried over $Na_2SO_4$, filtered and concentrated under reduced pressure.

The crude product was purified via flash chromatography using heptane and EtOAc as eluents to obtain Preparation 4d as a mixture of diastereoisomers.
MS: (M+H)$^+$=609.0.

Preparation 4e: Ethyl (2R)-2-[5-bromo-6-(2-furyl) thieno[2,3-d]pyrimidin-4-yl]oxy-3-(2-methoxyphenyl)propanoate 0.631 g 5-bromo-4-chloro-6-(2-furyl)thieno[2,3-d]pyrimidine (Preparation 2c) (2.00 mmol), 0.673 g ethyl (2R)-2-hydroxy-3-(2-methoxyphenyl)propanoate (Preparation 3ad) (3.00 mmol) and 0.195 g Cs$_2$CO$_3$ (6.00 mmol) were placed in a 25 mL flask. 10 mL tert-butanol was added and the mixture was stirred at 60° C. under N$_2$ until no further conversion was observed. The reaction mixture was diluted with DCM and brine, and then it was extracted with DCM. The combined organic layers were dried over Na$_2$SO$_4$, filtered and concentrated under reduced pressure. The crude product was purified via flash chromatography using heptane and EtOAc as eluents to obtain Preparation 4e.
$^1$H NMR (400 MHz, DMSO-d$_6$): 8.60 (s, 1H), 7.94 (d, 1H), 7.43 (d, 1H), 7.37 (dd, 1H), 7.22 (td, 1H), 6.96 (d, 1H), 6.86 (td, 1H), 6.77 (dd, 1H), 5.64 (dd, 1H), 4.10 (q, 2H), 3.79 (s, 3H), 3.87 (dd, 1H), 3.24 (dd, 1H), 1.10 (t, 3H).

Preparation 4f: Ethyl (2R)-2-[5-bromo-6-(5-chloro-2-furyl)thieno[2,3-d]pyrimidin-4-yl]oxy-3-[2-[(4-methoxyphenyl)methoxy]phenyl]propanoate 6.05 g 5-bromo-4-chloro-6-(5-chloro-2-furyl)thieno[2,3-d]pyrimidine (Preparation 2d) (17.3 mmol), 6.28 g ethyl (2R)-2-hydroxy-3-[2-[(4-methoxyphenyl)methoxy]phenyl]propanoate (Preparation 3ae) (19.0 mmol) and 19.7 g Cs$_2$CO$_3$ (60.5 mmol) were placed in a 250 mL flask. 60 mL tert-butanol was added and the mixture was stirred at 80° C. under N$_2$ until no further conversion was observed. Water was added, then it was extracted with EtOAc. The combined organic layers were dried over Na$_2$SO$_4$, filtered and concentrated under reduced pressure to obtain Preparation 4f.
MS: (M+H)$^+$=643.0.

Preparation 4g: Ethyl (2R)-2-[5-bromo-6-(5-chloro-2-furyl)thieno[2,3-d]pyrimidin-4-yl]oxy-3-[2-[[(2S)-tetrahydrofuran-2-yl]methoxy]phenyl]propanoate 0.315 g 5-bromo-4-chloro-6-(5-chloro-2-furyl)thieno[2,3-d]pyrimidine (Preparation 2d) (0.90 mmol), 0.267 g ethyl (2R)-2-hydroxy-3-[2-[[(2S)-tetrahydrofuran-2-yl]methoxy]phenyl]propanoate (Preparation 3af) (0.90 mmol) and 0.977 g Cs$_2$CO$_3$ (3.00 mmol) were placed in a 25 mL flask. 5 mL tert-butanol was added and the mixture was stirred at 65° C. under N$_2$ until no further conversion was observed. Water was added, the pH was set to 8 with 2 M HCl, then it was extracted with DCM. The combined organic layers were dried over Na$_2$SO$_4$, filtered, concentrated under reduced pressure. The crude product was purified via flash chromatography using heptane and EtOAc as eluents to obtain Preparation 4g.
MS: (M+H)$^+$=607.0.

Preparation 4h: Ethyl (2R)-2-[5-bromo-6-(4-fluoro-3-methoxy-phenyl)thieno[2,3-d]pyrimidin-4-yl]oxy-3-(2-tetrahydropyran-2-yloxyphenyl)propanoate 24.00 g 5-bromo-4-chloro-6-(4-fluoro-3-methoxy-phenyl)thieno[2,3-d]pyrimidine (Preparation 2e) (64.0 mmol), 22.69 g ethyl (2R)-2-hydroxy-3-(2-tetrahydropyran-2-yloxyphenyl)propanoate (Preparation 3ab-(R)) (77.0 mmol) and 62.8 g Cs$_2$CO$_3$ (63.0 mmol) were placed in a 250 mL flask. 150 mL tert-butanol was added and the mixture was stirred at 70° C. under N$_2$ until no further conversion was observed Water was added, then it was extracted with DCM. The combined organic layers were dried over Na$_2$SO$_4$, filtered, concentrated and purified via flash chromatography using heptane and EtOAc as eluents to obtain Preparation 4h as a mixture of diastereoisomers.
MS: (M+H)$^+$=631.0.

Preparation 4i: Methyl (2R)-2-(6-ethyl-5-iodo-thieno[2,3-d]pyrimidin-4-yl)oxy-3-phenyl-propanoate 5.00 g 4-chloro-6-ethyl-5-iodo-thieno[2,3-d]pyrimidine (Preparation 1d) (15.4 mmol), 3.47 g methyl (2R)-2-hydroxy-3-phenyl-propanoate (Preparation 3ag) (19.3 mmol) and 6.28 g Cs$_2$CO$_3$ (19.3 mmol) were placed in a 50 mL flask. 15 mL DMSO was added and the mixture was stirred at 60° C. under N$_2$ until no further conversion was observed. The reaction mixture was poured onto ice, the pH was adjusted to 4 with 2M HCl and the mixture was extracted with DCM. The combined organic layers were dried over MgSO$_4$, filtered and concentrated under reduced pressure. The crude product was purified via flash chromatography using heptane and EtOAc as eluents to obtain Preparation 4i.
$^1$H NMR (400 MHz, CDCl$_3$): 8.48 (s, 1H), 7.42 (d, 2H), 7.30 (t, 2H), 7.23 (m, 1H), 5.75 (dd, 1H), 3.73 (s, 3H), 3.44-3.40 (m, 2H), 2.93 (q, 2H), 1.33 (t, 3H).

Preparation 4j: Ethyl (2R)-2-(6-ethyl-5-iodo-thieno[2,3-d]pyrimidin-4-yl)oxy-3-(2-tetrahydropyran-2-yloxyphenyl)propanoate 3.25 g 4-chloro-6-ethyl-5-iodo-thieno[2,3-d]pyrimidine (Preparation 1d) (10.0 mmol), 3.24 g ethyl (2R)-2-hydroxy-3-(2-tetrahydropyran-2-yloxyphenyl)propanoate (Preparation 3ab-(R)) (11.0 mmol) and 9.77 g Cs$_2$CO$_3$ (30.0 mmol) were placed in a 100 mL flask. 50 mL tert-butanol was added and the mixture was stirred at 70° C. under N$_2$ until no further conversion was observed. Brine was added, then it was extracted with DCM. The combined organic layers were dried over Na$_2$SO$_4$, filtered and concentrated under reduced pressure. The crude product was purified via flash chromatography using heptane and EtOAc as eluents to obtain Preparation 4j as a mixture of diastereoisomers.
MS: (M+H)$^+$=583.0.

Preparation 4k: Ethyl (2R)-2-(5-iodo-6-prop-1-ynyl-thieno[2,3-d]pyrimidin-4-yl)oxy-3-(2-methoxyphenyl)propanoate 0.669 g 4-chloro-5-iodo-6-prop-1-ynyl-thieno[2,3-d]pyrimidine (Preparation 2f) (2.00 mmol), 0.673 g ethyl (2R)-2-hydroxy-3-(2-methoxyphenyl)propanoate (Preparation 3ad) (3.00 mmol) and 1.955 g Cs$_2$CO$_3$ (6.00 mmol) were placed in a 25 mL flask. 10 mL tert-butanol was added and the mixture was stirred at 60° C. under N$_2$ until no further conversion was observed. The reaction mixture was diluted with brine, and then it was extracted with DCM. The combined organic layers were dried over Na$_2$SO$_4$, filtered and concentrated under reduced pressure. The crude product was purified via flash chromatography using heptane and EtOAc as eluents to obtain Preparation 4k.

¹H NMR (400 MHz, CDCl₃): 8.52 (s, 1H), 7.36 (dd, 1H), 7.23 (dd, 1H), 6.89-6.84 (m, 2H), 5.78 (dd, 1H), 4.23-4.12 (m, 2H), 3.84 (s, 3H), 3.49 (dd, 1H), 3.39 (dd, 1H), 2.19 (s, 3H), 1.18 (t, 3H).
MS: (M+H)⁺=523.0.

Preparation 4l: Ethyl (2R)-2-(5-iodo-6-prop-1-ynyl-thieno[2,3-d]pyrimidin-4-yl)oxy-3-(2-tetrahydropyran-2-yloxyphenyl)propanoate 8.92 g 4-chloro-5-iodo-6-prop-1-ynyl-thieno[2,3-d]pyrimidine (Preparation 2f) (26.7 mmol), 8.83 g ethyl (2R)-2-hydroxy-3-(2-tetrahydropyran-2-yloxyphenyl)propanoate (Preparation 3ab-(R)) (30.0 mmol) and 29.3 g Cs₂CO₃ (90.0 mmol) were placed in a 500 mL flask. 300 mL tert-butanol was added and the mixture was stirred at 65° C. under N₂ until no further conversion was observed. Brine was added, then it was extracted with DCM. The combined organic layers were dried over Na₂SO₄, filtered, concentrated under reduced pressure. The crude product was purified via flash chromatography using heptane and EtOAc as eluents to obtain Preparation 4l as a mixture of diastereoisomers.
MS: (M+H)⁺=593.0

Preparation 4m: 2-(6-Ethyl-5-iodo-thieno[2,3-d]pyrimidin-4-yl)oxy-3-phenyl-propanoic acid 500 mg (2R)-2-hydroxy-3-phenyl-propanoic acid (2.77 mmol) was dissolved in 3 mL dry DMF, then 133 mg sodium hydride (3.32 mmol, 60% in mineral oil) was added and it was stirred for 15 minutes at room temperature. It was added dropwise to a DMF solution (5 mL) of 650 mg 4-chloro-6-ethyl-5-iodo-thieno[2,3-d]pyrimidine (Preparation 1d) (2.00 mmol) and the mixture was stirred for 1 hour. Then 2.5 mL 10% NaOH solution was added and the reaction mixture was stirred for 30 minutes. It was diluted with water and washed with Et₂O. The aqueous phase was acidified and the yellow precipitate was filtered and dried to obtain Preparation 4m.
¹H NMR (500 MHz, DMSO-d₆): 13.29 (s, 1H), 8.57 (s, 1H), 7.51 (m, 2H), 7.29 (m, 2H), 7.21 (m, 1H), 5.62 (dd, 1H), 3.36 (dd, 1H), 3.29 (dd, 1H), 2.91 (q, 2H), 1.26 (t, 3H).
HRMS calculated for C₁₇H₁₅IN₂O₃S: 453.9848. found: 454.9918 (M+H).

Preparation 4n: Ethyl (2R)-2-[5-bromo-6-(4-fluorophenyl)thieno[2,3-d]pyrimidin-4-yl]oxy-3-(2-methoxyphenyl)propanoate 687 mg 5-bromo-4-chloro-6-(4-fluorophenyl)thieno[2,3-d]pyrimidine (Preparation 2a) (2.00 mmol), 673 mg ethyl (2R)-2-hydroxy-3-(2-methoxyphenyl)propanoate (Preparation 3ad) (3.00 mmol) and 1.955 g Cs₂CO₃ (6.00 mmol) were placed in a 25 mL flask. 10 mL tert-butanol was added and the mixture was stirred at 60° C. under N₂ until no further conversion was observed. The reaction mixture was diluted with brine, and then it was extracted with DCM. The combined organic layers were dried over Na₂SO₄, filtered and concentrated under reduced pressure. The crude product was purified via flash chromatography using heptane and EtOAc as eluents to obtain Preparation 4n.
MS: (M+H)⁺=531.0.

Preparation 4o: Ethyl (2R)-2-[5-bromo-6-(3,4-difluorophenyl)thieno[2,3-d]pyrimidin-4-yl]oxy-3-(2-tetrahydropyran-2-yloxyphenyl)propanoate 6.0 g 5-bromo-4-chloro-6-(3,4-difluorophenyl)thieno[2,3-d]pyrimidine (Preparation 2g) (16.59 mmol), 5.97 g ethyl (2R)-2-hydroxy-3-(2-tetrahydropyran-2-yloxyphenyl)propanoate (Preparation 3ab-(R)) (18.25 mmol) and 18.93 g Cs₂CO₃ (58.1 mmol) were placed in a 250 mL flask. 100 mL tert-butanol was added and the mixture was stirred at 60° C. under N₂ until no further conversion was observed. Approximately 50 mL solvent was evaporated under reduced pressure, then it was diluted with water, the pH was set to 8 with 2 M HCl, and then it was extracted with DCM. The combined organic layers were dried over Na₂SO₄, filtered and concentrated under reduced pressure. The crude product was purified via flash chromatography using heptane and EtOAc as eluents to obtain Preparation 4o as a mixture of diastereoisomers.
¹H NMR (400 MHz, DMSO-d₆): 8.69 (d, 1H), 7.87 (m, 1H), 7.67 (m, 1H), 7.57 (m, 1H), 7.44 (m, 1H), 7.20 (m, 1H), 7.07 (m, 1H), 6.90 (t, 1H), 5.82/5.70 (dd, 1H), 5.62/5.56 (t, 1H), 4.22-4.08 (m, 2H), 3.75/3.65 (td, 1H), 3.61-3.45 (m, 2H), 3.20/3.16 (d, 1H), 2.10-1.48 (m, 6H), 1.17/1.14 (t, 3H).

Preparation 4p: Ethyl (2R)-2-[5-bromo-6-(4-fluorophenyl)thieno[2,3-d]pyrimidin-4-yl]oxy-3-[2-[[(2R)-tetrahydrofuran-2-yl]methoxy]phenyl]propanoate 4.12 g 5-bromo-4-chloro-6-(4-fluorophenyl)thieno[2,3-d]pyrimidine (Preparation 2a) (12.0 mmol) and 3.80 g ethyl (2R)-2-hydroxy-3-[2-[[(2R)-tetrahydrofuran-2-yl]methoxy]phenyl]propanoate (Preparation 3bj) (12.9 mmol) were dissolved in 30 mL tert-butanol, then 13.03 g Cs₂CO₃ (40.0 mmol) was added and the mixture was stirred at 65° C. under N₂ until no further conversion was observed. Then it was poured onto icy water, the pH was set to 6 with 2 M HCl, and it was filtered and washed with water to obtain Preparation 4p.
¹H NMR (400 MHz, DMSO-d₆): 8.67 (s, 1H), 7.76 (m, 2H), 7.42 (m, 2H), 7.38 (dd, 1H), 7.21 (dt, 1H), 6.98 (d, 1H), 6.86 (t, 1H), 5.71 (dd, 1H), 4.20-4.09 (m, 3H), 4.04-3.96 (m, 2H), 3.79-3.73 (m, 1H), 3.69-3.64 (m, 1H), 3.40 (dd, 1H), 3.22 (dd, 1H), 2.04-1.78 (m, 4H), 1.12 (t, 3H).

Preparation 4q: Ethyl (2R)-2-(6-ethyl-5-iodo-thieno[2,3-d]pyrimidin-4-yl)oxy-3-(2-methoxyphenyl)propanoate 2.809 g 4-chloro-6-ethyl-5-iodo-thieno[2,3-d]pyrimidine (Preparation 1d) (8.92 mmol), 1.00 g ethyl (2R)-2-hydroxy-3-(2-methoxyphenyl)propanoate (Preparation 3ad) (4.46 mmol) and 1.598 g Cs₂CO₃ (4.91 mmol) were dissolved in 5 mL dry DMSO and heated at 60° C. until no further conversion was observed. Then it was diluted with water, the pH was set to 7 with 2 M HCl, and then it was extracted with DCM. The combined organic layers were dried over Na₂SO₄, filtered and concentrated under reduced pressure and purified via flash chromatography using heptane and EtOAc as eluents to obtain Preparation 4q.
MS: (M+H)⁺=513.0.

Preparation 4r: Ethyl (2S)-2-(6-ethyl-5-iodo-thieno[2,3-d]pyrimidin-4-yl)oxy-3-(2-methoxyphenyl)propanoate 2.809 g 4-chloro-6-ethyl-5-iodo-thieno[2,3-d]pyrimidine (Preparation 1d) (8.92 mmol), 1.00 g ethyl (2S)-2-hydroxy-3-(2-methoxyphenyl)propanoate (Preparation 3bi) (4.46 mmol) and 1.598 g Cs₂CO₃ (4.91 mmol) were dissolved in 5 mL dry DMSO and heated at 60° C. until no further conversion was observed. Then it was diluted with water, the pH was set to 7 with 2 M HCl, and then it was extracted with DCM. The combined organic layers were dried over Na$_2$SO$_4$, filtered and concentrated under reduced pressure and purified via flash chromatography using heptane and EtOAc as eluents to obtain Preparation 4r.

MS: (M+H)$^+$=513.0.

Preparation 4s: Ethyl (2R)-2-[5-bromo-6-(4-fluoro-phenyl)thieno[2,3-d]pyrimidin-4-yl]oxy-3-[2-(2,2,2-trifluoroethoxy)phenyl]propanoate 5.39 g 5-bromo-4-chloro-6-(4-fluorophenyl)thieno[2,3-d]pyrimidine (Preparation 2a) (15.7 mmol) and 5.50 g ethyl (2R)-2-hydroxy-3-[2-(2,2,2-trifluoroethoxy)phenyl] propanoate (Preparation 3bl) (18.8 mmol) were dissolved in 60 mL tert-butanol, then 15.32 g Cs$_2$CO$_3$ (47.0 mmol) was added and the mixture was stirred at 60° C. under N$_2$ until no further conversion was observed. Then it was poured onto icy water, the pH was set to 6 with 2 M HCl, and it was filtered, washed with water to obtain Preparation 4s.

$^1$H NMR (400 MHz, CDCl$_3$): 8.53 (s, 1H), 7.64 (m, 2H), 7.43 (d, 1H), 7.27-7.16 (m, 3H), 6.97 (t, 1H), 6.82 (d, 1H), 5.75 (dd, 1H), 4.45-4.38 (m, 2H), 4.22 (q, 2H), 3.55 (dd, 1H), 3.33 (dd, 1H), 1.24 (t, 3H).

Preparation 4t: Ethyl (2R)-2-[5-bromo-6-(2,3-difluorophenyl)thieno[2,3-d]pyrimidin-4-yl]oxy-3-(2-tetrahydropyran-2-yloxyphenyl)propanoate 6.00 g Preparation 2h (16.59 mmol), 5.97 g Preparation 3ab-(R) (18.25 mmol) and 18.93 g Cs$_2$CO$_3$ (58.1 mmol) were placed in a 250 mL flask. 100 mL tert-butanol was added and the mixture was stirred at 60° C. under N$_2$ until no further conversion was observed. Approximately 50 mL solvent was evaporated under reduced pressure, then it was diluted with water, the pH was set to 8 with 2 M HCl, and then it was extracted with DCM. The combined organic layers were dried over Na$_2$SO$_4$, filtered and concentrated under reduced pressure. The crude product was purified via flash chromatography using heptane and EtOAc as eluents to obtain Preparation 4t as a mixture of diastereoisomers.

HRMS calculated for C$_{28}$H$_{25}$BrF$_2$N$_2$O$_5$S: 618.0636. found: 619.0695 (M+H).

Preparation 4u: Ethyl (2R)-2-[5-bromo-6-(4-fluorophenyl)thieno[2,3-d]pyrimidin-4-yl]oxy-3-[2-[[2-(2-fluorophenyl)pyrimidin-4-yl]methoxy]phenyl]propanoate 1.718 g (5 mmol) Preparation 2a and 2.18 g (6 mmol) Preparation 3bq were dissolved in 50 mL dioxane then 4.887 g Cs$_2$CO$_3$ (15 mmol) was added. The mixture was stirred at 70° C. under N$_2$ until no further conversion was observed. It was diluted with water, the pH was set to 7 with 2 M HCl, and then it was extracted with DCM. The combined organic layers were dried over Na$_2$SO$_4$, filtered and concentrated under reduced pressure. The crude product was purified via flash chromatography using heptane and EtOAc as eluents to obtain Preparation 4u.

MS: (M+H)$^+$=702.6, (M+2H)$^{2+}$=351.0.

Preparation 4v: Ethyl (2R)-2-[5-bromo-6-(4-fluorophenyl)thieno[2,3-d]pyrimidin-4-yl]oxy-3-[2-[[2-(2-methoxyphenyl)pyrimidin-4-yl]methoxy]phenyl]propanoate 20.0 g 5-bromo-4-chloro-6-(4-fluorophenyl)thieno[2,3-d]pyrimidine (Preparation 2a) (58.2 mmol), 23.77 g ethyl (2R)-2-hydroxy-3-[2-[[2-(2-methoxyphenyl)pyrimidin-4-yl]methoxy]phenyl]propanoate (Preparation 3bs) (58.2 mmol) and 56.89 g Cs$_2$CO$_3$ (174.6 mmol) were placed in a flask, then 250 mL abs. THF was added and the mixture was stirred at 70° C. under N$_2$ until no further conversion was observed. The reaction mixture was diluted with water, then it was extracted with DCM. The combined organic layers were dried over Na$_2$SO$_4$, filtered and concentrated under reduced pressure. The crude product was purified via flash chromatography using dichloromethane and methanol as eluents to obtain Preparation 4v.

MS: (M+H)$^+$=715.0, 717.2.

Preparation 4w: Ethyl (2S)-2-[5-bromo-6-(4-fluorophenyl)thieno[2,3-d]pyrimidin-4-yl]oxy-3-(2-tetrahydropyran-2-yloxyphenyl)propanoate 48.45 g 5-bromo-4-chloro-6-(4-fluorophenyl)thieno[2,3-d]pyrimidine (Preparation 2a) (141 mmol), 45.63 g ethyl (2S)-2-hydroxy-3-(2-tetrahydropyran-2-yloxyphenyl)propanoate (Preparation 3ab-(S)) (155 mmol) and 137.8 g Cs$_2$CO$_3$ (423 mmol) were placed in a 2 L flask. 1.4 L tert-butanol was added and the mixture was stirred at 70° C. under N$_2$ until no further conversion was observed. Approximately 1 L solvent was evaporated under reduced pressure, then it was diluted with water, the pH was set to 8 with 2 M HCl, and then it was extracted with DCM. The combined organic layers were dried over Na$_2$SO$_4$, filtered and concentrated under reduced pressure. The crude product was purified via flash chromatography using heptane and EtOAc as eluents to obtain Preparation 4w as a mixture of diastereoisomers.

MS: (M+H)=601.2.

Preparation 5a: 2-Chloro-3-methyl-4-(4,4,5,5-tetramethyl-1,3,2-dioxaborolan-2-yl)phenol Step A: (4-Bromo-2-chloro-phenoxy)-trimethyl-silane 20.8 g 4-bromo-2-chloro-phenol (100 mmol) was dissolved in 150 mL dry THF then 24.2 g HMDS (150 mmol) was added. The reaction mixture was stirred at 85° C. under argon atmosphere for 1.5 hours then concentrated under reduced pressure resulting in the product used without further purification.

$^1$H NMR (200 MHz, CDCl$_3$): 7.49 (d, 1H), 7.23 (dd, 1H), 6.75 (d, 1H), 0.26 (s, 9H).

Step B: 4-Bromo-2-chloro-3-methyl-phenol 48 mL "BuLi solution in hexanes (2.5 M, 120 mmol) was added dropwise to a solution of 12.1 g dry DIPA (120 mmol) in 250 mL dry THF at −78° C. under argon atmosphere. The mixture was stirred for 30 minutes at the same temperature then 28.0 g (4-bromo-2-chloro-phenoxy)-trimethyl-silane (100 mmol) was added dropwise. After 2.5 hours 21.3 g MeI (150 mmol) was added dropwise then the cooling bath was removed and the mixture was stirred overnight. The reaction was quenched with 100 mL NH$_4$OH solution and 200 mL NH$_4$Cl solution and extracted with EtOAc, dried over Na$_2$SO$_4$, filtered and concentrated under reduced pressure. The resulting dark mass was refluxed with pure hexane several times (150-150 mL aliquots) and decanted leaving a black tar behind. Combined organic phases were concentrated under reduced pressure affording 19.0 g crude product used without further purification.

$^1$H NMR (200 MHz, CDCl$_3$): 7.32 (d, 1H), 6.76 (d, 1H), 5.62 (s, 1H), 2.49 (s, 3H).

Step C: (4-Bromo-2-chloro-3-methyl-phenoxy)-trimethyl-silane 20.8 g HMDS (129 mmol) was added to the solution of 19.0 g 4-bromo-2-chloro-3-methyl-phenol (86.0 mmol) in 150 mL dry THF. The mixture was stirred at 85° C. under argon balloon for 1.5 hours and then concentrated under reduced pressure. The obtained product was used without further purification.

$^1$H NMR (200 MHz, CDCl$_3$): 7.30 (d, 1H), 6.63 (d, 1H), 2.50 (s, 3H), 0.28 (s, 9H).

Step D: 2-Chloro-3-methyl-4-(4,4,5,5-tetramethyl-1,3,2-dioxaborolan-2-yl)phenol

A solution of 25.2 g (4-bromo-2-chloro-3-methyl-phenoxy)-trimethyl-silane (86.0 mmol) in 250 mL dry THF was cooled to −78° C. under argon and then 38 mL ″BuLi in hexanes (2.5 M, 94.6 mmol) was added dropwise. After 5 minutes 19.2 g 2-isopropoxy-4,4,5,5-tetramethyl-1,3,2-dioxaborolane (103 mmol) was added dropwise. The cooling bath was removed and the mixture was slowly allowed to warm up to room temperature. Then the mixture was added to 200 mL NH$_4$Cl solution and extracted with EtOAc. Combined organic layers were concentrated under reduced pressure and passed through a pad of silica gel using hexane and EtOAc as eluents. The crude product was recrystallized from a mixture of EtOAc and hexane to obtain Preparation 5a.

$^1$H NMR (500 MHz, DMSO-d$_6$): 10.40 (s, 1H), 7.42 (d, 1H), 6.80 (d, 1H), 2.49 (s, 3H), 1.27 (s, 12H).

Preparation 5b: 1-[2-[2-Chloro-3-methyl-4-(4,4,5,5-tetramethyl-1,3,2-dioxaborolan-2-yl)phenoxy]ethyl]-4-methyl-piperazine 10.0 g 2-chloro-3-methyl-4-(4,4,5,5-tetramethyl-1,3,2-dioxaborolan-2-yl)phenol (Preparation 5a) (37.2 mmol), 8.7 g 2-(4-methylpiperazin-1-yl)ethanol (60.3 mmol) and 15.8 g PPh$_3$ (60.3 mmol) were dissolved in 100 mL dry toluene and then 27 mL diethyl azodicarboxylate (60.3 mmol, 40% solution in toluene) was added dropwise. The mixture was stirred at 50° C. under argon for 1.5 hours. The volatiles were evaporated under reduced pressure and 100 mL Et$_2$O was added. The precipitated white crystals were filtered off and washed with Et$_2$O. The filtrate was concentrated under reduced pressure and purified via flash chromatography using CHCl$_3$ and MeOH as eluents. The resulting light brown oil was crystallized from hexane to give Preparation 5b as an off-white solid.

$^1$H NMR (500 MHz, DMSO-d$_6$): 7.56 (d, 1H), 6.99 (d, 1H), 4.15 (t, 2H), 2.72 (t, 2H), 2.51 (s, 3H), 2.50 (br s, 4H), 2.29 (br s, 4H), 2.13 (s, 3H), 1.29 (s, 12H).

Preparation 5c: [2-Chloro-3-methyl-4-(4,4,5,5-tetramethyl-1,3,2-dioxaborolan-2-yl)phenoxy]-triisopropyl-silane Step A: (4-Bromo-2-chloro-phenoxy)-triisopropyl-silane 200 g 4-bromo-2-chloro-phenol (0.97 mol) and 126 mL TIPSCl (1.18 mol) were dissolved in 1.6 L DCM. 167 g imidazole (2.45 mol) was added and the mixture was stirred at room temperature for 2 hours. The volatiles were evaporated under reduced pressure and the residue was dissolved in 1.5 L EtOAc. The mixture was washed with brine, dried over Na$_2$SO$_4$, filtered and concentrated under reduced pressure. The triisopropylsilyl hydroxide impurity was removed by distillation (120° C. at 0.01 mmHg). The residue was filtered through a short pad of silica with hexane and concentrated under reduced pressure. The product (colourless oil) was used in the next step without further purification.

$^1$H NMR (400 MHz, CDCl$_3$): 7.49 (d, 1H), 7.21 (dd, 1H), 6.78 (d, 1H), 1.31 (septet, 3H), 1.14 (d, 18H).

MS (EI, 70 eV) m/z (% relative intensity, [ion]): 63 (30), 79 (24), 93 (41), 170 (17), 235 (19), 251 (16), 265 (24), 293 (23), 319 (77), 321 (100), 323 (28), 362 (1, [M$^+$]).

Step B: (4-Bromo-2-chloro-3-methyl-phenoxy)-triisopropyl-silane 76.0 mL dry DIPA (0.54 mol) was dissolved in 1.2 L dry THF under argon atmosphere and 51.2 mL ″BuLi solution (10 M in hexanes, 0.512 mol) was added dropwise at −78° C. The mixture was stirred for 45 minutes at the same temperature. 178 g (4-bromo-2-chloro-phenoxy)-triisopropyl-silane (0.488 mol) was added dropwise at −78° C. and the white suspension was stirred for 8 hours. 36.5 mL MeI (0.586 mmol) was added at this temperature and the reaction mixture was stirred overnight without further cooling. The volatiles were evaporated under reduced pressure. The residue was dissolved in 1.5 L EtOAc, washed with brine, dried over Na$_2$SO$_4$, filtered and concentrated under reduced pressure. The crude product was filtered through a short pad of silica using hexane as eluent and concentrated under reduced pressure to obtain the product as pale yellow oil.

$^1$H NMR (400 MHz, CDCl$_3$): 7.30 (d, 1H), 6.68 (d, 1H), 2.53 (s, 3H), 1.32 (septet, 3H), 1.14 (d, 18H).

Step C: [2-Chloro-3-methyl-4-(4,4,5,5-tetramethyl-1,3,2-dioxaborolan-2-yl)phenoxy]-triisopropyl-silane 178 g (4-bromo-2-chloro-3-methyl-phenoxy)-triisopropyl-silane (0.472 mol) was dissolved in 1.4 L dry THF under argon atmosphere and 52 mL ″BuLi solution (10 M in hexanes, 0.52 mol) was added dropwise at −78° C. The mixture was stirred for 5 minutes at this temperature. Then 116 mL 2-isopropoxy-4,4,5,5-tetramethyl-1,3,2-dioxaborolane (0.569 mol) was added and the mixture was allowed to warm up to room temperature. The volatiles were evaporated under reduced pressure. The residue was dissolved in 1.5 L EtOAc, washed with brine, dried over Na$_2$SO$_4$, filtered and concentrated under reduced pressure. The 2-isopropoxy-4,4,5,5-tetramethyl-1,3,2-dioxaborolane impurity was removed by distillation (80° C. at 0.01 mmHg). The crude product was triturated in MeOH affording Preparation 5c as a white solid.

$^1$H NMR (400 MHz, CDCl$_3$): 7.53 (d, 1H), 6.74 (d, 1H), 2.60 (s, 3H), 1.34 (s, 12H), 1.32 (m, 3H), 1.12 (d, 18H).

Preparation 5d: 2-(3-Chloro-4-methoxy-2-methyl-phenyl)-4,4,5,5-tetramethyl-1,3,2-dioxaborolane 5.371 g 2-chloro-3-methyl-4-(4,4,5,5-tetramethyl-1,3,2-dioxaborolan-2-yl)phenol (Preparation 5a) (20.0 mmol) and 15.74 g PPh$_3$ (60.0 mmol) were dissolved in 50 mL dry MeOH under N$_2$, then 13.82 g ditertbutyl azodicarboxylate (60.0 mmol) was added and the mixture was stirred at 50° C. for 2 hours. Then it was concentrated under reduced pressure and purified via flash chromatography using heptane and EtOAc as eluents to obtain Preparation 5d.

$^1$H NMR (400 MHz, DMSO-d$_6$): 7.59 (d, 1H), 6.98 (d, 1H), 3.85 (s, 3H), 2.52 (s, 3H), 1.29 (s, 12H).

MS (EI, 70 eV) m/z (% relative intensity, [ion]): 77 (21), 82 (100), 225 (29), 267 (18), 282 (32, [M]$^+$), 284 (11, [M]$^+$).

Preparation 5e: [2-Chloro-3-ethyl-4-(4,4,5,5-tetramethyl-1,3,2-dioxaborolan-2-yl)phenoxy]-triisopropylsilane Step A: (4-Bromo-2-chloro-3-ethyl-phenoxy)-triisopropylsilane 7.07 g (4-bromo-2-chloro-phenoxy)-triisopropyl-silane (19.4 mmol, see Step A at Preparation 5c) was dissolved in 60 mL dry THF under $N_2$ and was cooled to −78° C. with dry ice-acetone. 11.7 mL LDA (23.3 mmol in 2 M THF, EtPh) was added and the mixture was stirred for 1 hour. Then 4.23 g ethyl iodide (38.9 mmol) was added and the mixture was allowed to warm up to room temperature. It was quenched with saturated $NH_4Cl$ solution, extracted with EtOAc, dried over $Na_2SO_4$, filtered and concentrated under reduced pressure. The crude product was purified via flash chromatography using heptane as eluent to obtain a mixture of product and starting material. They were separated via reversed phase chromatography using pure MeCN as eluent.

MS (EI, 70 eV) m/z (% relative intensity, [ion]): 63 (15), 93 (65), 121 (26), 161 (15), 183 (13), 263 (10), 279 (14), 347 (71), 349 (100), 351 (28), 390 (1, [$M^+$]), 392 (1, [$M^+$]).

Step B: [2-Chloro-3-ethyl-4-(4,4,5,5-tetramethyl-1,3,2-dioxaborolan-2-yl)phenoxy]-triisopropyl-silane 1.08 g (4-bromo-2-chloro-3-ethyl-phenoxy)-triisopropyl-silane (2.76 mmol) was dissolved in 20 mL dry THF under $N_2$ and was cooled to −78° C. with dry ice-acetone. 1.9 mL "BuLi (3.03 mmol in 1.6 M hexanes) was added and the mixture was stirred for 5 minutes, then 1.02 mL 2-isopropoxy-4,4,5,5-tetramethyl-1,3,2-dioxaborolane (4.00 mmol) was added and the mixture was allowed to warm up to room temperature. It was quenched with saturated $NH_4Cl$ solution, extracted with EtOAc, dried over $Na_2SO_4$, filtered and concentrated under reduced pressure. The crude product was purified via flash chromatography using heptane and EtOAc as eluents to obtain Preparation 5e.

MS (EI, 70 eV) m/z (% relative intensity, [ion]): 55 (25), 83 (100), 93 (50), 225 (14), 295 (9), 395 (67), 397 (26).

Preparation 5f: 1-[2-[2-Chloro-3-fluoro-4-(4,4,5,5-tetramethyl-1,3,2-dioxaborolan-2-yl)phenoxy]ethyl]-4-methyl-piperazine Step A: 1-[2-(4-Bromo-3-fluoro-phenoxy)ethyl]-4-methyl-piperazine 1.91 g 4-bromo-3-fluoro-phenol (10.0 mmol), 1.73 g 2-(4-methylpiperazin-1-yl)ethanol (12.0 mmol) and 5.00 g immobilized $PPh_3$ (15.0 mmol) were dissolved in 30 mL dry toluene under $N_2$, then 2.99 g ditertbutyl azodicarboxylate (13.0 mmol) was added and the mixture was stirred at 50° C. for 6 hours. Then it was filtered, the filtrate was concentrated under reduced pressure and purified via flash chromatography using EtOAc and MeOH as eluents to obtain 1-[2-(4-bromo-3-fluoro-phenoxy)ethyl]-4-methyl-piperazine.

MS (M+H): 317.2.

Step B: 1-[2-(4-Bromo-2-chloro-3-fluoro-phenoxy)ethyl]-4-methyl-piperazine 2.35 g 1-[2-(4-bromo-3-fluoro-phenoxy)ethyl]-4-methyl-piperazine (7.41 mmol) was dissolved in 40 mL dry THF under $N_2$ and was cooled to −78° C. with dry ice-acetone. 7.2 mL LDA (14.4 mmol in 2 M THF, EtPh) was added and the mixture was stirred for 1 hour, then 2.10 g 1,1,1,2,2,2-hexachloroethane (8.89 mmol) was added and the mixture was allowed to warm up to room temperature. It was quenched with brine, extracted with DCM, dried over $Na_2SO_4$, filtered and concentrated under reduced pressure. The crude product was purified via flash chromatography using EtOAc and MeOH as eluents to obtain 1-[2-(4-bromo-2-chloro-3-fluoro-phenoxy)ethyl]-4-methyl-piperazine.

MS (M+H): 351.0.

Step C: 1-[2-[2-Chloro-3-fluoro-4-(4,4,5,5-tetramethyl-1,3,2-dioxaborolan-2-yl)phenoxy]ethyl]-4-methyl-piperazine 1.94 g 1-[2-(4-bromo-2-chloro-3-fluoro-phenoxy)ethyl]-4-methyl-piperazine (5.50 mmol) was dissolved in 25 mL dry THF under $N_2$ and was cooled to −78° C. with dry ice-acetone. 4.2 mL "BuLi (6.60 mmol in 1.6 M hexanes) was added and the mixture was stirred for 5 minutes, then 2.04 mL 2-isopropoxy-4,4,5,5-tetramethyl-1,3,2-dioxaborolane (10.0 mmol) was added and the mixture was allowed to warm up to room temperature. It was quenched with brine, extracted with DCM, dried over $Na_2SO_4$, filtered and concentrated under reduced pressure. The crude product was purified via flash chromatography using EtOAc and MeOH as eluents to obtain Preparation 5f.

MS (M+H): 399.2.

Preparation 5g: 2-Fluoro-3-methyl-4-(4,4,5,5-tetramethyl-1,3,2-dioxaborolan-2-yl)phenol Step A: (4-Bromo-2-fluoro-phenoxy)-triisopropyl-silane 3.82 g 4-bromo-2-fluoro-phenol (20.0 mmol) was dissolved in 50 mL DCM, then 5.14 mL TIPSCl (24.0 mmol) and 2.72 g imidazole (40.0 mmol) was added and the mixture was stirred at room temperature for 1 hour. Then it was concentrated under reduced pressure and purified via flash chromatography using heptane as eluent to obtain (4-bromo-2-fluoro-phenoxy)-triisopropyl-silane.

MS (EI, 70 eV) m/z (% relative intensity, [ion]): 63 (35), 77 (100), 105 (44), 153 (43), 182 (25), 233 (75), 235 (75), 261 (9), 263 (9), 303 (17), 305 (17), 346 (3, [$M^+$]), 348 (3, [$M^+$]).

Step B: (4-Bromo-2-fluoro-3-methyl-phenoxy)-triisopropyl-silane 6.50 g (4-bromo-2-fluoro-phenoxy)-triisopropyl-silane (18.7 mmol) was dissolved in 60 mL dry THF under $N_2$ and was cooled to −78° C. with dry ice-acetone. 11.2 mL LDA was added (22.5 mmol in 2 M THF, EtPh) and the mixture was stirred for 1 hour, then 2.3 mL MeI (37.4 mmol) was added and the mixture was allowed to warm up to room temperature. It was quenched with saturated $NH_4Cl$ solution, extracted with EtOAc, dried over $Na_2SO_4$, filtered and concentrated under reduced pressure. The crude product was purified via flash chromatography using heptane as eluent to obtain (4-bromo-2-fluoro-3-methyl-phenoxy)-triisopropyl-silane.

MS (EI, 70 eV) m/z (% relative intensity, [ion]): 63 (21), 77 (100), 61 (105), 167 (52), 196 (43), 247 (60), 249 (59), 275 (25), 277 (25), 317 (14), 319 (14), 360 (5, [$M^+$]), 362 (5, [$M^+$]).

Step C: [2-Fluoro-3-methyl-4-(4,4,5,5-tetramethyl-1,3,2-dioxaborolan-2-yl)phenoxy]-triisopropyl-silane 6.61 g (4-bromo-2-fluoro-3-methyl-phenoxy)-triisopropyl-silane (18.3 mmol) was dissolved in 80 mL dry THF under $N_2$ and was cooled to −78° C. with dry ice-acetone. 13.8 mL "BuLi (22.0 mmol in 1.6 M hexanes) was added and the mixture was stirred for 10 minutes, then 5.6 mL 2-isopropoxy-4,4,5,5-tetramethyl-1,3,2-dioxaborolane (27.4 mmol) was added and the mixture was allowed to warm up to room temperature. It was quenched with saturated $NH_4Cl$ solution, extracted with $Et_2O$, dried over $Na_2SO_4$, filtered and concentrated under reduced pressure. The crude product was purified via flash chromatography using heptane and EtOAc as eluents to obtain [2-fluoro-3-methyl-4-(4,4,5,5-tetramethyl-1,3,2-dioxaborolan-2-yl)phenoxy]-triisopropyl-silane.

MS (EI, 70 eV) m/z (% relative intensity, [ion]): 77 (39), 83 (100), 195 (26), 223 (20), 241 (10), 323 (4), 365 (4).

Step D: 2-Fluoro-3-methyl-4-(4,4,5,5-tetramethyl-1,3,2-dioxaborolan-2-yl)phenol 6.00 g [2-fluoro-3-methyl-4-(4,4,5,5-tetramethyl-1,3,2-dioxaborolan-2-yl)phenoxy]-triisopropyl-silane (14.7 mmol) was dissolved in 20 mL THF, then 16.2 mL TBAF (16.2 mmol in 1 M THF) was added and the mixture was stirred for 10 minutes. Then it was diluted with EtOAc and $Et_2O$, washed with water and brine, dried over $Na_2SO_4$, filtered and concentrated under reduced pressure. The crude product was purified via flash chromatography using heptane and EtOAc as eluents to obtain Preparation 5g.

$^1$H NMR (400 MHz, DMSO-$d_6$): 10.09 (s, 1H), 7.27 (dd, 1H), 6.75 (t, 1H), 2.36 (d, 3H), 1.27 (s, 12H).

MS (EI, 70 eV) m/z (% relative intensity, [ion]): 152 (100), 166 (18), 195 (21), 237 (18), 252 (19, [M$^+$]).

Preparation 5h: 1-Methyl-4-[2-[4-methyl-3-(4,4,5,5-tetramethyl-1,3,2-dioxaborolan-2-yl)phenoxy]ethyl]piperazine Step A: 1-[2-(3-Bromo-4-methyl-phenoxy)ethyl]-4-methyl-piperazine 0.50 g 3-bromo-4-methyl-phenol (2.67 mmol), 0.46 g 2-(4-methylpiperazin-1-yl)ethanol (3.21 mmol) and 0.84 g PPh$_3$ (3.21 mmol) was dissolved in 10 mL dry THF under N$_2$, then 1.47 mL diethyl azodicarboxylate (3.21 mmol, 40% in toluene) was added and the mixture was stirred at room temperature for 2 hours. Then it was concentrated under reduced pressure and purified via reversed phase chromatography using aqueous 0.1% TFA solution and MeCN as eluents to obtain 1-[2-(3-bromo-4-methyl-phenoxy)ethyl]-4-methyl-piperazine.

MS (M+H): 313.1.

Step B: 1-Methyl-4-[2-[4-methyl-3-(4,4,5,5-tetramethyl-1,3,2-dioxaborolan-2-yl)phenoxy] ethyl]piperazine 1.70 g 1-[2-(3-bromo-4-methyl-phenoxy)ethyl]-4-methyl-piperazine (5.43 mmol), 1.52 g 4,4,5,5-tetramethyl-2-(4,4,5,5-tetramethyl-1,3,2-dioxaborolan-2-yl)-1,3,2-dioxaborolane (5.97 mmol), 395 mg PdCl$_2$×dppf (0.54 mmol) and 1.60 g KOAc (16.3 mmol) were dissolved in 20 mL dry DMF under N$_2$. The mixture was stirred at 85° C. for 5 hours, then it was filtered through celite, diluted with Et$_2$O, washed with water, dried over Na$_2$SO$_4$, filtered and concentrated under reduced pressure. Then heptane was added, the solid impurities were filtered and the filtrate was concentrated under reduced pressure. The crude product was used as Preparation 5h without further purification.

MS (M+H): 361.2.

Preparation 5i: 2-(3-Chloro-5-fluoro-4-methoxy-2-methyl-phenyl)-4,4,5,5-tetramethyl-1,3,2-dioxaborolane Step A: 1-Bromo-3-chloro-5-fluoro-4-methoxy-2-methyl-benzene 13.01 g 3-chloro-1-fluoro-2-methoxy-4-methyl-benzene (74.5 mmol) was dissolved in 200 mL AcOH, then 4.1 mL bromine (80.0 mmol) was added and the mixture was stirred at room temperature. Additional 6 mL bromine needed to reach complete conversion. Then the mixture was poured onto icy water, the pH was carefully set to 8 with solid KOH and K$_2$CO$_3$, then saturated Na$_2$S$_2$O$_3$ solution was added until the brown color of bromine disappeared. Then it was extracted with Et$_2$O. The combined organics were washed with water, then brine, then dried over Na$_2$SO$_4$, filtered and concentrated under reduced pressure to give 1-bromo-3-chloro-5-fluoro-4-methoxy-2-methyl-benzene.

$^1$H NMR (400 MHz, CDCl$_3$): 7.29 (d, 1H), 3.95 (d, 3H), 2.47 (d, 3H).

MS (EI, 70 eV) m/z (% relative intensity, [ion]): 75 (26), 95 (42), 107 (25), 130 (96), 132 (35), 237 (57), 239 (74), 252 (77, [M$^+$]), 254 (100, [M$^+$]), 256 (23, [M$^+$]).

Step B: 2-(3-Chloro-5-fluoro-4-methoxy-2-methyl-phenyl)-4,4,5,5-tetramethyl-1,3,2-dioxaborolane 761 mg 1-bromo-3-chloro-5-fluoro-4-methoxy-2-methyl-benzene (3.0 mmol) was dissolved in 15 mL dry THF under N$_2$ and was cooled to −78° C. with dry ice-acetone. 2.1 mL $^n$BuLi (3.3 mmol in 1.6 M hexanes) was added and the mixture was stirred for 10 minutes, then 0.69 mL 2-isopropoxy-4,4,5,5-tetramethyl-1,3,2-dioxaborolane (3.4 mmol) was added and the mixture was allowed to warm up to room temperature. It was quenched with saturated NH$_4$Cl solution, extracted with DCM, dried over Na$_2$SO$_4$, filtered and concentrated under reduced pressure. The crude product was purified via flash chromatography using heptane and EtOAc as eluents to obtain Preparation 5i.

MS (EI, 70 eV) m/z (% relative intensity, [ion]): 200 (100), 201 (57), 243 (52), 285 (26), 300 (35, [M$^+$]), 302 (11, [M$^+$]).

Preparation 5j: 1-[3-Chloro-2-methoxy-4-methyl-5-(4,4,5,5-tetramethyl-1,3,2-dioxaborolan-2-yl)phenyl]-4-methyl-piperazine Step A: 1-(5-Bromo-3-chloro-2-methoxy-4-methyl-phenyl)-4-methyl-piperazine 1.27 g 1-bromo-3-chloro-5-fluoro-4-methoxy-2-methyl-benzene (5.00 mmol, see Step A at Preparation 5i) was dissolved in 15 mL dry THF under N$_2$ and was cooled to −78° C. with dry ice-acetone. Separately 0.58 mL 1-methylpiperazine (5.25 mmol) was dissolved also in 15 mL dry THF under N$_2$ and was cooled to 0° C. with icy water. Then 3.3 mL $^n$BuLi (5.25 mmol in 1.6 M hexanes) was added and the mixture was stirred for 10 minutes, then it was cooled to −78° C. with dry ice-acetone. This latter mixture was transferred to the THF solution of 1-bromo-3-chloro-5-fluoro-4-methoxy-2-methyl-benzene and the mixture was allowed to warm up to room temperature. Water and brine were added and the mixture was extracted with DCM, dried over Na$_2$SO$_4$, filtered and concentrated under reduced pressure. The crude product was purified via reversed phase chromatography using 25 mM aqueous NH$_4$HCO$_3$ solution and MeCN as eluents.

MS (M+H): 333.0.

Step B: 1-[3-Chloro-2-methoxy-4-methyl-5-(4,4,5,5-tetramethyl-1,3,2-dioxaborolan-2-yl)phenyl]-4-methyl-piperazine 334 mg 1-(5-bromo-3-chloro-2-methoxy-4-methyl-phenyl)-4-methyl-piperazine (1.00 mmol) was dissolved in 10 mL dry THF under N$_2$ and was cooled to −78° C. with dry ice-acetone. 0.66 mL $^n$BuLi (1.05 mmol in 1.6 M hexanes) was added and the mixture was stirred for 15 minutes, then 0.25 mL 2-isopropoxy-4,4,5,5-tetramethyl-1,3,2-dioxaborolane (1.20 mmol) was added and the mixture was allowed to warm up to room temperature. It was quenched with brine, extracted with DCM, dried over Na$_2$SO$_4$, filtered and concentrated under reduced pressure and used as Preparation 5j without further purification.

MS (M+H): 381.2.

Preparation 5k: 2-Chloro-6-methoxy-3-methyl-4-(4,4,5,5-tetramethyl-1,3,2-dioxaborolan-2-yl)phenol Step A: 4-Bromo-2-methoxy-5-methyl-phenol 1.38 g 2-methoxy-5-methyl-phenol (10.0 mmol) was dissolved in 20 mL THF, then 1.87 g NBS (10.5 mmol) was added and the mixture was stirred at room temperature for 2 hours. Then it was concentrated under reduced pressure and purified via flash chromatography using heptane and EtOAc as eluents to obtain 4-bromo-2-methoxy-5-methyl-phenol.

$^1$H NMR (400 MHz, CDCl$_3$): 7.00 (s, 1H), 6.82 (s, 1H), 5.46 (s, 1H), 3.87 (s, 3H), 2.30 (s, 3H).

MS (EI, 70 eV) m/z (% relative intensity, [ion]): 51 (44), 65 (40), 94 (88), 137 (22), 173 (29), 175 (30), 201 (83), 203 (78), 216 (100, [M$^+$]), 218 (96, [M$^+$]).

Step B: 4-Bromo-2-chloro-6-methoxy-3-methyl-phenol 1.09 g 4-bromo-2-methoxy-5-methyl-phenol (5.00 mmol) was dissolved in 20 mL THF, then 701 mg NCS (5.25 mmol) was added and the mixture was stirred at room temperature for 1 day. Then it was concentrated under reduced pressure and purified via reversed phase chromatography using aqueous 0.1% TFA solution and MeCN as eluents to obtain 4-bromo-2-chloro-6-methoxy-3-methyl-phenol.

$^1$H NMR (400 MHz, CDCl$_3$): 6.98 (s, 1H), 5.81 (s, 1H), 3.88 (s, 3H), 2.43 (s, 3H).

MS (EI, 70 eV) m/z (% relative intensity, [ion]): 63 (37), 128 (53), 171 (42), 209 (26), 237 (67), 250 (77, [M$^+$]), 252 (100, [M$^+$]), 254 (24, [M$^+$]).

Step C: (4-Bromo-2-chloro-6-methoxy-3-methyl-phenoxy)-triisopropyl-silane 772 mg 4-bromo-2-chloro-6-methoxy-3-methyl-phenol (3.07 mmol) and 788 µL TIPSCl (3.68 mmol) were dissolved in 10 mL DCM. 418 mg imidazole (6.14 mmol) was added and the mixture was stirred at room temperature overnight. Then it was concentrated under reduced pressure and purified via flash chromatography using heptane as eluent to obtain (4-bromo-2-chloro-6-methoxy-3-methyl-phenoxy)-triisopropyl-silane.

$^1$H NMR (400 MHz, CDCl$_3$): 6.95 (s, 1H), 3.77 (s, 3H), 2.44 (s, 3H), 1.30 (septet, 3H), 1.10 (d, 18H).

MS (EI, 70 eV) m/z (% relative intensity, [ion]): 59 (19), 183 (15), 279 (27), 308 (13), 348 (76), 350 (100), 352 (28), 363 (66), 365 (89), 367 (24).

Step D: [2-Chloro-6-methoxy-3-methyl-4-(4,4,5,5-tetramethyl-1,3,2-dioxaborolan-2-yl)phenoxy]-triisopropyl-silane 3.07 mmol (4-bromo-2-chloro-6-methoxy-3-methyl-phenoxy)-triisopropyl-silane was dissolved in 20 mL dry THF under N$_2$ and was cooled to −78° C. with dry ice-acetone. 2.1 mL $^n$BuLi (3.40 mmol in 1.6 M hexanes) was added and the mixture was stirred for 5 minutes, then 820 µL 2-isopropoxy-4,4,5,5-tetramethyl-1,3,2-dioxaborolane (4.00 mmol, dissolved in 5 mL dry THF) was added and the mixture was allowed to warm up to room temperature. It was quenched with saturated NH$_4$Cl solution, extracted with EtOAc, dried over Na$_2$SO$_4$, filtered and concentrated under reduced pressure. The crude product was purified via flash chromatography using heptane and EtOAc as eluents to obtain [2-chloro-6-methoxy-3-methyl-4-(4,4,5,5-tetramethyl-1,3,2-dioxaborolan-2-yl)phenoxy]-triisopropyl-silane.

MS (EI, 70 eV) m/z (% relative intensity, [ion]): 225 (14), 254 (10), 296 (13), 396 (67), 398 (26), 411 (100), 413 (39).

Step E: 2-Chloro-6-methoxy-3-methyl-4-(4,4,5,5-tetramethyl-1,3,2-dioxaborolan-2-yl)phenol 3.07 mmol [2-chloro-6-methoxy-3-methyl-4-(4,4,5,5-tetramethyl-1,3,2-dioxaborolan-2-yl)phenoxy]-triisopropyl-silane was dissolved in 5 mL THF, then 3.5 mL TBAF (3.50 mmol in 1 M THF) was added and the mixture was stirred for 10 minutes. Then it was diluted with EtOAc, washed with water and brine, dried over Na$_2$SO$_4$, filtered and concentrated under reduced pressure. The crude product was purified via flash chromatography using heptane and EtOAc as eluents to obtain Preparation 5k.

$^1$H NMR (400 MHz, DMSO-d$_6$): 9.71 (s, 1H), 7.09 (s, 1H), 3.79 (s, 3H), 2.44 (s, 3H), 1.28 (s, 12H).

MS (EI, 70 eV) m/z (% relative intensity, [ion]): 183 (23), 198 (100), 199 (52), 223 (13), 241 (9), 283 (6), 298 (51, [M$^+$]), 300 (17, [M$^+$]).

Preparation 5l: 2-Chloro-3,6-dimethyl-4-(4,4,5,5-tetramethyl-1,3,2-dioxaborolan-2-yl)phenol Step A: (4-Bromo-2-chloro-6-methyl-phenoxy)-triisopropyl-silane 5.00 g 4-bromo-2-chloro-6-methyl-phenol (22.6 mmol) and 5.80 mL TIPSCl (27.1 mmol) were dissolved in 50 mL DCM. 3.07 g imidazole (45.1 mmol) was added and the mixture was stirred at room temperature overnight. Then it was concentrated under reduced pressure and purified via flash chromatography using heptane as eluent to obtain (4-bromo-2-chloro-6-methyl-phenoxy)-triisopropyl-silane.

$^1$H NMR (400 MHz, CDCl$_3$): 7.31 (s, 1H), 7.15 (s, 1H), 2.62 (s, 3H), 1.39 (septet, 3H), 1.13 (d, 18H).

MS (EI, 70 eV) m/z (% relative intensity, [ion]): 93 (33), 183 (30), 307 (14), 333 (87), 335 (100), 337 (30).

Step B: (4-Bromo-2-chloro-3,6-dimethyl-phenoxy)-triisopropyl-silane 6.70 g (4-bromo-2-chloro-6-methyl-phenoxy)-triisopropyl-silane (17.7 mmol) was dissolved in 80 mL dry THF under N$_2$ and was cooled to −78° C. with dry ice-acetone. 10.6 mL LDA was added (21.2 mmol in 2 M THF, EtPh) and the mixture was stirred for 1 hour, then 2.2 mL MeI (35.4 mmol) was added and the mixture was allowed to warm up to room temperature. It was quenched with saturated NH$_4$Cl solution, extracted with Et$_2$O, dried over Na$_2$SO$_4$, filtered and concentrated under reduced pressure. The crude product was purified via flash chromatography using heptane as eluent. The unreacted starting material was separated via reversed phase chromatography using MeCN as eluent to obtain (4-bromo-2-chloro-3,6-dimethyl-phenoxy)-triisopropyl-silane.

$^1$H NMR (400 MHz, CDCl$_3$): 7.23 (s, 1H), 2.47 (s, 3H), 2.24 (s, 3H), 1.40 (septet, 3H), 1.13 (d, 18H).

MS (EI, 70 eV) m/z (% relative intensity, [ion]): 93 (23), 146 (17), 197 (26), 347 (76), 349 (100), 351 (27).

Step C: [2-Chloro-3,6-dimethyl-4-(4,4,5,5-tetramethyl-1,3,2-dioxaborolan-2-yl)phenoxy]-triisopropyl-silane 1.18 g (4-bromo-2-chloro-3,6-dimethyl-phenoxy)-triisopropyl-silane (3.00 mmol) was dissolved in 15 mL dry THF under N$_2$ and was cooled to −78° C. with dry ice-acetone. 2.25 mL $^n$BuLi (3.60 mmol in 1.6 M hexanes) was added and the mixture was stirred for 15 minutes, then 1.02 mL 2-isopropoxy-4,4,5,5-tetramethyl-1,3,2-dioxaborolane (5.00 mmol) was added and the mixture was allowed to warm up to room temperature. It was quenched with saturated NH$_4$Cl solution, extracted with Et$_2$O, dried over Na$_2$SO$_4$, filtered and concentrated under reduced pressure. The crude product was purified via flash chromatography using heptane and EtOAc as eluents to obtain [2-chloro-3,6-dimethyl-4-(4,4,5,5-tetramethyl-1,3,2-dioxaborolan-2-yl)phenoxy]-triisopropyl-silane.

MS (EI, 70 eV) m/z (% relative intensity, [ion]): 83 (100), 101 (30), 225 (14), 395 (54), 397 (21).

Step D: 2-Chloro-3,6-dimethyl-4-(4,4,5,5-tetramethyl-1,3,2-dioxaborolan-2-yl)phenol 968 mg [2-chloro-3,6-dimethyl-4-(4,4,5,5-tetramethyl-1,3,2-dioxaborolan-2-yl)phenoxy]-triisopropyl-silane (2.20 mmol) was dissolved in 10 mL THF, then 2.4 mL TBAF (2.40 mmol in 1 M THF) was added and the mixture was stirred for 5 minutes. Then it was diluted with Et$_2$O and EtOAc, washed with water and brine, dried over Na$_2$SO$_4$, filtered and concentrated under reduced pressure. The crude product was purified via flash chromatography using heptane and EtOAc as eluents to obtain Preparation 5l.

$^1$H NMR (400 MHz, CDCl$_3$): 7.48 (s, 1H), 5.89 (s, 1H), 2.58 (s, 3H), 2.26 (s, 3H), 1.35 (s, 12H).

MS (EI, 70 eV) m/z (% relative intensity, [ion]): 91 (14), 147 (22), 182 (100), 183 (61), 225 (43), 267 (14), 282 (26, [M$^+$]), 284 (9, [M$^+$]).

Preparation 5m: 2-Chloro-6-fluoro-3-methyl-4-(4,4,5,5-tetramethyl-1,3,2-dioxaborolan-2-yl)phenol Step A: 4-Bromo-2-chloro-6-fluoro-3-methyl-phenol 3.21 g 2-chloro-6-fluoro-3-methyl-phenol (20.0 mmol) was dissolved in 60 mL THF, then 3.74 g NBS (21.0 mmol) was added and the mixture was stirred at room temperature for 10 minutes. Then it was concentrated under reduced pressure and purified via flash chromatography using heptane and EtOAc as eluents to obtain 4-bromo-2-chloro-6-fluoro-3-methyl-phenol.

$^1$H NMR (400 MHz, CDCl$_3$): 7.25 (d, 1H), 5.63 (s, 1H), 2.44 (d, 3H).

MS (EI, 70 eV) m/z (% relative intensity, [ion]): 75 (37), 95 (36), 159 (100), 161 (31), 238 (47, [M$^+$]), 240 (61, [M$^+$]), 242 (15, [M$^+$]).

Step B: (4-Bromo-2-chloro-6-fluoro-3-methyl-phenoxy)-triisopropyl-silane 4.06 g 4-bromo-2-chloro-6-fluoro-3-methyl-phenol (19.9 mmol) and 4.35 mL TIPSCl (20.3 mmol) were dissolved in 50 mL DCM. 2.31 g imidazole (33.9 mmol) was added and the mixture was stirred at room temperature for 1 hour. Then it was concentrated under reduced pressure and purified via flash chromatography using heptane as eluent to obtain (4-bromo-2-chloro-6-fluoro-3-methyl-phenoxy)-triisopropyl-silane.

$^1$H NMR (400 MHz, CDCl$_3$): 7.21 (d, 1H), 2.45 (d, 3H), 1.32 (septet, 3H), 1.10 (d, 18H).

MS (EI, 70 eV) m/z (% relative intensity, [ion]): 77 (100), 97 (37), 187 (22), 215 (58), 267 (42), 269 (54), 311 (13), 351 (32), 353 (43).

Step C: [2-Chloro-6-fluoro-3-methyl-4-(4,4,5,5-tetramethyl-1,3,2-dioxaborolan-2-yl)phenoxy]-triisopropyl-silane 6.22 g (4-bromo-2-chloro-6-fluoro-3-methyl-phenoxy)-triisopropyl-silane (15.7 mmol) was dissolved in 65 mL dry THF under N$_2$ and was cooled to −78° C. with dry ice-acetone. 11.8 mL "BuLi (18.9 mmol in 1.6 M hexanes) was added and the mixture was stirred for 30 minutes, then 5.34 mL 2-isopropoxy-4,4,5,5-tetramethyl-1,3,2-dioxaborolane (26.2 mmol) was added and the mixture was allowed to warm up to room temperature. It was quenched with saturated NH$_4$Cl solution, extracted with DCM, dried over Na$_2$SO$_4$, filtered and concentrated under reduced pressure. The crude product was purified via flash chromatography using heptane and EtOAc as eluents to obtain [2-chloro-6-fluoro-3-methyl-4-(4,4,5,5-tetramethyl-1,3,2-dioxaborolan-2-yl)phenoxy]-triisopropyl-silane.

$^1$H NMR (400 MHz, CDCl$_3$): 7.37 (d, 1H), 2.54 (d, 3H), 1.33 (m, 15H), 1.10 (d, 18H).

MS (EI, 70 eV) m/z (% relative intensity, [ion]): 83 (100), 101 (18), 275 (8), 399 (7).

Step D: 2-Chloro-6-fluoro-3-methyl-4-(4,4,5,5-tetramethyl-1,3,2-dioxaborolan-2-yl)phenol 5.18 g [2-chloro-6-fluoro-3-methyl-4-(4,4,5,5-tetramethyl-1,3,2-dioxaborolan-2-yl)phenoxy]-triisopropyl-silane (11.7 mmol) was dissolved in 15 mL THF, then 12.9 mL TBAF (12.9 mmol in 1 M THF) was added and the mixture was stirred for 5 minutes. Then it was diluted with EtOAc, washed with pH 5 HCl solution, water and brine, dried over Na$_2$SO$_4$, filtered and concentrated under reduced pressure. The crude product was purified via flash chromatography using heptane and EtOAc as eluents to obtain Preparation 5m.

$^1$H NMR (400 MHz, CDCl$_3$): 7.45 (d, 1H), 5.74 (s, 1H), 2.56 (d, 3H), 1.34 (s, 12H).

MS (EI, 70 eV) m/z (% relative intensity, [ion]): 59 (30), 85 (17), 151 (23), 186 (100), 187 (63), 229 (49), 272 (25), 286 (22, [M$^+$]), 288 (7, [M$^+$]).

Preparation 5n: 3-[2-Chloro-3-methyl-4-(4,4,5,5-tetramethyl-1,3,2-dioxaborolan-2-yl)phenyl]-N,N-dimethyl-propan-1-amine Step A: 1-Bromo-3-chloro-4-iodo-2-methyl-benzene 7.93 g 4-bromo-2-chloro-1-iodo-benzene (25.0 mmol) was dissolved in 300 mL dry THF under N$_2$ and was cooled to −78° C. with dry ice-acetone. 13.8 mL LDA was added (27.5 mmol in 2 M THF, EtPh) and the mixture was stirred for 75 minutes, then 3.1 mL MeI (50.0 mmol) was added and the mixture was allowed to warm up to room temperature. It was quenched with saturated NH$_4$Cl solution and most of the volatiles were evaporated under reduced pressure. Then it was extracted with DCM, dried over Na$_2$SO$_4$, filtered and concentrated under reduced pressure. The crude product was purified via flash chromatography using heptane as eluent to obtain 1-bromo-3-chloro-4-iodo-2-methyl-benzene.

$^1$H NMR (400 MHz, CDCl$_3$): 7.55 (d, 1H), 7.17 (d, 1H), 2.62 (s, 3H).

MS (EI, 70 eV) m/z (% relative intensity, [ion]): 63 (27), 89 (47), 124 (35), 251 (43), 330 (81, [M$^+$]), 332 (100, [M$^+$]), 334 (25, [M$^+$]).

Step B: 3-(4-Bromo-2-chloro-3-methyl-phenyl)-N,N-dimethyl-prop-2-yn-1-amine 1.66 g 1-bromo-3-chloro-4-iodo-2-methyl-benzene (5.00 mmol), 626 µL N,N-dimethylprop-2-yn-1-amine (7.00 mmol), 176 mg PdCl$_2$(PPh$_3$)$_2$ (0.25 mmol) and 95 mg copper(I) iodide (0.50 mmol) were dissolved in 26 mL dry DIPA and the mixture was stirred at 40° C. under N$_2$ for 30 minutes. Then it was concentrated under reduced pressure and purified via flash chromatography using heptane and EtOAc as eluents. Then it was further purified via reversed phase chromatography using 25 mM aqueous NH$_4$HCO$_3$ solution and MeCN as eluents to obtain 3-(4-bromo-2-chloro-3-methyl-phenyl)-N,N-dimethyl-prop-2-yn-1-amine.

$^1$H NMR (400 MHz, CDCl$_3$): 7.38 (d, 1H), 7.16 (d, 1H), 3.52 (s, 2H), 2.52 (s, 3H), 2.38 (s, 6H). MS (M+H): 286.0.

Step C: 3-(4-Bromo-2-chloro-3-methyl-phenyl)-N,N-dimethyl-propan-1-amine 641 mg 3-(4-bromo-2-chloro-3-methyl-phenyl)-N,N-dimethyl-prop-2-yn-1-amine (2.13 mmol) was dissolved in 3 mL AcOH, then 300 mg red phosphorus and 5 mL HI (67% aqueous solution) was added. The mixture was heated to 180° C. for 20 minutes via microwave irradiation. After cooling to room temperature it was neutralized with 2 M NaOH, extracted with DCM, dried over Na$_2$SO$_4$, filtered and concentrated under reduced pressure. The crude product was purified via reversed phase chromatography using 25 mM aqueous NH$_4$HCO$_3$ solution and MeCN as eluents to obtain 3-(4-bromo-2-chloro-3-methyl-phenyl)-N,N-dimethyl-propan-1-amine.

$^1$H NMR (400 MHz, CDCl$_3$): 7.35 (d, 1H), 6.92 (d, 1H), 2.70 (t, 2H), 2.51 (s, 3H), 2.29 (t, 2H), 2.21 (s, 6H), 1.74 (quint, 2H). MS (M+H): 290.0.

Step D: 3-[2-Chloro-3-methyl-4-(4,4,5,5-tetramethyl-1,3,2-dioxaborolan-2-yl)phenyl]-N,N-dimethyl-propan-1-amine 378 mg 3-(4-bromo-2-chloro-3-methyl-phenyl)-N,N-dimethyl-propan-1-amine (1.30 mmol) was dissolved in 5 mL dry THF under N$_2$ and was cooled to −78° C. with dry ice-acetone. 0.94 mL ″BuLi (1.50 mmol in 1.6 M hexanes) was added and the mixture was stirred for 5 minutes, then 370 μL 2-isopropoxy-4,4,5,5-tetramethyl-1,3,2-dioxaborolane (1.80 mmol) was added and the mixture was allowed to warm up to room temperature. It was quenched with water and brine, extracted with EtOAc, dried over Na$_2$SO$_4$, filtered and concentrated under reduced pressure and used as Preparation 5n without further purification.

MS (M+H): 338.2.

Preparation 5o: [2-Bromo-3-methyl-4-(4,4,5,5-tetramethyl-1,3,2-dioxaborolan-2-yl)phenoxy]-triisopropyl-silane Step A: (2,4-Dibromophenoxy)-triisopropyl-silane 7.56 g 2,4-dibromophenol (30.0 mmol) and 7.7 mL TIPSCl (36.0 mmol) were dissolved in 100 mL DCM. 4.08 g imidazole (60.0 mmol) was added and the mixture was stirred at room temperature overnight. Then it was concentrated under reduced pressure and purified via flash chromatography using heptane as eluent to obtain (2,4-dibromophenoxy)-triisopropyl-silane.

MS (EI, 70 eV) m/z (% relative intensity, [ion]): 109 (39), 137 (43), 201 (22), 279 (24), 309 (27), 337 (20), 363 (48), 365 (100), 367 (52).

Step B: (2,4-Dibromo-3-methyl-phenoxy)-triisopropyl-silane 11.15 g (2,4-dibromophenoxy)-triisopropyl-silane (27.3 mmol) was dissolved in 100 mL dry THF under N$_2$ and was cooled to −78° C. with dry ice-acetone. 16.4 mL LDA (32.8 mmol in 2 M THF, EtPh) was added and the mixture was stirred for 1 hour, then 3.4 mL MeI (54.6 mmol) was added and the mixture was allowed to warm up to room temperature. It was quenched with saturated NH$_4$Cl solution, extracted with EtOAc, dried over Na$_2$SO$_4$, filtered and concentrated under reduced pressure. The crude product was purified via flash chromatography using heptane as eluent to obtain (2,4-dibromo-3-methyl-phenoxy)-triisopropyl-silane.

MS (EI, 70 eV) m/z (% relative intensity, [ion]): 139 (19), 161 (14), 351 (13), 377 (54), 379 (100), 381 (53).

Step C [2-Bromo-3-methyl-4-(4,4,5,5-tetramethyl-1,3,2-dioxaborolan-2-yl)phenoxy]-triisopropyl-silane 8.70 g (2,4-dibromo-3-methyl-phenoxy)-triisopropyl-silane (20.6 mmol) was dissolved in 50 mL dry THF under N$_2$ and was cooled to −78° C. with dry ice-acetone. 14.2 mL ″BuLi (22.7 mmol in 1.6 M hexanes) was added and the mixture was stirred for 1 minute, then 6.1 mL 2-isopropoxy-4,4,5,5-tetramethyl-1,3,2-dioxaborolane (30.0 mmol) was added and the mixture was allowed to warm up to room temperature. It was quenched with saturated NH$_4$Cl solution, extracted with EtOAc, dried over Na$_2$SO$_4$, filtered and concentrated under reduced pressure. The crude product was purified via reversed phase chromatography using MeCN as eluent to obtain Preparation 5o.

$^1$H NMR (400 MHz, CDCl$_3$): 7.57 (d, 1H), 6.71 (d, 1H), 2.65 (s, 3H), 1.37-1.27 (m, 15H), 1.13 (d, 18H).

MS (EI, 70 eV) m/z (% relative intensity, [ion]): 55 (54), 83 (100), 139 (27), 425 (53), 427 (54).

Preparation 5p: 1-[2-[2,3-Dichloro-4-(4,4,5,5-tetramethyl-1,3,2-dioxaborolan-2-yl)phenoxy] ethyl]-4-methyl-piperazine Step A: 4-Bromo-2,3-dichloro-phenol 1.63 g 2,3-dichlorophenol (10.0 mmol) was dissolved in 30 mL DCM and was cooled to 0° C. Then 512 μL bromine (10.0 mmol) was added and the mixture was allowed to warm up to room temperature and the mixture was stirred at room temperature overnight. Then it was washed with saturated Na$_2$S$_2$O$_3$ solution, dried over Na$_2$SO$_4$, filtered and concentrated under reduced pressure. The crude product was purified via flash chromatography using heptane and EtOAc as eluents to obtain a mixture of 6-bromo-2,3-dichloro-phenol and 4-bromo-2,3-dichloro-phenol.

MS (M−H): 239.0.

Step B: 1-[2-(4-Bromo-2,3-dichloro-phenoxy)ethyl]-4-methyl-piperazine 1.90 g mixture of 6-bromo-2,3-dichloro-phenol and 4-bromo-2,3-dichloro-phenol (7.85 mmol), 2.27 g 2-(4-methylpiperazin-1-yl)ethanol (15.7 mmol) and 4.12 g PPh$_3$ (15.7 mmol) were dissolved in 20 mL dry toluene under N$_2$, then 3.62 g ditertbutyl azodicarboxylate (15.7 mmol) was added and the mixture was stirred at room temperature overnight. Then it was concentrated under reduced pressure and the regioisomers were separated via flash chromatography using EtOAc and MeOH as eluents. The desired isomer was further purified via reversed phase chromatography using water and MeCN as eluents to obtain 1-[2-(4-bromo-2,3-dichloro-phenoxy)ethyl]-4-methyl-piperazine.

$^1$H NMR (400 MHz, DMSO-d$_6$): 7.69 (d, 1H), 7.16 (d, 1H), 4.20 (t, 2H), 2.72 (t, 2H), 2.42-2.18 (m, 8H), 2.13 (s, 3H). MS (M+H): 367.0.

Step C: 1-[2-[2,3-Dichloro-4-(4,4,5,5-tetramethyl-1,3,2-dioxaborolan-2-yl)phenoxy] ethyl]-4-methyl-piperazine 2.10 g 1-[2-(4-bromo-2,3-dichloro-phenoxy)ethyl]-4-methyl-piperazine (5.70 mmol) was dissolved in 25 mL dry THF under N$_2$ and was cooled to −78° C. with dry ice-acetone. 3.9 mL ″BuLi (6.28 mmol in 1.6 M hexanes) was added and the mixture was stirred for 5 minutes, then 2.0 mL 2-isopropoxy-4,4,5,5-tetramethyl-1,3,2-dioxaborolane (10.0 mmol) was added and the mixture was allowed to warm up to room temperature. It was quenched with brine, extracted with DCM, dried over Na$_2$SO$_4$, filtered and concentrated under reduced pressure. The crude product was purified via reversed phase chromatography using 25 mM aqueous NH$_4$HCO$_3$ solution and MeCN as eluents to obtain Preparation 5p.

MS (M+H): 415.2.

Preparation 5q: 1-[2-[[3-chloro-4-methyl-5-(4,4,5,5-tetramethyl-1,3,2-dioxaborolan-2-yl)-2-pyridyl]oxy] ethyl]-4-methyl-piperazine Step A: 5-Bromo-3-chloro-4-methyl-pyridin-2-ol 4.86 g 5-bromo-4-methyl-pyridin-2-ol (25.8 mmol) was dissolved in 250 mL THF, then 4.49 g NCS (33.6 mmol) was added and the mixture was stirred at 60° C. in dark for 45 minutes. Then it was concentrated under reduced pressure and crystallized from Et$_2$O and heptane to get an overweight product, which was crystallized from 100 mL MeCN to give 5-bromo-3-chloro-4-methyl-pyridin-2-ol.

¹H NMR (400 MHz, DMSO-d₆): 11.50 (br s, 1H), 7.74 (s, 1H), 2.36 (s, 3H). MS (M+H): 222.0, (M−H): 220.0.

Step B: 1-[2-[(5-Bromo-3-chloro-4-methyl-2-pyridyl)oxy]ethyl]-4-methyl-piperazine 2.326 g 5-bromo-3-chloro-4-methyl-pyridin-2-ol (10.45 mmol), 2.163 g 2-(4-methylpiperazin-1-yl)ethanol (15.00 mmol) and 3.935 g PPh₃ (15.00 mmol) were dissolved in 30 mL dry toluene under N₂, then 3.454 g ditertbutyl azodicarboxylate (15.00 mmol) was added and the mixture was stirred at room temperature under N₂ for 20 minutes. Then it was concentrated under reduced pressure and the structural isomers were separated via flash chromatography using EtOAc and MeOH as eluents. The isomer eluting earlier was collected as 1-[2-[(5-bromo-3-chloro-4-methyl-2-pyridyl)oxy]ethyl]-4-methyl-piperazine.

¹H NMR (400 MHz, DMSO-d₆): 8.24 (s, 1H), 4.41 (t, 2H), 2.68 (t, 2H), 2.48-2.15 (m, 11H), 2.12 (s, 3H). MS (M+H): 348.0.

Step C: 1-[2-[[3-Chloro-4-methyl-5-(4,4,5,5-tetramethyl-1,3,2-dioxaborolan-2-yl)-2-pyridyl]oxy]ethyl]-4-methyl-piperazine 1.917 g 1-[2-[(5-bromo-3-chloro-4-methyl-2-pyridyl)oxy]ethyl]-4-methyl-piperazine (5.50 mmol) was dissolved in 30 mL dry THF under N₂ and was cooled to −78° C. with dry ice-acetone. 4.1 mL ⁿBuLi (6.60 mmol in 1.6 M hexanes) was added and the mixture was stirred for 5 minutes, then 1.46 mL 2-isopropoxy-4,4,5,5-tetramethyl-1,3,2-dioxaborolane (7.15 mmol) was added and the mixture was allowed to warm up to room temperature. It was quenched with brine, extracted with DCM, dried over Na₂SO₄, filtered and concentrated under reduced pressure. The crude product was purified via flash chromatography using EtOAc and MeOH as eluents to obtain Preparation 5q.

MS (M+H): 396.2.

Preparation 5r: 1-[3-[2-Chloro-3-methyl-4-(4,4,5,5-tetramethyl-1,3,2-dioxaborolan-2-yl)phenyl]propyl]-4-methyl-piperazine Step A: 3-(4-Bromo-2-chloro-3-methyl-phenyl)prop-2-yn-1-ol 17.43 g 1-bromo-3-chloro-4-iodo-2-methyl-benzene (52.60 mmol, see Step A at Preparation 5n), 3.37 mL prop-2-yn-1-ol (57.86 mmol), 369 mg PdCl₂(PPh₃)₂ (0.53 mmol) and 501 mg copper(I) iodide (2.63 mmol) were dissolved in 100 mL dry DIPA and the mixture was stirred at 40° C. under N₂ for 20 minutes. Then it was concentrated under reduced pressure and purified via flash chromatography using heptane and EtOAc as eluents to obtain 3-(4-bromo-2-chloro-3-methyl-phenyl)prop-2-yn-1-ol.

¹H NMR (400 MHz, CDCl₃): 7.40 (d, 1H), 7.16 (d, 1H), 4.54 (d, 2H), 2.53 (s, 3H), 1.87 (t, 1H).

MS (EI, 70 eV) m/z (% relative intensity, [ion]): 63 (35), 115 (100), 223 (56), 258 (15, [M⁺]), 260 (18, [M⁺]), 262 (5, [M⁺]).

Step B: 3-(4-Bromo-2-chloro-3-methyl-phenyl)prop-2-ynyl methanesulfonate 5.427 g 3-(4-bromo-2-chloro-3-methyl-phenyl)prop-2-yn-1-ol (20.9 mmol) and 4.37 mL DIPEA (25.1 mmol) was dissolved in 50 mL dry DCM under N₂, then 1.78 mL methanesulfonyl chloride (23.0 mmol) was added carefully and the mixture was stirred for 10 minutes. Then it was concentrated under reduced pressure and purified via flash chromatography using heptane and EtOAc as eluents to obtain 3-(4-bromo-2-chloro-3-methyl-phenyl)prop-2-ynyl methanesulfonate.

¹H NMR (400 MHz, CDCl₃): 7.45 (d, 1H), 7.19 (d, 1H), 5.12 (s, 2H), 3.18 (s, 3H), 2.53 (s, 3H).

Step C: 1-[3-(4-Bromo-2-chloro-3-methyl-phenyl)prop-2-ynyl]-4-methyl-piperazine 4.31 g 3-(4-bromo-2-chloro-3-methyl-phenyl)prop-2-ynyl methanesulfonate (12.8 mmol) was dissolved in 120 mL MeCN, and the mixture was added to the stirred mixture of 2.65 g K₂CO₃ (19.2 mmol), 14.2 mL 1-methylpiperazine (127.7 mmol) and 120 mL MeCN. The mixture was stirred for 30 minutes, then it was filtered and the filtrate was concentrated under reduced pressure. Brine was added and the mixture was extracted with DCM, dried over Na₂SO₄, filtered and concentrated under reduced pressure to obtain 1-[3-(4-bromo-2-chloro-3-methyl-phenyl)prop-2-ynyl]-4-methyl-piperazine.

MS (M+H): 341.0.

Step D: 1-[3-(4-Bromo-2-chloro-3-methyl-phenyl)propyl]-4-methyl-piperazine 1.51 g 1-[3-(4-Bromo-2-chloro-3-methyl-phenyl)prop-2-ynyl]-4-methyl-piperazine (4.42 mmol) was dissolved in 15 mL AcOH, then 500 mg red phosphorus and 10 mL HI (67% aqueous solution) was added. The mixture was heated to 180° C. for 5 minutes via microwave irradiation. After cooling to room temperature it was neutralized with 2 M NaOH, extracted with DCM, dried over Na₂SO₄, filtered and concentrated under reduced pressure. The crude product was purified via reversed phase chromatography using 25 mM aqueous NH₄HCO₃ solution and MeCN as eluents to obtain 1-[3-(4-bromo-2-chloro-3-methyl-phenyl)propyl]-4-methyl-piperazine.

¹H NMR (400 MHz, DMSO-d₆): 7.50 (d, 1H), 7.13 (d, 1H), 2.68 (t, 2H), 2.47 (s, 3H), 2.46-2.15 (m, 10H), 2.13 (s, 3H), 1.67 (quint, 2H). MS (M+H): 345.0.

Step E: 1-[3-[2-Chloro-3-methyl-4-(4,4,5,5-tetramethyl-1,3,2-dioxaborolan-2-yl)phenyl] propyl]-4-methyl-piperazine 708 mg 1-[3-(4-bromo-2-chloro-3-methyl-phenyl)propyl]-4-methyl-piperazine (2.04 mmol) was dissolved in 10 mL dry THF under N₂ and was cooled to −78° C. with dry ice-acetone. 1.7 mL ⁿBuLi (2.70 mmol in 1.6 M hexanes) was added and the mixture was stirred for 5 minutes, then 0.61 mL 2-isopropoxy-4,4,5,5-tetramethyl-1,3,2-dioxaborolane (3.00 mmol) was added and the mixture was allowed to warm up to room temperature. It was quenched with brine, extracted with DCM, dried over Na₂SO₄, filtered and concentrated under reduced pressure. The crude product was purified via reversed phase chromatography using 25 mM aqueous NH₄HCO₃ solution and MeCN as eluents to obtain Preparation 5r.

MS (M+H): 393.4.

Preparation 5s: 1-[2-[2,3-dimethyl-4-(4,4,5,5-tetramethyl-1,3,2-dioxaborolan-2-yl)phenoxy] ethyl]-4-methyl-piperazine Step A: 4-Bromo-2,3-dimethyl-phenol 1.22 g 2,3-dimethylphenol (10.0 mmol) was dissolved in 50 mL MeCN, then 1.78 g NBS (10.0 mmol) was added and the mixture was stirred at room temperature overnight. Then it was concentrated under reduced pressure and purified via flash chromatography using heptane and EtOAc as eluents to obtain 4-bromo-2,3-dimethyl-phenol.

¹H NMR (400 MHz, CDCl₃): 7.24 (d, 1H), 6.52 (d, 1H), 4.68 (s, 1H), 2.37 (s, 3H), 2.22 (s, 3H).

MS (EI, 70 eV) m/z (% relative intensity, [ion]): 77 (45), 91 (62), 121 (100), 200 (76, [M⁺]), 202 (74, [M⁺]).

Step B: 1-[2-(4-Bromo-2,3-dimethyl-phenoxy)ethyl]-4-methyl-piperazine 1.54 g 4-bromo-2,3-dimethyl-phenol (7.66 mmol), 2.21 g 2-(4-methylpiperazin-1-yl)ethanol (15.3 mmol) and 6.03 g PPh$_3$ (23.0 mmol) were dissolved in 20 mL dry toluene under N$_2$, then 5.29 g ditertbutyl azodicarboxylate (23.0 mmol) was added and the mixture was stirred at 45° C. for 2 hours. Then it was concentrated under reduced pressure and purified via flash chromatography using EtOAc and MeOH as eluents to obtain 1-[2-(4-bromo-2,3-dimethyl-phenoxy)ethyl]-4-methyl-piperazine.

$^1$H NMR (400 MHz, CDCl$_3$): 7.31 (d, 1H), 6.58 (d, 1H), 4.06 (t, 2H), 2.83 (t, 2H), 2.70-2.38 (m, 8H), 2.36 (s, 3H), 2.29 (s, 3H), 2.20 (s, 3H).

Step C: 1-[2-[2,3-Dimethyl-4-(4,4,5,5-tetramethyl-1,3,2-dioxaborolan-2-yl)phenoxy] ethyl]-4-methyl-piperazine 2.10 g 1-[2-(4-bromo-2,3-dimethyl-phenoxy)ethyl]-4-methyl-piperazine (6.42 mmol) was dissolved in 25 mL dry THF under N$_2$ and was cooled to −78° C. with dry ice-acetone. 4.2 mL $^n$BuLi (6.74 mmol in 1.6 M hexanes) was added and the mixture was stirred for 15 minutes, then 1.44 mL 2-isopropoxy-4,4,5,5-tetramethyl-1,3,2-dioxaborolane (7.06 mmol) was added and the mixture was allowed to warm up to room temperature. It was quenched with brine, extracted with DCM, dried over Na$_2$SO$_4$, filtered and concentrated under reduced pressure. The crude product was purified via flash chromatography using heptane and EtOAc as eluents to obtain Preparation 5s.

$^1$H NMR (400 MHz, DMSO-d$_6$): 7.46 (d, 1H), 6.75 (d, 1H), 4.02 (t, 2H), 2.68 (t, 2H), 2.48 (br s, 4H), 2.38 (s, 3H), 2.30 (br s, 4H), 2.13 (s, 3H), 2.05 (s, 3H), 1.26 (s, 12H). MS (M+H): 375.4.

Preparation 5t: 2-(4-Bromo-3-chloro-2-methyl-phenyl)-4,4,5,5-tetramethyl-1,3,2-dioxaborolane 2.92 g 1-bromo-2-chloro-4-iodo-3-methyl-benzene (8.81 mmol) was dissolved in 30 mL dry THF under N$_2$ and 4.8 mL EtMgCl (9.69 mmol in 2 M THF) was added dropwise at room temperature. It was stirred for 10 minutes, then 5.4 mL 2-isopropoxy-4,4,5,5-tetramethyl-1,3,2-dioxaborolane (26.4 mmol) was added and the mixture was stirred for 10 minutes. Then it was concentrated under reduced pressure and purified via flash chromatography using heptane and EtOAc as eluents to obtain Preparation 5t.

$^1$H NMR (400 MHz, DMSO-d$_6$): 7.49 (d, 1H), 7.45 (d, 1H), 2.66 (s, 3H), 1.34 (s, 12H).

Preparation 5u: 1-[2-[2-Chloro-3-ethyl-4-(4,4,5,5-tetramethyl-1,3,2-dioxaborolan-2-yl)phenoxy]ethyl]-4-methyl-piperazine Step A: 1-[2-(4-Bromo-2-chloro-phenoxy)ethyl]-4-methyl-piperazine 10.373 g (50 mmol) 4-bromo-2-chlorophenol, 14.442 g 2-(4-methylpiperazin-1-yl)ethanol (100 mmol) and 26.229 g PPh$_3$ (100 mmol) were dissolved in 250 mL toluene, then 23.027 g ditertbutyl azodicarboxylate (100 mmol) was added. The mixture was stirred at 50° C. under N$_2$ until no further conversion was observed. The toluene was evaporated under reduced pressure and the residue was purified via flash chromatography using EtOAc and MeOH as eluents

MS (M+H)$^+$=333.0.

Step B: 1-[2-(4-Bromo-2-chloro-3-ethyl-phenoxy)ethyl]-4-methyl-piperazine 2.0 g (6 mmol) 1-[2-(4-bromo-2-chloro-phenoxy)ethyl]-4-methyl-piperazine was dissolved in 50 mL dry THF under N$_2$ and was cooled to −78° C. with dry ice-acetone. 6 mL LDA (12 mmol in 2 M THF) was added and the mixture was stirred for 3 hour, then 982 mg (6.3 mmol) iodoethane was added and the mixture was allowed to warm up to room temperature. It was quenched with saturated NH$_4$Cl solution, extracted with EtOAc, dried over Na$_2$SO$_4$, filtered and concentrated under reduced pressure.

MS (M+H)$^+$=360.8, 362.8.

Step C: 1-[2-[2-Chloro-3-ethyl-4-(4,4,5,5-tetramethyl-1,3,2-dioxaborolan-2-yl)phenoxy] ethyl]-4-methyl-piperazine 2099 mg (5.8 mmol) 1-[2-(4-bromo-2-chloro-3-ethyl-phenoxy)ethyl]-4-methyl-piperazine was dissolved in 30 mL dry THF under N$_2$ and was cooled to −78° C. with dry ice-acetone and 4.645 mL BuLi (11.61 mmol in 2.5 M THF) was added dropwise. It was stirred for 5 h, then 2.6 mL 2-isopropoxy-4,4,5,5-tetramethyl-1,3,2-dioxaborolane (12.77 mmol) was added and the mixture was stirred for 30 minutes. Then it was concentrated under reduced pressure and purified via flash chromatography using EtOAc and MeOH as eluents to obtain Preparation 5u.

MS: (M+H)$^+$=409.2

Preparation 5v: 1-[2-[3-Bromo-2-chloro-4-(4,4,5,5-tetramethyl-1,3,2-dioxaborolan-2-yl)phenoxy]ethyl]-4-methyl-piperazine Step A: (2-Chloro-4-iodo-phenoxy)-triisopropyl-silane 10.178 g 2-chloro-4-iodophenol (40.0 mmol), 11.06 g (80 mmol) K$_2$CO$_3$ and 10.17 mL TIPSCl (48.0 mmol) were dissolved in 100 mL ACN. The mixture was stirred at room temperature for 1 h. Then it was concentrated under reduced pressure and purified via flash chromatography using heptane as eluent to obtain (2-chloro-4-iodo-phenoxy)-triisopropyl-silane.

MS (EI, 70 eV) m/z (% relative intensity, [ion]): 63 (6.5), 93 (8), 155 (9), 170 (10), 281 (7), 297 (7.5), 311 (10), 339 (17), 367 (100), 368 (20), 369 (40), 370 (6.5), 410 (1.5, [M$^+$]).

Step B: (3-Bromo-2-chloro-4-iodo-phenoxy)-triisopropyl-silane 820 mg (2-chloro-4-iodo-phenoxy)-triisopropyl-silane (2 mmol) was dissolved in 10 mL dry THF under N$_2$ and was cooled to −78° C. with dry ice-acetone. 1.15 mL LDA (2.3 mmol in 2 M THF) was added and the mixture was stirred for 1 hour, then 814 mg (2.5 mmol) 1,2-dibromotetrachloroethane was added and the mixture was allowed to warm up to room temperature. It was quenched with saturated NH$_4$Cl solution, extracted with EtOAc, dried over Na$_2$SO$_4$, filtered and concentrated under reduced pressure. The crude product was purified via flash chromatography using heptane as eluent to obtain (3-bromo-2-chloro-4-iodo-phenoxy)-triisopropyl-silane.

MS (EI, 70 eV) m/z (% relative intensity, [ion]): 63 (21), 79 (20), 93 (48), 195 (18), 248 (15), 250 (19), 445 (75), 447 (100), 448 (18), 449 (26), 488 (0.4, [M$^+$]).

Step C: [3-Bromo-2-chloro-4-(4,4,5,5-tetramethyl-1,3,2-dioxaborolan-2-yl)phenoxy]-triisopropyl-silane 900 mg (3-bromo-2-chloro-4-iodo-phenoxy)-triisopropyl-silane (1.84 mmol) was dissolved in 10 mL dry THF under N$_2$ and 1.01 mL EtMgCl (2.02 mmol in 2 M THF) was added dropwise at room temperature. It was stirred for 10 minutes, then 0.47 mL 2-isopropoxy-4,4,5,5-tetramethyl-1,3,2-dioxaborolane (2.3 mmol) was added and the mixture was stirred for 10 minutes. Then it was concentrated under reduced pressure and purified via flash chromatography using heptane and EtOAc as eluents to obtain [3-bromo-2-chloro-4-(4,4,5,5-tetramethyl-1,3,2-dioxaborolan-2-yl)phenoxy]-triisopropyl-silane.

¹H-NMR (400 MHz, CDCl₃): 7.39 (d, 1H), 6.84 (d, 1H), 1.38 (s, 12H), 1.32 (m, 3H), 1.12 (d, 18H).

Step D: 3-Bromo-2-chloro-4-(4,4,5,5-tetramethyl-1,3,2-dioxaborolan-2-yl)phenol

The resulting intermediate was dissolved in 10 mL THF and 0.5 mL 1M tetrabutylammonium fluoride solution was added. The mixture was stirred at room temperature until no further conversion was observed. Volatiles were evaporated under reduced pressure. The residue was purified via flash chromatography using heptane and EtOAc as eluents to obtain 3-bromo-2-chloro-4-(4,4,5,5-tetramethyl-1,3,2-dioxaborolan-2-yl)phenol.

¹H-NMR (400 MHz, DMSO-d₆): 10.97 (s, 1H), 7.36 (d, 1H), 6.96 (d, 1H), 1.28 (s, 12H).

Step E: 1-[2-[3-Bromo-2-chloro-4-(4,4,5,5-tetramethyl-1,3,2-dioxaborolan-2-yl)phenoxy] ethyl]-4-methyl-piperazine 133 mg 3-bromo-2-chloro-4-(4,4,5,5-tetramethyl-1,3,2-dioxaborolan-2-yl)phenol (0.4 mmol) was dissolved in 5 mL toluene, 82 mg 2-(4-methylpiperazin-1-yl)ethanol (0.57 mmol) and 149 mg PPh₃ (0.57 mmol) were added, then 131 mg ditertbutyl azodicarboxylate (0.57 mmol) was added. The mixture was stirred at 50° C. under N₂ until no further conversion was observed. The toluene was evaporated under reduced pressure and the residue was purified via flash chromatography using EtOAc and MeOH as eluents to obtain 1-[2-[3-bromo-2-chloro-4-(4,4,5,5-tetramethyl-1,3,2-dioxaborolan-2-yl)phenoxy] ethyl]-4-methyl-piperazine (Preparation 5v).

MS: (M+H)⁺=459.2.

Preparation 5w: 1-[2-[2,3-Dichloro-4-(4,4,5,5-tetramethyl-1,3,2-dioxaborolan-2-yl)phenoxy]ethyl]-4-methyl-piperazine Step A: 1-[2-(4-Bromo-2,3-dichloro-phenoxy)ethyl]-4-methyl-piperazine 2.0 g (6 mmol) 1-[2-(4-bromo-2-chloro-phenoxy)ethyl]-4-methyl-piperazine (Preparation 5, Step A) was dissolved in 50 mL dry THF under N₂ and was cooled to −78° C. with dry ice-acetone. 6 mL LDA (12 mmol in 2 M THF) was added and the mixture was stirred for 3 hour, then 3125 mg (13.2 mmol) hexachloroethane was added and the mixture was allowed to warm up to room temperature. It was quenched with saturated NH₄Cl solution, extracted with EtOAc, dried over Na₂SO₄, filtered and concentrated under reduced pressure to obtain 1-[2-(4-bromo-2,3-dichloro-phenoxy)ethyl]-4-methyl-piperazine.

Step B: 1-[2-[2,3-Dichloro-4-(4,4,5,5-tetramethyl-1,3,2-dioxaborolan-2-yl)phenoxy]ethyl]-4-methyl-piperazine 1630 mg (4.43 mmol) 1-[2-(4-bromo-2,3-dichloro-phenoxy)ethyl]-4-methyl-piperazine was dissolved in 20 mL dry THF under N₂ and was cooled to −78° C. with dry ice-acetone and 3.9 mL BuLi (2.5 M THF) was added dropwise. It was stirred for 5 h, then 2.1 mL 2-isopropoxy-4,4,5,5-tetramethyl-1,3,2-dioxaborolane (10.2 mmol) was added and the mixture was stirred for 30 minutes. Then it was concentrated under reduced pressure and purified via flash chromatography using EtOAc and MeOH as eluents to obtain Preparation 5w.

MS: (M+H)⁺=415.0, 417.0.

Preparation 5x: (3-chloro-2-cyano-4-triisopropylsilyloxy-phenyl)boronic acid

Step A: (4-bromo-2-chloro-3-iodo-phenoxy)-triisopropyl-silane 10.91 g (4-bromo-2-chloro-phenoxy)-triisopropyl-silane (Preparation 5c, Step A) (30 mmol) was dissolved in 100 mL dry THF, then cooled to −78° C. At this temperature 20 mL (1.8 M in THF, 1.2 eq) LDA was added over 5 min. Resulting mixture further was stirred for 90 min. Then 9.89 g (39 mmol, 1.3 eq) I₂ was added at −78° C. in one portion. After 20 min stirring it was quenched with saturated NH₄Cl solution, extracted with EtOAc, dried over Na₂SO₄, filtered and concentrated under reduced pressure. The crude product was purified via flash chromatography using heptane as eluent to obtain (4-bromo-2-chloro-3-iodo-phenoxy)-triisopropyl-silane.

¹H NMR (400 MHz, DMSO-d₆): 7.59 (d, 1H), 6.97 (d, 1H), 1.31 (m, 3H), 1.06 (d, 18H).

Step B: 6-bromo-2-chloro-3-triisopropylsilyloxy-benzonitrile 3.62 g (4-bromo-2-chloro-3-iodo-phenoxy)-triisopropyl-silane (7.40 mmol) was dissolved in 20 mL dry DMF and 0.795 g (8.88 mmol, 1.2 eq) CuCN was added, then stirred overnight at 120° C. Reaction mixture was diluted with brine, and then extracted with EtOAc. Organic phase was dried over MgSO4, filtered and evaporated under reduced pressure. The crude product was purified by flash chromatography using heptane and EtOAc as eluents to obtain 6-bromo-2-chloro-3-triisopropylsilyloxy-benzonitrile.

¹H NMR (400 MHz, CDCl₃): 7.41 (d, 1H), 6.99 (d, 1H), 1.31 (m, 3H), 1.13 (d, 18H).

Step C: (3-chloro-2-cyano-4-triisopropylsilyloxy-phenyl)boronic acid 1.50 g 6-bromo-2-chloro-3-triisopropylsilyloxy-benzonitrile (3.85 mmol) was dissolved in 10 mL dry THF under N₂ and was cooled to −78° C. with dry ice-acetone. 1.85 mL nBuLi (4.63 mmol, 2.5 M in hexanes) was added and the mixture was stirred for 10 minutes, then 0.853 mL triethyl borate (5.01 mmol, 1.3 eq) was added and the mixture was allowed to warm up to room temperature. It was quenched with saturated NH4Cl solution, extracted with EtOAc, dried over Na₂SO₄, filtered and concentrated under reduced pressure to obtain (3-chloro-2-cyano-4-triisopropylsilyloxy-phenyl)boronic acid.

¹H NMR (400 MHz, DMSO-d₆): 8.52 (bs, 2H), 7.59 (d, 1H), 7.27 (d, 1H), 1.34 (m, 3H), 1.07 (d, 18H).

Preparation 5y: [2-chloro-3-(methoxymethoxy)-4-(4,4,5,5-tetramethyl-1,3,2-dioxaborolan-2-yl)phenoxy]-triisopropyl-silane Step A: 2-chloro-3-triisopropylsilyloxy-phenol To a stirred solution of 10.0 g 2-chlorobenzene-1,3-diol (69.17 mmol) in 100 mL dry MeCN, 19.12 g potassium carbonate (138.35 mmol, 2 eq) and 16.15 mL TIPSCl (76.09 mmol. 1.1 eq) was added. Resulting mixture was stirred for 30 min. Potassium carbonate was removed by filtration, then the filtrate was concentrated under reduced pressure. This crude product was purified by flash chromatography using heptane and EtOAc as eluents to obtain 2-chloro-3-triisopropylsilyloxy-phenol as colorless oil.

¹H NMR (400 MHz, CDCl₃): 7.01 (t, 1H), 6.65 (dd, 1H), 6.52 (dd, 1H), 5.62 (bs, 1H), 1.33 (m, 3H), 1.14 (d, 18H).

Step B: [2-chloro-3-(methoxymethoxy)phenoxy]-triisopropyl-silane 4.70 g 2-chloro-3-triisopropylsilyloxy-phenol (15.62 mmol) was dissolved in 50 mL dry THF, and then it was cooled to 0° C. under argon atmosphere. Then 0.687 g NaH (17.18 mmol, 1.1 eq, 60% in mineral oil) was added slowly and stirred for 15 min at this temperature. After addition of 1.41 mL MOMCl (18.74 mmol, 1.2 eq) resulting mixture was allowed to warm up to room temperature and stirred until no further conversion was observed. From the reaction mixture the inorganics were removed by filtration. The filtrate was evaporated under reduced pressure to obtain [2-chloro-3-(methoxymethoxy)phenoxy]-triisopropyl-silane as light-yellow oil, which was used in the next step without further purification.

$^1$H NMR (400 MHz, CDCl$_3$): 7.03 (t, 1H), 6.79 (dd, 1H), 6.63 (dd, 1H), 5.24 (s, 2H), 3.53 (s, 3H), 1.33 (m, 3H), 1.14 (d, 18H).

Step C: [2-chloro-3-(methoxymethoxy)-4-(4,4,5,5-tetramethyl-1,3,2-dioxaborolan-2-yl)phenoxy]-triisopropyl-silane 5.39 g [2-chloro-3-(methoxymethoxy)phenoxy]-triisopropyl-silane (15.62 mmol) was dissolved in 50 mL dry THF, and then it was cooled to −78° C. under argon atmosphere. Then 7.50 mL butyl lithium (18.74 mmol, 1.2 eq, 2.5 M in hexan) was added. Resulting mixture was stirred for 90 min. To the ortho-lithiated intermediate 4.78 mL 2-isopropoxy-4,4,5,5-tetramethyl-1,3,2-dioxaborolane (23.43 mmol, 1.5 eq) was added. After 30 min stirring at −78° C. we have observed full conversion. It was quenched with saturated NH$_4$Cl solution, extracted with EtOAc, dried over Na$_2$SO$_4$, filtered and concentrated under reduced pressure to obtain [2-chloro-3-(methoxymethoxy)-4-(4,4,5,5-tetramethyl-1,3,2-dioxaborolan-2-yl)phenoxy]-triisopropyl-silane as yellow oil.

$^1$H NMR (400 MHz, CDCl$_3$): 7.52 (d, 1H), 6.71 (d, 1H), 5.15 (s, 2H), 3.67 (s, 3H), 1.35 (s, 12H), 1.33 (m, 3H), 1.14 (d, 18H).

Preparation 6a: Ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-(2-tetrahydropyran-2-yloxyphenyl)propanoate 186.6 g ethyl (2R)-2-[5-bromo-6-(4-fluorophenyl)thieno[2,3-d]pyrimidin-4-yl]oxy-3-(2-tetra-hydropyran-2-yloxyphenyl)propanoate (Preparation 4a) (310.3 mmol) and 99.99 g 2-chloro-3-methyl-4-(4,4,5,5-tetramethyl-1,3,2-dioxaborolan-2-yl)phenol (Preparation 5a) (372.3 mmol) were dissolved in 1.2 L THF, then 202.2 g Cs$_2$CO$_3$ (620.6 mmol) dissolved in 300 mL water was added. Then 11.0 g AtaPhos (15.51 mmol) was added, and the mixture was stirred under nitrogen at reflux temperature until no further conversion was observed. Most of the volatiles were evaporated under reduced pressure, then it was diluted with dichloromethane and brine. After shaking the pH of the aqueous phase was set to 8 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer pair eluting later was collected as Preparation 6a.

$^1$H NMR (500 MHz, DMSO-d$_6$, 1:1 mixture of diastereomers): 10.27 (br s, 1H), 8.60 (s, 1H), 7.30 (m, 2H), 7.22 (m, 2H), 7.16/7.14 (d, 1H), 7.12 (m, 1H), 7.00 (d, 1H), 6.96 (d, 1H), 6.74/6.73 (t, 1H), 6.34/6.36 (d, 1H), 5.55/5.52 (m, 1H), 5.54/5.41 (dd, 1H), 4.06 (q, 2H), 3.68/3.54 (m, 2H), 3.10/3.07 (dd, 1H), 2.44 (dd, 1H), 1.98/1.90 (br s, 1H), 1.85/1.83 (s, 3H), 1.79 (br s, 2H), 1.64 (br s, 1H), 1.59 (br s, 1H), 1.54 (br s, 1H), 1.09/1.08 (t, 3H).

HRMS: (M+H)=663.1728 and 663.1717.

Preparation 6b: Ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[2-(pyrazin-2-ylmethoxy)phenyl] propanoate 2.52 g ethyl (2R)-2-[5-bromo-6-(4-fluorophenyl)thieno[2,3-d]pyrimidin-4-yl]oxy-3-[2-(pyrazin-2-ylmethoxy)phenyl]propanoate (Preparation 4b) (4.1 mmol) and 2.2 g 2-chloro-3-methyl-4-(4,4,5,5-tetramethyl-1,3,2-dioxaborolan-2-yl)phenol (Preparation 5a) (8.2 mmol) were dissolved in 30 mL 1,4-dioxane, then 2.67 g Cs$_2$CO$_3$ (8.2 mmol) dissolved in 15 mL water was added. Then 284 mg AtaPhos (0.41 mmol) was added, and the mixture was stirred under nitrogen at 100° C. until no further conversion was observed. Most of the volatiles were evaporated under reduced pressure, then it was diluted with dichloromethane and brine. After shaking the pH of the aqueous phase was set to 7 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer eluting later was collected as Preparation 6b.

$^1$H NMR (500 MHz, DMSO-d$_6$): 10.27 (s, 1H), 8.92 (d, 1H), 8.76-8.61 (m, 2H), 8.58 (s, 1H), 7.30 (m, 2H), 7.22 (m, 2H), 7.19 (m, 1H), 7.16 (d, 1H), 7.07 (dm, 1H), 6.97 (d, 1H), 6.76 (m, 1H), 6.30 (dm, 1H), 5.46 (dd, 1H), 5.30 (d, 1H), 5.25 (d, 1H), 4.07 (m, 1H), 4.04 (m, 1H), 3.16 (dd, 1H), 2.49 (dd, 1H), 1.80 (s, 3H), 1.08 (t, 3H).

HRMS: (M+H)=671.1533.

Preparation 6c: Ethyl (2R)-2-[(5S$_a$)-5-(3-chloro-4-hydroxy-2-methyl-phenyl)-6-(5-fluoro-2-furyl)thieno[2,3-d]pyrimidin-4-yl]oxy-3-(2-tetrahydropyran-2-yloxyphenyl)propanoate and Preparation 6q: Ethyl (2R)-2-[(5R$_a$)-5-(3-chloro-4-hydroxy-2-methyl-phenyl)-6-(5-fluoro-2-furyl)thieno[2,3-d]pyrimidin-4-yl]oxy-3-(2-tetrahydropyran-2-yloxyphenyl)propanoate 174.0 g ethyl (2R)-2-[5-bromo-6-(5-fluoro-2-furyl)thieno[2,3-d]pyrimidin-4-yl]oxy-3-(2-tetrahydropyran-2-yloxyphenyl)propanoate (Preparation 4c) (294.2 mmol) and 94.81 g 2-chloro-3-methyl-4-(4,4,5,5-tetramethyl-1,3,2-dioxaborolan-2-yl)phenol (Preparation 5a) (353.0 mmol) were dissolved in 1.18 L THF, then 191.7 g Cs$_2$CO$_3$ (588.4 mmol) dissolved in 300 mL water was added. Then 10.41 g AtaPhos (14.71 mmol) was added, and the mixture was stirred under nitrogen at 60° C. until no further conversion was observed. Most of the volatiles were evaporated under reduced pressure, then it was diluted with dichloromethane and brine. After shaking the pH of the aqueous phase was set to 8 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents.

The diastereoisomer pair eluting earlier was collected as Preparation 6q.

$^1$H NMR (500 MHz, DMSO-d$_6$, 1:1 mixture of diastereomers): 10.44 (s, 1H), 8.58 (s, 1H), 7.11 (t, 1H), 7.02/7.00 (d, 1H), 6.98 (d, 1H), 6.95/6.94 (d, 1H), 6.73 (t, 1H), 6.21/6.19 (d, 1H), 5.87 (dd, 1H), 5.71 (t, 1H), 5.55/5.49 (t, 1H), 5.47/5.34 (dd, 1H), 4.10 (q, 1H), 4.08 (q, 1H), 3.66 (m, 1H), 3.52 (m, 1H), 3.23 (dd, 1H), 2.33 (dd, 1H), 2.22/2.21 (t, 3H), 2.03-1.49 (m, 6H), 1.11/1.10 (t, 3H).

HRMS: (M+H)=653.1518

The diastereoisomer pair eluting later was collected as Preparation 6c.

$^1$H NMR (500 MHz, DMSO-d$_6$, 1:1 mixture of diastereomers): 10.40 (s, 1H), 8.58 (s, 1H), 7.15 (t, 1H), 7.10 (d, 1H), 7.04 (d, 1H), 7.01 (d, 1H), 6.81/6.80 (t, 1H), 6.38/6.36 (d, 1H), 5.89 (dd, 1H), 5.69 (t, 1H), 5.56/5.52 (t, 1H), 5.56/5.43 (dd, 1H), 4.05 (q, 2H), 3.68 (m, 1H), 3.54 (m, 1H), 3.13 (dd, 1H), 2.36 (dd, 1H), 1.95/1.94 (s, 3H), 1.82-1.51 (m, 6H), 1.09 (t, 3H).

HRMS: (M+H)=653.1485 and 653.1492.

Preparation 6d: Ethyl (2R)-2-[(5S$_a$)-5-(3-chloro-4-hydroxy-2-methyl-phenyl)-6-(2-furyl)thieno[2,3-d]pyrimidin-4-yl]oxy-3-(2-tetrahydropyran-2-yloxy-phenyl)propanoate 36.3 g ethyl (2R)-2-[5-bromo-6-(2-furyl)thieno[2,3-d]pyrimidin-4-yl]oxy-3-(2-tetrahydropyran-2-yloxyphenyl)propanoate (Preparation 4d) (63.3 mmol) and 18.7 g 2-chloro-3-methyl-4-(4,4,5,5-tetramethyl-1,3,2-dioxaborolan-2-yl)phenol (Preparation 5a) (69.6 mmol) were dissolved in 400 mL THF, then 32.6 g Cs$_2$CO$_3$ (100.0 mmol) dissolved in 100 mL water was added. Then 1.8 g AtaPhos (2.5 mmol) was added, and the mixture was stirred under nitrogen at reflux temperature until no further conversion was observed. Then it was diluted with dichloromethane and brine. After shaking the pH of the aqueous phase was set to 8 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer pair eluting later was collected as Preparation 6d.

$^1$H NMR (400 MHz, DMSO-d$_6$, 1:1 mixture of diastereomers): 10.40 (s, 8.58/8.57 (s, 1H), 7.80/7.79 (d, 1H), 7.15 (tm, 1H), 7.10 (d, 1H), 7.05 (d, 1H), 7.02 (d, 1H), 6.81 (m, 1H), 6.54 (dd, 1H), 6.39 (dm, 1H), 5.69 (dm, 1H), 5.57 (m, 1H), 5.55/5.43 (ddd, 1H), 4.06 (m, 2H), 3.68 (m, 1H), 3.54 (m, 1H), 3.33 (s, 3H), 3.13 (td 1H), 2.36 (m, 1H), 1.94/1.93 (s, 3H), 1.80 (m, 2H), 1.71-1.48 (m, 3H), 1.09 (td, 3H).

MS: (M+H)$^+$=635.0.

Preparation 6e: Ethyl (2R)-2-[(5S$_a$)-5-(3-chloro-4-hydroxy-2-methyl-phenyl)-6-(2-furyl)thieno[2,3-d]pyrimidin-4-yl]oxy-3-(2-methoxyphenyl)propanoate 2.013 g ethyl (2R)-2-[5-bromo-6-(2-furyl)thieno[2,3-d]pyrimidin-4-yl]oxy-3-(2-methoxyphenyl)propanoate (Preparation 4e) (4.0 mmol) and 1.396 g 2-chloro-3-methyl-4-(4,4,5,5-tetramethyl-1,3,2-dioxaborolan-2-yl)phenol (Preparation 5a) (5.2 mmol) were dissolved in 16 mL 1,4-dioxane, then 2.607 g Cs$_2$CO$_3$ (8.0 mmol) dissolved in 4 mL water was added. Then 57 mg AtaPhos (0.08 mmol) was added, rinsed with nitrogen, and heated at 110° C. via microwave irradiation until no further conversion was observed. Then it was diluted with dichloromethane and brine. After shaking the pH of the aqueous phase was set to 5 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer eluting later was collected as Preparation 6e.

$^1$H NMR (500 MHz, DMSO-d$_6$): 10.40 (br s, 1H), 8.57 (s, 1H), 7.79 (d, 1H), 7.18 (td, 1H), 7.08 (d, 1H), 7.04 (d, 1H), 6.91 (d, 1H), 6.77 (t, 1H), 6.53 (dd, 1H), 6.36 (dd, 1H), 5.67 (d, 1H), 5.40 (dd, 1H), 4.04 (m, 2H), 3.77 (s, 3H), 3.00 (dd, 1H), 2.42 (dd, 1H), 1.92 (s, 3H), 1.07 (t, 3H).

HRMS: (M+H)=565.1187.

Preparation 6f: Ethyl (2R)-2-[6-(5-chloro-2-furyl)-(5S$_a$)-5-(3-chloro-4-hydroxy-2-methyl-phenyl)-thieno[2,3-d]pyrimidin-4-yl]oxy-3-[2-[(4-methoxyphenyl)methoxy] phenyl]propanoate 11.11 g ethyl (2R)-2-[5-bromo-6-(5-chloro-2-furyl)thieno[2,3-d]pyrimidin-4-yl]oxy-3-[2-[(4-methoxyphenyl)methoxy]phenyl]propanoate (Preparation 4f) (17.28 mmol) and 7.0 g 2-chloro-3-methyl-4-(4,4,5,5-tetramethyl-1,3,2-dioxaborolan-2-yl)phenol (Preparation 5a) (26.0 mmol) were dissolved in 100 mL 1,4-dioxane, then 11.4 g Cs$_2$CO$_3$ (35.0 mmol) dissolved in 50 mL water was added. Then 1.22 g AtaPhos (1.73 mmol) was added, and the mixture was stirred under nitrogen at reflux temperature until no further conversion was observed. Then it was diluted with dichloromethane and brine. After shaking the pH of the aqueous phase was set to 6 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer eluting later was collected as Preparation 6f.

MS: (M+H)=705.0.

Preparation 6g: Ethyl (2R)-2-[6-(5-chloro-2-furyl)-(5S$_a$)-5-(3-chloro-4-hydroxy-2-methyl-phenyl)-thieno[2,3-d]pyrimidin-4-yl]oxy-3-[2-[[(2S)-tetrahydrofuran-2-yl] methoxy]phenyl]propanoate 547 mg ethyl (2R)-2-[5-bromo-6-(5-chloro-2-furyl)thieno[2,3-d]pyrimidin-4-yl]oxy-3-[2-[[(2S)-tetrahydrofuran-2-yl]methoxy]phenyl]propanoate (Preparation 4g) (0.752 mmol) and 403 mg 2-chloro-3-methyl-4-(4,4,5,5-tetramethyl-1,3,2-dioxaborolan-2-yl)phenol (Preparation 5a) (1.5 mmol) were dissolved in the mixture of 5 mL THF and 5 mL 1,4-dioxane, then 652 mg Cs$_2$CO$_3$ (2.0 mmol) dissolved in 5 mL water was added. Then 53 g AtaPhos (0.075 mmol) was added, rinsed with nitrogen, heated at 100° C. via microwave irradiation until no further conversion was observed. Then it was diluted with dichloromethane and brine. After shaking the pH of the aqueous phase was set to 6 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer eluting later was collected as Preparation 6g.

MS: (M+H)=669.0.

Preparation 6h: Ethyl (2R)-2-[(5S$_a$)-5-(3-chloro-4-hydroxy-2-methyl-phenyl)-6-(4-fluoro-3-methoxy-phenyl)thieno[2,3-d]pyrimidin-4-yl]oxy-3-(2-tetrahydropyran-2-yloxyphenyl)propanoate 22.0 g ethyl (2R)-2-[5-bromo-6-(4-fluoro-3-methoxy-phenyl)thieno[2,3-d]pyrimidin-4-yl]oxy-3-(2-tetrahydropyran-2-yloxyphenyl)propanoate (Preparation 4h) (34.84 mmol) and 11.23 g 2-chloro-3-methyl-4-(4,4,5,5-tetramethyl-1,3,2-dioxaborolan-2-yl)phenol (Preparation 5a) (41.80 mmol) were dissolved in 200 mL THF, then 34.05 g Cs$_2$CO$_3$ (104.5 mmol) dissolved in 200 mL water was added. Then 2.46 g AtaPhos (3.48 mmol) was added, and the mixture was stirred under nitrogen at 60° C. until no further conversion was observed. Then it was diluted with dichloromethane and brine. After shaking the pH of the aqueous phase was set to 7 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer pair eluting later was collected as Preparation 6h.

$^1$H NMR (400 MHz, DMSO-d$_6$, 1:1 mixture of diastereomers): 10.30 (s, 1H), 8.61/8.60 (s, 1H), 7.26/7.23 (d, 1H), 7.19/7.17 (d, 1H), 7.13 (m, 1H), 7.01 (d, 1H), 6.99 (d, 1H), 6.94 (m, 1H), 6.87 (dd, 1H), 6.74 (m, 1H), 6.30 (m, 1H), 5.56/5.53 (m, 1H), 5.53/5.42 (m, 1H), 4.07 (m, 2H), 3.68/3.56 (m, 2H), 3.59/3.58 (s, 3H), 3.15 (m, 1H), 2.42 (dd, 1H), 2.03-1.89 (br s, 1H), 1.86/1.84 (s, 3H), 1.79 (br s, 2H), 1.71-1.48 (br s, 3H), 1.10 (td, 3H).

MS: (M+H)=693.0.

Preparation 6i: Methyl (2R)-2-[(5S$_a$)-5-(3-chloro-4-hydroxy-2-methyl-phenyl)-6-ethyl-thieno[2,3-d]pyrimidin-4-yl]oxy-3-phenyl-propanoate and

Preparation 6n: Methyl (2R)-2-[(5R$_a$)-(3-chloro-4-hydroxy-2-methyl-phenyl)-6-ethyl-thieno[2,3-d]pyrimidin-4-yl]oxy-3-phenyl-propanoate 13.17 g methyl (2R)-2-(6-ethyl-5-iodo-thieno[2,3-d]pyrimidin-4-yl)oxy-3-phenyl-propanoate (Preparation 4o) (28.12 mmol) and 10.57 g 2-chloro-3-methyl-4-(4,4,5,5-tetramethyl-1,3,2-dioxaborolan-2-yl)phenol (Preparation 5a) (39.37 mmol) were dissolved in 100 mL 2-Me-THF, then 40 mL TBAOH (1 M aqueous solution) was added. Then 893 mg AtaPhos (1.406 mmol) was added, and the mixture was stirred under nitrogen at reflux temperature until no further conversion was observed. It was diluted with EtOAc and 1 mL HCl (2 M aqueous solution), then it was washed with water and brine. The organic layer was dried over Na$_2$SO$_4$, filtered and concentrated under reduced pressure. The diastereoisomers were separated via flash chromatography using heptane and ethyl acetate as eluents. The diastereoisomer eluting earlier was collected as Preparation 6n.

$^1$H NMR (500 MHz, DMSO-d$_6$): 10.22 (br, s 1H), 8.53 (s, 1H), 7.16 (m, 3H), 7.07 (d, 1H), 7.00 (d, 1H), 6.66 (m, 2H), 5.45 (dd, 1H), 3.54 (s, 3H), 2.93 (dd, 1H), 2.66 (dd, 1H), 2.62 (m, 2H), 1.99 (s, 3H), 1.15 (t, 3H).

HRMS: (M+H)=483.1137.

The diastereoisomer eluting later was collected as Preparation 6i.

$^1$H NMR (500 MHz, DMSO-d$_6$): 10.26 (br s, 1H), 8.52 (s, 1H), 7.14 (m, 3H), 6.97 (d, 1H), 6.94 (d, 1H), 6.65 (m, 2H), 5.30 (dd, 1H), 3.64 (s, 3H), 2.99 (dd, 1H), 2.66 (m, 2H), 2.54 (dd, 1H), 2.17 (s, 3H), 1.15 (t, 3H).

HRMS: (M+H)=483.1126.

Preparation 6j: Methyl (2R)-2-[6-ethyl-(5S$_a$)-5-(4-hydroxy-2-methyl-phenyl)thieno[2,3-d]pyrimidin-4-yl]oxy-3-phenyl-propanoate and

Preparation 6o: Methyl (2R)-2-[6-ethyl-(5R$_a$)-5-(4-hydroxy-2-methyl-phenyl)thieno[2,3-d]pyrimidin-4-yl]oxy-3-phenyl-propanoate 2.25 g methyl (2R)-2-(6-ethyl-5-iodo-thieno[2,3-d]pyrimidin-4-yl)oxy-3-phenyl-propanoate (Preparation 4i) (2.67 mmol) and 1.76 g 3-methyl-4-(4,4,5,5-tetramethyl-1,3,2-dioxaborolan-2-yl)phenol (8.0 mmol) were dissolved in 15 mL 2-Me-THF, then 2.75 g Ag$_2$CO$_3$ (10.0 mmol) was added. Then 309 mg Pd(PPh$_3$)$_4$ (0.267 mmol) was added, rinsed with nitrogen, heated at 100° C. via microwave irradiation until no further conversion was observed. It was diluted with ethyl acetate and brine. After shaking the pH of the aqueous phase was set to 5 with 2 M HCl. After phase separation the organic layer was dried over Na$_2$SO$_4$, filtered and concentrated under reduced pressure. The diastereoisomers were separated via flash chromatography using heptane and ethyl acetate as eluents. The diastereoisomer eluting earlier was collected as Preparation 6j.

$^1$H NMR (500 MHz, DMSO-d$_6$): 9.44 (s, 1H), 8.52 (s, 1H), 7.16 (m, 3H), 7.05 (d, 1H), 6.78 (d, 1H), 6.76 (dd, 1H), 6.70 (m, 2H), 5.47 (dd, 1H), 3.54 (s, 3H), 2.95 (dd, 1H), 2.68 (dd, 1H), 2.62 (m, 2H), 1.84 (s, 3H), 1.15 (t, 3H).

HRMS: (M+H)=449.1509.

The diastereoisomer eluting later was collected as Preparation 6o.

$^1$H NMR (500 MHz, DMSO-d$_6$): 9.64 (s, 1H), 8.50 (s, 1H), 7.14 (m, 3H), 6.94 (d, 1H), 6.82 (d, 1H), 6.77 (dd, 1H), 6.66 (m, 2H), 5.28 (dd, 1H), 3.64 (s, 3H), 2.97 (dd, 1H), 2.64 (m, 2H), 2.58 (dd, 1H), 2.08 (s, 3H), 1.14 (st, 3H).

HRMS: (M+H)=449.1540.

Preparation 6k: Ethyl (2R)-2-[(5S$_a$)-5-(3-chloro-4-hydroxy-2-methyl-phenyl)-6-ethyl-thieno[2,3-d]pyrimidin-4-yl]oxy-3-(2-tetrahydropyran-2-yloxy-phenyl)propanoate 5.0 g ethyl (2R)-2-(6-ethyl-5-iodo-thieno[2,3-d]pyrimidin-4-yl)oxy-3-(2-tetrahydropyran-2-yloxyphenyl)propanoate (Preparation 4j) (9.33 mmol) and 3.22 g 2-chloro-3-methyl-4-(4,4,5,5-tetramethyl-1,3,2-dioxaborolan-2-yl)phenol (Preparation 5a) (12.0 mmol) were dissolved in 60 mL THF, then 6.52 g Cs$_2$CO$_3$ (20.0 mmol) dissolved in 20 mL water was added. Then 330 mg AtaPhos (0.466 mmol) was added, and the mixture was stirred under nitrogen at 65° C. until no further conversion was observed. Then it was diluted with dichloromethane and brine. After shaking the pH of the aqueous phase was set to 8 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer pair eluting later was collected as Preparation 6k.

$^1$H NMR (400 MHz, DMSO-d$_6$, 1:1 mixture of diastereomers): 10.24 (br s, 1H), 8.52/8.51 (s, 1H), 7.13 (m, 1H), 7.05 (d, 1H), 7.01 (dm, 1H), 6.98 (d, 1H), 6.79 (m, 1H), 6.35 (m, 1H), 5.55/5.51 (m, 1H), 5.50 (dd, 1H), 5.37 (dd, 1H), 4.03 (m, 2H), 3.67 (m, 1H), 3.53 (m, 1H), 3.06 (dd, 1H), 2.65 (dd, 1H), 2.58 (m, 1H), 2.41 (m, 1H), 1.98/1.97 (s, 3H), 1.79 (m, 2H), 1.68-1.47 (m, 3H), 1.15 (t, 3H), 1.06 (td, 3H).

MS: (M+H)=597.2.

Preparation 6l: Ethyl (2R)-2-[(5S$_a$)-5-(3-chloro-4-hydroxy-2-methyl-phenyl)-6-prop-1-ynyl-thieno[2, 3-d]pyrimidin-4-yl]oxy-3-(2-methoxyphenyl)propanoate 472 mg ethyl (2R)-2-(5-iodo-6-prop-1-ynyl-thieno[2,3-d]pyrimidin-4-yl)oxy-3-(2-methoxyphenyl)propanoate (Preparation 4k) (0.90 mmol) and 403 mg 2-chloro-3-methyl-4-(4,4,5,5-tetramethyl-1,3,2-dioxaborolan-2-yl)phenol (Preparation 5a) (1.5 mmol) were dissolved in 10 mL 1,4-dioxane, then 652 mg Cs$_2$CO$_3$ (2.0 mmol) dissolved in 2 mL water was added. Then 64 mg AtaPhos (0.09 mmol) was added, rinsed with nitrogen, heated at 110° C. via microwave irradiation until no further conversion was observed. Then it was diluted with dichloromethane and brine. After shaking the pH of the aqueous phase was set to 5 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer eluting later was collected as Preparation 6l.

$^1$H NMR (500 MHz, DMSO-d$_6$): 10.34 (br s, 1H), 8.61 (s, 1H), 7.16 (m, 1H), 7.09 (d, 1H), 6.98 (d, 1H), 6.89 (dm, 1H), 6.69 (m, 1H), 6.19 (dm, 1H), 5.34 (dd, 1H), 4.08 (m, 1H), 4.03 (m, 1H), 3.75 (s, 3H), 3.01 (dd, 1H), 2.49 (dd, 1H), 2.08 (s, 3H), 2.03 (s, 3H), 1.07 (t, 3H).

HRMS: (M+H)=537.1247.

Preparation 6m: Ethyl (2R)-2-[(5S$_a$)-5-(3-chloro-4-hydroxy-2-methyl-phenyl)-6-prop-1-ynyl-thieno[2, 3-d]pyrimidin-4-yl]oxy-3-(2-tetrahydropyran-2-yloxyphenyl)propanoate 10.59 g ethyl (2R)-2-(5-iodo-6-prop-1-ynyl-thieno[2,3-d]pyrimidin-4-yl)oxy-3-(2-tetrahydropyran-2-yloxyphenyl)propanoate (Preparation 4l) (17.87 mmol) and 5.76 g 2-chloro-3-methyl-4-(4,4,5,5-tetramethyl-1,3,2-dioxaborolan-2-yl)phenol (Preparation 5a) (21.45 mmol) were dissolved in 100 mL THF, then 11.64 g Cs$_2$CO$_3$ (35.74 mmol) dissolved in 30 mL water was added. Then 1.26 g AtaPhos (1.79 mmol) was added, and the mixture was stirred under nitrogen at 60 C until no further conversion was observed. Then it was diluted with dichloromethane and brine. After shaking the pH of the aqueous phase was set to 8 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer pair eluting later was collected as Preparation 6m.

MS: (M+H)=607.0.

Preparation 6p: Ethyl (2R)-2-[(5S$_a$)-5-(3-chloro-4-hydroxy-2-methyl-phenyl)-6-(3,4-difluorophenyl)thieno[2,3-d]pyrimidin-4-yl]oxy-3-(2-tetrahydropyran-2-yloxyphenyl)propanoate 9.18 g ethyl (2R)-2-[(5S$_a$)-5-bromo-6-(3,4-difluorophenyl)thieno[2,3-d]pyrimidin-4-yl]oxy-3-(2-tetrahydropyran-2-yloxyphenyl)propanoate (Preparation 4o) (14.82 mmol) and 5.17 g 2-chloro-3-methyl-4-(4,4,5,5-tetramethyl-1,3,2-dioxaborolan-2-yl)phenol (Preparation 5a) (19.26 mmol) were dissolved in 50 mL THF, then 6.52 g Cs$_2$CO$_3$ (20 mmol) dissolved in 20 mL water was added. Then 525 mg AtaPhos (0.74 mmol) was added, and the mixture was stirred under nitrogen at reflux temperature until no further conversion was observed. Most of the volatiles were evaporated under reduced pressure, then it was diluted with dichloromethane and brine. After shaking the pH of the aqueous phase was set to 8 with 2 M HCl. After phase separation the aqueous phase was extracted with dichloromethane. The organic layers were combined and dried over Na$_2$SO$_4$, filtered and concentrated under reduced pressure. The diastereoisomers were separated via flash chromatography using heptane and ethyl acetate as eluents. The diastereoisomer pair eluting later was collected as Preparation 6p.

$^1$H NMR (500 MHz, DMSO-d$_6$, 1:1 mixture of diastereomers): 10.33 (br s, 1H), 8.63/8.62 (s, 1H), 7.47 (m, 1H), 7.30 (m, 1H), 7.19/7.17 (d, 1H), 7.13 (m, 2H), 7.00 (m, 2H), 6.76/6.76 (dd, 1H), 6.34/6.29 (d, 1H), 5.56/5.53 (m, 1H), 5.54/5.42 (dd, 1H), 4.07 (m, 2H), 3.68/3.54 (m, 2H), 3.11/3.08 (dd, 1H), 2.44 (dd, 1H), 2.05-1.89 (m, 1H), 1.86/1.84 (s, 3H), 1.80 (m, 2H), 1.72-1.45 (m, 3H), 1.09/1.08 (t, 3H).

MS: (M+H)=681.0

Preparation 6r: Ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[2-[[(2R)-tetrahydrofuran-2-yl]methoxy]phenyl]propanoate 7.22 g ethyl (2R)-2-[5-bromo-6-(4-fluorophenyl)thieno[2,3-d]pyrimidin-4-yl]oxy-3-[2-[[(2R)-tetrahydrofuran-2-yl]methoxy]phenyl]propanoate (Preparation 4p) (12.00 mmol) and 4.83 g 2-chloro-3-methyl-4-(4,4,5,5-tetramethyl-1,3,2-dioxaborolan-2-yl)phenol (Preparation 5a) (18.00 mmol) were dissolved in 60 mL dioxane, then 7.82 g Cs$_2$CO$_3$ (24.00 mmol) dissolved in 30 mL water was added. Then 708 mg AtaPhos (1.00 mmol) was added, and the mixture was stirred under nitrogen at reflux temperature until no further conversion was observed. Most of the volatiles were evaporated under reduced pressure, then it was diluted with dichloromethane and brine. After shaking the pH of the aqueous phase was set to 6 with 2 M HCl. After phase separation the aqueous phase was extracted with dichloromethane. The combined organic layers were dried over Na$_2$SO$_4$, filtered and concentrated under reduced pressure. The diastereoisomers were separated via flash chromatography using heptane and ethyl acetate as eluents. The diastereoisomer eluting later was collected as Preparation 6r.

$^1$H NMR (500 MHz, DMSO-d$_6$): 10.25 (br s, 1H), 8.60 (s, 1H), 7.30 (m, 2H), 7.21 (m, 2H), 7.14 (t, 1H), 7.12 (d, 1H), 6.95 (d, 1H), 6.90 (d, 1H), 6.70 (t, 1H), 6.32 (d, 1H), 5.43 (dd, 1H), 4.15 (m, 1H), 4.03 (m, 2H), 3.97 (dd, 1H), 3.93 (dd, 1H), 3.74 (m, 1H), 3.66 (m, 1H), 2.97 (dd, 1H), 2.48

(dd, 1H), 1.99 (m, 1H), 1.88 (m, 1H), 1.85 (s, 3H), 1.82 (m, 1H), 1.81 (m, 1H), 1.05 (t, 3H).

Preparation 6s: Ethyl (2R)-2-[5-(3-chloro-4-hydroxy-2-methyl-phenyl)-6-(4-fluorophenyl)thieno[2,3-d]pyrimidin-4-yl]oxy-3-[2-(2,2,2-trifluoroethoxy)phenyl] propanoate (mixture of diastereoisomers)

9.17 g ethyl (2R)-2-[5-bromo-6-(4-fluorophenyl)thieno[2,3-d]pyrimidin-4-yl]oxy-3-[2-(2,2,2-trifluoroethoxy)phenyl]propanoate (Preparation 4s) (15.35 mmol) and 4.95 g 2-chloro-3-methyl-4-(4,4,5,5-tetramethyl-1,3,2-dioxaborolan-2-yl)phenol (Preparation 5a) (18.42 mmol) were dissolved in 50 mL THF, then 15.00 g $Cs_2CO_3$ (46.05 mmol) dissolved in 50 mL water was added. Then 1.09 g AtaPhos (1.54 mmol) was added, and the mixture was stirred under nitrogen at 60° C. until no further conversion was observed. Then the most of the volatiles were evaporated under reduced pressure and it was diluted with brine. The pH was set to 6 with 2 M HCl, and the mixture was extracted with dichloromethane. The combined organic layers were dried over $Na_2SO_4$, filtered and concentrated under reduced pressure and purified via flash chromatography using heptane and ethyl acetate as eluents to Preparation 6s as a mixture of diastereoisomers.
$^1$H NMR (400 MHz, DMSO-$d_6$): 10.26 (br s, 1H), 8.60 (s, 1H), 7.32-7.26 (m, 2H), 7.24-7.17 (m, 3H), 7.15-7.11 (m, 1H), 7.03-6.94 (m, 2H), 6.82-6.68 (m, 1H), 6.33/6.19 (dd, 1H), 5.36/5.29 (dd, 1H), 4.83-4.64 (m, 2H), 4.09/4.04 (q, 2H), 3.15/3.01 (dd, 1H), 2.50/2.37 (dd, 1H), 2.32/1.85 (s, 3H), 1.11/1.07 (t, 3H).

Preparation 6t: Ethyl (2R)-2-[(5S$_a$)-5-(3-chloro-4-hydroxy-2-methyl-phenyl)-6-(2,3-difluorophenyl)thieno[2,3-d]pyrimidin-4-yl]oxy-3-(2-tetrahydropyran-2-yloxyphenyl)propanoate 9.18 g ethyl (2R)-2-[(5S$_a$)-5-bromo-6-(2,3-difluorophenyl)thieno[2,3-d]pyrimidin-4-yl]oxy-3-(2-tetrahydropyran-2-yloxyphenyl)propanoate (Preparation 4t) (14.82 mmol) and 5.17 g 2-chloro-3-methyl-4-(4,4,5,5-tetramethyl-1,3,2-dioxaborolan-2-yl)phenol (Preparation 5a) (19.26 mmol) were dissolved in 50 mL THF, then 6.52 g $Cs_2CO_3$ (20 mmol) dissolved in 20 mL water was added. Then 525 mg AtaPhos (0.74 mmol) was added, and the mixture was stirred under reflux temperature until no further conversion was observed. Most of the volatiles were evaporated under reduced pressure, and then it was diluted with dichloromethane and brine. After shaking the pH of the aqueous phase was set to 8 with 2 M HCl. After phase separation the aqueous phase was extracted with dichloromethane. The organic layers were combined and dried over $Na_2SO_4$, filtered and concentrated under reduced pressure. The diastereoisomers were separated via flash chromatography using heptane and ethyl acetate as eluents. The diastereoisomer pair eluting later was collected as Preparation 6t.
HRMS calculated for $C_{35}H_{31}ClF_2N_2O_6S$: 680.1559. found: 681.1618 and 681.1624 of the two isomers.

Preparation 6u: Ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[[2-(2-fluorophenyl)pyrimidin-4-yl]methoxy]phenyl]propanoate 1.407 g (2 mmol) Preparation 4u and 699 mg 2-chloro-3-methyl-4-(4,4,5,5-tetramethyl-1,3,2-dioxaborolan-2-yl) phenol (Preparation 5a) (2.6 mmol) were dissolved in 25 mL THF, then 912 mg $Cs_2CO_3$ (2.8 mmol) dissolved in 15 mL water was added. Then 71 mg AtaPhos (0.1 mmol) was added, and the mixture was stirred under nitrogen at 90° C. until no further conversion was observed. Most of the volatiles were evaporated under reduced pressure, then it was diluted with dichloromethane and brine. After shaking the pH of the aqueous phase was set to 6 with 2 M HCl. After phase separation the aqueous phase was extracted with dichloromethane. The organic layers were combined and dried over $Na_2SO_4$, filtered and concentrated under reduced pressure. The diastereoisomers were separated via flash chromatography using heptane and ethyl acetate as eluents. The diastereoisomer eluting later was collected as Preparation 6u.
MS: $(M+H)^+=764.6$.

Preparation 6v: ethyl (2R)-2-[5-(3-chloro-4-hydroxy-2-methyl-phenyl)-6-(4-fluorophenyl)thieno[2,3-d]pyrimidin-4-yl]oxy-3-[2-[[2-(2-methoxyphenyl)pyrimidin-4-yl]methoxy]phenyl]propanoate Using General Procedure (XXXIV) and Preparation 5a as the appropriate boronic acid derivative Preparation 6v was obtained as the mixture of diastereomers.
MS (ESI+): 777.2

Preparation 6w: Ethyl (2R)-2-[(5Ra)-5-(3-chloro-4-hydroxy-2-methyl-phenyl)-6-(4-fluorophenyl)thieno[2,3-d]pyrimidin-4-yl]oxy-3-(2-tetrahydropyran-2-yloxyphenyl)propanoate 186.6 g ethyl (2R)-2-[5-bromo-6-(4-fluorophenyl)thieno[2,3-d]pyrimidin-4-yl]oxy-3-(2-tetrahydropyran-2-yloxyphenyl)propanoate (Preparation 4a) (310.3 mmol) and 99.99 g 2-chloro-3-methyl-4-(4,4,5,5-tetramethyl-1,3,2-dioxaborolan-2-yl)phenol (Preparation 5a) (372.3 mmol) were dissolved in 1.2 L THF, then 202.2 g $Cs_2CO_3$ (620.6 mmol) dissolved in 300 mL water was added. Then 11.0 g AtaPhos (15.51 mmol) was added, and the mixture was stirred under nitrogen at reflux temperature until no further conversion was observed. Most of the volatiles were evaporated under reduced pressure, then it was diluted with dichloromethane and brine. After shaking the pH of the aqueous phase was set to 8 with 2 M HCl. After phase separation the aqueous phase was extracted with dichloromethane. The organic layers were combined and dried over $Na_2SO_4$, filtered and concentrated under reduced pressure. The diastereoisomers were separated via flash chromatography using heptane and ethyl acetate as eluents. The diastereoisomer pair eluting earlier was collected as Preparation 6w.
HRMS: (M+H)=663.1717 and 663.1746

Preparation 6x: ethyl (2S)-2-[5-(3-chloro-4-hydroxy-2-methyl-phenyl)-6-(4-fluorophenyl)thieno[2,3-d]pyrimidin-4-yl]oxy-3-(2-tetrahydropyran-2-yloxyphenyl)propanoate 186.6 g ethyl (2S)-2-[5-bromo-6-(4-fluorophenyl)thieno[2,3-d]pyrimidin-4-yl]oxy-3-(2-tetra-hydropyran-2-yloxyphenyl)propanoate (Preparation 4w) (310.3 mmol) and 99.99 g 2-chloro-3-methyl-4-(4,4,5,5-tetramethyl-1,3,2-dioxaborolan-2-yl)phenol (Preparation 5a) (372.3 mmol) were dissolved in 1.2 L THF, then 202.2 g $Cs_2CO_3$ (620.6 mmol) dissolved in 300 mL water was added. Then 11.0 g AtaPhos (15.51 mmol) was added, and the mixture was stirred under nitrogen at reflux temperature until no further conversion was observed. Most of the volatiles were evaporated under reduced pressure, then it was diluted with dichloromethane and brine. After shaking the pH of the aqueous phase was set to 8 with 2 M HCl. After phase separation the aqueous phase was extracted with dichloromethane. The organic layers were combined and dried over $Na_2SO_4$, filtered and concentrated under reduced pressure and the product was purified via flash chromatography using heptane and ethyl acetate as eluents to give Preparation 6x as a mixture of diastereoisomers.

MS: (M+H)=663.2.

Preparation 7a: Ethyl (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-tetrahydropyran-2-yloxyphenyl)propanoate 132.3 g ethyl (2R)-2-[(5S$_a$)-5-(3-chloro-4-hydroxy-2-methyl-phenyl)-6-(4-fluorophenyl)-thieno[2,3-d]pyrimidin-4-yl]oxy-3-(2-tetrahydropyran-2-yloxyphenyl)propanoate (Preparation 6a) (199.5 mmol), 43.17 g 2-(4-methylpiperazin-1-yl)ethanol (299.3 mmol) and 94.20 g $PPh_3$ (359.1 mmol) were dissolved in 1 L dry toluene, then 78.09 g ditertbutyl azodicarboxylate (339.2 mmol) was added. The mixture was stirred at 50° C. under $N_2$ until no further conversion was observed. 980 mL toluene was evaporated, then 500 mL $Et_2O$ was added, and the mixture was stirred and sonicated. The precipitated white crystals were filtered, washed with $Et_2O$ to give 65.9 g pure triphenylphosphin-eoxide. The filtrate was concentrated under reduced pressure and purified via flash chromatography using EtOAc and MeOH as eluents to obtain Preparation 7a.

MS: (M+H)$^+$=789.2.

Preparation 7b: Ethyl (2R)-2-[(5S$_a$)-5-[3-chloro-4-(2-dimethylaminoethyloxy)-2-methyl-phenyl]-6-(4-fluorophenyl)thieno[2,3-d]pyrimidin-4-yl]oxy-3-(2-tetrahydropyran-2-yloxyphenyl)propanoate 4.94 g ethyl (2R)-2-[(5S$_a$)-5-(3-chloro-4-hydroxy-2-methyl-phenyl)-6-(4-fluorophenyl)-thieno[2,3-d]pyrimidin-4-yl]oxy-3-(2-tetrahydropyran-2-yloxyphenyl)propanoate (Preparation 6a) (7.5 mmol), 1.34 g 2-(dimethylamino)ethanol (15 mmol) and 3.94 g $PPh_3$ (15 mmol) were dissolved in 30 mL dry toluene, then 3.45 g ditertbutyl azodicarboxylate (15 mmol) was added. The mixture was stirred at 50° C. under $N_2$ until no further conversion was observed. The toluene was evaporated under reduced pressure and the residue was purified via flash chromatography using DCM and MeOH as eluents to obtain Preparation 7b.

MS: (M+H)$^+$=734.2.

Preparation 7c: Ethyl (2R)-2-[(5S$_a$)-5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-(2-tetrahydropyran-2-yloxyphenyl)propanoate 11.55 g ethyl (2R)-2-[(5S$_a$)-5-(3-chloro-4-hydroxy-2-methyl-phenyl)-6-(5-fluoro-2-furyl)thieno[2,3-d]pyrimidin-4-yl]oxy-3-(2-tetrahydropyran-2-yloxyphenyl)propanoate (Preparation 6c) (7.5 mmol), 5.77 g 2-(4-methylpiperazin-1-yl)ethanol (40 mmol), and 10.49 g $PPh_3$ (40 mmol) were dissolved in 100 mL dry toluene, then 9.21 g ditertbutyl azodicarboxylate (40 mmol) was added. The mixture was stirred at 50° C. under $N_2$ until no further conversion was observed. The toluene was evaporated under reduced pressure and the residue was purified via flash chromatography using DCM and MeOH as eluents to obtain Preparation 7c.

MS: (M+H)$^+$=695.2.

Preparation 7d: Ethyl (2R)-2-[(5S$_a$)-5-[3-chloro-4-(2-dimethylaminoethyloxy)-2-methyl-phenyl]-6-(5-fluoro-2-furyl)thieno[2,3-d]pyrimidin-4-yl]oxy-3-(2-tetrahydropyran-2-yloxyphenyl)propanoate 2.87 g ethyl (2R)-2-[(5S$_a$)-5-(3-chloro-4-hydroxy-2-methyl-phenyl)-6-(5-fluoro-2-furyl)thieno[2,3-d]pyrimidin-4-yl]oxy-3-(2-tetrahydropyran-2-yloxyphenyl)propanoate (Preparation 6c) (5.05 mmol), 1.35 g 2-(dimethylamino)ethanol (15.15 mmol) and 3.98 g $PPh_3$ (15.15 mmol) were dissolved in 100 mL dry toluene, then 3.49 g ditertbutyl azodicarboxylate (15.15 mmol) was added. The mixture was stirred at 50° C. under $N_2$ until no further conversion was observed. The toluene was evaporated under reduced pressure and the residue was purified via flash chromatography using EtOAc and MeOH as eluents to obtain Preparation 7d.

MS: (M+H)$^+$=724.2.

Preparation 7e: Ethyl (2R)-2-[(5S$_a$)-5-[3-chloro-2-methyl-4-[2-(4-methylpiperazin-1-yl)ethoxy]phenyl]-6-(2-furyl)thieno[2,3-d]pyrimidin-4-yl]oxy-3-(2-tetrahydropyran-2-yloxyphenyl)propanoate 19.05 g ethyl (2R)-2-[(5S$_a$)-5-(3-chloro-4-hydroxy-2-methyl-phenyl)-6-(2-furyl)thieno[2,3-d]pyrimidin-4-yl]oxy-3-(2-tetrahydropyran-2-yloxyphenyl)propanoate (Preparation 6d) (30 mmol), 8.65 g 2-(4-methylpiperazin-1-yl)ethanol (60 mmol) and 15.74 g $PPh_3$ (60 mmol) were dissolved in 200 mL dry toluene, then 13.81 g ditertbutyl azodicarboxylate (60 mmol) was added. The mixture was stirred at 50° C. under $N_2$ until no further conversion was observed. The toluene was evaporated under reduced pressure and the residue was purified via flash chromatography using EtOAc and MeOH as eluents to obtain Preparation 7e.

MS: (M+H)$^+$=761.2.

Preparation 7f: Ethyl (2R)-2-[(5S$_a$)-5-[3-chloro-2-methyl-4-[2-(4-methylpiperazin-1-yl)ethoxy]phenyl]-6-(4-fluoro-3-methoxy-phenyl)thieno[2,3-d]pyrimidin-4-yl]oxy-3-(2-tetrahydropyran-2-yloxyphenyl)propanoate 13.5 g ethyl (2R)-2-[(5S$_a$)-5-(3-chloro-4-hydroxy-2-methyl-phenyl)-6-(4-fluoro-3-methoxy-phenyl)thieno[2,3-d]pyrimidin-4-yl]oxy-3-(2-tetrahydropyran-2-yloxyphenyl)propanoate (Preparation 6h) (13.5 mmol), 5.62 g 2-(4-methylpiperazin-1-yl)ethanol (39 mmol) and 10.22 g $PPh_3$ (39 mmol) were dissolved in 250 mL dry toluene, then 10.22 g ditertbutyl azodicarboxylate (39 mmol) was added. The mixture was stirred at 50° C. under $N_2$ until no further conversion was observed. The toluene was evaporated under reduced pressure and the residue was purified via flash chromatography using EtOAc and MeOH as eluents to obtain Preparation 7f.

MS: (M+H)$^+$=819.0.

Preparation 7g: Ethyl (2R)-2-[(5S$_a$)-5-[3-chloro-2-methyl-4-[2-(4-methylpiperazin-1-yl)ethoxy]phenyl]-6-ethyl-thieno[2,3-d]pyrimidin-4-yl]oxy-3-(2-tetrahydropyran-2-yloxyphenyl)propanoate 9.86 g ethyl (2R)-2-[(5S$_a$)-5-(3-chloro-4-hydroxy-2-methyl-phenyl)-6-ethyl-thieno[2,3-d]pyrimidin-4-yl]oxy-3-

(2-tetrahydropyran-2-yloxyphenyl)propanoate (Preparation 6k) (6.46 mmol), 1.73 g 2-(4-methylpiperazin-1-yl)ethanol (12.0 mmol) and 3.15 g PPh$_3$ (12.0 mmol) were dissolved in 40 mL dry toluene, then 2.76 g ditertbutyl azodicarboxylate (12.0 mmol) was added. The mixture was stirred at 50° C. under N$_2$ until no further conversion was observed. Toluene was evaporated under reduced pressure and the residue was purified via flash chromatography using EtOAc and MeOH as eluents to obtain Preparation 7g.
MS: (M+H)$^+$=723.2.

Preparation 7h: Ethyl (2R)-2-[(5S$_a$)-5-[3-chloro-2-methyl-4-[2-(4-methylpiperazin-1-yl)ethoxy]phenyl]-6-prop-1-ynyl-thieno[2,3-d]pyrimidin-4-yl]oxy-3-(2-tetrahydropyran-2-yloxyphenyl)propanoate 6.60 g ethyl (2R)-2-[(5S$_a$)-(3-chloro-4-hydroxy-2-methyl-phenyl)-6-prop-1-ynyl-thieno[2,3-d]pyrimidin-4-yl]oxy-3-(2-tetrahydropyran-2-yloxyphenyl)propanoate (Preparation 6m) (10.87 mmol), 2.88 g 2-(4-methylpiperazin-1-yl)ethanol (20 mmol) and 5.25 g PPh$_3$ (20 mmol) were dissolved in 450 mL dry toluene, then 4.61 g ditertbutyl azodicarboxylate (20 mmol) was added. The mixture was stirred at 50° C. under N$_2$ until no further conversion was observed. The toluene was evaporated under reduced pressure and the residue was purified via flash chromatography using EtOAc and MeOH as eluents to obtain Preparation 7h.
MS: (M+H)$^+$=733.2.

Preparation 7i: Ethyl (2R)-2-[6-(5-chloro-2-furyl)-5-(5S$_a$)-[3-chloro-2-methyl-4-[2-(4-methylpiperazin-1-yl)ethoxy]phenyl]thieno[2,3-d]pyrimidin-4-yl]oxy-3-[2-[(4-methoxyphenyl)methoxy]phenyl]propanoate 5.30 g ethyl (2R)-2-[6-(5-chloro-2-furyl)-5-(5S$_a$)-(3-chloro-4-hydroxy-2-methyl-phenyl)thieno[2,3-d]pyrimidin-4-yl]oxy-3-[2-[(4-methoxyphenyl)methoxy]phenyl] propanoate (Preparation 6f) (7.5 mmol), 2.16 g 2-(4-methylpiperazin-1-yl)ethanol (15 mmol) and 3.93 g PPh$_3$ (15 mmol) were dissolved in 30 mL dry toluene, then 3.45 g ditertbutyl azodicarboxylate (15 mmol) was added. The mixture was stirred at 50° C. under N$_2$ until no further conversion was observed. The toluene was evaporated under reduced pressure and the residue was purified via flash chromatography using EtOAc and MeOH as eluents to obtain Preparation 7i.
MS: (M+H)$^+$=831.0.

Preparation 7j: Ethyl (2R)-2-[(5S$_a$)-5-[3-chloro-2-methyl-4-[2-(4-methylpiperazin-1-yl)ethoxy]phenyl]-6-(3,4-difluorophenyl)thieno[2,3-d]pyrimidin-4-yl]oxy-3-(2-tetrahydropyran-2-yloxyphenyl)propanoate 6.85 g ethyl (2R)-2-[(5S$_a$)-5-(3-chloro-4-hydroxy-2-methyl-phenyl)-6-(3,4-difluorophenyl)thieno[2,3-d]pyrimidin-4-yl]oxy-3-(2-tetrahydropyran-2-yloxyphenyl)propanoate (Preparation 6p) (10.06 mmol), 2.90 g 2-(4-methylpiperazin-1-yl)ethanol (20.12 mmol) and 5.27 g PPh$_3$ (20.12 mmol) were dissolved in 20 mL dry toluene, then 4.63 g ditertbutyl azodicarboxylate (20.12 mmol) was added. The mixture was stirred at 50° C. under N$_2$ until no further conversion was observed. The toluene was evaporated under reduced pressure and the residue was purified via flash chromatography using EtOAc and MeOH as eluents to obtain Preparation 7j.
MS: (M+H)$^+$=681.0.

Preparation 7k: Ethyl (2R)-2-[(5S$_a$)-5-[3-chloro-2-methyl-4-[2-(4-methylpiperazin-1-yl)ethoxy]phenyl]-6-(2,3-difluorophenyl)thieno[2,3-d]pyrimidin-4-yl]oxy-3-(2-tetrahydropyran-2-yloxyphenyl) propanoate Step A: 5-Bromo-4-chloro-6-(2,3-difluorophenyl)thieno[2,3-d]pyrimidine
9.39 g 5-bromo-4-chloro-6-iodo-thieno[2,3-d]pyrimidine (Preparation 1a) (25 mmol), 9.00 g 2-(2,3-difluorophenyl)-4,4,5,5-tetramethyl-1,3,2-dioxaborolane (37.5 mmol), 16.29 g Cs$_2$CO$_3$ (50 mmol), and 0.912 g Pd(dppf)Cl$_2$ (1.25 mmol) were placed in a 250 mL flask. 100 mL THF and 50 mL water were added, and then stirred at 70° C. under N$_2$ until no further conversion was observed. The reaction mixture was extracted with EtOAc. The combined organic layers were dried over Na$_2$SO$_4$, filtered and concentrated under reduced pressure. The crude product was purified via flash chromatography using DCM and MeOH as eluents.
$^1$H NMR (500 MHz, DMSO-d$_6$): 9.07 (s, 1H), 7.71 (m, 1H), 7.46 (m, 2H).
HRMS calculated for C$_{12}$H$_4$BrClF$_2$N$_2$S: 359.8935. found: 360.9013 (M+H).

Step B: Ethyl (2R)-2-[5-bromo-6-(2,3-difluorophenyl)thieno[2,3-d]pyrimidin-4-yl]oxy-3-(2-tetrahydropyran-2-yloxyphenyl)propanoate
8.3 g 5-bromo-4-chloro-6-(2,3-difluorophenyl)thieno[2,3-d]pyrimidine (23 mmol), 7.48 g ethyl (2R)-2-hydroxy-3-(2-tetrahydropyran-2-yloxyphenyl)propanoate (Preparation 3ab-(R)) (25.4 mmol) and 26.23 g Cs$_2$CO$_3$ (80.5 mmol) were placed in a 250 mL flask. 100 mL tert-butanol was added and the mixture was stirred at 60° C. under N$_2$ until no further conversion was observed. The reaction mixture was diluted with brine, the pH was set between 6-7 with 2 M HCl, and then it was extracted with DCM. The combined organic layers were dried over Na$_2$SO$_4$, filtered and concentrated under reduced pressure. The crude product was purified via flash chromatography using heptane and EtOAc as eluents to obtain the product of Step B as a mixture of diastereoisomers.
$^1$H NMR (500 MHz, DMSO-d$_6$): 8.71 (d, 1H), 7.69 (m, 1H), 7.43 (m, 3H), 7.19 (m, 1H), 7.07 (m, 1H), 6.89 (t, 1H), 5.83/5.71 (dd, 1H), 5.60/5.56 (t, 1H), 4.15 (m, 2H), 3.75-3.18 (m, 4H), 1.99-1.56 (m, 4H), 1.82 (m, 2H), 1.15/1.16 (t, 3H).
HRMS calculated for C$_{28}$H$_{25}$BrF$_2$N$_2$O$_5$S: 618.0636. found: 619.0695 (M+H).

Step C: Ethyl (2R)-2-[(5S$_a$)-5-(3-chloro-4-hydroxy-2-methyl-phenyl)-6-(2,3-difluoro phenyl)thieno[2,3-d]pyrimidin-4-yl]oxy-3-(2-tetrahydropyran-2-yloxyphenyl)propanoate
8.75 g ethyl (2R)-2-[(5S$_a$)-5-bromo-6-(2,3-difluorophenyl)thieno[2,3-d]pyrimidin-4-yl]oxy-3-(2-tetrahydropyran-2-yloxyphenyl)propanoate (14.1 mmol) and 4.92 g 2-chloro-3-methyl-4-(4,4,5,5-tetramethyl-1,3,2-dioxaborolan-2-yl)phenol (Preparation 5a) (18.3 mmol) were dissolved in 50 mL THF, then 6.11 g Cs$_2$CO$_3$ (18.8 mmol) dissolved in 20 mL water was added. Then 0.5 g AtaPhos (0.7 mmol) was added, and the mixture was stirred under N$_2$ at reflux temperature until no further conversion was observed. The reaction mixture was diluted with brine and extracted with DCM. The organic combined layers were dried over Na₂SO₄, filtered and concentrated under reduced pressure. The diastereoisomers were separated via flash chromatography using heptane and EtOAc as eluents. The diastereoisomer pair eluting later was collected as the product of Step C.

¹H NMR (500 MHz, DMSO-$d_6$, 1:1 mixture of diastereomers): 10.24 (br s, 1H), 8.66/8.65 (s, 1H), 7.48 (m, 1H), 7.22 (m, 1H), 7.13 (m, 2H), 7.08 (d, 1H), 7.01 (d, 1H), 6.89 (d, 1H), 6.74 (t, 1H), 6.38/6.32 (d, 1H), 5.55 (m, 1H), 5.45 (dd, 1H), 4.04 (m, 2H), 3.68/3.54 (m, 2H), 3.32 (dd, 1H), 2.47 (dd, 1H), 2.06-1.48 (m, 6H), 1.90/1.88 (s, 3H), 1.07/1.06 (t, 3H).

HRMS calculated for $C_{35}H_{31}ClF_2N_2O_6S$: 680.1559. found: 681.1618/681.1624 (M+H).

Step D: Ethyl (2R)-2-[(5S$_a$)-5-[3-chloro-2-methyl-4-[2-(4-methylpiperazin-1-yl)ethoxy]phenyl]-6-(3,4-difluorophenyl)thieno[2,3-d]pyrimidin-4-yl]oxy-3-(2-tetrahydropyran-2-yloxyphenyl)propanoate 6.49 g ethyl (2R)-2-[(5S$_a$)-5-(3-chloro-4-hydroxy-2-methyl-phenyl)-6-(2,3-difluorophenyl)thieno[2,3-d]pyrimidin-4-yl]oxy-3-(2-tetrahydropyran-2-yloxyphenyl)propanoate (9.5 mmol), 2.75 g 2-(4-methylpiperazin-1-yl)ethanol (19 mmol) and 4.98 g PPh₃ (19 mmol) were dissolved in 20 mL dry toluene, then 4.38 g ditertbutyl azodicarboxylate (19 mmol) was added. The mixture was stirred at 50° C. under N₂ until no further conversion was observed. The toluene was evaporated under reduced pressure and the residue was purified via flash chromatography using EtOAc and MeOH as eluents to obtain Preparation 7k.

¹H NMR (500 MHz, DMSO-$d_6$, 1:1 mixture of diastereomers): 8.67 (s, 1H), 7.48 (m, 1H), 7.22-7.17 (m, 3H), 7.13 (t, 1H), 7.10 (d, 1H), 7.01 (d, 1H), 6.72 (t, 1H), 6.33/6.28 (d, 1H), 5.54/5.51 (m, 1H), 5.45 (dd, 1H), 4.18 (m, 2H), 4.03 (m, 2H), 3.68/3.54 (m, 2H), 3.02/2.99 (dd, 1H), 2.69 (t, 2H), 2.56 (m, 1H), 2.46 (br s, 4H), 2.22 (br s, 4H), 2.08 (s, 3H), 2.03-1.46 (m, 6H), 1.93/1.92 (s, 3H), 1.05 (t, 3H).

HRMS calculated for $C_{42}H_{45}ClF_2N_2O_6S$: 806.2716. found: 807.2763/807.2793 (M+H).

Preparation 7l: Ethyl (2R)-2-[(5Sa)-5-[3-chloro-2-methyl-4-[2-(dimethylamino)ethoxy]phenyl]-6-(2,3-difluorophenyl)thieno[2,3-d]pyrimidin-4-yl]oxy-3-(2-tetrahydropyran-2-yloxyphenyl)propanoate 6.85 g ethyl (2R)-2-[(5S$_a$)-5-(3-chloro-4-hydroxy-2-methyl-phenyl)-6-(2,3-difluorophenyl)thieno[2,3-d]pyrimidin-4-yl]oxy-3-(2-tetrahydropyran-2-yloxyphenyl)propanoate (Preparation 6t) (10.06 mmol), 1.793 g N,N-dimethylethanolamine (20.12 mmol) and 5.27 g PPh₃ (20.12 mmol) were dissolved in 20 mL dry toluene, then 4.63 g ditertbutyl azodicarboxylate (20.12 mmol) was added. The mixture was stirred at 50° C. under N₂ until no further conversion was observed. The toluene was evaporated under reduced pressure and the residue was purified via flash chromatography using EtOAc and MeOH as eluents to obtain Preparation 7l.

MS: (M+H)⁺=752.6.

Preparation 7m: Ethyl (2R)-2-[(5Sa)-5-[3-chloro-2-methyl-4-[2-(piperazin-1-yl)ethoxy]phenyl]-6-(4-fluorophenyl)thieno[2,3-d]pyrimidin-4-yl]oxy-3-(2-tetrahydropyran-2-yloxyphenyl)propanoate 862 mg ethyl (2R)-2-[(5S$_a$)-5-(3-chloro-4-hydroxy-2-methyl-phenyl)-6-(4-fluorophenyl)-thieno[2,3-d]pyrimidin-4-yl]oxy-3-(2-tetrahydropyran-2-yloxyphenyl)propanoate (Preparation 6a) (1.3 mmol), 338 mg N-(2-hydroxyethyl)piperazine (2.6 mmol) and 682 mg PPh₃ (2.6 mmol) were dissolved in 25 mL dry toluene, then 600 mg ditertbutyl azodicarboxylate (2.6 mmol) was added. The mixture was stirred at 50° C. under N₂ until no further conversion was observed. Toluene was evaporated, then 5 mL Et₂O was added, and the mixture was stirred and sonicated. The precipitated white crystals were filtered, washed with Et₂O. The filtrate was concentrated under reduced pressure and purified via flash chromatography using DCM and MeOH as eluents to obtain Preparation 7m.

MS: (M+H)⁺=775.2.

Preparation 7n: Ethyl (2R)-2-[(5Sa)-5-[3-chloro-2-methyl-4-[2-(4-ethylpiperazin-1-yl)ethoxy]phenyl]-6-(4-fluorophenyl)thieno[2,3-d]pyrimidin-4-yl]oxy-3-(2-tetrahydropyran-2-yloxyphenyl)propanoate 862 mg ethyl (2R)-2-[(5Sa)-5-(3-chloro-4-hydroxy-2-methyl-phenyl)-6-(4-fluorophenyl)-thieno[2,3-d]pyrimidin-4-yl]oxy-3-(2-tetrahydropyran-2-yloxyphenyl)propanoate (Preparation 6a) (1.3 mmol), 411 mg 2-(4-ethylpiperazin-1-yl)ethanol (2.6 mmol) and 682 mg PPh₃ (2.6 mmol) were dissolved in 25 mL dry toluene, then 600 mg ditertbutyl azodicarboxylate (2.6 mmol) was added. The mixture was stirred at 50° C. under N₂ until no further conversion was observed. Toluene was evaporated, then 5 mL Et₂O was added, and the mixture was stirred and sonicated. The precipitated white crystals were filtered, washed with Et₂O (PPh₃O). The filtrate was concentrated under reduced pressure and purified via flash chromatography using DCM and MeOH as eluents to obtain Preparation 7n.

MS: (M+H)⁺=802.4, 803.4.

Preparation 7o: Ethyl (2R)-2-[(5R$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-tetrahydropyran-2-yloxyphenyl)propanoate 132.3 g ethyl (2R)-2-[(5R$_a$)-5-(3-chloro-4-hydroxy-2-methyl-phenyl)-6-(4-fluorophenyl)-thieno[2,3-d]pyrimidin-4-yl]oxy-3-(2-tetrahydropyran-2-yloxyphenyl)propanoate (Preparation 6w) (199.5 mmol), 43.17 g 2-(4-methylpiperazin-1-yl)ethanol (299.3 mmol) and 94.20 g PPh₃ (359.1 mmol) were dissolved in 1 L dry toluene, then 78.09 g ditertbutyl azodicarboxylate (339.2 mmol) was added. The mixture was stirred at 50° C. under N₂ until no further conversion was observed. 980 mL toluene was evaporated, then 500 mL Et₂O was added, and the mixture was stirred and sonicated. The precipitated white crystals were filtered, washed with Et₂O to give 65.9 g pure triphenylphosphineoxide. The filtrate was concentrated under reduced pressure and purified via flash chromatography using EtOAc and MeOH as eluents to obtain Preparation 7o.

MS: (M+H)⁺=789.2.

Preparation 7p: Ethyl (2S)-2-[5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-tetrahydropyran-2-yloxyphenyl)propanoate 132.3 g ethyl (2S)-2-[5-(3-chloro-4-hydroxy-2-methyl-phenyl)-6-(4-fluorophenyl)-thieno[2,3-d]pyrimidin-4-yl]oxy-3-(2-tetrahydropyran-2-yloxyphenyl)propanoate (Preparation 6x) (199.5 mmol), 43.17 g 2-(4-methylpiperazin-1-yl)ethanol (299.3 mmol) and 94.20 g PPh₃ (359.1 mmol) were dissolved in 1 L dry toluene, then 78.09 g Preparation 8a: Ethyl (2R)-2-[(5S$_a$)-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-hydroxyphenyl)propanoate 199.5 mmol ethyl (2R)-2-[(5S$_a$)-[3-chloro-2-methyl-4-[2-(4-methylpiperazin-1-yl)ethoxy]-phenyl]-6-(4-fluorophenyl)thieno[2,3-d]pyrimidin-4-yl]oxy-3-(2-tetrahydropyran-2-yl-oxyphenyl)-propanoate (Preparation 7a) was dissolved in 1 L EtOH, then 1 L 1.25 M HCl in EtOH was added and the mixture was stirred at room temperature until no further conversion was observed. Most of the EtOH was evaporated, then Et$_2$O was added and the precipitated HCl salt (white solid) was filtered, washed with Et$_2$O. The HCl salt was carefully treated with saturated NaHCO$_3$ solution, extracted with DCM, the combined organic phases were dried over Na$_2$SO$_4$, filtered and concentrated under reduced pressure to give Preparation 8a.

$^1$H NMR (400 MHz, DMSO-d$_6$): 9.53 (br s, 1H), 8.60 (s, 1H), 7.30 (m, 2H), 7.28 (d, 1H), 7.21 (m, 2H), 7.16 (d, 1H), 6.97 (t, 1H), 6.72 (d, 1H), 6.53 (t, 1H), 6.20 (d, 1H), 5.46 (dd, 1H), 4.22 (m, 2H), 4.04 (m, 2H), 2.92 (dd, 1H), 2.75 (m, 2H), 2.53 (br s, 4H), 2.44 (dd, 1H), 2.36 (br s, 4H), 2.17 (s, 3H), 1.88 (s, 3H), 1.06 (t, 3H).

HRMS calculated for C$_{37}$H$_{38}$ClFN$_4$O$_5$S: 704.2235. found: 705.2288 (M+H).

Preparation 8b: Ethyl (2R)-2-[(5S$_a$)-[3-chloro-4-(2-dimethylaminoethyloxy)-2-methyl-phenyl]-6-(4-fluorophenyl)thieno[2,3-d]pyrimidin-4-yl]oxy-3-(2-hydroxyphenyl)propanoate 5.60 mmol ethyl (2R)-2-[(5S$_a$)-5-[3-chloro-4-(2-dimethylaminoethyloxy)-2-methyl-phenyl]-6-(4-fluorophenyl)thieno[2,3-d]pyrimidin-4-yl]oxy-3-(2-tetrahydropyran-2-yloxyphenyl)propanoate (Preparation 7b) was dissolved in 40 mL EtOH, then 20 mL 1.25 M HCl in EtOH was added and the mixture was stirred until no further conversion was observed. Water and saturated NaHCO$_3$ solution were added carefully and the mixture was extracted with DCM, the combined organic phases were dried over Na$_2$SO$_4$, filtered and concentrated under reduced pressure. The crude product was purified via flash chromatography using DCM and EtOAc as eluents to obtain Preparation 8b.

$^1$H NMR (500 MHz, DMSO-d$_6$): 9.53 (br s, 1H), 8.61 (s, 1H), 7.30 (m, 2H), 7.29 (d, 1H), 7.31 (m, 2H), 7.16 (d, 1H), 6.97 (m, 1H), 6.71 (dm, 1H), 6.52 (m, 1H), 6.18 (dm, 1H), 5.46 (dd, 1H), 4.20 (t, 2H), 4.04 (m, 2H), 2.92 (dd, 1H), 2.69 (t, 2H), 2.43 (dd, 1H), 2.22 (s, 6H), 1.88 (s, 3H), 1.06 (t, 3H).

HRMS calculated for C$_{34}$H$_{33}$ClFN$_3$O$_5$S: 649.1813. found: 650.1887 (M+H).

Preparation 8c: Ethyl (2R)-2-[(5S$_a$)-5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-(2-hydroxyphenyl)propanoate 184 mmol ethyl (2R)-2-[(5S$_a$)-5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-(2-tetrahydropyran-2-yloxyphenyl)propanoate (Preparation 7c) was dissolved in 1 L EtOH, then 1 L 1.25 M HCl in EtOH was added and the mixture was stirred at room temperature until no further conversion was observed. Most of the EtOH was evaporated, then Et$_2$O was added and the precipitated HCl salt (white solid) was filtered, washed with Et$_2$O. The HCl salt was carefully treated with saturated NaHCO$_3$ solution, extracted with DCM, the combined organic phases were dried over Na$_2$SO$_4$, filtered and concentrated under reduced pressure. The crude product was purified via flash chromatography using DCM and MeOH as eluents to obtain Preparation 8c.

$^1$H NMR (500 MHz, DMSO-d$_6$): 9.55 (s, 1H), 8.58 (s, 1H), 7.25 (s, 2H), 6.99 (t, 1H), 6.72 (d, 1H), 6.59 (t, 1H), 6.23 (d, 1H), 5.88 (dd, 1H), 5.72 (t, 1H), 5.47 (dd, 1H), 4.27 (t, 2H), 4.04 (m, 2H), 2.95 (dd, 1H), 2.77 (t, 2H), 2.53 (br s, 4H), 2.35 (dd, 1H), 2.30 (br s, 4H), 2.13 (s, 3H), 1.97 (s, 3H), 1.06 (t, 3H).

HRMS calculated for C$_{35}$H$_{36}$ClFN$_4$O$_6$S: 694.2028. found: 695.2106 (M+H).

Preparation 8d: Ethyl (2R)-2-[(5S$_a$)-5-[3-chloro-4-(2-dimethylaminoethyloxy)-2-methyl-phenyl]-6-(5-fluoro-2-furyl)thieno[2,3-d]pyrimidin-4-yl]oxy-3-(2-hydroxyphenyl)propanoate 30 mL 1.25 M HCl in EtOH was added to 1.5 mmol ethyl (2R)-2-[(5S$_a$)-5-[3-chloro-4-(2-dimethylaminoethyloxy)-2-methyl-phenyl]-6-(5-fluoro-2-furyl)thieno[2,3-d]pyrimidin-4-yl]oxy-3-(2-tetrahydropyran-2-yloxyphenyl)propanoate (Preparation 7d) and the mixture was stirred until no further conversion was observed. The reaction mixture was carefully diluted with saturated NaHCO$_3$ solution and the mixture was extracted with DCM, the combined organic phases were dried over Na$_2$SO$_4$, filtered and concentrated under reduced pressure. The crude product was purified via flash chromatography using EtOAc and MeOH as eluents to obtain Preparation 8d.

$^1$H NMR (500 MHz, DMSO-d$_6$): 9.56 (br s, 1H), 8.58 (s, 1H), 7.25 (s, 2H), 6.99 (td, 1H), 6.72 (dd, 1H), 6.59 (td, 1H), 6.23 (dd, 1H), 5.88 (dd, 1H), 5.71 (t, 1H), 5.48 (dd, 1H), 4.25 (m, 2H), 4.04 (m, 2H), 2.96 (dd, 1H), 2.71 (t, 2H), 2.35 (dd, 1H), 2.23 (s, 6H), 1.98 (s, 3H), 1.06 (t, 3H).

HRMS calculated for C$_{32}$H$_{31}$ClFN$_3$O$_6$S: 639.1606. found: 640.1679 (M+H).

Preparation 8e: Ethyl (2R)-2-[(5S$_a$)-5-[3-chloro-2-methyl-4-[2-(4-methylpiperazin-1-yl)ethoxy]phenyl]-6-(2-furyl)thieno[2,3-d]pyrimidin-4-yl]oxy-3-(2-hydroxyphenyl)propanoate 30 mmol ethyl (2R)-2-[(5S$_a$)-5-[3-chloro-2-methyl-4-[2-(4-methylpiperazin-1-yl)ethoxy]phenyl]-6-(2-furyl)thieno[2,3-d]pyrimidin-4-yl]oxy-3-(2-tetrahydropyran-2-yloxyphenyl)propanoate (Preparation 7e) was dissolved in 200 mL EtOH, then 200 mL 1.25 M HCl in EtOH was added and the mixture was stirred at room temperature until no further conversion was observed. Saturated NaHCO$_3$ solution was added, and the reaction mixture was extracted with DCM. The combined organic layers were dried over Na$_2$SO$_4$, filtered and concentrated under reduced pressure. The crude product was purified via flash chromatography using DCM and MeOH as eluents to obtain Preparation 8e.

$^1$H NMR (500 MHz, DMSO-d$_6$): 9.55 (s, 1H), 8.58 (s, 1H), 7.80 (d, 1H), 7.26 (d, 1H), 7.24 (d, 1H), 6.99 (t, 1H), 6.72 (d, 1H), 6.60 (t, 1H), 6.53 (dd, 1H), 6.24 (d, 1H), 5.69

(d, 1H), 5.48 (dd, 1H), 4.28 (t, 2H), 4.04 (m, 2H), 2.95 (dd, 1H), 2.78 (t, 2H), 2.51 (br s, 4H), 2.34 (dd, 1H), 2.31 (br s, 4H), 2.13 (br s, 3H), 1.96 (s, 3H), 1.06 (t, 3H).

HRMS calculated for $C_{35}H_{37}ClN_4O_6S$: 676.2122. found: 677.2194 (M+H).

Preparation 8f: Ethyl (2R)-2-[(5S$_a$)-6-(5-chloro-2-furyl)-5-[3-chloro-2-methyl-4-[2-(4-methylpiperazin-1-yl)ethoxy]phenyl]thieno[2,3-d]pyrimidin-4-yl]oxy-3-(2-hydroxyphenyl)propanoate 200 mL 1.25 M HCl in EtOH was added to 7 mmol ethyl (2R)-2-[6-(5-chloro-2-furyl)-5-(5S$_a$)-[3-chloro-2-methyl-4-[2-(4-methylpiperazin-1-yl)ethoxy]phenyl]thieno[2,3-d]pyrimidin-4-yl]oxy-3-[2-[(4-methoxyphenyl)methoxy]phenyl]propanoate (Preparation 7i) and the mixture was stirred at 80° C. until no further conversion was observed. Saturated NaHCO$_3$ solution was added to the reaction mixture, and it was extracted with DCM. The combined organic layers were dried over Na$_2$SO$_4$, filtered and concentrated under reduced pressure and purified via flash chromatography using DCM and MeOH as eluents to obtain Preparation 8f.

$^1$H NMR (500 MHz, DMSO-d$_6$): 9.56 (br s, 1H), 8.59 (s, 1H), 7.25 (s, 2H), 6.99 (t, 1H), 6.72 (d, 1H), 6.59 (t, 1H), 6.55 (d, 1H), 6.23 (d, 1H), 5.74 (d, 1H), 5.48 (dd, 1H), 4.28 (t, 2H), 4.04 (m, 2H), 2.95 (dd, 1H), 2.79 (t, 2H), 2.58 (br s, 4H), 2.44 (br s, 4H), 2.35 (dd, 1H), 2.23 (br s, 3H), 1.96 (s, 3H), 1.06 (t, 3H).

HRMS calculated for $C_{35}H_{36}Cl_2N_4O_6S$: 710.1733. found: 711.1797 (M+H).

Preparation 8g: Ethyl (2R)-2-[(5S$_a$)-5-[3-chloro-2-methyl-4-[2-(4-methylpiperazin-1-yl)ethoxy]phenyl]-6-(4-fluoro-3-methoxy-phenyl)thieno[2,3-d]pyrimidin-4-yl]oxy-3-(2-hydroxyphenyl)propanoate 19 mmol ethyl (2R)-2-[(5S$_a$)-5-[3-chloro-2-methyl-4-[2-(4-methylpiperazin-1-yl)ethoxy]phenyl]-6-(4-fluoro-3-methoxy-phenyl)thieno[2,3-d]pyrimidin-4-yl]oxy-3-(2-tetrahydropyran-2-yloxyphenyl)propanoate (Preparation 7f) was dissolved in 300 mL EtOH, then 150 mL 1.25 M HCl in EtOH was added and the mixture was stirred at room temperature until no further conversion was observed. Saturated NaHCO$_3$ solution was added and the mixture was extracted with DCM. The combined organic layers were dried over Na$_2$SO$_4$, filtered and concentrated under reduced pressure. The crude product was purified via flash chromatography using DCM and MeOH as eluents to obtain Preparation 8g.

$^1$H NMR (500 MHz, DMSO-d$_6$): 9.57 (br s, 1H), 8.61 (s, 1H), 7.31 (d, 1H), 7.24 (dd, 1H), 7.19 (d, 1H), 6.97 (td, 1H), 6.93 (ddd, 1H), 6.86 (dd, 1H), 6.71 (d, 1H), 6.53 (t, 1H), 6.16 (d, 1H), 5.46 (dd, 1H), 4.23 (m, 2H), 4.05 (m, 2H), 3.57 (s, 3H), 2.95 (dd, 1H), 2.73 (m, 2H), 2.72 (br s, 4H), 2.68 (br s, 4H), 2.41 (dd, 1H), 2.10 (s, 3H), 1.88 (s, 3H), 1.07 (t, 3H).

HRMS calculated for $C_{38}H_{40}ClFN_4O_6S$: 734.2341. found: 735.2406 (M+H).

Preparation 8h: Ethyl (2R)-2-[(5S$_a$)-5-[3-chloro-2-methyl-4-[2-(4-methylpiperazin-1-yl)ethoxy]phenyl]-6-ethyl-thieno[2,3-d]pyrimidin-4-yl]oxy-3-(2-hydroxyphenyl)propanoate 6 mmol ethyl (2R)-2-[(5S$_a$)-5-[3-chloro-2-methyl-4-[2-(4-methylpiperazin-1-yl)ethoxy]phenyl]-6-ethyl-thieno[2,3-d]pyrimidin-4-yl]oxy-3-(2-tetrahydropyran-2-yloxyphenyl)propanoate (Preparation 7g) was dissolved in 100 mL EtOH, then 40 mL 1.25 M HCl in EtOH was added and the mixture was stirred at room temperature until no further conversion was observed. Saturated NaHCO$_3$ solution was added and the reaction was extracted with DCM. The combined organic layers were dried over Na$_2$SO$_4$, filtered and concentrated under reduced pressure. The crude product was purified via flash chromatography using DCM and MeOH as eluents to obtain Preparation 8h.

$^1$H NMR (500 MHz, DMSO-d$_6$): 9.53 (s, 1H), 8.53 (s, 1H), 7.21 (d, 1H), 7.18 (d, 1H), 6.99 (t, 1H), 6.72 (d, 1H), 6.58 (t, 1H), 6.22 (d, 1H), 5.42 (dd, 1H), 4.25 (m, 2H), 4.02 (m, 2H), 2.90 (dd, 1H), 2.76 (m, 2H), 2.67 (m, 1H), 2.60 (m, 1H), 2.49 (br s, 4H), 2.41 (dd, 1H), 2.27 (br s, 4H), 2.11 (s, 3H), 2.01 (s, 3H), 1.17 (t, 3H), 1.05 (t, 3H).

HRMS calculated for $C_{33}H_{39}ClFN_4O_5S$: 638.2330. found: 639.2377 (M+H).

Preparation 8i: Ethyl (2R)-2-[(5S$_a$)-5-[3-chloro-2-methyl-4-[2-(4-methylpiperazin-1-yl)ethoxy]phenyl]-6-prop-1-ynyl-thieno[2,3-d]pyrimidin-4-yl]oxy-3-(2-hydroxyphenyl)propanoate 10 mmol ethyl (2R)-2-[(5S$_a$)-5-[3-chloro-2-methyl-4-[2-(4-methylpiperazin-1-yl)ethoxy]phenyl]-6-prop-1-ynyl-thieno[2,3-d]pyrimidin-4-yl]oxy-3-(2-tetrahydropyran-2-yloxyphenyl)propanoate (Preparation 7h) was dissolved in 100 mL EtOH, then 40 mL 1.25 M HCl in EtOH was added and the mixture was stirred at room temperature until no further conversion was observed. The most of the EtOH was evaporated then saturated NaHCO$_3$ solution was added and the mixture was extracted with DCM. The combined organic layers were dried over Na$_2$SO$_4$, filtered and concentrated under reduced pressure and purified via flash chromatography using DCM and MeOH as eluents to obtain Preparation 8i.

$^1$H NMR (500 MHz, DMSO-d$_6$): 9.53 (s, 1H), 8.62 (s, 1H), 7.24 (d, 1H), 7.19 (d, 1H), 6.97 (m, 1H), 6.70 (dm, 1H), 6.52 (m, 1H), 6.05 (dm, 1H), 5.41 (dd, 1H), 4.25 (t, 2H), 4.05 (m, 2H), 2.97 (dd, 1H), 2.76 (m, 1H), 2.74 (m, 1H), 2.51 (br s, 4H), 2.42 (dd, 1H), 2.26 (br s, 4H), 2.11 (s, 3H), 2.10 (s, 3H), 2.03 (s, 3H), 1.08 (t, 3H).

HRMS calculated for $C_{34}H_{37}ClN_4O_5S$: 648.2173. found: 649.2275 (M+H).

Preparation 8j: Ethyl (2R)-2-[5-[5-chloro-4-methyl-6-[2-(4-methylpiperazin-1-yl)ethoxy]-3-pyridyl]-6-(4-fluorophenyl)thieno[2,3-d]pyrimidin-4-yl]oxy-3-(2-hydroxyphenyl)propanoate (mixture of diastereoisomers)

Step A: Ethyl (2R)-2-[5-[5-chloro-4-methyl-6-[2-(4-methylpiperazin-1-yl)ethoxy]-3-pyridyl]-6-(4-fluorophenyl)thieno[2,3-d]pyrimidin-4-yl]oxy-3-(2-tetrahydropyran-2-yloxyphenyl)propanoate 1.504 g ethyl (2R)-2-[5-bromo-6-(4-fluorophenyl)thieno[2,3-d]pyrimidin-4-yl]oxy-3-(2-tetrahydropyran-2-yloxyphenyl)propanoate (Preparation 4a) (2.50 mmol) and 1.052 g 1-[2-[[3-chloro-4-methyl-5-(4,4,5,5-tetramethyl-1,3,2-dioxaborolan-2-yl)-2-pyridyl]oxy]ethyl]-4-methyl-piperazine (Preparation 5q) (2.66 mmol) were dissolved in 15 mL THF, then 1.63 g Cs$_2$CO$_3$ (5.00 mmol) dissolved in 5 mL water was added. Then 177 mg AtaPhos (0.25 mmol) was added, and the mixture was stirred under nitrogen at reflux temperature until no further conversion was observed. Then the mixture was diluted with brine, extracted with DCM, the combined organic phases were dried over Na$_2$SO$_4$, filtered and concentrated under reduced pressure, then purified via flash chromatography using EtOAc and MeOH as eluents.

Step B: Ethyl (2R)-2-[5-[5-chloro-4-methyl-6-[2-(4-methylpiperazin-1-yl)ethoxy]-3-pyridyl]-6-(4-fluorophenyl)thieno[2,3-d]pyrimidin-4-yl]oxy-3-(2-hydroxyphenyl)propanoate (mixture of diastereoisomers)

The obtained ethyl (2R)-2-[5-[5-chloro-4-methyl-6-[2-(4-methylpiperazin-1-yl)ethoxy]-3-pyridyl]-6-(4-fluorophenyl)thieno[2,3-d]pyrimidin-4-yl]oxy-3-(2-tetrahydropyran-2-yloxyphenyl)propanoate was dissolved in 50 mL EtOH, then 10 mL 1.25 M HCl in EtOH was added and the mixture was stirred at room temperature until no further conversion was observed. Saturated NaHCO$_3$ solution was added carefully and the mixture was extracted with DCM, the combined organic phases were dried over Na$_2$SO$_4$, filtered and concentrated under reduced pressure. The crude product was purified via flash chromatography using DCM and MeOH as eluents to give Preparation 8j as a mixture of diastereoisomers.

$^1$H NMR (400 MHz, DMSO-d$_6$): 9.57 (br s, 1H), 8.65/8.64 (s, 1H), 8.07/7.68 (s, 1H), 7.37-7.31 (m, 2H), 7.27-7.22 (m, 2H), 6.98/6.96 (td, 1H), 6.72/6.70 (dd, 1H), 6.54/6.48 (td, 1H), 6.29/6.05 (dd, 1H), 5.55/5.42 (dd, 1H), 4.60-4.41 (m, 2H), 4.07-4.01 (m, 2H), 3.05/2.92 (dd, 1H), 2.72/2.69 (t, 2H), 2.48-2.12 (m, 9H), 2.09 (s, 3H), 2.08/1.90 (s, 3H), 1.10/1.05 (t, 3H).

MS (M+H): 706.2.

Preparation 8k: Ethyl (2R)-2-[(5S$_a$)-5-[3-chloro-2-methyl-4-[2-(4-methylpiperazin-1-yl)ethoxy]phenyl]-6-(3,4-difluorophenyl)thieno[2,3-d]pyrimidin-4-yl]oxy-3-(2-hydroxyphenyl)propanoate 7.85 g ethyl (2R)-2-[(5S$_a$)-5-[3-chloro-2-methyl-4-[2-(4-methylpiperazin-1-yl)ethoxy] phenyl]-6-(3,4-difluorophenyl)thieno[2,3-d]pyrimidin-4-yl]oxy-3-(2-tetrahydropyran-2-yloxyphenyl)propanoate (Preparation 7j) (9.72 mmol) was dissolved in 70 mL EtOH, then 50 mL 1.25 M HCl in EtOH was added and the mixture was stirred at room temperature until no further conversion was observed. The most of the EtOH was evaporated then water and saturated NaHCO$_3$ solution were added and the mixture was extracted with DCM. The combined organic layers were dried over Na$_2$SO$_4$, filtered and concentrated under reduced pressure. The crude product was purified via flash chromatography using DCM and MeOH as eluents to obtain Preparation 8k.

$^1$H NMR (500 MHz, DMSO-d$_6$): 9.54 (s, 1H), 8.63 (s, 1H), 7.46 (m, 1H), 7.32 (m, 1H), 7.30 (d, 1H), 7.18 (d, 1H), 7.11 (m, 1H), 6.97 (t, 1H), 6.71 (d, 1H), 6.53 (t, 1H), 6.19 (d, 1H), 5.46 (dd, 1H), 4.23 (m, 2H), 4.04 (m, 2H), 2.92 (dd, 1H), 2.73 (m, 2H), 2.50 (br s, 4H), 2.43 (dd, 1H), 2.25 (br s, 4H), 2.10 (s, 3H), 1.89 (s, 3H), 1.06 (t, 3H).

HRMS calculated for C$_{37}$H$_{37}$ClF$_2$N$_4$O$_5$S: 722.2141. found: 723.2211 (M+H).

Preparation 8l: Ethyl (2R)-2-[(5S$_a$)-5-(3-chloro-4-methoxy-2-methyl-phenyl)-6-(4-fluorophenyl)thieno[2,3-d]pyrimidin-4-yl]oxy-3-(2-hydroxyphenyl)propanoate Step A: Ethyl (2R)-2-[(5S$_a$)-5-(3-chloro-4-methoxy-2-methyl-phenyl)-6-(4-fluorophenyl)thieno[2,3-d]pyrimidin-4-yl]oxy-3-(2-tetrahydropyran-2-yloxyphenyl)propanoate 12.47 g ethyl (2R)-2-[5-bromo-6-(4-fluorophenyl)thieno[2,3-d]pyrimidin-4-yl]oxy-3-(2-tetra-hydropyran-2-yloxyphenyl)propanoate (Preparation 4a) (20.7 mmol) and 8.20 g 2-(3-chloro-4-methoxy-2-methyl-phenyl)-4,4,5,5-tetramethyl-1,3,2-dioxaborolane (Preparation 5d) (29.0 mmol) were dissolved in 145 mL THF, then 13.50 g Cs$_2$CO$_3$ (41.50 mmol) dissolved in 48 mL water was added. Then 1.17 g AtaPhos (1.66 mmol) was added, and the mixture was stirred under nitrogen at reflux temperature until no further conversion was observed. Then most of the volatiles were evaporated and the residue was diluted with brine. The pH was set to 6 with 2 M HCl, and the mixture was extracted with DCM. The combined organic layers were dried over Na$_2$SO$_4$, filtered and concentrated under reduced pressure, then purified via flash chromatography using heptane and EtOAc as eluents. The diastereoisomer pair eluting later was collected as ethyl (2R)-2-[(5S$_a$)-5-(3-chloro-4-methoxy-2-methyl-phenyl)-6-(4-fluorophenyl)thieno[2,3-d]pyrimidin-4-yl]oxy-3-(2-tetrahydropyran-2-yloxyphenyl)propanoate.

Step B: Ethyl (2R)-2-[(5S$_a$)-5-(3-chloro-4-methoxy-2-methyl-phenyl)-6-(4-fluorophenyl)thieno[2,3-d]pyrimidin-4-yl]oxy-3-(2-hydroxyphenyl)propanoate The product of Step A was dissolved in 300 mL EtOH, then 150 mL 1.25 M HCl in EtOH was added and the mixture was stirred at room temperature until no further conversion was observed. Most of the EtOH was evaporated, then saturated NaHCO$_3$ solution was added carefully, and the mixture was extracted with DCM, dried over Na$_2$SO$_4$, filtered and concentrated under reduced pressure. The crude product was purified via flash chromatography using DCM and MeOH as eluents to give Preparation 8l.

$^1$H NMR (500 MHz, DMSO-d$_6$): 9.52 (s, 1H), 8.61 (s, 1H), 7.30 (m, 3H), 7.22 (t, 2H), 7.14 (d, 1H), 6.97 (t, 1H), 6.71 (d, 1H), 6.53 (t, 1H), 6.18 (d, 1H), 5.45 (dd, 1H), 4.04 (m, 2H), 3.90 (s, 3H), 2.91 (dd, 1H), 2.44 (dd, 1H), 1.89 (s, 3H), 1.06 (t, 3H).

HRMS calculated for C$_{31}$H$_{26}$ClFN$_2$O$_5$S: 592.1235. found 593.1307 (M+H).

Preparation 8m: Ethyl (2R)-2-[(5S$_a$)-5-[3-chloro-2-methyl-4-[2-(4-methylpiperazin-1-yl)ethoxy]phenyl]-6-(2,3-difluorophenyl)thieno[2,3-d]pyrimidin-4-yl]oxy-3-(2-hydroxyphenyl)propanoate 9.72 mmol ethyl (2R)-2-[(5S$_a$)-5-[3-chloro-2-methyl-4-[2-(4-methylpiperazin-1-yl)ethoxy] phenyl]-6-(2,3-difluorophenyl)thieno[2,3-d]pyrimidin-4-yl]oxy-3-(2-tetrahydropyran-2-yloxyphenyl)propanoate (Preparation 7k) was dissolved in 70 mL EtOH, then 60 mL 1.25 M HCl in EtOH was added and the mixture was stirred at room temperature until no further conversion was observed. Ice and saturated NaHCO$_3$ solution were added and the mixture was extracted with DCM. The combined organic layers were dried over Na$_2$SO$_4$, filtered and concentrated under reduced pressure. The crude product was purified via flash chromatography using EtOAc and MeOH as eluents to obtain Preparation 8m.

$^1$H NMR (500 MHz, DMSO-d$_6$): 9.54 (br s, 1H), 8.66 (s, 1H), 7.48 (m, 1H), 7.22-7.18 (m, 3H), 7.09 (m, 1H), 6.97 (t, 1H), 6.72 (d, 1H), 6.52 (t, 1H), 6.21 (d, 1H), 5.47 (dd, 1H), 4.18 (m, 2H), 4.02 (m, 2H), 2.86 (dd, 1H), 2.72 (m, 2H), 2.53 (dd, 1H), 2.51 (br s, 4H), 2.39 (br s, 4H), 2.19 (br s, 3H), 1.94 (s, 3H), 1.04 (t, 3H).

HRMS calculated for C$_{37}$H$_{37}$ClF$_2$N$_4$O$_5$S: 722.2141. found 723.2177 (M+H).

Preparation 8n: Ethyl (2R)-2-[(5S$_a$)-[3-chloro-2-methyl-4-[2-(dimethylamino)ethoxy] phenyl]-6-(2,3-difluorophenyl)thieno[2,3-d]pyrimidin-4-yl]oxy-3-(2-hydroxyphenyl)propanoate 7.85 g ethyl (2R)-2-[(5S$_a$)-5-[3-chloro-2-methyl-4-[2-dimethylaminoethoxy]phenyl]-6-(2,3-difluorophenyl)thieno

[2,3-d]pyrimidin-4-yl]oxy-3-(2-tetrahydropyran-2-yloxyphenyl)propanoate (Preparation 7l) (9.72 mmol) was dissolved in 70 mL EtOH, then 50 mL 1.25 M HCl in EtOH was added and the mixture was stirred at room temperature until no further conversion was observed. The most of the EtOH was evaporated then water and saturated NaHCO$_3$ solution were added and the mixture was extracted with DCM. The combined organic layers were dried over Na$_2$SO$_4$, filtered and concentrated under reduced pressure. The crude product was purified via flash chromatography using DCM and MeOH as eluents to obtain Preparation 8n.
MS: (M+H)$^+$=667.8.

Preparation 8o: Ethyl (2R)-2-[(5S$_a$)-[3-chloro-2-methyl-4-[2-(piperazin-1-yl)ethoxy] phenyl]-6-(4-fluorophenyl)thieno[2,3-d]pyrimidin-4-yl]oxy-3-(2-hydroxyphenyl)propanoate 900 mg ethyl (2R)-2-[(5S$_a$)-[3-chloro-2-methyl-4-[2-(piperazin-1-yl)ethoxy]-phenyl]-6-(4-fluorophenyl)thieno[2,3-d]pyrimidin-4-yl]oxy-3-(2-tetrahydropyran-2-yl-oxyphenyl)-propanoate (Preparation 7m) was dissolved in 5 mL EtOH, then 5 mL 1.25 M HCl in EtOH was added and the mixture was stirred at room temperature until no further conversion was observed. Most of the EtOH was evaporated, then Et$_2$O was added and the precipitated HCl salt (white solid) was filtered, washed with Et$_2$O. The HCl salt was carefully treated with saturated NaHCO$_3$ solution, extracted with DCM, the combined organic phases were dried over Na$_2$SO$_4$, filtered and concentrated under reduced pressure to give Preparation 8o.
MS: (M+H)$^+$=691.0.

Preparation 8p: Ethyl (2R)-2-[(5S$_a$)-[3-chloro-2-methyl-4-[2-(4-ethylpiperazin-1-yl)ethoxy] phenyl]-6-(4-fluorophenyl)thieno[2,3-d]pyrimidin-4-yl]oxy-3-(2-hydroxyphenyl)propanoate 952 mg ethyl (2R)-2-[(5S$_a$)-[3-chloro-2-methyl-4-[2-(4-ethylpiperazin-1-yl)ethoxy]-phenyl]-6-(4-fluorophenyl)thieno[2,3-d]pyrimidin-4-yl]oxy-3-(2-tetrahydropyran-2-yl-oxyphenyl)-propanoate (Preparation 7n) was dissolved in 5 mL EtOH, then 5 mL 1.25 M HCl in EtOH was added and the mixture was stirred at room temperature until no further conversion was observed. Most of the EtOH was evaporated, then Et$_2$O was added and the precipitated HCl salt (white solid) was filtered, washed with Et$_2$O. The HCl salt was carefully treated with saturated NaHCO$_3$ solution, extracted with DCM, the combined organic phases were dried over Na$_2$SO$_4$, filtered and concentrated under reduced pressure to give Preparation 8p.
MS: (M+H)$^+$=719.2.

Preparation 8q: Ethyl (2R)-2-[(5R$_a$)-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-hydroxyphenyl)propanoate 199.5 mmol ethyl (2R)-2-[(5R$_a$)-[3-chloro-2-methyl-4-[2-(4-methylpiperazin-1-yl)ethoxy]-phenyl]-6-(4-fluorophenyl)thieno[2,3-d]pyrimidin-4-yl]oxy-3-(2-tetrahydropyran-2-yl-oxyphenyl)-propanoate (Preparation 7o) was dissolved in 1 L EtOH, then 1 L 1.25 M HCl in EtOH was added and the mixture was stirred at room temperature until no further conversion was observed. Most of the EtOH was evaporated, then Et$_2$O was added and the precipitated HCl salt (white solid) was filtered, washed with Et$_2$O. The HCl salt was carefully treated with saturated NaHCO$_3$ solution, extracted with DCM, the combined organic phases were dried over Na$_2$SO$_4$, filtered and concentrated under reduced pressure to give Preparation 8q.
MS: (M+H)=705.2.

Preparation 8r: Ethyl (2S)-2-[(5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-hydroxyphenyl)propanoate 199.5 mmol ethyl (2S)-2-[(5-[3-chloro-2-methyl-4-[2-(4-methylpiperazin-1-yl)ethoxy]-phenyl]-6-(4-fluorophenyl)thieno[2,3-d]pyrimidin-4-yl]oxy-3-(2-tetrahydropyran-2-yl-oxyphenyl)-propanoate (Preparation 7p) was dissolved in 1 L EtOH, then 1 L 1.25 M HCl in EtOH was added and the mixture was stirred at room temperature until no further conversion was observed. Most of the EtOH was evaporated, then Et$_2$O was added and the precipitated HCl salt (white solid) was filtered, washed with Et$_2$O. The HCl salt was carefully treated with saturated NaHCO$_3$ solution, extracted with DCM, the combined organic phases were dried over Na$_2$SO$_4$, filtered and concentrated under reduced pressure to give Preparation 8r.
MS: (M+H)=705.2.

Unless otherwise specified, most of the compounds of Preparation 9aa to 9er were obtained using General Procedures 9A to 9H described below.

General Procedure 9A:

The appropriate acetal (1.0 eq.) was stirred with 2N HCl solution (3 mL/mmol) at 60° C. until no further conversion was observed. Reaction mixture was cooled to 0° C., then NaOH (5.7 eq.) was added portionwise. The pH was adjusted to 8 using 10% K$_2$CO$_3$ solution, then sodium borohydride (2.0 eq.) was added portionwise keeping the temperature under 5° C. and the mixture was stirred for 30 min at 0° C. Reaction mixture was extracted with EtOAc, the combined organic phases were dried over Na$_2$SO$_4$, filtered and concentrated under reduced pressure. The crude product was purified via flash chromatography using heptane and EtOAc as eluents.

General Procedure 9B:

The appropriate acetal (1.0 eq.) was stirred with 1N HCl solution (3 mL/mmol) at 50° C. for 45 min. Reaction mixture was cooled to 0° C., then NaOH (2.85 eq.) was added portionwise. The pH was adjusted to 8 using 10% K$_2$CO$_3$ solution, then sodium borohydride (2.0 eq.) was added portionwise keeping the temperature under 5° C. and stirred for 30 min at 0° C. Reaction mixture was extracted with EtOAc, the combined organic phases were dried over Na$_2$SO$_4$, filtered and concentrated under reduced pressure. The crude product was purified via flash chromatography using heptane and EtOAc as eluents.

General Procedure 9C:

To the mixture of the appropriate amidine hydrochloride (1.2 eq.) and (E)-4-(dimethylamino)-1,1-dimethoxy-but-3-en-2-one (Preparation 9a1, 1.0 eq.) in dry methanol (0.5 mL/mmol) sodium methoxide (1.2 eq.) was added portionwise and the mixture was stirred at 75° C. for 2 h. The reaction mixture was cooled and concentrated under reduced pressure. To the residue water was added and it was extracted with DCM. The combined organic layers were dried over MgSO$_4$, filtered and concentrated under reduced pressure. The crude product was purified via flash chromatography using heptane and EtOAc as eluents.

General Procedure 9D:

To the mixture of the appropriate hydrazine hydrochloride (1.2 eq.) and (E)-4-(dimethylamino)-1,1-dimethoxy-but-3-en-2-one (Preparation 9a1, 1.0 eq.) in dry methanol (0.5 mL/mmol) sodium methoxide (1.2 eq.) was added portionwise and the mixture was stirred at 75° C. for 2 h. The reaction mixture was cooled and concentrated under reduced pressure. To the residue water was added and it was extracted with DCM. The combined organic phases were dried over $MgSO_4$, filtered and concentrated under reduced pressure. The crude product was purified via flash chromatography using heptane and EtOAc as eluents.

General Procedure 9E:

To the solution of the appropriate methylsulfonyl derivative (Preparation 9a3 1.0 eq.) in dry acetonitrile (3 ml/mmol) $K_2CO_3$ (2.0 eq.) and the appropriate amine (1.5 eq.) were added, and stirred at 70° C. until no further conversion was observed. The reaction mixture was cooled, filtered, the precipitate was washed with EtOAc, then the filtrate was concentrated under reduced pressure. Crude product was purified via flash chromatography using heptane and EtOAc as eluents.

General Procedure 9F:

To the solution of 1H-pyrazole (1.0 eq.) in DMF (0.5 mL/mmol) KOH (1.0 eq.) was added, then it was cooled to 0° C., and the appropriate halide was added (1.0 eq.) dropwise. The mixture was stirred at room temperature until no further conversion was observed. The mixture was diluted with DCM and washed with water. The organic layer was dried over $MgSO_4$, filtered and concentrated under reduced pressure. The crude product was purified via flash chromatography using heptane and EtOAc as eluents.

General Procedure 9G:

To the suspension of sodium hydride (1.10 eq.) in tetrahydrofurane (0.20 mL/mmol) was added the solution of pyrazole (1.0 eq.) in tetrahydrofurane (0.12 mL/mmol) dropwise, while the temperature was kept under 20° C. After the mixture was stirred at room temperature for 30 minutes, the appropriate halide (1.20 eq.) was added and the mixture was stirred further at same temperature for 16 hours. Next, the reaction mixture was refluxed for 15 hours. After completion the resulting precipitate was filtered off, the filtrate was concentrated then the residue was poured onto a mixture of water and ethyl acetate. The phases were separated, and the aqueous layer was extracted with ethyl acetate. The combined organic layers were dried over $Na_2SO_4$, filtered and concentrated under reduced pressure. The crude product was purified via distillation.

General Procedure 9H:

To the solution of appropriate alkyl pyrazole (1.0 eq.) in dry tetrahydrofurane (1.5 mL/mmol) n-butyllithium (1.10 eq.) was added dropwise at −70° C. The mixture was stirred further at same temperature for 30 minutes; afterwards allowed to warm up to 0° C. in approx. 30 minutes, and cooled in a dry ice bath. N,N-dimethylformamide (1.10 eq.) was added dropwise at −70° C., then the reaction mixture was stirred at room temperature overnight. The mixture was cooled to 15° C., and saturated ammonium chloride solution was added dropwise to the mixture at 15° C., then the mixture was poured into saturated ammonium chloride solution. The phases were separated, the aqueous layer was extracted with ethyl acetate. The combined organic layers were dried over $Na_2SO_4$, and concentrated under reduced pressure. The residue was used in the next step without further purification. To the solution of the appropriate crude aldehyde (1.0 eq.) in ethanol (0.5 mL/mmol) sodium borohydride (1.30 eq.) was added portionwise at −15° C. then the reaction mixture was stirred at room temperature for 1 h. The mixture was poured onto crushed ice and stirred for 16 hours. The precipitate was filtered off, and the filtrate was concentrated under reduced pressure. The oily phase was separated, and the aqueous layer was extracted with ethyl acetate. The combined organic layers were dried over $Na_2SO_4$, and concentrated to dryness.

Preparation 9a1: (E)-4-(Dimethylamino)-1,1-dimethoxy-but-3-en-2-one 502.1 g 1,1-dimethoxypropan-2-one (4.25 mol) and 506.4 g 1,1-dimethoxy-N,N-dimethyl-methanamine (4.25 mol) were mixed in a 2 L flask and stirred at 105° C. for 3 hours. The formed MeOH was removed continuously via distillation. When MeOH formation stopped (at 65° C. head temperature) the reaction mixture was vacuum distilled (decreasing the pressure slowly to 30 mbar) to remove side products and unreacted starting materials. The crude product was distilled at 0.1 mbar. Fractions were collected between 107-118° C. head temperature (bath temperature 160-165° C.) to give a yellow oil.

$^1$H NMR (500 MHz, DMSO-$d_6$): 7.59 (d, 1H), 5.17 (d, 1H), 4.42 (s, 1H), 3.25 (s, 6H), 3.09 (s, 3H), 2.78 (s, 3H).

Preparation 9a2:
4-(Dimethoxymethyl)-2-methylsulfanyl-pyrimidine 198 g sodium methoxide (3.67 mmol) was dissolved in 3 L MeOH and cooled to 0° C. 322 g thiocarbamide (4.23 mol) was added portionwise and the mixture was stirred for 1 hour. Then 488 g (E)-4-(dimethylamino)-1,1-dimethoxy-but-3-en-2-one (Preparation 9a1) (2.82 mol) was added dropwise at 0° C., then it was heated to 70° C. for 4 hours. It was cooled to room temperature, 237 mL methyl iodide (3.81 mol) was added dropwise, keeping the temperature below 28° C., and the resulting mixture was stirred overnight at room temperature. It was filtered, the filtrate was concentrated under reduced pressure, diluted with EtOAc, washed with water and brine. The combined aqueous layers were extracted with EtOAc. The combined organic layers were dried over $Na_2SO_4$, filtered and concentrated under reduced pressure. The residue was dissolved in 500 mL $Et_2O$, filtered through a pad of silica, using $Et_2O$ as eluent. The filtrate was concentrated under reduced pressure to give a light brown oil.

$^1$H NMR (400 MHz, DMSO-$d_6$): 8.69 (d, 1H), 7.23 (d, 1H), 5.22 (s, 1H), 3.33 (s, 6H), 2.52 (s, 3H).

Preparation 9a3:
4-(Dimethoxymethyl)-2-methylsulfonyl-pyrimidine

To solution of 180 g 4-(dimethoxymethyl)-2-methylsulfanyl-pyrimidine (Preparation 9a2, 940 mmol) in 1.5 L methanol and 1.5 L $H_2O$ 752 g Oxone (potassium peroxymonosulfate, 1220 mmol) was added portionwise at −5° C., then stirred at 0° C. overnight. The reaction mixture was concentrated under reduced pressure to half volume using a 30° C. bath and then the mixture was filtered, and the precipitates were was washed with DCM. The filtrate was extracted with DCM. The combined organic layers were dried over $MgSO_4$, filtered and concentrated under reduced pressure to give a light brown oil.

$^1$H NMR (400 MHz, CDCl$_3$): 8.98 (d, 1H), 7.97 (d, 1H), 5.36 (s, 1H), 3.47 (s, 6H), 3.39 (s, 3H).

Preparation 9a4: 2-Methylsulfonyl-4-(tetrahydropyran-2-yloxymethyl)pyrimidine Step A:

To solution of 7.24 g (2-methylsulfanylpyrimidin-4-yl)methanol (Preparation 9aa, 47.5 mmol) and 30.0 g 3,4-dihydro-2H-pyran (357 mmol) in 150 mL DCM 452 mg of p-toluenesulfonic acid monohydrate (2.30 mmol) was added and it was stirred at room temperature for 2 h. The reaction mixture was diluted with DCM, then it was washed with water and saturated aq. NaHCO$_3$. The organic layer was dried over Na$_2$SO$_4$ and concentrated under reduced pressure. The residue was purified via flash chromatography using heptane and EtOAc as eluents to give 2-methylsulfanyl-4-(tetrahydropyran-2-yloxymethyl)pyrimidine.

MS: (M+H)$^+$=241.2.

Step B:

To solution of 11.4 g 2-methylsulfanyl-4-(tetrahydropyran-2-yloxymethyl)pyrimidine (47.5 mmol) in 500 mL DCM 24.6 g MCPBA (3-chloroperoxybenzoic acid, 143 mmol) was added portionwise at 0° C. and stirred at this temperature for 1 h. The precipitates were filtered off, and the filtrate was washed water and saturated aq. NaHCO$_3$. The organic layer was dried over Na$_2$SO$_4$ and concentrated under reduced pressure. The residue was purified via flash chromatography using heptane and EtOAc as eluents to give the title product.

$^1$H NMR (400 MHz, CDCl$_3$): 9.05 (d, 1H), 7.86 (d, 1H), 4.83 (d, 1H), 4.80 (m, 1H), 4.74 (d, 1H), 3.77 (m, 1H), 3.48 (m, 1H), 3.41 (s, 3H), 1.88-1.40 (m, 6H).

Preparation 9a5: 5-(Dimethoxymethyl)-1H-pyrazole

To the mixture of the 4.11 g hydrazine hydrochloride (60.0 mmol) and 8.66 g (E)-4-(dimethylamino)-1,1-dimethoxy-but-3-en-2-one (Preparation 9a1, 50.0 mmol) in dry methanol 3.241 g sodium methoxide (60.0 mmol) was added portionwise and the mixture was stirred at 50° C. for 45 min. The reaction mixture was cooled and concentrated under reduced pressure. To the residue water was added and it was extracted with DCM. The combined organic layers were dried over MgSO$_4$ and concentrated under reduced pressure. The crude product was purified via flash chromatography using heptane and EtOAc as eluents to give the title product.

$^1$H NMR (400 MHz, CDCl$_3$): 12.78 (br s, 1H), 7.68 (s, 1H), 6.22 (d, 1H), 5.37 (s, 1H), 3.24 (s, 6H).

Preparation 9aa: (2-Methylsulfanylpyrimidin-4-yl)methanol

Starting from 4-(dimethoxymethyl)-2-methylsulfanyl-pyrimidine (Preparation 9a2) using General Procedure 9A the title product was obtained as white crystals.

$^1$H NMR (400 MHz, DMSO-d$_6$): 8.61 (d, 1H), 7.25 (d, 1H), 5.63 (t, 1H), 4.49 (d, 2H), 2.49 (s, 3H).

Preparation 9ab: [2-(2-Methoxyethylsulfanyl)pyrimidin-4-yl]methanol

Step A:

1.51 g sodium methoxide (28.0 mmol) was dissolved in 15 mL MeOH and cooled to 0° C. 2.44 g thiocarbamide (32.0 mol) was added portionwise and the mixture was stirred for 1 hour. Then 3.46 g (E)-4-(dimethylamino)-1,1-dimethoxy-but-3-en-2-one (Preparation 9a1) (20.0 mol) was added dropwise at 0° C., then it was heated to 80° C. and stirred there for 2 hours. It was cooled to room temperature, 4.17 g 1-bromo-2-methoxy-ethane (30 mmol) was added and the mixture was stirred for 1 hour at 50° C., then overnight at room temperature. It was filtered, the filtrate was concentrated under reduced pressure, diluted with EtOAc, washed with water and brine. The organic layer was dried over Na$_2$SO$_4$ and concentrated under reduced pressure. The residue was purified via flash chromatography using heptane and ethyl-acetate as eluents to give a light yellow oil (4-(dimethoxymethyl)-2-(2-methoxyethylsulfanyl)pyrimidine).

$^1$H NMR (400 MHz, DMSO-d$_6$): 8.68 (d, 1H), 7.24 (d, 1H), 5.23 (s, 1H), 3.59 (t, 2H), 3.33 (s, 6H), 3.32 (t, 2H), 3.28 (s, 3H).

Step B:

Starting from this material using General Procedure 9A the title product was obtained.

$^1$H NMR (400 MHz, DMSO-d$_6$): 8.60 (d, 1H), 7.25 (d, 1H), 5.63 (t, 1H), 4.48 (d, 2H), 3.57 (t, 2H), 3.29 (t, 2H), 3.27 (s, 3H).

Preparation 9ac: [2-(3-Methoxypropylsulfanyl)pyrimidin-4-yl]methanol

Step A:

1.51 g sodium methoxide (28.0 mmol) was dissolved in 15 mL MeOH and cooled to 0° C. 2.44 g thiocarbamide (32.0 mol) was added portionwise and the mixture was stirred for 1 hour. Then 3.46 g (E)-4-(dimethylamino)-1,1-dimethoxy-but-3-en-2-one (Preparation 9a1) (20.0 mol) was added dropwise at 0° C., then it was heated at 80° C. for 2 hours. It was cooled to room temperature, 4.59 g 1-bromo-3-methoxy-propane (30 mmol) was added and was stirred 1 hour at 50° C., then overnight at room temperature. It was filtered, the filtrate was concentrated under reduced pressure, diluted with EtOAc, washed with water and brine. The organic layer was dried over Na$_2$SO$_4$, filtered and concentrated under reduced pressure. The residue was purified using flash chromatography using heptane and ethyl-acetate as eluents to give a light yellow oil (4-(dimethoxymethyl)-2-(3-methoxypropylsulfanyl)pyrimidine).

$^1$H NMR (400 MHz, DMSO-d$_6$): 8.68 (d, 1H), 7.23 (d, 1H), 5.22 (s, 1H), 3.43 (t, 2H), 3.33 (s, 6H), 3.24 (s, 3H), 3.14 (m, 2H), 1.90 (m, 2H).

Step B:

Starting from this material using General Procedure 9A the title product was obtained.

$^1$H NMR (400 MHz, DMSO-d$_6$): 8.60 (d, 1H), 7.24 (d, 1H), 5.63 (t, 1H), 4.48 (d, 2H), 3.42 (t, 2H), 3.24 (s, 3H), 3.12 (t, 2H) 1.88 (m, 2H).

Preparation 9ad: (2-Ethoxypyrimidin-4-yl)methanol

Step A:

To the solution of 1500 mg 4-(dimethoxymethyl)-2-methylsulfonyl-pyrimidine (Preparation 9a3, 6.46 mmol) in 60 mL ethanol 527 mg sodium ethoxide (7.75 mmol) was added and stirred at room temperature for 1 h. The volatiles were evaporated under reduced pressure and the residue was purified via flash chromatography using heptane and EtOAc as eluents to give 4-(dimethoxymethyl)-2-ethoxy-pyrimidine.

MS: (M+H)$^+$=199.2.

Step B:

Starting from this material using General Procedure 9A the title product was obtained.

MS: (M+H)$^+$=155.2

Preparation 9ae: (2-Isopropoxypyrimidin-4-yl)methanol

Step A:

To the solution of 1500 mg 4-(dimethoxymethyl)-2-methylsulfonyl-pyrimidine (Preparation 9a3, 6.46 mmol) in 50 mL propan-2-ol the solution of 310 mg sodium hydride (60%, 7.75 mmol) in 10 ml propan-2-ol was added and stirred at room temperature for 1 h. The volatiles were evaporated under reduced pressure and the residue was purified via flash chromatography using heptane and EtOAc as eluents to give 4-(dimethoxymethyl)-2-isopropoxy-pyrimidine.

MS: $(M+H)^+=213.2$.

Step B:

Starting from this material using General Procedure 9A the title product was obtained.

MS: $(M+H)^+=169.2$

Preparation 9af: (2-Propoxypyrimidin-4-yl)methanol

Step A:

To the solution of 1500 mg 4-(dimethoxymethyl)-2-methylsulfonyl-pyrimidine (Preparation 9a3, 6.46 mmol) in 50 mL propan-1-ol the solution of 310 mg sodium hydride (60%, 7.75 mmol) in 10 ml propan-1-ol was added and stirred at room temperature for 1 h. The volatiles were evaporated under reduced pressure and the residue was purified via flash chromatography using heptane and EtOAc as eluents to give 4-(dimethoxymethyl)-2-propoxy-pyrimidine.

MS: $(M+H)^+=213.2$.

Step B:

Starting from this material using General Procedure 9A the title product was obtained.

MS: $(M+H)=169.2$

Preparation 9ag: [2-(2-Methoxyethoxy)pyrimidin-4-yl]methanol

Step A:

2-Methoxyethanol (10 mL) was cooled to 0° C. and 413 mg of sodium hydride (60%, 10.33 mmol) was added portionwise, then 2.00 g 4-(dimethoxymethyl)-2-methylsulfonyl-pyrimidine (Preparation 9a3) (8.61 mmol) was added and stirred at room temperature for 1 h. The reaction mixture was concentrated under reduced pressure. To the residue water was added and it was extracted with DCM. The combined organic layers were dried over $MgSO_4$ and concentrated under reduced pressure to give 4-(dimethoxymethyl)-2-(2-methoxyethoxy)pyrimidine.

MS: $(M+H)^+=229.2$.

Step B:

Starting from this material using General Procedure 9A the title product was obtained.

MS: $(M+H)^+=185.2$

Preparation 9ah: [2-(2-Ethoxyethoxy)pyrimidin-4-yl]methanol

Step A:

20 mL 2-ethoxyethanol was cooled to 0° C., then 240 mg sodium hydride (6.00 mmol) was added portionwise and the mixture was stirred at this temperature for 15 min. The solution of 1.16 g 4-(dimethoxymethyl)-2-methylsulfonyl-pyrimidine (Preparation 9a3, 5.00 mmol) in 3 mL 2-ethoxyethanol was added, then cooling was removed and reaction mixture was stirred at room temperature for 2 h. Brine was added then the mixture was extracted with DCM. The combined organic layers were dried over $MgSO_4$ and concentrated under reduced pressure. The residue was purified via flash chromatography using heptane and EtOAc as eluents to give 4-(dimethoxymethyl)-2-(2-ethoxyethoxy)pyrimidine.

$^1$H NMR (400 MHz, $CDCl_3$): 8.54 (d, 1H), 7.17 (d, 1H), 5.18 (s, 1H), 4.53 (t, 2H), 3.82 (t, 2H), 3.59 (q, 2H), 3.42 (s, 6H), 1.22 (t, 3H).

Step B:

Starting from this material using General Procedure 9A the title product was obtained.

$^1$H NMR (400 MHz, $CDCl_3$): 8.47 (d, 1H), 6.95 (d, 1H), 4.71 (br s, 2H), 4.56 (t, 2H), 3.84 (t, 2H), 3.62 (q, 2H), 1.25 (t, 3H).

Preparation 9ai: [2-(2,2,2-Trifluoroethoxy)pyrimidin-4-yl]methanol

Step A:

To the solution of 5.00 g 4-(dimethoxymethyl)-2-methylsulfonyl-pyrimidine (Preparation 9a3, 21.5 mmol) in 54 ml dry acetonitrile 5.95 g $K_2CO_3$ (43.1 mmol) and 3.24 g 2,2,2-trifluoroethanol (32.3 mmol) were added, and stirred at 60° C. until no further conversion was observed. The reaction mixture was cooled, filtered, the precipitate was washed with EtOAc, then the filtrate was concentrated under reduced pressure. The crude product was purified via flash chromatography using heptane and EtOAc as eluents to give 4-(dimethoxymethyl)-2-(2,2,2-trifluoroethoxy)pyrimidine.

$^1$H NMR (400 MHz, DMSO-$d_6$): 8.74 (d, 1H), 7.32 (d, 1H), 5.25 (s, 1H), 5.05 (q, 2H), 3.34 (s, 6H).

Step B:

Starting from this material using General Procedure 9A the title product was obtained.

$^1$H NMR (400 MHz, DMSO-$d_6$): 8.65 (d, 1H), 7.32 (d, 1H), 5.69 (t, 1H), 5.02 (q, 2H), 4.51 (d, 2H).

Preparation 9aj: [2-(3,3,3-Trifluoropropoxy)pyrimidin-4-yl]methanol

Step A:

To the solution of 2.00 g Preparation 9a3 (8.61 mmol) in acetonitrile 2.38 g $K_2CO_3$ (17.2 mmol), then 3,3,3-trifluoropropan-1-ol were added and the so obtained mixture was stirred for 10 h at 60° C. The reaction mixture was cooled, filtered and the filtrate concentrated under reduced pressure. The residue was purified via flash chromatography using heptane and ethyl-acetate as eluents to give 4-(dimethoxymethyl)-2-(3,3,3-trifluoropropoxy)pyrimidine.

$^1$H NMR (400 MHz, DMSO-$d_6$): 8.68 (d, 1H), 7.22 (d, 1H), 5.22 (s, 1H), 4.53 (t, 2H), 3.33 (s, 6H), 2.83 (m, 2H).

Step B:

Starting from this material using General Procedure 9A the title product was obtained.

$^1$H NMR (400 MHz, DMSO-$d_6$): 8.59 (d, 1H), 7.22 (d, 1H), 5.63 (t, 1H), 4.49 (m, 4H), 2.81 (m, 2H).

Preparation 9ak: (2-Phenoxypyrimidin-4-yl)methanol

Step A:

To the solution of 1.50 g Preparation 9a3 (6.46 mmol) in 50 mL THF 2.14 g $K_2CO_3$ (15.5 mmol), then 729 mg of phenol (7.75 mmol) were added and the so obtained mixture was stirred for 3 days at room temperature. The reaction mixture was concentrated under reduced pressure. The residue was purified via flash chromatography using heptane and ethyl-acetate as eluents to give 4-(dimethoxymethyl)-2-phenoxy-pyrimidine.

MS: (M+H)$^+$=247.2.

Step B:

Starting from this material using General Procedure 9A the title product was obtained.

MS: (M+H)$^+$=203.2

Preparation 9al: (2-Aminopyrimidin-4-yl)methanol

Step A:

To the stirred mixture of 2.29 g of guanidine hydrochloride (24.0 mmol) and 8 mL of methanol 1.30 g sodium methoxide (24.0 mmol) and 3.46 g Preparation 9a1 (20.0 mmol) were added, then stirred at 75° C. for 2 h. The reaction mixture was cooled, concentrated under reduced pressure, then 30 mL water was added. The formed precipitate was filtered, washed with water and dried to give 4-(dimethoxymethyl)pyrimidin-2-amine.

$^1$H NMR (400 MHz, DMSO-d$_6$): 8.26 (d, 1H), 6.71 (br s, 2H), 6.61 (d, 1H), 5.00 (s, 1H), 3.28 (s, 6H).

Step B:

The solution of 5.01 g 4-(dimethoxymethyl)pyrimidin-2-amine (29.5 mmol) in 100 mL 2N aq. HCl was stirred at 60° C. for 5 h. Reaction mixture was cooled to 0° C., then 7.60 g NaOH (190 mmol) was added portionwise. The pH was adjusted to 8 using 10% K$_2$CO$_3$ solution, then 2.24 g sodium borohydride (59.0 mmol) was added portionwise keeping the temperature under 5° C. and stirred for 30 min at 0° C. The reaction mixture was extracted with EtOAc, the combined organic phases were dried over Na$_2$SO$_4$ and concentrated under reduced pressure. The crude product was purified via flash chromatography (MeOH—containing 1% NH$_3$— and DCM).

$^1$H NMR (400 MHz, DMSO-d$_6$): 8.20 (d, 1H), 6.66 (d, 1H), 6.49 (br s, 2H), 5.35 (t, 1H), 4.30 (d, 2H).

Preparation 9am:
[2-(Methylamino)pyrimidin-4-yl]methanol

To the 2M solution of methylamine in THF (3 mL) 232 mg 4-(dimethoxymethyl)-2-methylsulfonyl-pyrimidine (Preparation 9a3, 1.00 mmol) was added and it was stirred at room temperature for 1 h. The reaction mixture was concentrated under reduced pressure, the residue was diluted with EtOAc and washed with brine. The organic layer was dried over MgSO$_4$ and concentrated under reduced pressure. To the residue 3 mL 2N HCl was added and it was stirred at 60° C. for 2 h. Than it was cooled to 0° C., the pH was adjusted to 9 using 2N NaOH solution, and then 76 mg sodium borohydride (2.0 mmol) was added and the mixture was stirred for 1 h. The reaction mixture was extracted with EtOAc, the combined organic layers were dried over MgSO$_4$ and concentrated under reduced pressure to give the title product.

MS: (M+2H)$^+$=141.4.

Preparation 9an:
[2-(Dimethylamino)pyrimidin-4-yl]methanol

To 3 mL dimethylamine solution (2M in THF, 6 mmol) 232 mg 4-(dimethoxymethyl)-2-methylsulfonyl-pyrimidine (Preparation 9a3, 1.00 mmol) was added and it was stirred at room temperature for 1 h. The reaction mixture was concentrated under reduced pressure, the residue was diluted with EtOAc and washed with brine. The organic layer was dried over MgSO$_4$ and concentrated under reduced pressure. To the residue 3 mL 2N HCl was added and it was stirred at 60° C. for 2 h. It was cooled to 0° C., the pH was adjusted to 9 using 2N NaOH solution, and then 76 mg sodium borohydride (2.0 mmol) was added and stirred for 1 h. The reaction mixture was extracted with EtOAc, and the combined organic layers were dried over MgSO$_4$ and concentrated under reduced pressure to give the title product.

MS: (M+H)$^+$=154.4.

Preparation 9ao:
[2-(2-Methoxyethylamino)pyrimidin-4-yl]methanol

Step A:

Starting from 4-(dimethoxymethyl)-2-methylsulfonyl-pyrimidine (Preparation 9a3) and 2-methoxyethanamine using General Procedure 9E 4-(dimethoxymethyl)-N-(2-methoxyethyl)pyrimidin-2-amine was obtained.

$^1$H NMR (400 MHz, CDCl$_3$): 8.32 (d, 1H), 6.73 (d, 1H), 5.61 (br s, 1H), 5.08 (s, 1H), 3.62 (m, 2H) 3.56 (m, 2H), 3.38 (s, 6H), 3.36 (s, 3H).

Step B:

Starting from this material using General Procedure 9A the title product was obtained.

$^1$H NMR (400 MHz, CDCl$_3$): 8.22 (d, 1H), 6.48 (d, 1H), 5.64 (br s, 1H), 4.57 (s, 2H), 3.65 (m, 2H) 3.58 (m, 2H), 3.49 (s, 1H), 3.39 (s, 3H).

Preparation 9ap: [2-[2-Methoxyethyl(methyl)amino]pyrimidin-4-yl]methanol

Step A:

Starting from 4-(dimethoxymethyl)-2-methylsulfonyl-pyrimidine (Preparation 9a3) and 2-methoxy-N-methyl-ethanamine as amine reagent using General Procedure 9E 4-(dimethoxymethyl)-N-(2-methoxyethyl)-N-methyl-pyrimidin-2-amine was obtained.

$^1$H NMR (400 MHz, CDCl$_3$): 8.32 (d, 1H), 6.66 (d, 1H), 5.04 (s, 1H), 3.82 (t, 2H) 3.58 (t, 2H), 3.40 (s, 6H), 3.34 (s, 3H), 3.21 (s, 3H).

Step B:

Starting from this product using General Procedure 9A the title product was obtained.

$^1$H NMR (400 MHz, CDCl$_3$): 8.25 (d, 1H), 6.39 (d, 1H), 4.57 (d, 2H), 3.90 (br s, 1H), 3.85 (t, 2H) 3.61 (t, 2H), 3.37 (s, 3H), 3.24 (s, 3H).

Preparation 9aq:
[2-(4-Methylpiperazin-1-yl)pyrimidin-4-yl]methanol

Step A:

Starting from 4-(dimethoxymethyl)-2-methylsulfonyl-pyrimidine (Preparation 9a3) and 1-methylpiperazine using General Procedure 9E 4-(dimethoxymethyl)-2-(4-methylpiperazin-1-yl)pyrimidine was obtained.

$^1$H NMR (400 MHz, CDCl$_3$): 8.34 (d, 1H), 6.70 (d, 1H), 5.06 (s, 1H), 3.85 (m, 4H), 3.41 (s, 6H), 2.46 (m, 4H), 2.34 (s, 3H).

Step B:

Starting from 4-(dimethoxymethyl)-2-(4-methylpiperazin-1-yl)pyrimidine using General Procedure 9A the title product was obtained.

$^1$H NMR (400 MHz, DMSO-d$_6$): 8.33 (d, 1H), 6.72 (d, 1H), 5.41 (t, 1H), 4.35 (d, 2H), 3.70 (m, 4H), 2.36 (m, 4H), 2.22 (s, 3H).

Preparation 9ar:
(2-(Morpholin-4-yl)pyrimidin-4-yl)methanol

Step A:

3.50 g Preparation 9a3 (15.1 mmol) was stirred in 23 mL morpholine at room temperature for 2 h. The reaction mixture was concentrated under reduced pressure and the residue was purified via flash chromatography using heptane and ethyl-acetate as eluents to give 4-[4-(dimethoxymethyl) pyrimidin-2-yl]morpholine.

$^1$H NMR (400 MHz, DMSO-$d_6$): 8.42 (d, 1H), 6.71 (d, 1H), 5.06 (s, 1H), 3.67 (m, 8H), 3.31 (s, 6H).

Step B:

Starting from 4-[4-(dimethoxymethyl)pyrimidin-2-yl] morpholine using General Procedure 9A the title product was obtained.

$^1$H NMR (400 MHz, DMSO-$d_6$): 8.36 (d, 1H), 6.76 (d, 1H), 5.43 (t, 1H), 4.36 (d, 2H), 3.65 (m, 8H).

Preparation 9as:
[2-(1H-[1,2,3]Triazol-1-yl)pyrimidin-4-yl]methanol

Step A:

To the solution of 829 mg 1H-[1,2,3]triazole (12.0 mmol) in acetone 2.07 g $K_2CO_3$ (15.0 mmol), then Preparation 9a3 were added and the mixture was stirred for 2 h at room temperature. The reaction mixture was filtered and concentrated under reduced pressure. The residue was purified via flash chromatography using heptane and ethyl-acetate as eluents to give 4-(dimethoxymethyl)-2-(1H-[1,2,3]triazol-1-yl)pyrimidine as white crystals.

$^1$H NMR (400 MHz, DMSO-$d_6$): 9.06 (d, 1H), 8.89 (d, 1H), 8.01 (d, 1H), 7.70 (d, 1H), 5.44 (s, 1H), 3.40 (s, 6H).

Note: 4-(dimethoxymethyl)-2-(1H-[1,2,3]triazol-2-yl)pyrimidine was also obtained.

$^1$H NMR (400 MHz, DMSO-$d_6$): 9.03 (d, 1H), 8.24 (s, 2H), 7.66 (d, 1H), 5.42 (s, 1H), 3.39 (s, 6H).

Step B:

Starting from 1.40 g 4-(dimethoxymethyl)-2-(1H-[1,2,3] triazol-1-yl)pyrimidine using General Procedure 9A the title product was obtained.

$^1$H NMR (400 MHz, DMSO-$d_6$): 8.97 (d, 1H), 8.88 (d, 1H), 7.99 (d, 1H), 7.70 (d, 1H), 5.86 (t, 1H), 4.69 (d, 2H).

Preparation 9at:
[2-(Benzylamino)pyrimidin-4-yl]methanol

To the solution of 0.32 mL benzylamine in 4 mL DCM 460 mg 4-(dimethoxymethyl)-2-methylsulfonyl-pyrimidine (Preparation 9a3, 2.00 mmol) was added and it was stirred at 40° C. for 16 h. The reaction mixture was diluted with DCM and washed with brine. The organic layer was dried over $MgSO_4$ and concentrated under reduced pressure. To the residue 6 mL 2N HCl was added and it was stirred at 60° C. for 2 h. It was cooled to 0° C., the pH was adjusted to 9 using 2N NaOH solution, and then 152 mg sodium borohydride (2.0 mmol) was added and stirred for 1 h. The reaction mixture was extracted with EtOAc, the combined organic layers were dried over $MgSO_4$ filtered and concentrated under reduced pressure to give the title product.

MS: $(M+H)^+$=216.2.

Preparation 9au:
[2-(Cyclopropylmethoxy)pyrimidin-4-yl]methanol

Step A:

10 mL cyclopropylmethanol was cooled to 0° C., then 1.10 g sodium hydride (27.5 mmol) was added portionwise and the mixture was stirred at this temperature for 30 min. This mixture was added to 953 mg of 2-methylsulfonyl-4-(tetrahydropyran-2-yloxymethyl)pyrimidine (Preparation 9a4, 3.50 mmol) and it was stirred at room temperature for 30 min. Water was added then the mixture was extracted with DCM. The combined organic layers were dried over $MgSO_4$, filtered and concentrated under reduced pressure. The residue was purified via flash chromatography using heptane and EtOAc as eluents to give 2-(cyclopropylmethoxy)-4-(tetrahydropyran-2-yloxymethyl)pyrimidine.

MS: $(M+H)^+$=265.2.

Step B:

To the solution of 732 mg of 2-(cyclopropylmethoxy)-4-(tetrahydropyran-2-yloxymethyl)pyrimidine (2.77 mmol) in 50 mL EtOH 160 mg pyridinium p-toluenesulfonate (0.64 mmol) was added and the mixture was stirred at 50° C. for 16 h. The mixture was concentrated under reduced pressure, the residue was purified via flash chromatography using heptane and EtOAc as eluents to give the title product.

$^1$H NMR (400 MHz, DMSO-$d_6$): 8.55 (d, 1H), 7.16 (d, 1H), 5.59 (t, 1H), 4.45 (m, 2H), 4.11 (d, 2H), 1.25 (m, 1H), 0.55 (m, 2H), 0.33 (m, 2H).

Preparation 9aw:
[2-(4-Pyridylmethoxy)pyrimidin-4-yl]methanol

To the solution of 164 mg of 4-pyridylmethanol (1.50 mmol) in 3 mL DMF 80 mg of sodium hydride (60%, 2.0 mmol) was added at 0° C. and stirred at room temperature for 30 min. This mixture was added to the solution of 272 mg of 2-methylsulfonyl-4-(tetrahydropyran-2-yloxymethyl) pyrimidine (Preparation 9a4, 1.00 mmol) in 1 mL DMF. The mixture was stirred at room temperature for 1 h, then it was diluted with water, and extracted with DCM. The combined organic layers were dried over $Na_2SO_4$ and concentrated under reduced pressure. The residue was dissolved in 15 mL EtOH then 160 mg pyridinium p-toluenesulfonate (0.64 mmol) was added and stirred at 50° C. for 16 h. The mixture was concentrated under reduced pressure, the residue diluted with water, and extracted with DCM. The combined organic layers were dried over $Na_2SO_4$ and concentrated under reduced pressure. The residue was purified via flash chromatography using heptane and EtOAc as eluents to give the title product.

MS: $(M+H)^+$=218.2.

Preparation 9ax:
(2-Benzyloxypyrimidin-4-yl)methanol

Step A:

To 4.25 mL phenylmethanol cooled to 0° C. 545 mg sodium hydride (13.6 mmol) was added portionwise and the mixture was stirred at room temperature for 30 min. This mixture was added to 460 mg of 2-methylsulfonyl-4-(tetrahydropyran-2-yloxymethyl)pyrimidine (Preparation 9a4, 1.69 mmol) and it was stirred at room temperature for 1 h. Water was added then the mixture was extracted with DCM. The combined organic layers were dried over $MgSO_4$ and concentrated under reduced pressure. The residue was purified via flash chromatography using heptane and EtOAc as eluents to give 2-benzyloxy-4-(tetrahydropyran-2-yloxymethyl)pyrimidine.

MS: (M+H)$^+$=301.2.

Step B:

To the solution of 408 mg of 2-benzyloxy-4-(tetrahydropyran-2-yloxymethyl)pyrimidine (1.36 mmol) in 50 mL EtOH 79 mg pyridinium p-toluenesulfonate (0.30 mmol) was added and the mixture was stirred at 50° C. for 16 h. The mixture was concentrated under reduced pressure, the residue was purified via flash chromatography using heptane and EtOAc as eluents to give the title product.

$^1$H NMR (400 MHz, DMSO-d$_6$): 8.59 (d, 1H), 7.47-7.30 (m, 5H), 7.21 (d, 1H), 5.62 (t, 1H), 5.37 (s, 2H), 4.49 (m, 2H).

Preparation 9ay: {2-[(1-methyl-1H-imidazol-5-yl)methoxy]pyrimidin-4-yl}methanol

To the solution of 224 mg of (1-methyl-1H-imidazol-5-yl)methanol (2.00 mmol) in 5 mL DMF 158 mg of sodium hydride (60%, 3.95 mmol) was added at 0° C. and it was stirred at room temperature for 30 min. This mixture was added to the solution of 500 mg of 2-methylsulfonyl-4-(tetrahydropyran-2-yloxymethyl)pyrimidine (Preparation 9a4, 1.84 mmol) in 1 mL DMF. The reaction mixture was stirred at room temperature for 1 h, then it was diluted with water, and extracted with DCM. The combined organic layers were dried over Na$_2$SO$_4$ and concentrated under reduced pressure. The residue was dissolved in 5 mL HCl in EtOH (1.25M) and stirred at room temperature for 1 h. The mixture was concentrated under reduced pressure, the residue diluted with water, and extracted with DCM. The combined organic layers were dried over Na$_2$SO$_4$ and concentrated under reduced pressure. The residue was purified via flash chromatography using heptane and EtOAc as eluents to give the title product.

MS: (M+H)$^+$=221.2.

Preparation 9ba: (2-Ethylpyrimidin-4-yl)methanol

Step A:

Starting from propanamidine hydrochloride using General Procedure 9C 4-(dimethoxymethyl)-2-ethyl-pyrimidine was obtained.

MS: (M+H)$^+$=183.2.

Step B:

Starting from this material using General Procedure 9A the title product was obtained.

$^1$H NMR (400 MHz, DMSO-d$_6$): 8.69 (d, 1H), 7.37 (d, 1H), 5.59 (t, 1H), 4.52 (d, 2H), 2.84 (q, 2H), 1.25 (t, 3H).

Preparation 9bb: (2-Propylpyrimidin-4-yl)methanol

Step A.

Starting from butanamidine hydrochloride using General Procedure 9C 4-(dimethoxymethyl)-2-propyl-pyrimidine was obtained.

MS: (M+H)$^+$=197.2.

Step B:

Starting from this material using General Procedure 9A the title product was obtained.

$^1$H NMR (400 MHz, DMSO-d$_6$): 8.68 (d, 1H), 7.36 (d, 1H), 5.59 (t, 1H), 4.51 (d, 2H), 2.79 (t, 2H), 1.75 (h, 2H), 0.90 (t, 3H).

Preparation 9bc: (2-Butylpyrimidin-4-yl)methanol

Step A:

Starting from n-pentanamidine hydrochloride using General Procedure 9C 2-butyl-4-(dimethoxymethyl)pyrimidine was obtained.

$^1$H NMR (400 MHz, DMSO-d$_6$): 8.77 (d, 1H), 7.36 (d, 1H), 5.25 (s, 1H), 3.32 (s, 6H), 2.87 (t, 2H), 1.73 (m, 2H), 1.32 (m, 2H), 0.90 (t, 3H).

Step B:

Starting from this material using General Procedure 9A the title product was obtained.

$^1$H NMR (400 MHz, DMSO-d$_6$): 8.70 (d, 1H), 7.36 (d, 1H), 5.59 (t, 1H), 4.51 (d, 2H), 2.81 (t, 2H), 1.70 (m, 2H), 1.31 (m, 2H), 0.89 (t, 3H).

Preparation 9bd: (2-Isopropylpyrimidin-4-yl)methanol

Step A:

Starting from 2-methylpropanamidine hydrochloride using General Procedure 9C 4-(dimethoxymethyl)-2-isopropyl-pyrimidine was obtained.

$^1$H NMR (400 MHz, DMSO-d$_6$): 8.79 (d, 1H), 7.36 (d, 1H), 5.25 (s, 1H), 3.34 (s, 6H), 3.14 (h, 1H), 1.27 (d, 6H).

Step B:

Starting from this material using General Procedure 9A the title product was obtained.

$^1$H NMR (400 MHz, DMSO-d$_6$): 8.70 (d, 1H), 7.37 (d, 1H), 5.59 (t, 1H), 4.52 (d, 2H), 3.08 (h, 1H), 1.25 (d, 6H).

Preparation 9be: (2-Cyclopropylpyrimidin-4-yl)methanol

Step A:

Starting from cyclopropanecarboxamidine hydrochloride using General Procedure 9C 2-cyclopropyl-4-(dimethoxymethyl)pyrimidine was obtained.

$^1$H NMR (400 MHz, DMSO-d$_6$): 8.67 (d, 1H), 7.28 (d, 1H), 5.20 (s, 1H), 3.31 (s, 6H), 2.20 (m, 1H), 1.07-0.96 (m, 4H).

Step B:

Starting from this material using General Procedure 9A the title product was obtained.

$^1$H NMR (400 MHz, DMSO-d$_6$): 8.59 (d, 1H), 7.29 (d, 1H), 5.56 (t, 1H), 4.47 (d, 2H), 2.14 (m, 1H), 1.03-0.92 (m, 4H).

Preparation 9bf: (2-Isobutylpyrimidin-4-yl)methanol

Step A:

Starting from 3-methylbutanamidine hydrochloride using General Procedure 9C 4-(dimethoxymethyl)-2-isobutyl-pyrimidine was obtained.

$^1$H NMR (400 MHz, DMSO-d$_6$): 8.77 (d, 1H), 7.36 (d, 1H), 5.25 (s, 1H), 3.32 (s, 6H), 2.75 (d, 2H), 2.22 (m, 1H), 0.89 (d, 6H).

Step B:

Starting from this material using General Procedure 9A the title product was obtained.

$^1$H NMR (400 MHz, DMSO-d$_6$): 8.69 (d, 1H), 7.37 (d, 1H), 5.59 (t, 1H), 4.51 (d, 2H), 2.69 (d, 2H), 2.19 (m, 1H), 0.88 (d, 6H).

Preparation 9bg: [2-(Cyclopropylmethyl)pyrimidin-4-yl]methanol

Step A:

Starting from 2-cyclopropylacetamidine hydrochloride using General Procedure 9C 2-(cyclopropylmethyl)-4-(dimethoxymethyl)pyrimidine was obtained.

$^1$H NMR (400 MHz, DMSO-d$_6$): 8.79 (d, 1H), 7.38 (d, 1H), 5.26 (s, 1H), 3.34 (s, 6H), 2.78 (d, 2H), 1.18 (m, 1H), 0.46 (m, 2H), 0.22 (m, 2H).

Step B:

Starting from this material using General Procedure 9A the title product was obtained.

$^1$H NMR (400 MHz, DMSO-d$_6$): 8.70 (d, 1H), 7.39 (d, 1H), 5.59 (t, 1H), 4.52 (d, 2H), 2.71 (d, 2H), 1.17 (m, 1H), 0.45 (m, 2H), 0.25 (m, 2H).

Preparation 9bh: (2-tert-Butylpyrimidin-4-yl)methanol

Step A:

Starting from 2,2-dimethylpropanamidine hydrochloride using General Procedure 9C 2-tert-butyl-4-(dimethoxymethyl)pyrimidine was obtained.

$^1$H NMR (400 MHz, DMSO-d$_6$): 8.80 (d, 1H), 7.34 (d, 1H), 5.25 (s, 1H), 3.34 (s, 6H), 1.35 (s, 9H).

Step B:

Starting from this material using General Procedure 9A the title product was obtained.

$^1$H NMR (400 MHz, DMSO-d$_6$): 8.72 (d, 1H), 7.35 (d, 1H), 5.57 (t, 1H), 4.52 (d, 2H), 1.33 (s, 9H).

Preparation 9bi: (2-Cyclopentylpyrimidin-4-yl)methanol

Step A:

Starting from cyclopentanecarboxamidine hydrochloride using General Procedure 9C 2-cyclopentyl-4-(dimethoxymethyl)pyrimidine was obtained.

MS: (M+H)$^+$=223.2.

Step B:

Starting from this material using General Procedure 9A the title product was obtained.

$^1$H NMR (400 MHz, DMSO-d$_6$): 8.68 (d, 1H), 7.34 (d, 1H), 5.57 (t, 1H), 4.51 (d, 2H), 3.25 (p, 1H), 1.98 (m, 2H), 1.87-1.57 (m, 6H).

Preparation 9bj: [2-(Trifluoromethyl)pyrimidin-4-yl]methanol

Step A:

The mixture of 500 mg Preparation 9a1 (2.89 mmol) and 356 mg 2,2,2-trifluoroacetamidine (3.18 mmol) was heated at 110° C. for 40 min in a microwave reactor. The crude product was purified via flash chromatography using heptane and EtOAc as eluents to give 4-(dimethoxymethyl)-2-(trifluoromethyl)pyrimidine.

$^1$H NMR (400 MHz, CDCl$_3$): 8.97 (d, 1H), 7.77 (d, 1H), 5.36 (s, 1H), 3.48 (s, 6H).

Step B:

Starting from this material using General Procedure 9A the title product was obtained.

$^1$H NMR (400 MHz, CDCl$_3$): 8.90 (d, 1H), 7.65 (d, 1H), 5.87 (br s, 1H), 4.91 (d, 2H).

Preparation 9bk: [2-(Methoxymethyl)pyrimidin-4-yl]methanol

Step A:

Starting from 2-methoxyacetamidine hydrochloride using General Procedure 9C 4-(dimethoxymethyl)-2-(methoxymethyl)pyrimidine was obtained.

$^1$H NMR (400 MHz, DMSO-d$_6$): 8.86 (d, 1H), 7.47 (d, 1H), 5.30 (s, 1H), 4.58 (s, 2H), 3.37 (s, 3H), 3.34 (s, 6H).

Step B:

Starting from this material using General Procedure 9A the title product was obtained.

$^1$H NMR (400 MHz, DMSO-d$_6$): 8.77 (d, 1H), 7.47 (d, 1H), 5.66 (t, 1H), 4.55 (d, 2H), 4.53 (s, 2H), 3.36 (s, 3H).

Preparation 9bl: [2-(2-Methoxyethyl)pyrimidin-4-yl]methanol

Step A:

Starting from 3-methoxypropanamidine hydrochloride using General Procedure 9C 4-(dimethoxymethyl)-2-(2-methoxyethyl)pyrimidine was obtained.

$^1$H NMR (400 MHz, DMSO-d$_6$): 8.78 (d, 1H), 7.38 (d, 1H), 5.25 (s, 1H), 3.80 (t, 2H), 3.33 (s, 6H), 3.22 (s, 3H), 3.11 (t, 2H).

Note: 2-[4-(dimethoxymethyl)pyrimidin-2-yl]-N,N-dimethyl-ethanamine was also obtained.

MS: (M+H)$^+$=226.2. (See also at Step A of Preparation 9bm)

Step B:

Starting from this material using General Procedure 9A the title product was obtained.

$^1$H NMR (400 MHz, DMSO-d$_6$): 8.70 (d, 1H), 7.39 (d, 1H), 5.60 (t, 1H), 4.52 (d, 2H), 3.78 (t, 2H), 3.22 (s, 3H), 3.06 (t, 2H).

Preparation 9bm: [2-(2-Dimethylaminoethyl)pyrimidin-4-yl]methanol

Step A:

To the mixture of 1.63 g 3-(dimethylamino)propanamidine dihydrochloride (8.67 mmol) and 1.25 g (E)-4-(dimethylamino)-1,1-dimethoxy-but-3-en-2-one (Preparation 9a1, 7.23 mmol) in 4 mL dry methanol sodium methoxide (17.3 mmol) was added portionwise and the mixture was stirred at 75° C. for 2 h. The reaction mixture was cooled and concentrated under reduced pressure. Water was added to the residue and it was extracted with EtOAc. The combined organic layers were dried over MgSO$_4$ and concentrated under reduced pressure to give 2-[4-(dimethoxymethyl)pyrimidin-2-yl]-N,N-dimethyl-ethanamine.

MS: (M+H)$^+$=226.2.

Step B:

1.474 g crude 2-[4-(dimethoxymethyl)pyrimidin-2-yl]-N,N-dimethyl-ethanamine obtained in Step A was stirred with 20 mL 2N HCl solution at 60° C. for 2 h. The reaction mixture was cooled to 0° C., then 1.52 NaOH (3.8 mmol) was added portionwise. The pH was adjusted to 8 using 10% K$_2$CO$_3$ solution, then 492 mg sodium borohydride (13.0 mmol) was added portionwise keeping the temperature under 5° C. and stirred for 30 min at 0° C. Reaction mixture was salted (4 g NaCl) then extracted with 2-Me-THF. The combined organic layers were dried over Na$_2$SO$_4$ and concentrated under reduced pressure to give the title product.

$^1$H NMR (400 MHz, DMSO-d$_6$): 8.69 (d, 1H), 7.39 (d, 1H), 5.64 (br s, 1H), 4.52 (s, 2H), 3.01 (m, 2H), 2.80 (m, 2H), 2.25 (s, 6H).

Preparation 9bn:
[2-(Ethoxymethyl)pyrimidin-4-yl]methanol

Step A:

Starting from 2-ethoxyacetamidine hydrochloride using General Procedure 9C 4-(dimethoxymethyl)-2-(ethoxymethyl)pyrimidine was obtained.

$^1$H NMR (400 MHz, DMSO-$d_6$): 8.86 (d, 1H), 7.46 (d, 1H), 5.29 (s, 1H), 4.61 (s, 2H), 3.58 (q, 2H), 3.33 (s, 6H), 1.16 (t, 3H).

Step B:

Starting from this material using General Procedure 9A the title product was obtained.

$^1$H NMR (400 MHz, DMSO-$d_6$): 8.77 (d, 1H), 7.47 (d, 1H), 5.65 (t, 1H), 4.56 (m, 4H), 3.57 (q, 2H), 1.14 (t, 3H).

Preparation 9bo:
[2-(4-Chlorophenyl)pyrimidin-4-yl]methanol

Step A:

Starting from 4-chlorobenzamidine hydrochloride using General Procedure 9C 2-(4-chlorophenyl)-4-(dimethoxymethyl)pyrimidine was obtained.

$^1$H NMR (400 MHz, DMSO-$d_6$): 8.97 (d, 1H), 8.40 (m, 2H), 7.61 (m, 2H), 7.50 (d, 1H), 5.38 (s, 1H), 3.39 (s, 6H).

Step B:

Starting from this material using General Procedure 9A the title product was obtained.

$^1$H NMR (400 MHz, DMSO-$d_6$): 8.89 (d, 1H), 8.39 (m, 2H), 7.59 (m, 2H), 7.52 (d, 1H), 5.71 (t, 1H), 4.64 (d, 2H).

Preparation 9bp:
[2-(2-Methoxyphenyl)pyrimidin-4-yl]methanol

Step A:

Starting from 2-methoxybenzamidine acetic acid salt using General Procedure 9C 4-(dimethoxymethyl)-2-(2-methoxyphenyl)pyrimidine was obtained.

$^1$H NMR (400 MHz, DMSO-$d_6$): 8.93 (d, 1H), 7.55-7.44 (m, 3H), 7.16 (d, 1H), 7.06 (m, 1H), 5.31 (s, 1H), 3.76 (s, 3H), 3.37 (s, 6H).

Step B:

261 mg 4-(dimethoxymethyl)-2-(2-methoxyphenyl)pyrimidine (1.00 mmol) was dissolved in 2 mL HCl in dioxane (4M solution), then 2 mL water was added and this mixture was stirred at 50° C. for 16 h. The reaction mixture was cooled to 0° C., then 320 mg NaOH (8.0 mmol) was added portionwise. The pH was adjusted to 8 using 10% $K_2CO_3$ solution, then 76 mg sodium borohydride (2.0 mmol) was added and the mixture was stirred for 30 min at 0° C. The reaction mixture was diluted with 5 mL water and extracted with EtOAc. The combined organic phases were dried over $Na_2SO_4$ and concentrated under reduced pressure. The crude product was purified via flash chromatography using heptane and EtOAc as eluents to give the title product.

$^1$H NMR (400 MHz, DMSO-$d_6$): 8.84 (d, 1H), 7.50-7.42 (m, 3H), 7.14 (d, 1H), 7.03 (m, 1H), 5.66 (t, 1H), 4.58 (d, 2H), 3.75 (s, 3H).

Preparation 9bq:
[2-(2-Pyridyl)pyrimidin-4-yl]methanol

Step A:

Starting from pyridine-2-carboxamidine hydrochloride using General Procedure 9C 4-(dimethoxymethyl)-2-(2-pyridyl)pyrimidine was obtained.

MS: (M+H)$^+$=232.2.

Step B:

Starting from this material using General Procedure 9A the title product was obtained.

$^1$H NMR (400 MHz, DMSO-$d_6$): 8.94 (d, 1H), 8.74 (d, 1H), 8.37 (d, 1H), 7.97 (m, 1H), 7.60 (d, 1H), 7.52 (m, 1H), 5.74 (t, 1H), 4.67 (d, 2H).

Preparation 9br:
[2-(3-Pyridyl)pyrimidin-4-yl]methanol

Step A:

Starting from pyridine-3-carboxamidine hydrochloride using General Procedure 9C 4-(dimethoxymethyl)-2-(3-pyridyl)pyrimidine was obtained.

MS: (M+H)$^+$=232.2.

Step B:

Starting from this material using General Procedure 9A the title product was obtained.

$^1$H NMR (400 MHz, DMSO-$d_6$): 9.51 (dd, 1H), 8.93 (d, 1H), 8.72 (dd, 1H), 8.66 (m, 1H), 7.56 (m, 2H), 5.73 (t, 1H), 4.67 (d, 2H).

Preparation 9bs:
[2-(4-Pyridyl)pyrimidin-4-yl]methanol

Step A:

Starting from pyridine-4-carboxamidine hydrochloride using General Procedure 9C 4-(dimethoxymethyl)-2-(4-pyridyl)pyrimidine was obtained.

MS: (M+H)$^+$=232.2.

Step B:

Starting from this material using General Procedure 9A the title product was obtained.

$^1$H NMR (400 MHz, DMSO-$d_6$): 8.98 (d, 1H), 8.77 (m, 2H), 8.25 (m, 2H), 7.63 (d, 1H), 5.76 (t, 1H), 4.68 (d, 2H).

Preparation 9bt:
[2-(3-Furyl)pyrimidin-4-yl]methanol

Step A:

Starting from furan-3-carboxamidine hydrochloride using General Procedure 9C 4-(dimethoxymethyl)-2-(3-furyl)pyrimidine was obtained.

$^1$H NMR (400 MHz, DMSO-$d_6$): 8.85 (d, 1H), 8.43 (br s, 1H), 7.83 (dd, 1H), 7.39 (d, 1H), 7.04 (dd, 1H), 5.31 (s, 1H), 3.36 (s, 6H).

Step B:

Starting from this material using General Procedure 9A the title product was obtained.

$^1$H NMR (400 MHz, DMSO-$d_6$): 8.77 (d, 1H), 8.39 (br s, 1H), 7.80 (dd, 1H), 7.40 (d, 1H), 7.02 (dd, 1H), 5.65 (t, 1H), 4.58 (d, 2H).

Preparation 9bu:
[2-(3-Thienyl)pyrimidin-4-yl]methanol

Step A:

Starting from thiophene-3-carboxamidine hydrochloride using General Procedure 9C 4-(dimethoxymethyl)-2-(3-thienyl)pyrimidine was obtained.

$^1$H NMR (400 MHz, DMSO-$d_6$): 8.89 (d, 1H), 8.39 (dd, 1H), 7.81 (dd, 1H), 7.67 (dd, 1H), 7.40 (d, 1H), 5.33 (s, 1H), 3.38 (s, 6H).

Step B:

Starting from this material using General Procedure 9A the title product was obtained.

¹H NMR (400 MHz, DMSO-d₆): 8.81 (d, 1H), 8.36 (dd, 1H), 7.80 (dd, 1H), 7.65 (dd, 1H), 7.42 (d, 1H), 5.66 (t, 1H), 4.60 (d, 2H).

Preparation 9bv:
[2-(2-Thienyl)pyrimidin-4-yl]methanol

Step A:

Starting from thiophene-2-carboxamidine hydrochloride using General Procedure 9C 4-(dimethoxymethyl)-2-(2-thienyl)pyrimidine was obtained.

MS: (M+H)⁺=237.2.

Step B:

Starting from this material using General Procedure 9A the title product was obtained.

¹H NMR (400 MHz, DMSO-d₆): 8.77 (d, 1H), 7.93 (dd, 1H), 7.76 (dd, 1H), 7.40 (d, 1H), 7.20 (dd, 1H), 5.68 (t, 1H), 4.58 (d, 2H).

Preparation 9bw:
(2-(1H-Pyrazol-1-yl)pyrimidin-4-yl)methanol

Step A:

To the stirred mixture of 4.18 g of pyrazole-1-carboxamidine hydrochloride (28.5 mmol) and 120 mL of ethanol 4.05 g of Na₂HPO₄ (28.5 mmol) and 4.12 g of Preparation 9a1 (23.78 mmol) were added, then it was stirred at 85° C. for 10 h. The reaction mixture was cooled, concentrated under reduced pressure, and the crude product was purified via flash chromatography using heptane and EtOAc as eluents to give 4-(dimethoxymethyl)-2-(1H-pyrazol-1-yl)-pyrimidine.

¹H NMR (400 MHz, DMSO-d₆): 8.92 (d, 1H), 8.65 (d, 1H), 7.87 (br s, 1H), 7.50 (d, 1H), 6.62 (dd, 1H), 5.36 (s, 1H), 3.38 (s, 6H).

Step B:

Starting from this material using General Procedure 9A the title product was obtained.

¹H NMR (400 MHz, DMSO-d₆): 8.84 (d, 1H), 8.65 (d, 1H), 7.84 (br s, 1H), 7.51 (d, 1H), 6.59 (dd, 1H), 5.77 (t, 1H), 4.63 (d, 2H).

Preparation 9bx:
(2-Thiazol-2-ylpyrimidin-4-yl)methanol

Step A:

To the stirred mixture of 1.00 g of thiazole-2-carboxamidine hydrochloride (6.11 mmol) and 3 mL of methanol 330 mg sodium methoxide (6.11 mmol) and 1.05 g of Preparation 9a1 (6.11 mmol) were added, then it was stirred at 75° C. for 7 h. The reaction mixture was cooled, concentrated under reduced pressure, brine was added and it was extracted with DCM. The combined organic phases were dried over Na₂SO₄ and concentrated under reduced pressure. The crude product was purified via flash chromatography using heptane and EtOAc as eluents to give 2-[4-(dimethoxymethyl)pyrimidin-2-yl]thiazole.

MS: (M+H)⁺=238.2.

Step B:

Starting from this material using General Procedure 9A the title product was obtained.

¹H NMR (400 MHz, DMSO-d₆): 8.91 (d, 1H), 8.03 (dd, 2H), 7.61 (d, 1H), 5.78 (t, 1H), 4.65 (d, 2H).

Preparation 9by: (2-Benzylpyrimidin-4-yl)methanol

Step A:

Starting from 2-phenylacetamidine hydrochloride using General Procedure 9C 2-benzyl-4-(dimethoxymethyl)pyrimidine was obtained.

MS: (M+H)⁺=245.2.

Step B:

Starting from this material using General Procedure 9A the title product was obtained.

¹H NMR (400 MHz, DMSO-d₆): 8.71 (d, 1H), 7.39 (d, 1H), 7.28 (m, 4H), 7.20 (m, 1H), 5.61 (t, 1H), 4.52 (d, 2H), 4.16 (s, 2H).

Preparation 9bz:
[2-(Phenoxymethyl)pyrimidin-4-yl]methanol

Step A:

Starting from 2-phenoxyacetamidine hydrochloride using General Procedure 9C 4-(dimethoxymethyl)-2-(phenoxymethyl)pyrimidine was obtained.

MS: (M+H)⁺=261.2.

Step B:

Starting from this material using General Procedure 9A the title product was obtained.

¹H NMR (400 MHz, DMSO-d₆): 8.81 (d, 1H), 7.51 (d, 1H), 7.28 (m, 2H), 6.95 (m, 3H), 5.68 (t, 1H), 5.21 (s, 2H), 4.57 (d, 2H).

Preparation 9ca: (5-Bromopyrimidin-4-yl)methanol

Step A:

To the solution of 3.90 g of 4-(dimethoxymethyl)pyrimidine (25.3 mmol) in 100 mL AcOH 4.15 g sodium acetate (50.6 mmol) and 8.08 g bromine (50.6 mmol) were added and the mixture was stirred at 40° C. for 7 h. Reaction mixture was concentrated under reduced pressure, DCM was added to the residue, and it was washed with saturated aq. NaHCO₃. The organic phase was dried over Na₂SO₄ and concentrated under reduced pressure. The crude product was purified via flash chromatography using heptane and EtOAc as eluents to give 5-bromo-4-(dimethoxymethyl)pyrimidine.

¹H NMR (400 MHz, DMSO-d₆): 9.18 (s, 1H), 9.06 (s, 1H), 5.51 (s, 1H), 3.40 (s, 6H).

Step B:

Starting from this material using General Procedure 9A the title product was obtained.

¹H NMR (400 MHz, DMSO-d₆): 9.14 (s, 1H), 8.94 (s, 1H), 5.49 (t, 1H), 4.62 (d, 2H).

Preparation 9cb:
(5-Bromo-2-methoxy-pyrimidin-4-yl)methanol

Step A:

Starting from methyl carbamimidate hydrochloride using General Procedure 9C 4-(dimethoxymethyl)-2-methoxy-pyrimidine was obtained.

¹H NMR (400 MHz, DMSO-d₆): 8.66 (d, 1H), 7.18 (d, 1H), 5.20 (s, 1H), 3.92 (s, 3H) 3.33 (s, 6H).

Step B:

To the solution of 5.49 g of 4-(dimethoxymethyl)-2-methoxy-pyrimidine (30.0 mmol) in 100 mL AcOH 4.92 g sodium acetate (60.0 mmol) and 9.59 g bromine (60.0 mmol) were added and stirred at 40° C. for 24 h. The reaction mixture was concentrated under reduced pressure, to the residue DCM was added, and it was washed with saturated aq. NaHCO₃. The organic phase was dried over Na$_2$SO$_4$ and concentrated under reduced pressure. The crude product was purified via flash chromatography using heptane and EtOAc as eluents to give 5-bromo-4-(dimethoxymethyl)-2-methoxy-pyrimidine.

$^1$H NMR (400 MHz, DMSO-d$_6$): 8.79 (s, 1H), 5.41 (s, 1H), 3.93 (s, 3H), 3.40 (s, 6H).

Step C:
Starting from this material using General Procedure 9A the title product was obtained.

$^1$H NMR (400 MHz, DMSO-d$_6$): 8.68 (s, 1H), 5.41 (t, 1H), 4.54 (d, 2H), 3.94 (s, 3H).

Preparation 9cc:
[2-Methoxy-5-(3-thienyl)pyrimidin-4-yl]methanol

Step A:
To the solution of 766 mg of 5-bromo-4-(dimethoxymethyl)-2-methoxy-pyrimidine (the product of Preparation 9cb, Step B, 2.91 mmol) in 15 mL THF-water (1:1) 934 mg 4,4,5,5-tetramethyl-2-(3-thienyl)-1,3,2-dioxaborolane (4.45 mmol), 1.96 g Cs$_2$CO$_3$ (6.00 mmol) and 522 mg tetrakis(triphenylphosphine)palladium(0) (0.450 mmol) were added and the mixture was heated under N$_2$ in a microwave reactor at 110° C. for 30 h. The reaction mixture was filtered; the filtrate was concentrated under reduced pressure. The residue was purified via flash chromatography using heptane and ethyl-acetate as eluents to give 4-(dimethoxymethyl)-2-methoxy-5-(3-thienyl)pyrimidine.

MS: (M+H)$^+$=267.2.

Step B:
Starting from this material using General Procedure 9A the title product was obtained.

$^1$H NMR (400 MHz, DMSO-d$_6$): 8.62 (s, 1H), 7.76 (m, 1H), 7.70 (m, 1H), 7.39 (dd, 1H), 5.39 (t, 1H), 4.49 (d, 2H), 3.98 (s, 3H).

Preparation 9cd:
(2,6-Dimethoxypyrimidin-4-yl)methanol

Step A:
To the mixture of 12.16 g O-methylisourea hydrochloride (110 mmol) and 20.0 g ethyl 4,4-dimethoxy-3-oxo-butanoate (91.6 mmol) in dry methanol 5.94 g sodium methoxide (110 mmol) was added portionwise and the mixture was stirred at 75° C. for 2 h. The reaction mixture was cooled, celite was added and the volatiles were removed under reduced pressure. The crude product was purified via flash chromatography using heptane and EtOAc as eluents to give 4-(dimethoxymethyl)-2-methoxy-1H-pyrimidin-6-one.

$^1$H NMR (400 MHz, DMSO-d$_6$): 12.37 (br s, 1H), 6.03 (s, 1H), 5.08 (s, 1H), 3.87 (s, 3H), 3.57 (m, 4H), 1.15 (t, 6H).

Step B:
To the solution of 2.00 g 4-(dimethoxymethyl)-2-methoxy-1H-pyrimidin-6-one (8.76 mmol) in 8 mL DMF 1612 mg phosphoryl chloride (10.5 mmol) was added dropwise at 0° C. and it was stirred at this temperature for 30 min. The mixture was diluted with 40 mL DCM and it was poured onto ice. The organic layer was washed with water, then it was dried over MgSO$_4$ and concentrated under reduced pressure. The residue was dissolved in 30 mL methanol and 946 mg sodium methoxide (17.52 mmol) was added at 0° C., and it was stirred at this temperature for 1 h. Celite was added and the volatiles were removed under reduced pressure. The crude product was purified via flash chromatography using heptane and EtOAc as eluents to give 4-(dimethoxymethyl)-2,6-dimethoxy-pyrimidine.

MS: (M+H)$^+$=243.2.

Step C:
Starting from this material using General Procedure 9A the title product was obtained.

$^1$H NMR (400 MHz, DMSO-d$_6$): 6.53 (br s, 1H), 5.53 (t, 1H), 4.40 (dd, 2H), 3.89 (s, 3H), 3.86 (s, 3H).

Preparation 9ce: (6-Chloropyrimidin-4-yl)methanol

Step A:
To the solution of 3.00 g chloromethyl benzoate (17.59 mmol) in 21 mL MeCN 5.799 g NaI (38.69 mmol) was added. The reaction mixture was stirred at room temperature for 14 h. The precipitate was filtered and the organic phase was concentrated to give iodomethyl benzoate as yellow oil.

Step B:
Preparation of Activated Zinc:

Zinc was washed quickly with 10% HCl followed with water then ethanol then diethyl ether. The activated zinc was stored under argon.

An excess of activated zinc was suspended in 3 mL THF, treated with 349 mg 1,2-dibromoethane (160 μL, 1.857 mmol) and the resulting mixture was heated at 60° C. under argon for 30 minutes. The reaction mixture was allowed to cool to room temperature, treated with 154 mg trimethylchlorosilane (180 μL, 1.418 mmol) and the resulting mixture was stirred at room temperature for 30 minutes. The reaction mixture was treated with 64.5 mg LiCl (1.521 mmol) and the resulting mixture was stirred at room temperature for 30 minutes.

A solution of iodomethyl benzoate (1.60 g, 6.11 mmol) in 3 mL THF was added and the resulting mixture was stirred at room temperature for 1.5 h. This reaction mixture was added to a solution of 537 mg 4,6-dichloropyrimidine (3.605 mmol) and 502 mg tris[tris(3,5-bis(trifluoromethyl)-phenyl)phosphine]palladium(0) {Superstable Pd(0) Catalyst} (0.180 mmol) in 6 mL THF and the resulting mixture was stirred at room temperature under argon for 18 h. The reaction mixture was filtered through celite, diluted with saturated ammonium chloride solution and extracted with ethyl acetate. The ethyl acetate layers were combined, dried on magnesium sulfate and concentrated under reduced pressure. The residue was purified by column chromatography.

Step C:
To the solution of 800 mg (6-chloropyrimidin-4-yl) methyl benzoate (3.217 mmol) in 32 mL MeOH 17 mg NaOMe (0.315 mmol) was added. It was stirred at room temperature for 2.5 h. The reaction mixture was concentrated under reduced pressure, and the residue was purified by flash chromatography to give the title product.

$^1$H NMR (200 MHz, CDCl$_3$): 8.94 (s, 1H), 7.47 (s, 1H), 4.76 (s, 2H).

Preparation 9cf:
(2-Methoxy-6-methyl-pyrimidin-4-yl)methanol

To the solution of 1.00 g methyl 2-methoxy-6-methyl-pyrimidine-4-carboxylate (5.49 mmol) in 15 mL abs THF 12 mL DIBAL-H (1M in THF) was added and it was stirred at room temperature for 30 min, then further 12 mL DIBAL-H was added. After 1 h the excess of DIBAL-H was quenched with propan-2-ol, then with water. Saturated aq. NaF solution was added to the reaction mixture, then it was extracted with DCM. The combined organic phases were dried over Na$_2$SO$_4$ and concentrated under reduced pressure. The crude product was purified via flash chromatography using heptane and EtOAc as eluents to give the title product.

¹H NMR (400 MHz, DMSO-d₆): 7.07 (s, 1H), 5.55 (t, 1H), 4.43 (m, 2H), 3.86 (s, 3H), 2.40 (s, 3H).

Preparation 9cg: (6-Phenylpyrimidin-4-yl)methanol

To the solution of 1.00 g ethyl 6-phenylpyrimidine-4-carboxylate (4.38 mmol) in 15 mL MeOH 175 mg NaBH₄ (4.63 mmol) was added at room temperature and it was stirred at 70° C. for 3 h. The reaction mixture was concentrated, and the residue was diluted with saturated aq. K₂CO₃ and it was extracted with DCM. The combined organic phases were dried over Na₂SO₄ and concentrated under reduced pressure. The crude product was purified via flash chromatography using heptane and EtOAc as eluents to give the title product.
¹H NMR (400 MHz, CDCl₃): 8.97 (s, 1H), 8.11 (d, 2H), 7.68-7.45 (m, 4H), 5.45 (d, 2H).

Preparation 9ch: (2-Chloropyrimidin-4-yl)methanol

To the solution of 1860 mg methyl 2-chloropyrimidine-4-carboxylate (10.78 mmol) in 11 mL THF 21.6 mL DIBAL-H (1M in THF, 21.6 mmol) was added dropwise at −70° C. and it was stirred at this temperature for 16 h. 5 mL MeOH was added to it at −50° C., then 5 mL water was added to it at 0° C. It was filtered through celite. The filtrate was concentrated under reduced pressure, and then it was purified via flash chromatography using heptane and EtOAc as eluents.
¹H NMR (200 MHz, CDCl₃): 8.60 (d, 1H), 7.38 (d, 1H), 4.79 (s, 2H).

Preparation 9da: (1-Ethyl-1H-pyrazol-5-yl)methanol

Step A:
Using bromoethane in General Procedure 9G 1-ethyl-1H-pyrazole was obtained.
Step B:
Starting from 1-ethyl-1H-pyrazole using General Procedure 9H the title product was obtained.
¹H NMR (400 MHz, CDCl₃): 7.36 (d, 1H), 6.15 (d, 1H), 4.66 (br s, 2H), 4.18 (q, 2H), 2.99 (br s, 1H), 1.42 (t, 3H).

Preparation 9db: (1-Propyl-1H-pyrazol-5-yl)methanol

Step A:
Using 1-bromopropane in General Procedure 9G 1-propylpyrazole was obtained.
MS: (M+H)⁺=111.2.
Step B:
Starting from 1-propyl-1H-pyrazole using General Procedure 9H the title product was obtained.
¹H NMR (400 MHz, CDCl₃): 7.34 (d, 1H), 6.14 (d, 1H), 4.64 (s, 2H), 4.07 (dd, 2H), 1.85 (m, 2H), 0.89 (t, 3H).
MS: (M+H)⁺=141.2.

Preparation 9dc: [1-(Propan-2-yl)-1H-pyrazol-5-yl]methanol

Step A:
Using 2-bromopropane in General Procedure 9G 1-isopropylpyrazole was obtained.
Step B:
Starting from 1-isopropylpyrazole using General Procedure 9H the title product was obtained.

¹H NMR (400 MHz, DMSO-d₆): 7.32 (d, 1H), 6.10 (d, 1H), 5.21 (t, 1H), 4.60 (h, 1H), 4.50 (d, 2H), 1.36 (d, 6H).
MS: (M+H)⁺=141.2.

Preparation 9dd: (1-Butyl-1H-pyrazol-5-yl)methanol

Starting from 1-butylpyrazole using General Procedure 9H the title product was obtained.
¹H NMR (400 MHz, DMSO-d₆): 7.30 (d, 1H), 6.12 (d, 1H), 5.23 (t, 1H), 4.49 (d, 2H), 4.06 (t, 2H), 1.72 (m, 2H), 1.26 (m, 2H), 0.88 (t, 3H).
MS: (M+H)⁺=155.2.

Preparation 9de: [1-(3-Methylbutyl)-1H-pyrazol-5-yl]methanol

Step A:
Using 1-bromo-3-methyl-butane in General Procedure 9F 1-(3-methylbutyl)-1H-pyrazole was obtained.
¹H NMR (400 MHz, DMSO-d₆): 7.71 (d, 1H), 7.40 (d, 1H), 6.20 (t, 1H), 4.11 (t, 2H), 1.65 (q, 2H), 1.44 (h, 1H), 0.89 (d, 6H).
Step B:
Starting from 1-(3-methylbutyl)-1H-pyrazole using General Procedure 9H the title product was obtained.
¹H NMR (400 MHz, DMSO-d₆): 7.30 (d, 1H), 6.12 (d, 1H), 5.25 (t, 1H), 4.49 (d, 2H), 4.08 (m, 2H), 1.63 (m, 2H), 1.55 (h, 1H), 0.90 (d, 6H).

Preparation 9df: [1-(Cyclopropylmethyl)-1H-pyrazol-5-yl]methanol

Starting from 1-(cyclopropylmethyl)-1H-pyrazole using General Procedure 9H the title product was obtained.
¹H NMR (400 MHz, DMSO-d₆): 7.31 (d, 1H), 6.14 (d, 1H), 5.26 (t, 1H), 4.51 (d, 2H), 3.96 (d, 2H), 1.24 (m, 1H), 0.51-0.24 (m, 4H).
MS: (M+H)⁺=153.2.

Preparation 9dg: (1-Cyclopentyl-1H-pyrazol-5-yl)methanol

Step A:
Using bromocyclopentane in General Procedure 9G 1-cyclopentyl-1H-pyrazole was obtained.
Step B:
Starting from 1-cyclopentyl-1H-pyrazole using General Procedure 9H the title product was obtained.
¹H NMR (400 MHz, DMSO-d₆): 7.31 (d, 1H), 6.11 (d, 1H), 5.20 (t, 1H), 4.77 (p, 1H), 4.51 (d, 2H), 1.99 (m, 2H), 1.91 (m, 2H), 1.82 (m, 2H), 1.61 (m, 2H).
MS: (M+H)⁺=167.2.

Preparation 9dh: (1-Cyclohexyl-1H-pyrazol-5-yl)methanol

Step A:
Using bromocyclohexane in General Procedure 9G 1-cyclohexyl-1H-pyrazole was obtained.
MS: (M+H)⁺=151.2.
Step B:
Starting from 1-cyclohexyl-1H-pyrazole using General Procedure 9H the title product was obtained.
¹H NMR (400 MHz, CDCl₃): 7.44 (s, 1H), 6.17 (s, 1H), 4.70 (d, 2H), 4.20 (m, 1H), 2.05-1.21 (m, 10H).
MS: (M+H)⁺=181.2.

Preparation 9di: (1-(Tetrahydro-2H-pyran-4-yl)-1H-pyrazol-5-yl)methanol

Step A:

The mixture of 596 mg pyrazole (8.75 mmol), 2.89 g 4-bromo-tetrahydropyran (17.5 mmol) and 1.47 g sodium hydrogen carbonate (17.5 mmol) was stirred at 120° C. for 10 days. After completion it was diluted with diethyl ether (30 mL), the precipitate was filtered off and the volatiles were removed under reduced pressure at room temperature. The crude oil was diluted with diethyl ether (20 mL) and washed with water. The aqueous phase was extracted with ethyl acetate. The combined organic layers were dried over $Na_2SO_4$ and concentrated under reduced pressure. The residue was purified by column chromatography (eluent: dichloromethane:ethanol=100:1) to give 1-(tetrahydro-2H-pyran-4-yl)-1H-pyrazole.

MS: $(M+H)^+=153.2$.

Step B:

Starting from 1-(tetrahydro-2H-pyran-4-yl)-1H-pyrazole using General Procedure 9H the title product was obtained.

$^1$H NMR (400 MHz, $CDCl_3$): 7.46 (d, 1H), 6.19 (d, 1H), 4.71 (s, 2H), 4.46 (m, 1H), 4.12 (dd, 2H), 3.55 (m, 2H), 2.34 (m, 2H), 1.88 (m, 2H).

MS: $(M+H)^+=183.1$.

Preparation 9dj: {1-[2-(Dimethylamino)ethyl]-1H-pyrazol-5-yl}methanol

Step A:

The mixture of 5 g 1H-pyrazole (79.44 mmol), 11.64 g 2-chloro-N,N-dimethylethylamine hydrochloride (80.79 mmol) and 30.0 g potassium carbonate (220.32 mmol) in 100 mL DMF was stirred at 60° C. for 14 hours. After completion the volatiles were removed under reduced pressure. The residue was diluted with chloroform (100 mL) and washed with water. The organic layer was dried over $Na_2SO_4$ and concentrated under reduced pressure. The residue was diluted with ethanol (20 mL) and 34 mL HCl (5N in EtOH) was added. The precipitate was filtered off, washed with diethyl ether and dried to give N,N-dimethyl-2-(1H-pyrazol-1-yl)-ethanamine.

MS: $(M+H)^+=140.2$.

Step B:

Starting from N,N-dimethyl-2-(1H-pyrazol-1-yl)-ethanamine using General Procedure 9H the title product was obtained.

$^1$H NMR (400 MHz, $CDCl_3$): 7.47 (br s, 1H), 6.25 (br s, 1H), 4.54 (s, 2H), 4.27 (m, 2H), 2.73 (m, 2H), 2.21 (s, 6H).

MS: $(M+H)^+=170.1$.

Preparation 9dk: [1-(4-Methoxybenzyl)-1H-pyrazol-5-yl]methanol

Step A:

Using 1-(bromomethyl)-4-methoxy-benzene in General Procedure 9G 1-(4-methoxybenzyl)-1H-pyrazole was obtained.

Step B:

Starting from 1-(4-methoxybenzyl)-1H-pyrazole using General Procedure 9H the title product was obtained.

$^1$H NMR (400 MHz, $CDCl_3$): 7.47 (d, 1H), 7.14 (m, 2H), 6.85 (m, 2H), 6.24 (d, 1H), 5.35 (s, 2H), 4.60 (s, 2H), 3.78 (s, 3H).

MS: $(M+H)^+=219.1$.

Preparation 9dl: [1-(4,4,4-Trifluorobutyl)-1H-pyrazol-5-yl]methanol

Step A:

Using 4-bromo-1,1,1-trifluoro-butane in General Procedure 9F 1-(4,4,4-trifluorobutyl)-1H-pyrazole was obtained.

$^1$H NMR (400 MHz, DMSO-$d_6$): 7.75 (d, 1H), 7.46 (d, 1H), 6.24 (t, 1H), 4.19 (t, 2H), 2.26-2.13 (m, 2H), 1.98 (m, 2H).

Step B:

Starting from 1-(4,4,4-trifluorobutyl)-1H-pyrazole using General Procedure 9H the title product was obtained.

$^1$H NMR (400 MHz, DMSO-$d_6$): 7.36 (d, 1H), 6.16 (d, 1H), 5.29 (br s, 1H), 4.50 (d, 2H), 4.16 (t, 2H), 2.31-2.18 (m, 2H), 1.99 (m, 2H).

Preparation 9dm: (1-Pentyl-1H-pyrazol-5-yl)methanol

Step A:

Using 1-bromopentane in General Procedure 9F 1-pentyl-1H-pyrazole was obtained.

$^1$H NMR (400 MHz, DMSO-$d_6$): 7.70 (d, 1H), 7.41 (d, 1H), 6.20 (t, 1H), 4.08 (t, 2H), 1.75 (p, 2H), 1.28 (m, 2H), 1.17 (m, 2H), 0.84 (t, 3H).

Step B:

Starting from 1-pentyl-1H-pyrazole using General Procedure 9H the title product was obtained.

$^1$H NMR (400 MHz, DMSO-$d_6$): 7.31 (d, 1H), 6.12 (d, 1H), 5.25 (t, 1H), 4.49 (d, 2H), 4.05 (t, 2H), 1.74 (p, 2H), 1.34-1.17 (m, 4H), 0.86 (t, 3H).

Preparation 9dn and Preparation 9do: (1R or S)-1-(1-pentyl-1H-pyrazol-5-yl)ethanol and (1S or R)-1-(1-pentyl-1H-pyrazol-5-yl)ethanol To the solution of 2.00 g 1-pentyl-1H-pyrazole (Preparation 9dm, Step A, 14.47 mmol) in 30 mL dry THF 10 mL n-BuLi (1.6 M, 16 mmol) was added dropwise at −78° C. and the mixture was stirred for 1 h at this temperature, then 848 mg acetaldehyde (20.0 mmol) was added dropwise and stirred for 90 min at −78° C. The mixture was poured into cooled saturated aq. $NH_4Cl$ solution. Phases were separated; the aqueous phase was extracted with EtOAc. The combined organic layers were dried over $MgSO_4$ and concentrated under reduced pressure. The residue was purified via flash chromatography using heptane and EtOAc as eluents to give 1-(2-pentylpyrazol-3-yl)ethanol.

$^1$H NMR (400 MHz, DMSO-$d_6$): 7.30 (d, 1H), 6.11 (d, 1H), 5.24 (d, 1H), 4.80 (m, 1H), 4.08 (m, 2H), 1.75 (p, 2H), 1.41 (d, 3H), 1.35-1.15 (m, 4H), 0.86 (t, 3H).

The enantiomers were separated via chiral chromatography column: AD, eluents: heptane/EtOH. The product eluting earlier was collected as Preparation 9dn, and the product eluting later was collected as Preparation 9do.

Preparation 9dp: [1-(2-Methoxyethyl)-1H-pyrazol-5-yl]methanol

Step A:

Starting from 5-(dimethoxymethyl)-1H-pyrazole (Preparation 9a5) and 1-bromo-2-methoxy-ethane using General Procedure 9F 5-(dimethoxymethyl)-1-(2-methoxyethyl)-1H-pyrazole was obtained.

$^1$H NMR (400 MHz, DMSO-$d_6$): 7.40 (d, 1H), 6.25 (d, 1H), 5.62 (s, 1H), 4.25 (t, 2H), 3.65 (t, 2H), 3.24 (s, 6H), 3.22 (s, 3H).

Note: 3-(dimethoxymethyl)-1-(2-methoxyethyl)-1H-pyrazole was also obtained.

$^1$H NMR (400 MHz, DMSO-d$_6$): 7.65 (d, 1H), 6.18 (d, 1H), 5.33 (s, 1H), 4.22 (t, 2H), 3.65 (t, 2H), 3.24 (s, 6H), 3.21 (s, 3H).

Step B:

Starting from 5-(dimethoxymethyl)-1-(2-methoxyethyl)-1H-pyrazole using General Procedure 9B the title product was obtained.

$^1$H NMR (400 MHz, DMSO-d$_6$): 7.33 (d, 1H), 6.13 (d, 1H), 5.22 (t, 1H), 4.50 (d, 2H), 4.24 (t, 2H), 3.65 (t, 2H), 3.20 (s, 3H).

Preparation 9dq:
[1-(3-Methoxypropyl)-1H-pyrazol-5-yl]methanol

Step A:

Starting from 5-(dimethoxymethyl)-1H-pyrazole (Preparation 9a5) and 1-bromo-3-methoxy-propane using General Procedure 9F 5-(dimethoxymethyl)-1-(3-methoxypropyl)-1H-pyrazole was obtained.

$^1$H NMR (400 MHz, DMSO-d$_6$): 7.40 (d, 1H), 6.25 (d, 1H), 5.59 (s, 1H), 4.12 (t, 2H), 3.29 (t, 2H), 3.25 (s, 6H), 3.23 (s, 3H), 1.96 (m, 2H).

Note: 3-(dimethoxymethyl)-1-(3-methoxypropyl)-1H-pyrazole was also obtained.

$^1$H NMR (400 MHz, DMSO-d$_6$): 7.66 (d, 1H), 6.18 (d, 1H), 5.33 (s, 1H), 4.11 (t, 2H), 3.25 (t, 2H), 3.23 (s, 6H), 3.21 (s, 3H), 1.97 (m, 2H).

Step B:

Starting from 5-(dimethoxymethyl)-1-(3-methoxypropyl)-1H-pyrazole using General Procedure 9B the title product was obtained.

$^1$H NMR (400 MHz, DMSO-d$_6$): 7.33 (d, 1H), 6.13 (d, 1H), 5.24 (t, 1H), 4.48 (d, 2H), 4.11 (t, 2H), 3.28 (t, 2H), 3.22 (s, 3H), 1.97 (m, 2H).

Preparation 9dr:
[1-(2-Ethoxyethyl)-1H-pyrazol-5-yl]methanol

Step A:

Starting from 5-(dimethoxymethyl)-1H-pyrazole (Preparation 9a5) and 1-bromo-2-ethoxy-ethane using General Procedure 9F 5-(dimethoxymethyl)-1-(2-ethoxyethyl)-1H-pyrazole was obtained.

$^1$H NMR (400 MHz, DMSO-d$_6$): 7.40 (d, 1H), 6.25 (d, 1H), 5.65 (s, 1H), 4.24 (t, 2H), 3.68 (t, 2H), 3.38 (m, 2H), 3.24 (s, 6H), 1.06 (t, 3H).

Note: 3-(dimethoxymethyl)-1-(2-ethoxyethyl)pyrazole was also obtained.

$^1$H NMR (400 MHz, DMSO-d$_6$): 7.65 (d, 1H), 6.19 (d, 1H), 5.33 (s, 1H), 4.21 (t, 2H), 3.69 (t, 2H), 3.39 (q, 2H), 3.24 (s, 6H), 1.05 (t, 3H).

Step B:

Starting from 5-(dimethoxymethyl)-1-(2-ethoxyethyl)-1H-pyrazole using General Procedure 9B the title product was obtained.

$^1$H NMR (400 MHz, DMSO-d$_6$): 7.33 (d, 1H), 6.13 (d, 1H), 5.20 (t, 1H), 4.51 (d, 2H), 4.23 (t, 2H), 3.68 (t, 2H), 3.38 (q, 2H), 1.05 (t, 3H).

Preparation 9ds: {1-[2-(2-Methoxyethoxy)ethyl]-1H-pyrazol-5-yl}methanol

Step A:

Starting from 5-(dimethoxymethyl)-1H-pyrazole (Preparation 9a5) and 1-(2-bromoethoxy)-2-methoxy-ethane using General Procedure 9F 5-(dimethoxymethyl)-1-[2-(2-methoxyethoxy)ethyl]-1H-pyrazole was obtained.

$^1$H NMR (400 MHz, DMSO-d$_6$): 7.40 (d, 1H), 6.25 (d, 1H), 5.67 (s, 1H), 4.25 (t, 2H), 3.72 (t, 2H), 3.47 (m, 2H), 3.39 (m, 2H), 3.25 (s, 6H), 3.21 (s, 3H).

Note: 3-(dimethoxymethyl)-1-[2-(2-methoxyethoxy)ethyl]-1H-pyrazole was also obtained.

$^1$H NMR (400 MHz, DMSO-d$_6$): 7.66 (d, 1H), 6.19 (d, 1H), 5.33 (s, 1H), 4.22 (t, 2H), 3.74 (t, 2H), 3.48 (m, 2H), 3.39 (m, 2H), 3.24 (s, 6H), 3.21 (s, 3H).

Step B:

Starting from 5-(dimethoxymethyl)-1-[2-(2-methoxyethoxy)ethyl]-1H-pyrazole using General Procedure 9B the title product was obtained.

$^1$H NMR (400 MHz, DMSO-d$_6$): 7.33 (d, 1H), 6.13 (d, 1H), 5.19 (t, 1H), 4.51 (d, 2H), 4.24 (t, 2H), 3.72 (t, 2H), 3.46 (m, 2H), 3.38 (m, 2H), 3.20 (s, 3H).

Preparation 9dt:
(1-tert-Butyl-1H-pyrazol-5-yl)methanol

Step A:

Starting from tert-butylhydrazine hydrochloride using General Procedure 9D 1-tert-butyl-5-(dimethoxymethyl)-1H-pyrazole was obtained.

$^1$H NMR (400 MHz, DMSO-d$_6$): 7.34 (d, 1H), 6.34 (d, 1H), 5.74 (s, 1H), 3.24 (s, 6H), 1.57 (s, 9H).

Note: 1-tert-butyl-3-(dimethoxymethyl)-1H-pyrazole was also obtained.

$^1$H NMR (400 MHz, DMSO-d$_6$): 7.75 (d, 1H), 6.18 (d, 1H), 5.34 (s, 1H), 3.24 (s, 6H), 1.50 (s, 9H).

Step B:

Starting from 1-tert-butyl-5-(dimethoxymethyl)-1H-pyrazole using General Procedure 9B the title product was obtained.

$^1$H NMR (400 MHz, DMSO-d$_6$): 7.27 (d, 1H), 6.19 (d, 1H), 5.31 (t, 1H), 4.61 (d, 2H), 1.56 (s, 9H).

Preparation 9du:
[1-(2,2,2-Trifluoroethyl)-1H-pyrazol-5-yl]methanol

Step A:

Starting from 2,2,2-trifluoroethylhydrazine (70 w/w % in water) using General Procedure 9D in absence of sodium methoxide 5-(dimethoxymethyl)-1-(2,2,2-trifluoroethyl)-4,5-dihydro-1H-pyrazol-5-ol was obtained.

$^1$H NMR (400 MHz, DMSO-d$_6$): 6.83 (t, 1H), 6.03 (s, 1H), 4.30 (s, 1H), 3.95 (m, 1H), 3.47 (m, 1H), 3.40 (d, 6H), 2.88 (m, 1H), 2.50 (m, 1H).

Step B:

Starting from 5-(dimethoxymethyl)-1-(2,2,2-trifluoroethyl)-4,5-dihydro-1H-pyrazol-5-ol using General Procedure 9B the title product was obtained.

$^1$H NMR (400 MHz, DMSO-d$_6$): 7.48 (d, 1H), 6.27 (d, 1H), 5.46 (t, 1H), 5.08 (q, 2H), 4.56 (d, 2H).

Preparation 9dv:
[1-(cyclohexylmethyl)-1H-pyrazol-5-yl]methanol and

Preparation 9dw:
[1-(cyclohexylmethyl)-1H-pyrazol-3-yl]methanol

Step A:

Starting from cyclohexylmethylhydrazine hydrochloride using General Procedure 9D 1-(cyclohexylmethyl)-5-(dimethoxymethyl)-1H-pyrazole was obtained. This product eluted first.

¹H NMR (400 MHz, DMSO-d₆): 7.38 (d, 1H), 6.25 (d, 1H), 5.59 (s, 1H), 3.91 (d, 2H), 3.24 (s, 6H), 1.89 (m, 1H), 1.66 (m, 2H), 1.61 (m, 2H), 1.48 (d, 2H), 1.16 (m, 2H), 0.95 (dd, 2H).

Note: The secondly eluted product was the 1-(cyclohexylmethyl)-3-(dimethoxymethyl)-1H-pyrazole.

¹H NMR (400 MHz, DMSO-d₆): 7.64 (d, 1H), 7.17 (d, 1H), 5.33 (s, 1H), 3.91 (d, 2H), 3.23 (s, 6H), 1.77 (m, 1H), 1.66 (m, 2H), 1.60 (m, 2H), 1.47 (d, 2H), 1.16 (m, 2H), 0.92 (dd, 2H).

Step B1:

Starting from 1-(cyclohexylmethyl)-5-(dimethoxymethyl)-1H-pyrazole using General Procedure 9B [1-(cyclohexylmethyl)-1H-pyrazol-5-yl]methanol was obtained.

¹H NMR (400 MHz, DMSO-d₆): 7.31 (d, 1H), 6.12 (d, 1H), 5.24 (t, 1H), 4.48 (d, 2H), 3.90 (d, 2H), 1.84 (m, 1H) 1.69-1.55 (m, 3H), 1.49 (m, 2H), 1.15 (m, 3H), 0.96 (m, 2H).

Step B2:

Starting from 1-(cyclohexylmethyl)-3-(dimethoxymethyl)-1H-pyrazole using General Procedure 9B [1-(cyclohexylmethyl)-1H-pyrazol-3-yl]methanol was obtained.

¹H NMR (400 MHz, DMSO-d₆): 7.56 (d, 1H), 6.13 (d, 1H), 4.94 (t, 1H), 4.37 (d, 2H), 3.85 (d, 2H), 1.75 (m, 1H) 1.69-1.56 (m, 3H), 1.49 (m, 2H), 1.15 (m, 3H), 0.91 (m, 2H).

Preparation 9ea: [6-(2-Furyl)-2-pyridyl]methanol

To the solution of 940 mg (6-bromo-2-pyridyl)methanol (5.00 mmol) in 20 mL dioxane 1.94 g 2-(2-furyl)-4,4,5,5-tetramethyl-1,3,2-dioxaborolane (10.0 mmol), 4.89 g $Cs_2CO_3$ (15.0 mmol) and 577 mg tetrakis(triphenylphosphine)palladium(0) (0.50 mmol) were added, and it was stirred under $N_2$ at 70° C. for 16 h. The reaction mixture was concentrated under reduced pressure. The residue was purified via flash chromatography using heptane and ethylacetate as eluents to give the title product.

MS: (M+H)⁺=176.2.

Preparation 9eb: [6-(2-Thienyl)-2-pyridyl]methanol

To the solution of 624 mg (6-bromo-2-pyridyl)methanol (3.30 mmol) in 15 mL dioxane 850 mg 2-thienylboronic acid (6.60 mmol), 3.25 g $Cs_2CO_3$ (10.0 mmol) and 385 mg tetrakis(triphenylphosphine)palladium(0) (0.33 mmol) were added, and it was stirred under $N_2$ at 70° C. for 16 h. The reaction mixture was concentrated under reduced pressure. The residue was purified via flash chromatography using heptane and ethyl-acetate as eluents to give the title product.

MS: (M+H)⁺=192.2.

Preparation 9ec:
(1-Butyl-1H-1,2,3-triazol-5-yl)methanol

Step A:

To the solution of 690 mg 1H-[1,2,3]triazole (10.0 mmol) in 5 mL DMF 1.50 g $K_2CO_3$ (11.0 mmol) and 1.50 g bromobutane (11.0 mmol) were added and the mixture was stirred at room temperature for 16 h. The reaction mixture was poured into 50 mL water and extracted with DCM. The combined organic phases were dried over $Na_2SO_4$ and concentrated under reduced pressure. The regioisomers were separated via flash chromatography using heptane and EtOAc as eluents: 2-butyl-2H-[1,2,3]triazole eluted first then 1-butyl-1H-[1,2,3]triazole.

¹H NMR (400 MHz, DMSO-d₆) of 1-butyl-1H-[1,2,3] triazole: 7.62 (m, 1H), 7.53 (m, 1H), 4.32 (m, 2H), 1.82 (m, 2H), 1.27 (m, 2H), 0.87 (m, 3H).

Step B:

To the cooled solution of 428 mg 1-butyl-1H-[1,2,3] triazole (3.40 mmol) in 15 mL THF under $N_2$ 2.35 mL BuLi (1.6M, 3.74 mmol) was added at −78° C., and it was stirred for 15 min, then 0.300 mL DMF (3.74 mmol) was added. The reaction mixture was stirred at room temperature for 24 h. It was poured onto 50 mL ice-water, and extracted with EtOAc. The combined organic phases were dried over $Na_2SO_4$ and concentrated under reduced pressure. The residue was dissolved in 20 mL EtOH and 250 mg sodium borohydride (6.50 mmol) was added at 0° C. and stirred for 1 h at this temperature, then it was stirred at room temperature for 16 h. Then 1 mL water was added, and the volatiles were removed under reduced pressure. The residue was diluted with EtOAc and washed with brine. The organic phase was dried over $Na_2SO_4$ and concentrated under reduced pressure. The residue was purified via flash chromatography using heptane and EtOAc as eluents to give the title product.

¹H NMR (400 MHz, DMSO-d₆): 7.59 (s, 1H), 5.46 (t, 1H), 4.58 (d, 2H), 4.32 (t, 2H), 1.79 (m, 2H), 1.29 (m, 2H), 0.90 (m, 3H).

Preparation 9ed: [1-(3-Methoxypropyl)-1H-1,2,3-triazol-5-yl]methanol

Step A:

To the solution of 690 mg 1H-[1,2,3]triazole (10.0 mmol) in 5 mL acetonitrile 1.50 g $K_2CO_3$ (11.0 mmol) and 1.68 g 1-bromo-3-methoxy-propane (11.0 mmol) were added and the mixture was stirred at room temperature for 24 h. The reaction mixture was filtered and concentrated under reduced pressure. The regioisomers were separated via flash chromatography using heptane and EtOAc as eluents: 2-(3-methoxypropyl)-1H-[1,2,3]triazole eluted first then 1-(3-methoxypropyl)-1H-[1,2,3]triazole.

¹H NMR (400 MHz, DMSO-d₆) of 1-(3-methoxypropyl)-1H-[1,2,3]triazole: 8.12 (d, 1H), 7.72 (d, 1H), 4.42 (t, 2H), 3.29 (t, 2H), 3.23 (s, 3H), 2.04 (m, 2H).

Step B:

To the cooled solution of 378 mg 1-(3-methoxypropyl)-1H-[1,2,3]triazole (2.70 mmol) in 12 mL THF under $N_2$ 1.90 mL BuLi (1.6M, 3.04 mmol) was added at −78° C., and it was stirred for 30 min, then 0.220 mL DMF (3.00 mmol) was added. The reaction mixture was stirred at room temperature for 4 h. It was poured onto 40 mL ice-water, and extracted with EtOAc. The combined organic phases were dried over $Na_2SO_4$ and concentrated under reduced pressure. The residue was dissolved in 16 mL EtOH and 200 mg sodium borohydride (5.29 mmol) was added at 0° C. and stirred for 1 h at this temperature, then it was stirred at room temperature for 16 h. Then 1 mL water was added, and the volatiles were removed under reduced pressure. The residue was diluted with EtOAc and washed with brine. The organic phase was dried over $Na_2SO_4$ and concentrated under reduced pressure. The residue was purified via flash chromatography using heptane and EtOAc as eluents to give the title product.

¹H NMR (400 MHz, DMSO-d₆): 7.60 (s, 1H), 5.46 (t, 1H), 4.57 (d, 2H), 4.37 (t, 2H), 3.31 (t, 2H), 3.23 (s, 3H), 2.04 (m, 2H).

Preparation 9ee:
(1-Phenyl-1H-1,2,3-triazol-5-yl)methanol

Step A:
(Tang, Bo-Xiao et al *Synthesis* 2008, 1707)

The mixture of 207 mg 1H-[1,2,3]triazole (3.00 mmol), 735 mg iodobenzene (3.60 mmol), 57 mg copper(I)oxide (0.60 mmol), 216 mg 1,10-phenantroline (1.20 mmol), and 2.35 g TBAF hydrate (9.00 mmol) was heated at 115° C. for 22 h under argon. The reaction mixture was diluted with EtOAc and washed with brine. The organic phase was dried over $Na_2SO_4$ and concentrated under reduced pressure. The residue was purified via flash chromatography using heptane and EtOAc as eluents to give 1-phenyl-1H-[1,2,3]triazole.

$^1$H NMR (400 MHz, DMSO-$d_6$): 8.84 (d, 1H), 7.99 (d, 1H), 7.92 (m, 2H), 7.61 (m, 2H), 7.49 (m, 1H).

Step B:
To the cooled solution of 216 mg 1-phenyl-1H-[1,2,3]triazole (1.50 mmol) in 7 mL THF under $N_2$ 1.00 mL BuLi (1.6M, 1.60 mmol) was added at −78° C., and it was stirred for 15 min, then 0.130 mL DMF (1.63 mmol) was added. The reaction mixture was stirred at room temperature for 90 min. It was poured onto 30 mL ice-water, and extracted with EtOAc. The combined organic phases were dried over $Na_2SO_4$ and concentrated under reduced pressure. The residue was dissolved in 9 mL EtOH and 111 mg sodium borohydride (2.94 mmol) was added at 0° C. and stirred for 1 h at this temperature, then it was stirred at room temperature for 16 h. Then 1 mL water was added and the reaction mixture was concentrated under reduced pressure. The residue was diluted with EtOAc and washed with brine. The organic phase was dried over $Na_2SO_4$ and concentrated under reduced pressure to give the title product.

MS: $(M+H)^+$=176.2.

Preparation 9ef:
[1-(2-Methoxyethyl)-1H-1,2,3-triazol-5-yl]methanol

Step A:
To the solution of 2.50 g ethyl 1H-[1,2,3]triazole-5-carboxylate (17.7 mmol) in 20 mL acetonitrile and in 3 mL DMF 3.19 g $K_2CO_3$ (23.1 mmol) and 3.20 g 1-bromo-2-methoxy-ethane (23.1 mmol) were added and the mixture was stirred at 35° C. for 24 h. Then it was filtered and concentrated under reduced pressure. The regioisomers were separated via flash chromatography using heptane and EtOAc as eluents: ethyl 2-(2-methoxyethyl)-2H-[1,2,3]triazole-4-carboxylate eluted first followed by ethyl 1-(2-methoxyethyl)-1H-1,2,3-triazole-5-carboxylate.

$^1$H NMR (400 MHz, DMSO-$d_6$) of ethyl 1-(2-methoxyethyl)-1H-1,2,3-triazole-5-carboxylate: 8.22 (s, 1H), 4.59 (t, 2H), 4.43 (q, 2H), 3.76 (t, 2H), 3.36 (s, 3H), 1.42 (t, 3H).

Step B:
To the solution of 223 mg ethyl 1-(2-methoxyethyl)-1H-1,2,3-triazole-5-carboxylate (1.12 mmol) in 5 mL EtOH 105 mg sodium borohydride (2.78 mmol) was added at 0° C. and the mixture was stirred for 1 h at this temperature, then it was stirred at room temperature for 16 h. Then 1 mL water was added, and the reaction mixture was concentrated under reduced pressure. The residue was digerated with DCM, the solids were filtered off and the filtrate was concentrated under reduced pressure to give the title product as yellow oil.

$^1$H NMR (400 MHz, DMSO-$d_6$): 7.64 (s, 1H), 4.69 (s, 2H), 4.61 (t, 2H), 3.85 (t, 2H), 3.37 (s, 3H).

Preparation 9eg:
4-(2-Hydroxyethyl)-1-methyl-piperazin-2-one

To the mixture of 450 mg 1-methylpiperazin-2-one (3.00 mmol) and 1.00 g $K_2CO_3$ (7.24 mmol) in 5 mL THF 1 mL 2-bromoethanol (14.1 mmol) was added and the mixture was stirred at 65° C. for 16 h. The mixture was cooled to room temperature, filtered and concentrated under reduced pressure. The residue was purified via flash chromatography using DCM and MeOH to give 4-(2-hydroxyethyl)-1-methyl-piperazin-2-one.

MS: $(M+H)^+$=159.4.

Preparation 9eh:
2-[4-(2,2,2-Trifluoroethyl)piperazin-1-yl]ethanol

Step A:
To a solution of 5.208 g 2-piperazin-1-ylethanol (40 mmol) in 250 mL dry ethanol 8.063 g 4-dimethylaminopyridine (66 mmol) and 12.1 mL (2,2,2-trifluoroacetyl) 2,2,2-trifluoroacetate (87 mmol) was added in portions and the mixture was stirred at room temperature until no further conversion was observed. The mixture was concentrated under reduced pressure and purified via flash chromatography using EtOAc and MeOH as eluents to give 2,2,2-trifluoro-1-[4-(2-hydroxyethyl)piperazin-1-yl]ethanone.

Step B:
To a mixture of 3.300 g 2,2,2-trifluoro-1-[4-(2-hydroxyethyl)piperazin-1-yl]ethanone (14.6 mmol) and 1.988 g imidazole (29.2 mmol) in 50 mL THF 4.7 mL chloro(triisopropyl)silane (21.9 mmol) was added dropwise and it was stirred at room temperature until no further conversion was observed. Then the volatiles were evaporated under reduced pressure and the residue was purified via flash chromatography using heptane and EtOAc as eluents to give 2,2,2-trifluoro-1-[4-(2-triisopropylsilyloxyethyl)piperazin-1-yl]ethanone.

MS (EI, 70 eV) m/z (% relative intensity, [ion]): 166 (5), 195 (100), 339 (11), 382 (1, [M$^+$]).

Step C:
To a solution of 1.55 g 2,2,2-trifluoro-1-[4-(2-triisopropylsilyloxyethyl)piperazin-1-yl]ethanone (4.0 mmol) in 15 mL THF 12 mL $BH_3$×THF (1.0 M in THF, 12 mmol) was added with stirring and it was heated at 45° C. until no further conversion was observed. The mixture was cooled to room temperature, the excess of $BH_3$ was decomposed by the addition of MeOH. The volatiles were evaporated under reduced pressure and the residue was co-evaporated with MeOH again. Then the crude product was purified via flash chromatography using heptane and EtOAc as eluents to give triisopropyl-[2-[4-(2,2,2-trifluoroethyl)piperazin-1-yl]ethoxy]silane.

MS (EI, 70 eV) m/z (% relative intensity, [ion]): 138 (7), 165 (5), 181 (100) 325 (9), 368 (4, [M$^+$]).

Step D:
To a solution of 0.536 g triisopropyl-[2-[4-(2,2,2-trifluoroethyl)piperazin-1-yl]ethoxy]silane (1.45 mmol) in 10 mL THF 1.52 mL TBAF (1.0 M in THF) was added and it was stirred at room temperature until no further conversion was observed. The volatiles were evaporated under reduced pressure and the residue was purified via flash chromatography using EtOAc and MeOH as eluents to give the title product.

$^1$H NMR (400 MHz, CDCl$_3$): 3.64 (t, 2H), 3.06 (br s, 2H), 2.98 (q, 2H), 2.78-2.68 (m, 4H), 2.63-2.53 (m, 5H).

Preparation 9ei:
2-[4-(2,2-Difluoroethyl)piperazin-1-yl]ethanol

Step A:
To a solution of 3.254 g 2-piperazin-1-ylethanol (25 mmol) in 60 mL dry ethanol 7.82 g 4-dimethylaminopyridine (64 mmol) and 8 mL (2,2-difluoroacetyl) 2,2-difluoroacetate (64 mmol) was added and stirred at room temperature. Later a second portion of 7.82 g 4-dimethylaminopyridine (64 mmol) and 8 mL (2,2-difluoroacetyl) 2,2-difluoroacetate (64 mmol) were added and the mixture was stirred at room temperature until no further conversion was observed. The mixture was concentrated under reduced pressure and purified via flash chromatography using EtOAc and MeOH as eluents to give 2,2-difluoro-1-[4-(2-hydroxyethyl)piperazin-1-yl]ethanone.
Step B:
1.800 g 2,2-difluoro-1-[4-(2-hydroxyethyl)piperazin-1-yl]ethanone (8.65 mmol) and 1.178 g imidazole (17.3 mmol) were dissolved in 25 mL THF and 2.8 mL chloro(triisopropyl)silane (13.0 mmol) was added dropwise to the solution, which was stirred at room temperature until no further conversion was observed. Then the volatiles were evaporated under reduced pressure and the residue was purified via flash chromatography using heptane and EtOAc as eluents to give 2,2-difluoro-1-[4-(2-triisopropylsilyloxyethyl)piperazin-1-yl]ethanone.
MS (EI, 70 eV) m/z (% relative intensity, [ion]): 148 (4), 177 (100), 321 (5), 364 (1, [M$^+$]).
Step C:
To a solution of 1.40 g 2,2-difluoro-1-[4-(2-triisopropylsilyloxyethyl)piperazin-1-yl]ethanone (3.84 mmol) in 15 mL THF 7.7 mL BH$_3$×THF (1.0 M in THF) was added with stirring and the mixture was heated at 45° C. until no further conversion was observed. After cooling to room temperature the excess of BH$_3$ was decomposed by the addition of MeOH. The volatiles were evaporated under reduced pressure and the residue was co-evaporated with MeOH again. Then the crude product was purified via flash chromatography using heptane and EtOAc as eluents to give 2-[4-(2,2-difluoroethyl)piperazin-1-yl]ethoxy-triisopropyl-silane.
MS (EI, 70 eV) m/z (% relative intensity, [ion]): 59 (5), 70 (7), 97 (5), 120 (9), 147 (3), 163 (100), 307 (3) 350 (1, [M$^+$]).
Step 2 D:
To a solution of 0.547 g 2-[4-(2,2-difluoroethyl)piperazin-1-yl]ethoxy-triisopropyl-silane (1.56 mmol) in 10 mL THF 1.64 mL TBAF (1.0 M in THF) was added and the mixture was stirred at room temperature until no further conversion was observed. The volatiles were evaporated under reduced pressure and the residue was purified via flash chromatography using EtOAc and MeOH as eluents to give the title product.
$^1$H NMR (400 MHz, CDCl$_3$): 5.87 (tt, 1H), 3.60 (t, 2H), 2.74 (td, 2H), 2.66-2.41 (m, 10H).

Preparation 9ej: [2-[4-Methoxy-2-(trifluoromethyl)phenyl]pyrimidin-4-yl]methanol Step A: N'-Hydroxy-4-methoxy-2-(trifluoromethyl)benzamidine
1 eq. hydroxylamine hydrochloride was dissolved in MeOH (1 ml/mmol) and 1 eq. NaHCO$_3$ was added. The mixture was stirred at room temperature for 20 min, then (4-methoxy-2-(trifluoromethyl)benzonitrile was added and the mixture was heated to reflux until no further conversion was observed. MeOH was partially evaporated, residue was filtered and dried under reduced pressure.
Step B: 4-(Dimethoxymethyl)-2-[4-methoxy-2-(trifluoromethyl)phenyl]pyrimidine
Using General Procedure 9C and this intermediate, 4-(dimethoxymethyl)-2-[4-methoxy-2-(trifluoromethyl)phenyl]pyrimidine was obtained.

HRMS calculated for C$_{15}$H$_{15}$N$_2$O$_3$F$_3$: 328.1035. found: 329.1099 (M+H).
$^1$H NMR (500 MHz, DMSO-d$_6$): 3.35 (s, 6H), 3.91 (s, 3H), 5.31 (s, 1H), 7.35 (m, 1H), 7.36 (m, 1H) 7.54 (d, 1H), 7.75 (d, 1H), 8.96 (d, 1H).
$^{13}$C NMR (125 MHz, DMSO-d$_6$): 54.1, 56.3, 103.0, 107.7, 112.9, 116.8, 124.1, 129.1, 130.6, 134.1, 158.7, 160.3, 165.0, 165.5.
Step C: [2-[4-Methoxy-2-(trifluoromethyl)phenyl]pyrimidin-4-yl]methanol
Starting from 4-(dimethoxymethyl)-2-[4-methoxy-2-(trifluoromethyl)phenyl]pyrimidine using General Procedure 9A Preparation 9ej was obtained.
MS: (M+H)$^+$=285.2.

Preparation 9ek: [1-(4-Pyridylmethyl)pyrazol-5-yl]methanol

Step A: 4-[[5-(Dimethoxymethyl)pyrazol-1-yl]methyl]pyridine
Starting from (hydrazinomethyl)pyridine dihydrochloride using General Procedure 9D 4-[[5-(dimethoxymethyl)pyrazol-1-yl]methyl]pyridine was obtained.
$^1$H NMR: (500 MHz, DMSO-d$_6$): 3.17 (s, 6H), 5.40 (s, 2H), 5.55 (s, 1H), 6.37 (d, 1 h), 7.02 (d, 2H), 7.51 (d, 1H), 8.50 (d, 2H).
$^{13}$C NMR (125 MHz, DMSO-d$_6$): 52.2, 53.3, 97.3, 106.7, 122.3, 139.0, 140.0, 147.1, 150.1.
Step B: [2-(4-Pyridylmethyl)pyrazol-3-yl]methanol
Starting from 4-[5-(dimethoxymethyl)pyrazol-1-yl]pyridine using General Procedure 9B Preparation 9ek was obtained.
$^1$H NMR: (500 MHz, DMSO-d$_6$)=4.46 (d, 2H), 5.35 (br, 1H), 5.40 (s, 2H), 6.25 (d, 1H), 7.04 (dm, 2H), 7.43 (d, 1H), 8.49 (dm, 2H).
$^{13}$C NMR: (125 MHz, DMSO-d$_6$)=51.6, 54.3, 105.9, 122.4, 138.9, 143.5, 147.2, 150.1.

Preparation 9el: [1-(2-Methoxyphenyl)pyrazol-3-yl]methanol and

Preparation 9em: [1-(2-Methoxyphenyl)pyrazol-5-yl]methanol

Step A: 3-(Dimethoxymethyl)-1-(2-methoxyphenyl)pyrazole and 5-(dimethoxymethyl)-1-(2-methoxyphenyl)pyrazole
Starting from 2-methoxyphenylhydrazine hydrochloride using General Procedure 9D 3-(dimethoxymethyl)-1-(2-methoxyphenyl)pyrazole was obtained as the product eluting first.
MS: (M+H)$^+$=249.2.
The product eluting second was 3-(dimethoxymethyl)-2-(2-methoxyphenyl)pyrazole.
MS: (M+H)$^+$=249.2.
Step B1: [1-(2-Methoxyphenyl)pyrazol-3-yl]methanol
Starting from 3-(dimethoxymethyl)-1-(2-methoxyphenyl)pyrazole using General Procedure 9B [1-(2-methoxyphenyl)pyrazol-3-yl]methanol was obtained as Preparation 9el.
$^1$H NMR (400 MHz, CDCl$_3$): 8.08 (d, 1H), 7.60 (dd, 1H), 7.34 (m, 1H), 7.23 (m, 1H), 7.06 (td, 1H), 6.42 (d, 1H), 5.13 (t, 1H), 4.49 (d, 2H), 3.86 (s, 3H).

Step B2: [1-(2-Methoxyphenyl)pyrazol-5-yl]methanol

Starting from 5-(dimethoxymethyl)-1-(2-methoxyphenyl) pyrazole using General Procedure 9B [1-(2-methoxyphenyl)pyrazol-5-yl]methanol was obtained as Preparation 9em.

$^1$H NMR (400 MHz, CDCl$_3$): 7.55 (d, 1H), 7.47 (m, 1H), 7.30 (m, 1H), 7.21 (m, 1H), 7.07 (td, 1H), 6.35 (m, 1H), 5.14 (t, 1H), 4.28 (d, 2H), 3.75 (s, 3H).

Preparation 9en:
[1-[(2-Methoxyphenyl)methyl]pyrazol-5-yl]methanol and

Preparation 9eo:
[1-[(2-Methoxyphenyl)methyl]pyrazol-3-yl]methanol

Step A: 5-(Dimethoxymethyl)-1-[(2-methoxyphenyl)methyl]pyrazole and 3-(dimethoxymethyl)-1-[(2-methoxyphenyl)methyl]pyrazole Starting from (2-methoxyphenyl)methylhydrazine hydrochloride using General Procedure 9D 5-(dimethoxymethyl)-1-[(2-methoxyphenyl)methyl]pyrazole was obtained as the product eluting first.

$^1$H NMR (500 MHz, DMSO-d$_6$): 3.19 (s, 6H), 3.83 (s, 3H), 5.28 (s, 2H), 5.53 (s, 1H), 6.33 (d, 1H), 6.56 (dm 1H), 6.84 (m, 1H), 7.01 (dm, 1H), 7.25 (m, 1H), 7.46 (d, 1H).

$^{13}$C NMR (500 MHz, DMSO-d$_6$): 48.2, 53.1, 55.2, 97.2, 106.2, 111.0, 120.7, 128.0, 129.1, 138.5.

The product eluting second was 3-(dimethoxymethyl)-1-[(2-methoxyphenyl) methyl]pyrazole.

$^1$H NMR (500 MHz, DMSO-d$_6$): 3.23 (s, 6H), 3.82 (s, 3H), 5.25 (s, 2H), 5.33 (s, 1H), 6.22 (d, 1H), 6.82 (dm, 1H), 6.89 (m, 1H), 7.03 (dm, 1H), 7.29 (m, 1H), 7.69 (d, 1H).

$^{13}$C NMR (500 MHz, DMSO-d$_6$): 50.5, 52.9, 55.9, 99.8, 104.0, 111.3, 120.8, 129.0, 129.6, 131.6.

Step B1: [2-[(2-Methoxyphenyl)methyl]pyrazol-3-yl]methanol

Starting from 5-(dimethoxymethyl)-1-[(2-methoxyphenyl)methyl]pyrazole using General Procedure 9B [1-[(2-methoxyphenyl)methyl]pyrazol-5-yl]methanol was obtained as Preparation 9en.

$^1$H NMR (400 MHz, CDCl$_3$): 7.39 (d, 1H), 7.25 (m, 1H), 7.02 (m, 1H), 6.84 (m, 1H), 6.53 (m, 1H), 6.22 (d, 1H), 5.29 (m, 2H), 5.28 (m, 1H), 4.46 (d, 2H), 3.83 (s, 3H).

Step B2: [1-[(2-Methoxyphenyl)methyl]pyrazol-3-yl]methanol

Starting from 3-(dimethoxymethyl)-1-[(2-methoxyphenyl)methyl]pyrazole using General Procedure 9B [1-[(2-methoxyphenyl)methyl]pyrazol-3-yl]methanol was obtained as Preparation 9eo.

$^1$H NMR (400 MHz, CDCl$_3$): 7.63 (d, 1H), 7.29 (m, 1H), 7.02 (m, 1H), 6.89 (m, 2H), 6.19 (d, 1H), 5.21 (s, 2H), 4.97 (t, 1H), 4.38 (d, 2H), 3.82 (s, 3H).

Preparation 9ep:
[1-(2-Ethoxyethyl)pyrazol-5-yl]methanol

Step A: 5-(Dimethoxymethyl)-1-(2-ethoxyethyl)pyrazole

Starting from 5-(dimethoxymethyl)-1H-pyrazole (Preparation 9a5) and 2-bromoethyl ethyl ether using General Procedure 9F 5-(dimethoxymethyl)-1-(2-ethoxyethyl)pyrazole was obtained.

MS: (M+H)$^+$=215.2.

Step B: [1-(2-Ethoxyethyl)pyrazol-5-yl]methanol

Starting from 5-(dimethoxymethyl)-1-(2-ethoxyethyl) pyrazole, using General Procedure 9B [2-(2-ethoxyethyl) pyrazol-3-yl]methanol (Preparation 9ep) was obtained.

HRMS calculated for $C_8H_{14}N_2O_2$: 170.1055. found: 171.1135 (M+H).

Preparation 9eq:
[2-(2-Fluorophenyl)pyrimidin-4-yl]methanol

Step A: 2-Fluoro-N'-hydroxy-benzamidine 11.48 g (165 mmol) hydroxylamine hydrochloride and 13.87 g (165 mmol) NaHCO$_3$ were dissolved in 120 mL MeOH and stirred at room temperature for 30 min. 10 g (82.6 mmol) 2-fluorobenzonitrile was added and the mixture was stirred at 75° C. until no further conversion was observed. Solvent was partially evaporated, residue was filtered, washed with MeOH, filtrate was concentrated. It was diluted with water and extracted with EtOAc. The combined organic phases were dried over Na$_2$SO$_4$, filtered and concentrated under reduced pressure.

Step B: 2-Fluorobenzamidine 12.67 g 2-fluoro-N'-hydroxy-benzamidine (81.55 mmol) was dissolved in AcOH at 0° C. and 9.24 mL (97.86 mmol) Ac$_2$O was added. Mixture was stirred at room temperature until no further conversion was observed. 630 mg 10% Pd/C was added and the mixture was stirred under 4 bar H$_2$ until no further conversion was observed. Mixture was filtered on celite and volatiles were removed in vacou to obtain 2-fluorobenzamidine.

MS: (M+H)$^+$=139.4.

Step C: 4-(Dimethoxymethyl)-2-(2-fluorophenyl)pyrimidine

Starting from 2-fluorobenzamidine using General Procedure 9C 4-(dimethoxymethyl)-2-(2-fluorophenyl)pyrimidine was obtained.

MS: (M+H)$^+$=249.2.

Step D: [2-(2-Fluorophenyl)pyrimidin-4-yl]methanol

Starting from 4-(dimethoxymethyl)-2-(2-fluorophenyl) pyrimidine using General Procedure 9A, [2-(2-fluorophenyl)pyrimidin-4-yl]methanol (Preparation 9 eq) was obtained.

MS: (M+H)$^+$=205.2.

Preparation 9er: [2-[2-(trideuteriomethoxy)phenyl]pyrimidin-4-yl]methanol

Step A: N',2-dihydroxybenzamidine 17.5 g H$_2$N—OH×HCl (252 mmol) was dissolved in 250 mL methanol, then 21.1 g NaHCO$_3$ (252 mmol) was added and it was stirred at rt for 30 minutes. Then 15.0 g 2-hydroxybenzonitrile (126 mmol) was added and refluxed for 5 h. The mixture was cooled to 0° C., it was filtered, and the filtrate was concentrated to dryness. 75 mL water was added and it was extracted with 3×75 mL ethylacetate. The combined organic layer was dried over MgSO$_4$ to give light yellow-brown crystals.

MS (ESI+): 153.2

Step B: 2-[4-(dimethoxymethyl)pyrimidin-2-yl]phenol 18.0 g N'-hydroxy-2-methoxy-benzamidine (118 mmol) was dissolved in 350 mL acetic acid and 13.4 mL acetic anhydride (14.49 g, 141.9 mmol) was added dropwise at 40° C. Then it was stirred at 50° C. for 45 minutes to reach 100% conversion by HPLC. 1.26 g Pd/C (7 m/m %, Pd on C, Strem Catalog No: 46-1900) was added and the mixture was stirred under 4 bar H$_2$ atmosphere for 4 hours to reach 100% conversion. Then it was filtered through Celite, washed with acetic acid and the filtrate was concentrated to dryness, then to the crude product 20 mL of diethylether was added and the so obtained mixture was sonicated for 10 minutes. It was filtered, precipitates were washed with 30 mL diethylether, and then precipitates were dried to give light yellow crystals. The obtained amidine acetic acid salt was used without further purification.

The crude amidine was dissolved in 350 mL methanol, then 16.0 g sodium methoxyde (295 mmol) was added portionwise at room temperature, then 28.7 g (E)-4-(dimethylamino)-1,1-dimethoxy-but-3-en-2-one (Preparation 9a1) (166 mmol) was added, and the reaction mixture was refluxed for 3 hours. The volatiles were evaporated, then 150 ml brine was added and the pH was set to 6 using 2N HCl. The mixture was extracted with 3×150 mL ethylacetate. The combined organic layers were dried over magnesium sulphate, filtered and concentrated. The crude product was purified via flash chromatography using heptane and ethylacetate as eluents to give the title compound as a light yellow oil.

MS (ESI+): 247.2

Step C: 4-(dimethoxymethyl)-2-[2-(trideuteriomethoxy)phenyl]pyrimidine

To the solution of 5.06 g 2-[4-(dimethoxymethyl)pyrimidin-2-yl]phenol (20.5 mmol) in 60 ml DMF 7.70 g cesium carbonate (23.6 mmol) was added and the reaction mixture was stirred at room temperature for 6 hours, then at 35° C. for 1 hour. Reaction mixture was concentrated under reduced pressure (55° C., 10 mbar), then 60 ml brine was added, and it was extracted with 3×60 ml ethylacetate. Combined organic layer was dried over magnesium sulphate, filtered and concentrated. The crude product was purified via flash chromatography using heptane and ethylacetate as eluents.

MS (ESI+): 264.2

Step D: [2-[2-(trideuteriomethoxy)phenyl]pyrimidin-4-yl]methanol

5N HCl (22 ml, 1.2 ml/mmol) was diluted with dioxan 22 ml (1.2 ml/mmol) then 4.81 g of 4-(dimethoxymethyl)-2-[2-(trideuteriomethoxy)phenyl]pyrimidine (18.27 mmol) was added and the reaction mixture was stirred under argon at 50° C. for 16 h to reach 98% conversion by HPLC. Reaction mixture was cooled to 0° C. The pH was adjusted to 9 by the portionwise addition of 5.6 g sodium hydroxyde (140 mmol) and $K_2CO_3$ solution (aq, 10%). At 0° C. 795 mg sodium borohydride (1.15 eq, 21 mmol) was added portionwise to the reaction mixture and it was stirred for 30 min. Then 20 ml brine was added and it was extracted with 2×60 ml of ethyl acetate. To the water phase 30 ml of saturated $NH_4Cl$ solution was added, and it was extracted with 2×60 ml of ethyl acetate again. Organic layers were combined, dried over magnesium sulphate, filtered and concentrated. The crude product was purified on ISCO 80 g silica gold column using heptane and ethylacetate as eluents to give Preparation 9er as white crystals.

MS (ESI+): 220.2

Preparation 10a: Ethyl (2R)-2-[(5S$_a$)-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[(2-methylsulfanylpyrimidin-4-yl)methoxy]phenyl]propanoate 1.77 g ethyl (2R)-2-[(5S$_a$)-5-[3-chloro-2-methyl-4-[2-(4-methylpiperazin-1-yl)ethoxy] phenyl]-6-(4-fluorophenyl)thieno[2,3-d]pyrimidin-4-yl]oxy-3-(2-hydroxyphenyl)propanoate (Preparation 8a) (2.5 mmol), 1.17 g (2-methylsulfanylpyrimidin-4-yl)methanol (Preparation 9aa) (7.5 mmol) and 1.97 g PPh$_3$ (7.5 mmol) were dissolved in 50 mL dry toluene, then 1.74 g ditertbutyl azodicarboxylate (7.5 mmol) was added. The mixture was stirred at 50° C. under nitrogen until no further conversion was observed. The toluene was evaporated under reduced pressure and the residue was purified via flash chromatography using DCM and MeOH as eluents.

$^1$H NMR (500 MHz, DMSO-d$_6$): 8.70 (d, 1H), 8.58 (s, 1H), 7.34 (d, 1H), 7.31 (d, 1H), 7.30 (m, 2H), 7.22 (m, 2H), 7.17 (t, 1H), 7.16 (d, 1H), 6.98 (d, 1H), 6.74 (t, 1H), 6.31 (d, 1H), 5.47 (dd, 1H), 5.17 (d, 1H), 5.11 (d, 1H), 4.20 (m, 1H), 4.16 (m, 1H), 4.06 (m, 2H), 3.12 (dd, 1H), 2.69 (m, 2H), 2.56 (dd, 1H), 2.50 (s, 3H), 2.46 (br s, 4H), 2.24 (br s, 4H), 2.10 (s, 3H), 1.86 (s, 3H), 1.06 (t, 3H).

HRMS calculated for $C_{43}H_{44}ClFN_6O_5S_2$: 842.2487. found: 843.2660 (M+H).

Preparation 10b: Ethyl (2R)-2-[(5S$_a$)-5-[3-chloro-4-(2-dimethylaminoethyloxy)-2-methyl-phenyl]-6-(4-fluorophenyl)thieno[2,3-d]pyrimidin-4-yl]oxy-3-[2-[(2-methylsulfanylpyrimidin-4-yl)methoxy]phenyl]propanoate 0.975 g ethyl (2R)-2-[(5S$_a$)-5-[3-chloro-4-(2-dimethylaminoethyloxy)-2-methyl-phenyl]-6-(4-fluorophenyl)thieno[2,3-d]pyrimidin-4-yl]oxy-3-(2-hydroxyphenyl)propanoate (Preparation 8b) (1.5 mmol), 0.702 g (2-methylsulfanylpyrimidin-4-yl)methanol (Preparation 9aa) (4.5 mmol) and 1.180 g PPh$_3$ (4.5 mmol) were dissolved in 50 mL dry toluene, then 1.036 g ditertbutyl azodicarboxylate (4.5 mmol) was added. The mixture was stirred at 50° C. under nitrogen until no further conversion was observed. The toluene was evaporated under reduced pressure, Et$_2$O was added, and the mixture was stirred and sonicated. The precipitated white crystals were filtered, washed with Et$_2$O. The filtrate was concentrated and purified via flash chromatography using DCM and MeOH as eluents.

$^1$H NMR (500 MHz, DMSO-d$_6$): 8.69 (d, 1H), 8.60 (s, 1H), 7.34 (d, 1H), 7.30 (d, 1H), 7.30 (dd, 2H), 7.23 (t, 2H), 7.17 (d, 1H), 7.16 (t, 1H), 6.98 (d, 1H), 6.74 (t, 1H), 6.29 (dd, 1H), 5.47 (dd, 1H), 5.17 (d, 1H), 5.11 (d, 1H), 4.19 (t, 1H), 4.15 (t, 1H), 4.08 (m, 1H), 4.05 (m, 1H), 3.13 (d, 1H), 2.64 (t, 2H), 2.56 (d, 1H), 2.50 (s, 3H), 2.19 (s, 6H), 1.85 (s, 3H), 1.06 (t, 3H).

HRMS calculated for $C_{40}H_{39}ClFN_5O_5S_2$: 787.2065. found: 788.2148 (M+H).

Preparation 10c: Ethyl (2R)-2-[(5S$_a$)-5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-[2-[(2-methylsulfanylpyrimidin-4-yl)methoxy]phenyl]propanoate 1.39 g ethyl (2R)-2-[(5S$_a$)-5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-(2-hydroxyphenyl)propanoate (Preparation 8c) (2.00 mmol), 0.94 g (2-methylsulfanylpyrimidin-4-yl)methanol (Preparation 9aa) (6.00 mmol) and 1.57 g PPh$_3$ (6.00 mmol) were dissolved in 40 mL dry toluene, then 1.38 g ditertbutyl azodicarboxylate (6.00 mmol) was added. The mixture was stirred at 50° C. under nitrogen until no further conversion was observed. The toluene was evaporated under reduced pressure and the residue was purified via flash chromatography using DCM and MeOH as eluents.

$^1$H NMR (500 MHz, DMSO-d$_6$): 8.70 (d, 1H), 8.57 (s, 1H), 7.35 (d, 1H), 7.27 (d, 1H), 7.25 (d, 1H), 7.19 (m, 1H), 7.00 (dm, 1H), 6.81 (m, 1H), 6.35 (dm, 1H), 5.89 (dd, 1H), 5.71 (t, 1H), 5.48 (dd, 1H), 5.18 (d, 1H), 5.12 (d, 1H), 4.26 (m, 1H), 4.22 (m, 1H), 4.08 (m, 1H), 4.05 (m, 1H), 3.15 (dd,

1H), 2.50 (s, 3H), 2.50 (br s, 4H), 2.49 (dd, 1H), 2.27 (br s, 4H), 2.11 (s, 3H), 1.95 (s, 3H), 1.06 (t, 3H).

HRMS calculated for $C_{41}H_{42}ClFN_6O_6S_2$: 832.2280. found: 833.2332 (M+H).

Preparation 10d: Ethyl (2R)-2-[(5S$_a$)-[3-chloro-2-methyl-4-[2-(4-ethylpiperazin-1-yl)ethoxy]phenyl]-6-(4-fluorophenyl)thieno[2,3-d]pyrimidin-4-yl]oxy-3-[2-[(2-methylsulfanylpyrimidin-4-yl)methoxy]phenyl]propanoate 1.80 g ethyl (2R)-2-[(5S$_a$)-5-[3-chloro-2-methyl-4-[2-(4-ethylpiperazin-1-yl)ethoxy] phenyl]-6-(4-fluorophenyl)thieno[2,3-d]pyrimidin-4-yl]oxy-3-(2-hydroxyphenyl)propanoate (Preparation 8p) (2.5 mmol), 1.17 g (2-methylsulfanylpyrimidin-4-yl)methanol (Preparation 9aa) (7.5 mmol) and 1.97 g PPh$_3$ (7.5 mmol) were dissolved in 50 mL dry toluene, then 1.74 g ditertbutyl azodicarboxylate (7.5 mmol) was added. The mixture was stirred at 50° C. under nitrogen until no further conversion was observed. The toluene was evaporated under reduced pressure and the residue was purified via flash chromatography using DCM and MeOH as eluents.

HRMS calculated for $C_{44}H_{46}ClFN_6O_5S_2$: 856.2644. found: 857.2743 (M+H).

Preparation 10e: Ethyl (2R)-2-[(5R$_a$)-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[(2-methylsulfanylpyrimidin-4-yl)methoxy]phenyl]propanoate 1.77 g ethyl (2R)-2-[(5R$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-hydroxyphenyl)propanoate (Preparation 8q) (2.5 mmol), 1.17 g (2-methylsulfanylpyrimidin-4-yl)methanol (Preparation 9aa) (7.5 mmol) and 1.97 g PPh$_3$ (7.5 mmol) were dissolved in 50 mL dry toluene, then 1.74 g ditertbutyl azodicarboxylate (7.5 mmol) was added. The mixture was stirred at 50° C. under nitrogen until no further conversion was observed. The toluene was evaporated under reduced pressure and the residue was purified via flash chromatography using DCM and MeOH as eluents.

MS: (M+H)=843.2

Preparation 10f: Ethyl (2S)-2-[5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[(2-methylsulfanylpyrimidin-4-yl)methoxy]phenyl]propanoate 1.77 g ethyl (2S)-2-[(5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-hydroxyphenyl)propanoate (Preparation 8r) (2.5 mmol), 1.17 g (2-methylsulfanylpyrimidin-4-yl)methanol (Preparation 9aa) (7.5 mmol) and 1.97 g PPh$_3$ (7.5 mmol) were dissolved in 50 mL dry toluene, then 1.74 g ditertbutyl azodicarboxylate (7.5 mmol) was added. The mixture was stirred at 50° C. under nitrogen until no further conversion was observed. The toluene was evaporated under reduced pressure and the residue was purified via flash chromatography using DCM and MeOH as eluents.

MS: (M+H)=843.2

Preparation 11a: Ethyl (2R)-2-[5-(3-chloro-2-ethyl-4-hydroxy-phenyl)-6-(2-furyl)thieno[2,3-d]pyrimidin-4-yl]oxy-3-(2-methoxyphenyl)propanoate (mixture of diastereoisomers)

403 mg ethyl (2R)-2-[5-bromo-6-(2-furyl)thieno[2,3-d]pyrimidin-4-yl]oxy-3-(2-methoxyphenyl)propanoate (Preparation 4e) (0.80 mmol), 371 mg [2-chloro-3-ethyl-4-(4,4,5,5-tetramethyl-1,3,2-dioxaborolan-2-yl)phenoxy]-triisopropyl-silane (Preparation 5e) (0.85 mmol), 57 mg Ataphos (0.08 mmol) and 652 mg Cs$_2$CO$_3$ (2.00 mmol) were dissolved in 8 mL dioxane and 2 mL water. The mixture was heated to 110° C. for 15 minutes via microwave irradiation. Then water was added and the pH was set to 6 with 2 M HCl. Then it was extracted with DCM, dried over Na$_2$SO$_4$, filtered and concentrated under reduced pressure and purified via reversed phase chromatography, using MeCN as eluent to obtain ethyl (2R)-2-[5-(3-chloro-2-ethyl-4-triisopropylsilyloxy-phenyl)-6-(2-furyl)thieno[2,3-d]pyrimidin-4-yl]oxy-3-(2-methoxyphenyl)propanoate (MS (M+H): 735.2). Then it was dissolved in 2 mL toluene, 0.45 mL TBAF (0.45 mmol in 1 M THF) was added and the mixture was stirred for 5 minutes. Then it was diluted with DCM, washed with water and brine, dried over Na$_2$SO$_4$, filtered and concentrated under reduced pressure. The crude product was purified via flash chromatography, using heptane and EtOAc as eluents to obtain Preparation 11a as a mixture of diastereoisomers.

MS (M+H): 579.2 for both diastereomers.

Preparation 11b: Ethyl (2R)-2-[5-(3-fluoro-4-hydroxy-2-methyl-phenyl)-6-(2-furyl)thieno[2,3-d]pyrimidin-4-yl]oxy-3-(2-methoxyphenyl)propanoate (mixture of diastereoisomers)

503 mg ethyl (2R)-2-[5-bromo-6-(2-furyl)thieno[2,3-d]pyrimidin-4-yl]oxy-3-(2-methoxyphenyl)propanoate (Preparation 4e) (1.00 mmol), 378 mg 2-fluoro-3-methyl-4-(4,4,5,5-tetramethyl-1,3,2-dioxaborolan-2-yl)phenol (Preparation 5g) (1.50 mmol), 21 mg Ataphos (0.03 mmol) and 652 mg Cs$_2$CO$_3$ (2.00 mmol) were dissolved in 8 mL dioxane and 2 mL water. The mixture was heated to 110° C. for 10 minutes via microwave irradiation. Then water was added and the pH was set to 6 with 2 M HCl. Then it was extracted with DCM, dried over Na$_2$SO$_4$, filtered and concentrated under reduced pressure. The crude product was purified via flash chromatography, using heptane and EtOAc as eluents to obtain Preparation 11b as a mixture of diastereoisomers.

MS (M+H): 549.0, (M−H): 547.0 for both diastereomers.

Preparation 12: 4-Chloro-5-[3-chloro-2-methyl-4-[2-(4-methylpiperazin-1-yl)ethoxy] phenyl]thieno[2,3-d]pyrimidine 25.00 g 4-chloro-5-iodo-thieno[2,3-d]pyrimidine (Preparation 1c) (84.31 mmol), 39.94 g 1-[2-[2-chloro-3-methyl-4-(4,4,5,5-tetramethyl-1,3,2-dioxaborolan-2-yl)phenoxy]ethyl]-4-methyl-piperazine (Preparation 5b) (101.2 mmol) and 53.69 g K$_3$PO$_4$ (252.9 mmol) were dissolved in 300 mL DME and 200 mL water. 946 mg palladium acetate (4.221 mmol) and 3.021 g "BuPAd$_2$ (8.433 mmol) were added, and then the mixture was stirred at 60° C. under argon atmosphere until no further conversion was observed. Then the DME was evaporated and the precipitated solid was filtered off and washed with water. To the filtered solid 100 mL MeCN was added and it was sonicated, and then it was filtered to give a pale yellow solid as Preparation 12.

$^1$H NMR (400 MHz, DMSO-d$_6$): 8.98 (s, 1H), 7.97 (s, 1H), 7.22 (d, 1H), 7.09 (s, 1H), 4.25-4.16 (m, 2H), 2.76 (t, 2H), 2.54 (br s, 4H), 2.32 (br s, 4H), 2.14 (s, 3H), 2.06 (s, 3H).

Preparation 13: 4-Chloro-5-[3-chloro-2-methyl-4-[2-(4-methylpiperazin-1-yl)ethoxy] phenyl]-6-iodo-thieno[2,3-d]pyrimidine 21.95 g 4-chloro-5-[3-chloro-2-methyl-4-[2-(4-methylpiperazin-1-yl)ethoxy]phenyl] thieno-[2,3-d]pyrimidine (Preparation 12) (50.20 mmol) was dissolved in 500 mL dry THF under N$_2$ and then it was cooled to −78° C. 50.20 mL lithium diisopropylamide (100.4 mmol, 2 M in THF, EtPh, hexanes) was added and the mixture was stirred at −78° C. for 1 hour. Then 25.48 g iodine (100.4 mmol) was added and the mixture was allowed to warm up to room temperature. The volatiles were evaporated; the residue was diluted with DCM, washed with 10% sodium thiosulphate solution. The aqueous layer was extracted with DCM. The combined organic phases were dried over Na$_2$SO$_4$, filtered and concentrated. 50 mL MeCN was added and it was sonicated for 10 minutes, filtered, washed with MeCN to give a pale yellow solid as Preparation 13.

$^1$H NMR (500 MHz, DMSO-d$_6$): 8.93 (s, 1H), 7.15 (d, 1H), 7.13 (d, 1H), 4.22 (t, 2H), 2.77 (t, 2H), 2.56 (br s, 4H), 2.34 (br s, 4H), 2.16 (s, 3H), 2.00 (s, 3H).

Preparation 14: 4-Chloro-5-[3-chloro-2-methyl-4-[2-(4-methylpiperazin-1-yl)ethoxy] phenyl]-6-(2-furyl) thieno[2,3-d]pyrimidine 3.00 g 4-chloro-5-[3-chloro-2-methyl-4-[2-(4-methylpiperazin-1-yl)ethoxy]phenyl]-6-iodo-thieno[2,3-d]pyrimidine (Preparation 13) (5.32 mmol), 2.06 g 2-(2-furyl)-4,4,5,5-tetramethyl-1,3,2-dioxaborolane (9.05 mmol), 377 mg Ata-Phos (0.53 mmol) and 5.205 g cesium carbonate (15.97 mmol) were placed in an 250 mL flask. 80 mL dioxane and 20 mL water were added, and then stirred at 70° C. under argon atmosphere until no further conversion was observed. Brine was added to the reaction mixture and it was extracted with EtOAc. The combined organic phases were dried over MgSO$_4$, filtered and evaporated under reduced pressure, and then purified by flash chromatography using DCM/MeOH as eluents to give Preparation 14.

$^1$H NMR (500 MHz, DMSO-d$_6$): 8.93 (s, 1H), 7.86 (d, 1H), 7.24 (d, 1H), 7.19 (d, 1H), 6.55 (d, 1H), 5.65 (d, 1H), 4.23 (t, 2H), 2.78 (t, 2H), 2.15 (s, 3H), 2.04 (s, 3H).

Preparation 15a: Methyl (2R)-2-[(5S$_a$)-5-(3-chloro-4-hydroxy-2-methyl-5-nitro-phenyl)-6-ethyl-thieno [2,3-d]pyrimidin-4-yl]oxy-3-phenyl-propanoate 483 mg methyl (2R)-2-[(5S$_a$)-5-(3-chloro-4-hydroxy-2-methyl-phenyl)-6-ethyl-thieno[2,3-d]pyrimidin-4-yl]oxy-3-phenyl-propanoate (Preparation 6i) (1.00 mmol) was dissolved in 10 mL MeCN, then 139 mg nitronium tetrafluoroborate (1.05 mmol) suspended in 10 mL MeCN was added and the mixture was stirred at 0° C. for 50 minutes. The volatiles were evaporated under reduced pressure and the crude product was purified via flash chromatography, using heptane and EtOAc as eluents to obtain Preparation 15a.

$^1$H NMR (400 MHz, DMSO-d$_6$): 11.19 (br s, 1H), 8.59 (s, 1H), 7.87 (s, 1H), 7.14 (m, 3H), 6.72 (m, 2H), 5.59 (dd, 1H), 3.53 (s, 3H), 2.97 (dd, 1H), 2.74-2.61 (m, 3H), 2.07 (s, 3H), 1.18 (t, 3H).

HRMS calculated for C$_{25}$H$_{22}$ClN$_3$O$_6$S: 527.0918. found: 528.0986 (M+H).

Preparation 15b: Methyl (2R)-2-[(5S$_a$)-5-(5-amino-3-chloro-4-hydroxy-2-methyl-phenyl)-6-ethyl-thieno [2,3-d]pyrimidin-4-yl]oxy-3-phenyl-propanoate 1.339 g methyl (2R)-2-[(5S$_a$)-5-(3-chloro-4-hydroxy-2-methyl-5-nitro-phenyl)-6-ethyl-thieno[2,3-d]pyrimidin-4-yl]oxy-3-phenyl-propanoate (Preparation 15a) (2.536 mmol) was dissolved in 40 mL MeOH. 270 mg Selcat Q6 was added and the mixture was stirred at 40° C. under 4 atm. H$_2$ pressure for 90 minutes. Then it was filtered through celite and the volatiles were evaporated under reduced pressure. The crude product was purified via flash chromatography, using heptane and EtOAc as eluents to obtain Preparation 15b.

$^1$H NMR (400 MHz, DMSO-d$_6$): 8.78 (br s, 1H), 8.52 (s, 1H), 7.16 (m, 3H), 6.67 (m, 2H), 6.58 (s, 1H), 5.45 (dd, 1H), 4.88 (br s, 2H), 3.51 (s, 3H), 2.92 (dd, 1H), 2.78 (dd, 1H), 2.72-2.59 (m, 2H), 1.86 (s, 3H), 1.17 (t, 3H).

HRMS calculated for C$_{25}$H$_{24}$ClN$_3$O$_4$S: 497.1176. found: 498.1259 (M+H).

Preparation 15c: Methyl (2R)-2-[(5S$_a$)-5-[7-chloro-2-(chloromethyl)-6-methyl-1,3-benzoxazol-5-yl]-6-ethyl-thieno[2,3-d]pyrimidin-4-yl]oxy-3-phenyl-propanoate 100 mg methyl (2R)-2-[(5S$_a$)-5-(5-amino-3-chloro-4-hydroxy-2-methyl-phenyl)-6-ethyl-thieno[2,3-d]pyrimidin-4-yl]oxy-3-phenyl-propanoate (Preparation 15b) (0.20 mmol) was dissolved in 0.5 mL dry toluene under N$_2$. 57 μL triethyl-ortochloroacetate (0.30 mmol) was added and the mixture was stirred at 100° C. for 1 hour. The volatiles were evaporated under reduced pressure. The crude product was purified via flash chromatography, using heptane and EtOAc as eluents to obtain Preparation 15c.

MS (M+H): 556.0.

Preparation 15d: Methyl (2R)-2-[(5S$_a$)-5-(3-chloro-4-hydroxy-5-iodo-2-methyl-phenyl)-6-ethyl-thieno [2,3-d]pyrimidin-4-yl]oxy-3-phenyl-propanoate 483 mg methyl (2R)-2-[(5S$_a$)-5-(3-chloro-4-hydroxy-2-methyl-phenyl)-6-ethyl-thieno[2,3-d]pyrimidin-4-yl]oxy-3-phenyl-propanoate (Preparation 6i) (1.0 mmol) was dissolved in 5 mL EtOH, then 305 mg iodine (1.2 mmol) and 405 mg Ag$_2$SO$_4$ (1.3 mmol) were added and the mixture was stirred at room temperature for 90 minutes. Then it was filtered, the filtrate was concentrated under reduced pressure and the crude product was purified via flash chromatography, using heptane and EtOAc as eluents to obtain Preparation 15d.

$^1$H NMR (400 MHz, DMSO-d$_6$): 10.10 (br s, 1H), 8.55 (s, 1H), 7.64 (s, 1H), 7.15 (m, 3H), 6.63 (m, 2H), 5.49 (dd, 1H), 3.58 (s, 1H), 3.00 (dd, 1H), 2.69 (dd, 1H), 2.65 (m, 2H), 1.99 (s, 3H), 1.17 (t, 3H).

HRMS calculated for C$_{25}$H$_{22}$ClIN$_2$O$_4$S: 608.0034. found: 609.0130 (M+H).

Preparation 15e: Methyl (2R)-2-[(5S$_a$)-5-(3,5-di-chloro-4-hydroxy-2-methyl-phenyl)-6-ethyl-thieno[2,3-d]pyrimidin-4-yl]oxy-3-phenyl-propanoate 483 mg methyl (2R)-2-[(5S$_a$)-5-(3-chloro-4-hydroxy-2-methyl-phenyl)-6-ethyl-thieno[2,3-d]pyrimidin-4-yl]oxy-3-phenyl-propanoate (Preparation 6i) (1.0 mmol) was dissolved in 5 mL THF, then 147 mg NCS (1.1 mmol) was added and the mixture was stirred at 50° C. for 3 hours. The volatiles were evaporated under reduced pressure and the crude product was purified via flash chromatography, using heptane and EtOAc as eluents to obtain Preparation 15e.

$^1$H NMR (400 MHz, DMSO-d$_6$): 10.21 (s, 1H), 8.56 (s, 1H), 7.33 (s, 1H), 7.16 (m, 3H), 6.66 (m, 2H), 5.52 (dd, 1H), 3.55 (s, 3H), 2.98 (dd, 1H), 2.70-2.60 (m, 3H), 1.99 (s, 3H), 1.17 (t, 3H).

HRMS calculated for C$_{25}$H$_{22}$Cl$_2$N$_2$O$_4$S: 516.0677. found: 517.0772 (M+H).

Preparation 15f: Methyl (2R)-2-[(5S$_a$)-5-(5-bromo-3-chloro-4-hydroxy-2-methyl-phenyl)-6-ethyl-thieno[2,3-d]pyrimidin-4-yl]oxy-3-phenyl-propanoate 169 mg methyl (2R)-2-[(5S$_a$)-5-(3-chloro-4-hydroxy-2-methyl-phenyl)-6-ethyl-thieno[2,3-d]pyrimidin-4-yl]oxy-3-phenyl-propanoate (Preparation 6i) (0.35 mmol) was dissolved in 2 mL THF, then 64 mg NBS (0.36 mmol) was added and the mixture was stirred at 50° C. for 10 minutes. The volatiles were evaporated under reduced pressure and the crude product was purified via flash chromatography, using heptane and EtOAc as eluents to obtain Preparation 15f.

$^1$H NMR (400 MHz, DMSO-d$_6$): 10.10 (br s, 1H), 8.54 (s, 1H), 7.44 (s, 1H), 7.15 (m, 3H), 6.65 (m, 2H), 5.50 (dd, 1H), 3.55 (s, 3H), 2.98 (dd, 1H), 2.70-2.59 (m, 3H), 1.97 (s, 1H), 1.16 (t, 3H).

MS (M+H): 561.0, (M–H): 559.0.

Unless otherwise specified, compounds of Preparation 16a to 16g were obtained using General Procedure 16A described below.

General Procedure 16A:

2.5 eq. 4-chloro-6-ethyl-5-iodo-thieno[2,3-d]pyrimidine (Preparation 1d), 1.0 eq. of the appropriate alcohol and 1.5 eq. cesium carbonate were dissolved in dry DMSO (0.25 M for Preparation 1d). The mixture was stirred at 100° C. under nitrogen until no further conversion was observed. The reaction mixture was cooled to room temperature, it was diluted with water, the pH was set to 7 with 2 M HCl, and then it was extracted with ethyl acetate. The combined organic phases were dried over Na$_2$SO$_4$, filtered, concentrated under reduced pressure and purified via flash chromatography using heptane and ethyl acetate as eluents.

Preparation 16a: Ethyl (2R)-3-(1,3-benzodioxol-4-yl)-2-(6-ethyl-5-iodo-thieno[2,3-d]pyrimidin-4-yl)oxy-propanoate Using General Procedure 16A and ethyl (2R)-3-(1,3-benzodioxol-4-yl)-2-hydroxy-propanoate (Preparation 3bg) as the appropriate alcohol we obtained Preparation 16a.

$^1$H NMR (400 MHz, CDCl$_3$): 8.49 (s, 1H), 6.90 (dd, 1H), 6.75 (t, 1H), 6.73 (dt, 1H), 5.92 (dd, 2H), 5.82 (t, 1H), 4.20 (dq, 2H), 3.40 (d, 2H), 2.93 (q, 2H), 1.33 (t, 3H), 1.21 (t, 3H).

Preparation 16b: Ethyl (2R)-3-(2,3-dihydrobenzofuran-7-yl)-2-(6-ethyl-5-iodo-thieno[2,3-d]pyrimidin-4-yl)oxy-propanoate Using General Procedure 16A and ethyl (2R)-3-(2,3-dihydrobenzofuran-7-yl)-2-hydroxy-propanoate (Preparation 3bd) as the appropriate alcohol we obtained Preparation 16b.

$^1$H NMR (400 MHz, CDCl$_3$): 8.48 (s, 1H), 7.17 (d, 1H), 7.08 (d, 1H), 6.76 (t, 1H), 5.81 (dd, 1H), 4.54 (dt, 2H), 4.19 (dq, 2H), 3.44-3.32 (m, 2H), 3.19 (t, 2H), 2.92 (q, 2H), 1.32 (t, 3H), 1.20 (t, 3H).

Preparation 16c: Ethyl (2S)-3-(2,3-dihydrobenzofuran-7-yl)-2-(6-ethyl-5-iodo-thieno[2,3-d]pyrimidin-4-yl)oxy-propanoate Using General Procedure 16A and ethyl (2S)-3-(2,3-dihydrobenzofuran-7-yl)-2-hydroxy-propanoate (Preparation 3be) as the appropriate alcohol we obtained Preparation 16c.

$^1$H NMR (400 MHz, CDCl$_3$): 8.48 (s, 1H), 7.17 (d, 1H), 7.08 (d, 1H), 6.76 (t, 1H), 5.81 (dd, 1H), 4.54 (dt, 2H), 4.19 (dq, 2H), 3.44-3.32 (m, 2H), 3.19 (t, 2H), 2.92 (q, 2H), 1.32 (t, 3H), 1.20 (t, 3H).

Preparation 16d: Ethyl 3-(benzofuran-7-yl)-2-(6-ethyl-5-iodo-thieno[2,3-d]pyrimidin-4-yl)oxy-propanoate Using General Procedure 16A and ethyl 3-(benzofuran-7-yl)-2-hydroxy-propanoate (Preparation 3bb) as the appropriate alcohol we obtained Preparation 16d.

$^1$H NMR (400 MHz, CDCl$_3$): 8.47 (s, 1H), 7.61 (d, 1H), 7.49 (d, 1H), 7.36 (d, 1H), 7.16 (t, 1H), 6.76 (d, 1H), 5.94 (dd, 1H), 4.18 (dq, 2H), 3.79-3.66 (m, 2H), 2.90 (q, 2H), 1.31 (t, 3H), 1.16 (t, 3H).

Preparation 16e: Ethyl (2S)-2-(6-ethyl-5-iodo-thieno[2,3-d]pyrimidin-4-yl)oxy-3-(2-fluorophenyl)propanoate Using General Procedure 16A and ethyl (2S)-3-(2-fluorophenyl)-2-hydroxy-propanoate (Preparation 3az) as the appropriate alcohol we obtained Preparation 16e.

$^1$H NMR (400 MHz, CDCl$_3$): 8.48 (s, 1H), 7.45 (dt, 1H), 7.23 (m, 1H), 7.06 (t, 1H), 7.04 (t, 1H), 5.78 (dd, 1H), 4.19 (m, 2H), 3.53-3.41 (m, 2H), 2.92 (q, 2H), 1.33 (t, 3H), 1.20 (t, 3H).

Preparation 16f: Ethyl (2R)-2-(6-ethyl-5-iodo-thieno[2,3-d]pyrimidin-4-yl)oxy-3-(2-fluorophenyl)propanoate Using General Procedure 16A and ethyl (2R)-3-(2-fluorophenyl)-2-hydroxy-propanoate (Preparation 3ba) as the appropriate alcohol we obtained Preparation 16f.

$^1$H NMR (400 MHz, CDCl$_3$): 8.48 (s, 1H), 7.45 (dt, 1H), 7.23 (m, 1H), 7.06 (t, 1H), 7.04 (t, 1H), 5.78 (dd, 1H), 4.19 (m, 2H), 3.53-3.41 (m, 2H), 2.92 (q, 2H), 1.33 (t, 3H), 1.20 (t, 3H).

Preparation 16g: Ethyl (2S)-3-(1,3-benzodioxol-4-yl)-2-(6-ethyl-5-iodo-thieno[2,3-d]pyrimidin-4-yl)oxy-propanoate Using General Procedure 16A and ethyl (2S)-3-(1,3-benzodioxol-4-yl)-2-hydroxy-propanoate (Preparation 3bh) as the appropriate alcohol we obtained Preparation 16g.

¹H NMR (400 MHz, CDCl₃): 8.49 (s, 1H), 6.90 (dd, 1H), 6.75 (t, 1H), 6.73 (dt, 1H), 5.92 (dd, 2H), 5.82 (t, 1H), 4.20 (dq, 2H), 3.40 (d, 2H), 2.93 (q, 2H), 1.33 (t, 3H), 1.21 (t, 3H).

Preparation 17a: Ethyl (2R)-3-(1,3-benzodioxol-4-yl)-2-[(5R$_a$)-5-(3-chloro-4-hydroxy-2-methyl-phenyl)-6-ethyl-thieno[2,3-d]pyrimidin-4-yl]oxy-propanoate and Preparation 17b: Ethyl (2R)-3-(1,3-benzodioxol-4-yl)-2-[(5S$_a$)-5-(3-chloro-4-hydroxy-2-methyl-phenyl)-6-ethyl-thieno[2,3-d]pyrimidin-4-yl]oxy-propanoate 0.482 g ethyl (2R)-3-(1,3-benzodioxol-4-yl)-2-(6-ethyl-5-iodo-thieno[2,3-d]pyrimidin-4-yl)oxy-propanoate (Preparation 16a) (0.92 mmol), 0.737 g 2-chloro-3-methyl-4-(4,4,5,5-tetramethyl-1,3,2-dioxaborolan-2-yl)phenol (Preparation 5a) (2.74 mmol), 0.041 g Pd(OAc)₂ (0.18 mmol) 0.130 g ⁿBuPAd₂ (0.36 mmol), 2.7 mL Bu₄NOH solution (2.7 mmol, 1.0 M in water) and 6.6 mL DME were heated under nitrogen at 100° C. for 10 min in microwave reactor with stirring. The pH of the mixture was set to 6 with 2 M HCl, and then it was extracted with MTBE. The combined organic phases were dried over Na₂SO₄, filtered and concentrated under reduced pressure. The diastereomers were separated via flash chromatography using heptane and EtOAc as eluents, collecting the diastereomer eluting earlier as Preparation 17a, and the diastereomer eluting later as Preparation 17b. Preparation 17a: ¹H NMR (500 MHz, DMSO-d₆): 10.28 (br s, 1H), 8.53 (s, 1H), 6.91 (d, 1H), 6.88 (d, 1H), 6.73 (d, 1H), 6.58 (t, 1H), 5.95 (s, 2H), 5.82 (d, 1H), 5.30 (dd, 1H), 4.09 (m, 2H), 2.97 (dd, 1H), 2.65 (m, 2H), 2.44 (dd, 1H), 2.15 (s, 3H), 1.15 (t, 3H), 1.09 (t, 3H). Preparation 17b: ¹H NMR (500 MHz, DMSO-d₆): 10.23 (br s, 1H), 8.54 (s, 1H), 7.03 (d, 1H), 6.96 (d, 1H), 6.75 (d, 1H), 6.62 (t, 1H), 5.96 (s, 1H), 5.94 (s, 1H), 5.92 (d, 1H), 5.43 (dd, 1H), 4.02 (m, 2H), 2.86 (dd, 1H), 2.62 (m, 2H), 2.58 (dd, 1H), 1.95 (s, 3H), 1.15 (t, 3H), 1.04 (t, 3H).

Preparation 17c: Ethyl (2R)-2-[(5S$_a$)-5-(3-chloro-4-hydroxy-2-methyl-phenyl)-6-ethyl-thieno[2,3-d]pyrimidin-4-yl]oxy-3-(2,3-dihydrobenzofuran-7-yl)propanoate 0.525 g ethyl (2R)-3-(2,3-dihydrobenzofuran-7-yl)-2-(6-ethyl-5-iodo-thieno[2,3-d]pyrimidin-4-yl)oxy-propanoate (Preparation 16b) (1.0 mmol), 0.670 g 2-chloro-3-methyl-4-(4,4,5,5-tetramethyl-1,3,2-dioxaborolan-2-yl)phenol (Preparation 5a) (2.5 mmol), 0.063 g AtaPhos (0.09 mmol), 2.5 mL Bu₄NOH solution (2.5 mmol, 1.0 M in water) and 4.5 mL 2-MeTHF were heated under nitrogen at 100° C. for 10 mins in a microwave reactor with stirring. The pH of the mixture was set to 6 with 2 M HCl, and then it was extracted with MTBE. The combined organic phases were dried over Na₂SO₄, filtered and concentrated under reduced pressure. The diastereomers were separated via flash chromatography using heptane and EtOAc as eluents, collecting the diastereomer eluting later as Preparation 17c.

¹H NMR (500 MHz, DMSO-d₆): 10.23 (br s, 1H), 8.52 (s, 1H), 7.04 (d, 1H), 7.02 (d, 1H), 6.96 (d, 1H), 6.62 (t, 1H), 6.12 (d, 1H), 5.38 (dd, 1H), 4.49 (m, 2H), 4.02 (m, 2H), 3.11 (t, 2H), 2.87 (dd, 1H), 2.61 (m, 2H), 2.45 (dd, 1H), 1.95 (s, 3H), 1.15 (t, 3H), 1.05 (t, 3H).

Preparation 17d: Ethyl (2S)-2-[(5R$_a$)-5-(3-chloro-4-hydroxy-2-methyl-phenyl)-6-ethyl-thieno[2,3-d]pyrimidin-4-yl]oxy-3-(2,3-dihydrobenzofuran-7-yl)propanoate 0.525 g ethyl (2S)-3-(2,3-dihydrobenzofuran-7-yl)-2-(6-ethyl-5-iodo-thieno[2,3-d]pyrimidin-4-yl)oxy-propanoate (Preparation 16c) (1.0 mmol), 0.670 g 2-chloro-3-methyl-4-(4,4,5,5-tetramethyl-1,3,2-dioxaborolan-2-yl)phenol (Preparation 5a) (2.5 mmol), 0.063 g AtaPhos (0.09 mmol), 2.5 mL Bu₄NOH solution (2.5 mmol, 1.0 M in water) and 4.5 mL 2-MeTHF were heated under nitrogen at 100° C. for 10 mins in a microwave reactor with stirring. The pH of the mixture was set to 6 with 2 M HCl, and then it was extracted with MTBE. The combined organic phases were dried over Na₂SO₄, filtered and concentrated under reduced pressure. The diastereomers were separated via flash chromatography using heptane and EtOAc as eluents, collecting the diastereomer eluting later as Preparation 17d.

¹H NMR (500 MHz, DMSO-d₆): 10.23 (br s, 1H), 8.52 (s, 1H), 7.04 (d, 1H), 7.02 (d, 1H), 6.96 (d, 1H), 6.62 (t, 1H), 6.12 (d, 1H), 5.38 (dd, 1H), 4.49 (m, 2H), 4.02 (m, 2H), 3.11 (t, 2H), 2.87 (dd, 1H), 2.61 (m, 2H), 2.45 (dd, 1H), 1.95 (s, 3H), 1.15 (t, 3H), 1.05 (t, 3H).

Preparation 17e: Ethyl (2R)-3-(benzofuran-7-yl)-2-[(5S$_a$)-5-(3-chloro-4-hydroxy-2-methyl-phenyl)-6-ethyl-thieno[2,3-d]pyrimidin-4-yl]oxy-propanoate and Preparation 17f: Ethyl (2S)-3-(benzofuran-7-yl)-2-[(5R$_a$)-5-(3-chloro-4-hydroxy-2-methyl-phenyl)-6-ethyl-thieno[2,3-d]pyrimidin-4-yl]oxy-propanoate 0.647 g Ethyl 3-(benzofuran-7-yl)-2-(6-ethyl-5-iodo-thieno[2,3-d]pyrimidin-4-yl)oxy-propanoate (Preparation 16d) (1.24 mmol), 0.766 g 2-chloro-3-methyl-4-(4,4,5,5-tetramethyl-1,3,2-dioxaborolan-2-yl)phenol (Preparation 5a) (2.85 mmol), 0.087 g AtaPhos (0.12 mmol), 2.5 mL Bu₄NOH solution (2.5 mmol, 1.0 M in water) and 5 mL 2-MeTHF were heated under nitrogen at 100° C. for 10 mins in a microwave reactor with stirring. The pH of the mixture was set to 6 with 2 M HCl, it was filtered through a pad of celite, and the pad was washed both with water and MTBE. The phases were then separated, the aqueous layer was extracted with MTBE. The combined organic phases were dried over Na₂SO₄, filtered and concentrated. The four stereoisomer containing mixture was first separated via flash chromatography using heptane and EtOAc as eluents, and collecting the racemic mixture eluting later. Then further separation of the mixture was accomplished by chiral chromatography, Column: AD, Eluents: heptane/EtOH. The enantiomer eluting earlier was collected as Preparation 17e with ee>99.8% and the enantiomer eluting later was collected as Preparation 17f with ee: 99.6%.

¹H NMR (500 MHz, DMSO-d₆): 10.25 (br s, 1H), 8.52 (s, 1H), 7.97 (d, 1H), 7.49 (m, 1H), 7.06 (d, 1H), 7.04 (t, 1H), 7.01 (d, 1H), 6.91 (d, 1H), 6.36 (m, 1H), 5.57 (dd, 1H), 3.98 (m, 1H), 3.93 (m, 1H), 3.22 (dd, 1H), 2.90 (dd, 1H), 2.65 (m, 1H), 2.60 (m, 1H), 1.96 (s, 3H), 1.15 (t, 3H), 0.94 (t, 3H).

Preparation 17g: Ethyl (2S)-2-[(5R$_a$)-5-(3-chloro-4-hydroxy-2-methyl-phenyl)-6-ethyl-thieno[2,3-d]pyrimidin-4-yl]oxy-3-(2-fluorophenyl)propanoate 0.425 g Ethyl (2S)-2-(6-ethyl-5-iodo-thieno[2,3-d]pyrimidin-4-yl)oxy-3-(2-fluorophenyl)propanoate (Preparation 16e) (0.85 mmol), 0.570 g 2-chloro-3-methyl-4-(4,4,5,5-tetramethyl-1,3,2-dioxaborolan-2-yl)phenol (Preparation 5a) (2.12 mmol), 0.053 g AtaPhos (0.075 mmol), 2.13 mL Bu$_4$NOH solution (2.13 mmol, 1.0 M in water) and 4 mL 2-MeTHF were heated under nitrogen at 100° C. for 10 mins in a microwave reactor with stirring. The pH of the mixture was set to 6 with 2 M HCl, it was filtered through a pad of celite, the pad was washed both with water and MTBE. The phases were then separated, the aqueous layer was extracted with MTBE. The combined organic phases were dried over Na$_2$SO$_4$, filtered and concentrated under reduced pressure. The diastereomers were separated via flash chromatography using heptane and EtOAc as eluents, collecting the diastereomer eluting later as Preparation 17g.

$^1$H NMR (500 MHz, DMSO-d$_6$): 10.23 (s, 1H), 8.54 (s, 1H), 7.24 (m, 1H), 7.09 (ddd, 1H), 7.05 (d, 1H), 6.98 (d, 1H), 6.97 (td, 1H), 6.45 (td, 1H), 5.42 (dd, 1H), 4.00 (m, 2H), 2.93 (dd, 1H), 2.72 (dd, 1H), 2.63 (m, 2H), 1.97 (s, 3H), 1.15 (t, 3H), 1.02 (t, 3H).

Preparation 17h: Ethyl (2R)-2-[(5S$_a$)-5-(3-chloro-4-hydroxy-2-methyl-phenyl)-6-ethyl-thieno[2,3-d]pyrimidin-4-yl]oxy-3-(2-fluorophenyl)propanoate 0.425 g Ethyl (2R)-2-(6-ethyl-5-iodo-thieno[2,3-d]pyrimidin-4-yl)oxy-3-(2-fluorophenyl)propanoate (Preparation 16f) (0.85 mmol), 0.570 g 2-chloro-3-methyl-4-(4,4,5,5-tetramethyl-1,3,2-dioxaborolan-2-yl)phenol (Preparation 5a) (2.12 mmol), 0.053 g AtaPhos (0.075 mmol), 2.13 mL Bu$_4$NOH solution (2.13 mmol, 1.0 M in water) and 4 mL 2-MeTHF were heated under nitrogen at 100° C. for 10 mins in a microwave reactor with stirring. The pH of the mixture was set to 6 with 2 M HCl, it was filtered through a pad of celite, the pad was washed both with water and MTBE. The phases were then separated, the aqueous layer was extracted with MTBE. The combined organic phases were dried over Na$_2$SO$_4$, filtered and concentrated under reduced pressure. The diastereomers were separated via flash chromatography using heptane and EtOAc as eluents, collecting the diastereomer eluting later as Preparation 17h.

$^1$H NMR (500 MHz, DMSO-d$_6$): 10.23 (s, 1H), 8.54 (s, 1H), 7.24 (m, 1H), 7.09 (ddd, 1H), 7.05 (d, 1H), 6.98 (d, 1H), 6.97 (td, 1H), 6.45 (td, 1H), 5.42 (dd, 1H), 4.00 (m, 2H), 2.93 (dd, 1H), 2.72 (dd, 1H), 2.63 (m, 2H), 1.97 (s, 3H), 1.15 (t, 3H), 1.02 (t, 3H).

Preparation 17i: Ethyl (2S)-3-(1,3-benzodioxol-4-yl)-2-[(5S$_a$)-5-(3-chloro-4-hydroxy-2-methyl-phenyl)-6-ethyl-thieno[2,3-d]pyrimidin-4-yl]oxy-propanoate and

Preparation 17j: Ethyl (2S)-3-(1,3-benzodioxol-4-yl)-2-[(5R$_a$)-5-(3-chloro-4-hydroxy-2-methyl-phenyl)-6-ethyl-thieno[2,3-d]pyrimidin-4-yl]oxy-propanoate 0.482 g ethyl (2S)-3-(1,3-benzodioxol-4-yl)-2-(6-ethyl-5-iodo-thieno[2,3-d]pyrimidin-4-yl)oxy-propanoate (Preparation 16g) (0.92 mmol), 0.737 g 2-chloro-3-methyl-4-(4,4,5,5-tetramethyl-1,3,2-dioxaborolan-2-yl)phenol (Preparation 5a) (2.74 mmol), 0.041 g Pd(OAc)$_2$ (0.18 mmol), 0.130 g $^n$BuPAd$_2$ (0.36 mmol), 2.7 mL Bu$_4$NOH solution (2.7 mmol, 1.0 M in water) and 6.6 mL DME were heated under nitrogen at 100° C. for 10 mins in a microwave reactor with stirring. The pH of the mixture was set to 6 with 2 M HCl, and then it was extracted with MTBE. The combined organic phases were dried over Na$_2$SO$_4$, filtered and concentrated under reduced pressure. The diastereomers were separated via flash chromatography using heptane and EtOAc as eluents, collecting the diastereomer eluting earlier as Preparation 17i, and the diastereomer eluting later as Preparation 17j. Preparation 17i: $^1$H NMR (500 MHz, DMSO-d$_6$): 10.28 (br s, 1H), 8.53 (s, 1H), 6.91 (d, 1H), 6.88 (d, 1H), 6.73 (d, 1H), 6.58 (t, 1H), 5.95 (s, 2H), 5.82 (d, 1H), 5.30 (dd, 1H), 4.09 (m, 2H), 2.97 (dd, 1H), 2.65 (m, 2H), 2.44 (dd, 1H), 2.15 (s, 3H), 1.15 (t, 3H), 1.09 (t, 3H). Preparation 17j: $^1$H NMR (500 MHz, DMSO-d$_6$): 10.23 (br s, 1H), 8.54 (s, 1H), 7.03 (d, 1H), 6.96 (d, 1H), 6.75 (d, 1H), 6.62 (t, 1H), 5.96 (s, 1H), 5.94 (s, 1H), 5.92 (d, 1H), 5.43 (dd, 1H), 4.02 (m, 2H), 2.86 (dd, 1H), 2.62 (m, 2H), 2.58 (dd, 1H), 1.95 (s, 3H), 1.15 (t, 3H), 1.04 (t, 3H).

Preparation 18a: Ethyl (2R)-2-[(5S$_a$)-5-(3-chloro-4-hydroxy-5-methoxy-2-methyl-phenyl)-6-prop-1-ynyl-thieno[2,3-d]pyrimidin-4-yl]oxy-3-(2-methoxyphenyl)propanoate 444 mg ethyl (2R)-2-(5-iodo-6-prop-1-ynyl-thieno[2,3-d]pyrimidin-4-yl)oxy-3-(2-methoxyphenyl)propanoate (Preparation 4k) (0.85 mmol), 297 mg 2-chloro-6-methoxy-3-methyl-4-(4,4,5,5-tetramethyl-1,3,2-dioxaborolan-2-yl)phenol (Preparation 5k) (1.00 mmol), 62 mg PdCl$_2$×dppf (0.085 mmol) and 326 mg Cs$_2$CO$_3$ (1.00 mmol) were dissolved in 8 mL dioxane and 2 mL water. The mixture was heated to 110° C. for 10 minutes via microwave irradiation. Then it was diluted with brine, neutralized with 2 M HCl, extracted with DCM, dried over Na$_2$SO$_4$, filtered and concentrated under reduced pressure. The crude product was purified via flash chromatography, using heptane and EtOAc as eluents. The diastereoisomer eluting earlier was collected as Preparation 18a.

$^1$H NMR (400 MHz, DMSO-d$_6$): 9.60 (br s, 1H), 8.62 (s, 1H), 7.15 (t, 1H), 6.89 (s, 1H), 6.87 (d, 1H), 6.66 (t, 1H), 6.05 (dd, 1H), 5.32 (dd, 1H), 4.11 (m, 2H), 3.86 (s, 3H), 3.75 (s, 3H), 3.10 (dd, 1H), 2.37 (dd, 1H), 2.06 (s, 3H), 2.05 (s, 3H), 1.11 (t, 3H).

HRMS calculated for C$_{29}$H$_{27}$ClN$_2$O$_6$S: 566.1278. found: 567.1360 (M+H).

Preparation 18b: Ethyl (2R)-2-[5-(3-chloro-4-hydroxy-2,5-dimethyl-phenyl)-6-prop-1-ynyl-thieno[2,3-d]pyrimidin-4-yl]oxy-3-(2-methoxyphenyl)propanoate (mixture of diastereoisomers)

522 mg ethyl (2R)-2-(5-iodo-6-prop-1-ynyl-thieno[2,3-d]pyrimidin-4-yl)oxy-3-(2-methoxyphenyl)propanoate (Preparation 4k) (1.00 mmol), 351 mg 2-chloro-3,6-dimethyl-4-(4,4,5,5-tetramethyl-1,3,2-dioxaborolan-2-yl)phenol (Preparation 5l) (1.24 mmol), 73 mg PdCl$_2$×dppf (0.10 mmol) and 489 mg Cs$_2$CO$_3$ (1.50 mmol) were dissolved in 8 mL dioxane and 2 mL water. The mixture was heated to 110° C. for 12 minutes via microwave irradiation. Then it was diluted with brine, neutralized with 2 M HCl, extracted with DCM, dried over Na$_2$SO$_4$, filtered and concentrated under reduced pressure. The crude product was purified via flash chromatography, using heptane and EtOAc as eluents to obtain Preparation 18b as a mixture of diastereoisomers.

$^1$H NMR (400 MHz, DMSO-$d_6$): 9.25 (br s, 1H), 8.61 (s, 1H), 7.14 (t, 1H), 7.06/6.94 (s, 1H), 6.87 (d, 1H), 6.65/6.61 (t, 1H), 6.11/6.06 (dd, 1H), 5.33/5.25 (dd, 1H), 4.14-4.02 (m, 2H), 3.75 (s, 3H), 3.09/3.05 (dd, 1H), 2.44-2.34 (m, 1H), 2.27/2.26 (s, 3H), 2.18/2.09 (s, 3H), 2.04/2.02 (s, 3H), 1.09 (t, 3H).

HRMS calculated for $C_{29}H_{27}ClN_2O_5S$: 550.1329. found: 551.1412 (M+H).

Preparation 18c: Ethyl (2R)-2-[(5S$_a$)-5-(3-chloro-5-fluoro-4-hydroxy-2-methyl-phenyl)-6-prop-1-ynyl-thieno[2,3-d]pyrimidin-4-yl]oxy-3-(2-methoxyphenyl)propanoate 522 mg ethyl (2R)-2-(5-iodo-6-prop-1-ynyl-thieno[2,3-d]pyrimidin-4-yl)oxy-3-(2-methoxyphenyl)propanoate (Preparation 4k) (1.00 mmol), 403 mg 2-chloro-6-fluoro-3-methyl-4-(4,4,5,5-tetramethyl-1,3,2-dioxaborolan-2-yl)phenol (Preparation 5m) (1.5 mmol), 71 mg AtaPhos (0.1 mmol) and 652 mg $Cs_2CO_3$ (2.00 mmol) were dissolved in 8 mL dioxane and 2 mL water. The mixture was heated to 100° C. for 15 minutes via microwave irradiation. Then it was diluted with brine, neutralized with 2 M HCl, extracted with DCM, dried over $Na_2SO_4$, filtered and concentrated under reduced pressure. The crude product was purified via flash chromatography, using heptane and EtOAc as eluents. The diastereoisomer eluting later was collected as Preparation 18c.

$^1$H NMR (400 MHz, DMSO-$d_6$): 10.56 (br s, 1H), 8.64 (s, 1H), 7.17 (dt, 1H), 7.13 (d, 1H), 6.90 (d, 1H), 6.69 (t, 1H), 6.23 (dd, 1H), 5.41 (dd, 1H), 4.11-4.01 (m, 2H), 3.75 (s, 3H), 3.03 (dd, 1H), 2.52 (dd, 1H), 2.06 (m, 6H), 1.08 (t, 3H).

HRMS calculated for $C_{28}H_{24}ClFN_2O_5S$: 554.1078. found: 555.1166 (M+H).

Preparation 19a: Ethyl 3-(benzofuran-4-yl)-2-(5-iodo-6-prop-1-ynyl-thieno[2,3-d]pyrimidin-4-yl)oxy-propanoate 2.676 g 4-chloro-5-iodo-6-prop-1-ynyl-thieno[2,3-d]pyrimidine (Preparation 2f) (8 mmol), 0.937 g ethyl 3-(benzofuran-4-yl)-2-hydroxy-propanoate (Preparation 3bc) (4 mmol) and 1.955 g $Cs_2CO_3$ (6 mmol) were placed in a flask. 20 mL dry DMSO was added and the mixture was stirred at room temperature until no further conversion was observed. It was diluted with water, the pH was set to 8 with 2 M HCl, and then it was extracted with DCM. The combined organic phases were dried over $Na_2SO_4$ filtered and concentrated under reduced pressure and purified via flash chromatography using heptane and ethyl acetate as eluents to give Preparation 19a.

$^1$H NMR (400 MHz, $CDCl_3$): 8.50 (s, 1H), 7.64 (d, 1H), 7.40 (d, 1H), 7.33 (d, 1H), 7.22 (t, 1H), 6.94 (d, 1H), 5.82 (dd, 1H), 4.17 (m, 2H), 3.71-3.59 (m, 2H), 2.18 (s, 3H).

Preparation 20a: Ethyl (2R)-3-(benzofuran-4-yl)-2-[(5S$_a$)-5-(3-chloro-4-hydroxy-2-methyl-phenyl)-6-prop-1-ynyl-thieno[2,3-d]pyrimidin-4-yl]oxy-propanoate and Preparation 20b: Ethyl (2S)-3-(benzofuran-4-yl)-2-[(5R$_a$)-5-(3-chloro-4-hydroxy-2-methyl-phenyl)-6-prop-1-ynyl-thieno[2,3-d]pyrimidin-4-yl]oxy-propanoate 0.850 g ethyl 3-(benzofuran-4-yl)-2-(5-iodo-6-prop-1-ynyl-thieno[2,3-d]pyrimidin-4-yl)oxy-propanoate (Preparation 19a) (1.6 mmol), 0.859 g 2-chloro-3-methyl-4-(4,4,5,5-tetramethyl-1,3,2-dioxaborolan-2-yl)phenol (Preparation 5a) (3.2 mmol), 0.110 g AtaPhos (0.16 mmol) and 1.043 g $Cs_2CO_3$ (3.2 mmol) were placed in a microwave reactor tube. 16 mL Dioxane and 4.8 mL $H_2O$ were added and the mixture was heated under nitrogen at 80° C. for 10 mins in microwave reactor. The mixture was filtered through a pad of celite, the pad was washed both with water and MTBE. The pH of the filtrate was adjusted to 7 with 2 M HCl, and then it was shaken. The aqueous phase was extracted with MTBE, the combined organic layers were dried over $Na_2SO_4$, filtered and concentrated under reduced pressure. The mixture containing four stereoisomers was first separated via flash chromatography using heptane and EtOAc as eluents and the racemic mixture eluting later was collected. Then this mixture was separated by chiral chromatography, Column: AD, Eluents: heptane/ethanol. The product eluting earlier was collected as Preparation 20a with ee: 96.8%, the product eluting later was collected as Preparation 20b with ee>99.8%.

$^1$H NMR (500 MHz, DMSO-$d_6$): 10.31 (br s, 1H), 8.62 (s, 1H), 7.95 (dd, 1H), 7.41 (dd, 1H), 7.13 (dd, 1H), 7.05 (dd, 1H), 7.00 (dd, 1H), 6.82 (dd, 1H), 6.28 (dd, 1H), 5.49 (dd, 1H), 3.98 (m, 1H), 3.91 (m, 1H), 3.16 (dd, 1H), 2.98 (dd, 1H), 2.09 (s, 3H), 2.03 (s, 3H), 0.97 (t, 3H).

Preparation 21: Methyl (2R)-2-(6-bromo-5-iodo-thieno[2,3-d]pyrimidin-4-yl)oxy-3-phenyl-propanoate 15.39 g 6-bromo-4-chloro-5-iodo-thieno[2,3-d]pyrimidine (Preparation 1e) (41 mmol), 11.08 g methyl (2R)-2-hydroxy-3-phenyl-propanoate (61.5 mmol) and 26.71 g cesium carbonate (82 mmol) were placed in a 100 mL flask. 40 mL dry DMSO was added and the mixture was stirred at 70° C. under argon atmosphere until no further conversion was observed. The reaction mixture was poured onto 200 mL water, and then pH was set to ~5. The precipitated product was collected by filtration.

MS (M+H)=519.0.

Preparation 22: Methyl (2R)-2-[6-bromo-(5S$_a$)-5-(3-chloro-4-hydroxy-2-methyl-phenyl)thieno[2,3-d]pyrimidin-4-yl]oxy-3-phenyl-propanoate 1.557 g methyl (2R)-2-(6-bromo-5-iodo-thieno[2,3-d]pyrimidin-4-yl)oxy-3-phenyl-propanoate (Preparation 21) (3.0 mmol), 1.289 g 2-chloro-3-methyl-4-(4,4,5,5-tetramethyl-1,3,2-dioxaborolan-2-yl)phenol (Preparation 5a) (4.8 mmol), 219 mg Pd(ddpf)$Cl_2$ (0.3 mmol) and 2.931 g cesium carbonate (9.0 mmol) were placed in a 30 mL microwave tube. After addition of 12 mL dioxane and 6 mL water reaction was heated at 120° C. under nitrogen with stirring for 25 min in a microwave reactor. Water was added to the reaction mixture and the pH was set to 5 with 2 M HCl. The resulting mixture was extracted with DCM. The combined organic phases were dried over $Na_2SO_4$, filtered and concentrated under reduced pressure. Diastereoisomers were separated via flash chromatography using heptane and ethyl acetate as eluents. The diastereoisomer eluting later was collected as Preparation 22.

MS (M+H)=532.0.

Preparation 23a: [2-Chloro-4-(4-chlorothieno[2,3-d]pyrimidin-5-yl)-3-methyl-phenoxy]-triisopropyl-silane 34.50 g 4-chloro-5-iodo-thieno[2,3-d]pyrimidine (Preparation 1c) (116.3 mmol), 59.32 g [2-chloro-3-methyl-4-(4, 4,5,5-tetramethyl-1,3,2-dioxaborolan-2-yl)phenoxy]-triisopropyl-silane (Preparation 5c) (139.6 mmol), 653 mg Pd(OAc)$_2$ (2.908 mmol), 2.085 g ″BuPAd$_2$ (5.817 mmol) and 74.09 g K$_3$PO$_4$ (349.0 mmol) were placed in a 1 L flask. After addition of 450 mL DME and 150 mL water the reaction was stirred under nitrogen at 60° C. until no further conversion was observed. To the reaction mixture saturated aq. NH$_4$Cl was added and then it was extracted with EtOAc. The combined organic layers were dried over MgSO$_4$ and concentrated under reduced pressure. The obtained solid was sonicated in acetonitrile/water (3:1) and collected by filtration to give Preparation 23a.

$^1$H NMR (400 MHz, DMSO-d$_6$): 8.95 (s, 1H), 7.98 (s, 1H), 7.13 (d, 1H), 6.91 (d, 1H), 2.05 (s, 3H), 1.40-1.29 (m, 3H), 1.10 (dd, 18H).

Preparation 23b: 4-Chloro-5-(3-chloro-2-methyl-phenyl)thieno[2,3-d]pyrimidine

Step A:
The mixture of 4.26 g (3-chloro-2-methyl-phenyl)boronic acid (25.0 mmol) and 2.954 g 2,3-dimethylbutane-2,3-diol (25.0 mmol) was dissolved in 125 mL 2-Me-THF and 0.2 g dry Amberlyst 15 H$^+$ ion-exchange resin (previously co-evaporated with toluene) was added and the mixture was stirred at room temperature until no further conversion was observed. The solution was filtered through a pad of celite, it was washed with 2-MeTHF and the filtrate was evaporated under reduced pressure to give 2-(3-chloro-2-methyl-phenyl)-4,4,5,5-tetramethyl-1,3,2-dioxaborolane. The obtained material was used without further purification.

Step B:
3.558 g 4-chloro-5-iodo-thieno[2,3-d]pyrimidine (Preparation 1c) (12.0 mmol), 3.636 g 2-(3-chloro-2-methyl-phenyl)-4,4,5,5-tetramethyl-1,3,2-dioxaborolane (Step A, 14.4 mmol), 67.4 mg Pd(OAc)$_2$ (0.3 mmol), 0.215 g ″BuPAd$_2$ (0.6 mmol) and 7.645 g K$_3$PO$_4$ (36.0 mmol) were placed in a flask. After the addition of 45 mL DME and 15 mL water the mixture was stirred under nitrogen at 60° C. until no further conversion was observed. To the reaction mixture saturated aq. NH$_4$Cl was added and it was extracted with EtOAc. The combined organic layers were dried over MgSO$_4$ and concentrated under reduced pressure. The crude material was purified via flash chromatography using heptane and EtOAc as eluents to obtain Preparation 23b.

$^1$H NMR (400 MHz, CDCl$_3$): 8.89 (s, 1H), 7.47 (dd, 1H), 7.43 (s, 1H), 7.20 (t, 1H), 7.14 (dd, 1H), 2.14 (s, 3H).

Preparation 24a: [2-Chloro-4-(4-chloro-6-iodo-thieno[2,3-d]pyrimidin-5-yl)-3-methyl-phenoxy]-triisopropyl-silane 38.00 g [2-chloro-4-(4-chlorothieno[2,3-d]pyrimidin-5-yl)-3-methyl-phenoxy]-triisopropyl-silane (Preparation 23a) (81.27 mmol) was dissolved in 1 L dry THF then cooled to −78° C. under argon atmosphere. 48.76 mL lithium diisopropylamide (97.53 mmol, 2 M in THF, EtPh, hexanes) was added and the mixture was stirred at −78° C. for 1 hour. Then 24.75 g iodine (97.53 mmol) was added and the mixture was allowed to warm up to room temperature. Saturated aq. NH$_4$Cl was added to the reaction mixture and it was extracted with EtOAc. The combined organic layers were washed with Na$_2$S$_2$O$_3$ solution, then dried over Na$_2$SO$_4$ and concentrated under reduced pressure. The obtained solid was sonicated in acetonitrile/water (3:1) and collected by filtration.

$^1$H NMR (400 MHz, DMSO-d$_6$): 8.91 (s, 1H), 7.05 (d, 1H), 6.97 (d, 1H), 1.99 (s, 3H), 1.39-1.30 (m, 3H), 1.10 (dd, 18H).

Preparation 24b: 4-Chloro-5-(3-chloro-2-methyl-phenyl)-6-iodo-thieno[2,3-d] pyrimidine 1.48 g 4-chloro-5-(3-chloro-2-methyl-phenyl)thieno[2,3-d]pyrimidine (Preparation 23b) (5.0 mmol) was dissolved in 30 mL dry THF then cooled to −78° C. under argon atmosphere. 2.75 mL lithium diisopropylamide (5.5 mmol, 2 M in THF, EtPh, hexanes) was added and the mixture was stirred at −78° C. for 1 hour. Then 1.675 g iodine (6.5 mmol) was added and the mixture was allowed to warm up to room temperature. Saturated aq. NH$_4$Cl was added to the reaction mixture and it was extracted with EtOAc. The combined organic layers were washed with Na$_2$S$_2$O$_3$ solution, then dried over Na$_2$SO$_4$ and concentrated under reduced pressure. The residue was purified via flash chromatography using heptane and EtOAc as eluents to obtain Preparation 24b.

$^1$H NMR (400 MHz, CDCl$_3$): 8.82 (s, 1H), 7.52 (dd, 1H), 7.25 (t, 1H), 7.05 (dd, 1H), 2.09 (s, 3H).

Preparation 25: Ethyl (2R)-2-[(5S$_a$)-5-(3-chloro-4-hydroxy-2-methyl-phenyl)-6-iodo-thieno[2,3-d]pyrimidin-4-yl]oxy-3-(2-methoxyphenyl)propanoate 37.85 g [2-chloro-4-(4-chloro-6-iodo-thieno[2,3-d]pyrimidin-5-yl)-3-methyl-phenoxy]-triisopropyl-silane (Preparation 24a) (63.7 mmol), 15.71 g methyl (2R)-2-hydroxy-3-(2-methoxyphenyl)propanoate (Preparation 3ad) (70 mmol) and 62.3 g Cs$_2$CO$_3$ (191 mmol) were placed in a 500 mL flask. 150 mL tert-butanol was added and the mixture was stirred at 65° C. until no further conversion was observed. It was diluted with icy water, the pH was set to 6 with 2 M HCl, and then it was extracted with ethyl acetate. The combined organic layers were dried over Na$_2$SO$_4$ and concentrated under reduced pressure. The residue was dissolved in 100 mL THF, 76.4 mL TBAF (1M in THF) was added and the mixture was stirred at room temperature until no further conversion was observed. Approximately 50 mL solvent was evaporated under reduced pressure, then it was diluted with ethyl acetate, washed with water and brine. The organic layer was dried over Na$_2$SO$_4$ and concentrated under reduced pressure and purified via flash chromatography using heptane and ethyl acetate as eluents. The diastereoisomer eluting later was collected as Preparation 25.

$^1$H NMR (500 MHz, DMSO-d$_6$): 10.33 (s, 1H), 8.55 (s, 1H), 7.18 (t, 1H), 7.00 (d, 1H), 6.98 (d, 1H), 6.90 (d, 1H), 6.75 (t, 1H), 6.29 (d, 1H), 5.36 (dd, 1H), 4.03 (m, 2H), 3.76 (s, 3H), 2.99 (dd, 1H), 2.42 (dd, 1H), 1.97 (s, 3H), 1.06 (t, 3H).

HRMS: (M+H)=625.0055.

Preparation 26a: Ethyl (2R)-2-[5-[3-chloro-2-methyl-4-[2-(4-methylpiperazin-1-yl)ethoxy] phenyl]-6-iodo-thieno[2,3-d]pyrimidin-4-yl]oxy-3-(2-tetrahydropyran-2-yloxyphenyl)propanoate 7.1 g 4-chloro-5-[3-chloro-2-methyl-4-[2-(4-methylpiperazin-1-yl)ethoxy]phenyl]-6-iodo-thieno[2,3-d]pyrimidine (Preparation 13) (12.6 mmol), 4.45 g ethyl (2R)-2-hydroxy-3-(2-tetrahydropyran-2-yloxyphenyl)propanoate (Preparation 3ab-(R)) (15.12 mmol) and 12.32 g Cs$_2$CO$_3$ (32.81 mmol) were placed in a 250 mL flask. 100 mL tert-butanol and 50 mL DMSO was added and the mixture was stirred at 90° C. until no further conversion was observed. It was diluted with ethyl acetate and then it was washed with brine. The organic layer was dried over $Na_2SO_4$, filtered and concentrated under reduced pressure and purified via flash chromatography using ethyl acetate and methanol as eluents to obtain Preparation 26a as a mixture of diastereomers.
MS: (M+H)=821.0.

Preparation 26b: Ethyl (2R)-2-[5-[3-chloro-2-methyl-4-[2-(4-methylpiperazin-1-yl)ethoxy]phenyl]-6-iodo-thieno[2,3-d]pyrimidin-4-yl]oxy-3-(2-hydroxyphenyl)propanoate 6.7 g ethyl (2R)-2-[5-[3-chloro-2-methyl-4-[2-(4-methyl-piperazin-1-yl)ethoxy]phenyl]-6-iodo-thieno[2,3-d]pyrimidin-4-yl]oxy-3-(2-tetrahydropyran-2-yloxyphenyl)propanoate (Preparation 26a) (8.15 mmol) was dissolved in 75 mL ethanol, then 75 mL HCl (1.25 M in ethanol) was added and the mixture was stirred at room temperature until no further conversion was observed. It was concentrated under reduced pressure and purified via flash chromatography using ethyl acetate and methanol as eluents to obtain Preparation 26b as a mixture of diastereomers.
MS: (M+H)=737.0.

Preparation 26c: Ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-iodo-thieno[2,3-d] pyrimidin-4-yl]oxy-propanoate 5.5 g ethyl (2R)-2-[5-[3-chloro-2-methyl-4-[2-(4-methyl-piperazin-1-yl)ethoxy]phenyl]-6-iodo-thieno[2,3-d]pyrimidin-4-yl]oxy-3-(2-hydroxyphenyl)propanoate (Preparation 26b) (7.46 mmol), 2.3 g (1-butyl-1H-pyrazol-5-yl)methanol (Preparation 9dd) (14.92 mmol) and 3.91 g triphenyl phosphine (14.92 mmol) were dissolved in 100 mL abs. toluene, then 2.6 g ditertbutyl azodicarboxylate (14.92 mmol) was added. The mixture was stirred at 50° C. under nitrogen until no further conversion was observed. It was concentrated under reduced pressure and purified via flash chromatography using ethyl acetate and methanol as eluents to obtain Preparation 26c as a mixture of diastereomers.
MS: $(M+H)^+$=873.0.

Preparation 27: Ethyl (2R)-2-[(5$S_a$)-5-[3-chloro-2-methyl-4-[2-(4-methylpiperazin-1-yl)ethoxy]phenyl]-6-(4-fluoro-3-methoxy-phenyl)thieno[2,3-d]pyrimidin-4-yl]oxy-3-[2-[(2-methoxypyrimidin-4-yl)methoxy]phenyl]propanoate 441 mg ethyl (2R)-2-[(5$S_a$)-5-[3-chloro-2-methyl-4-[2-(4-methylpiperazin-1-yl)ethoxy]phenyl]-6-(4-fluoro-3-methoxy-phenyl)thieno[2,3-d]pyrimidin-4-yl]oxy-3-(2-hydroxyphenyl)propanoate (Preparation 8g) (0.6 mmol), 252 mg (2-methoxypyrimidin-4-yl)methanol (1.8 mmol) and 472 mg triphenyl phosphine (1.8 mmol) were dissolved in 10 mL abs. toluene, then 414 mg ditertbutyl azodicarboxylate (1.8 mmol) was added. The mixture was stirred at 50° C. under nitrogen until no further conversion was observed. It was concentrated under reduced pressure and purified via flash chromatography using dichloromethane and methanol as eluents to obtain Preparation 27.
MS: (M+H)=856.6.

Preparation 28a: Ethyl (2R)-2-[(5$S_a$)-5-[3-chloro-2-methyl-4-[2-(4-methylpiperazin-1-yl)ethoxy]phenyl]-6-(4-fluoro-3-hydroxy-phenyl)thieno[2,3-d] pyrimidin-4-yl]oxy-3-[2-[(2-methoxypyrimidin-4-yl)methoxy]phenyl]propanoate 857 mg ethyl (2R)-2-[(5$S_a$)-5-[3-chloro-2-methyl-4-[2-(4-methylpiperazin-1-yl)ethoxy] phenyl]-6-(4-fluoro-3-methoxy-phenyl)thieno[2,3-d]pyrimidin-4-yl]oxy-3-[2-[(2-methoxy pyrimidin-4-yl)methoxy]phenyl]propanoate (Preparation 27) (1.0 mmol) was dissolved in 20 mL DCM, and 5.3 mL $BBr_3$ (1M in DCM, 5.3 mmol) was added at 0° C. The mixture was stirred at 0° C. until no further conversion was observed. It was diluted with water, the pH was set to 6 with $NaHCO_3$ (saturated aqueous solution), and then it was extracted with dichloromethane. The combined organic phases were dried over $Na_2SO_4$ and concentrated under reduced pressure and purified via flash chromatography using dichloromethane and methanol as eluents to obtain Preparation 28a.
$^1$H NMR (400 MHz, DMSO-$d_6$): 10.15 (br s, 1H), 8.66 (d, 1H), 8.59 (s, 1H), 7.29 (d, 1H), 7.28 (d, 1H), 7.17 (t, 1H), 7.16 (d, 1H), 7.13 (dd, 1H), 6.99 (d, 1H), 6.87 (dd, 1H), 6.75 (t, 1H), 6.65 (m, 1H), 6.32 (d, 1H), 5.48 (dd, 1H), 5.16 (d, 1H), 5.10 (d, 1H), 4.23 (m, 1H), 4.17 (m, 1H), 4.05 (m, 2H), 3.91 (s, 3H), 3.11 (dd, 1H), 2.89-2.47 (br s, 8H), 2.77 (br s, 2H), 2.57 (dd, 1H), 2.42 (br s, 3H), 1.89 (s, 3H), 1.05 (t, 3H).
MS: (M+H)=843.2.

Preparation 28b: Ethyl (2R)-2-[5-(3-chloro-4-methoxy-2-methyl-phenyl)-6-(4-fluoro-3-hydroxy-phenyl)thieno[2,3-d]pyrimidin-4-yl]oxy-3-[2-[(2-methoxypyrimidin-4-yl)methoxy]phenyl]propanoate Step A:
To the solution of 3.212 g 4-chloro-5-iodo-thieno[2,3-d] pyrimidine (Preparation 1c, 10.83 mmol), 6.897 g $K_3PO_4$ (32.49 mmol), 388 mg bis(1-adamantyl)-butyl-phosphane (1.083 mmol) in 50 ml dimethoxyethane and 15 ml water 4.609 g 2-(3-chloro-4-methoxy-2-methyl-phenyl)-4,4,5,5-tetramethyl-1,3,2-dioxaborolane (Preparation 5d, 16.31 mmol) and 729 mg palladium(II) acetate (1.083 mmol) was added, and it was stirred at 60° C. for 2 h under nitrogen atmosphere. The reaction mixture was diluted with water and the pH was adjusted to 7 using 2N HCl. It was extracted with DCM, the combined organic phases were dried over $Na_2SO_4$ and concentrated under reduced pressure. The residue was purified via flash chromatography using heptane and EtOAc as eluents to give 4-chloro-5-(3-chloro-4-methoxy-2-methyl-phenyl)thieno[2,3-d]pyrimidine.
$^1$H NMR (400 MHz, DMSO-$d_6$): 8.98 (s, 1H), 7.98 (s, 1H), 7.25 (d, 1H), 7.09 (d, 1H), 3.91 (s, 3H), 2.07 (s, 3H).
Step B:
2.706 g of the product of Step A (8.35 mmol) was dissolved in 50 ml THF, the mixture was cooled to −78° C. and 5 mL lithium diisopropylamide (2M in THF, 10 mmol) was added dropwise and the mixture was stirred at this temperature for 30 minutes. Additional 4.5 mL lithium diisopropylamide (2M in THF, 9 mmol) was added dropwise, and the stirring was continued at −78° C. for 30 minutes and then 4.223 g of iodine (16.64 mmol) was added to the reaction mixture. After 30 minutes it was left to warm to room temperature. Water then saturated aq. $NH_4Cl$ solution was added to the mixture and then it was extracted with diethylether. The combined organic phases were dried over $Na_2SO_4$ and concentrated under reduced pressure. The residue was purified via flash chromatography using heptane and EtOAc as eluents to give 4-chloro-5-(3-chloro-4-methoxy-2-methyl-phenyl)-6-iodo-thieno[2,3-d]pyrimidine.
MS: $(M+H)^+$=452.0.
Step C:
2.055 g of the product of Step B (4.57 mmol), 1.540 g 2-[4-fluoro-3-(methoxymethoxy)phenyl]-4,4,5,5-tetramethyl-1,3,2-dioxaborolane (Preparation BA5, 5.459 mmol) and 2.965 g cesium carbonate (9.10 mmol) were dissolved in 30 mL dioxane and 10 mL water, and 322 mg bis(di-tert-butyl(4-dimethylaminophenyl)phosphine) dichloropalladium(II) (AtaPhos, 0.4548 mmol) was added. The reaction mixture was stirred under nitrogen at 55° C. until no further conversion was observed. The reaction mixture was cooled to room temperature, it was diluted with water and the pH was adjusted to 7 using 2 M HCl. It was extracted with DCM, the combined organic phases were dried over $Na_2SO_4$ and concentrated under reduced pressure. The residue was purified via flash chromatography using heptane and EtOAc as eluents to give 4-chloro-5-(3-chloro-4-methoxy-2-methyl-phenyl)-6-[4-fluoro-3-(methoxymethoxy)phenyl]thieno[2,3-d]pyrimidine.

MS: $(M+H)^+$=479.0.

Step D:

To 1.824 g of the product of Step C (3.805 mmol) and 2.529 g ethyl (2R)-2-hydroxy-3-[2-[(2-methoxypyrimidin-4-yl)methoxy]phenyl]propanoate (Preparation 3ah, 7.610 mmol) in 40 mL tert-butanol 5.005 g cesium carbonate (15.36 mmol) was added and it was stirred at 65° C. until no further conversion was obtained. The reaction mixture was cooled to room temperature, it was diluted with water and the pH was adjusted to 7 using 2 M HCl. It was extracted with DCM, the combined organic phases were dried over $Na_2SO_4$ and concentrated under reduced pressure. The residue was purified via flash chromatography using heptane and EtOAc as eluents to give ethyl (2R)-2-[5-(3-chloro-4-methoxy-2-methyl-phenyl)-6-[4-fluoro-3-(methoxymethoxy)phenyl]thieno[2,3-d]pyrimidin-4-yl]oxy-3-[2-[(2-methoxypyrimidin-4-yl)methoxy]phenyl]propanoate.

MS: $(M+H)^+$=775.0.

Step E:

1.373 g of the product of Step D (1.771 mmol) was dissolved in 50 mL HCl (1.25 M in EtOH) and the mixture was stirred at 50° C. until no further conversion was observed. It was cooled to room temperature then saturated aq. $NaHCO_3$ solution was added to the reaction mixture, and it was extracted with DCM. The combined organic phases were dried over $Na_2SO_4$ and concentrated under reduced pressure. The residue was purified via flash chromatography using heptane and EtOAc as eluents to give Preparation 28b.

HRMS calculated for $C_{37}H_{32}ClFN_4O_7S$: 730.1664. found 731.1746 (M+H).

Preparation 29: Ethyl (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-[(2-chloropyrimidin-4-yl)methoxy]phenyl]propanoate Using Step A of General Procedure (Ia) and (2-chloropyrimidin-4-yl)methanol as the appropriate alcohol derivative Preparation 29 was obtained.

HRMS calculated for $C_{42}H_{41}Cl_2FN_6O_5S$: 830.2220. found 831.2275 (M+H).

Preparation 30: Ethyl (2R)-2-[5-[3-chloro-2-methyl-4-[2-(4-methylpiperazin-1-yl)ethoxy]phenyl]-6-iodo-thieno[2,3-d]pyrimidin-4-yl]oxy-3-[2-[[2-(2-methoxyphenyl)pyrimidin-4-yl]methoxy]phenyl]propanoate 43.00 g 4-chloro-5-[3-chloro-2-methyl-4-[2-(4-methylpiperazin-1-yl)ethoxy]phenyl]-6-iodo-thieno[2,3-d]pyrimidine (Preparation 13) (76.33 mmol), 34.3 g (2R)-2-hydroxy-3-[2-[[2-(2-methoxyphenyl)pyrimidin-4-yl]methoxy]phenyl]propanoate (Preparation 3br) (83.9 mmol) and 74.62 g $Cs_2CO_3$ (229 mmol) were placed in a 1 L flask. 200 mL tert-butanol and 200 mL DMSO were added and the mixture was stirred at 80° C. under $N_2$ until no further conversion was observed. Reaction mixture was diluted with water then it was extracted with DCM. The combined organic layers were dried over $Na_2SO_4$, filtered and concentrated under reduced pressure. Residue was dissolved in 250 mL EtOH and 250 1.25 M HCl in EtOH and the mixture was stirred at room temperature until no further conversion was observed. Most of the EtOH was evaporated, then the HCl salt was carefully treated with saturated 10% $K_2CO_3$ solution, extracted with DCM, the combined organic phases were dried over $Na_2SO_4$, filtered and concentrated under reduced pressure. The crude product was purified via flash chromatography using MeOH and EtOAc as eluents to obtain Preparation 30.

HRMS calculated for $C_{43}H_{44}ClIN_6O_6S$: 934.1776. found: 468.0966 and 468.0966 for the two diastereomers (M+2H).

Preparation 31: Ethyl (2R)-2-[5-[3-chloro-2-methyl-4-[2-(4-methylpiperazin-1-yl)ethoxy]phenyl]-6-(4-hydroxyphenyl)thieno[2,3-d]pyrimidin-4-yl]oxy-3-[2-[[2-(2-methoxyphenyl)pyrimidin-4-yl]methoxy]phenyl]propanoate Using General Procedure (XXXIIIa) and 4-hydroxyphenylboronic acid as the appropriate boronic acid derivative Preparation 31 was obtained as a mixture of diastereomers.

HRMS calculated $C_{49}H_{49}ClN_6O_7S$: 900.3072. found 451.1630 (M+2H).

Preparation 32: Ethyl (2R)-2-[5-[3-chloro-2-methyl-4-[2-(4-methylpiperazin-1-yl)ethoxy]phenyl]-6-(4-hydroxyphenyl)thieno[2,3-d]pyrimidin-4-yl]oxy-3-[2-[[1-(2,2,2-trifluoroethyl)pyrazol-5-yl]methoxy]phenyl]propanoate 386 mg (1 mmol) 5-bromo-4-chloro-6-[4-(methoxymethoxy)phenyl]thieno[2,3-d] pyrimidine (Preparation 21), and 403 mg (1.05 mmol) ethyl 2-hydroxy-3-[2-[[2-(2,2,2-trifluoroethyl)pyrazol-3-yl]methoxy]phenyl]propanoate (Preparation 3bp) were dissolved in 6 mL dioxane, then 977 mg (3 mmol) $Cs_2CO_3$ was added. The mixture was stirred at 70° C. under $N_2$ until no further conversion was observed. Then 0.473 g (1.16 mmol) Preparation 5b, 71 mg AtaPhos (0.1 mmol) and 5 mL $H_2O$ were added, and the mixture was stirred under nitrogen at 70° C. until no further conversion was observed. Most of the volatiles were evaporated under reduced pressure, then it was diluted with dichloromethane and brine. After shaking the pH of the aqueous phase was set to 5 with 2 M HCl. After phase separation the aqueous phase was extracted with dichloromethane. The organic layers were combined and dried over $Na_2SO_4$, filtered and concentrated under reduced pressure. The product was separated via flash chromatography using DCM and MeOH as eluents. This intermediate was dissolved in 3 mL 1.25 M HCl/EtOH and stirred at 50° C. until no further conversion was observed. Mixture was poured into ice-water, pH was adjusted to 6 with saturated $NaHCO_3$ solution and extracted with dichloromethane. The organic layers were combined and dried over $Na_2SO_4$, filtered and concentrated under reduced pressure. The product was separated via flash chromatography using DCM and MeOH as eluents to obtain Preparation 32.

MS: $(M+H)^+$=865.2; (M−H)−=863.0.

Preparation 33: Ethyl (2R)-2-[(5S$_a$)-5-[3-chloro-2-methyl-4-[2-(4-methylpiperazin-1-yl)ethoxy]phenyl]-6-(4-hydroxyphenyl)thieno[2,3-d]pyrimidin-4-yl]oxy-3-[2-[[2-(2,2,2-trifluoroethoxy]phenyl]propanoate Step A:
386 mg (1 mmol) 5-bromo-4-chloro-6-[4-(methoxymethoxy)phenyl]thieno[2,3-d]pyrimidine (Preparation 21), 351 mg (1.2 mmol) ethyl (2R)-2-hydroxy-3-[2-(2,2,2-trifluoroethoxy)phenyl]propanoate (Preparation 3bl) and 977 mg (3 mmol) Cs$_2$CO$_3$ were dissolved in 6 ml dioxane and stirred at 70° C. under N$_2$ until no further conversion was observed. Then 473 mg (1.2 mmol) Preparation 5b, 71 mg (0.1 mmol) Ataphos, and 5 mL H$_2$O were added to the mixture and stirred at 70° C. under N$_2$ until no further conversion was observed. It was diluted with brine, the pH was set to 6 with 2 M HCl, and then it was extracted with DCM. The combined organic layers were dried over Na$_2$SO$_4$, filtered and concentrated under reduced pressure. The crude product was purified via flash chromatography using DCM and MeOH as eluents. The diastereoisomer eluting later was collected.
MS: (M+H)+=829.2.

Step B:
This intermediate was dissolved in 3 mL 1.25 M HCl/EtOH and 4 mL EtOH and stirred at 50° C. until no further conversion was observed. Mixture was poured into ice-water, the pH was set to 6 with 2 M HCl, and then it was extracted with DCM. The combined organic layers were dried over Na$_2$SO$_4$, filtered and concentrated under reduced pressure. The crude product was purified via flash chromatography using DCM and MeOH as eluents to obtain Preparation 33.
MS: (M+H)$^+$=785.2. (M−H)$^−$=783.0.

Preparation 34: 2-(2-methyl-2,6-diazaspiro[3.3]heptan-6-yl)ethanol

Step A: 2-(2-tert-butoxycarbonyl-2,6-diazaspiro[3.3]heptan-6-yl)ethanol
1.441 g (5 mmol) 2,6-diazaspiro[3.3]heptane-2-carboxylic acid tert-butyl ester hemioxylate was dissolved in 10 ml ACN, then 1.25 g (10 mmol) 2-bromoethanol and 2.073 g (15 mmol) K$_2$CO$_3$ were added and the mixture was heated to reflux for 16 hours. Mixture was then filtered and concentrated in vacuo and purified via flash chromatography using DCM and MeOH as eluents.
MS (EI, 70 eV) m/z (% relative intensity, [ion]): 55 (35), 56 (37), 57 (70), 82 (33), 155 (100), 169 (17), 211 (56), 242 (2, [M$^+$]).

Step B: 2-(2-methyl-2,6-diazaspiro[3.3]heptan-6-yl)ethanol
0.464 g (1.9 mmol) of the intermediate obtained from the above Step A was dissolved in 10 ml dry THF and cooled to 0° C. 5.7 ml 1M (in THF) LiAlH$_4$ solution was added under N$_2$ and the mixture was heated to reflux until no further conversion was observed. Then 215 μl water, 215 μl 15% NaOH solution were added and the mixture was stirred at 0° C. overnight. Mixture was filtered, filtrate was concentrated in vacuo to obtain Preparation 34.
$^1$H-NMR (500 MHz, dmso-d6) δ ppm 4.34 (br, 1H), 3.28 (t, 2H), 3.13 (s, 4H), 3.1 (s, 4H), 2.34 (t, 2H), 2.12 (s, 3H).
$^{13}$C-NMR: (500 MHz, dmso-d6) δ ppm 66.2, 64.8, 61.8, 59.7, 46.1.

Preparation 35a: 1-iodoethyl acetate

Using General Procedure (XXXVII) and acetyl chloride as the appropriate alkanoyl-chloride derivative Preparation 35a was obtained.
$^1$H NMR (400 MHz, CDCl$_3$) δ 6.84 (q, 1H), 2.20 (d, 3H), 2.09 (s, 3H)

Preparation 35b: 1-iodoethyl 2,2-dimethylpropanoate

Using General Procedure (XXXVII) and 2,2-dimethylpropanoyl chloride as the appropriate alkanoyl-chloride derivative Preparation 35b was obtained.
$^1$H NMR (400 MHz, CDCl$_3$) δ 6.87 (q, 1H), 2.22 (d, 3H), 1.21 (s, 9H)

Preparation 35c: 1-iodoethyl propanoate

Using General Procedure (XXXVII) and propanoyl chloride as the appropriate alkanoyl-chloride derivative Preparation 35c was obtained.
$^1$H NMR (400 MHz, CDCl$_3$) δ 6.88 (q, 1H), 2.37 (q, 2H), 2.22 (d, 3H), 1.17 (t, 3H)

Preparation 35d: 1-iodoethyl 2-methylpropanoate

Using General Procedure (XXXVII) and 2-methylpropanoyl chloride as the appropriate alkanoyl-chloride derivative Preparation 35d was obtained.
$^1$H NMR (400 MHz, CDCl$_3$) δ 6.88 (q, 1H), 2.56 (sept, 1H), 2.22 (d, 3H), 1.19 (d, 6H)

Preparation 35e: 1-iodoethyl 2-methoxyacetate

Using General Procedure (XXXVII) and methoxyacetyl chloride as the appropriate alkanoyl-chloride derivative Preparation 35e was obtained.
$^1$H NMR (400 MHz, CDCl$_3$) δ 6.94 (q, 1H), 4.06 (s, 2H), 3.49 (s, 3H), 2.24 (d, 3H)

Preparation 36: Ethyl (2R)-2-[5-(3-chloro-2-cyano-4-hydroxy-phenyl)-6-(4-fluorophenyl)thieno[2,3-d]pyrimidin-4-yl]oxy-3-[2-[[2-(2-methoxyphenyl)pyrimidin-4-yl]methoxy]phenyl]propanoate Using General Procedure (XXXIV, Step A) and (3-chloro-2-cyano-4-triisopropylsilyloxy-phenyl)boronic acid (Preparation 5x) as the appropriate boronic acid we observed complete desililation during the Suzuki-coupling. After purification of the crude product by flash chromatography using heptane and EtOAc as eluents the ethyl (2R)-2-[5-(3-chloro-2-cyano-4-hydroxy-phenyl)-6-(4-fluorophenyl)thieno[2,3-d]pyrimidin-4-yl]oxy-3-[2-[[2-(2-methoxyphenyl)pyrimidin-4-yl]methoxy]phenyl]propanoate was obtained as a mixture of the diastereoisomers.
MS: (M+H)=788.0

Preparation 37: Ethyl (2R)-2-[5-[3-chloro-2-(methoxymethoxy)-4-[2-(4-methylpiperazin-1-yl)ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate Using General Procedure (XXXIV, Step A) and [2-chloro-3-(methoxymethoxy)-4-(4,4,5,5-tetramethyl-1,3,2-dioxaborolan-2-yl)phenoxy]-triisopropyl-silane (Preparation 5y) as the appropriate boronic ester. The crude product was purified by flash chromatography using heptane and EtOAc as eluents the ethyl (2R)-2-[5-[3-chloro-2-(methoxymethoxy)-4-triisopropylsilyloxy-phenyl]-6-(4-fluorophenyl)thieno[2,3-d]pyrimidin-4-yl]oxy-3-[2-[[2-(2- methoxyphenyl)pyrimidin-4-yl]methoxy]phenyl]
propanoate intermediate was obtained as a mixture of the diastereoisomers.

MS (M+H): 979.2.

The resulting intermediate was dissolved in dry THF and 1.2 eq (1 M in THF) tetrabutylammonium fluoride solution was added. The mixture was stirred at room temperature until no further conversion was observed. Volatiles were evaporated under reduced pressure. The residue was purified via flash chromatography using heptane and EtOAc as eluents to obtain ethyl (2R)-2-[5-[3-chloro-4-hydroxy-2-(methoxymethoxy)phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate as a diastereoisomer mixture.

MS (M–H): 821.0.

Using General Procedure (XXXVIII) and this intermediate as the appropriate phenol derivative and 2-(4-methylpiperazin-1-yl)ethanol as the appropriate alcohol Preparation 37 was obtained as a mixture of the diastereoisomers.

MS (M+H): 948.8.

Preparation 38: Ethyl (2R)-2-[5-[3-chloro-2-hydroxy-4-[2-(4-methylpiperazin-1-yl)ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate 2.00 g ethyl (2R)-2-[5-[3-chloro-2-(methoxymethoxy)-4-[2-(4-methylpiperazin-1-yl)ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate (Preparation 37) (2.10 mmol) was dissolved in 20 ml 1.25 M HCl in EtOH and stirred at room temperature until no further conversion was observed. The pH was adjusted to ~6 and with $NH_4CO_3$, and then it was extracted with EtOAc. Organic phase was dried over $Na_2SO_4$, filtered and evaporated under reduced pressure to obtain Preparation 38 as a mixture of the diastereoisomers.

MS (M+H): 904.8.

Preparation BA1: 4,4,5,5-tetramethyl-2-thieno[3,2-b]thiophen-3-yl-1,3,2-dioxaborolane 0.782 g 3-bromothieno[3,2-b]thiophene (3.6 mmol), 3.626 g 4,4,5,5-tetramethyl-2-(4,4,5,5-tetramethyl-1,3,2-dioxaborolan-2-yl)-1,3,2-dioxaborolane (14 mmol), 0.783 g $PdCl_2 \times dppf$ (1.07 mmol) and 2.102 g KOAc (21.4 mmol) were dissolved in 4 mL dioxane under $N_2$. It was heated to 60° C. for 5 hours. The reaction mixture was cooled down and filtered through celite. The filtrate was concentrated and purified via flash chromatography using heptane and EtOAc as eluents to give Preparation BA1.

$^1$H NMR (500 MHz, DMSO-$d_6$): 8.11 (d, 1H), 7.67 (dd, 1H), 7.45 (d, 1H), 1.32 (s, 12H).

HRMS calculated for $C_{12}H_{15}BO_2S_2$: 266.0607. found: 267.0682 (M+H).

Preparation BA2: 4,4,5,5-tetramethyl-2-thieno[3,2-b]thiophen-2-yl-1,3,2-dioxaborolane 0.982 g thieno[3,2-b]thiophene (7.0 mmol) was dissolved in 40 mL THF under $N_2$ and cooled to −78° C. 7 ml ″BuLi (1.6 M in hexanes, 7.0 mmol) was added and the mixture was stirred at −78° C. for 1 hour. Then 1.6 mL 2-isopropoxy-4,4,5,5-tetramethyl-1,3,2-dioxaborolane (7.7 mmol) was added and after 10 minutes stirring the mixture was allowed to warm up to room temperature. It was quenched with saturated aq. $NH_4Cl$ solution, then extracted with THF, dried over $Na_2SO_4$, filtered and concentrated and purified via flash chromatography using heptane and EtOAc as eluents to give Preparation BA2.

MS (EI, 70 eV) m/z (% relative intensity, [ion]): 120 (19), 165 (25), 166 (100), 167 (44), 180 (17), 206 (22), 223 (60), 266 (68, [M$^+$]).

Preparation BA3: 2-[4-fluoro-3-(methoxymethyl)phenyl]-4,4,5,5-tetramethyl-1,3,2-dioxaborolane 0.801 g LiCl (19 mmol) was heated at 250° C. for 10 minutes under $N_2$. Then it was cooled to room temperature and the flask was charged with 0.911 g Mg (38 mmol) and 30 mL dry THF. The Mg was activated with 0.15 mL $iBu_2AlH$ (1 M in THF, 0.15 mmol) for 10 minutes, then it was cooled to 0° C. and 3.313 g 4-bromo-1-fluoro-2-(methoxymethyl)benzene (15 mmol) was added. After formation of the Grignard reagent (appr. 30 minutes) at 0° C. 4 mL 2-isopropoxy-4,4,5,5-tetramethyl-1,3,2-dioxaborolane (20 mmol) was added and the reaction mixture was stirred for 30 minutes, then filtered through celite, diluted with EtOAc and washed with saturated aq. $NH_4Cl$. The aqueous phase was back-extracted with EtOAc. The combined organic phases were dried over $Na_2SO_4$, filtered, concentrated and purified via flash chromatography using heptane and EtOAc as eluents to give Preparation BA3.

MS (EI, 70 eV) m/z (% relative intensity, [ion]): 59 (21), 85 (20), 134 (24), 135 (100), 136 (28), 150 (30), 165 (24), 166 (43), 167 (95), 192 (20), 251 (44, [M$^+$]).

Preparation BA4: 2-(5-fluoro-2-furyl)-4,4,5,5-tetramethyl-1,3,2-dioxaborolane

In a 2 L flask 57.7 g 5-bromo-2-furoic acid (300 mmol) and 108.1 g Selectfluor (300 mmol) were added to 900 mL pentane, than 270 mL saturated $NaHCO_3$ solution (300 mmol) was added in portions. The reaction mixture was stirred at room temperature for 1 hour. The layers were separated, and the aqueous layer was extracted with pentane. The combined organic layers were dried over $MgSO_4$, than filtered into a dried 3-necked 4 L flask. The resulting solution was diluted with 450 mL dry THF under $N_2$, than cooled to −78° C. 18 mL ″BuLi (10 M in hexanes, 180 mmol) was added dropwise (T<−65° C.) than the reaction mixture was stirred for 5 minutes. 36 mL 2-isopropoxy-4,4,5,5-tetramethyl-1,3,2-dioxaborolane (180 mmol) was added slowly (T<−70° C.) and the reaction mixture was stirred for 10 minutes. Cooling was removed, and the reaction mixture was warmed up to −15° C. than quenched with 600 mL saturated aq. $NH_4Cl$ solution and stirred for 15 minutes. The layers were separated and the aqueous layer was extracted with $Et_2O$. The combined organic layers were dried over $MgSO_4$, filtered and concentrated to give Preparation BA4.

MS (EI, 70 eV) m/z (% relative intensity, [ion]): 85.1 (21), 112.2 (20), 126.1 (26), 127.1 (100), 169.1 (21), 197.0 (14), 212.0 (21, [M$^+$]).

$^1$H NMR (400 MHz, DMSO-$d_6$): 7.08 (t, 1H), 5.86 (dd, 1H), 1.26 (s, 12H).

Preparation BA5: 2-[4-fluoro-3-(methoxymethoxy)phenyl]-4,4,5,5-tetramethyl-1,3,2-dioxaborolane Step A:

1.91 g 5-bromo-2-fluoro-phenol (10 mmol) was dissolved in acetone (5 mL). 1.20 g chloro(methoxy)methane (15 mmol) and 2.76 g $K_2CO_3$ (20 mmol) was added and the reaction mixture was stirred at room temperature until no further conversion was observed. The volatiles were evaporated under reduced pressure, and the residue was diluted with water and extracted with DCM. The combined organic layers were dried over $Na_2SO_4$ and concentrated under reduced pressure. The crude product was purified via flash chromatography using heptane and EtOAc as eluents to obtain 4-bromo-1-fluoro-2-(methoxymethoxy)benzene.

$^1$H NMR (400 MHz, $CDCl_3$): 7.37 (dd, 1H), 7.13-7.09 (m, 1H), 6.99 (dd, 1H), 5.22 (s, 2H), 3.54 (s, 3H).

MS (EI, 70 eV) m/z (% relative intensity, [ion]): 63 (40), 81 (71), 82 (45), 94 (100), 96 (35), 161 (91), 163 (87), 175 (34), 177 (35), 204 (28), 206 (27), 234 (91, [M$^+$]), 236 (89, [M$^+$]).

Step B:

0.319 g LiCl (7.5 mmol) was heated at 250° C. for 10 minutes under $N_2$. Then it was cooled to room temperature and the flask was charged with 0.366 g Mg (15 mmol) and 15 mL dry THF. The Mg was activated with 0.06 mL $iBu_2AlH$ (1 M in THF, 0.06 mmol) for 10 minutes, then it was cooled to 0° C. and 1.416 g 4-bromo-1-fluoro-2-(methoxymethoxy)benzene (6 mmol) was added. After formation of the Grignard reagent (appr. 30 minutes) at 0° C. 1.5 mL 2-isopropoxy-4,4,5,5-tetramethyl-1,3,2-dioxaborolane (7.5 mmol) was added and the reaction mixture was stirred for 30 minutes, then filtered through celite, diluted with EtOAc and washed with saturated aq. $NH_4Cl$. The aqueous phase was extracted with EtOAc. The combined organic phases were dried over $Na_2SO_4$ and concentrated under reduced pressure and purified via flash chromatography using heptane and EtOAc as eluents to obtain Preparation BA5.

$^1$H NMR (400 MHz, $CDCl_3$): 7.60 (dd, 1H), 7.48-7.44 (m, 1H), 7.10 (dd, 1H), 5.27 (s, 2H), 3.56 (s, 3H), 1.35 (s, 12H).

MS (EI, 70 eV) m/z (% relative intensity, [ion]): 57 (42), 59 (54), 83 (31), 85 (30), 138 (40), 151 (51), 152 (54), 153 (42), 166 (100), 237 (31), 252 (69), 282 (49, [M$^+$]).

Compounds of the invention display axial chirality. They can be isolated as a mixture of atropoisomers or as individual atropoisomers ($S_a$ or $R_a$).

General Procedure (Ia)

Step A:

1 eq. ethyl (2R)-2-[(5$S_a$)-5-[3-chloro-2-methyl-4-[2-(4-methylpiperazin-1-yl)ethoxy] phenyl]-6-(4-fluorophenyl)thieno[2,3-d]pyrimidin-4-yl]oxy-3-(2-hydroxyphenyl)propanoate (Preparation 8a), 2 eq. of the appropriate alcohol and 2 eq. triphenyl phosphine were dissolved in abs. toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:

The obtained intermediate was dissolved in dioxane-water 1:1 (10 mL/mmol) and 10 eq LiOH×$H_2O$ was added. The mixture was stirred at room temperature until no further conversion was observed. Then it was diluted with brine, neutralized with 2 M HCl, extracted with dichloromethane. The combined organic phases were dried over $Na_2SO_4$, filtered and concentrated under reduced pressure and purified via preparative reversed phase chromatography using 25 mM aqueous $NH_4HCO_3$ solution and MeCN as eluents.

General Procedure (Ib)

Step A:

1 eq. ethyl (2R)-2-[(5$S_a$)-5-[3-chloro-2-methyl-4-[2-(4-methylpiperazin-1-yl)ethoxy] phenyl]-6-(4-fluorophenyl)thieno[2,3-d]pyrimidin-4-yl]oxy-3-[2-[(2-methylsulfanyl pyrimidin-4-yl)methoxy]phenyl]propanoate (Preparation 10a), 3.0 eq. of the appropriate boronic acid derivative and 3.0 eq. copper(I) thiophenecarboxylate were dissolved in dry THF (0.1 M for Preparation 10a), then 0.15 eq. Pd(PPh$_3$)$_4$ was added. The mixture was stirred at 70° C. under nitrogen until no further conversion was observed. Then it was concentrated under reduced pressure and the crude intermediate was purified via flash chromatography using dichloromethane and methanol as eluents.

Step B:

The obtained intermediate was dissolved in dioxane-water 1:1 (10 mL/mmol) and 10 eq LiOH×$H_2O$ was added. The mixture was stirred at room temperature until no further conversion was observed. Then it was diluted with brine, neutralized with 2 M HCl, extracted with DCM. The combined organic phases were dried over $Na_2SO_4$, filtered and concentrated under reduced pressure and purified via preparative reversed phase chromatography using 5 mM aqueous $NH_4HCO_3$ solution and MeCN as eluents.

Example 1 (2R)-2-{[(5$S_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-methoxyphenyl)propanoic acid Using General Procedure (Ia) and methanol as the appropriate alcohol, Example 1 was obtained. HRMS calculated for $C_{36}H_{36}ClFN_4O_5S$: 690.2079. found 691.2147 (M+H).

Example 2 (2R)-2-{[(5$S_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-{2-[(2R)-tetrahydrofuran-2-ylmethoxy]phenyl}propanoic acid Using General Procedure (Ia) and [(2R)-tetrahydrofuran-2-yl]methanol as the appropriate alcohol, Example 2 was obtained. HRMS calculated for $C_{40}H_{42}ClFN_4O_6S$: 760.2498. found 761.2550 (M+H).

Example 3 (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(2,2,2-trifluoroethoxy)phenyl]propanoic acid Step A:

211 mg ethyl (2R)-2-[(5$S_a$)-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-hydroxyphenyl)propanoate (Preparation 8a) (0.3 mmol) and 138 mg $K_2CO_3$ (1.0 mmol) were dissolved in 2 mL DMF, then 232 mg 2,2,2-trifluoroethyl trifluoromethanesulfonate (1.0 mmol) was added. The mixture was stirred at room temperature under nitrogen until no further conversion was observed. Then it was diluted with brine, neutralized with 2 M HCl, extracted with dichloromethane, dried over $Na_2SO_4$, filtered and concentrated under reduced pressure.

Step B:

The obtained intermediate was dissolved in 8 mL dioxane-water 1:1 and 150 mg LiOH×H$_2$O (3.57 mmol) was added. The mixture was stirred at room temperature until no further conversion was observed. Then it was diluted with brine, neutralized with 2 M HCl, extracted with dichloromethane, dried over Na$_2$SO$_4$, filtered and concentrated under reduced pressure and purified via preparative reversed phase chromatography using 5 mM aqueous NH$_4$HCO$_3$ solution and MeCN as eluents to obtain Example 3. HRMS calculated for C$_{37}$H$_{35}$ClF$_4$N$_4$O$_5$S: 758.1953. found 759.1999 (M+H).

Example 4 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(2,2-difluoroethoxy)phenyl]propanoic acid Using General Procedure (Ia) and 2,2-difluoroethanol as the appropriate alcohol, Example 4 was obtained. HRMS calculated for C$_{37}$H$_{36}$ClF$_3$N$_4$O$_5$S: 740.2047. found 741.2119 (M+H).

Example 5 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1R or S)-1-(1-pentyl-1H-pyrazol-5-yl)ethoxy]phenyl}propanoic acid Using General Procedure (Ia) and (1R or S)-1-(1-pentyl-1H-pyrazol-5-yl)ethanol (Preparation 9dn) as the appropriate alcohol, Example 5 was obtained. HRMS calculated for C$_{45}$H$_{50}$ClFN$_6$O$_5$S: 840.3236. found 421.1674 (M+2H).

Example 6 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1S or R)-1-(1-pentyl-1H-pyrazol-5-yl)ethoxy]phenyl}propanoic acid Using General Procedure (Ia) and (1S or R)-1-(1-pentyl-1H-pyrazol-5-yl)ethanol (Preparation 9do) as the appropriate alcohol, Example 6 was obtained. HRMS calculated for C$_{45}$H$_{50}$ClFN$_6$O$_5$S: 840.3236. found 421.1679 (M+2H).

Example 7 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(6-methoxy-2-phenylpyrimidin-4-yl)methoxy]phenyl}propanoic acid Using General Procedure (Ia) and (6-methoxy-2-phenylpyrimidin-4-yl)methanol (prepared according to Tabei K. et al., *J. Heterocyclic Chem.* 1985 22, 569-574,) as the appropriate alcohol, Example 7 was obtained. HRMS calculated for C$_{47}$H$_{44}$ClFN$_6$O$_6$S: 874.2716. found 438.1444 (M+2H).

Example 8 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2,6-dimethoxypyrimidin-4-yl)methoxy]phenyl}propanoic acid Using General Procedure (Ia) and (2,6-dimethoxypyrimidin-4-yl)methanol (Preparation 9cd) as the appropriate alcohol, Example 8 was obtained. HRMS calculated for C$_{42}$H$_{42}$ClFN$_6$O$_7$S: 828.2508. found 415.1340 (M+2H).

Example 9 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(5-methyl-1,2-oxazol-3-yl)methoxy]phenyl}propanoic acid Using General Procedure (Ia) and (5-methyl-1,2-isoxazol-3-yl)methanol as the appropriate alcohol, Example 9 was obtained. HRMS calculated for C$_{40}$H$_{39}$ClFN$_5$O$_6$S: 771.2294. found 386.6226 (M+2H).

Example 10 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(5-fluoropyridin-2-yl)methoxy]phenyl}propanoic acid Using General Procedure (Ia) and (5-fluoro-2-pyridyl)methanol as the appropriate alcohol, Example 10 was obtained. HRMS calculated for C$_{41}$H$_{38}$ClF$_2$N$_5$O$_5$S: 785.2250. found 393.6212 (M+2H).

Example 11 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[6-(furan-2-yl)pyridin-2-yl]methoxy}phenyl)propanoic acid Using General Procedure (Ia) and [6-(2-furyl)-2-pyridyl]methanol (Preparation 9ea) as the appropriate alcohol, Example 11 was obtained. HRMS calculated for C$_{45}$H$_{41}$ClFN$_5$O$_6$S: 833.2450. found 417.6304 (M+2H).

Example 12 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[6-(morpholin-4-yl)pyridin-2-yl]methoxy}phenyl)propanoic acid Using General Procedure (Ia) and (6-(morpholin-4-yl)-pyridin-2-yl)methanol (prepared according to WO 02/42305 A1) as the appropriate alcohol, Example 12 was obtained. HRMS calculated for C$_{45}$H$_{46}$ClFN$_6$O$_6$S: 852.2872. found 427.1494 (M+2H).

Example 13 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(6-ethoxypyridin-2-yl)methoxy]phenyl}propanoic acid Using General Procedure (Ia) and (6-ethoxy-2-pyridyl)methanol as the appropriate alcohol, Example 13 was obtained. HRMS calculated for C$_{43}$H$_{43}$ClFN$_5$O$_6$S: 811.2607. found 406.6361 (M+2H).

Example 14 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(pyridin-2-ylmethoxy)phenyl]propanoic acid Using General Procedure (Ia) and 2-pyridylmethanol as the appropriate alcohol, Example 14 was obtained. HRMS calculated for C$_{41}$H$_{39}$ClFN$_5$O$_5$S: 767.2344. found 384.6257 (M+2H).

Example 15 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(cyclohexylmethyl)-1H-pyrazol-3-yl]methoxy}phenyl)propanoic acid Using General Procedure (Ia) and [1-(cyclohexylmethyl)-1H-pyrazol-3-yl]methanol (Preparation 9dw) as the appropriate alcohol, Example 15 was obtained. HRMS calculated for $C_{46}H_{50}ClFN_6O_5S$: 852.3236. found 427.1688 (M+2H).

Example 16 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-methylpyridin-4-yl)methoxy]phenyl}propanoic acid Using General Procedure (Ia) and (2-methyl-4-pyridyl)methanol as the appropriate alcohol, Example 16 was obtained. HRMS calculated for $C_{42}H_{41}ClFN_5O_5S$: 781.2501. found 391.6327 (M+2H).

Example 17 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(trifluoromethyl)pyridin-4-yl]methoxy}phenyl)propanoic acid Using General Procedure (Ia) and [2-(trifluoromethyl)-4-pyridyl]methanol as the appropriate alcohol, Example 17 was obtained. HRMS calculated for $C_{42}H_{38}ClF_4N_5O_5S$: 835.2218. found 836.2334 (M+H).

Example 18 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(thiophen-2-yl)pyridin-4-yl]methoxy}phenyl)propanoic acid Using General Procedure (Ia) and [2-(2-thienyl)-4-pyridyl]methanol (Preparation 9eb) as the appropriate alcohol, Example 18 was obtained. HRMS calculated for $C_{45}H_{41}ClFN_5O_5S_2$: 849.2222. found 425.6192 (M+2H).

Example 19 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-chloropyridin-4-yl)methoxy]phenyl}propanoic acid Using General Procedure (Ia) and (2-chloro-4-pyridyl)methanol as the appropriate alcohol, Example 19 was obtained. HRMS calculated for $C_{41}H_{38}Cl_2FN_5O_5S$: 801.1955. found 802.2017 (M+H).

Example 20 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(morpholin-4-yl)pyridin-4-yl]methoxy}phenyl)propanoic acid Using General Procedure (Ia) and [2-(morpholin-4-yl)pyridin-4-yl]methanol as the appropriate alcohol, Example 20 was obtained. HRMS calculated for $C_{45}H_{46}ClFN_6O_6S$: 852.2872. found 427.1490 (M+2H).

Example 21 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-methoxypyridin-4-yl)methoxy]phenyl}propanoic acid Using General Procedure (Ia) and (2-methoxy-4-pyridyl)methanol as the appropriate alcohol, Example 21 was obtained. HRMS calculated for $C_{42}H_{41}ClFN_5O_6S$: 797.2450. found 399.6302 (M+2H).

Example 22 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyethoxy)pyridin-4-yl]methoxy}phenyl)propanoic acid Using General Procedure (Ia) and [2-(2-methoxyethoxy)pyridin-4-yl]methanol as the appropriate alcohol, Example 22 was obtained. HRMS calculated for $C_{44}H_{45}ClFN_5O_7S$: 841.2712. found 421.6410 (M+2H).

Example 23 (2R)-3-{2-[(2-tert-butylpyrimidin-4-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ia) and (2-tert-butylpyrimidin-4-yl)methanol (Preparation 9bh) as the appropriate alcohol, Example 23 was obtained. HRMS calculated for $C_{44}H_{46}ClFN_6O_5S$: 824.2923. found 413.1528 (M+2H).

Example 24 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(propan-2-yl)pyrimidin-4-yl]methoxy}phenyl)propanoic acid Using General Procedure (Ia) and (2-isopropylpyrimidin-4-yl)methanol (Preparation 9bd) as the appropriate alcohol, Example 24 was obtained. HRMS calculated for $C_{43}H_{44}ClFN_6O_5S$: 810.2766. found 406.1465 (M+2H).

Example 25 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(trifluoromethyl)pyrimidin-4-yl]methoxy}phenyl)propanoic acid Using General Procedure (Ia) and (2-trifluoromethylpyrimidin-4-yl)methanol (Preparation 9bj) as the appropriate alcohol, Example 25 was obtained. HRMS calculated for $C_{41}H_{37}ClF_4N_6O_5S$: 836.2171. found 837.2295 (M+H).

Example 26 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-cyclopropylpyrimidin-4-yl)methoxy]phenyl}propanoic acid Using General Procedure (Ia) and (2-cyclopropylpyrimidin-4-yl)methanol (Preparation 9be) as the appropriate alcohol, Example 26 was obtained. HRMS calculated for $C_{43}H_{42}ClFN_6O_5S$: 808.2610. found 405.1363 (M+2H).

Example 27 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-chlorophenyl)pyrimidin-4-yl]methoxy}phenyl)propanoic acid Using General Procedure (Ia) and [2-(4-chlorophenyl)pyrimidin-4-yl]methanol (Preparation 9bo) as the appropriate alcohol, Example 27 was obtained. HRMS calculated for $C_{46}H_{41}Cl_2FN_6O_5S$: 878.2220. found 879.2355 (M+H).

Example 28 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-cyclopentylpyrimidin-4-yl)methoxy]phenyl}propanoic acid Using General Procedure (Ia) and (2-cyclopentylpyrimidin-4-yl)methanol (Preparation 9bi) as the appropriate alcohol, Example 28 was obtained. HRMS calculated for $C_{45}H_{46}ClFN_6O_5S$: 836.2923. found 419.1537 (M+2H).

Example 29 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-phenylpyrimidin-4-yl)methoxy]phenyl}propanoic acid Using General Procedure (Ia) and (2-phenylpyrimidin-4-yl)methanol as the appropriate alcohol, Example 29 was obtained. HRMS calculated for $C_{46}H_{42}ClFN_6O_5S$: 844.2610. found 423.1363 (M+2H).

Example 30 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid Using General Procedure (Ia) and [2-(2-methoxyphenyl)pyrimidin-4-yl]methanol (Preparation 9bp) as the appropriate alcohol, Example 30 was obtained. HRMS calculated for $C_{47}H_{44}ClFN_6O_6S$: 874.2716. found 438.1415 (M+2H).

Example 31 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(pyridin-2-yl)pyrimidin-4-yl]methoxy}phenyl)propanoic acid Using General Procedure (Ia) and [2-(2-pyridyl)pyrimidin-4-yl]methanol (Preparation 9bq) as the appropriate alcohol, Example 31 was obtained. HRMS calculated for $C_{45}H_{41}ClFN_7O_5S$: 845.2562. found 423.6373 (M+2H).

Example 32 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(pyridin-3-yl)pyrimidin-4-yl]methoxy}phenyl)propanoic acid Using General Procedure (Ia) and [2-(3-pyridyl)pyrimidin-4-yl]methanol (Preparation 9br) as the appropriate alcohol, Example 32 was obtained. HRMS calculated for $C_{45}H_{41}ClFN_7O_5S$: 845.2562. found 423.6337 (M+2H).

Example 33 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(thiophen-2-yl)pyrimidin-4-yl]methoxy}phenyl)propanoic acid Using General Procedure (Ia) and [2-(2-thienyl)pyrimidin-4-yl]methanol (Preparation 9bv) as the appropriate alcohol, Example 33 was obtained. HRMS calculated for $C_{44}H_{40}ClFN_6O_5S_2$: 850.2174. found 851.2245 (M+H).

Example 34 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(pyridin-4-yl)pyrimidin-4-yl]methoxy}phenyl)propanoic acid Using General Procedure (Ia) and [2-(4-pyridyl)pyrimidin-4-yl]methanol (Preparation 9bs) as the appropriate alcohol, Example 34 was obtained. HRMS calculated for $C_{45}H_{41}ClFN_7O_5S$: 845.2562. found 423.6358 (M+2H).

Example 35 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(furan-3-yl)pyrimidin-4-yl]methoxy}phenyl)propanoic acid Using General Procedure (Ia) and [2-(3-furyl)pyrimidin-4-yl]methanol (Preparation 9bt) as the appropriate alcohol, Example 35 was obtained. HRMS calculated for $C_{44}H_{40}ClFN_6O_6S$: 834.2403. found 835.2443 (M+H).

Example 36 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(1,3-thiazol-2-yl)pyrimidin-4-yl]methoxy}phenyl)propanoic acid Using General Procedure (Ia) and [2-(2-thiazolyl)pyrimidin-4-yl]methanol (Preparation 9bx) as the appropriate alcohol, Example 36 was obtained. HRMS calculated for $C_{43}H_{39}ClFN_7O_5S_2$: 851.2127. found 426.6120 (M+2H).

Example 37 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-ethylpyrimidin-4-yl)methoxy]phenyl}propanoic acid Using General Procedure (Ia) and (2-ethylpyrimidin-4-yl)methanol (Preparation 9ba) as the appropriate alcohol, Example 37 was obtained. HRMS calculated for $C_{42}H_{42}ClFN_6O_5S$: 796.2610. found 399.1381 (M+2H).

Example 38 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methylpropyl)pyrimidin-4-yl]methoxy}phenyl)propanoic acid Using General Procedure (Ia) and [2-(2-methylpropyl)pyrimidin-4-yl]methanol (Preparation 9bf) as the appropriate alcohol, Example 38 was obtained. HRMS calculated for $C_{44}H_{46}ClFN_6O_5S$: 824.2923. found 825.2998 (M+H).

Example 39 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(cyclopropylmethyl)pyrimidin-4-yl]methoxy}phenyl)propanoic acid Using General Procedure (Ia) and [2-(cyclopropylmethyl)pyrimidin-4-yl]methanol (Preparation 9bg) as the appropriate alcohol, Example 39 was obtained. HRMS calculated for $C_{44}H_{44}ClFN_6O_5S$: 822.2766. found 412.1458 (M+2H).

Example 40 (2R)-3-{2-[(2-benzylpyrimidin-4-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ia) and (2-benzylpyrimidin-4-yl)methanol (Preparation 9by) as the appropriate alcohol, Example 40 was obtained. HRMS calculated for $C_{47}H_{44}ClFN_6O_5S$: 858.2766. found 430.1471 (M+2H).

Example 41 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-propylpyrimidin-4-yl)methoxy]phenyl}propanoic acid Using General Procedure (Ia) and (2-propylpyrimidin-4-yl)methanol (Preparation 9bb) as the appropriate alcohol, Example 41 was obtained. HRMS calculated for $C_{43}H_{44}ClFN_6O_5S$: 810.2766. found 406.1459 (M+2H).

Example 42 (2R)-3-{2-[(2-butylpyrimidin-4-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ia) and (2-butylpyrimidin-4-yl)methanol (Preparation 9bc) as the appropriate alcohol, Example 42 was obtained. HRMS calculated for $C_{44}H_{46}ClFN_6O_5S$: 824.2923. found 413.1500 (M+2H).

Example 43 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(dimethylamino)ethyl]pyrimidin-4-yl}methoxy)phenyl]propanoic acid Using General Procedure (Ia) and [2-[2-(dimethylamino)ethyl]pyrimidin-4-yl]methanol (Preparation 9bm) as the appropriate alcohol, Example 43 was obtained. HRMS calculated for $C_{44}H_{47}ClFN_7O_5S$: 839.3032. found 420.6614 (M+2H).

Example 44 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyethyl)pyrimidin-4-yl]methoxy}phenyl)propanoic acid Using General Procedure (Ia) and [2-(2-methoxyethyl)pyrimidin-4-yl]methanol (Preparation 9bl) as the appropriate alcohol, Example 44 was obtained. HRMS calculated for $C_{43}H_{44}ClFN_6O_6S$: 826.2716. found 414.1439 (M+2H).

Example 45 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(methoxymethyl)pyrimidin-4-yl]methoxy}phenyl)propanoic acid Using General Procedure (Ia) and [2-(methoxymethyl)pyrimidin-4-yl]methanol (Preparation 9bk) as the appropriate alcohol, Example 45 was obtained. HRMS calculated for $C_{42}H_{42}ClFN_6O_6S$: 812.2559. found 813.2622 (M+H).

Example 46 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(phenoxymethyl)pyrimidin-4-yl]methoxy}phenyl)propanoic acid Using General Procedure (Ia) and [2-(phenoxymethyl)pyrimidin-4-yl]methanol (Preparation 9bz) as the appropriate alcohol, Example 46 was obtained. HRMS calculated for $C_{47}H_{44}ClFN_6O_6S$: 874.2716. found 875.2790 (M+H).

Example 47 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(ethoxymethyl)pyrimidin-4-yl]methoxy}phenyl)propanoic acid Using General Procedure (Ia) and [2-(ethoxymethyl)pyrimidin-4-yl]methanol (Preparation 9bn) as the appropriate alcohol, Example 47 was obtained. HRMS calculated for $C_{43}H_{44}ClFN_6O_6S$: 826.2716. found 827.2783 (M+H).

Example 48 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[(2-methoxyethyl)(methyl)amino]pyrimidin-4-yl}methoxy)phenyl]propanoic acid Using General Procedure (Ia) and [2-[2-methoxyethyl(methyl)amino]pyrimidin-4-yl]methanol (Preparation 9ap) as the appropriate alcohol, Example 48 was obtained. HRMS calculated for $C_{44}H_{47}ClFN_7O_6S$: 855.2981. found 428.6583 (M+2H).

Example 49 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(1H-pyrazol-1-yl)pyrimidin-4-yl]methoxy}phenyl)propanoic acid Using General Procedure (Ia) and (2-(1H-pyrazol-1-yl)pyrimidin-4-yl)methanol (Preparation 9bw) as the appropriate alcohol, Example 49 was obtained. HRMS calculated for $C_{43}H_{40}ClFN_8O_5S$: 834.2515. found 418.1327 (M+2H).

Example 50 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-methylpiperazin-1-yl)pyrimidin-4-yl]methoxy}phenyl)propanoic acid Using General Procedure (Ia) and [2-(4-methylpiperazin-1-yl)pyrimidin-4-yl]methanol (Preparation 9aq) as the appropriate alcohol, Example 50 was obtained. HRMS calculated for $C_{45}H_{48}ClFN_8O_5S$: 866.3141. found 434.1640 (M+2H).

Example 51 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(1H-1,2,3-triazol-1-yl)pyrimidin-4-yl]methoxy}phenyl)propanoic acid Using General Procedure (Ia) and [2-(1H-1,2,3-triazol-1-yl)pyrimidin-4-yl]methanol (Preparation 9 as) as the appropriate alcohol, Example 51 was obtained. HRMS calculated for $C_{42}H_{39}ClFN_9O_5S$: 835.2467. found 418.6292 (M+2H).

Example 52 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(morpholin-4-yl)pyrimidin-4-yl]methoxy}phenyl)propanoic acid Using General Procedure (Ia) and (2-(morpholin-4-yl)pyrimidin-4-yl)methanol (Preparation 9ar) as the appropriate alcohol, Example 52 was obtained. HRMS calculated for $C_{44}H_{45}ClFN_7O_6S$: 853.2825. found 427.6484 (M+2H).

Example 53 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[(2-methoxyethyl)amino]pyrimidin-4-yl}methoxy)phenyl]propanoic acid Using General Procedure (Ia) and [2-(2-methoxyethylamino)pyrimidin-4-yl]methanol (Preparation 9ao) as the appropriate alcohol, Example 53 was obtained. HRMS calculated for $C_{43}H_{45}ClFN_7O_6S$: 841.2825. found 421.6505 (M+2H).

Example 54 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-methoxypyrimidin-4-yl)methoxy]phenyl}propanoic acid Using General Procedure (Ia) and (2-methoxypyrimidin-4-yl)methanol as the appropriate alcohol, Example 54 was obtained. HRMS calculated for $C_{41}H_{40}ClFN_6O_6S$: 798.2403. found 400.1284 (M+2H).

Example 55 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(propan-2-yloxy)pyrimidin-4-yl]methoxy}phenyl)propanoic acid Using General Procedure (Ia) and (2-isopropoxypyrimidin-4-yl)methanol (Preparation 9ae) as the appropriate alcohol, Example 55 was obtained. HRMS calculated for $C_{43}H_{44}ClFN_6O_6S$: 826.2716. found 414.1442 (M+2H).

Example 56 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-phenoxypyrimidin-4-yl)methoxy]phenyl}propanoic acid Using General Procedure (Ia) and (2-phenoxypyrimidin-4-yl)methanol (Preparation 9ak) as the appropriate alcohol, Example 56 was obtained. HRMS calculated for $C_{46}H_{42}ClFN_6O_6S$: 860.2559. found 431.1333 (M+2H).

Example 57 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-ethoxypyrimidin-4-yl)methoxy]phenyl}propanoic acid Using General Procedure (Ia) and (2-ethoxypyrimidin-4-yl)methanol (Preparation 9ad) as the appropriate alcohol, Example 57 was obtained. HRMS calculated for $C_{42}H_{42}ClFN_6O_6S$: 812.2559. found 407.1342 (M+2H).

Example 58 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2,2,2-trifluoroethoxy)pyrimidin-4-yl]methoxy}phenyl)propanoic acid Using General Procedure (Ia) and [2-(2,2,2-trifluoroethoxy)pyrimidin-4-yl]methanol (Preparation 9ai) as the appropriate alcohol, Example 58 was obtained. HRMS calculated for $C_{42}H_{39}ClF_4N_6O_6S$: 866.2276. found 434.1195 (M+2H).

Example 59 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(pyridin-4-ylmethoxy)pyrimidin-4-yl]methoxy}phenyl)propanoic acid Using General Procedure (Ia) and [2-(4-pyridylmethoxy)pyrimidin-4-yl]methanol (Preparation 9aw) as the appropriate alcohol, Example 59 was obtained. HRMS calculated for $C_{46}H_{43}ClFN_7O_6S$: 875.2668. found 438.6442 (M+2H).

Example 60 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[(1-methyl-1H-imidazol-5-yl)methoxy]pyrimidin-4-yl}methoxy)phenyl]propanoic acid Using General Procedure (Ia) and {2-[(1-methyl-1H-imidazol-5-yl)methoxy]pyrimidin-4-yl}methanol (Preparation 9ay) as the appropriate alcohol, Example 60 was obtained. HRMS calculated for $C_{45}H_{44}ClFN_8O_6S$: 878.2777. found 440.1451 (M+2H).

Example 61 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-propoxypyrimidin-4-yl)methoxy]phenyl}propanoic acid Using General Procedure (Ia) and (2-propoxypyrimidin-4-yl)methanol (Preparation 9af) as the appropriate alcohol, Example 61 was obtained. HRMS calculated for $C_{43}H_{44}ClFN_6O_6S$: 826.2716. found 414.1423 (M+2H).

Example 62 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3,3,3-trifluoropropoxy)pyrimidin-4-yl]methoxy}phenyl)propanoic acid Using General Procedure (Ia) and [2-(3,3,3-trifluoropropoxy)pyrimidin-4-yl]methanol (Preparation 9aj) as the appropriate alcohol, Example 62 was obtained. HRMS calculated for $C_{43}H_{41}ClF_4N_6O_6S$: 880.2433. found 441.1294 (M+2H).

Example 63 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyethoxy)pyrimidin-4-yl]methoxy}phenyl)propanoic acid Using General Procedure (Ia) and [2-(2-methoxyethoxy)pyrimidin-4-yl]methanol (Preparation 9ag) as the appropriate alcohol, Example 63 was obtained. HRMS calculated for $C_{43}H_{44}ClFN_6O_7S$: 842.2665. found 422.1385 (M+2H).

Example 64 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-ethoxyethoxy)pyrimidin-4-yl]methoxy}phenyl)propanoic acid Using General Procedure (Ia) and [2-(2-ethoxyethoxy)pyrimidin-4-yl]methanol (Preparation 9ah) as the appropriate alcohol, Example 64 was obtained. HRMS calculated for $C_{44}H_{46}ClFN_6O_7S$: 856.2821. found 429.1497 (M+2H).

Example 65 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(methylsulfanyl)pyrimidin-4-yl]methoxy}phenyl)propanoic acid Using General Procedure (Ia) and (2-methylsulfanylpyrimidin-4-yl)methanol (Preparation 9aa) as the appropriate alcohol, Example 65 was obtained. HRMS calculated for $C_{41}H_{40}ClFN_6O_5S_2$: 814.2174. found 815.2260 (M+H).

Example 66 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[(3-methoxypropyl)sulfanyl]pyrimidin-4-yl}methoxy)phenyl]propanoic acid Using General Procedure (Ia) and [2-(3-methoxypropylsulfanyl)pyrimidin-4-yl]methanol (Preparation 9ac) as the appropriate alcohol, Example 66 was obtained. HRMS calculated for $C_{44}H_{46}ClFN_6O_6S_2$: 872.2593. found 437.1384 (M+2H).

Example 67 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[(2-methoxyethyl)sulfanyl]pyrimidin-4-yl}methoxy)phenyl]propanoic acid Using General Procedure (Ia) and [2-(2-methoxyethylsulfanyl)pyrimidin-4-yl]methanol (Preparation 9ab) as the appropriate alcohol, Example 67 was obtained. HRMS calculated for $C_{43}H_{44}ClFN_6O_6S_2$: 858.2436. found 430.1286 (M+2H).

Example 68 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(pyrimidin-4-ylmethoxy)phenyl]propanoic acid Using General Procedure (Ia) and pyrimidin-4-ylmethanol as the appropriate alcohol, Example 68 was obtained. HRMS calculated for $C_{40}H_{38}ClFN_6O_5S$: 768.2297. found 769.2358 (M+H).

Example 69 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-methyl-1H-pyrazol-5-yl)methoxy]phenyl}propanoic acid Using General Procedure (Ia) and (1-methyl-1H-imidazol-5-yl)methanol as the appropriate alcohol, Example 69 was obtained. HRMS calculated for $C_{40}H_{40}ClFN_6O_5S$: 770.2453. found 771.2527 (M+H).

Example 70 (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ia) and (1-tert-butyl-1H-pyrazol-5-yl)methanol (Preparation 9dt) as the appropriate alcohol, Example 70 was obtained. HRMS calculated for $C_{43}H_{46}ClFN_6O_5S$: 812.2923. found 813.3030 (M+H).

Example 71 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(propan-2-yl)-1H-pyrazol-5-yl]methoxy}phenyl)propanoic acid Using General Procedure (Ia) and [1-(propan-2-yl)-1H-pyrazol-5-yl]methanol (Preparation 9dc) as the appropriate alcohol, Example 71 was obtained. HRMS calculated for $C_{42}H_{44}ClFN_6O_5S$: 798.2766. found 400.1469 (M+2H).

Example 72 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-cyclopentyl-1H-pyrazol-5-yl)methoxy]phenyl}propanoic acid Using General Procedure (Ia) and (1-cyclopentyl-1H-pyrazol-5-yl)methanol (Preparation 9dg) as the appropriate alcohol, Example 72 was obtained. HRMS calculated for $C_{44}H_{46}ClFN_6O_5S$: 824.2923. found 413.1559 (M+2H).

Example 73 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-cyclohexyl-1H-pyrazol-5-yl)methoxy]phenyl}propanoic acid Using General Procedure (Ia) and (1-cyclohexyl-1H-pyrazol-5-yl)methanol (Preparation 9dh) as the appropriate alcohol, Example 73 was obtained. HRMS calculated for $C_{45}H_{48}ClFN_6O_5S$: 838.3079. found 839.3165 (M+H).

Example 74 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-phenyl-1H-pyrazol-5-yl)methoxy]phenyl}propanoic acid Using General Procedure (Ia) and (1-phenyl-1H-pyrazol-5-yl)methanol as the appropriate alcohol, Example 74 was obtained. HRMS calculated for $C_{45}H_{42}ClFN_6O_5S$: 832.2610. found 833.2656 (M+H).

Example 75 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(tetrahydro-2H-pyran-4-yl)-1H-pyrazol-5-yl]methoxy}phenyl)propanoic acid Using General Procedure (Ia) and (1-(tetrahydro-2H-pyran-4-yl)-1H-pyrazol-5-yl)methanol (Preparation 9di) as the appropriate alcohol, Example 75 was obtained. HRMS calculated for $C_{44}H_{46}ClFN_6O_6S$: 840.2872. found 841.2913 (M+H).

Example 76 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-ethyl-1H-pyrazol-5-yl)methoxy]phenyl}propanoic acid Using General Procedure (Ia) and (1-ethyl-1H-pyrazol-5-yl)methanol (Preparation 9da) as the appropriate alcohol, Example 76 was obtained. HRMS calculated for $C_{41}H_{42}ClFN_6O_5S$: 784.2610. found 785.2679 (M+H).

Example 77 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2,2,2-trifluoroethyl)-1H-pyrazol-5-yl]methoxy}phenyl)propanoic acid Using General Procedure (Ia) and [1-(2,2,2-trifluoroethyl)-1H-pyrazol-5-yl]methanol (Preparation 9du) as the appropriate alcohol, Example 77 was obtained. HRMS calculated for $C_{41}H_{39}ClF_4N_6O_5S$: 838.2327. found 839.2389 (M+H).

Example 78 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(cyclopropylmethyl)-1H-pyrazol-5-yl]methoxy}phenyl)propanoic acid Using General Procedure (Ia) and [1-(cyclopropylmethyl)-1H-pyrazol-5-yl]methanol (Preparation 9df) as the appropriate alcohol, Example 78 was obtained. HRMS calculated for $C_{43}H_{44}ClFN_6O_5S$: 810.2766. found 406.1464 (M+2H).

Example 79 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(4-methoxybenzyl)-1H-pyrazol-5-yl]methoxy}phenyl)propanoic acid Using General Procedure (Ia) and [1-(4-methoxybenzyl)-1H-pyrazol-5-yl]methanol (Preparation 9dk) as the appropriate alcohol, Example 79 was obtained. HRMS calculated for $C_{47}H_{46}ClFN_6O_6S$: 876.2872. found 439.1531 (M+2H).

Example 80 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(cyclohexylmethyl)-1H-pyrazol-5-yl]methoxy}phenyl)propanoic acid Using General Procedure (Ia) and [1-(cyclohexylmethyl)-1H-pyrazol-5-yl]methanol (Preparation 9dv) as the appropriate alcohol, Example 80 was obtained. HRMS calculated for $C_{46}H_{50}ClFN_6O_5S$: 852.3236. found 427.1679 (M+2H).

Example 81 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-propyl-1H-pyrazol-5-yl)methoxy]phenyl}propanoic acid Using General Procedure (Ia) and (1-propyl-1H-pyrazol-5-yl)methanol (Preparation 9db) as the appropriate alcohol, Example 81 was obtained. HRMS calculated for $C_{42}H_{44}ClFN_6O_5S$: 798.2766. found 400.1433 (M+2H).

Example 82 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(3-methylbutyl)-1H-pyrazol-5-yl]methoxy}phenyl)propanoic acid Using General Procedure (Ia) and [1-(3-methylbutyl)-1H-pyrazol-5-yl]methanol (Preparation 9de) as the appropriate alcohol, Example 82 was obtained. HRMS calculated for $C_{44}H_{48}ClFN_6O_5S$: 826.3079. found 827.3123 (M+H).

Example 83 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ia) and (1-butyl-1H-pyrazol-5-yl)methanol (Preparation 9dd) as the appropriate alcohol, Example 83 was obtained. HRMS calculated for $C_{43}H_{46}ClFN_6O_5S$: 812.2923. found 407.1551 (M+2H).

Example 84 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(4,4,4-trifluorobutyl)-1H-pyrazol-5-yl]methoxy}phenyl)propanoic acid Using General Procedure (Ia) and [1-(4,4,4-trifluorobutyl)-1H-pyrazol-5-yl]methanol (Preparation 9dl) as the appropriate alcohol, Example 84 was obtained. HRMS calculated for $C_{43}H_{43}ClF_4N_6O_5S$: 866.2640. found 434.1385 (M+2H).

Example 85 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-pentyl-1H-pyrazol-5-yl)methoxy]phenyl}propanoic acid Using General Procedure (Ia) and (1-pentyl-1H-pyrazol-5-yl)methanol (Preparation 9dm) as the appropriate alcohol, Example 85 was obtained. HRMS calculated for $C_{44}H_{48}ClFN_6O_5S$: 826.3079. found 827.3206 (M+H).

Example 86 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(3-methoxypropyl)-1H-pyrazol-5-yl]methoxy}phenyl)propanoic acid Using General Procedure (Ia) and [1-(3-methoxypropyl)-1H-pyrazol-5-yl]methanol (Preparation 9dq) as the appropriate alcohol, Example 86 was obtained. HRMS calculated for $C_{43}H_{46}ClFN_6O_6S$: 828.2872. found 415.1505 (M+2H).

Example 87 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({1-[2-(dimethylamino)ethyl]-1H-pyrazol-5-yl}methoxy)phenyl]propanoic acid Using General Procedure (Ia) and {1-[2-(dimethylamino)ethyl]-1H-pyrazol-5-yl}methanol (Preparation 9dj) as the appropriate alcohol, Example 87 was obtained. HRMS calculated for $C_{43}H_{47}ClFN_7O_5S$: 827.3032. found 414.6592 (M+2H).

Example 88 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2-methoxyethyl)-1H-pyrazol-5-yl]methoxy}phenyl)propanoic acid Using General Procedure (Ia) and [1-(2-methoxyethyl)-1H-pyrazol-5-yl]methanol (Preparation 9dp) as the appropriate alcohol, Example 88 was obtained. HRMS calculated for $C_{42}H_{44}ClFN_6O_6S$: 814.2716. found 408.1423 (M+2H).

Example 89 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2-ethoxyethyl)-1H-pyrazol-5-yl]methoxy}phenyl)propanoic acid Using General Procedure (Ia) and [1-(2-ethoxyethyl)-1H-pyrazol-5-yl]methanol (Preparation 9dr) as the appropriate alcohol, Example 89 was obtained. HRMS calculated for $C_{43}H_{46}ClFN_6O_6S$: 828.2872. found 415.1510 (M+2H).

Example 90 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({1-[2-(2-methoxyethoxy)ethyl]-1H-pyrazol-5-yl}methoxy)phenyl]propanoic acid Using General Procedure (Ia) and {1-[2-(2-methoxyethoxy)ethyl]-1H-pyrazol-5-yl}methanol (Preparation 9ds) as the appropriate alcohol, Example 90 was obtained. HRMS calculated for $C_{44}H_{48}ClFN_6O_7S$: 858.2978. found 430.1571 (M+2H).

Example 91 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(pyrazin-2-ylmethoxy)phenyl]propanoic acid Using General Procedure (Ia) and pyrazin-2-ylmethanol as the appropriate alcohol, Example 91 was obtained. HRMS calculated for $C_{40}H_{38}ClFN_6O_5S$: 768.2297. found 769.2422 (M+H).

Example 92 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-methyl-1H-imidazol-5-yl)methoxy]phenyl}propanoic acid Using General Procedure (Ia) and (1-methyl-1H-imidazol-5-yl)methanol as the appropriate alcohol, Example 92 was obtained. HRMS calculated for $C_{40}H_{40}ClFN_6O_5S$: 770.2453. found 771.2523 (M+H).

Example 93 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(pyrimidin-5-ylmethoxy)phenyl]propanoic acid Using General Procedure (Ia) and pyrimidin-5-ylmethanol as the appropriate alcohol, Example 93 was obtained. HRMS calculated for $C_{40}H_{38}ClFN_6O_5S$: 768.2297. found 769.2379 (M+H).

Example 94 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(1-phenyl-1H-1,2,3-triazol-5-yl)methoxy]phenyl}propanoic acid Using General Procedure (Ia) and (1-phenyl-1H-1,2,3-triazol-5-yl)methanol (Preparation 9ee) as the appropriate alcohol, Example 94 was obtained. HRMS calculated for $C_{44}H_{41}ClFN_7O_5S$: 833.2562. found 834.2620 (M+H).

Example 95 (2R)-3-{2-[(1-butyl-1H-1,2,3-triazol-5-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ia) and (1-butyl-1H-1,2,3-triazol-5-yl)methanol (Preparation 9ec) as the appropriate alcohol, Example 95 was obtained. HRMS calculated for $C_{42}H_{45}ClFN_7O_5S$: 813.2875. found 814.2964 (M+H).

Example 96 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(3-methoxypropyl)-1H-1,2,3-triazol-5-yl]methoxy}phenyl)propanoic acid Using General Procedure (Ia) and [1-(3-methoxypropyl)-1H-1,2,3-triazol-5-yl]methanol (Preparation 9ed) as the appropriate alcohol, Example 96 was obtained. HRMS calculated for $C_{42}H_{45}ClFN_7O_6S$: 829.2825. found 830.2876 (M+H).

Example 97 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2-methoxyethyl)-1H-1,2,3-triazol-5-yl]methoxy}phenyl)propanoic acid Using General Procedure (Ia) and [1-(2-methoxyethyl)-1H-1,2,3-triazol-5-yl]methanol (Preparation 9ef) as the appropriate alcohol, Example 97 was obtained. HRMS calculated for $C_{41}H_{43}ClFN_7O_6S$: 815.2668. found 408.6427 (M+2H).

Example 98 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(1,3-oxazol-4-ylmethoxy)phenyl]propanoic acid Using General Procedure (Ia) and oxazol-4-ylmethanol as the appropriate alcohol, Example 98 was obtained. HRMS calculated for $C_{39}H_{37}ClFN_5O_6S$: 757.2137. found 758.2245 (M+H).

Example 99 (2R)-3-{2-[(5-bromo-2-methoxypyrimidin-4-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ia) and (5-bromo-2-methoxypyrimidin-4-yl)methanol (Preparation 9cb) as the appropriate alcohol, Example 99 was obtained. HRMS calculated for C$_{41}$H$_{39}$BrClFN$_6$O$_6$S: 876.1508. found 439.0864 (M+2H).

Example 100 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-methoxy-5-(thiophen-3-yl)pyrimidin-4-yl]methoxy}phenyl)propanoic acid Using General Procedure (Ia) and [2-methoxy-5-(3-thienyl)pyrimidin-4-yl]methanol (Preparation 9 cc) as the appropriate alcohol, Example 100 was obtained. HRMS calculated for C$_{45}$H$_{42}$ClFN$_6$O$_6$S$_2$: 880.2280. found 441.1229 (M+2H).

Example 101 (2R)-3-{2-[(5-bromopyrimidin-4-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ia) and (5-bromopyrimidin-4-yl)methanol (Preparation 9ca) as the appropriate alcohol, Example 101 was obtained. HRMS calculated for C$_{40}$H$_{37}$BrClFN$_6$O$_5$S: 846.1402. found 424.0775 (M+2H).

Example 102 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(4-methyl-4H-1,2,4-triazol-3-yl)methoxy]phenyl}propanoic acid Using General Procedure (Ia) and (4-methyl-4H-1,2,4-triazol-3-yl)methanol as the appropriate alcohol, Example 102 was obtained. HRMS calculated for C$_{39}$H$_{39}$ClFN$_7$O$_5$S: 771.2406. found 772.2411 (M+H).

Example 103 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(2-fluoroethoxy)phenyl]propanoic acid Using General Procedure (Ia) and 2-fluoroethanol as the appropriate alcohol, Example 103 was obtained. HRMS calculated for C$_{37}$H$_{37}$ClF$_2$N$_4$O$_5$S: 722.2141. found 723.2244 (M+H).

Example 104 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(2-methoxyethoxy)phenyl]propanoic acid Using General Procedure (Ia) and 2-methoxyethanol as the appropriate alcohol, Example 104 was obtained. HRMS calculated for C$_{38}$H$_{40}$ClFN$_4$O$_6$S: 734.2341. found 735.2455 (M+H).

Example 105 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[2-(2-methoxyethoxy)ethoxy]phenyl}propanoic acid Using General Procedure (Ia) and 2-(2-methoxyethoxy)ethanol as the appropriate alcohol, Example 105 was obtained. HRMS calculated for C$_{40}$H$_{44}$ClFN$_4$O$_7$S: 778.2603. found 390.1362 (M+2H).

Example 106 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{2-[2-(2-methoxyethoxy)ethoxy]ethoxy}phenyl)propanoic acid Using General Procedure (Ia) and 2-[2-(2-methoxyethoxy)ethoxy]ethanol as the appropriate alcohol, Example 106 was obtained. HRMS calculated for C$_{42}$H$_{48}$ClFN$_4$O$_8$S: 822.2865. found 412.1520 (M+2H).

Example 107 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-methoxyphenyl)pyrimidin-4-yl]methoxy}phenyl)propanoic acid Using General Procedure (Ib) and (4-methoxyphenyl)boronic acid as the appropriate boronic acid derivative, Example 107 was obtained. HRMS calculated for C$_{47}$H$_{44}$ClFN$_6$O$_6$S: 874.2716. found 438.1407 (M+2H).

Example 108 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(6-methylpyridin-3-yl)pyrimidin-4-yl]methoxy}phenyl)propanoic acid Using General Procedure (Ib) and (6-methyl-3-pyridyl)boronic acid as the appropriate boronic acid derivative, Example 108 was obtained. HRMS calculated for C$_{46}$H$_{43}$ClFN$_7$O$_5$S: 859.2719. found 430.6436 (M+2H).

Example 109 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[6-(trifluoromethyl)pyridin-3-yl]pyrimidin-4-yl}methoxy)phenyl]propanoic acid Using General Procedure (Ib) and [6-(trifluoromethyl)-3-pyridyl]boronic acid as the appropriate boronic acid derivative, Example 109 was obtained. HRMS calculated for C$_{46}$H$_{40}$ClF$_4$N$_7$O$_5$S: 913.2436. found 914.2521 (M+H).

Example 110 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(6-chloropyridin-3-yl)pyrimidin-4-yl]methoxy}phenyl)propanoic acid Using General Procedure (Ib) and (6-chloro-3-pyridyl)boronic acid as the appropriate boronic acid derivative, Example 110 was obtained. HRMS calculated for C$_{45}$H$_{40}$Cl$_2$FN$_7$O$_5$S: 879.2173. found 440.6161 (M+2H).

Example 111 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(6-methoxypyridin-3-yl)pyrimidin-4-yl]methoxy}phenyl)propanoic acid Using General Procedure (Ib) and (6-methoxy-3-pyridyl)boronic acid as the appropriate boronic acid derivative, Example 111 was obtained. HRMS calculated for C$_{46}$H$_{43}$ClFN$_7$O$_6$S: 875.2668. found 438.6403 (M+2H).

Example 112 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-methoxyphenyl)pyrimidin-4-yl]methoxy}phenyl)propanoic acid Using General Procedure (Ib) and (3-methoxyphenyl)boronic acid as the appropriate boronic acid derivative, Example 112 was obtained. HRMS calculated for C$_{47}$H$_{44}$ClFN$_6$O$_6$S: 874.2716. found 875.2836 (M+H).

Example 113 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methylphenyl)pyrimidin-4-yl]methoxy}phenyl)propanoic acid Using General Procedure (Ib) and o-tolylboronic acid as the appropriate boronic acid derivative, Example 113 was obtained. HRMS calculated for C$_{47}$H$_{44}$ClFN$_6$O$_5$S: 858.2766. found 430.1464 (M+2H).

Example 114 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoic acid Using General Procedure (Ib) and (2-fluorophenyl)boronic acid as the appropriate boronic acid derivative, Example 114 was obtained. HRMS calculated for C$_{46}$H$_{41}$ClF$_2$N$_6$O$_5$S: 862.2516. found 432.1342 (M+2H).

Example 115 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-ethoxyphenyl)pyrimidin-4-yl]methoxy}phenyl)propanoic acid Using General Procedure (Ib) and (2-ethoxyphenyl)boronic acid as the appropriate boronic acid derivative, Example 115 was obtained. HRMS calculated for C$_{39}$H$_{38}$ClFN$_6$O$_7$S: 788.2195. found 395.1179 (M+2H).

Example 116 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methylpyridin-3-yl)pyrimidin-4-yl]methoxy}phenyl)propanoic acid Using General Procedure (Ib) and (2-methyl-3-pyridyl)boronic acid as the appropriate boronic acid derivative, Example 116 was obtained. HRMS calculated for C$_{46}$H$_{43}$ClFN$_7$O$_5$S: 859.2719. found 430.6429 (M+2H).

Example 117 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(furan-2-yl)pyrimidin-4-yl]methoxy}phenyl)propanoic acid Using General Procedure (Ib) and 2-furylboronic acid as the appropriate boronic acid derivative, Example 117 was obtained. HRMS calculated for C$_{44}$H$_{40}$ClFN$_6$O$_6$S: 834.2403. found 418.1278 (M+2H).

Example 118 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methylpyridin-4-yl)pyrimidin-4-yl]methoxy}phenyl)propanoic acid Using General Procedure (Ib) and (2-methyl-4-pyridyl)boronic acid as the appropriate boronic acid derivative, Example 118 was obtained. HRMS calculated for C$_{46}$H$_{43}$ClFN$_7$O$_5$S: 859.2719. found 430.6409 (M+2H).

Example 119 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-chloropyridin-4-yl)pyrimidin-4-yl]methoxy}phenyl)propanoic acid Using General Procedure (Ib) and (2-chloro-4-pyridyl)boronic acid as the appropriate boronic acid derivative, Example 119 was obtained. HRMS calculated for C$_{45}$H$_{40}$Cl$_2$FN$_7$O$_5$S: 879.2173. found 440.6186 (M+2H).

Example 120 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-methylpyridin-4-yl)pyrimidin-4-yl]methoxy}phenyl)propanoic acid Using General Procedure (Ib) and (3-methyl-4-pyridyl)boronic acid as the appropriate boronic acid derivative, Example 120 was obtained. HRMS calculated for C$_{46}$H$_{43}$ClFN$_7$O$_5$S: 859.2719. found 860.2808 (M+H).

Example 121 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methylthiophen-3-yl)pyrimidin-4-yl]methoxy}phenyl)propanoic acid Using General Procedure (Ib) and (2-methyl-3-thienyl)boronic acid as the appropriate boronic acid derivative, Example 121 was obtained. HRMS calculated for C$_{45}$H$_{42}$ClFN$_6$O$_5$S$_2$: 864.2331. found 433.1239 (M+2H).

Example 122 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(5-methylpyridin-3-yl)pyrimidin-4-yl]methoxy}phenyl)propanoic acid Using General Procedure (Ib) and (5-methyl-3-pyridyl)boronic acid as the appropriate boronic acid derivative, Example 122 was obtained. HRMS calculated for C$_{46}$H$_{43}$ClFN$_7$O$_5$S: 859.2719. found 430.6450 (M+2H).

Example 123 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-methylpyridin-3-yl)pyrimidin-4-yl]methoxy}phenyl)propanoic acid Using General Procedure (Ib) and (4-methyl-3-pyridyl) boronic acid as the appropriate boronic acid derivative, Example 123 was obtained. HRMS calculated for C$_{46}$H$_{43}$ClFN$_7$O$_5$S: 859.2719. found 430.6434 (M+2H).

Example 124 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(4-methylthiophen-3-yl)pyrimidin-4-yl]methoxy}phenyl)propanoic acid Using General Procedure (Ib) and (4-methyl-3-thienyl) boronic acid as the appropriate boronic acid derivative, Example 124 was obtained. HRMS calculated for C$_{45}$H$_{42}$ClFN$_6$O$_5$S$_2$: 864.2331. found 433.1256 (M+2H).

Example 125 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(1H-pyrazol-5-ylmethoxy)phenyl]propanoic acid Step A:
1.058 g ethyl (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-hydroxyphenyl)propanoate (Preparation 8a) (1.5 mmol), 982 mg [1-(4-methoxybenzyl)-1H-pyrazol-5-yl]methanol (Preparation 9dk) (4.5 mmol) and 1.18 g PPh$_3$ (4.5 mmol) were dissolved in 30 mL dry toluene, then 1.036 g ditertbutyl azodicarboxylate (4.5 mmol) was added. The mixture was stirred at 50° C. under nitrogen until no further conversion was observed. The volatiles were evaporated under reduced pressure, and the crude intermediate was purified via flash chromatography using dichloromethane and methanol as eluents.

Step B:
226 mg (0.25 mmol) from the obtained intermediate was dissolved in 13 mL TFA and it was stirred at 100° C. for 1 hour. The volatiles were evaporated under reduced pressure, then the residue was diluted with DCM, washed with saturated aqueous NaHCO$_3$ solution. The organic layer was dried over Na$_2$SO$_4$, filtered and concentrated under reduced pressure.

Step C:
The obtained crude intermediate was dissolved in 6 mL dioxane-water 1:1 and 105 mg LiOH×H$_2$O (2.5 mmol) was added. The mixture was stirred at room temperature until no further conversion was observed. Then it was diluted with brine, neutralized with 2 M HCl, extracted with DCM, dried over Na$_2$SO$_4$, filtered and concentrated under reduced pressure and purified via preparative reversed phase chromatography using 5 mM aqueous NH$_4$HCO$_3$ solution and MeCN as eluents to give Example 125. HRMS calculated for C$_{39}$H$_{38}$ClFN$_6$O$_5$S: 756.2297. found 757.2303 (M+H).

General Procedure (IIa)
Step A:
1 eq. ethyl (2R)-2-[(5S$_a$)-5-[3-chloro-4-(2-dimethylaminoethyloxy)-2-methyl-phenyl]-6-(4-fluorophenyl)thieno[2,3-d]pyrimidin-4-yl]oxy-3-(2-hydroxyphenyl)propanoate (Preparation 8b) (0.3 mmol) and 2 eq. of the appropriate alcohol and 2 eq. triphenyl phosphine were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:
The obtained intermediate was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure. The crude product was purified via preparative reversed phase chromatography using 5 mM aqueous NH$_4$HCO$_3$ solution and MeCN as eluents.

General Procedure (IIb)
Step A:
1 eq. ethyl (2R)-2-[(5S$_a$)-5-[3-chloro-4-(2-dimethylaminoethyloxy)-2-methyl-phenyl]-6-(4-fluorophenyl)thieno[2,3-d]pyrimidin-4-yl]oxy-3-[2-[(2-methylsulfanylpyrimidin-4-yl)methoxy]phenyl]propanoate (Preparation 10b), 3.0 eq. of the appropriate boronic acid derivative and 3.0 eq. copper(I) thiophenecarboxylate were dissolved in dry THF (0.1 M for Preparation 10b), then 0.15 eq. Pd(PPh$_3$)$_4$ was added. The mixture was stirred at 70° C. under nitrogen until no further conversion was observed. Then it was concentrated under reduced pressure and the crude intermediate was purified via flash chromatography using dichloromethane and methanol as eluents.

Step B:
The obtained intermediate was dissolved in dioxane-water 1:1 (10 mL/mmol) and 10 eq LiOH×H$_2$O was added. The mixture was stirred at until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 5 mM aqueous NH$_4$HCO$_3$ solution and MeCN as eluents.

Example 126 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-{2-[(2R)-tetrahydrofuran-2-ylmethoxy]phenyl}propanoic acid Using General Procedure (IIa) and [(2R)-tetrahydrofuran-2-yl]methanol as the appropriate alcohol, Example 126 was obtained. HRMS calculated for C$_{37}$H$_{37}$ClFN$_3$O$_6$S: 705.2076. found 706.2163 (M+H).

Example 127 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-[2-(2,2,2-trifluoroethoxy)phenyl]propanoic acid Step A:
195 mg ethyl (2R)-2-[(5S$_a$)-5-[3-chloro-4-(2-dimethylaminoethyloxy)-2-methyl-phenyl]-6-(4-fluorophenyl)thieno[2,3-d]pyrimidin-4-yl]oxy-3-(2-hydroxyphenyl)propanoate (Preparation 8b) (0.3 mmol) and 138 mg K$_2$CO$_3$ (1.0 mmol) were dissolved in 2 mL DMF, then 232 mg 2,2,2-trifluoroethyl trifluoromethanesulfonate (1.0 mmol) was added. The mixture was stirred at room temperature under nitrogen until no further conversion was observed. Then it was diluted with brine, neutralized with 2 M HCl, and extracted with DCM. The combined organic phases were dried over Na$_2$SO$_4$, filtered and concentrated under reduced pressure.
Step B:

The obtained intermediate was dissolved in 8 mL dioxane-water 1:1 and 150 mg LiOH×H$_2$O (3.57 mmol) was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 5 mM aqueous NH$_4$HCO$_3$ solution and MeCN as eluents to obtain Example 127. HRMS calculated for C$_{34}$H$_{30}$ClF$_4$N$_3$O$_5$S: 703.1531. found 704.1634 (M+H).

Example 128 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(pyridin-4-yl)pyrimidin-4-yl]methoxy}phenyl)propanoic acid Using General Procedure (IIa) and [2-(4-pyridyl)pyrimidin-4-yl]methanol (Preparation 9bs) as the appropriate alcohol, Example 128 was obtained. HRMS calculated for C$_{42}$H$_{36}$ClFN$_6$O$_5$S: 790.2140. found 396.1147 (M+2H).

Example 129 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(morpholin-4-yl)pyrimidin-4-yl]methoxy}phenyl)propanoic acid Using General Procedure (IIa) and (2-(morpholin-4-yl)pyrimidin-4-yl)methanol (Preparation 9ar) as the appropriate alcohol, Example 129 was obtained. HRMS calculated for C$_{41}$H$_{40}$ClFN$_6$O$_6$S: 798.2403. found 799.2458 (M+H).

Example 130 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-{2-[(2-ethoxypyrimidin-4-yl)methoxy]phenyl}propanoic acid Using General Procedure (IIa) and (2-ethoxypyrimidin-4-yl)methanol (Preparation 9ad) as the appropriate alcohol, Example 130 was obtained. HRMS calculated for C$_{39}$H$_{37}$ClFN$_5$O$_6$S: 757.2137. found 758.2212 (M+H).

Example 131 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2,2,2-trifluoroethoxy)pyrimidin-4-yl]methoxy}phenyl)propanoic acid Using General Procedure (IIa) and [2-(2,2,2-trifluoroethoxy)pyrimidin-4-yl]methanol (Preparation 9ai) as the appropriate alcohol, Example 131 was obtained. HRMS calculated for C$_{39}$H$_{34}$ClF$_4$N$_5$O$_6$S: 811.1854. found 812.1956 (M+H).

Example 132 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[1-(2,2,2-trifluoroethyl)-1H-pyrazol-5-yl]methoxy}phenyl)propanoic acid Using General Procedure (IIa) and [1-(2,2,2-trifluoroethyl)-1H-pyrazol-5-yl]methanol (Preparation 9du) as the appropriate alcohol, Example 132 was obtained. HRMS calculated for C$_{38}$H$_{34}$ClF$_4$N$_5$O$_5$S: 783.1905. found 784.1969 (M+H).

Example 133 (2R)-3-{2-[(1-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}propanoic acid Using General Procedure (IIa) and (1-butyl-1H-pyrazol-5-yl)methanol (Preparation 9dd) as the appropriate alcohol, Example 133 was obtained. HRMS calculated for C$_{40}$H$_{41}$ClFN$_5$O$_5$S: 757.2501. found 758.2596 (M+H).

Example 134 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-[2-(pyrazin-2-ylmethoxy)phenyl]propanoic acid Using General Procedure (IIa) and pyrazin-2-ylmethanol as the appropriate alcohol, Example 134 was obtained. HRMS calculated for C$_{37}$H$_{33}$ClFN$_5$O$_5$S: 713.1875. found 714.1931 (M+H).

Example 135 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid Using General Procedure (IIb) and (2-methoxyphenyl)boronic acid as the appropriate boronic acid, Example 135 was obtained. HRMS calculated for C$_{44}$H$_{39}$ClFN$_5$O$_6$S: 819.2294. found 410.6206 (M+2H).

Example 136 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-methylpyridin-4-yl)pyrimidin-4-yl]methoxy}phenyl)propanoic acid Using General Procedure (IIb) and (2-methyl-4-pyridyl)boronic acid as the appropriate boronic acid, Example 136 was obtained. HRMS calculated for C$_{43}$H$_{38}$ClFN$_6$O$_5$S: 804.2297. found 403.1234 (M+2H).

Example 137 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(3-methylpyridin-4-yl)pyrimidin-4-yl]methoxy}phenyl)propanoic acid Using General Procedure (IIb) and (3-methyl-4-pyridyl)boronic acid as the appropriate boronic acid, Example 137 was obtained. HRMS calculated for C$_{43}$H$_{38}$ClFN$_6$O$_5$S: 804.2297. found 403.1237 (M+2H).

Example 138 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(4-methylpyridin-3-yl)pyrimidin-4-yl]methoxy}phenyl)propanoic acid Using General Procedure (IIb) and (4-methyl-3-pyridyl)boronic acid as the appropriate boronic acid, Example 138 was obtained. HRMS calculated for $C_{43}H_{38}ClFN_6O_5S$: 804.2297. found 403.1220 (M+2H).

General Procedure (IIIa)

1.0 eq. of ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[2-(pyrazin-2-ylmethoxy)phenyl]propanoate (Preparation 6b), 2.0 eq. of the appropriate alcohol and 2.0 eq. triphenylphosphine were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents. The obtained intermediate was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

Example 139 (2R)-2-{[(5S$_a$)-5-(3-chloro-2-methyl-4-{[(3R)-1-methylpyrrolidin-3-yl]methoxy}phenyl)-6-(4-fluorophenyl)thieno[2,3-d]pyrimidin-4-yl]oxy}-3-[2-(pyrazin-2-ylmethoxy)phenyl]propanoic acid Using General Procedure (IIIa) and [(3R)-1-methylpyrrolidin-3-yl]methanol as the appropriate alcohol, Example 139 was obtained. HRMS calculated for $C_{39}H_{35}ClFN_5O_5S$: 739.2031. found 740.2136 (M+H).

Example 140 (2R)-2-{[(5S$_a$)-5-(3-chloro-2-methyl-4-{[(3S)-1-methylpyrrolidin-3-yl]methoxy}phenyl)-6-(4-fluorophenyl)thieno[2,3-d]pyrimidin-4-yl]oxy}-3-[2-(pyrazin-2-ylmethoxy)phenyl]propanoic acid Using General Procedure (IIIa) and [(3S)-1-methylpyrrolidin-3-yl]methanol as the appropriate alcohol, Example 140 was obtained. HRMS calculated for $C_{39}H_{35}ClFN_5O_5S$: 739.2031. found 740.2095 (M+H).

Example 141 (2R)-2-{[(5S$_a$)-5-{3-chloro-2-methyl-4-[((3S or R)-1-methylpiperidin-3-yl)oxy]phenyl}-6-(4-fluorophenyl)thieno[2,3-d]pyrimidin-4-yl]oxy}-3-[2-(pyrazin-2-ylmethoxy)phenyl]propanoic acid and Example 142 (2R)-2-{[(5S$_a$)-5-{3-chloro-2-methyl-4-[((3R or S)-1-methylpiperidin-3-yl)oxy]phenyl}-6-(4-fluorophenyl)thieno[2,3-d]pyrimidin-4-yl]oxy}-3-[2-(pyrazin-2-ylmethoxy)phenyl]propanoic acid and Example 143 (2R)-2-{[(5S$_a$)-5-{3-chloro-2-methyl-4-[(1-methylpyrrolidin-2-yl)methoxy]phenyl}-6-(4-fluorophenyl)thieno[2,3-d]pyrimidin-4-yl]oxy}-3-[2-(pyrazin-2-ylmethoxy)phenyl]propanoic acid
(mixture of diastereoisomers)

0.470 g ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[2-(pyrazin-2-ylmethoxy)phenyl]propanoate (Preparation 6b) (0.7 mmol), 0.330 g 1-methylpiperidin-3-ol (2.0 mmol), and 0.524 g triphenyl phosphine (2.0 mmol) were dissolved in 15 mL dry toluene, then 0.461 g ditertbutyl azodicarboxylate (2.0 mmol) was added. The mixture was stirred at 50° C. under nitrogen. During the reaction rearrangement of the methylpiperidine moiety was also observed. When no further conversion was observed, the volatiles were evaporated under reduced pressure, and the constitutional isomers were separated via flash chromatography using DCM and MeOH as eluents. The mixture of compounds eluting earlier were the precursors of Example 141 and 142, while the mixture of compounds eluting later were the precursors of Example 143. The obtained precursor derivatives were separately dissolved in dioxane-water 1:1 (10 mL/mmol) and 10 eq LiOH×H$_2$O was added. The mixtures were stirred at room temperature until no further conversion was observed. Then they were individually diluted with brine, neutralized with 2 M HCl, extracted with DCM. The combined organic phases were dried over Na$_2$SO$_4$, filtered and concentrated under reduced pressure and purified separately via preparative reversed phase chromatography using 25 mM aqueous NH$_4$HCO$_3$ solution and MeCN as eluents to obtain Example 141 [HRMS calculated for $C_{39}H_{35}ClFN_5O_5S$: 739.2031. found 740.2119 (M+H)], Example 142 [HRMS calculated for $C_{39}H_{35}ClFN_5O_5S$: 739.2031. found 740.2088 (M+H)], and Example 143 [HRMS calculated for $C_{39}H_{35}ClFN_5O_5S$: 739.2031. found 740.2101 and 740.2078 (M+H)].

Example 144 (2R)-2-{[(5S$_a$)-5-{3-chloro-2-methyl-4-[(1-methylazepan-3-yl)methoxy]phenyl}-6-(4-fluorophenyl)thieno[2,3-d]pyrimidin-4-yl]oxy}-3-[2-(pyrazin-2-ylmethoxy)phenyl]propanoic acid
(mixture of diastereoisomers)

Using General Procedure (IIIa) and 2-(1-methyl-2-piperidyl)ethanol as the appropriate alcohol in the course of the reaction the ring-expansion of the piperidyl moiety was observed, thus Example 144 was obtained. HRMS calculated for $C_{41}H_{39}ClFN_5O_5S$: 767.2344. found 768.2399 and 768.2398 (M+H).

Example 145 (2R)-2-{[(5S$_a$)-5-{3-chloro-2-methyl-4-[(1-methylpyrrolidin-3-yl)methoxy]phenyl}-6-(4-fluorophenyl)thieno[2,3-d]pyrimidin-4-yl]oxy}-3-[2-(pyrazin-2-ylmethoxy)phenyl]propanoic acid
(mixture of diastereoisomers)

Using General Procedure (IIIa) and (1-methylpyrrolidin-3-yl)methanol as the appropriate alcohol, Example 145 was obtained. HRMS calculated for $C_{39}H_{35}ClFN_5O_5S$: 739.2031. found 740.2081 (M+H).

Example 146 (2R)-2-{[(5S$_a$)-5-{3-chloro-2-methyl-4-[3-(1-methylpyrrolidin-2-yl)propoxy]phenyl}-6-(4-fluorophenyl)thieno[2,3-d]pyrimidin-4-yl]oxy}-3-[2-(pyrazin-2-ylmethoxy)phenyl]propanoic acid
(mixture of diastereoisomers)

Using General Procedure (IIIa) and 2-(1-methyl-3-piperidyl)ethanol as the appropriate alcohol in the course of the reaction the ring-contraction of the piperidyl moiety was observed, thus Example 146 was obtained. HRMS calculated for $C_{41}H_{39}ClFN_5O_5S$: 767.2344. found 768.2454 (M+H).

Example 147 (2R)-2-{[(5S$_a$)-5-{3-chloro-4-[3-(dimethylamino)propoxy]-2-methylphenyl}-6-(4-fluorophenyl)thieno[2,3-d]pyrimidin-4-yl]oxy}-3-[2-(pyrazin-2-ylmethoxy)phenyl]propanoic acid Using General Procedure (IIIa) and 3-(dimethylamino)propan-1-ol as the appropriate alcohol, Example 147 was obtained. HRMS calculated for $C_{38}H_{35}ClFN_5O_5S$: 727.2031. found 728.2085 (M+H).

Example 148 (2R)-2-{[(5S$_a$)-5-{3-chloro-2-methyl-4-[2-(morpholin-4-yl)ethoxy]phenyl}-6-(4-fluorophenyl)thieno[2,3-d]pyrimidin-4-yl]oxy}-3-[2-(pyrazin-2-ylmethoxy)phenyl]propanoic acid Using General Procedure (IIIa) and 2-(morpholin-4-yl)ethanol as the appropriate alcohol, Example 148 was obtained. HRMS calculated for $C_{39}H_{35}ClFN_5O_6S$: 755.1981. found 756.2052 (M+H).

General Procedure (IVa)

Step A:

1 eq. ethyl (2R)-2-[(5S$_a$)-5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-(2-hydroxyphenyl)propanoate (Preparation 8c), 2 eq. of the appropriate alcohol and 2 eq. triphenyl phosphine were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:

The obtained intermediate was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

Example 149 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-methoxyphenyl)propanoic acid Using General Procedure (IVa) and methanol as the appropriate alcohol, Example 149 was obtained. HRMS calculated for $C_{34}H_{34}ClFN_4O_6S$: 680.1872. found 681.1947 (M+H).

Example 150 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2R)-tetrahydrofuran-2-ylmethoxy]phenyl}propanoic acid Using General Procedure (IVa) and [(2R)-tetrahydrofuran-2-yl]methanol as the appropriate alcohol, Example 150 was obtained. HRMS calculated for $C_{38}H_{40}ClFN_4O_7S$: 750.2290. found 751.2375 (M+H).

Example 151 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[2-(methylamino)-2-oxoethoxy]phenyl}propanoic acid Using General Procedure (IVa) and 2-hydroxy-N-methyl-acetamide as the appropriate alcohol, Example 151 was obtained. HRMS calculated for $C_{36}H_{37}ClFN_5O_7S$: 737.2086. found 738.2195 (M+H).

Example 152 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[2-(cyclopentylamino)-2-oxoethoxy]phenyl}propanoic acid Using General Procedure (IVa) and N-cyclopentyl-2-hydroxy-acetamide as the appropriate alcohol, Example 152 was obtained. HRMS calculated for $C_{40}H_{43}ClFN_5O_7S$: 791.2556. found 792.2658 (M+H).

Example 153 (2R)-3-{2-[2-(benzylamino)-2-oxoethoxy]phenyl}-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}propanoic acid Using General Procedure (IVa) and N-benzyl-2-hydroxy-acetamide as the appropriate alcohol, Example 153 was obtained. HRMS calculated for $C_{42}H_{41}ClFN_5O_7S$: 813.2399. found 814.2492 (M+H).

Example 154 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[2-oxo-2-(propylamino)ethoxy]phenyl}propanoic acid Using General Procedure (IVa) and 2-hydroxy-N-propyl-acetamide as the appropriate alcohol, Example 154 was obtained. HRMS calculated for $C_{38}H_{41}ClFN_5O_7S$: 765.2399. found 766.2459 (M+H).

Example 155 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{2-oxo-2-[(2-phenylethyl)amino]ethoxy}phenyl)propanoic acid Using General Procedure (IVa) and 2-hydroxy-N-2-phenylethyl-acetamide as the appropriate alcohol, Example 155 was obtained. HRMS calculated for $C_{43}H_{43}ClFN_5O_7S$: 827.2556. found 828.2580 (M+H).

Example 156 (2R)-3-{2-[2-(butylamino)-2-oxoethoxy]phenyl}-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}propanoic acid Using General Procedure (IVa) and N-butyl-2-hydroxy-acetamide as the appropriate alcohol, Example 156 was obtained. HRMS calculated for $C_{39}H_{43}ClFN_5O_7S$: 779.2556. found 780.2614 (M+H).

Example 157 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{2-[(2-methoxyethyl)amino]-2-oxoethoxy}phenyl)propanoic acid Using General Procedure (IVa) and 2-hydroxy-N-(2-methoxyethyl)acetamide as the appropriate alcohol, Example 157 was obtained. HRMS calculated for C$_{38}$H$_{41}$ClFN$_5$O$_8$S: 781.2348. found 782.2478 (M+H).

Example 158 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(2,2,2-trifluoroethoxy)phenyl]propanoic acid Step A:

209 mg ethyl (2R)-2-[(5S$_a$)-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-hydroxyphenyl)propanoate (Preparation 8c) (0.3 mmol) and 138 mg K$_2$CO$_3$ (1.0 mmol) were dissolved in 2 mL DMF, then 232 mg 2,2,2-trifluoroethyl trifluoromethanesulfonate (1.0 mmol) was added. The mixture was stirred at room temperature under nitrogen until no further conversion was observed. Then it was diluted with brine, neutralized with 2 M HCl, extracted with DCM. The combined organic phases were dried over Na$_2$SO$_4$, filtered and concentrated under reduced pressure.

Step B:

The obtained intermediate was dissolved in 8 mL dioxane-water 1:1 and 150 mg LiOH×H$_2$O (3.57 mmol) was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 5 mM aqueous NH$_4$HCO$_3$ solution and MeCN as eluents to obtain Example 158. HRMS calculated for C$_{35}$H$_{33}$ClF$_4$N$_4$O$_6$S: 748.1745. found 749.1819 (M+H).

Example 159 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[4-(trifluoromethyl)pyridin-2-yl]methoxy}phenyl)propanoic acid Using General Procedure (IVa) and [4-(trifluoromethyl)-2-pyridyl]methanol as the appropriate alcohol, Example 159 was obtained. HRMS calculated for C$_{40}$H$_{36}$ClF$_4$N$_5$O$_6$S: 825.2011. found 413.6085 (M+2H).

Example 160 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-methoxy-6-methylpyrimidin-4-yl)methoxy]phenyl}propanoic acid Using General Procedure (IVa) and (2-methoxy-6-methyl-pyrimidin-4-yl)methanol (Preparation 9cf) as the appropriate alcohol, Example 160 was obtained. HRMS calculated for C$_{40}$H$_{40}$ClFN$_6$O$_7$S: 802.2352. found 402.1241 (M+2H).

Example 161 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(6-methylpyrimidin-4-yl)methoxy]phenyl}propanoic acid Using General Procedure (IVa) and (6-methylpyrimidin-4-yl)methanol as the appropriate alcohol, Example 161 was obtained. HRMS calculated for C$_{39}$H$_{38}$ClFN$_6$O$_6$S: 772.2246. found 387.1188 (M+2H).

Example 162 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(6-methoxypyrimidin-4-yl)methoxy]phenyl}propanoic acid Using General Procedure (IVa) and (6-methoxypyrimidin-4-yl)methanol (Preparation 9ce) as the appropriate alcohol, Example 162 was obtained. HRMS calculated for C$_{39}$H$_{38}$ClFN$_6$O$_7$S: 788.2195. found 395.1165 (M+2H).

Example 163 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(5-fluoropyridin-2-yl)methoxy]phenyl}propanoic acid Using General Procedure (IVa) and (5-fluoro-2-pyridyl)methanol as the appropriate alcohol, Example 163 was obtained. HRMS calculated for C$_{39}$H$_{36}$ClF$_2$N$_5$O$_6$S: 775.2043. found 776.2161 (M+H).

Example 164 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[6-(trifluoromethyl)pyridin-2-yl]methoxy}phenyl)propanoic acid Using General Procedure (IVa) and [6-(trifluoromethyl)-2-pyridyl]methanol as the appropriate alcohol, Example 164 was obtained. HRMS calculated for C$_{40}$H$_{36}$ClF$_4$N$_5$O$_6$S: 825.2011. found 826.2100 (M+H).

Example 165 (2R)-2-{[(5R$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(pyridin-2-ylmethoxy)phenyl]propanoic acid and

Example 166 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(pyridin-2-ylmethoxy)phenyl]propanoic acid Step A:

591 mg 4-chloro-5-[3-chloro-2-methyl-4-[2-(4-methylpiperazin-1-yl)ethoxy]phenyl]-6-iodo-thieno[2,3-d]pyrimidine (Preparation 13) (1.05 mmol), 915 mg ethyl (2R)-2-hydroxy-3-[2-(2-pyridylmethoxy)phenyl]propanoate (Preparation 3bn) (1.045 mmol) and 977 mg Cs$_2$CO$_3$ (3.0 mmol) were placed in a flask. 10 mL tert-butanol was added and the mixture was stirred at 60° C. until no further conversion was observed. Then it was diluted with brine and extracted with dichloromethane. The combined organic phases were dried over Na$_2$SO$_4$, filtered and concentrated under reduced pressure and purified via preparative reversed phase chromatography using 5 mM aqueous $NH_4HCO_3$ solution and MeCN as eluents to obtain ethyl (2R)-2-[5-[3-chloro-2-methyl-4-[2-(4-methylpiperazin-1-yl)ethoxy]phenyl]-6-iodo-thieno[2,3-d]pyrimidin-4-yl]oxy-3-[2-(2-pyridylmethoxy)phenyl]propanoate as a mixture of diastereoisomers. MS: (M+H)=828.0.

Step B:

518 mg ethyl (2R)-2-[5-[3-chloro-2-methyl-4-[2-(4-methylpiperazin-1-yl)ethoxy]phenyl]-6-iodo-thieno[2,3-d]pyrimidin-4-yl]oxy-3-[2-(2-pyridylmethoxy)phenyl]propanoate (0.625 mmol) and 565 mg 2-(5-fluoro-2-furyl)-4,4,5,5-tetramethyl-1,3,2-dioxaborolane (2.66 mmol) were dissolved in 5 ml 1,4-dioxane, then 407 mg $Cs_2CO_3$ (1.25 mmol) dissolved in 1 mL water was added. Then 46 mg $PdCl_2 \times dppf$ (0.0625 mmol) was added. The mixture was heated at 100° C. via microwave irradiation until no further conversion was observed. Then it was diluted with brine, extracted with DCM. The combined organic phases were dried over $Na_2SO_4$, filtered and concentrated under reduced pressure and purified via preparative reversed phase chromatography using 5 mM aqueous $NH_4HCO_3$ solution and MeCN as eluents.

Step C:

The obtained intermediate was dissolved in 10 mL dioxane-water 1:1 (10 mL/mmol) and 200 mg $LiOH \times H_2O$ (4.77 mmol) was added. The mixture was stirred at room temperature until no further conversion was observed. Then it was diluted with brine, neutralized with 2 M HCl, extracted with DCM, dried over $Na_2SO_4$, filtered and concentrated under reduced pressure and purified via preparative reversed phase chromatography using 5 mM aqueous $NH_4HCO_3$ solution and MeCN as eluents. The diastereoisomer eluting earlier was collected as Example 165. HRMS calculated for $C_{39}H_{37}ClFN_5O_6S$: 757.2137. found 379.6156 (M+2H). The diastereoisomer eluting later was collected as Example 166. HRMS calculated for $C_{39}H_{37}ClFN_5O_6S$: 757.2137. found 379.6159 (M+2H).

Example 167 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(trifluoromethyl)pyridin-4-yl]methoxy}phenyl)propanoic acid Using General Procedure (IVa) and [2-(trifluoromethyl)-4-pyridyl]methanol as the appropriate alcohol, Example 167 was obtained. HRMS calculated for $C_{40}H_{36}ClF_4N_5O_6S$: 825.2011. found 826.2124 (M+H).

Example 168 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-methoxypyridin-4-yl)methoxy]phenyl}propanoic acid Using General Procedure (IVa) and (2-methoxy-4-pyridyl)methanol as the appropriate alcohol, Example 168 was obtained. HRMS calculated for $C_{40}H_{39}ClFN_5O_7S$: 787.2243. found 394.6210 (M+2H).

Example 169 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(trifluoromethyl)pyrimidin-4-yl]methoxy}phenyl)propanoic acid Using General Procedure (IVa) and [2-(trifluoromethyl)pyrimidin-4-yl]methanol (Preparation 9bj) as the appropriate alcohol, Example 169 was obtained. HRMS calculated for $C_{39}H_{35}ClF_4N_6O_6S$: 826.1963. found 827.2059 (M+H).

Example 170 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-cyclopropylpyrimidin-4-yl)methoxy]phenyl}propanoic acid Using General Procedure (IVa) and (2-cyclopropylpyrimidin-4-yl)methanol (Preparation 9be) as the appropriate alcohol, Example 170 was obtained. HRMS calculated for $C_{41}H_{40}ClFN_6O_6S$: 798.2403. found 400.1265 (M+2H).

Example 171 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(thiophen-2-yl)pyrimidin-4-yl]methoxy}phenyl)propanoic acid Using General Procedure (IVa) and [2-(2-thienyl)pyrimidin-4-yl]methanol (Preparation 9bv) as the appropriate alcohol, Example 171 was obtained. HRMS calculated for $C_{42}H_{38}ClFN_6O_6S_2$: 840.1967. found 421.1070 (M+2H).

Example 172 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(pyridin-4-yl)pyrimidin-4-yl]methoxy}phenyl)propanoic acid Using General Procedure (IVa) and [2-(4-pyridyl)pyrimidin-4-yl]methanol (Preparation 9bs) as the appropriate alcohol, Example 172 was obtained. HRMS calculated for $C_{43}H_{39}ClFN_7O_6S$: 835.2355. found 418.6246 (M+2H).

Example 173 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(thiophen-3-yl)pyrimidin-4-yl]methoxy}phenyl)propanoic acid Using General Procedure (IVa) and [2-(3-thienyl)pyrimidin-4-yl]methanol (Preparation 9bu) as the appropriate alcohol, Example 173 was obtained. HRMS calculated for $C_{42}H_{38}ClFN_6O_6S_2$: 840.1967. found 841.2059 (M+H).

Example 174 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(2-methoxyethyl)pyrimidin-4-yl]methoxy}phenyl)propanoic acid Using General Procedure (IVa) and [2-(2-methoxyethyl)pyrimidin-4-yl]methanol (Preparation 9bl) as the appropriate alcohol, Example 174 was obtained. HRMS calculated for $C_{41}H_{42}ClFN_6O_7S$: 816.2508. found 409.1335 (M+2H).

Example 175 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(morpholin-4-yl)pyrimidin-4-yl]methoxy}phenyl)propanoic acid Using General Procedure (IVa) and (2-(morpholin-4-yl)pyrimidin-4-yl)methanol (Preparation 9ar) as the appropriate alcohol, Example 175 was obtained. HRMS calculated for $C_{42}H_{43}ClFN_7O_7S$: 843.2617. found 422.6360 (M+2H).

Example 176 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-methoxypyrimidin-4-yl)methoxy]phenyl}propanoic acid Using General Procedure (IVa) and (2-methoxypyrimidin-4-yl)methanol as the appropriate alcohol, Example 176 was obtained. HRMS calculated for $C_{39}H_{38}N_6O_7FSCl$: 788.2195. found 789.2289 (M+H).

Example 177 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-ethoxypyrimidin-4-yl)methoxy]phenyl}propanoic acid Using General Procedure (IVa) and (2-ethoxypyrimidin-4-yl)methanol (Preparation 9ad) as the appropriate alcohol, Example 177 was obtained. HRMS calculated for $C_{40}H_{40}ClFN_6O_7S$: 802.2352. found 402.1255 (M+2H).

Example 178 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(2,2,2-trifluoroethoxy)pyrimidin-4-yl]methoxy}phenyl)propanoic acid Using General Procedure (IVa) and [2-(2,2,2-trifluoroethoxy)pyrimidin-4-yl]methanol (Preparation 9ai) as the appropriate alcohol, Example 178 was obtained. HRMS calculated for $C_{40}H_{37}ClF_4N_6O_7S$: 856.2069. found 857.2110 (M+H).

Example 179 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(pyrimidin-4-ylmethoxy)phenyl]propanoic acid Using General Procedure (IVa) and pyrimidin-4-ylmethanol as the appropriate alcohol, Example 179 was obtained. HRMS calculated for $C_{38}H_{36}ClFN_6O_6S$: 758.2090. found 759.2166 (M+H).

Example 180 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(1-methyl-1H-pyrazol-5-yl)methoxy]phenyl}propanoic acid Using General Procedure (IVa) and (1-methyl-1H-pyrazol-5-yl)methanol as the appropriate alcohol, Example 180 was obtained. HRMS calculated for $C_{38}H_{38}ClFN_6O_6S$: 760.2246. found 761.2343 (M+H).

Example 181 (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}propanoic acid Using General Procedure (IVa) and (1-tert-butyl-1H-pyrazol-5-yl)methanol (Preparation 9dt) as the appropriate alcohol, Example 181 was obtained. HRMS calculated for $C_{41}H_{44}ClFN_6O_6S$: 802.2716. found 402.1422 (M+2H).

Example 182 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(propan-2-yl)-1H-pyrazol-5-yl]methoxy}phenyl)propanoic acid Using General Procedure (IVa) and [1-(propan-2-yl)-1H-pyrazol-5-yl]methanol (Preparation 9dc) as the appropriate alcohol, Example 182 was obtained. HRMS calculated for $C_{40}H_{42}ClFN_6O_6S$: 788.2559. found 789.2663 (M+H).

Example 183 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(1-cyclopentyl-1H-pyrazol-5-yl)methoxy]phenyl}propanoic acid Using General Procedure (IVa) and (1-cyclopentyl-1H-pyrazol-5-yl)methanol (Preparation 9dg) as the appropriate alcohol, Example 183 was obtained. HRMS calculated for $C_{42}H_{44}ClFN_6O_6S$: 814.2716. found 815.2796 (M+H).

Example 184 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(1-ethyl-1H-pyrazol-5-yl)methoxy]phenyl}propanoic acid Using General Procedure (IVa) and (1-ethyl-1H-pyrazol-5-yl)methanol (Preparation 9da) as the appropriate alcohol, Example 184 was obtained. HRMS calculated for $C_{39}H_{40}ClFN_6O_6S$: 774.2403. found 388.1265 (M+2H).

Example 185 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid Using General Procedure (IVa) and [1-(2,2,2-trifluoroethyl)-1H-pyrazol-5-yl]methanol (Preparation 9du) as the appropriate alcohol, Example 185 was obtained. HRMS calculated for $C_{39}H_{37}ClF_4N_6O_6S$: 828.2120. found 415.1131 (M+2H).

Example 186 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(cyclopropylmethyl)-1H-pyrazol-5-yl]methoxy}phenyl)propanoic acid Using General Procedure (IVa) and [1-(cyclopropylmethyl)-1H-pyrazol-5-yl]methanol (Preparation 9df) as the appropriate alcohol, Example 186 was obtained. HRMS calculated for $C_{41}H_{42}ClFN_6O_6S$: 800.2559. found 401.1355 (M+2H).

Example 187 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(1-propyl-1H-pyrazol-5-yl)methoxy]phenyl}propanoic acid Using General Procedure (IVa) and (1-propyl-1H-pyrazol-5-yl)methanol (Preparation 9 db) as the appropriate alcohol, Example 187 was obtained. HRMS calculated for $C_{40}H_{42}ClFN_6O_6S$: 788.2559. found 395.1357 (M+2H).

Example 188 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}propanoic acid Using General Procedure (IVa) and (1-butyl-1H-pyrazol-5-yl)methanol (Preparation 9dd) as the appropriate alcohol, Example 188 was obtained. HRMS calculated for $C_{41}H_{44}ClFN_6O_6S$: 802.2716. found 402.1447 (M+2H).

Example 189 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(pyrazin-2-ylmethoxy)phenyl]propanoic acid Using General Procedure (IVa) and pyrazin-2-ylmethanol as the appropriate alcohol, Example 189 was obtained. HRMS calculated for $C_{38}H_{36}ClFN_6O_6S$: 758.2090. found 759.2159 (M+H).

Example 190 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(pyrimidin-5-ylmethoxy)phenyl]propanoic acid Using General Procedure (IVa) and pyrimidin-5-ylmethanol as the appropriate alcohol, Example 190 was obtained. HRMS calculated for $C_{38}H_{36}ClFN_6O_6S$: 758.2090. found 759.2198 (M+H).

Example 191 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(1,3-oxazol-4-ylmethoxy)phenyl]propanoic acid Using General Procedure (IVa) and 1,3-oxazol-4-ylmethanol as the appropriate alcohol, Example 191 was obtained. HRMS calculated for $C_{37}H_{35}ClFN_5O_7S$: 747.1930. found 748.1970 (M+H).

Example 192 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[2-(dimethylamino)ethoxy]phenyl}propanoic acid Using General Procedure (IVa) and 2-(dimethylamino)ethanol as the appropriate alcohol Example 192 was obtained. HRMS calculated for $C_{37}H_{41}ClFN_5O_6S$: 737.2450. found 369.6277 (M+2H).

Example 193 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(2-hydroxyethoxy)phenyl]propanoic acid Using General Procedure (IVa) and ethylene glycol as the appropriate alcohol, Example 193 was obtained. HRMS calculated for $C_{35}H_{36}ClFN_4O_7S$: 710.1977. found 711.2037 (M+H).

Example 194 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[2-(2-methoxyethoxy)phenyl]propanoic acid Using General Procedure (IVa) and 2-methoxyethanol as the appropriate alcohol, Example 194 was obtained. HRMS calculated for $C_{36}H_{38}ClFN_4O_7S$: 724.2134. found 725.2224 (M+H).

Example 195 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[2-(2-hydroxyethoxy)ethoxy]phenyl}propanoic acid Using General Procedure (IVa) and 2-(2-hydroxyethoxy)ethanol as the appropriate alcohol, Example 195 was obtained. HRMS calculated for $C_{37}H_{40}ClFN_4O_8S$: 754.2239. found 755.2279 (M+H).

Example 196 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[2-(2-methoxyethoxy)ethoxy]phenyl}propanoic acid Using General Procedure (IVa) and 2-(2-methoxyethoxy)ethanol as the appropriate alcohol, Example 196 was obtained. HRMS calculated for $C_{38}H_{42}ClFN_4O_8S$: 768.2396. found 769.2481 (M+H).

Example 197 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{2-[2-(2-methoxyethoxy)ethoxy]ethoxy}phenyl)propanoic acid Using General Procedure (IVa) and 2-[2-(2-methoxyethoxy)ethoxy]ethanol as the appropriate alcohol, Example 197 was obtained. HRMS calculated for $C_{40}H_{46}ClFN_4O_9S$: 812.2658. found 407.1384 (M+2H).

Example 198 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(3-methylpyridin-4-yl)pyrimidin-4-yl]methoxy}phenyl)propanoic acid Step A:
417 mg ethyl (2R)-2-[(5S$_a$)-5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-[2-[(2-methylsulfanylpyrimidin-4-yl)methoxy]phenyl]propanoate (Preparation 10c) (0.5 mmol), 205 mg (3-methyl-4-pyridyl)boronic acid (1.5 mmol) and 286 mg copper(I) thiophenecarboxylate (1.5 mmol) were dissolved in 5 mL dry THF, then 58 mg Pd(PPh$_3$)$_4$ (0.05 mmol) was added. The mixture was stirred at 70° C. under nitrogen until no further conversion was observed. Then it was concentrated under reduced pressure and the crude intermediate was purified via flash chromatography using DCM and MeOH as eluents.

Step B:
The obtained intermediate was dissolved in 3 mL methanol and 150 mg NaOH (3.75 mmol) was added. The mixture was stirred at room temperature until no further conversion was observed. Then it was diluted with brine, neutralized with 2 M HCl, extracted with DCM. The combined organic phases were dried over $Na_2SO_4$, filtered and concentrated under reduced pressure and purified via preparative reversed phase chromatography using 5 mM aqueous $NH_4HCO_3$ solution and MeCN as eluents to obtain Example 198. HRMS calculated for $C_{44}H_{41}ClFN_7O_6S$: 849.2512. found 425.6338 (M+2H).

General Procedure (Va)

Step A:

1 eq. ethyl (2R)-2-[(5S$_a$)-5-[3-chloro-4-(2-dimethylaminoethyloxy)-2-methyl-phenyl]-6-(5-fluoro-2-furyl)thieno[2,3-d]pyrimidin-4-yl]oxy-3-(2-hydroxyphenyl)propanoate (Preparation 8d), 2 eq. of the appropriate alcohol and 2 eq. triphenyl phosphine were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:

The obtained intermediate was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, extracted with dichloromethane. The combined organic phases were dried over $Na_2SO_4$, filtered and concentrated under reduced pressure and purified via preparative reversed phase chromatography using 25 mM aqueous $NH_4HCO_3$ solution and MeCN as eluents.

Example 199 (2R)-2-{[(5S$_a$)-5-{3-chloro-4-[2-(dimethylamino)ethoxy]-2-methylphenyl}-6-(5-fluoro-furan-2-yl)thieno[2,3-d]pyrimidin-4-yl]oxy}-3-(2-methoxyphenyl)propanoic acid Using General Procedure (Va) and methanol as the appropriate alcohol, Example 199 was obtained. HRMS calculated for $C_{31}H_{29}ClFN_3O_6S$: 625.1450. found 626.1509 (M+H).

Example 200 (2R)-2-{[(5S$_a$)-5-{3-chloro-4-[2-(dimethylamino)ethoxy]-2-methylphenyl}-6-(5-fluoro-furan-2-yl)thieno[2,3-d]pyrimidin-4-yl]oxy}-3-[2-(2,2,2-trifluoroethoxy)phenyl]propanoic acid Step A:

192 mg (2R)-2-[(5S$_a$)-5-[3-chloro-4-(2-dimethylaminoethyloxy)-2-methyl-phenyl]-6-(5-fluoro-2-furyl)thieno[2,3-d]pyrimidin-4-yl]oxy-3-(2-hydroxyphenyl)propanoate (Preparation 8d) (0.3 mmol) and 138 mg $K_2CO_3$ (1.0 mmol) were dissolved in 2 mL DMF, then 232 mg 2,2,2-trifluoroethyl trifluoromethanesulfonate (1.0 mmol) was added. The mixture was stirred at room temperature under nitrogen until no further conversion was observed. Then it was diluted with brine, neutralized with 2 M HCl, extracted with DCM, dried over $Na_2SO_4$, filtered and concentrated under reduced pressure.

Step B:

The obtained intermediate was dissolved in 8 mL dioxane-water 1:1 and 150 mg LiOH×H$_2$O (3.57 mmol) was added. The mixture was stirred at room temperature until no further conversion was observed. Then it was diluted with brine, neutralized with 2 M HCl, extracted with DCM. The combined organic phases were dried over $Na_2SO_4$, filtered and concentrated under reduced pressure and purified via preparative reversed phase chromatography using 5 mM aqueous $NH_4HCO_3$ solution and MeCN as eluents to obtain Example 200. HRMS calculated for $C_{32}H_{28}ClF_4N_3O_6S$: 693.1323. found 694.1382 (M+H).

Example 201 (2R)-2-{[(5S$_a$)-5-{3-chloro-4-[2-(dimethylamino)ethoxy]-2-methylphenyl}-6-(5-fluoro-furan-2-yl)thieno[2,3-d]pyrimidin-4-yl]oxy}-3-(2-{[2-(trifluoromethyl)pyrimidin-4-yl]methoxy}phenyl)propanoic acid Using General Procedure (Va) and [2-(trifluoromethyl)pyrimidin-4-yl]methanol (Preparation 9bj) as the appropriate alcohol Example 201 was obtained. HRMS calculated for $C_{36}H_{30}ClF_4N_5O_6S$: 771.1541. found 772.1604 (M+H).

Example 202 (2R)-2-{[(5S$_a$)-5-{3-chloro-4-[2-(dimethylamino)ethoxy]-2-methylphenyl}-6-(5-fluoro-furan-2-yl)thieno[2,3-d]pyrimidin-4-yl]oxy}-3-(2-{[2-(morpholin-4-yl)pyrimidin-4-yl]methoxy}phenyl) propanoic acid Using General Procedure (Va) and (2-(morpholin-4-yl)pyrimidin-4-yl)methanol (Preparation 9ar) as the appropriate alcohol Example 202 was obtained. HRMS calculated for $C_{39}H_{38}ClFN_6O_7S$: 788.2195. found 395.1179 (M+2H).

Example 203 (2R)-2-{[(5S$_a$)-5-{3-chloro-4-[2-(dimethylamino)ethoxy]-2-methylphenyl}-6-(5-fluoro-furan-2-yl)thieno[2,3-d]pyrimidin-4-yl]oxy}-3-(2-{[2-(2,2,2-trifluoroethoxy)pyrimidin-4-yl]methoxy}phenyl)propanoic acid Using General Procedure (Va) and [2-(2,2,2-trifluoroethoxy)pyrimidin-4-yl]methanol (Preparation 9ai) as the appropriate alcohol Example 203 was obtained. HRMS calculated for $C_{37}H_{32}ClF_4N_5O_7S$: 801.1647. found 802.1706 (M+H).

Example 204 (2R)-2-{[(5S$_a$)-5-{3-chloro-4-[2-(dimethylamino)ethoxy]-2-methylphenyl}-6-(5-fluoro-furan-2-yl)thieno[2,3-d]pyrimidin-4-yl]oxy}-3-{2-[(1-ethyl-1H-pyrazol-5-yl)methoxy]phenyl}propanoic acid Using General Procedure (Va) and (1-ethyl-1H-pyrazol-5-yl)methanol (Preparation 9da) as the appropriate alcohol Example 204 was obtained. HRMS calculated for $C_{36}H_{35}ClFN_5O_6S$: 719.1981. found 720.2064 (M+H).

Example 205 (2R)-2-{[(5S$_a$)-5-{3-chloro-4-[2-(dimethylamino)ethoxy]-2-methylphenyl}-6-(5-fluoro-furan-2-yl)thieno[2,3-d]pyrimidin-4-yl]oxy}-3-(2-{[1-(2,2,2-trifluoroethyl)-1H-pyrazol-5-yl]methoxy}phenyl)propanoic acid Using General Procedure (Va) and [1-(2,2,2-trifluoroethyl)-1H-pyrazol-5-yl]methanol (Preparation 9du) as the appropriate alcohol Example 205 was obtained. HRMS calculated for $C_{36}H_{32}ClF_4N_5O_6S$: 773.1698. found 774.1771 (M+H).

Example 206 (2R)-2-{[(5S$_a$)-5-{3-chloro-4-[2-(dimethylamino)ethoxy]-2-methylphenyl}-6-(5-fluoro-furan-2-yl)thieno[2,3-d]pyrimidin-4-yl]oxy}-3-[2-(pyrazin-2-ylmethoxy)phenyl]propanoic acid Using General Procedure (Va) and pyrazin-2-ylmethanol as the appropriate alcohol Example 206 was obtained. HRMS calculated for $C_{35}H_{31}ClFN_5O_6S$: 703.1668. found 704.1726 (M+H).

General Procedure (VIa)

Step A:

1 eq. ethyl (2R)-2-[(5S$_a$)-5-[3-chloro-2-methyl-4-[2-(4-methylpiperazin-1-yl)ethoxy] phenyl]-6-(2-furyl)thieno[2,3-d]pyrimidin-4-yl]oxy-3-(2-hydroxyphenyl)propanoate (Preparation 8e), 2 eq. of the appropriate alcohol and 2 eq. triphenylphosphine were dissolved in dry toluene (0.2 M for the phenol), then 2 eq. ditertbutyl azodicarboxylate was added. The mixture was stirred at 50° C. under nitrogen until no further conversion was observed. Then it was concentrated under reduced pressure and the crude intermediate was purified via flash chromatography using EtOAc and MeOH as eluents.

Step B:

The obtained intermediate was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

Example 207 (2R)-2-{[-[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-hydroxyphenyl)propanoic acid Ethyl (2R)-2-[(5S$_a$)-5-[3-chloro-2-methyl-4-[2-(4-methylpiperazin-1-yl)ethoxy]phenyl]-6-(2-furyl)thieno[2,3-d]pyrimidin-4-yl]oxy-3-(2-hydroxyphenyl)propanoate (Preparation 8e) was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents to obtain Example 207. HRMS calculated for C$_{33}$H$_{33}$ClN$_4$O$_6$S: 648.1809. found 649.1862 (M+H).

Example 208 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1R)-1-(pyridin-4-yl)ethoxy]phenyl}propanoic acid Using General Procedure (VIa) and (1R)-1-(4-pyridyl)ethanol as the appropriate alcohol, Example 208 was obtained. HRMS calculated for C$_{40}$H$_{40}$ClN$_5$O$_6$S: 753.2388. found 377.6276 (M+2H).

Example 209 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-methoxyphenyl)propanoic acid Using General Procedure (VIa) and methanol as the appropriate alcohol, Example 209 was obtained. HRMS calculated for C$_{34}$H$_{35}$ClN$_4$O$_6$S: 662.1966. found 663.2028 (M+H).

Example 210 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(propan-2-yloxy)phenyl]propanoic acid Using General Procedure (VIa) and 2-propanol as the appropriate alcohol, Example 210 was obtained. HRMS calculated for C$_{36}$H$_{39}$ClN$_4$O$_6$S: 690.2279. found 691.2344 (M+H).

Example 211 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2R)-tetrahydrofuran-2-ylmethoxy]phenyl}propanoic acid Using General Procedure (VIa) and [(2R)-tetrahydrofuran-2-yl]methanol as the appropriate alcohol, Example 211 was obtained. HRMS calculated for C$_{38}$H$_{41}$ClN$_4$O$_7$S: 732.2384. found 733.2453 (M+H).

Example 212 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(cyclopentyloxy)phenyl]propanoic acid Using General Procedure (VIa) and cyclopentanol as the appropriate alcohol, Example 212 was obtained. HRMS calculated for C$_{38}$H$_{41}$ClN$_4$O$_6$S: 716.2435. found 717.2481 (M+H).

Example 213 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(5,6,7,8-tetrahydroquinolin-8-yloxy)phenyl]propanoic acid Using General Procedure (VIa) and 5,6,7,8-tetrahydroquinolin-8-ol as the appropriate alcohol, Example 213 was obtained as mixture of the diastereoisomers. HRMS calculated for C$_{42}$H$_{42}$ClN$_5$O$_6$S: 779.2544. found 390.6369 (M+2H) and 390.6355 (M+2H).

Example 214 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-methylpyrrolidin-3-yl)oxy]phenyl}propanoic acid Using General Procedure (VIa) and 1-methylpyrrolidin-3-ol as the appropriate alcohol, Example 214 was obtained as mixture of the diastereoisomers. HRMS calculated for C$_{38}$H$_{42}$ClN$_5$O$_6$S: 731.2544. found 366.6362 (M+2H) and 366.6354 (M+2H).

Example 215 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-ethoxyphenyl)propanoic acid Using General Procedure (VIa) and ethanol as the appropriate alcohol, Example 215 was obtained. HRMS calculated for C$_{35}$H$_{37}$ClN$_4$O$_6$S: 676.2122. found 677.2216 (M+H).

Example 216 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(prop-2-yn-1-yloxy)phenyl]propanoic acid Using General Procedure (VIa) and prop-2-yn-1-ol as the appropriate alcohol, Example 216 was obtained. HRMS calculated for $C_{36}H_{35}ClN_4O_6S$: 686.1966. found 687.2056 (M+H).

Example 217 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[2-(dimethylamino)-2-oxoethoxy]phenyl}propanoic acid Using General Procedure (VIa) and 2-hydroxy-N,N-dimethyl-acetamide as the appropriate alcohol, Example 217 was obtained. HRMS calculated for $C_{37}H_{40}ClN_5O_7S$: 733.2337. found 734.2407 (M+H).

Example 218 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[2-(methylamino)-2-oxoethoxy]phenyl}propanoic acid Using General Procedure (VIa) and 2-hydroxy-N-methyl-acetamide as the appropriate alcohol, Example 218 was obtained. HRMS calculated for $C_{36}H_{38}ClN_5O_7S$: 719.2180. found 720.2263 (M+H).

Example 219 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[2-oxo-2-(phenylamino)ethoxy]phenyl}propanoic acid Using General Procedure (VIa) and 2-hydroxy-N-phenyl-acetamide as the appropriate alcohol, Example 219 was obtained. HRMS calculated for $C_{41}H_{40}ClN_5O_7S$: 781.2337. found 391.6225 (M+2H).

Example 220 (2R)-3-{2-[2-(butylamino)-2-oxoethoxy]phenyl}-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Using General Procedure (VIa) and N-butyl-2-hydroxy-acetamide as the appropriate alcohol, Example 220 was obtained. HRMS calculated for $C_{39}H_{44}ClN_5O_7S$: 761.2650. found 762.2703 (M+H).

Example 221 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(2,2,2-trifluoroethoxy)phenyl]propanoic acid Step A:

677 mg ethyl (2R)-2-[(5S$_a$)-5-[3-chloro-2-methyl-4-[2-(4-methylpiperazin-1-yl)ethoxy]phenyl]-6-(2-furyl)thieno[2,3-d]pyrimidin-4-yl]oxy-3-(2-hydroxyphenyl)propanoate (Preparation 8e) (1 mmol) and 276 mg $K_2CO_3$ (2.0 mmol) were dissolved in 5 mL DMF, then 141 μL 2,2,2-trifluoroethyl trifluoromethanesulfonate (1.2 mmol) was added. The mixture was stirred at room temperature under nitrogen until no further conversion was observed. Then it was diluted with brine, neutralized with 2 M HCl, extracted with dichloromethane, and the combined organic phases were dried over $Na_2SO_4$, filtered and concentrated under reduced pressure.

Step B:

The obtained intermediate was dissolved in 10 mL dioxane-water 1:1 and 420 mg LiOH×H$_2$O (10.0 mmol) was added. The mixture was stirred at room temperature until no further conversion was observed. Then it was diluted with brine, neutralized with 2 M HCl, extracted with dichloromethane, the combined organic phases were dried over $Na_2SO_4$, filtered and concentrated under reduced pressure and purified via preparative reversed phase chromatography using 25 mM aqueous $NH_4HCO_3$ solution and MeCN as eluents to obtain Example 207. HRMS calculated for $C_{35}H_{34}ClF_3N_4O_6S$: 730.1840. found 731.1875 (M+H).

Example 222 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(4-chloropyridin-2-yl)methoxy]phenyl}propanoic acid Using General Procedure (VIa) and (4-chloro-2-pyridyl)methanol as the appropriate alcohol, Example 222 was obtained. HRMS calculated for $C_{39}H_{37}Cl_2N_5O_6S$: 773.1842. found 387.6008 (M+2H).

Example 223 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(4-methoxypyridin-2-yl)methoxy]phenyl}propanoic acid Using General Procedure (VIa) and (4-methoxy-2-pyridyl)methanol as the appropriate alcohol, Example 223 was obtained. HRMS calculated for $C_{40}H_{40}ClN_5O_7S$: 769.2337. found 385.6252 (M+2H).

Example 224 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(6-phenylpyrimidin-4-yl)methoxy]phenyl}propanoic acid Using General Procedure (VIa) and (6-phenylpyrimidin-4-yl)methanol (Preparation 9cg) as the appropriate alcohol, Example 224 was obtained. HRMS calculated for $C_{44}H_{41}ClN_6O_6S$: 816.2497. found 409.1321 (M+2H).

Example 225 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1,3-dimethyl-1H-pyrazol-5-yl)methoxy]phenyl}propanoic acid Using General Procedure (VIa) and (1,3-dimethyl-1H-pyrazol-5-yl)methanol as the appropriate alcohol, Example 225 was obtained. HRMS calculated for $C_{39}H_{41}ClN_6O_6S$: 756.2497. found 379.1313 (M+2H).

Example 226 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(3-cyclopropyl-1-methyl-1H-pyrazol-5-yl)methoxy]phenyl}propanoic acid Using General Procedure (VIa) and (3-cyclopropyl-1-methyl-1H-pyrazol-5-yl)methanol as the appropriate alcohol, Example 226 was obtained. HRMS calculated for $C_{41}H_{43}ClN_6O_6S$: 782.2653. found 392.1398 (M+2H).

Example 227 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-methyl-3-phenyl-1H-pyrazol-5-yl)methoxy]phenyl}propanoic acid Using General Procedure (VIa) and (1-methyl-3-phenyl-1H-pyrazol-5-yl)methanol as the appropriate alcohol, Example 227 was obtained. HRMS calculated for $C_{44}H_{43}ClN_6O_6S$: 818.2653. found 819.2735 (M+H).

Example 228 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[3-(furan-2-yl)-1-methyl-1H-pyrazol-5-yl]methoxy}phenyl)propanoic acid Using General Procedure (VIa) and [3-(furan-2-yl)-1-methyl-1H-pyrazol-5-yl]methanol as the appropriate alcohol, Example 228 was obtained. HRMS calculated for $C_{42}H_{41}ClN_6O_7S$: 808.2446. found 809.2524 (M+H).

Example 229 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(cyclopropylmethoxy)phenyl]propanoic acid Using General Procedure (VIa) and cyclopropylmethanol as the appropriate alcohol, Example 229 was obtained. HRMS calculated for $C_{37}H_{39}N_4O_6SCl$: 702.2279. found 703.2374 (M+H).

Example 230 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(isoquinolin-3-ylmethoxy)phenyl]propanoic acid Using General Procedure (VIa) and isoquinolin-3-ylmethanol as the appropriate alcohol Example 230 was obtained. HRMS calculated for $C_{43}H_{40}ClN_5O_6S$: 789.2388. found 395.6256 (M+2H).

Example 231 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(5-chloropyridin-2-yl)methoxy]phenyl}propanoic acid Using General Procedure (VIa) and (5-chloro-2-pyridyl)methanol as the appropriate alcohol, Example 231 was obtained. HRMS calculated for $C_{39}H_{37}Cl_2N_5O_6S$: 773.1842. found 774.1921 (M+H).

Example 232 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(5-fluoropyridin-2-yl)methoxy]phenyl}propanoic acid Using General Procedure (VIa) and (5-fluoro-2-pyridyl)methanol as the appropriate alcohol, Example 232 was obtained. HRMS calculated for $C_{39}H_{37}ClFN_5O_6S$: 757.2137. found 758.2199 (M+H).

Example 233 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(5-methoxypyridin-2-yl)methoxy]phenyl}propanoic acid Using General Procedure (VIa) and (5-methoxy-2-pyridyl)methanol as the appropriate alcohol, Example 233 was obtained. HRMS calculated for $C_{40}H_{40}ClN_5O_7S$: 769.2337. found 385.6241 (M+2H).

Example 234 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(quinolin-2-ylmethoxy)phenyl]propanoic acid Using General Procedure (VIa) and quinolin-2-ylmethanol as the appropriate alcohol, Example 234 was obtained. HRMS calculated for $C_{43}H_{40}ClN_5O_6S$: 789.2388. found 395.6253 (M+2H).

Example 235 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(6-methylpyridin-2-yl)methoxy]phenyl}propanoic acid Using General Procedure (VIa) and (6-methyl-2-pyridyl)methanol as the appropriate alcohol, Example 235 was obtained. HRMS calculated for $C_{40}H_{40}ClN_5O_6S$: 753.2388. found 377.6262 (M+2H).

Example 236 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(6-chloropyridin-2-yl)methoxy]phenyl}propanoic acid Using General Procedure (VIa) and (6-chloro-2-pyridyl)methanol as the appropriate alcohol, Example 236 was obtained. HRMS calculated for $C_{39}H_{37}Cl_2N_5O_6S$: 773.1842. found 774.1906 (M+H).

Example 237 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[6-(pyrrolidin-1-yl)pyridin-2-yl]methoxy}phenyl)propanoic acid Using General Procedure (VIa) and (6-pyrrolidin-1-yl-2-pyridyl)methanol as the appropriate alcohol, Example 237 was obtained. HRMS calculated for $C_{43}H_{45}ClN_6O_6S$: 808.2810. found 405.1472 (M+2H).

Example 238 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(6-methoxypyridin-2-yl)methoxy]phenyl}propanoic acid Using General Procedure (VIa) and (6-methoxy-2-pyridyl)methanol as the appropriate alcohol, Example 238 was obtained. HRMS calculated for $C_{40}H_{40}ClN_5O_7S$: 769.2337. found 770.2432 (M+H).

Example 239 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(cyclopentylmethoxy)phenyl]propanoic acid Using General Procedure (VIa) and cyclopentylmethanol as the appropriate alcohol, Example 239 was obtained. HRMS calculated for $C_{39}H_{43}ClN_4O_6S$: 730.2592. found 731.2639 (M+H).

Example 240 (2R)-3-[2-(benzyloxy)phenyl]-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Using General Procedure (VIa) and phenylmethanol as the appropriate alcohol, Example 240 was obtained. HRMS calculated for $C_{40}H_{39}ClN_4O_6S$: 738.2279. found 739.2319 (M+H).

Example 241 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(pyridin-2-ylmethoxy)phenyl]propanoic acid Using General Procedure (VIa) and 2-pyridylmethanol as the appropriate alcohol, Example 241 was obtained. HRMS calculated for $C_{39}H_{38}ClN_5O_6S$: 739.2231. found 370.6197 (M+2H).

Example 242 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(pyridin-3-ylmethoxy)phenyl]propanoic acid Using General Procedure (VIa) and 3-pyridylmethanol as the appropriate alcohol, Example 242 was obtained. HRMS calculated for $C_{39}H_{38}ClN_5O_6S$: 739.2231. found 370.6178 (M+2H).

Example 243 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(pyridazin-3-ylmethoxy)phenyl]propanoic acid Using General Procedure (VIa) and pyridazin-3-ylmethanol as the appropriate alcohol, Example 243 was obtained. HRMS calculated for $C_{38}H_{37}ClN_6O_6S$: 740.2184. found 741.2227 (M+H).

Example 244 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(furan-2-ylmethoxy)phenyl]propanoic acid Using General Procedure (VIa) and 2-furylmethanol as the appropriate alcohol, Example 244 was obtained. HRMS calculated for $C_{38}H_{37}ClN_4O_7S$: 728.2071. found 729.2112 (M+H).

Example 245 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(thiophen-2-ylmethoxy)phenyl]propanoic acid Using General Procedure (VIa) and 2-thienylmethanol as the appropriate alcohol, Example 245 was obtained. HRMS calculated for $C_{38}H_{37}ClN_4O_6S_2$: 744.1843. found 745.1895 (M+H).

Example 246 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-methyl-1H-pyrazol-3-yl)methoxy]phenyl}propanoic acid Using General Procedure (VIa) and (1-methyl-1H-pyrazol-3-yl)methanol as the appropriate alcohol, Example 246 was obtained. HRMS calculated for $C_{38}H_{39}ClN_6O_6S$: 742.2340. found 372.1234 (M+2H).

Example 247 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2-methylpyrimidin-4-yl)methoxy]phenyl}propanoic acid Using General Procedure (VIa) and (2-methylpyrimidin-4-yl)methanol as the appropriate alcohol, Example 247 was obtained. HRMS calculated for $C_{39}H_{39}ClN_6O_6S$: 754.2340. found 755.2446 (M+H).

Example 248 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[2-(trifluoromethyl)pyrimidin-4-yl]methoxy}phenyl)propanoic acid Using General Procedure (VIa) and [2-(trifluoromethyl)pyrimidin-4-yl]methanol (Preparation 9bj) as the appropriate alcohol, Example 248 was obtained. HRMS calculated for $C_{39}H_{36}ClF_3N_6O_6S$: 808.2058. found 809.2126 (M+H).

Example 249 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2-chloropyrimidin-4-yl)methoxy]phenyl}propanoic acid Using General Procedure (VIa) and (2-chloropyrimidin-4-yl)methanol (Preparation 9ch) as the appropriate alcohol, Example 249 was obtained. HRMS calculated for $C_{38}H_{36}Cl_2N_6O_6S$: 774.1794. found 775.1863 (M+H).

Example 250 (2R)-3-{2-[(2-aminopyrimidin-4-yl)methoxy]phenyl}-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Using General Procedure (VIa) and (2-aminopyrimidin-4-yl)methanol (Preparation 9al) as the appropriate alcohol, Example 250 was obtained. HRMS calculated for $C_{38}H_{38}ClN_7O_6S$: 755.2293. found 378.6217 (M+2H).

Example 251 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[2-(dimethylamino)pyrimidin-4-yl]methoxy}phenyl)propanoic acid Using General Procedure (VIa) and [2-(dimethylamino)pyrimidin-4-yl]methanol (Preparation 9an) as the appropriate alcohol, Example 251 was obtained. HRMS calculated for $C_{40}H_{42}ClN_7O_6S$: 783.2606. found 392.6366 (M+2H).

Example 252 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[2-(morpholin-4-yl)pyrimidin-4-yl]methoxy}phenyl)propanoic acid Using General Procedure (VIa) and (2-(morpholin-4-yl)pyrimidin-4-yl)methanol (Preparation 9ar) as the appropriate alcohol, Example 252 was obtained. HRMS calculated for $C_{42}H_{44}ClN_7O_7S$: 825.2711. found 413.6424 (M+2H).

Example 253 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[2-(methylamino)pyrimidin-4-yl]methoxy}phenyl)propanoic acid Using General Procedure (VIa) and [2-(methylamino)pyrimidin-4-yl]methanol (Preparation 9am) as the appropriate alcohol, Example 253 was obtained. HRMS calculated for $C_{39}H_{40}ClN_7O_6S$: 769.2449. found 385.6305 (M+2H).

Example 254 (2R)-3-(2-{[2-(benzylamino)pyrimidin-4-yl]methoxy}phenyl)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Using General Procedure (VIa) and [2-(benzylamino)pyrimidin-4-yl]methanol (Preparation 9 at) as the appropriate alcohol, Example 254 was obtained. HRMS calculated for $C_{45}H_{44}ClN_7O_6S$: 845.2762. found 423.6479 (M+2H).

Example 255 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2-methoxypyrimidin-4-yl)methoxy]phenyl}propanoic acid Using General Procedure (VIa) and (2-methoxypyrimidin-4-yl)methanol as the appropriate alcohol Example 255 was obtained. HRMS calculated for $C_{39}H_{39}ClN_6O_7S$: 770.2289. found 771.2344 (M+H).

Example 256 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[2-(cyclopropylmethoxy)pyrimidin-4-yl]methoxy}phenyl)propanoic acid Using General Procedure (VIa) and [2-(cyclopropylmethoxy)pyrimidin-4-yl]methanol (Preparation 9au) as the appropriate alcohol, Example 256 was obtained. HRMS calculated for $C_{42}H_{43}ClN_6O_7S$: 810.2602. found 406.1380 (M+2H).

Example 257 (2R)-3-(2-{[2-(benzyloxy)pyrimidin-4-yl]methoxy}phenyl)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Using General Procedure (VIa) and (2-benzyloxypyrimidin-4-yl)methanol as the appropriate alcohol, Example 257 was obtained. HRMS calculated for $C_{45}H_{43}ClN_6O_7S$: 846.2602. found 424.1407 (M+2H).

Example 258 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(pyridin-4-ylmethoxy)phenyl]propanoic acid Using General Procedure (VIa) and 4-pyridylmethanol as the appropriate alcohol, Example 258 was obtained. HRMS calculated for $C_{39}H_{38}ClN_5O_6S$: 739.2231. found 370.6187 (M+2H).

Example 259 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(pyrimidin-4-ylmethoxy)phenyl]propanoic acid Using General Procedure (VIa) and pyrimidin-4-ylmethanol as the appropriate alcohol, Example 259 was obtained. HRMS calculated for $C_{38}H_{37}ClN_6O_6S$: 740.2184. found 741.2259 (M+H).

Example 260 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-methyl-1H-pyrazol-5-yl)methoxy]phenyl}propanoic acid Using General Procedure (VIa) and (1-methyl-1H-pyrazol-5-yl)methanol as the appropriate alcohol, Example 260 was obtained. HRMS calculated for $C_{38}H_{39}ClN_6O_6S$: 742.2340. found 743.2404 (M+H).

Example 261 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[1-(propan-2-yl)-1H-pyrazol-5-yl]methoxy}phenyl)propanoic acid Using General Procedure (VIa) and [1-(propan-2-yl)-1H-pyrazol-5-yl]methanol (Preparation 9dc) as the appropriate alcohol, Example 261 was obtained. HRMS calculated for $C_{40}H_{43}ClN_6O_6S$: 770.2653. found 771.2726 (M+H).

Example 262 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-cyclopentyl-1H-pyrazol-5-yl)methoxy]phenyl}propanoic acid Using General Procedure (VIa) and (1-cyclopentyl-1H-pyrazol-5-yl)methanol (Preparation 9dg) as the appropriate alcohol, Example 262 was obtained. HRMS calculated for $C_{42}H_{45}ClN_6O_6S$: 796.2810. found 797.2835 (M+H).

Example 263 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-phenyl-1H-pyrazol-5-yl)methoxy]phenyl}propanoic acid Using General Procedure (VIa) and (1-phenyl-1H-pyrazol-5-yl)methanol as the appropriate alcohol, Example 263 was obtained. HRMS calculated for $C_{43}H_{41}ClN_6O_6S$: 804.2497. found 805.2575 (M+H).

Example 264 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-ethyl-1H-pyrazol-5-yl)methoxy]phenyl}propanoic acid Using General Procedure (VIa) and (1-ethyl-1H-pyrazol-5-yl)methanol (Preparation 9da) as the appropriate alcohol, Example 264 was obtained. HRMS calculated for C$_{39}$H$_{41}$ClN$_6$O$_6$S: 756.2497. found 757.2597 (M+H).

Example 265 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[1-(2,2,2-trifluoroethyl)-1H-pyrazol-5-yl]methoxy}phenyl)propanoic acid Using General Procedure (VIa) and [1-(2,2,2-trifluoroethyl)-1H-pyrazol-5-yl]methanol (Preparation 9du) as the appropriate alcohol, Example 265 was obtained. HRMS calculated for C$_{39}$H$_{38}$ClF$_3$N$_6$O$_6$S: 810.2214. found 406.1175 (M+2H).

Example 266 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(oxetan-2-ylmethoxy)phenyl]propanoic acid Using General Procedure (VIa) and oxetan-2-ylmethanol as the appropriate alcohol, Example 266 was obtained as a mixture of diastereoisomers. HRMS calculated for C$_{37}$H$_{39}$ClN$_4$O$_7$S: 718.2228. found 719.2296 (M+H) and found 719.2283 (M+H).

Example 267 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-methyl-1H-imidazol-4-yl)methoxy]phenyl}propanoic acid Using General Procedure (VIa) and (1-methyl-1H-imidazol-4-yl)methanol as the appropriate alcohol, Example 267 was obtained. HRMS calculated for C$_{38}$H$_{39}$ClN$_6$O$_6$S: 742.2340. found 372.1233 (M+2H).

Example 268 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(5-methylpyrazin-2-yl)methoxy]phenyl}propanoic acid Using General Procedure (VIa) and (5-methylpyrazin-2-yl)methanol as the appropriate alcohol Example 268 was obtained. HRMS calculated for C$_{39}$H$_{39}$ClN$_6$O$_6$S: 754.2340. found 755.2408 (M+H).

Example 269 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(5-chloropyrazin-2-yl)methoxy]phenyl}propanoic acid Using General Procedure (VIa) and (5-chloropyrazin-2-yl)methanol as the appropriate alcohol, Example 269 was obtained. HRMS calculated for C$_{38}$H$_{36}$Cl$_2$N$_6$O$_6$S: 774.1794. found 775.1817 (M+H).

Example 270 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(5-methoxypyrazin-2-yl)methoxy]phenyl}propanoic acid Using General Procedure (VIa) and (5-methoxypyrazin-2-yl)methanol as the appropriate alcohol, Example 270 was obtained. HRMS calculated for C$_{39}$H$_{39}$ClN$_6$O$_7$S: 770.2289. found 771.2329 (M+H).

Example 271 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2-methylpyrimidin-5-yl)methoxy]phenyl}propanoic acid Using General Procedure (VIa) and (2-methylpyrimidin-5-yl)methanol as the appropriate alcohol, Example 271 was obtained. HRMS calculated for C$_{39}$H$_{39}$ClN$_6$O$_6$S: 754.2340. found 755.2422 (M+H).

Example 272 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[2-(pyrrolidin-1-yl)pyrimidin-5-yl]methoxy}phenyl)propanoic acid Using General Procedure (VIa) and (2-pyrrolidin-1-ylpyrimidin-5-yl)methanol as the appropriate alcohol, Example 272 was obtained. HRMS calculated for C$_{42}$H$_{44}$ClN$_7$O$_6$S: 809.2762. found 405.6443 (M+2H).

Example 273 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-{[2-(morpholin-4-yl)pyrimidin-5-yl]methoxy}phenyl)propanoic acid Using General Procedure (VIa) and (2-(morpholin-4-yl)pyrimidin-5-yl)methanol as the appropriate alcohol, Example 273 was obtained. HRMS calculated for C$_{42}$H$_{44}$ClN$_7$O$_7$S: 825.2711. found 413.6424 (M+2H).

Example 274 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2-methoxypyrimidin-5-yl)methoxy]phenyl}propanoic acid Using General Procedure (VIa) and (2-methoxypyrimidin-5-yl)methanol as the appropriate alcohol, Example 274 was obtained. HRMS calculated for C$_{39}$H$_{39}$ClN$_6$O$_7$S: 770.2289. found 771.2398 (M+H).

Example 275 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(pyrazin-2-ylmethoxy)phenyl]propanoic acid Using General Procedure (VIa) and pyrazin-2-ylmethanol as the appropriate alcohol, Example 275 was obtained. HRMS calculated for C$_{38}$H$_{37}$ClN$_6$O$_6$S: 740.2184. found 741.2255 (M+H).

Example 276 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-methyl-1H-imidazol-5-yl)methoxy]phenyl}propanoic acid Using General Procedure (VIa) and (1-methyl-1H-imidazol-5-yl)methanol as the appropriate alcohol, Example 276 was obtained. HRMS calculated for C$_{38}$H$_{39}$ClN$_6$O$_6$S: 742.2340. found 372.1237 (M+2H).

Example 277 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(pyrimidin-5-ylmethoxy)phenyl]propanoic acid Using General Procedure (VIa) and pyrimidin-5-ylmethanol as the appropriate alcohol, Example 277 was obtained. HRMS calculated for C$_{38}$H$_{37}$ClN$_6$O$_6$S: 740.2184. found 741.2266 (M+H).

Example 278 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(1,3-thiazol-5-ylmethoxy)phenyl]propanoic acid Using General Procedure (VIa) and 1,3-thiazol-5-ylmethanol as the appropriate alcohol, Example 278 was obtained. HRMS calculated for C$_{37}$H$_{36}$ClN$_5$O$_6$S$_2$: 745.1796. found 746.1855 (M+H).

Example 279 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-methyl-1H-pyrazol-4-yl)methoxy]phenyl}propanoic acid Using General Procedure (VIa) and (1-methyl-1H-pyrazol-4-yl)methanol as the appropriate alcohol, Example 279 was obtained. HRMS calculated for C$_{38}$H$_{39}$ClN$_6$O$_6$S: 742.2340. found 372.1243 (M+2H).

Example 280 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(1,3-oxazol-4-ylmethoxy)phenyl]propanoic acid Using General Procedure (VIa) and 1,3-oxazol-4-ylmethanol as the appropriate alcohol, Example 280 was obtained. HRMS calculated for C$_{37}$H$_{36}$ClN$_5$O$_7$S: 729.2024. found 730.2116 (M+H).

Example 281 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(1,3-thiazol-4-ylmethoxy)phenyl]propanoic acid Using General Procedure (VIa) and 1,3-thiazol-4-ylmethanol as the appropriate alcohol, Example 281 was obtained. HRMS calculated for C$_{37}$H$_{36}$ClN$_5$O$_6$S$_2$: 745.1796. found 746.1867 (M+H).

Example 282 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2-methyl-2H-indazol-3-yl)methoxy]phenyl}propanoic acid Using General Procedure (VIa) and (2-methyl-2H-indazol-3-yl)methanol as the appropriate alcohol, Example 282 was obtained. HRMS calculated for C$_{42}$H$_{41}$ClN$_6$O$_6$S: 792.2497. found 397.1336 (M+2H).

Example 283 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(5-phenylpyrimidin-2-yl)methoxy]phenyl}propanoic acid Using General Procedure (VIa) and (5-phenylpyrimidin-2-yl)methanol as the appropriate alcohol, Example 283 was obtained. HRMS calculated for C$_{44}$H$_{41}$ClN$_6$O$_6$S: 816.2497. found 817.2539 (M+H).

Example 284 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(isoquinolin-1-ylmethoxy)phenyl]propanoic acid Using General Procedure (VIa) and isoquinolin-1-ylmethanol as the appropriate alcohol, Example 284 was obtained. HRMS calculated for C$_{43}$H$_{40}$ClN$_5$O$_6$S: 789.2388. found 395.6266 (M+2H).

Example 285 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(3-chloropyridin-2-yl)methoxy]phenyl}propanoic acid Using General Procedure (VIa) and (3-chloro-2-pyridyl)methanol as the appropriate alcohol, Example 285 was obtained. HRMS calculated for C$_{39}$H$_{37}$Cl$_2$N$_5$O$_6$S: 773.1842. found 774.1881 (M+H).

Example 286 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(pyrimidin-2-ylmethoxy)phenyl]propanoic acid Using General Procedure (VIa) and pyrimidin-2-ylmethanol as the appropriate alcohol, Example 286 was obtained. HRMS calculated for C$_{38}$H$_{37}$ClN$_6$O$_6$S: 740.2184. found 741.2229 (M+H).

Example 287 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(1-methyl-1H-imidazol-2-yl)methoxy]phenyl}propanoic acid Using General Procedure (VIa) and (1-methyl-1H-imidazol-2-yl)methanol as the appropriate alcohol, Example 287 was obtained. HRMS calculated for C$_{38}$H$_{39}$ClN$_6$O$_6$S: 742.2340. found 372.1246 (M+2H).

Example 288 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(3,3,3-trifluoropropoxy)phenyl]propanoic acid Using General Procedure (VIa) and 3,3,3-trifluoropropan-1-ol as the appropriate alcohol, Example 288 was obtained. HRMS calculated for C$_{36}$H$_{36}$ClF$_3$N$_4$O$_6$S: 744.1996. found 745.2037 (M+H).

Example 289 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[2-(pyridin-2-yl)ethoxy]phenyl}propanoic acid Using General Procedure (VIa) and 2-(2-pyridyl)ethanol as the appropriate alcohol, Example 289 was obtained. HRMS calculated for $C_{40}H_{40}ClN_5O_6S$: 753.2388. found 377.6280 (M+2H).

Example 290 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(2-methoxyethoxy)phenyl]propanoic acid Using General Procedure (VIa) and 2-methoxyethanol as the appropriate alcohol, Example 290 was obtained. HRMS calculated for $C_{36}H_{39}ClN_4O_7S$: 706.2228. found 707.2279 (M+H).

Example 291 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(2-phenoxyethoxy)phenyl]propanoic acid Using General Procedure (VIa) and 2-phenoxyethanol as the appropriate alcohol, Example 291 was obtained. HRMS calculated for $C_{41}H_{41}ClN_4O_7S$: 768.2384. found 769.2459 (M+H).

Example 292 (2R)-3-{2-[2-(benzyloxy)ethoxy]phenyl}-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Using General Procedure (VIa) and 2-benzyloxyethanol as the appropriate alcohol, Example 292 was obtained. HRMS calculated for $C_{42}H_{43}ClN_4O_7S$: 782.2541. found 392.1344 (M+2H).

Example 293 (2S)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2R)-tetrahydrofuran-2-ylmethoxy]phenyl}propanoic acid 503 mg 4-chloro-5-[3-chloro-2-methyl-4-[2-(4-methylpiperazin-1-yl)ethoxy]phenyl]-6-(2-furyl)thieno[2,3-d]pyrimidine (Preparation 14) (1 mmol), 353 mg ethyl (2S)-2-hydroxy-3-[2-[[(2R)-tetrahydrofuran-2-yl]methoxy]phenyl]propanoate (Preparation 3bm) (1.2 mmol) and 986 mg cesium carbonate (3 mmol) were dissolved in 10 mL dry tertbutanol. The mixture was stirred at 60° C. under nitrogen until no further conversion was observed. The reaction mixture was cooled to room temperature, then 5 mL 2 M LiOH solution was added. The mixture was stirred at room temperature until no further conversion was observed. Then it was diluted with brine, neutralized with 2 M HCl, extracted with DCM. The combined organic phases were dried over $Na_2SO_4$, filtered and concentrated under reduced pressure. The crude product was purified via preparative reversed phase chromatography using 25 mM aqueous $NH_4HCO_3$ solution and MeCN as eluents. Diastereoisomer eluting later was collected as Example 293. HRMS calculated for $C_{38}H_{41}ClN_4O_7S$: 732.2384. found 733.2476 (M+H).

Example 294 (2R)-3-{2-[(1-benzyl-1H-1,2,3-triazol-4-yl)methoxy]phenyl}-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid and Example 295 (2R)-3-{2-[(1-benzyl-1H-1,2,3-triazol-5-yl)methoxy]phenyl}-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid To a THF solution of 310 mg ethyl (2R)-2-[(5S$_a$)-5-[3-chloro-2-methyl-4-[2-(4-methylpiperazin-1-yl)ethoxy]phenyl]-6-(2-furyl)thieno[2,3-d]pyrimidin-4-yl]oxy-3-(2-prop-2-ynoxyphenyl)propanoate (see Step A of Example 216) (0.433 mmol), 86 mg benzyl azide (0.649 mmol) and 3 mg Cp*Ru(PPh$_3$)$_2$Cl were added and the mixture was stirred at 70° C. until no further conversion was observed. Then it was concentrated under reduced pressure and the crude product was purified via flash chromatography using DCM and MeOH as eluents to obtain the mixture of triazole regioisomers. Then 185 mg of this mixture (0.218 mmol) was dissolved in 5 mL dioxane/water (1:1) and 92 mg LiOH×H$_2$O was added. The mixture was stirred at room temperature until no further conversion was observed. Then it was diluted with brine, neutralized with 2 M HCl, extracted with DCM. The combined organic phases were dried over $Na_2SO_4$, filtered and concentrated under reduced pressure. The regioisomers were separated and purified via preparative reversed phase chromatography using 25 mM aqueous $NH_4HCO_3$ solution and MeCN as eluents. Regioisomer eluting earlier was collected as Example 294. HRMS calculated for $C_{43}H_{42}ClN_7O_6S$: 819.2606. found 410.6375 (M+2H). Regioisomer eluting later was collected as Example 295. HRMS calculated for $C_{43}H_{42}ClN_7O_6S$: 819.2606. found 410.6381 (M+2H).

Example 296 (2R)-2-{[(5S$_a$)-5-{3-chloro-2-methyl-4-[2-(4-methyl-4-oxidopiperazin-1-yl)ethoxy]phenyl}-6-(furan-2-yl)thieno[2,3-d]pyrimidin-4-yl]oxy}-3-(2-methoxyphenyl)propanoic acid During the synthesis of Example 209, Example 296 was formed and isolated as a side product. HRMS calculated for $C_{34}H_{35}ClN_4O_7S$: 678.1915. found 679.1966 (M+H).

Example 297 (2R)-2-{[(5S$_a$)-5-{3-chloro-2-methyl-4-[2-(4-methyl-1,4-dioxidopiperazin-1-yl)ethoxy]phenyl}-6-(furan-2-yl)thieno[2,3-d]pyrimidin-4-yl]oxy}-3-(2-methoxyphenyl)propanoic acid 200 mg (2R)-2-{[(5S$_a$)-5-{3-chloro-2-methyl-4-[2-(4-methylpiperazin-1-yl)ethoxy] phenyl}-6-(furan-2-yl)thieno[2,3-d]pyrimidin-4-yl]oxy}-3-(2-methoxyphenyl)propanoic acid (Example 209) was dissolved in 1 mL methanol and 5 µL 50% aqueous hydrogen peroxide solution was added. The reaction mixture was stirred at room temperature overnight. Then water was added and the mixture was extracted with DCM. The organic phase was dried over $Na_2SO_4$, filtered and concentrated under reduced pressure. The crude product was purified via preparative reversed phase chromatography using 25 mM aqueous $NH_4HCO_3$ solution and MeCN as eluents to obtain Example 297. HRMS calculated for $C_{34}H_{35}ClN_4O_8S$: 694.1864. found 695.1911 (M+H).

General Procedure (VIIa)
Step A:
1.0 eq. of ethyl (2R)-2-[(5S$_a$)-5-(3-chloro-4-hydroxy-2-methyl-phenyl)-6-(2-furyl)thieno[2,3-d]pyrimidin-4-yl]oxy-3-(2-methoxyphenyl)propanoate (Preparation 6e), 2.0 eq. of the appropriate alcohol and 2.0 eq. triphenylphosphine were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure, the crude ester was purified via flash chromatography using DCM and MeOH as eluents.
Step B:
The obtained ester was dissolved in dioxane-water 1:1 (10 mL/mmol) and 10 eq. LiOH×H$_2$O was added. The mixture was stirred at room temperature until no further conversion was observed. The reaction mixture was diluted with brine, neutralized with 2 M HCl, extracted with DCM. The combined organic phases were dried over Na$_2$SO$_4$, concentrated under reduced pressure and purified via preparative reversed phase chromatography using 25 mM aqueous NH$_4$HCO$_3$ solution and MeCN as eluents.

Example 298 (2R)-2-{[(5S$_a$)-5-(3-chloro-2-methyl-4-{[(2S)-1-methylpyrrolidin-2-yl]methoxy}phenyl)-6-(furan-2-yl)thieno[2,3-d]pyrimidin-4-yl]oxy}-3-(2-methoxyphenyl)propanoic acid Using General Procedure (VIIa) and [(2S)-1-methylpyrrolidin-2-yl]methanol as the appropriate alcohol, Example 298 was obtained. HRMS calculated for C$_{33}$H$_{32}$ClN$_3$O$_6$S: 633.1700. found 634.1771 (M+H).

Example 299 (2R)-2-{[(5S$_a$)-5-(3-chloro-2-methyl-4-{[(2R)-1-methylpyrrolidin-2-yl]methoxy}phenyl)-6-(furan-2-yl)thieno[2,3-d]pyrimidin-4-yl]oxy}-3-(2-methoxyphenyl)propanoic acid Using General Procedure (VIIa) and [(2R)-1-methylpyrrolidin-2-yl]methanol as the appropriate alcohol, Example 299 was obtained. HRMS calculated for C$_{33}$H$_{32}$ClN$_3$O$_6$S: 633.1700. found 634.1774 (M+H).

Example 300 (2R)-2-{[(5S$_a$)-5-{3-chloro-2-methyl-4-[(3R or S)-(1-methylazepan-3-yl)oxy]phenyl}-6-(furan-2-yl)thieno[2,3-d]pyrimidin-4-yl]oxy}-3-(2-methoxyphenyl)propanoic acid Using General Procedure (VIIa) and (1-methyl-2-piperidyl)methanol as the appropriate alcohol, Example 300 was obtained collecting only the later eluting diastereomer (absolute configuration not confirmed). HRMS calculated for C$_{34}$H$_{34}$ClN$_3$O$_6$S: 647.1857. found 648.1916 (M+H).

Example 301 (2R)-2-{[(5S$_a$)-5-{3-chloro-2-methyl-4-[((3R or S)-1-methylpiperidin-3-yl)oxy]phenyl}-6-(furan-2-yl)thieno[2,3-d]pyrimidin-4-yl]oxy}-3-(2-methoxyphenyl)propanoic acid and Example 302 (2R)-2-{[(5S$_a$)-5-{3-chloro-2-methyl-4-[((3S or R)-1-methylpiperidin-3-yl)oxy]phenyl}-6-(furan-2-yl)thieno[2,3-d]pyrimidin-4-yl]oxy}-3-(2-methoxyphenyl)propanoic acid Using General Procedure (VIIa) and 1-methylpiperidin-3-ol as the appropriate alcohol Example 301 was obtained collecting the earlier eluting diastereomer (absolute configuration not determined) HRMS calculated for C$_{33}$H$_{32}$ClN$_3$O$_6$S: 633.1700. found 634.1771 (M+H), and Example 302 was obtained collecting the later eluting diastereomer (absolute configuration not determined). HRMS calculated for C$_{33}$H$_{32}$ClN$_3$O$_6$S: 633.1700. found 634.1763 (M+H).

Example 303 (2R)-2-{[(5S$_a$)-5-{3-chloro-2-methyl-4-[(1-methylpyrrolidin-3-yl)oxy]phenyl}-6-(furan-2-yl)thieno[2,3-d]pyrimidin-4-yl]oxy}-3-(2-methoxyphenyl)propanoic acid Using General Procedure (VIIa) and 1-methylpyrrolidin-3-ol as the appropriate alcohol, Example 303 was obtained. HRMS calculated for C$_{32}$H$_{30}$ClN$_3$O$_6$S: 619.1500. found 620.1544 (M+H).

Example 304 (2R)-2-{[(5S$_a$)-5-{3-chloro-2-methyl-4-[(1-methylpiperidin-4-yl)oxy]phenyl}-6-(furan-2-yl)thieno[2,3-d]pyrimidin-4-yl]oxy}-3-(2-methoxyphenyl)propanoic acid Using General Procedure (VIIa) and 1-methylpiperidin-4-ol as the appropriate alcohol, Example 304 was obtained. HRMS calculated for C$_{33}$H$_{32}$ClN$_3$O$_6$S: 633.1700. found 634.1753 (M+H).

Example 305 (2R)-2-({(5S$_a$)-5-[3-chloro-2-methyl-4-((3S or R)-pyrrolidin-3-yloxy)phenyl]-6-(furan-2-yl)thieno[2,3-d]pyrimidin-4-yl}oxy)-3-(2-methoxyphenyl) propanoic acid and Example 306 (2R)-2-({(5S$_a$)-5-[3-chloro-2-methyl-4-((3R or S)-pyrrolidin-3-yloxy)phenyl]-6-(furan-2-yl)thieno[2,3-d]pyrimidin-4-yl}oxy)-3-(2-methoxyphenyl)propanoic acid Using General Procedure (VIIa) and pyrrolidin-3-ol as the appropriate alcohol Example 305 was obtained collecting the earlier eluting diastereomer (absolute configuration not confirmed) HRMS calculated for C$_{31}$H$_{28}$ClN$_3$O$_6$S: 605.1387. found 606.1472 (M+H), and Example 306 was obtained collecting the later eluting diastereomer (absolute configuration not confirmed). HRMS calculated for C$_{31}$H$_{28}$ClN$_3$O$_6$S: 605.1387. found 606.1461 (M+H).

Example 307 (2R)-2-({(5S$_a$)-5-[4-((3S or R)-1-azabicyclo[2.2.2]oct-3-yloxy)-3-chloro-2-methyl-phenyl]-6-(furan-2-yl)thieno[2,3-d]pyrimidin-4-yl}oxy)-3-(2-methoxyphenyl)propanoic acid and Example 308 (2R)-2-({(5S$_a$)-5-[4-((3R or S)-1-azabicyclo[2.2.2]oct-3-yloxy)-3-chloro-2-methyl-phenyl]-6-(furan-2-yl)thieno[2,3-d]pyrimidin-4-yl}oxy)-3-(2-methoxyphenyl)propanoic acid Using General Procedure (VIIa) and quinuclidin-3-ol as the appropriate alcohol, Example 307 was obtained collecting the earlier eluting diastereomer (absolute configuration not confirmed) HRMS calculated for C$_{34}$H$_{32}$ClN$_3$O$_6$S: 645.1700. found 646.1799 (M+H), and Example 308 was obtained collecting the later eluting diastereomer (absolute configuration not confirmed). HRMS calculated for $C_{34}H_{32}ClN_3O_6S$: 645.1700. found 646.1746 (M+H).

Example 309 (2R)-2-{[(5S$_a$)-5-{3-chloro-2-methyl-4-[((2S or R)-1-methylpiperidin-2-yl)methoxy]phenyl}-6-(furan-2-yl)thieno[2,3-d]pyrimidin-4-yl]oxy}-3-(2-methoxyphenyl)propanoic acid Using General Procedure (VIIa) and (1-methyl-2-piperidyl)methanol as the appropriate alcohol, Example 309 was obtained collecting the earlier eluting diastereomer (absolute configuration not confirmed). HRMS calculated for $C_{34}H_{34}ClN_3O_6S$: 647.1857. found 648.1934 (M+H).

Example 310 (2R)-2-{[(5S$_a$)-5-{3-chloro-2-methyl-4-[(1-methylpyrrolidin-3-yl)methoxy] phenyl}-6-(furan-2-yl)thieno[2,3-d]pyrimidin-4-yl]oxy}-3-(2-methoxyphenyl)propanoic acid Using General Procedure (VIIa) and (1-methylpyrrolidin-3-yl)methanol as the appropriate alcohol, Example 310 was obtained. HRMS calculated for $C_{33}H_{32}ClN_3O_6S$: 633.1700. found 634.1775 (M+H).

Example 311 (2R)-2-{[(5S$_a$)-5-{3-chloro-2-methyl-4-[(1-methylpiperidin-4-yl)methoxy] phenyl}-6-(furan-2-yl)thieno[2,3-d]pyrimidin-4-yl]oxy}-3-(2-methoxyphenyl)propanoic acid Using General Procedure (VIIa) and (1-methyl-4-piperidyl)methanol as the appropriate alcohol, Example 311 was obtained. HRMS calculated for $C_{34}H_{34}ClN_3O_6S$: 647.1857. found 648.1911 (M+H).

Example 312 (2R)-2-{[(5S$_a$)-5-(3-chloro-4-{[1-(2-methoxyethyl)pyrrolidin-3-yl]methoxy}-2-methylphenyl)-6-(furan-2-yl)thieno[2,3-d]pyrimidin-4-yl]oxy}-3-(2-methoxyphenyl)propanoic acid Using General Procedure (VIIa) and [1-(2-methoxyethyl)pyrrolidin-3-yl]methanol as the appropriate alcohol, Example 312 was obtained. HRMS calculated for $C_{35}H_{36}ClN_3O_7S$: 677.1962. found 678.2026 (M+H).

Example 313 (2R)-2-{[(5S$_a$)-5-{3-chloro-4-[(1,4-dimethylpiperazin-2-yl)methoxy]-2-methylphenyl}-6-(furan-2-yl)thieno[2,3-d]pyrimidin-4-yl]oxy}-3-(2-methoxyphenyl)propanoic acid Using General Procedure (VIIa) and (1,4-dimethylpiperazin-2-yl)methanol as the appropriate alcohol, Example 313 was obtained. HRMS calculated for $C_{34}H_{35}ClN_4O_6S$: 662.1966. found 663.2004 (M+H).

Example 314 (2R)-2-{[(5S$_a$)-5-{3-chloro-2-methyl-4-[(4-methylmorpholin-2-yl)methoxy] phenyl}-6-(furan-2-yl)thieno[2,3-d]pyrimidin-4-yl]oxy}-3-(2-methoxyphenyl)propanoic acid Using General Procedure (VIIa) and (4-methylmorpholin-2-yl)methanol as the appropriate alcohol, Example 314 was obtained. HRMS calculated for $C_{33}H_{32}ClN_3O_7S$: 649.1649. found 650.1710 (M+H).

Example 315 (2R)-2-({(5S$_a$)-5-[3-chloro-2-methyl-4-(morpholin-2-ylmethoxy)phenyl]-6-(furan-2-yl)thieno[2,3-d]pyrimidin-4-yl}oxy)-3-(2-methoxyphenyl)propanoic acid Using General Procedure (VIIa) and morpholin-2-ylmethanol as the appropriate alcohol, Example 315 was obtained. HRMS calculated for $C_{32}H_{30}ClN_3O_7S$: 635.1493. found 636.1518 (M+H).

Example 316 (2R)-2-{[(5S$_a$)-5-{3-chloro-2-methyl-4-[2-(1-methylpyrrolidin-2-yl)ethoxy] phenyl}-6-(furan-2-yl)thieno[2,3-d]pyrimidin-4-yl]oxy}-3-(2-methoxyphenyl)propanoic acid Using General Procedure (VIIa) and 2-(1-methylpyrrolidin-2-yl)ethanol as the appropriate alcohol, Example 316 was obtained. HRMS calculated for $C_{34}H_{34}ClN_3O_6S$: 647.1857. found 648.1909 (M+H).

Example 317 (2R)-2-{[(5S$_a$)-5-{3-chloro-2-methyl-4-[2-(1-methylpiperidin-4-yl)ethoxy]phenyl}-6-(furan-2-yl)thieno[2,3-d]pyrimidin-4-yl]oxy}-3-(2-methoxyphenyl)propanoic acid Using General Procedure (VIIa) and 2-(1-methyl-4-piperidyl)ethanol as the appropriate alcohol, Example 317 was obtained. HRMS calculated for $C_{35}H_{36}ClN_3O_6S$: 661.2013. found 662.2056 (M+H).

Example 318 (2R)-2-{[(5S$_a$)-5-{3-chloro-2-methyl-4-[2-(4-methylmorpholin-2-yl)ethoxy]phenyl}-6-(furan-2-yl)thieno[2,3-d]pyrimidin-4-yl]oxy}-3-(2-methoxyphenyl)propanoic acid Using General Procedure (VIIa) and 2-(4-methylmorpholin-2-yl)ethanol as the appropriate alcohol, Example 318 was obtained collecting only the later eluting diastereomer (absolute configuration not confirmed). HRMS calculated for $C_{34}H_{34}ClN_3O_7S$: 663.1806. found 664.1881 (M+H).

Example 319 (2R)-2-({(5S$_a$)-5-[4-(2-aminoethoxy)-3-chloro-2-methylphenyl]-6-(furan-2-yl)thieno[2,3-d]pyrimidin-4-yl}oxy)-3-(2-methoxyphenyl)propanoic acid Using General Procedure (VIIa) and 2-aminoethanol as the appropriate alcohol, Example 319 was obtained. HRMS calculated for $C_{29}H_{26}ClN_3O_6S$: 579.1231. found 580.1301 (M+H).

Example 320 (2R)-2-{[(5S$_a$)-5-{3-chloro-4-[2-(dimethylamino)ethoxy]-2-methylphenyl}-6-(furan-2-yl)thieno[2,3-d]pyrimidin-4-yl]oxy}-3-(2-methoxyphenyl)propanoic acid Using General Procedure (VIIa) and 2-(dimethylamino)ethanol as the appropriate alcohol, Example 320 was obtained. HRMS calculated for $C_{31}H_{30}ClN_3O_6S$: 607.1544. found 608.1617 (M+H).

Example 321 (2R)-2-{[(5S$_a$)-5-{3-chloro-2-methyl-4-[2-(4-methyl-3-oxopiperazin-1-yl)ethoxy]phenyl}-6-(furan-2-yl)thieno[2,3-d]pyrimidin-4-yl]oxy}-3-(2-methoxyphenyl)propanoic acid Using General Procedure (VIIa) and 4-(2-hydroxyethyl)-1-methyl-piperazin-2-one (Preparation 9eg) as the appropriate alcohol, Example 321 was obtained. HRMS calculated for $C_{34}H_{33}ClN_4O_7S$: 676.1758. found 677.1850 (M+H).

Example 322 (2R)-2-{[(5S$_a$)-5-{3-chloro-4-[2-(4-ethylpiperazin-1-yl)ethoxy]-2-methylphenyl}-6-(furan-2-yl)thieno[2,3-d]pyrimidin-4-yl]oxy}-3-(2-methoxyphenyl)propanoic acid Using General Procedure (VIIa) and 2-(4-ethylpiperazin-1-yl)ethanol as the appropriate alcohol, Example 322 was obtained. HRMS calculated for $C_{35}H_{37}ClN_4O_6S$: 676.2122. found 677.2186 (M+H).

Example 323 (2R)-2-{[(5S$_a$)-5-{4-[2-(4-acetylpiperazin-1-yl)ethoxy]-3-chloro-2-methylphenyl}-6-(furan-2-yl)thieno[2,3-d]pyrimidin-4-yl]oxy}-3-(2-methoxyphenyl)propanoic acid Step A:
141 mg ethyl (2R)-2-[(5S$_a$)-5-(3-chloro-4-hydroxy-2-methyl-phenyl)-6-(2-furyl)thieno[2,3-d]pyrimidin-4-yl]oxy-3-(2-methoxyphenyl)propanoate (Preparation 6e) (0.25 mmol), 0.092 mL 2-piperazin-1-ylethanol (0.75 mmol) and 197 mg triphenylphosphine (0.75 mmol) were dissolved in 5 mL dry toluene, then 173 mg ditertbutyl azodicarboxylate (0.75 mmol) was added. The mixture was stirred at 50° C. under nitrogen until no further conversion was observed. The volatiles were evaporated under reduced pressure and the crude ester was purified via flash chromatography using DCM and MeOH as eluents resulting the intermediate product ethyl (2R)-2-[(5S$_a$)-5-[3-chloro-2-methyl-4-(2-piperazin-1-ylethoxy)phenyl]-6-(2-furyl)thieno[2,3-d]pyrimidin-4-yl]oxy-3-(2-methoxyphenyl)propanoate. $^1$H NMR (500 MHz, DMSO-d$_6$): 8.58 (s, 1H), 7.79 (dd, 1H), 7.25 (d, 1H), 7.24 (d, 1H), 7.18 (m, 1H), 6.91 (d, 1H), 6.75 (m, 1H), 6.52 (dd, 1H), 6.33 (d, 1H), 5.69 (dd, 1H), 5.41 (dd, 1H), 4.27 (m, 2H), 4.05 (m, 1H), 4.02 (m, 1H), 3.76 (s, 3H), 2.97 (dd, 1H), 2.73 (t, 2H), 2.64 (m, 4H), 2.43 (brm, 4H), 2.43 (dd, 1H), 1.94 (s, 3H), 1.06 (t, 3H).

Step B:
87 mg ethyl (2R)-2-[(5S$_a$)-5-[3-chloro-2-methyl-4-(2-piperazin-1-ylethoxy)phenyl]-6-(2-furyl)thieno[2,3-d]pyrimidin-4-yl]oxy-3-(2-methoxyphenyl)propanoate (0.13 mmol) and 0.036 mL triethylamine (0.26 mmol) were dissolved in 1 mL dry DCM at room temperature. 0.018 mL acetyl chloride (0.26 mmol) was added and the reaction mixture was stirred until no further conversion was observed. The reaction was quenched with water and the mixture was extracted with DCM. The combined organic phases were washed with water, dried with Na$_2$SO$_4$ and concentrated under reduced pressure. Crude ethyl (2R)-2-[(5S$_a$)-5-[4-[2-(4-acetylpiperazin-1-yl)ethoxy]-3-chloro-2-methyl-phenyl]-6-(2-furyl)thieno[2,3-d]pyrimidin-4-yl]oxy-3-(2-methoxyphenyl)propanoate was dissolved in a mixture of 1 mL dioxane and 1 mL water and 11 mg LiOH×H$_2$O (0.26 mmol) was added. The mixture was stirred at room temperature until no further conversion was observed. The reaction mixture was diluted with brine, neutralized with 2 M HCl, extracted with DCM, dried with Na$_2$SO$_4$, concentrated under reduced pressure and purified via preparative reversed phase chromatography resulting Example 323. HRMS calculated for $C_{37}H_{35}ClN_4O_7S$: 690.1915. found 691.1996 (M+H).

Example 324 (2R)-2-{[(5S$_a$)-5-(3-chloro-2-methyl-4-{2-[4-(propan-2-yl)piperazin-1-yl]ethoxy}phenyl)-6-(furan-2-yl)thieno[2,3-d]pyrimidin-4-yl]oxy}-3-(2-methoxyphenyl)propanoic acid Using General Procedure (VIIa) and 2-(4-isopropylpiperazin-1-yl)ethanol as the appropriate alcohol, Example 324 was obtained. HRMS calculated for $C_{36}H_{39}ClN_4O_6S$: 690.2279. found 691.2335 (M+H).

Example 325 (2R)-2-{[(5S$_a$)-5-{3-chloro-2-methyl-4-[2-(4-phenylpiperazin-1-yl)ethoxy]phenyl}-6-(furan-2-yl)thieno[2,3-d]pyrimidin-4-yl]oxy}-3-(2-methoxyphenyl)propanoic acid Using General Procedure (VIIa) and 2-(4-phenylpiperazin-1-yl)ethanol as the appropriate alcohol, Example 325 was obtained. HRMS calculated for $C_{39}H_{37}ClN_4O_6S$: 724.2122. found 725.2187 (M+H).

Example 326 (2R)-2-{[(5S$_a$)-5-(4-{2-[4-(2-amino-2-oxoethyl)piperazin-1-yl]ethoxy}-3-chloro-2-methylphenyl)-6-(furan-2-yl)thieno[2,3-d]pyrimidin-4-yl]oxy}-3-(2-methoxyphenyl)propanoic acid 81 mg ethyl (2R)-2-[(5S$_a$)-5-[3-chloro-2-methyl-4-(2-piperazin-1-ylethoxy)phenyl]-6-(2-furyl)thieno[2,3-d]pyrimidin-4-yl]oxy-3-(2-methoxyphenyl)propanoate (as described in Step A of Example 323) (0.12 mmol) was dissolved in 2 mL dry THF. 41 mg 2-bromoacetamide (0.30 mmol) and 98 mg Cs$_2$CO$_3$ (0.30 mmol) were added at room temperature and the mixture was heated at 70° C. until no further conversion was observed. The mixture was concentrated under reduced pressure and the crude product was hydrolyzed by the addition of 3 mL NaOH solution (10 m/m %) in aqueous methanol (90% methanol). The mixture was stirred at room temperature until no further conversion was observed. The reaction mixture was diluted with brine, neutralized with 2 M HCl, extracted with DCM. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents resulting Example 326. HRMS calculated for $C_{35}H_{36}ClN_5O_7S$: 705.2024. found 706.2112 (M+H).

Example 327 (2R)-2-{[(5S$_a$)-5-(3-chloro-2-methyl-4-{2-[4-(2,2,2-trifluoroethyl)piperazin-1-yl]ethoxy}phenyl)-6-(furan-2-yl)thieno[2,3-d]pyrimidin-4-yl]oxy}-3-(2-methoxyphenyl)propanoic acid Using General Procedure (VIIa) and 2-[4-(2,2,2-trifluoroethyl)piperazin-1-yl]ethanol (Preparation 9eh) as the appropriate alcohol, Example 327 was obtained. HRMS calculated for $C_{35}H_{34}ClF_3N_4O_6S$: 730.1840. found 731.1919 (M+H).

Example 328 (2R)-2-{[(5S$_a$)-5-(3-chloro-4-{2-[4-(2,2-difluoroethyl)piperazin-1-yl]ethoxy}-2-methylphenyl)-6-(furan-2-yl)thieno[2,3-d]pyrimidin-4-yl]oxy}-3-(2-methoxyphenyl)propanoic acid Using General Procedure (VIIa) and 2-[4-(2,2-difluoroethyl)piperazin-1-yl]ethanol (Preparation 9ei) as the appropriate alcohol, Example 328 was obtained. HRMS calculated for $C_{35}H_{35}ClF_2N_4O_6S$: 712.1934. found 713.1978 (M+H).

Example 329 (2R)-2-{[(5S$_a$)-5-{4-[2-(4-benzylpiperazin-1-yl)ethoxy]-3-chloro-2-methylphenyl}-6-(furan-2-yl)thieno[2,3-d]pyrimidin-4-yl]oxy}-3-(2-methoxyphenyl)propanoic acid Step A:

75 mg ethyl (2R)-2-[(5S$_a$)-5-[3-chloro-2-methyl-4-(2-piperazin-1-ylethoxy)phenyl]-6-(2-furyl)thieno[2,3-d]pyrimidin-4-yl]oxy-3-(2-methoxyphenyl)propanoate (as described in Step A of Example 323) (0.115 mmol) and 0.013 mL benzaldehyde (0.127 mmol) were dissolved in 1 mL dry DCM. 37 mg sodium triacetoxyborohydride (0.173 mmol) was added and the reaction mixture was stirred at room temperature until no further conversion was observed. The reaction was quenched with NaHCO$_3$ solution and extracted with DCM. The combined organic phases were dried with Na$_2$SO$_4$ and concentrated under reduced pressure. The crude product was purified using flash chromatography eluting with DCM-MeOH gradient.

Step B:

The ester (product of Step A) was hydrolyzed by the addition of 3 mL NaOH solution (10 m/m %) in aqueous methanol (90% methanol). The mixture was stirred at room temperature until no further conversion was observed. The reaction mixture was diluted with brine, neutralized with 2 M HCl, extracted with DCM. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents resulting Example 329. HRMS calculated for C$_{40}$H$_{39}$ClN$_4$O$_6$S: 738.2279. found 739.2322 (M+H).

Example 330 (2R)-2-{[(5S$_a$)-5-(3-chloro-4-{2-[4-(2-methoxyethyl)piperazin-1-yl]ethoxy}-2-methylphenyl)-6-(furan-2-yl)thieno[2,3-d]pyrimidin-4-yl]oxy}-3-(2-methoxyphenyl)propanoic acid Step A:

135 mg ethyl (2R)-2-[(5S$_a$)-5-[3-chloro-2-methyl-4-(2-piperazin-1-ylethoxy)phenyl]-6-(2-furyl)thieno[2,3-d]pyrimidin-4-yl]oxy-3-(2-methoxyphenyl)propanoate (as described in Step A of Example 323) (0.20 mmol) was dissolved in 1.5 mL dry THF. 0.040 mL 1-bromo-2-methoxy-ethane (0.40 mmol) and 130 mg Cs$_2$CO$_3$ (0.40 mmol) were added at room temperature and the mixture was heated at 70° C. until no further conversion was observed. The mixture was concentrated under reduced pressure and the crude product was purified using flash chromatography eluting with a DCM-MeOH gradient.

Step B:

The ester obtained in Step A was hydrolyzed by adding 3 mL NaOH solution (10 m/m %) in aqueous methanol (90% methanol). The mixture was stirred at room temperature until no further conversion was observed. The reaction mixture was diluted with brine, neutralized with 2 M HCl, extracted with DCM. The combined organic phases were dried with Na$_2$SO$_4$, concentrated under reduced pressure and purified via preparative reversed phase chromatography using 25 mM aqueous NH$_4$HCO$_3$ solution and MeCN as eluents resulting Example 330. HRMS calculated for C$_{36}$H$_{39}$ClN$_4$O$_7$S: 706.2228. found 707.2273 (M+H).

Example 331 (2R)-2-{[(5S$_a$)-5-{3-chloro-2-methyl-4-[2-(methylamino)ethoxy]phenyl}-6-(furan-2-yl)thieno[2,3-d]pyrimidin-4-yl]oxy}-3-(2-methoxyphenyl)propanoic acid Using General Procedure (VIIa) and 2-(methylamino)ethanol as the appropriate alcohol, Example 331 was obtained. HRMS calculated for C$_{30}$H$_{28}$ClN$_3$O$_6$S: 593.1387. found 594.1455 (M+H).

Example 332 (2R)-2-{[(5S$_a$)-5-(3-chloro-2-methyl-4-{[(4-methylpiperazin-1-yl)acetyl]oxy}phenyl)-6-(furan-2-yl)thieno[2,3-d]pyrimidin-4-yl]oxy}-3-(2-methoxyphenyl)propanoic acid 100 mg ethyl (2R)-2-[(5S$_a$)-5-(3-chloro-4-hydroxy-2-methyl-phenyl)-6-(2-furyl)thieno[2,3-d]pyrimidin-4-yl]oxy-3-(2-methoxyphenyl)propanoate (Preparation 6e) (0.18 mmol) was dissolved in 0.5 mL dioxane and a solution of 37 mg LiOH×H$_2$O (0.88 mmol) in 0.5 mL water was added to it. The mixture was stirred at room temperature for 30 minutes, quenched with water, acidified with dilute hydrochloric acid solution and extracted with DCM. The combined organic phases were dried with Na$_2$SO$_4$ and concentrated under reduced pressure. The crude product was re-dissolved in 2 mL dry DCM, 64 mg 2-(4-methylpiperazin-1-yl)acetic acid (0.40 mmol), 208 mg PyBOP (0.40 mmol) and 0.060 mL triethylamine (0.44 mmol) were added. The mixture was stirred at room temperature until no further conversion was observed. Further DCM was added and the organic phase was washed with water, dried with Na$_2$SO$_4$ and concentrated under reduced pressure. The crude product was purified with preparative HPLC resulting Example 332. HRMS calculated for C$_{34}$H$_{33}$ClN$_4$O$_7$S: 676.1758. found 677.1846 (M+H).

Example 333 (2R)-2-{[(5R$_a$)-5-{3-fluoro-2-methyl-4-[2-(4-methylpiperazin-1-yl)ethoxy]phenyl}-6-(furan-2-yl)thieno[2,3-d]pyrimidin-4-yl]oxy}-3-(2-methoxyphenyl)propanoic acid and

Example 334 (2R)-2-{[(5S$_a$)-5-{3-fluoro-2-methyl-4-[2-(4-methylpiperazin-1-yl)ethoxy]phenyl}-6-(furan-2-yl)thieno[2,3-d]pyrimidin-4-yl]oxy}-3-(2-methoxyphenyl)propanoic acid 501 mg ethyl (2R)-2-[5-(3-fluoro-4-hydroxy-2-methyl-phenyl)-6-(2-furyl)thieno[2,3-d]pyrimidin-4-yl]oxy-3-(2-methoxyphenyl)propanoate (Preparation 11b, mixture of diastereomers) (0.913 mmol), 198 mg 2-(4-methylpiperazin-1-yl)ethanol (1.37 mmol) and 480 mg triphenylphosphine (1.83 mmol) were dissolved in 10 mL dry toluene, then 420 mg ditertbutyl azodicarboxylate (1.83 mmol) was added. The mixture was stirred at 50° C. under nitrogen for 45 minutes. The volatiles were evaporated under reduced pressure and the crude ester was purified using flash chromatography (eluents: EtOAc and MeOH). The obtained ester was dissolved in a mixture of 4 mL dioxane and 2 mL water and 200 mg LiOH×H$_2$O was added. The reaction mixture was stirred at room temperature for 1.5 hours, quenched by the addition of brine and neutralized with 2 M HCl. The mixture was extracted with DCM, dried with Na$_2$SO$_4$, concentrated under reduced pressure and purified via preparative reversed phase chromatography using 25 mM aqueous NH$_4$HCO$_3$ solution and MeCN as eluents. Example 333 was obtained as the diastereoisomer eluting earlier from the preparative HPLC column [HRMS calculated for $C_{34}H_{35}FN_4O_6S$: 646.2261. found 647.2365 (M+H)], and Example 334 was obtained as the diastereoisomer eluting later from the preparative HPLC column [HRMS calculated for $C_{34}H_{35}FN_4O_6S$: 646.2261. found 647.2302 (M+H)].

Example 335 (2R)-2-{[(5S$_a$)-5-{3-chloro-2-ethyl-4-[2-(4-methylpiperazin-1-yl)ethoxy]phenyl}-6-(furan-2-yl)thieno[2,3-d]pyrimidin-4-yl]oxy}-3-(2-methoxyphenyl)propanoic acid and Example 336 (2R)-2-{[(5R$_a$)-5-{3-chloro-2-ethyl-4-[2-(4-methylpiperazin-1-yl)ethoxy]phenyl}-6-(furan-2-yl)thieno[2,3-d]pyrimidin-4-yl]oxy}-3-(2-methoxyphenyl)propanoic acid 250 mg ethyl ((2R)-2-[5-(3-chloro-2-ethyl-4-hydroxyphenyl)-6-(2-furyl)thieno[2,3-d] pyrimidin-4-yl]oxy-3-(2-methoxyphenyl)propanoate (Preparation 11a, mixture of diastereomers) (0.40 mmol), 115 mg 2-(4-methylpiperazin-1-yl)ethanol (0.80 mmol) and 210 mg triphenylphosphine (0.80 mmol) were dissolved in 5 mL dry toluene, then 184 mg ditertbutyl azodicarboxylate (0.80 mmol) was added. The mixture was stirred at 50° C. under nitrogen for 1 hour. The volatiles were evaporated under reduced pressure and the crude ester was purified using flash chromatography (eluents: EtOAc and MeOH). The obtained ester was dissolved in a mixture of 4 mL dioxane and 2 mL water and 100 mg LiOH×H$_2$O was added. The reaction mixture was stirred at 30° C. for 1 hour. Water was added to the mixture and pH was set to 4-5 with 2 M HCl. The mixture was extracted with DCM, dried with Na$_2$SO$_4$, concentrated under reduced pressure and purified via preparative reversed phase chromatography using 25 mM aqueous NH$_4$HCO$_3$ solution and MeCN as eluents. Example 335 was obtained as the diastereoisomer eluting later from the preparative HPLC column [HRMS calculated for $C_{35}H_{37}ClN_4O_6S$: 676.2122. found 677.2204 (M+H)], while Example 336 was obtained as the diastereoisomer eluting earlier from the preparative HPLC column [HRMS calculated for $C_{35}H_{37}ClN_4O_6S$: 676.2122. found 677.2181 (M+H)].

Example 337 (2R)-2-{[5-{3-chloro-2-fluoro-4-[2-(4-methylpiperazin-1-yl)ethoxy]phenyl}-6-(furan-2-yl)thieno[2,3-d]pyrimidin-4-yl]oxy}-3-(2-methoxyphenyl)propanoic acid (mixture of diastereoisomers)

503 mg ethyl (2R)-2-[5-bromo-6-(2-furyl)thieno[2,3-d]pyrimidin-4-yl]oxy-3-(2-methoxyphenyl)propanoate (Preparation 4e) (1.00 mmol), 900 mg 1-[2-[2-chloro-3-fluoro-4-(4,4,5,5-tetramethyl-1,3,2-dioxaborolan-2-yl)phenoxy]ethyl]-4-methyl-piperazine (Preparation 5f) (2.20 mmol), 35 mg Ataphos (0.05 mmol) and 977 mg Cs$_2$CO$_3$ (3.00 mmol) were dissolved in 10 mL dioxane and 2 mL water. It was heated to 110° C. for 15 minutes via microwave irradiation. Then it was diluted with brine, extracted with DCM, and the combined organic phases were dried over Na$_2$SO$_4$, filtered and concentrated under reduced pressure and purified via reversed phase chromatography, using 25 mM aqueous NH$_4$HCO$_3$ solution and MeCN as eluents. The obtained ester was dissolved in a mixture of 5 mL dioxane and 5 mL water and 200 mg LiOH×H$_2$O was added. The reaction mixture was stirred at room temperature until no further conversion was observed. Water was added to the mixture and pH was set between 4-5 with 2 M HCl. The mixture was extracted with DCM, and the combined organic phases were dried with Na$_2$SO$_4$, concentrated under reduced pressure and purified via preparative reversed phase chromatography resulting Example 337. HRMS calculated for $C_{33}H_{32}ClFN_4O_6S$: 666.1715. found 667.1792 (M+H).

General Procedure (VIIIa)

Step A:

1.0 eq. 4-chloro-5-[3-chloro-2-methyl-4-[2-(4-methylpiperazin-1-yl)ethoxy]phenyl]-6-(2-furyl)thieno[2,3-d]pyrimidine (Preparation 14), 1.2 eq. of the appropriate alcohol and 3.0 eq. cesium carbonate were dissolved in dry tertbutanol or dry DMSO (0.2 M for Preparation 14). The mixture was stirred at 60° C. under nitrogen until no further conversion was observed. The reaction mixture was cooled to room temperature then it was diluted with brine and extracted with DCM. The combined organic phases were dried over MgSO$_4$ and evaporated under reduced pressure. The crude product was purified via flash chromatography using EtOAc/MeOH as eluents.

Step B:

The product of Step A was dissolved in dioxane/H$_2$O (1:1, 0.2 M for the product of Step A) and 10 eq. LiOH×H$_2$O was added then it was stirred at room temperature until no further conversion was observed. The reaction mixture was diluted with brine, neutralized with 2 M HCl, and extracted with DCM. The combined organic phases were dried over Na$_2$SO$_4$, concentrated under reduced pressure and purified via preparative reversed phase chromatography using 25 mM aqueous NH$_4$HCO$_3$ solution and MeCN as eluents.

Example 338 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(difluoromethoxy)phenyl]propanoic acid Using General Procedure (VIIIa) and methyl (2R)-3-[2-(difluoromethoxy)phenyl]-2-hydroxy-propanoate (Preparation 3aj) as the appropriate alcohol, the diastereoisomer eluting later was collected as Example 338. HRMS calculated for $C_{34}H_{33}ClF_2N_4O_6S$: 698.1777. found 699.1866 (M+H).

Example 339 (2R)-{[(5R$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}(phenyl)ethanoic acid and Example 340 (2R)-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}(phenyl)ethanoic acid Using General Procedure (VIIIa) and methyl (2R)-2-hydroxy-2-phenyl-acetate as the appropriate alcohol, the diastereoisomer eluting earlier was collected as Example 339 and the diastereoisomer eluting later was collected as Example 340. HRMS calculated for $C_{32}H_{31}ClN_4O_5S$: 618.1704. found 619.1766 (M+H) and 619.1768 (M+H).

Example 341 (2S)-2-{[(5R$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-fluorophenyl)propanoic acid Using General Procedure (VIIIa) and ethyl (2S)-3-(2-fluorophenyl)-2-hydroxy-propanoate (Preparation 3az) as the appropriate alcohol, the diastereoisomer eluting later was collected as Example 341. HRMS calculated for $C_{33}H_{32}ClFN_4O_5S$: 650.1766. found 651.1825 (M+H).

Example 342 (2R,3S)-2-{[(5R$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-hydroxy-3-phenylpropanoic acid and Example 343 (2R,3S)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-hydroxy-3-phenylpropanoic acid Using General Procedure (VIIIa) and methyl (2R,3S)-2,3-dihydroxy-3-phenyl-propanoate as the appropriate alcohol, the diastereoisomer eluting earlier was collected as Example 342 and the diastereoisomer eluting later was collected as Example 343. HRMS calculated for $C_{33}H_{33}ClN_4O_6S$: 648.1809. found 649.1879 (M+H) and 649.1875 (M+H).

Example 344 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-methoxy-5-methylphenyl)propanoic acid Using General Procedure (VIIIa) and ethyl (2R)-2-hydroxy-3-(2-methoxy-5-methyl-phenyl)propanoate (Preparation 3 at) as the appropriate alcohol, the diastereoisomer eluting later was collected as Example 344. HRMS calculated for $C_{35}H_{37}ClN_4O_6S$: 676.2122. found 677.2176 (M+H).

Example 345 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(5-fluoro-2-methoxyphenyl)propanoic acid Using General Procedure (VIIIa) and ethyl (2R)-3-(5-fluoro-2-methoxy-phenyl)-2-hydroxy-propanoate (Preparation 3ar) as the appropriate alcohol, the diastereoisomer eluting later was collected as Example 345. HRMS calculated for $C_{34}H_{34}ClFN_4O_6S$: 680.1872. found 681.1947 (M+H).

Example 346 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(4-fluoro-2-methoxyphenyl)propanoic acid Using General Procedure (VIIIa) and ethyl (2R)-3-(4-fluoro-2-methoxy-phenyl)-2-hydroxy-propanoate (Preparation 3 as) as the appropriate alcohol, the diastereoisomer eluting later was collected as Example 346. HRMS calculated for $C_{34}H_{34}ClFN_4O_6S$: 680.1872. found 681.1915 (M+H).

Example 347 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(3-methylphenyl)propanoic acid Using General Procedure (VIIIa) and methyl (2R)-2-hydroxy-3-(m-tolyl)propanoate (Preparation 3ap) as the appropriate alcohol, the diastereoisomer eluting later was collected as Example 347. HRMS calculated for $C_{34}H_{35}ClN_4O_5S$: 646.2017. found 647.2073 (M+H).

Example 348 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(3-fluorophenyl)propanoic acid Using General Procedure (VIIIa) and methyl (2R)-3-(3-fluorophenyl)-2-hydroxy-propanoate (Preparation 3ak) as the appropriate alcohol, the diastereoisomer eluting later was collected as Example 348. HRMS calculated for $C_{33}H_{32}ClFN_4O_5S$: 650.1766. found 651.1818 (M+H).

Example 349 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(3-methoxyphenyl)propanoic acid Using General Procedure (VIIIa) and methyl (2R)-2-hydroxy-3-(3-methoxyphenyl)propanoate (Preparation 3al) as the appropriate alcohol, the diastereoisomer eluting later was collected as Example 349. HRMS calculated for $C_{34}H_{35}ClN_4O_6S$: 662.1966. found 663.2043 (M+H).

Example 350 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2,3-difluorophenyl)propanoic acid Using General Procedure (VIIIa) and methyl (2R)-3-(2,3-difluorophenyl)-2-hydroxy-propanoate (Preparation 3am) as the appropriate alcohol, the diastereoisomer eluting later was collected as Example 350. HRMS calculated for $C_{33}H_{31}ClF_2N_4O_5S$: 668.1672. found 669.1729 (M+H).

Example 351 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-methoxy-3-methylphenyl)propanoic acid Using General Procedure (VIIIa) and ethyl (2R)-2-hydroxy-3-(2-methoxy-3-methyl-phenyl)propanoate (Preparation 3au) as the appropriate alcohol, the diastereoisomer eluting later was collected as Example 351. HRMS calculated for $C_{35}H_{37}ClN_4O_6S$: 676.2122. found 677.2221 (M+H).

Example 352 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(3-fluoro-2-methoxyphenyl)propanoic acid Using General Procedure (VIIIa) and ethyl (2R)-3-(3-fluoro-2-methoxy-phenyl)-2-hydroxy-propanoate (Preparation 3aq) as the appropriate alcohol, the diastereoisomer eluting later was collected as Example 352. HRMS calculated for $C_{34}H_{34}ClFN_4O_6S$: 680.1872. found 681.1963 (M+H).

Example 353 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-[2-(trifluoromethyl)phenyl]propanoic acid Using General Procedure (VIIIa) and methyl (2R)-2-hydroxy-3-[2-(trifluoromethyl)phenyl]propanoate (Preparation 3an) as the appropriate alcohol, the diastereoisomer eluting later was collected as Example 353. HRMS calculated for $C_{34}H_{32}ClF_3N_4O_5S$: 700.1734. found 701.1803 (M+H).

Example 354 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-methylphenyl)propanoic acid Using General Procedure (VIIIa) and methyl (2R)-2-hydroxy-3-(o-tolyl)propanoate (Preparation 3ao) as the appropriate alcohol, the diastereoisomer eluting later was collected as Example 354. HRMS calculated for $C_{34}H_{35}ClN_4O_5S$: 646.2017. found 647.2087 (M+H).

Example 355 (2R)-3-[2-(aminomethyl)phenyl]-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Step A:
252 mg 4-chloro-5-[3-chloro-2-methyl-4-[2-(4-methylpiperazin-1-yl)ethoxy]phenyl]-6-(2-furyl)thieno[2,3-d]pyrimidine (Preparation 14) (0.50 mmol), 196 mg ethyl (2R)-3-[2-[(tert-butoxycarbonylamino)methyl]phenyl]-2-hydroxy-propanoate (Preparation 3aw) (0.60 mmol) and 488 mg cesium carbonate (1.50 mmol) were dissolved in dry tertbutanol (0.1 M for Preparation 14). The mixture was stirred at 60° C. under nitrogen until no further conversion was observed. The mixture was cooled to room temperature, then it was diluted with brine and extracted with EtOAc. The combined organic phases were dried over MgSO$_4$, filtered and concentrated, and then purified by flash chromatography on silica gel using EtOAc/MeOH as eluents to give ethyl (2R)-3-[2-[(tert-butoxycarbonylamino)methyl] phenyl]-2-[5-[3-chloro-2-methyl-4-[2-(4-methylpiperazin-1-yl) ethoxy]phenyl]-6-(2-furyl)thieno[2,3-d]pyrimidin-4-yl]oxy-propanoate.
Step B:
198 mg ethyl (2R)-3-[2-[(tert-butoxycarbonylamino) methyl]phenyl]-2-[5-[3-chloro-2-methyl-4-[2-(4-methylpiperazin-1-yl)ethoxy]phenyl]-6-(2-furyl)thieno[2,3-d]pyrimidin-4-yl]oxy-propanoate (0.250 mmol) was dissolved in 10 mL dry DCM, then 1 mL TFA was added and it was stirred at room temperature until no further conversion was observed, and then reaction mixture was washed with saturated NaHCO$_3$. The organic layer was dried over MgSO$_4$, filtered and the volatiles were evaporated under reduced pressure to give ethyl (2R)-3-[2-(aminomethyl)phenyl]-2-[5-[3-chloro-2-methyl-4-[2-(4-methylpiperazin-1-yl) ethoxy]phenyl]-6-(2-furyl)thieno[2,3-d]pyrimidin-4-yl]oxy-propanoate.
Step C:
56 mg ethyl (2R)-3-[2-(aminomethyl)phenyl]-2-[5-[3-chloro-2-methyl-4-[2-(4-methylpiperazin-1-yl)ethoxy]phenyl]-6-(2-furyl)thieno[2,3-d]pyrimidin-4-yl]oxy-propanoate (0.081 mmol) was dissolved in 1 mL dioxane/water (1:1) and 68 mg LiOH×H$_2$O was added. The mixture was stirred at room temperature until no further conversion was observed. Then it was diluted with brine, neutralized with 2 M HCl, extracted with DCM. The combined organic phases were dried over Na$_2$SO$_4$, filtered, concentrated and purified via preparative reversed phase chromatography using 25 mM aqueous NH$_4$HCO$_3$ solution and MeCN as eluents. The diastereoisomer eluting later was collected as Example 355. HRMS calculated for $C_{34}H_{36}ClN_5O_5S$: 661.2126. found 331.6148 (M+2H).

Example 356 (2R)-3-{2-[(acetylamino)methyl]phenyl}-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Step A:
100 mg ethyl (2R)-3-[2-(aminomethyl)phenyl]-2-[5-[3-chloro-2-methyl-4-[2-(4-methylpiperazin-1-yl)ethoxy]phenyl]-6-(2-furyl)thieno[2,3-d]pyrimidin-4-yl]oxy-propanoate (0.145 mmol) (Step B of Example 355) and 611 triethyl amine (435 mol) were dissolved in 5 mL DCM, and then 12 μl acetyl chloride (174 mol) was added. Reaction mixture was stirred at room temperature until no further conversion was observed. The crude mixture was purified via flash chromatography using EtOAc/MeOH as eluents to give ethyl (2R)-3-[2-(acetamidomethyl)phenyl]-2-[5-[3-chloro-2-methyl-4-[2-(4-methylpiperazin-1-yl)ethoxy]phenyl]-6-(2-furyl)thieno[2,3-d]pyrimidin-4-yl]oxy-propanoate.
Step B:
73 mg ethyl (2R)-3-[2-(acetamidomethyl)phenyl]-2-[5-[3-chloro-2-methyl-4-[2-(4-methylpiperazin-1-yl)ethoxy] phenyl]-6-(2-furyl)thieno[2,3-d]pyrimidin-4-yl]oxy-propanoate (0.10 mmol) was dissolved in 2 mL dioxane/water (1:1) and 84 mg LiOH×H$_2$O (2.0 mmol) was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated and purified via preparative reverse phase chromatography using 25 mM aqueous NH$_4$HCO$_3$ solution and MeCN as eluents. The diastereoisomer eluting later was collected as Example 356. HRMS calculated for $C_{36}H_{38}ClN_5O_6S$: 703.2231. found 704.231 (M+H).

Example 357 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-fluorophenyl)propanoic acid Using General Procedure (VIIIa) and ethyl (2R)-3-(2-fluorophenyl)-2-hydroxy-propanoate (Preparation 3ba) as the appropriate alcohol, the diastereoisomer eluting later was collected as Example 357. HRMS calculated for $C_{33}H_{32}ClFN_4O_5S$: 650.1766. found 651.1827 (M+H).

Example 358 (2R)-3-{2-[(tert-butoxycarbonyl)amino]phenyl}-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}propanoic acid Using General Procedure (VIIIa) and ethyl (2R)-3-[2-(tert-butoxycarbonylamino)phenyl]-2-hydroxy-propanoate (Preparation 3av) as the appropriate alcohol, the diastereoisomer eluting later was collected as Example 358. HRMS calculated for $C_{38}H_{42}ClN_5O_7S$: 747.2493. found 748.2538 (M+H).

Example 359 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2,3-dihydro-1-benzofuran-7-yl)propanoic acid Using General Procedure (VIIIa) and ethyl (2R)-3-(2,3-dihydrobenzofuran-7-yl)-2-hydroxy-propanoate (Preparation 3bd) as the appropriate alcohol, the diastereoisomer eluting later was collected as Example 359. HRMS calculated for $C_{35}H_{35}ClN_4O_6S$: 674.1966. found 675.2033 (M+H).

Example 360 (2S)-2-{[(5R$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2,3-dihydro-1-benzofuran-7-yl)propanoic acid Using General Procedure (VIIIa) and ethyl (2S)-3-(2,3-dihydrobenzofuran-7-yl)-2-hydroxy-propanoate (Preparation 3be) as the appropriate alcohol, the diastereoisomer eluting later was collected as Example 360. HRMS calculated for $C_{35}H_{35}ClN_4O_6S$: 674.1966. found 675.2025 (M+H).

Example 361 (2S)-2-{[(5R$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2,2,2-trifluoroethyl)sulfanyl]phenyl}propanoic acid Using General Procedure (VIIIa) and ethyl (2S)-2-hydroxy-3-[2-(2,2,2-trifluoroethylsulfanyl)phenyl]propanoate (Preparation 3ax) as the appropriate alcohol, the diastereoisomer eluting later was collected as Example 361. HRMS calculated for $C_{35}H_{34}ClF_3N_4O_5S_2$: 746.1611. found 747.1678 (M+H).

Example 362 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-{2-[(2,2,2-trifluoroethyl)sulfanyl]phenyl}propanoic acid Using General Procedure (VIIIa) and ethyl (2R)-2-hydroxy-3-[2-(2,2,2-trifluoroethylsulfanyl)phenyl]propanoate (Preparation 3ay) as the appropriate alcohol, the diastereoisomer eluting later was collected as Example 362 was obtained. HRMS calculated for $C_{35}H_{34}ClF_3N_4O_5S_2$: 746.1611. found 747.1682 (M+H).

General Procedure (IXa)

Step A:

1 eq. of ethyl (2R)-2-[6-(5-chloro-2-furyl)-(5S$_a$)-5-[3-chloro-2-methyl-4-[2-(4-methylpiperazin-1-yl)ethoxy]phenyl]thieno[2,3-d]pyrimidin-4-yl]oxy-3-(2-hydroxyphenyl)propanoate (Preparation 8f), 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen. After no further conversion observed the volatiles were evaporated under reduced pressure and the crude ester was purified via flash chromatography using EtOAc and MeOH as eluents.

Step B:

The product of Step A was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$ and concentrated under reduced pressure. The residue was purified via preparative reversed phase chromatography using 25 mM aqueous NH$_4$HCO$_3$ solution and MeCN as eluents.

Example 363 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-methoxyphenyl)propanoic acid Using General Procedure (IXa) and methanol as the appropriate alcohol, Example 363 was obtained. HRMS calculated for $C_{34}H_{34}Cl_2N_4O_6S$: 696.1576. found 697.1656 (M+H).

Example 364 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-{2-[(2R)-tetrahydrofuran-2-ylmethoxy]phenyl}propanoic acid Using General Procedure (IXa) and [(2R)-tetrahydrofuran-2-yl]methanol as the appropriate alcohol, Example 364 was obtained. HRMS calculated for $C_{38}H_{40}Cl_2N_4O_7S$: 766.1995. found 767.2056 (M+H).

Example 365 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-[2-(2,2,2-trifluoroethoxy)phenyl]propanoic acid 214 mg ethyl (2R)-2-[6-(5-chloro-2-furyl)-(5S$_a$)-5-[3-chloro-2-methyl-4-[2-(4-methylpiperazin-1-yl)ethoxy]phenyl]thieno[2,3-d]pyrimidin-4-yl]oxy-3-(2-hydroxyphenyl)propanoate (Preparation 8f) (0.300 mmol) and 138 mg K$_2$CO$_3$ (1.00 mmol) were dissolved in 2 mL DMF, then 232 mg 2,2,2-trifluoroethyl trifluoromethanesulfonate (1.00 mmol) was added. The mixture was stirred at room temperature under nitrogen for 7 hours. Then it was diluted with brine, neutralized with 2 M HCl, and extracted with DCM. The combined organic phases were dried over Na$_2$SO$_4$ and concentrated under reduced pressure. The crude product was dissolved in 8 mL dioxane-water (1:1) and 126 mg LiOH× H$_2$O (3.00 mmol) was added. The mixture was stirred at room temperature for 1 hour. Then it was diluted with brine, neutralized with 2 M HCl, and extracted with DCM. The combined organic phases were dried over Na$_2$SO$_4$, concentrated under reduced pressure and the residue was purified via preparative reversed phase chromatography using 5 mM aqueous NH$_4$HCO$_3$ solution and MeCN as eluents to give Example 365. HRMS calculated for $C_{35}H_{33}Cl_2F_3N_4O_6S$: 764.145. found 765.1523 (M+H).

Example 366 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-[2-(pyridin-2-ylmethoxy)phenyl]propanoic acid Using General Procedure (IXa) and 2-pyridylmethanol as the appropriate alcohol, Example 366 was obtained. HRMS calculated for $C_{39}H_{37}Cl_2N_5O_6S$: 773.1842. found 387.5992 (M+2H).

Example 367 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-{[2-(trifluoromethyl)pyrimidin-4-yl]methoxy}phenyl)propanoic acid Using General Procedure (IXa) and [2-(trifluoromethyl)pyrimidin-4-yl]methanol (Preparation 9bj) as the appropriate alcohol, Example 367 was obtained. HRMS calculated for $C_{39}H_{35}Cl_2F_3N_6O_6S$: 842.1668. found 843.175 (M+H).

Example 368 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-{[2-(morpholin-4-yl)pyrimidin-4-yl]methoxy}phenyl)propanoic acid Using General Procedure (IXa) and (2-(morpholin-4-yl)pyrimidin-4-yl)methanol (Preparation 9ar) as the appropriate alcohol, Example 368 was obtained. HRMS calculated for $C_{42}H_{43}Cl_2N_7O_7S$: 859.2322. found 430.6247 (M+2H).

Example 369 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-{2-[(2-methoxypyrimidin-4-yl)methoxy]phenyl}propanoic acid Using General Procedure (IXa) and (2-methoxypyrimidin-4-yl)methanol as the appropriate alcohol, Example 369 was obtained. HRMS calculated for $C_{39}H_{38}Cl_2N_6O_7S$: 804.19. found 805.2032 (M+H).

Example 370 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-[2-(pyrimidin-4-ylmethoxy)phenyl]propanoic acid Using General Procedure (IXa) and pyrimidin-4-ylmethanol as the appropriate alcohol, Example 370 was obtained. HRMS calculated for $C_{38}H_{36}Cl_2N_6O_6S$: 774.1794. found 775.182 (M+H).

Example 371 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-{2-[(1-methyl-1H-pyrazol-5-yl)methoxy]phenyl}propanoic acid Using General Procedure (IXa) and (1-methyl-1H-pyrazol-5-yl)methanol as the appropriate alcohol, Example 371 was obtained. HRMS calculated for $C_{38}H_{38}Cl_2N_6O_6S$: 776.1951. found 777.1999 (M+H).

Example 372 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-{2-[(1-ethyl-1H-pyrazol-5-yl)methoxy]phenyl}propanoic acid Using General Procedure (IXa) and (1-ethyl-1H-pyrazol-5-yl)methanol (Preparation 9da) as the appropriate alcohol, Example 372 was obtained. HRMS calculated for $C_{39}H_{40}Cl_2N_6O_6S$: 790.2107. found 396.1113 (M+2H).

Example 373 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-{[1-(2,2,2-trifluoroethyl)-1H-pyrazol-5-yl]methoxy}phenyl)propanoic acid Using General Procedure (IXa) and [1-(2,2,2-trifluoroethyl)-1H-pyrazol-5-yl]methanol (Preparation 9du) as the appropriate alcohol, Example 373 was obtained. HRMS calculated for $C_{39}H_{37}Cl_2F_3N_6O_6S$: 844.1824. found 845.186 (M+H).

Example 374 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-[2-(pyrazin-2-ylmethoxy)phenyl]propanoic acid Using General Procedure (IXa) and pyrazin-2-ylmethanol as the appropriate alcohol, Example 374 was obtained. HRMS calculated for $C_{38}H_{36}Cl_2N_6O_6S$: 774.1794. found 775.1824 (M+H).

Example 375 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-[2-(pyrimidin-5-ylmethoxy)phenyl]propanoic acid Using General Procedure (IXa) and pyrimidin-5-ylmethanol as the appropriate alcohol, Example 375 was obtained. HRMS calculated for $C_{38}H_{36}Cl_2N_6O_6S$: 774.1794. found 775.1869 (M+H).

Example 376 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-[2-(1,3-oxazol-4-ylmethoxy)phenyl]propanoic acid Using General Procedure (IXa) and 1,3-oxazol-4-ylmethanol as the appropriate alcohol, Example 376 was obtained. HRMS calculated for $C_{37}H_{35}Cl_2N_5O_7S$: 763.1634. found 764.1685 (M+H).

Example 377 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-{2-[(2S)-tetrahydrofuran-2-ylmethoxy]phenyl}propanoic acid Step A:
228 mg of ethyl (2R)-2-[6-(5-chloro-2-furyl)-(5S$_a$)-5-(3-chloro-4-hydroxy-2-methyl-phenyl)thieno[2,3-d]pyrimidin-4-yl]oxy-3-[2-[[(2S)-tetrahydrofuran-2-yl]methoxy]phenyl]propanoate (Preparation 6g, 0.340 mmol), 101 mg 2-(4-methylpiperazin-1-yl)ethanol (0.70 mmol), and 184 mg PPh$_3$ (0.700 mmol) were dissolved in 2 mL dry toluene, then 161 mg ditertbutyl azodicarboxylate (0.700 mmol) was added. The mixture was stirred at 50° C. under nitrogen until no further conversion observed, than the volatiles were evaporated under reduced pressure and the residue was purified via flash chromatography using EtOAc and MeOH as eluents.

Step B:
The product of Step A was dissolved in 6 mL dioxane-water 1:1 and 150 mg LiOH×H$_2$O was added. The mixture was stirred at room temperature until no further conversion was observed. Then it was diluted with brine, neutralized with 2 M HCl, extracted with DCM, then the combined organic phases were dried over Na$_2$SO$_4$ and concentrated under reduced pressure. The residue was purified via preparative reversed phase chromatography using 25 mM aqueous NH$_4$HCO$_3$ solution and MeCN as eluents to give Example 377. HRMS calculated for $C_{38}H_{40}Cl_2N_4O_7S$: 766.1995. found 767.2095 (M+H).

General Procedure (Xa)
Step A:
1 eq. ethyl (2R)-2-[(5S$_a$)-5-[3-chloro-2-methyl-4-[2-(4-methylpiperazin-1-yl)ethoxy] phenyl]-6-(4-fluoro-3-methoxy-phenyl)thieno[2,3-d]pyrimidin-4-yl]oxy-3-(2-hydroxyphenyl)propanoate (Preparation 8g), 2 eq. of the appropriate alcohol and 2 eq. triphenyl phosphine were dissolved in dry toluene (5 mL/mmol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.
Step B:
The obtained intermediate was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, extracted with DCM. The combined organic phases were dried over Na$_2$SO$_4$, concentrated under reduced pressure and purified via preparative reversed phase chromatography using 25 mM aqueous NH$_4$HCO$_3$ solution and MeCN as eluents.

Example 378 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-(2-methoxyphenyl)propanoic acid Using General Procedure (Xa) and methanol as the appropriate alcohol, Example 378 was obtained. HRMS calculated for C$_{37}$H$_{38}$ClFN$_4$O$_6$S: 720.2185. found 721.2243 (M+H).

Example 379 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-{2-[(2R)-tetrahydrofuran-2-ylmethoxy]phenyl}propanoic acid Using General Procedure (Xa) and [(2R)-tetrahydrofuran-2-yl]methanol as the appropriate alcohol, Example 379 was obtained. HRMS calculated for C$_{41}$H$_{44}$ClFN$_4$O$_7$S: 790.2603. found 791.2670 (M+H).

Example 380 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-[2-(2,2,2-trifluoroethoxy)phenyl]propanoic acid Step A:
221 mg ethyl (2R)-2-[(5S$_a$)-5-[3-chloro-2-methyl-4-[2-(4-methylpiperazin-1-yl)ethoxy] phenyl]-6-(4-fluoro-3-methoxy-phenyl)thieno[2,3-d]pyrimidin-4-yl]oxy-3-(2-hydroxyphenyl)propanoate (Preparation 8g) (0.3 mmol) and 138 mg K$_2$CO$_3$ (1.0 mmol) were dissolved in 2 mL DMF, then 232 mg 2,2,2-trifluoroethyl trifluoromethanesulfonate (1.0 mmol) was added. The mixture was stirred at room temperature under nitrogen until no further conversion was observed. Then it was diluted with brine, neutralized with 2 M HCl, extracted with DCM. The combined organic phases were dried over Na$_2$SO$_4$, filtered and concentrated under reduced pressure.
Step B:
The obtained intermediate was dissolved in 8 mL dioxane-water 1:1 and 150 mg LiOH×H$_2$O (3.57 mmol) was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 5 mM aqueous NH$_4$HCO$_3$ solution and MeCN as eluents to obtain Example 380. HRMS calculated for C$_{38}$H$_{37}$ClF$_4$N$_4$O$_6$S: 788.2058. found 789.2133 (M+H).

Example 381 (2R)-2-{[(5S$_a$)-5-{3-chloro-2-methyl-4-[2-(4-methylpiperazin-1-yl)ethoxy] phenyl}-6-(4-fluoro-3-methoxyphenyl)thieno[2,3-d]pyrimidin-4-yl]oxy}-3-[2-(pyridin-2-ylmethoxy)phenyl]propanoic acid Using General Procedure (Xa) and 2-pyridylmethanol as the appropriate alcohol, Example 381 was obtained. HRMS calculated for C$_{42}$H$_{41}$ClFN$_5$O$_6$S: 797.2450. found 399.6308 (M+2H).

Example 382 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-(2-{[2-(trifluoromethyl)pyrimidin-4-yl]methoxy}phenyl)propanoic acid Using General Procedure (Xa) and [2-(trifluoromethyl)pyrimidin-4-yl]methanol (Preparation 9bj) as the appropriate alcohol, Example 382 was obtained. HRMS calculated for C$_{42}$H$_{39}$ClF$_4$N$_6$O$_6$S: 866.2276. found 867.2352 (M+H).

Example 383 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-{2-[(2-methoxypyrimidin-4-yl)methoxy]phenyl}propanoic acid Using General Procedure (Xa) and (2-methoxypyrimidin-4-yl)methanol as the appropriate alcohol, Example 383 was obtained. HRMS calculated for C$_{42}$H$_{42}$ClFN$_6$O$_7$S: 828.2508. found 415.1343 (M+2H).

Example 384 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-{2-[(1-ethyl-1H-pyrazol-5-yl)methoxy]phenyl}propanoic acid Using General Procedure (Xa) and (1-ethyl-1H-pyrazol-5-yl)methanol (Preparation 9da) as the appropriate alcohol, Example 384 was obtained. HRMS calculated for C$_{42}$H$_{44}$ClFN$_6$O$_6$S: 814.2716. found 408.1436 (M+2H).

Example 385 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-{2-[(1-propyl-1H-pyrazol-5-yl)methoxy]phenyl}propanoic acid Using General Procedure (Xa) and (1-propyl-1H-pyrazol-5-yl)methanol (Preparation 9 db) as the appropriate alcohol, Example 385 was obtained. HRMS calculated for C$_{43}$H$_{46}$ClFN$_6$O$_6$S: 828.2872. found 415.1536 (M+2H).

Example 386 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-[2-(pyrazin-2-ylmethoxy)phenyl]propanoic acid Using General Procedure (Xa) and pyrazin-2-ylmethanol as the appropriate alcohol, Example 386 was obtained. HRMS calculated for $C_{41}H_{40}ClFN_6O_6S$: 798.2403. found 799.2474 (M+H).

Example 387 (2R)-2-{[(5S$_a$)-5-{3-chloro-2-methyl-4-[2-(4-methylpiperazin-1-yl)ethoxy]phenyl}-6-(4-fluoro-3-methoxyphenyl)thieno[2,3-d]pyrimidin-4-yl]oxy}-3-[2-(2-methoxyethoxy)phenyl]propanoic acid Using General Procedure (Xa) and 2-methoxyethanol as the appropriate alcohol, Example 387 was obtained. HRMS calculated for $C_{39}H_{42}ClFN_4O_7S$: 764.2447. found 765.2502 (M+H).

General Procedure (XIa)
Step A:
1 eq. methyl (2R)-2-[(5S$_a$)-5-(3-chloro-4-hydroxy-2-methyl-phenyl)-6-ethyl-thieno[2,3-d]pyrimidin-4-yl]oxy-3-phenyl-propanoate (Preparation 6i), 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.
Step B:
The obtained intermediate was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, extracted with DCM, and the combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XIb)
Step A:
1 eq. methyl (2R)-2-[(5R$_a$)-5-(3-chloro-4-hydroxy-2-methyl-phenyl)-6-ethyl-thieno[2,3-d]pyrimidin-4-yl]oxy-3-phenyl-propanoate (Preparation 6n), 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.
Step B:
The obtained intermediate was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, extracted with DCM, and the combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XIc)
Step A:
1 eq. methyl (2R)-2-[6-ethyl-(5S$_a$)-5-(4-hydroxy-2-methyl-phenyl)thieno[2,3-d]pyrimidin-4-yl]oxy-3-phenyl-propanoate (Preparation 6j), 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.
Step B:
The obtained intermediate was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, extracted with DCM, and the combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XId)
Step A:
1 eq. methyl (2R)-2-[6-ethyl-(5R$_a$)-5-(4-hydroxy-2-methyl-phenyl)thieno[2,3-d]pyrimidin-4-yl]oxy-3-phenyl-propanoate (Preparation 6o), 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.
Step B:
The obtained intermediate was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, extracted with DCM, and the combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XIe)
Step A:
1 eq. phenol derivative, 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.
Step B:
The obtained intermediate was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, extracted with DCM, and the combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XIf)
1 eq. ester was dissolved in dioxane-water 1:1 (10 mL/mmol) and 10 eq. LiOH×H$_2$O was added and the mixture was stirred at room temperature until no further conversion was observed. Then it was diluted with brine, neutralized with 2 M HCl, extracted with DCM, and the combined organic phases were dried over $Na_2SO_4$, filtered and concentrated under reduced pressure. If necessary it was purified via preparative reversed phase chromatography using MeCN and 25 mM aqueous $NH_4HCO_3$ solution as eluents.

Example 388 (2R)-2-{[(5$S_a$)-5-(3-chloro-4-hydroxy-2-methylphenyl)-6-ethylthieno[2,3-d]pyrimidin-4-yl]oxy}-3-phenylpropanoic acid Methyl (2R)-2-[(5$S_a$)-5-(3-chloro-4-hydroxy-2-methylphenyl)-6-ethyl-thieno[2,3-d] pyrimidin-4-yl]oxy-3-phenyl-propanoate (Preparation 6i) was hydrolyzed according to General Procedure (XIf) to give Example 388. HRMS calculated for $C_{24}H_{21}ClN_2O_4S$: 468.0911. found 469.0997 (M+H).

Example 389 (2R)-2-{[(5$R_a$)-5-(3-chloro-4-hydroxy-2-methylphenyl)-6-ethylthieno[2,3-d]pyrimidin-4-yl]oxy}-3-phenylpropanoic acid Methyl (2R)-2-[(5$R_a$)-5-(3-chloro-4-hydroxy-2-methylphenyl)-6-ethyl-thieno[2,3-d] pyrimidin-4-yl]oxy-3-phenyl-propanoate (Preparation 6n) was hydrolyzed according to General Procedure (XIf) to give Example 389. HRMS calculated for $C_{24}H_{21}ClN_2O_4S$: 468.0911. found 469.0982 (M+H).

Example 390 (2R)-2-[((5$S_a$)-5-{3-chloro-4-[2-(dimethylamino)-2-oxoethoxy]-2-methylphenyl}-6-ethylthieno[2,3-d]pyrimidin-4-yl)oxy]-3-phenylpropanoic acid Using General Procedure (XIa) and 2-hydroxy-N,N-dimethyl-acetamide as the appropriate alcohol, Example 390 was obtained. HRMS calculated for $C_{28}H_{28}ClN_3O_5S$: 553.1438. found 554.1538 (M+H).

Example 391 (2R)-2-[((5$S_a$)-5-{3-chloro-2-methyl-4-[2-oxo-2-(pyrrolidin-1-yl)ethoxy]phenyl}-6-ethyl-thieno[2,3-d]pyrimidin-4-yl)oxy]-3-phenylpropanoic acid Using General Procedure (XIa) and 2-hydroxy-1-pyrrolidin-1-yl-ethanone as the appropriate alcohol, Example 391 was obtained. HRMS calculated for $C_{30}H_{30}ClN_3O_5S$: 579.1595. found 580.1673 (M+H).

Example 392 (2R)-2-[((5$S_a$)-5-{3-chloro-2-methyl-4-[2-(4-methylpiperazin-1-yl)-2-oxoethoxy]phenyl}-6-ethylthieno[2,3-d]pyrimidin-4-yl)oxy]-3-phenyl-propanoic acid Using General Procedure (XIa) and 2-hydroxy-1-(4-methylpiperazin-1-yl)ethanone as the appropriate alcohol, Example 392 was obtained. HRMS calculated for $C_{31}H_{33}ClN_4O_5S$: 608.1860. found 609.1948 (M+H).

Example 393 (2R)-2-[((5$S_a$)-5-{3-chloro-2-methyl-4-[2-(morpholin-4-yl)-2-oxoethoxy]phenyl}-6-ethyl-thieno[2,3-d]pyrimidin-4-yl)oxy]-3-phenylpropanoic acid Using General Procedure (XIa) and 2-hydroxy-1-(morpholin-4-yl)ethanone as the appropriate alcohol, Example 393 was obtained. HRMS calculated for $C_{30}H_{30}ClN_3O_6S$: 595.1544. found 596.1626 (M+H).

Example 394 (2R)-2-({(5$S_a$)-5-[4-(benzyloxy)-3-chloro-2-methylphenyl]-6-ethylthieno[2,3-d]pyrimidin-4-yl}oxy)-3-phenylpropanoic acid Using General Procedure (XIa) and phenylmethanol as the appropriate alcohol, Example 394 was obtained. HRMS calculated for $C_{31}H_{27}ClN_2O_4S$: 558.1380. found 559.1465 (M+H).

Example 395 (2R)-2-({(5$S_a$)-5-[3-chloro-2-methyl-4-(pyridin-4-ylmethoxy)phenyl]-6-ethylthieno[2,3-d]pyrimidin-4-yl}oxy)-3-phenylpropanoic acid Using General Procedure (XIa) and 4-pyridylmethanol as the appropriate alcohol, Example 395 was obtained. HRMS calculated for $C_{30}H_{26}ClN_3O_4S$: 559.1333. found 560.1396 (M+H).

Example 396 (2R)-2-[((5$S_a$)-5-{3-chloro-2-methyl-4-[2-(pyridin-3-yl)ethoxy]phenyl}-6-ethylthieno[2,3-d]pyrimidin-4-yl)oxy]-3-phenylpropanoic acid Using General Procedure (XIa) and 2-(3-pyridyl)ethanol as the appropriate alcohol, Example 396 was obtained. HRMS calculated for $C_{31}H_{28}ClN_3O_4S$: 573.1489. found 574.1559 (M+H).

Example 397 (2R)-2-[((5$S_a$)-5-{3-chloro-2-methyl-4-[2-(pyridin-4-yl)ethoxy]phenyl}-6-ethylthieno[2,3-d]pyrimidin-4-yl)oxy]-3-phenylpropanoic acid Using General Procedure (XIa) and 2-(4-pyridyl)ethanol as the appropriate alcohol, Example 397 was obtained. HRMS calculated for $C_{31}H_{28}ClN_3O_4S$: 573.1489. found 574.1562 (M+H).

Example 398 (2R)-2-{[(5$S_a$)-5-(4-butoxy-3-chloro-2-methylphenyl)-6-ethylthieno[2,3-d] pyrimidin-4-yl]oxy}-3-phenylpropanoic acid Using General Procedure (XIa) and butan-1-ol as the appropriate alcohol, Example 398 was obtained. HRMS calculated for $C_{28}H_{29}ClN_2O_4S$: 524.1537. found 525.1619 (M+H).

Example 399 (2R)-2-[((5$S_a$)-5-{3-chloro-2-methyl-4-[3-(pyridin-4-yl)propoxy]phenyl}-6-ethylthieno[2,3-d]pyrimidin-4-yl)oxy]-3-phenylpropanoic acid Using General Procedure (XIa) and 3-(4-pyridyl)propan-1-ol as the appropriate alcohol, Example 399 was obtained. HRMS calculated for $C_{32}H_{30}ClN_3O_4S$: 587.1646. found 588.1732 (M+H).

Example 400 (2R)-2-[((5$S_a$)-5-{3-chloro-4-[3-(dimethylamino)propoxy]-2-methylphenyl}-6-ethylthieno[2,3-d]pyrimidin-4-yl)oxy]-3-phenylpropanoic acid Using General Procedure (XIa) and 3-(dimethylamino)propan-1-ol as the appropriate alcohol, Example 400 was obtained. HRMS calculated for $C_{29}H_{32}ClN_3O_4S$: 553.1802. found 554.1891 (M+H).

Example 401 (2R)-2-[((5S$_a$)-5-{3-chloro-2-methyl-4-[3-(2-oxopyrrolidin-1-yl)propoxy]phenyl}-6-ethyl-thieno[2,3-d]pyrimidin-4-yl)oxy]-3-phenylpropanoic acid Using General Procedure (XIa) and 1-(3-hydroxypropyl)pyrrolidin-2-one as the appropriate alcohol, Example 401 was obtained. HRMS calculated for C$_{31}$H$_{32}$ClN$_3$O$_5$S: 593.1751. found 594.1826 (M+H).

Example 402 (2R)-2-[((5S$_a$)-5-{3-chloro-2-methyl-4-[3-(4-methylpiperazin-1-yl)propoxy]phenyl}-6-ethylthieno[2,3-d]pyrimidin-4-yl)oxy]-3-phenylpropanoic acid Using General Procedure (XIa) and 3-(4-methylpiperazin-1-yl)propan-1-ol as the appropriate alcohol, Example 402 was obtained. HRMS calculated for C$_{32}$H$_{37}$ClN$_4$O$_4$S: 608.2224. found 609.2304 (M+H).

Example 403 (2R)-2-[((5S$_a$)-5-{3-chloro-4-[3-(1H-imidazol-1-yl)propoxy]-2-methylphenyl}-6-ethylthieno[2,3-d]pyrimidin-4-yl)oxy]-3-phenylpropanoic acid Using General Procedure (XIa) and 3-(1H-imidazol-1-yl)propan-1-ol as the appropriate alcohol, Example 403 was obtained. HRMS calculated for C$_{30}$H$_{29}$ClN$_4$O$_4$S: 576.1598. found 577.1698 (M+H).

Example 404 (2R)-2-{[(5S$_a$)-5-(3-chloro-4-{3-[(ethylcarbamoyl)amino]propoxy}-2-methylphenyl)-6-ethylthieno[2,3-d]pyrimidin-4-yl]oxy}-3-phenylpropanoic acid Using General Procedure (XIa) and 1-ethyl-3-(3-hydroxypropyl)urea as the appropriate alcohol, Example 404 was obtained. HRMS calculated for C$_{30}$H$_{33}$ClN$_4$O$_5$S: 596.1860. found 597.1943 (M+H).

Example 405 (2R)-2-({(5S$_a$)-5-[3-chloro-4-(3-hydroxypropoxy)-2-methylphenyl]-6-ethylthieno[2,3-d]pyrimidin-4-yl}oxy)-3-phenylpropanoic acid Using General Procedure (XIa) and propane-1,3-diol as the appropriate alcohol, Example 405 was obtained. HRMS calculated for C$_{27}$H$_{27}$ClN$_2$O$_5$S: 526.1329. found 527.1402 (M+H).

Example 406 (2R)-2-[((5S$_a$)-5-{3-chloro-2-methyl-4-[3-(methylsulfonyl)propoxy]phenyl}-6-ethylthieno[2,3-d]pyrimidin-4-yl)oxy]-3-phenylpropanoic acid Using General Procedure (XIa) and 3-methylsulfonylpropan-1-ol as the appropriate alcohol, Example 406 was obtained. HRMS calculated for C$_{28}$H$_{29}$ClN$_2$O$_6$S$_2$: 588.1156. found 589.1242 (M+H).

Example 407 (2R)-2-[((5S$_a$)-5-{3-chloro-4-[2-(dimethylamino)ethoxy]-2-methylphenyl}-6-ethylthieno[2,3-d]pyrimidin-4-yl)oxy]-3-phenylpropanoic acid Using General Procedure (XIa) and 2-(dimethylamino)ethanol as the appropriate alcohol, Example 407 was obtained. HRMS calculated for C$_{28}$H$_{30}$ClN$_3$O$_4$S: 539.1646. found 540.1742 (M+H).

Example 408 (2R)-2-[((5R$_a$)-5-{3-chloro-4-[2-(dimethylamino)ethoxy]-2-methylphenyl}-6-ethylthieno[2,3-d]pyrimidin-4-yl)oxy]-3-phenylpropanoic acid Using General Procedure (XIb) and 2-(dimethylamino)ethanol as the appropriate alcohol, Example 408 was obtained. HRMS calculated for C$_{28}$H$_{30}$ClN$_3$O$_4$S: 539.1646. found 540.1744 (M+H).

Example 409 (2R)-2-[((5S$_a$)-5-{4-[2-(dimethylamino)ethoxy]-2-methylphenyl}-6-ethylthieno[2,3-d]pyrimidin-4-yl)oxy]-3-phenylpropanoic acid Using General Procedure (XIc) and 2-(dimethylamino)ethanol as the appropriate alcohol, Example 409 was obtained. HRMS calculated for C$_{28}$H$_{31}$N$_3$O$_4$S: 505.2035. found 506.2096 (M+H).

Example 410 (2R)-2-[((5R$_a$)-5-{4-[2-(dimethylamino)ethoxy]-2-methylphenyl}-6-ethylthieno[2,3-d]pyrimidin-4-yl)oxy]-3-phenylpropanoic acid Using General Procedure (XId) and 2-(dimethylamino)ethanol as the appropriate alcohol, Example 410 was obtained. HRMS calculated for C$_{28}$H$_{31}$N$_3$O$_4$S: 505.2035. found 506.2109 (M+H).

Example 411 (2R)-2-{[(5S$_a$)-5-(3-chloro-4-{2-[(2-hydroxyethyl)(methyl)amino]ethoxy}-2-methylphenyl)-6-ethylthieno[2,3-d]pyrimidin-4-yl]oxy}-3-phenylpropanoic acid Using General Procedure (XIa) and 2-[2-hydroxyethyl(methyl)amino]ethanol as the appropriate alcohol, Example 411 was obtained. HRMS calculated for C$_{29}$H$_{32}$ClN$_3$O$_5$S: 569.1751. found 570.1837 (M+H).

Example 412 (2R)-2-{[(5S$_a$)-5-(4-{2-[bis(2-hydroxyethyl)amino]ethoxy}-3-chloro-2-methylphenyl)-6-ethylthieno[2,3-d]pyrimidin-4-yl]oxy}-3-phenylpropanoic acid Using General Procedure (XIa) and 2-[bis(2-hydroxyethyl)amino]ethanol as the appropriate alcohol, Example 412 was obtained. HRMS calculated for C$_{30}$H$_{34}$ClN$_3$O$_6$S: 599.1857. found 600.1939 (M+H).

Example 413 (2R)-2-[((5S$_a$)-5-{3-chloro-4-[2-(4-hydroxypiperidin-1-yl)ethoxy]-2-methylphenyl}-6-ethylthieno[2,3-d]pyrimidin-4-yl)oxy]-3-phenylpropanoic acid Using General Procedure (XIa) and 1-(2-hydroxyethyl)piperidin-4-ol as the appropriate alcohol, Example 413 was obtained. HRMS calculated for C$_{31}$H$_{34}$ClN$_3$O$_5$S: 595.1908. found 596.1976 (M+H).

Example 414 (2R)-2-[((5R$_a$)-5-{3-chloro-2-methyl-4-[2-(4-methylpiperazin-1-yl)ethoxy]phenyl}-6-ethylthieno[2,3-d]pyrimidin-4-yl)oxy]-3-phenylpropanoic acid Using General Procedure (XIb) and 2-(4-methylpiperazin-1-yl)ethanol as the appropriate alcohol, Example 414 was obtained. HRMS calculated for C$_{31}$H$_{35}$ClN$_4$O$_4$S: 594.2068. found 595.2138 (M+H).

Example 415 (2R)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]-3-phenylpropanoic acid Using General Procedure (XIa) and 2-(4-methylpiperazin-1-yl)ethanol as the appropriate alcohol, Example 415 was obtained. HRMS calculated for $C_{31}H_{35}ClN_4O_4S$: 594.2068. found 595.2148 (M+H).

Example 416 (2R)-2-[(6-ethyl-(5R$_a$)-5-{2-methyl-4-[2-(4-methylpiperazin-1-yl)ethoxy]phenyl}thieno[2,3-d]pyrimidin-4-yl)oxy]-3-phenylpropanoic acid Using General Procedure (XId) and 2-(4-methylpiperazin-1-yl)ethanol as the appropriate alcohol, Example 416 was obtained. HRMS calculated for $C_{31}H_{36}N_4O_4S$: 560.2457. found 561.2524 (M+H).

Example 417 (2R)-2-[(6-ethyl-(5S$_a$)-5-{2-methyl-4-[2-(4-methylpiperazin-1-yl)ethoxy]phenyl}thieno[2,3-d]pyrimidin-4-yl)oxy]-3-phenylpropanoic acid Using General Procedure (XIc) and 2-(4-methylpiperazin-1-yl)ethanol as the appropriate alcohol, Example 417 was obtained. HRMS calculated for $C_{31}H_{36}N_4O_4S$: 560.2457. found 561.2536 (M+H).

Example 418 (2R)-2-[((5S$_a$)-5-{3-chloro-4-[2-(1H-imidazol-1-yl)ethoxy]-2-methylphenyl}-6-ethylthieno[2,3-d]pyrimidin-4-yl)oxy]-3-phenylpropanoic acid Using General Procedure (XIa) and 2-(1H-imidazol-1-yl)ethanol as the appropriate alcohol, Example 418 was obtained. HRMS calculated for $C_{29}H_{27}ClN_4O_4S$: 562.1442. found 563.1537 (M+H).

Example 419 (2R)-2-[((5S$_a$)-5-{3-chloro-2-methyl-4-[2-(2-oxoimidazolidin-1-yl)ethoxy]phenyl}-6-ethylthieno[2,3-d]pyrimidin-4-yl)oxy]-3-phenylpropanoic acid Using General Procedure (XIa) and 1-(2-hydroxyethyl)imidazolidin-2-one as the appropriate alcohol, Example 419 was obtained. HRMS calculated for $C_{29}H_{29}ClN_4O_5S$: 580.1547. found 581.1613 (M+H).

Example 420 (2R)-2-[((5S$_a$)-5-{3-chloro-2-methyl-4-[2-(morpholin-4-yl)ethoxy]phenyl}-6-ethylthieno[2,3-d]pyrimidin-4-yl)oxy]-3-phenylpropanoic acid Using General Procedure (XIa) and 2-(morpholin-4-yl)ethanol as the appropriate alcohol, Example 420 was obtained. HRMS calculated for $C_{30}H_{32}ClN_3O_5S$: 581.1751. found 582.1847 (M+H).

Example 421 (2R)-2-[((5R$_a$)-5-{3-chloro-2-methyl-4-[2-(morpholin-4-yl)ethoxy]phenyl}-6-ethylthieno[2,3-d]pyrimidin-4-yl)oxy]-3-phenylpropanoic acid Using General Procedure (XIb) and 2-(morpholin-4-yl)ethanol as the appropriate alcohol, Example 421 was obtained. HRMS calculated for $C_{30}H_{32}ClN_3O_5S$: 581.1751. found 582.1853 (M+H).

Example 422 (2R)-2-[((5S$_a$)-5-{4-[2-(acetylamino)ethoxy]-3-chloro-2-methylphenyl}-6-ethylthieno[2,3-d]pyrimidin-4-yl)oxy]-3-phenylpropanoic acid Using General Procedure (XIa) and N-(2-hydroxyethyl)acetamide as the appropriate alcohol, Example 422 was obtained. HRMS calculated for $C_{28}H_{28}ClN_3O_5S$: 553.1438. found 554.1511 (M+H).

Example 423 (2R)-2-({(5S$_a$)-5-[3-chloro-4-(2-hydroxyethoxy)-2-methylphenyl]-6-ethylthieno[2,3-d]pyrimidin-4-yl}oxy)-3-phenylpropanoic acid Using General Procedure (XIa) and ethylene glycol as the appropriate alcohol, Example 423 was obtained. HRMS calculated for $C_{26}H_{25}ClN_2O_5S$: 512.1173. found 513.1256 (M+H).

Example 424 (2R)-2-({(5S$_a$)-5-[3-chloro-4-(2-methoxyethoxy)-2-methylphenyl]-6-ethylthieno[2,3-d]pyrimidin-4-yl}oxy)-3-phenylpropanoic acid Using General Procedure (XIa) and 2-methoxyethanol as the appropriate alcohol, Example 424 was obtained. HRMS calculated for $C_{27}H_{27}ClN_2O_5S$: 526.1329. found 527.1400 (M+H).

Example 425 (2R)-2-[((5S$_a$)-5-{3-chloro-4-[2-(2-methoxyethoxy)ethoxy]-2-methylphenyl}-6-ethylthieno[2,3-d]pyrimidin-4-yl)oxy]-3-phenylpropanoic acid Using General Procedure (XIa) and 2-(2-methoxyethoxy)ethanol as the appropriate alcohol, Example 425 was obtained. HRMS calculated for $C_{29}H_{31}ClN_2O_6S$: 570.1591. found 571.1690 (M+H).

Example 426 (2R)-2-{[(5S$_a$)-5-(3-chloro-4-hydroxy-2-methyl-5-nitrophenyl)-6-ethylthieno[2,3-d]pyrimidin-4-yl]oxy}-3-phenylpropanoic acid Methyl (2R)-2-[(5S$_a$)-5-(3-chloro-4-hydroxy-2-methyl-5-nitro-phenyl)-6-ethyl-thieno[2,3-d]pyrimidin-4-yl]oxy-3-phenyl-propanoate (Preparation 15a) was hydrolyzed according to General Procedure (XIf) to give Example 426. HRMS calculated for $C_{24}H_{20}ClN_3O_6S$: 513.0761. found 514.0840 (M+H).

Example 427 (2R)-2-{[(5S$_a$)-5-(5-bromo-3-chloro-4-hydroxy-2-methylphenyl)-6-ethylthieno[2,3-d]pyrimidin-4-yl]oxy}-3-phenylpropanoic acid Methyl (2R)-2-[(5S$_a$)-5-(5-bromo-3-chloro-4-hydroxy-2-methyl-phenyl)-6-ethyl-thieno[2,3-d]pyrimidin-4-yl]oxy-3-phenyl-propanoate (Preparation 15f) was hydrolyzed according to General Procedure (XIf) to give Example 427. HRMS calculated for $C_{24}H_{20}BrClN_2O_4S$: 546.0016. found 547.0106 (M+H).

Example 428 (2R)-2-{[(5S$_a$)-5-(3,5-dichloro-4-hydroxy-2-methylphenyl)-6-ethylthieno[2,3-d]pyrimidin-4-yl]oxy}-3-phenylpropanoic acid Methyl (2R)-2-[(5S$_a$)-5-(3,5-dichloro-4-hydroxy-2-methyl-phenyl)-6-ethyl-thieno[2,3-d]pyrimidin-4-yl]oxy-3-phenyl-propanoate (Preparation 15e) was hydrolyzed according to General Procedure (XIf) to give Example 428. HRMS calculated for $C_{24}H_{20}Cl_2N_2O_4S$: 502.0521. found 503.0582 (M+H).

Example 429 (2R)-2-{[(5R$_a$)-5-(3,5-dichloro-4-hydroxy-2-methylphenyl)-6-ethylthieno[2,3-d]pyrimidin-4-yl]oxy}-3-phenylpropanoic acid 40 mg methyl (2R)-2-[6-ethyl-(5R$_a$)-5-(4-hydroxy-2-methyl-phenyl)thieno[2,3-d]pyrimidin-4-yl]oxy-3-phenyl-propanoate (Preparation 6o) (0.089 mmol) was dissolved in 2 mL THF and 26 mg NCS (0.193 mmol) was added. The mixture was stirred at 55° C. until no further conversion was observed. Then the volatiles were evaporated under reduced pressure and the crude intermediate was purified via flash chromatography using heptane and EtOAc as eluents. The obtained intermediate was hydrolyzed according to General Procedure (XIf) to give Example 429. HRMS calculated for $C_{24}H_{20}Cl_2N_2O_4S$: 502.0521. found 503.0587 (M+H).

Example 430 (2R)-2-[((5S$_a$)-5-{3-chloro-4-hydroxy-2-methyl-5-[(4-methylpiperazin-1-yl)methyl]phenyl}-6-ethylthieno[2,3-d]pyrimidin-4-yl)oxy]-3-phenylpropanoic acid 483 mg methyl (2R)-2-[(5S$_a$)-5-(3-chloro-4-hydroxy-2-methyl-phenyl)-6-ethyl-thieno[2,3-d]pyrimidin-4-yl]oxy-3-phenyl-propanoate (Preparation 6i) (1.0 mmol) and 140 mg hexamethylenetetramine (1.0 mmol) were dissolved in 10 mL TFA and stirred at 90° C. for 3 hours. The cooled reaction mixture was poured onto 100 mL icy water and the precipitated solid was filtered and dried. Then it was dissolved in 20 mL EtOH, 167 μL 1-methylpiperazine (1.5 mmol) and 636 mg Na(OAc)$_3$H (3.0 mmol) were added and the mixture was stirred at room temperature until no further conversion was observed. Then it was diluted with water, extracted with DCM, combined organic phases were dried over Na$_2$SO$_4$, filtered and concentrated under reduced pressure. The crude intermediate was purified via reversed phase chromatography using aqueous 0.1% TFA solution and MeCN as eluents. The intermediate obtained in Step A was hydrolyzed according to General Procedure (XIf) to give Example 430. HRMS calculated for $C_{30}H_{33}ClN_4O_4S$: 580.1911. found 581.1972 (M+H).

Example 431 (2R)-2-{[(5S$_a$)-5-(5-amino-3-chloro-4-hydroxy-2-methylphenyl)-6-ethylthieno[2,3-d]pyrimidin-4-yl]oxy}-3-phenylpropanoic acid Methyl (2R)-2-[(5S$_a$)-5-(5-amino-3-chloro-4-hydroxy-2-methyl-phenyl)-6-ethyl-thieno[2,3-d]pyrimidin-4-yl]oxy-3-phenyl-propanoate (Preparation 15b) was hydrolyzed according to General Procedure (XIf) to give Example 431. HRMS calculated for $C_{24}H_{22}ClN_3O_4S$: 483.1020. found 484.1083 (M+H).

Example 432 (2R)-2-({(5S$_a$)-5-[3-chloro-4-hydroxy-2-methyl-5-(4-methylpiperazin-1-yl)phenyl]-6-ethylthieno[2,3-d]pyrimidin-4-yl}oxy)-3-phenyl-propanoic acid 1.00 g immobilized PPh$_3$ (3.00 mmol) and 761 mg iodine (3.00 mmol) were dissolved in 5 mL DCM and stirred for 15 minutes, then 272 mg imidazole (4.00 mmol) was added, and the mixture was stirred for 10 minutes. Then 115 μL 2-[2-hydroxyethyl(methyl)amino]ethanol (1.00 mmol) was added, and the mixture was stirred for 1 hour. Then it was filtered, the filtrate was washed with saturated Na$_2$S$_2$O$_3$ solution and brine, dried over Na$_2$SO$_4$, filtered and concentrated under reduced pressure. To the formed 2-iodo-N-(2-iodoethyl)-N-methyl-ethanamine 100 mg methyl (2R)-2-[(5S$_a$)-5-(5-amino-3-chloro-4-hydroxy-2-methyl-phenyl)-6-ethyl-thieno[2,3-d]pyrimidin-4-yl]oxy-3-phenyl-propanoate (Preparation 15b) (0.20 mmol), 42 mg NaHCO$_3$ (0.50 mmol) and 2 mL EtOH were added and the mixture was stirred at reflux temperature overnight. Then it was diluted with EtOAc, washed with water and brine. The combined organic phases were dried over Na$_2$SO$_4$, filtered and concentrated under reduced pressure. The crude intermediate was purified via flash chromatography, using EtOAc and MeOH as eluents. The obtained intermediate was hydrolyzed according to General Procedure (XIf) to give Example 432. HRMS calculated for $C_{29}H_{31}ClN_4O_4S$: 566.1755. found 567.1794 (M+H).

Example 433 (2R)-2-({(5S$_a$)-5-[3-chloro-5-(formylamino)-4-hydroxy-2-methylphenyl]-6-ethylthieno[2,3-d]pyrimidin-4-yl}oxy)-3-phenylpropanoic acid 35 mg methyl (2R)-2-[(5S$_a$)-5-(5-amino-3-chloro-4-hydroxy-2-methyl-phenyl)-6-ethyl-thieno[2,3-d]pyrimidin-4-yl]oxy-3-phenyl-propanoate (Preparation 15b) (0.07 mmol) was dissolved in 0.5 mL dry toluene under N$_2$. 23 μL triethyl-orthoformate (0.136 mmol) was added and the mixture was stirred at 100° C. for 2.5 hours. Then the volatiles were evaporated under reduced pressure and the residue was purified via flash chromatography, using heptane and EtOAc as eluents. The obtained intermediate was hydrolyzed according to General Procedure (XIf) to give Example 433. HRMS calculated for $C_{25}H_{22}ClN_3O_5S$: 511.0969. found 512.1048 (M+H).

Example 434 (2R)-2-[((5S$_a$)-5-{3-chloro-4-methoxy-2-methyl-5-[(4-methylpiperazin-1-yl)methyl]phenyl}-6-ethylthieno[2,3-d]pyrimidin-4-yl)oxy]-3-phenylpropanoic acid Step A:
408 mg methyl (2R)-2-[(5S$_a$)-5-(5-bromo-3-chloro-4-hydroxy-2-methyl-phenyl)-6-ethyl-thieno[2,3-d]pyrimidin-4-yl]oxy-3-phenyl-propanoate (Preparation 15f) (0.73 mmol) was dissolved in 4 mL MeOH, then 444 mg immobilized PPh$_3$ (1.33 mmol) and 306 mg ditertbutyl azodicarboxylate (1.33 mmol) were added and the mixture was stirred at 50° C. under nitrogen until no further conversion was observed. Then the mixture was filtered, the filtrate was concentrated under reduced pressure and the residue was purified via flash chromatography using heptane and EtOAc as eluents to obtain methyl (2R)-2-[(5S$_a$)-5-(5-bromo-3-chloro-4-methoxy-2-methyl-phenyl)-6-ethyl-thieno[2,3-d]pyrimidin-4-yl]oxy-3-phenyl-propanoate.
Step B:
195 mg of the bromo derivative (0.34 mmol) synthesized in step A was dissolved in 3 mL THF, then 309 mg potassium 1-methyl-4-trifluoroboratomethylpiperazine (1.70 mmol), 8 mg Pd(OAc)$_2$ (0.034 mmol), 28 mg SPhos (0.068 mmol), 665 mg Cs$_2$CO$_3$ (2.04 mmol) and 0.3 mL water were added, and the mixture was heated to 90° C. for 10 minutes via microwave irradiation. Then the volatiles were evaporated under reduced pressure, the residue was diluted with brine, extracted DCM, and the combined organic phases were dried over Na$_2$SO$_4$, filtered and concentrated under reduced pressure. The obtained intermediate was hydrolyzed according to General Procedure (XIf) to give Example 434. HRMS calculated for $C_{31}H_{35}ClN_4O_4S$: 594.2068. found 595.2145 (M+H).

Example 435 (2R)-2-[((5S$_a$)-5-{3-chloro-2-methyl-4-[2-(4-methylpiperazin-1-yl)ethoxy]-5-nitrophenyl}-6-ethylthieno[2,3-d]pyrimidin-4-yl)oxy]-3-phenylpropanoic acid Using General Procedure (XIe), methyl (2R)-2-[(5S$_a$)-5-(3-chloro-4-hydroxy-2-methyl-5-nitro-phenyl)-6-ethyl-thieno[2,3-d]pyrimidin-4-yl]oxy-3-phenyl-propanoate (Preparation 15a) as the phenol and 2-(4-methylpiperazin-1-yl)ethanol as the appropriate alcohol, Example 435 was obtained. HRMS calculated for $C_{31}H_{34}ClN_5O_6S$: 639.1918. found 640.1984 (M+H).

Example 436 (2R)-2-[((5S$_a$)-5-{3,5-dichloro-2-methyl-4-[2-(4-methylpiperazin-1-yl)ethoxy]phenyl}-6-ethylthieno[2,3-d]pyrimidin-4-yl)oxy]-3-phenylpropanoic acid Using General Procedure (XIe) with methyl (2R)-2-[(5S$_a$)-5-(3,5-dichloro-4-hydroxy-2-methyl-phenyl)-6-ethyl-thieno[2,3-d]pyrimidin-4-yl]oxy-3-phenyl-propanoate (Preparation 15e) as the phenol and 2-(4-methylpiperazin-1-yl)ethanol as the appropriate alcohol, Example 436 was obtained. HRMS calculated for $C_{31}H_{34}Cl_2N_4O_4S$: 628.1678. found 629.1776 (M+H).

Example 437 (2R)-2-[((5S$_a$)-5-{5-amino-3-chloro-2-methyl-4-[2-(4-methylpiperazin-1-yl)ethoxy]phenyl}-6-ethylthieno[2,3-d]pyrimidin-4-yl)oxy]-3-phenylpropanoic acid Using General Procedure (XIe) with methyl (2R)-2-[(5S$_a$)-5-(5-amino-3-chloro-4-hydroxy-2-methyl-phenyl)-6-ethyl-thieno[2,3-d]pyrimidin-4-yl]oxy-3-phenyl-propanoate (Preparation 15b) as the phenol and 2-(4-methylpiperazin-1-yl)ethanol as the appropriate alcohol, Example 437 was obtained. HRMS calculated for $C_{31}H_{36}ClN_5O_4S$: 609.2177. found 610.2226 (M+H).

Example 438 (2R)-2-{[(5S$_a$)-5-(5-chloro-4-hydroxy-2-methylphenyl)-6-ethylthieno[2,3-d]pyrimidin-4-yl]oxy}-3-phenylpropanoic acid 100 mg methyl (2R)-2-[6-ethyl-(5S$_a$)-5-(4-hydroxy-2-methyl-phenyl)thieno[2,3-d]pyrimidin-4-yl]oxy-3-phenyl-propanoate (Preparation 6j) (0.223 mmol) was dissolved in 5 mL THF, then 31 mg NCS (0.234 mmol) was added. The reaction mixture was stirred at 60° C. overnight. Two monochlorinated and a dichlorinated intermediate were formed. The volatiles were evaporated under reduced pressure and the isomers were separated via preparative reversed phase chromatography using 40 mM aqueous NH$_4$OAc solution (pH was set to 4 with AcOH) and MeCN as eluents. The monochlorinated regioisomer eluting earlier was collected. The obtained intermediate was hydrolyzed according to General Procedure (XIf) to give Example 438. HRMS calculated for $C_{24}H_{21}ClN_2O_4S$: 468.0911. found 469.0981 (M+H).

Example 439 (2R)-2-{[(5R$_a$)-5-(5-chloro-4-hydroxy-2-methylphenyl)-6-ethylthieno[2,3-d]pyrimidin-4-yl]oxy}-3-phenylpropanoic acid 105 mg methyl (2R)-2-[6-ethyl-(5R$_a$)-5-(4-hydroxy-2-methyl-phenyl)thieno[2,3-d] pyrimidin-4-yl]oxy-3-phenyl-propanoate (Preparation 6o) (0.234 mmol) was dissolved in 5 mL THF, then 34 mg NCS (0.257 mmol) was added. The mixture was stirred at 60° C. overnight. Two monochlorinated and a dichlorinated intermediate were formed. The volatiles were evaporated under reduced pressure, and the mixture was hydrolyzed according to General Procedure (XIf). The isomer mixture was separated via preparative reversed phase chromatography using 40 mM aqueous NH$_4$OAc solution (pH was set to 4 with AcOH) and MeCN as eluents. The monochlorinated regioisomer eluting later was collected as Example 439. HRMS calculated for $C_{24}H_{21}ClN_2O_4S$: 468.0911. found 469.0987 (M+H).

Example 440 (2R)-2-[(6-ethyl-(5S$_a$)-5-{2-methyl-5-[2-(4-methylpiperazin-1-yl)ethoxy]phenyl}thieno[2,3-d]pyrimidin-4-yl)oxy]-3-phenylpropanoic acid and (2S)-2-[(6-ethyl-(5R$_a$)-5-{2-methyl-5-[2-(4-methylpiperazin-1-yl)ethoxy]phenyl}thieno[2,3-d]pyrimidin-4-yl)oxy]-3-phenylpropanoic acid (racemic)

45 mg 2-(6-ethyl-5-iodo-thieno[2,3-d]pyrimidin-4-yl)oxy-3-phenyl-propanoic acid (Preparation 4m) (0.10 mmol), 108 mg 1-methyl-4-[2-[4-methyl-3-(4,4,5,5-tetramethyl-1,3,2-dioxaborolan-2-yl)phenoxy]ethyl]piperazine (Preparation 5h) (0.30 mmol), 18 mg Pd$_2$ dba$_3$ (0.02 mmol), 14 mg "BuPAd$_2$ (0.04 mmol) and 55 mg K$_2$CO$_3$ (0.40 mmol) were dissolved in 2 mL DME and 0.5 mL water. The mixture was heated to 120° C. for 10 minutes via microwave irradiation. Then the mixture was cooled to room temperature, filtered, washed with saturated NaHCO$_3$ solution. The filtrate was washed with Et$_2$O, then it was acidified with 2 M HCl and extracted with DCM. The combined organic phases were dried over Na$_2$SO$_4$, filtered and concentrated under reduced pressure. The diastereomers were separated and purified via preparative reversed phase chromatography using 40 mM aqueous NH$_4$OAc solution (pH was set to 4 with AcOH) and MeCN as eluents. The diastereoisomer pair eluting later was collected as Example 440. HRMS calculated for $C_{31}H_{36}N_4O_4S$: 560.2457. found 561.2549 (M+H).

Example 441 (2R)-2-{[(5S$_a$)-5-(8-chloro-7-methyl-3-oxo-3,4-dihydro-2H-1,4-benzoxazin-6-yl)-6-ethyl-thieno[2,3-d]pyrimidin-4-yl]oxy}-3-phenylpropanoic acid 100 mg methyl (2R)-2-[(5S$_a$)-5-(5-amino-3-chloro-4-hydroxy-2-methyl-phenyl)-6-ethyl-thieno[2,3-d]pyrimidin-4-yl]oxy-3-phenyl-propanoate (Preparation 15b) (0.20 mmol) was dissolved in 1 mL dry THF under N$_2$ and was cooled to 0° C. Then 42 mg K$_2$CO$_3$ (0.30 mmol) and 19 µL bromoacetyl bromide (0.22 mmol) were added and the mixture was stirred for 30 minutes, then heated to 50° C. and stirred overnight. Then it was concentrated under reduced pressure and purified via flash chromatography, using heptane and EtOAc as eluents. The obtained ester was hydrolyzed according to General Procedure (XIf) to give Example 441. HRMS calculated for $C_{26}H_{22}ClN_3O_5S$: 523.0969. found 524.1062 (M+H).

Example 442 (2R)-2-[((5S$_a$)-5-{7-chloro-2-[(dimethylamino)methyl]-6-methyl-1-benzofuran-5-yl}-6-ethylthieno[2,3-d]pyrimidin-4-yl)oxy]-3-phenylpropanoic acid 152 mg methyl (2R)-2-[(5S$_a$)-5-(3-chloro-4-hydroxy-5-iodo-2-methyl-phenyl)-6-ethyl-thieno[2,3-d]pyrimidin-4- yl]oxy-3-phenyl-propanoate (Preparation 15d) (0.25 mmol), 33 mg N,N-dimethylprop-2-yn-1-amine (0.40 mmol), 18 mg PdCl$_2$(PPh$_3$)$_2$ (0.025 mmol) and 5 mg copper(I) iodide (0.025 mmol) were dissolved in 1 mL DIPA under N$_2$. The mixture was stirred at 50° C. for 30 minutes. Then it was concentrated under reduced pressure and purified via flash chromatography, using heptane and EtOAc as eluents. The obtained intermediate was hydrolyzed according to General Procedure (XIf) to give Example 442. HRMS calculated for C$_{29}$H$_{28}$ClN$_3$O$_4$S: 549.1489. found 505.0959 (M+H–Me$_2$NH).

Example 443 (2R)-2-{[(5S$_a$)-5-(7-chloro-6-methyl-1-benzofuran-5-yl)-6-ethylthieno[2,3-d]pyrimidin-4-yl]oxy}-3-phenylpropanoic acid 110 mg methyl (2R)-2-[(5S$_a$)-5-(3-chloro-4-hydroxy-5-iodo-2-methyl-phenyl)-6-ethyl-thieno[2,3-d]pyrimidin-4-yl]oxy-3-phenyl-propanoate (Preparation 15d) (0.18 mmol), 51 µL ethynyl(trimethyl)silane (0.36 mmol), 6.3 mg PdCl$_2$(PPh$_3$)$_2$ (0.009 mmol) and 1.7 mg copper(I) iodide (0.009 mmol) were dissolved in 2 mL DIPA under N$_2$. The mixture was stirred at 50° C. for 10 minutes, then 0.22 mL TBAF (1 M in THF, 0.22 mmol) was added and the mixture was stirred for additional 20 minutes. Then the volatiles were evaporated under reduced pressure and the residue was purified via flash chromatography, using heptane and EtOAc as eluents. The obtained intermediate was hydrolyzed according to General Procedure (XIf) to give Example 443. HRMS calculated for C$_{26}$H$_{21}$ClN$_2$O$_4$S: 492.0911. found 493.0999 (M+H).

Example 444 (2R)-2-{[(5S$_a$)-5-(7-chloro-2,6-dimethyl-1,3-benzoxazol-5-yl)-6-ethylthieno[2,3-d]pyrimidin-4-yl]oxy}-3-phenylpropanoic acid 50 mg methyl (2R)-2-[(5S$_a$)-5-(5-amino-3-chloro-4-hydroxy-2-methyl-phenyl)-6-ethyl-thieno[2,3-d]pyrimidin-4-yl]oxy-3-phenyl-propanoate (Preparation 15b) (0.10 mmol) was dissolved in 0.5 mL dry toluene under N$_2$. 27 µL triethyl-orthoacetate (0.15 mmol) was added and the mixture was stirred at 100° C. for 2.5 hours. Then the volatiles were evaporated under reduced pressure and the residue was purified via flash chromatography, using heptane and EtOAc as eluents. The obtained intermediate was hydrolyzed according to General Procedure (XIf) to give Example 444. HRMS calculated for C$_{26}$H$_{22}$ClN$_3$O$_4$S: 507.1020. found 508.1114 (M+H).

Example 445 (2R)-2-[((5S$_a$)-5-{7-chloro-6-methyl-2-[(4-methylpiperazin-1-yl)methyl]-1,3-benzoxazol-5-yl}-6-ethylthieno[2,3-d]pyrimidin-4-yl)oxy]-3-phenylpropanoic acid 56 mg methyl (2R)-2-[(5S$_a$)-5-[7-chloro-2-(chloromethyl)-6-methyl-1,3-benzoxazol-5-yl]-6-ethyl-thieno[2,3-d]pyrimidin-4-yl]oxy-3-phenyl-propanoate (Preparation 15c) (0.10 mmol) was dissolved in 2 mL dry THF under N$_2$. 20 mg 4-methyl-piperazine (0.20 mmol) was added and the mixture was stirred at room temperature for 1 hour. Then the volatiles were evaporated under reduced pressure and the obtained crude intermediate was hydrolyzed according to General Procedure (XIf) to give Example 445. HRMS calculated for C$_{31}$H$_{32}$ClN$_5$O$_4$S: 605.1864. found 606.1937 (M+H).

Example 446 (2R)-2-({(5S$_a$)-5-[7-chloro-6-methyl-2-(morpholin-4-ylmethyl)-1,3-benzoxazol-5-yl]-6-ethylthieno[2,3-d]pyrimidin-4-yl}oxy)-3-phenylpropanoic acid 56 mg methyl (2R)-2-[(5S$_a$)-5-[7-chloro-2-(chloromethyl)-6-methyl-1,3-benzoxazol-5-yl]-6-ethyl-thieno[2,3-d]pyrimidin-4-yl]oxy-3-phenyl-propanoate (Preparation 15c) (0.10 mmol) was dissolved in 2 mL dry THF under N$_2$. 18 mg morpholine (0.20 mmol) was added and the mixture was stirred at room temperature overnight. The volatiles were evaporated under reduced pressure and the obtained crude intermediate was hydrolyzed according to General Procedure (XIf) to give Example 446. HRMS calculated for C$_{30}$H$_{29}$ClN$_4$O$_5$S: 592.1547. found 593.1613 (M+H).

Example 447 (2R)-2-{[6-ethyl-(5S$_a$)-5-(4-hydroxy-2-methylphenyl)thieno[2,3-d]pyrimidin-4-yl]oxy}-3-phenylpropanoic acid Methyl (2R)-2-[6-ethyl-(5S$_a$)-5-(4-hydroxy-2-methylphenyl)thieno[2,3-d]pyrimidin-4-yl] oxy-3-phenyl-propanoate (Preparation 6j) was hydrolyzed according to General Procedure (XIf) to give Example 447. HRMS calculated for C$_{24}$H$_{22}$N$_2$O$_4$S: 434.1300. found 435.1358 (M+H).

Example 448 (2R)-2-{[6-ethyl-(5R$_a$)-5-(4-hydroxy-2-methylphenyl)thieno[2,3-d]pyrimidin-4-yl]oxy}-3-phenylpropanoic acid Methyl (2R)-2-[6-ethyl-(5R$_a$)-5-(4-hydroxy-2-methylphenyl)thieno[2,3-d]pyrimidin-4-yl] oxy-3-phenyl-propanoate (Preparation 6o) was hydrolyzed according to General Procedure (XIf) to give Example 448. HRMS calculated for C$_{24}$H$_{22}$N$_2$O$_4$S: 434.1300. found 435.1369 (M+H).

Example 449 (2R)-2-{[(5S$_a$)-5-(3-chloro-2-methylphenyl)-6-ethylthieno[2,3-d]pyrimidin-4-yl]oxy}-3-phenylpropanoic acid and (2S)-2-{[(5R$_a$)-5-(3-chloro-2-methylphenyl)-6-ethylthieno[2,3-d]pyrimidin-4-yl]oxy}-3-phenylpropanoic acid (racemic)

373 mg 2-(6-ethyl-5-iodo-thieno[2,3-d]pyrimidin-4-yl) oxy-3-phenyl-propanoic acid (Preparation 4m) (0.82 mmol), 280 mg (3-chloro-2-methyl-phenyl)boronic acid (1.64 mmol), 151 mg Pd$_2$dba$_3$ (0.164 mmol), 118 mg "BuPAd$_2$ (0.329 mmol) and 795 mg K$_2$CO$_3$ (5.75 mmol) were dissolved in 15 mL DME and 3 mL water. The mixture was heated to 80° C. for 30 minutes via microwave irradiation. Then it was cooled to room temperature, filtered, washed with saturated NaHCO$_3$ solution. The filtrate was washed with Et$_2$O, then it was acidified with 2 M HCl and extracted with DCM, the combined organic phases were dried over Na$_2$SO$_4$, filtered and concentrated under reduced pressure. The diastereomers were separated and purified via preparative reversed phase chromatography using 40 mM aqueous NH$_4$OAc solution (pH was set to 4 with AcOH) and MeCN as eluents. Diastereoisomer pair eluting earlier was collected as Example 449. HRMS calculated for C$_{24}$H$_{21}$ClN$_2$O$_3$S: 452.0961. found 453.1045 (M+H).

Example 450 (2R)-2-{[(5S$_a$)-5-(3-chloro-2-methyl-phenyl)-6-ethylthieno[2,3-d]pyrimidin-4-yl]oxy}-3-phenylpropanoic acid and Example 451 (2R)-2-{[(5R$_a$)-5-(3-chloro-2-methyl-phenyl)-6-ethylthieno[2,3-d]pyrimidin-4-yl]oxy}-3-phenylpropanoic acid 150 mg methyl (2R)-2-(6-ethyl-5-iodo-thieno[2,3-d]pyrimidin-4-yl)oxy-3-phenyl-propanoate (Preparation 4i) (0.320 mmol), 164 mg (3-chloro-2-methyl-phenyl)boronic acid (0.961 mmol), 74 mg Pd(PPh$_3$)$_4$ (0.064 mmol), and 265 mg Ag$_2$CO$_3$ (0.961 mmol) were dissolved in 6 mL DME. It was heated to 100° C. for 10 minutes via microwave irradiation. Then the mixture was cooled to room temperature, and the volatiles were evaporated under reduced pressure. The diastereoisomers were separated via flash chromatography, using heptane and EtOAc as eluents. The diastereoisomer eluting earlier was collected and hydrolyzed according to General Procedure (XIf) to give Example 450. HRMS calculated for C$_{24}$H$_{21}$ClN$_2$O$_3$S: 452.0961. found 453.1040 (M+H). The diastereoisomer eluting later was collected and hydrolyzed according to General Procedure (XIf) to give Example 451. HRMS calculated for C$_{24}$H$_{21}$ClN$_2$O$_3$S: 452.0961. found 453.1044 (M+H).

Example 452 (2R)-2-{[6-ethyl-(5S$_a$)-5-(3-hydroxy-2-methylphenyl)thieno[2,3-d]pyrimidin-4-yl]oxy}-3-phenylpropanoic acid and (2S)-2-{[6-ethyl-(5R$_a$)-5-(3-hydroxy-2-methylphenyl)thieno[2,3-d]pyrimidin-4-yl]oxy}-3-phenylpropanoic acid (racemic)

45 mg 2-(6-ethyl-5-iodo-thieno[2,3-d]pyrimidin-4-yl)oxy-3-phenyl-propanoic acid (Preparation 4m) (0.10 mmol), 70 mg 2-methyl-3-(4,4,5,5-tetramethyl-1,3,2-dioxaborolan-2-yl)phenol (0.30 mmol), 18 mg Pd$_2$ dba$_3$ (0.02 mmol), 14 mg "BuPAd$_2$ (0.04 mmol) and 55 mg K$_2$CO$_3$ (0.40 mmol) were dissolved in 2 mL DME and 0.5 mL water. It was heated to 90° C. for 30 minutes via microwave irradiation. Then the mixture was cooled to room temperature, filtered, washed with saturated NaHCO$_3$ solution. The filtrate was washed with Et$_2$O, then it was acidified with 2 M HCl and extracted with DCM. The combined organic phases were dried over Na$_2$SO$_4$, filtered and concentrated under reduced pressure. The diastereomers were separated and purified via preparative reversed phase chromatography using 40 mM aqueous NH$_4$OAc solution (pH was set to 4 with AcOH) and MeCN as eluents. The diastereoisomer pair eluting earlier was collected as Example 452. HRMS calculated for C$_{24}$H$_{22}$N$_2$O$_4$S: 434.1300. found 435.1371 (M+H).

General Procedure (XIIa)
Step A:
1 eq. ethyl (2R)-2-[(5S$_a$)-5-[3-chloro-2-methyl-4-[2-(4-methylpiperazin-1-yl)ethoxy] phenyl]-6-ethyl-thieno[2,3-d]pyrimidin-4-yl]oxy-3-(2-hydroxyphenyl)propanoate (Preparation 8h), 2 eq. of the appropriate alcohol and 2. eq triphenyl phosphine were dissolved in abs. toluene (0.2 M for the phenol), then 2 eq ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:
The product of Step A was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reversed phase chromatography using 25 mM aqueous NH$_4$HCO$_3$ solution and MeCN as eluents.

General Procedure (XIIb)
Step A:
1 eq. of the appropriate phenol, 2 eq. 2-(4-methylpiperazin-1-yl)ethanol and 2 eq. triphenyl phosphine were dissolved in abs. toluene (5 mL/mmol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:
The product of Step A was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reversed phase chromatography using 25 mM aqueous NH$_4$HCO$_3$ solution and MeCN as eluents.

Example 453 (2R)-2-[((5S$_a$)-5-{3-chloro-2-methyl-4-[2-(4-methylpiperazin-1-yl)ethoxy] phenyl}-6-ethylthieno[2,3-d]pyrimidin-4-yl)oxy]-3-(2-methoxyphenyl)propanoic acid Using General Procedure (XIIa) and methanol as the appropriate alcohol, Example 453 was obtained. HRMS calculated for C$_{32}$H$_{37}$ClN$_4$O$_5$S: 624.2173. found 625.2259 (M+H).

Example 454 (2R)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]-3-[2-(2,2,2-trifluoroethoxy)phenyl]propanoic acid Step A:
192 mg ethyl (2R)-2-[(5S$_a$)-5-[3-chloro-2-methyl-4-[2-(4-methylpiperazin-1-yl)ethoxy]phenyl]-6-ethyl-thieno[2,3-d]pyrimidin-4-yl]oxy-3-(2-hydroxyphenyl)propanoate (Preparation 8h) (0.3 mmol) and 138 mg K$_2$CO$_3$ (1.0 mmol) were dissolved in 2 mL DMF, then 232 mg 2,2,2-trifluoroethyl trifluoromethanesulfonate (1.0 mmol) was added. The mixture was stirred at room temperature under nitrogen until no further conversion was observed. Then it was diluted with brine, neutralized with 2 M HCl, and extracted with DCM The combined organic phases were dried over Na$_2$SO$_4$ and concentrated under reduced pressure.

Step B:
The product of Step A was dissolved in 8 mL dioxane-water 1:1 and 150 mg LiOH×H$_2$O (3.57 mmol) was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reversed phase chromatography using 5 mM aqueous $NH_4HCO_3$ solution and MeCN as eluents to obtain Example 454. HRMS calculated for $C_{33}H_{36}ClF_3N_4O_5S$: 692.2047. found 693.2151 (M+H).

Example 455 (2R)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]-3-{2-[(2-methoxypyrimidin-4-yl)methoxy]phenyl}propanoic acid Using General Procedure (XIIa) and (2-methoxypyrimidin-4-yl)methanol as the appropriate alcohol, Example 455 was obtained. HRMS calculated for $C_{37}H_{41}ClN_6O_6S$: 732.2497. found 367.1311 (M+2H).

Example 456 (2R)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]-3-{2-[(1-ethyl-1H-pyrazol-5-yl)methoxy]phenyl}propanoic acid Using General Procedure (XIIa) and (1-ethyl-1H-pyrazol-5-yl)methanol (Preparation 9da) as the appropriate alcohol, Example 456 was obtained. HRMS calculated for $C_{37}H_{43}ClN_6O_5S$: 718.2704. found 360.144 (M+2H).

Example 457 (2R)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]-3-[2-(2-methoxyethoxy)phenyl]propanoic acid Using General Procedure (XIIa) and 2-methoxyethanol as the appropriate alcohol, Example 457 was obtained. HRMS calculated for $C_{34}H_{41}ClN_4O_6S$: 668.2435. found 335.1297 (M+2H).

Example 458 (2R)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]-3-(2,3-dihydro-1-benzofuran-7-yl)propanoic acid Using General Procedure (XIIb) and ethyl (2R)-2-[(5Sa)-5-(3-chloro-4-hydroxy-2-methyl-phenyl)-6-ethyl-thieno[2,3-d]pyrimidin-4-yl]oxy-3-(2,3-dihydrobenzofuran-7-yl)propanoate (Preparation 17c) as the appropriate phenol, Example 458 were obtained. HRMS calculated for $C_{33}H_{37}ClN_4O_5S$: 636.2173. found 637.2233 (M+H).

Example 459 (2S)-2-[((5R$_a$)-5-{3-chloro-2-methyl-4-[2-(4-methylpiperazin-1-yl)ethoxy]phenyl}-6-ethylthieno[2,3-d]pyrimidin-4-yl)oxy]-3-(2,3-dihydro-1-benzofuran-7-yl)propanoic acid Using General Procedure (XIIb) and ethyl (2S)-2-[(5R$_a$)-5-(3-chloro-4-hydroxy-2-methyl-phenyl)-6-ethyl-thieno[2,3-d]pyrimidin-4-yl]oxy-3-(2,3-dihydrobenzofuran-7-yl)propanoate (Preparation 17d) as the appropriate phenol, Example 459 were obtained. HRMS calculated for $C_{33}H_{37}ClN_4O_5S$: 636.2173. found 637.2236 (M+H).

Example 460 (2R)-3-(1,3-benzodioxol-4-yl)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]propanoic acid Using General Procedure (XIIb) and ethyl (2R)-3-(1,3-benzodioxol-4-yl)-2-[(5S$_a$)-5-(3-chloro-2-hydroxy-2-methyl-phenyl)-6-ethyl-thieno[2,3-d]pyrimidin-4-yl]oxy-propanoate (Preparation 17b) as the appropriate phenol, Example 460 was obtained. HRMS calculated for $C_{32}H_{35}ClN_4O_6S$: 638.1966. found 639.2067 (M+H).

Example 461 (2R)-3-(1-benzofuran-7-yl)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]propanoic acid Using General Procedure (XIIb) and ethyl (2R)-3-(benzofuran-7-yl)-2-[(5S$_a$)-5-(3-chloro-4-hydroxy-2-methyl-phenyl)-6-ethyl-thieno[2,3-d]pyrimidin-4-yl]oxy-propanoate (Preparation 17e) as the appropriate phenol, Example 461 was obtained. HRMS calculated for $C_{33}H_{35}ClN_4O_5S$: 634.2017. found 635.2069 (M+H).

Example 462 (2S)-3-(1-benzofuran-7-yl)-2-[((5R$_a$)-5-{3-chloro-2-methyl-4-[2-(4-methylpiperazin-1-yl)ethoxy]phenyl}-6-ethylthieno[2,3-d]pyrimidin-4-yl)oxy]propanoic acid Using General Procedure (XIIb) and ethyl (2S)-3-(benzofuran-7-yl)-2-[(5R$_a$)-5-(3-chloro-4-hydroxy-2-methyl-phenyl)-6-ethyl-thieno[2,3-d]pyrimidin-4-yl]oxy-propanoate (Preparation 17f) as the appropriate phenol, Example 462 was obtained. HRMS calculated for $C_{33}H_{35}ClN_4O_5S$: 634.2017. found (M+H).

Example 463 (2R)-2-[((5S$_a$)-5-{3-chloro-2-methyl-4-[2-(4-methylpiperazin-1-yl)ethoxy]phenyl}-6-ethylthieno[2,3-d]pyrimidin-4-yl)oxy]-3-(2-fluorophenyl)propanoic acid Using General Procedure (XIIb) and ethyl (2R)-2-[(5S$_a$)-5-(3-chloro-4-hydroxy-2-methyl-phenyl)-6-ethyl-thieno[2,3-d]pyrimidin-4-yl]oxy-3-(2-fluorophenyl)propanoate (Preparation 17h) as the phenol, Example 463 was obtained. HRMS calculated for $C_{31}H_{34}ClFN_4O_4S$: 612.1973. found 613.205 (M+H).

Example 464 (2S)-2-[((5R$_a$)-5-{3-chloro-2-methyl-4-[2-(4-methylpiperazin-1-yl)ethoxy]phenyl}-6-ethylthieno[2,3-d]pyrimidin-4-yl)oxy]-3-(2-fluorophenyl)propanoic acid Using General Procedure (XIIb) and ethyl (2S)-2-[(5R$_a$)-5-(3-chloro-4-hydroxy-2-methyl-phenyl)-6-ethyl-thieno[2,3-d]pyrimidin-4-yl]oxy-3-(2-fluorophenyl)propanoate (Preparation 17g) as the phenol, Example 464 was obtained. HRMS calculated for $C_{31}H_{34}ClFN_4O_4S$: 612.1973. found 613.2053 (M+H).

General Procedure (XIIIa)
Step A:
1 eq. ethyl (2R)-2-[(5S$_a$)-5-(3-chloro-4-hydroxy-2-methyl-phenyl)-6-prop-1-ynyl-thieno[2,3-d]pyrimidin-4-yl]oxy-3-(2-methoxyphenyl)propanoate (Preparation 6l), 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.
Step B:
The product of Step A was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over $Na_2SO_4$, concentrated under reduced pressure and the residue was purified via preparative reversed phase chromatography using 25 mM aqueous $NH_4HCO_3$ solution and MeCN as eluents.
General Procedure (XIIIb)
Step A:

1 eq. phenol derivative, 2 eq. of the appropriate alcohol and 2 eq. $PPh_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.
Step B:

The product of Step A was dissolved in dioxane-water 1:1 (10 mL/mmol) and 10 eq. LiOH×$H_2O$ was added. The mixture was stirred at room temperature until no further conversion was observed. Then it was diluted with brine, neutralized with 2 M HCl, and extracted with DCM. The combined organic phases were dried over $Na_2SO_4$, concentrated under reduced pressure and the residue was purified via preparative reversed phase chromatography using 25 mM aqueous $NH_4HCO_3$ solution and MeCN as eluents.
General Procedure (XIIIc)

1 eq. ester was dissolved in dioxane-water 1:1 (10 mL/mmol) and 10 eq. LiOH×$H_2O$ was added and the mixture was stirred at room temperature until no further conversion was observed. Then it was diluted with brine, neutralized with 2 M HCl, and extracted with DCM. The combined organic phases were dried over $Na_2SO_4$ and concentrated under reduced pressure. If necessary the product was purified via preparative reversed phase chromatography using MeCN and 25 mM aqueous $NH_4HCO_3$ solution as eluents.

Example 465 (2R)-2-{[(5$S_a$)-5-{3-chloro-2-methyl-4-[2-(1-methylpiperidin-4-yl)ethoxy]phenyl}-6-(prop-1-yn-1-yl)thieno[2,3-d]pyrimidin-4-yl]oxy}-3-(2-methoxyphenyl)propanoic acid Using General Procedure (XIIIa) and 2-(1-methyl-4-piperidyl)ethanol as the appropriate alcohol, Example 465 was obtained. HRMS calculated for $C_{34}H_{36}ClN_3O_5S$: 633.2064. found 634.2136 (M+H).

Example 466 (2R)-2-{[(5$S_a$)-5-(3-chloro-4-{2-[di(propan-2-yl)amino]ethoxy}-2-methylphenyl)-6-(prop-1-yn-1-yl)thieno[2,3-d]pyrimidin-4-yl]oxy}-3-(2-methoxyphenyl)propanoic acid Using General Procedure (XIIIa) and 2-(diisopropylamino)ethanol as the appropriate alcohol, Example 466 was obtained. HRMS calculated for $C_{34}H_{38}ClN_3O_5S$: 635.2221. found 636.2310 (M+H).

Example 467 (2R)-2-{[(5$S_a$)-5-{3-chloro-4-[2-(dimethylamino)ethoxy]-2-methylphenyl}-6-(prop-1-yn-1-yl)thieno[2,3-d]pyrimidin-4-yl]oxy}-3-(2-methoxyphenyl)propanoic acid Using General Procedure (XIIIa) and 2-(dimethylamino)ethanol as the appropriate alcohol, Example 467 was obtained. HRMS calculated for $C_{30}H_{30}ClN_3O_5S$: 579.1595. found 580.1663 (M+H).

Example 468 (2R)-2-{[(5$S_a$)-5-{3-chloro-2-methyl-4-[2-(pyrrolidin-1-yl)ethoxy]phenyl}-6-(prop-1-yn-1-yl)thieno[2,3-d]pyrimidin-4-yl]oxy}-3-(2-methoxyphenyl)propanoic acid Using General Procedure (XIIIa) and 2-pyrrolidin-1-ylethanol as the appropriate alcohol, Example 468 was obtained. HRMS calculated for $C_{32}H_{32}ClN_3O_5S$: 605.1751. found 606.1822 (M+H).

Example 469 (2R)-2-{[(5$S_a$)-5-{3-chloro-2-methyl-4-[2-(piperidin-1-yl)ethoxy]phenyl}-6-(prop-1-yn-1-yl)thieno[2,3-d]pyrimidin-4-yl]oxy}-3-(2-methoxyphenyl)propanoic acid Using General Procedure (XIIIa) and 2-(1-piperidyl)ethanol as the appropriate alcohol, Example 469 was obtained. HRMS calculated for $C_{33}H_{34}ClN_3O_5S$: 619.1908. found 620.2011 (M+H).

Example 470 (2R)-2-{[(5$R_a$)-5-(3-chloro-5-fluoro-4-methoxy-2-methylphenyl)-6-(prop-1-yn-1-yl)thieno[2,3-d]pyrimidin-4-yl]oxy}-3-(2-methoxyphenyl)propanoic acid and Example 471 (2R)-2-{[(5$S_a$)-5-(3-chloro-5-fluoro-4-methoxy-2-methylphenyl)-6-(prop-1-yn-1-yl)thieno[2,3-d]pyrimidin-4-yl]oxy}-3-(2-methoxyphenyl)propanoic acid 522 mg ethyl (2R)-2-(5-iodo-6-prop-1-ynyl-thieno[2,3-d]pyrimidin-4-yl)oxy-3-(2-methoxyphenyl)propanoate (Preparation 4k) (1.00 mmol), 451 mg 2-(3-chloro-5-fluoro-4-methoxy-2-methyl-phenyl)-4,4,5,5-tetramethyl-1,3,2-dioxaborolane (Preparation 5i) (1.50 mmol), 73 mg $PdCl_2$× dppf (0.10 mmol) and 652 mg $Cs_2CO_3$ (2.00 mmol) were dissolved in 10 mL dioxane and 2.5 mL water, and heated under nitrogen at 110° C. for 10 minutes in a microwave reactor. Then reaction mixture was diluted with brine, neutralized with 2 M HCl, and extracted with DCM. The combined organic phases were dried over $Na_2SO_4$, concentrated under reduced pressure and the residue was purified via flash chromatography, using heptane and EtOAc as eluents, then it was hydrolyzed according to General Procedure (XIIIc). The diastereoisomer eluting earlier was collected as Example 470. HRMS calculated for $C_{27}H_{22}ClFN_2O_5S$: 540.0922. found 541.0987 (M+H). The diastereoisomer eluting later was collected as Example 471. HRMS calculated for $C_{27}H_{22}ClFN_2O_5S$: 540.0922. found 541.1009 (M+H).

Example 472 (2R)-2-({(5$R_a$)-5-[3-chloro-4-methoxy-2-methyl-5-(4-methylpiperazin-1-yl)phenyl]-6-(prop-1-yn-1-yl)thieno[2,3-d]pyrimidin-4-yl}oxy)-3-(2-methoxyphenyl)propanoic acid and Example 473 (2R)-2-({(5$S_a$)-5-[3-chloro-4-methoxy-2-methyl-5-(4-methylpiperazin-1-yl)phenyl]-6-(prop-1-yn-1-yl)thieno[2,3-d]pyrimidin-4-yl}oxy)-3-(2-methoxyphenyl)propanoic acid 418 mg ethyl (2R)-2-(5-iodo-6-prop-1-ynyl-thieno[2,3-d]pyrimidin-4-yl)oxy-3-(2-methoxyphenyl)propanoate (Preparation 4k) (0.80 mmol), 381 mg 1-[3-chloro-2-methoxy-4-methyl-5-(4,4,5,5-tetramethyl-1,3,2-dioxaborolan-2-yl)phenyl]-4-methyl-piperazine (Preparation 5j) (1.00 mmol), 58 mg PdCl$_2$×dppf (0.08 mmol) and 391 mg Cs$_2$CO$_3$ (1.20 mmol) were dissolved in 10 mL dioxane and 2 mL water and was heated under nitrogen at 110° C. for 10 minutes in a microwave reactor. Then reaction mixture was diluted with brine, and extracted with DCM. The combined organic phases were dried over Na$_2$SO$_4$, concentrated under reduced pressure and the residue was purified via flash chromatography, using heptane and EtOAc as eluents, then it was hydrolyzed according to General Procedure (XIIIc). The diastereoisomer eluting earlier was collected as Example 472. HRMS calculated for C$_{32}$H$_{33}$ClN$_4$O$_5$S: 620.1860. found 621.1929 (M+H). The diastereoisomer eluting later was collected as Example 473. HRMS calculated for C$_{32}$H$_{33}$ClN$_4$O$_5$S: 620.1860. found 621.1929 (M+H).

Example 474 (2R)-2-{[(5R$_a$)-5-{3-chloro-2,5-dimethyl-4-[2-(4-methylpiperazin-1-yl)ethoxy]phenyl}-6-(prop-1-yn-1-yl)thieno[2,3-d]pyrimidin-4-yl]oxy}-3-(2-methoxyphenyl)propanoic acid and Example 475 (2R)-2-{[(5S$_a$)-5-{3-chloro-2,5-dimethyl-4-[2-(4-methylpiperazin-1-yl)ethoxy]phenyl}-6-(prop-1-yn-1-yl)thieno[2,3-d]pyrimidin-4-yl]oxy}-3-(2-methoxyphenyl)propanoic acid Using General Procedure (XIIIb), diastereoisomer mixture of ethyl (2R)-2-[5-(3-chloro-4-hydroxy-2,5-dimethyl-phenyl)-6-prop-1-ynyl-thieno[2,3-d]pyrimidin-4-yl]oxy-3-(2-methoxyphenyl)propanoate (Preparation 18b) as the phenol and 2-(4-methylpiperazin-1-yl)ethanol as the appropriate alcohol Example 474 and Example 475 were obtained. The diastereoisomer eluting earlier was collected as Example 474. HRMS calculated for C$_{34}$H$_{37}$ClN$_4$O$_5$S: 648.2173. found 649.2252 (M+H). The diastereoisomer eluting later was collected as Example 475. HRMS calculated for C$_{34}$H$_{37}$ClN$_4$O$_5$S: 648.2173. found 649.2251 (M+H).

Example 476 (2R)-2-{[(5S$_a$)-5-{3-chloro-5-fluoro-2-methyl-4-[2-(4-methylpiperazin-1-yl)ethoxy]phenyl}-6-(prop-1-yn-1-yl)thieno[2,3-d]pyrimidin-4-yl]oxy}-3-(2-methoxyphenyl)propanoic acid Using General Procedure (XIIIb), ethyl (2R)-2-[(5S$_a$)-5-(3-chloro-5-fluoro-4-hydroxy-2-methyl-phenyl)-6-prop-1-ynyl-thieno[2,3-d]pyrimidin-4-yl]oxy-3-(2-methoxyphenyl)propanoate (Preparation 18c) as the phenol and 2-(4-methylpiperazin-1-yl)ethanol as the appropriate alcohol Example 476 was obtained. HRMS calculated for C$_{33}$H$_{34}$ClFN$_4$O$_5$S: 652.1922. found 653.2005 (M+H).

Example 477 (2R)-2-{[(5S$_a$)-5-{3-chloro-5-methoxy-2-methyl-4-[2-(4-methylpiperazin-1-yl)ethoxy]phenyl}-6-(prop-1-yn-1-yl)thieno[2,3-d]pyrimidin-4-yl]oxy}-3-(2-methoxyphenyl)propanoic acid To 57 mg ethyl (2R)-2-[(5S$_a$)-5-(3-chloro-4-hydroxy-5-methoxy-2-methyl-phenyl)-6-prop-1-ynyl-thieno[2,3-d]pyrimidin-4-yl]oxy-3-(2-methoxyphenyl)propanoate (Preparation 18a) (0.10 mmol), 29 mg 2-(4-methylpiperazin-1-yl) ethanol (0.20 mmol) and 100 mg immobilized PPh$_3$ (0.30 mmol) 1 mL dry toluene was added followed by 52 mg 3-(dimethylcarbamoylimino)-1,1-dimethyl-urea (0.30 mmol). The mixture was stirred at 50° C. under nitrogen until no further conversion was observed. Then the mixture was filtered, the filtrate was concentrated under reduced pressure and the residue was purified via flash chromatography using EtOAc and MeOH as eluents. The obtained intermediate was hydrolyzed according to General Procedure (XIIIc) to give Example 477. HRMS calculated for C$_{34}$H$_{37}$ClN$_4$O$_6$S: 664.2122. found 665.2200 (M+H).

Example 478 (2R)-2-{[(5R$_a$)-5-{3-chloro-4-[3-(dimethylamino)propyl]-2-methylphenyl}-6-(prop-1-yn-1-yl)thieno[2,3-d]pyrimidin-4-yl]oxy}-3-(2-methoxyphenyl)propanoic acid and Example 479 (2R)-2-{[(5S$_a$)-5-{3-chloro-4-[3-(dimethylamino)propyl]-2-methylphenyl}-6-(prop-1-yn-1-yl)thieno[2,3-d]pyrimidin-4-yl]oxy}-3-(2-methoxyphenyl)propanoic acid 522 mg ethyl (2R)-2-(5-iodo-6-prop-1-ynyl-thieno[2,3-d]pyrimidin-4-yl)oxy-3-(2-methoxyphenyl)propanoate (Preparation 4k) (1.00 mmol), 1.30 mmol 3-[2-chloro-3-methyl-4-(4,4,5,5-tetramethyl-1,3,2-dioxaborolan-2-yl)phenyl]-N,N-dimethyl-propan-1-amine (Preparation 5n), 71 mg AtaPhos (0.10 mmol) and 652 mg Cs$_2$CO$_3$ (2.00 mmol) were dissolved in 8 mL dioxane and 2 mL water, and heated under nitrogen at 100° C. for 15 minutes in a microwave reactor. The reaction mixture was diluted with brine and extracted with DCM. The combined organic phases were dried over Na$_2$SO$_4$, concentrated under reduced pressure and the residue was purified via flash chromatography, using EtOAc and MeOH as eluents. The obtained intermediate was hydrolyzed according to General Procedure (XIIIc). The diastereoisomer eluting earlier was collected as Example 478. HRMS calculated for C$_{31}$H$_{32}$ClN$_3$O$_4$S: 577.1802. found 578.1876 (M+H). The diastereoisomer eluting later was collected as Example 479. HRMS calculated for C$_{31}$H$_{32}$ClN$_3$O$_4$S: 577.1802. found 578.1881 (M+H).

Example 480 (2R)-2-{[(5S$_a$)-5-(3-chloro-4-hydroxy-2-methylphenyl)-6-(prop-1-yn-1-yl)thieno[2,3-d]pyrimidin-4-yl]oxy}-3-(2-methoxyphenyl)propanoic acid Ethyl (2R)-2-[(5S$_a$)-5-(3-chloro-4-hydroxy-2-methyl-phenyl)-6-prop-1-ynyl-thieno[2,3-d]pyrimidin-4-yl]oxy-3-(2-methoxyphenyl)propanoate (Preparation 6l) was hydrolyzed according to General Procedure (XIIIc) to give Example 480. HRMS calculated for C$_{26}$H$_{21}$ClN$_2$O$_5$S: 508.0860. found 509.0940 (M+H).

General Procedure (XIVa)
Step A:
1 eq. ethyl (2R)-2-[(5S$_a$)-5-[3-chloro-2-methyl-4-[2-(4-methylpiperazin-1-yl)ethoxy] phenyl]-6-prop-1-ynyl-thieno[2,3-d]pyrimidin-4-yl]oxy-3-(2-hydroxyphenyl)propanoate (Preparation 8i), 2 eq. of the appropriate alcohol and 2 eq. triphenyl phosphine were dissolved in abs. toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.

Step B:

The product of Step A was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reversed phase chromatography using 25 mM aqueous NH$_4$HCO$_3$ solution and MeCN as eluents.

Example 481 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-ethoxyphenyl)propanoic acid Using General Procedure (XIVa) and ethanol as the appropriate alcohol, Example 481 was obtained. HRMS calculated for C$_{34}$H$_{37}$ClN$_4$O$_5$S: 648.2173. found 649.2249 (M+H).

Example 482 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(2-methoxyphenyl)pyrimidin-4-yl]methoxy}phenyl)propanoic acid Using General Procedure (XIVa) and [2-(2-methoxyphenyl)pyrimidin-4-yl]methanol (Preparation 9bp) as the appropriate alcohol, Example 482 was obtained. HRMS calculated for C$_{44}$H$_{43}$ClN$_6$O$_6$S: 818.2653. found 410.1394 (M+2H).

Example 483 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(3-methylpyridin-4-yl)pyrimidin-4-yl]methoxy}phenyl)propanoic acid Step A:

1.30 g ethyl (2R)-2-[(5S$_a$)-5-[3-chloro-2-methyl-4-[2-(4-methylpiperazin-1-yl)ethoxy] phenyl]-6-prop-1-ynyl-thieno[2,3-d]pyrimidin-4-yl]oxy-3-(2-hydroxyphenyl)propanoate (Preparation 8i) (2.0 mmol), 0.94 g (2-methylsulfanylpyrimidin-4-yl)methanol (Preparation 9aa) (6.0 mmol) and 1.57 g PPh$_3$ (6.0 mmol) were dissolved in 40 mL dry toluene, then 1.38 g di-tert-butyl azodicarboxylate (6.0 mmol) was added. The mixture was stirred at 50° C. under nitrogen. If needed, the addition of (2-methylsulfanylpyrimidin-4-yl)methanol (Preparation 9aa) (6.0 mmol), PPh$_3$ (6.0 mmol) and ditertbutyl azodicarboxylate (6.0 mmol) can be repeated. When no further conversion was observed the volatiles were evaporated and the residue was purified via flash chromatography using DCM and MeOH as eluents, to obtain ethyl (2R)-2-[(5S$_a$)-5-[3-chloro-2-methyl-4-[2-(4-methylpiperazin-1-yl)ethoxy]phenyl]-6-prop-1-ynyl-thieno[2,3-d]pyrimidin-4-yl]oxy-3-[2-[(2-methylsulfanylpyrimidin-4-yl)methoxy]phenyl]propanoate. HRMS calculated for C$_{40}$H$_{43}$ClN$_6$O$_5$S$_2$: 787.2498. found 787.2464 (M+H).

Step B:

0.572 g ethyl (2R)-2-[(5S$_a$)-5-[3-chloro-2-methyl-4-[2-(4-methylpiperazin-1-yl)ethoxy] phenyl]-6-prop-1-ynyl-thieno[2,3-d]pyrimidin-4-yl]oxy-3-[2-[(2-methylsulfanylpyrimidin-4-yl)methoxy]phenyl]propanoate (0.44 mmol), 0.179 g (3-methyl-4-pyridyl)boronic acid (1.31 mmol), 0.25 g copper(I) thiophene-2-carboxylate (1.31 mmol) and 51 mg Pd(PPh$_3$)$_4$ were dissolved in 5 mL dry THF heated under nitrogen at 70° C. If needed, the addition of reagents was repeated. When no further conversion was observed, the volatiles were evaporated and the residue was purified via flash chromatography using DCM and MeOH as eluents.

Step C:

The product of Step B was dissolved in 5 mL dioxane-water 1:1 and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reverse phase chromatography using 25 mM aqueous NH$_4$HCO$_3$ solution and MeCN as eluents to furnish Example 483. HRMS calculated for C$_{43}$H$_{42}$ClN$_7$O$_5$S: 803.2657. found 402.6401 (M+2H).

Example 484 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(2-methoxyethyl)pyrimidin-4-yl]methoxy}phenyl)propanoic acid Using General Procedure (XIVa) and [2-(2-methoxyethyl)pyrimidin-4-yl]methanol (Preparation 9bl) as the appropriate alcohol, Example 484 was obtained. HRMS calculated for C$_{40}$H$_{43}$ClN$_6$O$_6$S: 770.2653. found 386.1410 (M+2H).

Example 485 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(morpholin-4-yl)pyrimidin-4-yl]methoxy}phenyl)propanoic acid Using General Procedure (XIVa) and (2-(morpholin-4-yl)pyrimidin-4-yl)methanol (Preparation 9ar) as the appropriate alcohol, Example 485 was obtained. HRMS calculated for C$_{41}$H$_{44}$ClN$_7$O$_6$S: 797.2762. found 399.6446 (M+2H).

Example 486 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-{2-[(2-methoxypyrimidin-4-yl)methoxy]phenyl}propanoic acid Using General Procedure (XIVa) and (2-methoxypyrimidin-4-yl)methanol as the appropriate alcohol, Example 486 was obtained. HRMS calculated for C$_{38}$H$_{39}$ClN$_6$O$_6$S: 742.2340. found 743.2424 (M+H).

Example 487 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(2,2,2-trifluoroethoxy)pyrimidin-4-yl]methoxy}phenyl)propanoic acid Using General Procedure (XIVa) and [2-(2,2,2-trifluoroethoxy)pyrimidin-4-yl]methanol (Preparation 9ai) as the appropriate alcohol, Example 487 was obtained. HRMS calculated for C$_{39}$H$_{38}$ClF$_3$N$_6$O$_6$S: 810.2214. found 811.2323 (M+H).

Example 488 (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}propanoic acid Using General Procedure (XIVa) and (1-tert-butyl-1H-pyrazol-5-yl)methanol (Preparation 9dt) as the appropriate alcohol, Example 488 was obtained. HRMS calculated for $C_{40}H_{45}ClN_6O_5S$: 756.2861. found 379.1485 (M+2H).

Example 489 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[1-(2,2,2-trifluoroethyl)-1H-pyrazol-5-yl]methoxy}phenyl)propanoic acid Using General Procedure (XIVa) and [1-(2,2,2-trifluoroethyl)-1H-pyrazol-5-yl]methanol (Preparation 9du) as the appropriate alcohol, Example 489 was obtained. HRMS calculated for $C_{38}H_{38}ClF_3N_6O_5S$: 782.2265. found 783.2353 (M+H).

Example 490 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}propanoic acid Using General Procedure (XIVa) and (1-butyl-1H-pyrazol-5-yl)methanol (Preparation 9dd) as the appropriate alcohol, Example 490 was obtained. HRMS calculated for $C_{40}H_{45}ClN_6O_5S$: 756.2861. found 757.2953 (M+H).

Example 491 (2S)-3-(1-benzofuran-4-yl)-2-{[(5R$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}propanoic acid Step A:

0.137 g ethyl (2S)-3-(benzofuran-4-yl)-2-[(5R$_a$)-5-(3-chloro-4-hydroxy-2-methyl-phenyl)-6-prop-1-ynyl-thieno[2,3-d]pyrimidin-4-yl]oxy-propanoate (Preparation 20b) (0.25 mmol), 0.072 g 2-(4-methylpiperazin-1-yl)ethanol (0.5 mmol) and 0.166 g PPh$_3$ (0.5 mmol) were dissolved in 4 mL dry toluene and 0.115 g ditertbutyl azodicarboxylate (0.5 mmol) was added and it was heated at 50° C. If needed, the addition of reagents can be repeated. When no further conversion was observed the volatiles were evaporated under reduced pressure and the residue was purified via flash chromatography using EtOAc and MeOH as eluents.

Step B:

The product of Step A was dissolved in 10 mL dioxane-water 1:1 and 0.200 g LiOH×H$_2$O (5.88 mmol) was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reverse phase chromatography using 25 mM aqueous NH$_4$HCO$_3$ solution and MeCN as eluents to furnish Example 491. HRMS calculated for $C_{34}H_{33}ClN_4O_5S$: 644.1860. found 645.1934 (M+H).

Example 492 (2R)-3-(1-benzofuran-4-yl)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}propanoic acid Step A:

0.137 g ethyl (2R)-3-(benzofuran-4-yl)-2-[(5S$_a$)-5-(3-chloro-4-hydroxy-2-methyl-phenyl)-6-prop-1-ynyl-thieno[2,3-d]pyrimidin-4-yl]oxy-propanoate (Preparation 20a) (0.25 mmol), 0.072 g 2-(4-methylpiperazin-1-yl)ethanol (0.5 mmol) and 0.166 g PPh$_3$ (0.5 mmol) were dissolved in 4 mL dry toluene and 0.115 g ditertbutyl azodicarboxylate (0.5 mmol) was added and it was heated at 50° C. If needed, the addition of reagents can be repeated. When no further conversion was observed the volatiles were evaporated under reduced pressure and the residue was purified via flash chromatography using EtOAc and MeOH as eluents.

Step B:

The product of Step A was dissolved in 10 mL dioxane-water 1:1 and 0.200 g LiOH×H$_2$O (5.88 mmol) was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reverse phase chromatography using 25 mM aqueous NH$_4$HCO$_3$ solution and MeCN as eluents to furnish Example 492. HRMS calculated for $C_{34}H_{33}ClN_4O_5S$: 644.1860. found 645.1935 (M+H).

General Procedure (XVa)

Step A:

1 eq. methyl (2R)-2-[6-bromo-(5S$_a$)-5-(3-chloro-4-hydroxy-2-methyl-phenyl)thieno[2,3-d]pyrimidin-4-yl]oxy-3-phenyl-propanoate (Preparation 22), 2.5 eq. of the appropriate boronic ester or boronic acid and 2.5 eq. Cs$_2$CO$_3$ were dissolved in THF-water (4:1) (12.5 ml/mmol of Preparation 22), then 0.1 eq Pd(dppf)Cl$_2$ was added. The mixture was heated under nitrogen at 110° C. in a microwave reactor until no further conversion was observed. Then it was diluted with brine, neutralized with 2 M HCl, and extracted with DCM. The combined organic phases were dried over Na$_2$SO$_4$, concentrated under reduced pressure and the residue was purified via flash chromatography using heptane and ethyl acetate as eluents.

Step B:

1 eq. of the product of Step A, 2 eq. 2-(4-methylpiperazin-1-yl)ethanol and 2 eq. PPh$_3$ were dissolved in dry toluene (5 mL/mmol of the product of Step A), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step C

The product of Step B was dissolved in dioxane-water 1:1 (10 mL/mmol product of Step B) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reversed phase chromatography using 25 mM aqueous NH$_4$HCO$_3$ solution and MeCN as eluents.

General Procedure (XVb)
Step A:

1 eq. phenol derivative, 2 eq. 2-(4-methylpiperazin-1-yl)ethanol and 2 eq. triphenyl phosphine were dissolved in dry toluene (5 mL/mmol of phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:

The product of Step A was dissolved in dioxane-water 1:1 (10 mL/mmol product of Step A) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and the residue was purified via preparative reversed phase chromatography using 25 mM aqueous NH$_4$HCO$_3$ solution and MeCN as eluents.

Example 493 (2R)-2-[(6-[(1Z)-but-1-en-1-yl]-(5S$_a$)-5-{3-chloro-2-methyl-4-[2-(4-methylpiperazin-1-yl)ethoxy]phenyl}thieno[2,3-d]pyrimidin-4-yl)oxy]-3-phenylpropanoic acid Step A:

8.45 g 4-chloro-5,6-diiodo-thieno[2,3-d]pyrimidine (Preparation 1b) (20 mmol), 5.41 g methyl (2R)-2-hydroxy-3-phenyl-propanoate (Preparation 3ag) (30 mmol) and 13.03 g Cs$_2$CO$_3$ (40 mmol) were placed in a flask. 20 mL DMSO was added and the mixture was stirred at 60° C. until no further conversion was observed. It was diluted with water, the pH was set to 5 with 2 M HCl, and then it was extracted with dichloromethane. The combined organic layers were dried over Na$_2$SO$_4$, concentrated under reduced pressure, and purified via flash chromatography using heptane and ethyl acetate as eluents to obtain methyl (2R)-2-(5,6-diiodothieno[2,3-d]pyrimidin-4-yl)oxy-3-phenyl-propanoate. $^1$H NMR (400 MHz, DMSO-d$_6$): 8.49 (s, 1H), 7.42 (m, 2H), 7.30 (m, 2H), 7.25 (m, 1H), 5.78 (dd, 1H), 3.75 (s, 3H), 3.50-3.35 (m, 2H).

Step B:

230 mg methyl (2R)-2-(5,6-diiodothieno[2,3-d]pyrimidin-4-yl)oxy-3-phenyl-propanoate (0.4 mmol), 14 mg Pd(PPh$_3$)$_2$Cl (0.02 mmol) and 4 mg CuI (0.02 mmol) were dissolved in 3 mL DIPA, then but-1-yne was bubbled through the reaction mixture, which was stirred at 30° C. until no further conversion was observed. The reaction mixture was concentrated under reduced pressure and purified via flash chromatography using heptane and ethyl acetate as eluents to obtain methyl (2R)-2-(6-but-1-ynyl-5-iodo-thieno[2,3-d]pyrimidin-4-yl)oxy-3-phenyl-propanoate. $^1$H NMR (400 MHz, CDCl$_3$): 8.52 (s, 1H), 7.43 (m, 2H), 7.29 (m, 2H), 7.22 (m, 1H), 5.76 (dd, 1H), 3.73 (s, 3H), 3.49-3.35 (m, 2H), 2.54 (q, 2H), 1.31 (t, 3H).

Step C:

189 mg methyl (2R)-2-(6-but-1-ynyl-5-iodo-thieno[2,3-d]pyrimidin-4-yl)oxy-3-phenyl-propanoate (0.383 mmol) and 155 mg 2-chloro-3-methyl-4-(4,4,5,5-tetramethyl-1,3,2-dioxaborolan-2-yl)phenol (Preparation 5a) (0.6 mmol) were dissolved in 3 mL 2-methyl-tetrahydrofurane, 600 μL tetrabutyl ammonium hydroxyde (1M in water, 0.6 mmol) was added. Then 27 mg AtaPhos (0.038 mmol) was added and the reaction mixture was heated under nitrogen at 110° C. in a microwave reactor until no further conversion was observed. Then reaction mixture was diluted with dichloromethane and brine, the pH was set to 5 with 2 M HCl, and extracted with dichloromethane. The combined organic layers were dried over Na$_2$SO$_4$ and concentrated under reduced pressure. The residue was purified via flash chromatography using heptane and ethyl acetate as eluents. The diastereoisomer eluting later was collected as methyl (2R)-2-[6-but-1-ynyl-(5S$_a$)-5-(2-chloro-4-hydroxy-3-methyl-phenyl)thieno[2,3-d]pyrimidin-4-yl]oxy-3-phenyl-propanoate. MS: (M+H)=507.0.

Step D:

50 mg methyl (2R)-2-[6-but-1-ynyl-(5S$_a$)-5-(2-chloro-4-hydroxy-3-methyl-phenyl)thieno[2,3-d]pyrimidin-4-yl]oxy-3-phenyl-propanoate (0.1 mmol) and 2 mg Pd/BaCO$_3$ (5 m/m %) (0.001 mmol) was dissolved in 10 mL methanol. Then 2.5 mL H$_2$ was added and the reaction mixture was stirred at room temperature until no further conversion was observed. The volatiles were evaporated under reduced pressure and the crude intermediate was purified via preparative reversed phase chromatography using 25 mM aqueous NH$_4$HCO$_3$ solution and MeCN to obtain methyl (2R)-2-[6-[(1Z)-but-1-enyl]-(5S$_a$)-5-(2-chloro-4-hydroxy-3-methyl-phenyl)thieno[2,3-d]pyrimidin-4-yl]oxy-3-phenyl-propanoate. $^1$H NMR (500 MHz, DMSO-d$_6$): 10.35 (br s, 1H), 8.54 (s, 1H), 7.15 (m, 3H), 7.07 (d, 1H), 7.01 (d, 1H), 6.65 (m, 2H), 6.31 (dt, 1H), 6.14 (d, 1H), 5.44 (dd, 1H), 3.56 (s, 3H), 2.95 (dd, 1H), 2.65 (dd, 1H), 2.16 (g, 2H), 2.00 (s, 3H), 0.96 (t, 3H). HRMS: (M+H)=509.1324.

Step E:

20 mg methyl (2R)-2-[6-[(1Z)-but-1-enyl]-(5S$_a$)-5-(2-chloro-4-hydroxy-3-methyl-phenyl)thieno[2,3-d]pyrimidin-4-yl]oxy-3-phenyl-propanoate (0.039 mmol), 12 mg 2-(4-methylpiperazin-1-yl)ethanol (0.08 mmol) and 26 mg triphenyl phosphine (0.08 mmol) were dissolved in 3 mL dry toluene, then 18 mg ditertbutyl azodicarboxylate (0.08 mmol) was added. The mixture was stirred at 40° C. under nitrogen until no further conversion was observed. The volatiles were evaporated under reduced pressure and the residue was purified via flash chromatography using ethyl acetate and methanol as eluents.

Step F:

The product of Step E was dissolved in 1 mL dioxane-water (1:1) and 17 mg LiOH×H$_2$O (0.4 mmol) was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure, and the residue was purified via preparative reversed phase chromatography using 25 mM aqueous NH$_4$HCO$_3$ solution and MeCN as eluents to obtain Example 493. HRMS calculated for C$_{33}$H$_{37}$ClN$_4$O$_4$S: 620.2224. found (M+H).

Example 494 (2R)-2-{[(5S$_a$)-5-{3-chloro-2-methyl-4-[2-(4-methylpiperazin-1-yl)ethoxy]phenyl}-6-(2-methylprop-1-en-1-yl)thieno[2,3-d]pyrimidin-4-yl]oxy}-3-phenylpropanoic acid Using General Procedure (XVa) and 4,4,5,5-tetramethyl-2-(2-methylprop-1-enyl)-1,3,2-dioxaborolane as the appropriate boronic ester, Example 494 was obtained. HRMS calculated for C$_{33}$H$_{37}$ClN$_4$O$_4$S: 620.2224. found 621.2287 (M+H).

Example 495 (2R)-2-{[(5S$_a$)-5-{3-chloro-2-methyl-4-[2-(4-methylpiperazin-1-yl)ethoxy]phenyl}-6-(4-methylthiophen-2-yl)thieno[2,3-d]pyrimidin-4-yl]oxy}-3-phenylpropanoic acid Using General Procedure (XVa) and 4,4,5,5-tetramethyl-2-(4-methyl-2-thienyl)-1,3,2-dioxaborolane as the appropriate boronic ester, Example 495 was obtained. HRMS calculated for $C_{34}H_{35}ClN_4O_4S_2$: 662.1788. found 663.1884 (M+H).

Example 496 (2R)-2-{[6-(1-benzofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-phenylpropanoic acid Using General Procedure (XVa) and 2-(benzofuran-2-yl)-4,4,5,5-tetramethyl-1,3,2-dioxaborolane as the appropriate boronic ester, Example 496 was obtained. HRMS calculated for $C_{37}H_{35}ClN_4O_5S$: 682.2017. found 683.2084 (M+H).

Example 497 (2R)-2-{[6-(1-benzothiophen-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-phenylpropanoic acid Using General Procedure (XVa) and 2-(benzothiophen-2-yl)-4,4,5,5-tetramethyl-1,3,2-dioxaborolane as the appropriate boronic ester, Example 497 was obtained. HRMS calculated for $C_{37}H_{35}ClN_4O_4S_2$: 698.1788. found 699.1879 (M+H).

Example 498 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-phenylpropanoic acid Using General Procedure (XVa) and 2-(4-fluorophenyl)-4,4,5,5-tetramethyl-1,3,2-dioxaborolane as the appropriate boronic ester, Example 498 was obtained. HRMS calculated for $C_{35}H_{34}ClFN_4O_4S$: 660.1973. found 661.2042 (M+H).

Example 499 (2R)-2-{[(5S$_a$)-5-{3-chloro-2-methyl-4-[2-(4-methylpiperazin-1-yl)ethoxy]phenyl}-6-(5-methylfuran-2-yl)thieno[2,3-d]pyrimidin-4-yl]oxy}-3-phenylpropanoic acid Using General Procedure (XVa) and 4,4,5,5-tetramethyl-2-(5-methyl-2-furyl)-1,3,2-dioxaborolane as the appropriate boronic ester, Example 499 was obtained. HRMS calculated for $C_{34}H_{35}ClN_4O_5S$: 646.2017. found 647.2091 (M+H).

Example 500 (2R)-2-{[(5S$_a$)-5-{3-chloro-2-methyl-4-[2-(4-methylpiperazin-1-yl)ethoxy]phenyl}-6-(5-methylthiophen-2-yl)thieno[2,3-d]pyrimidin-4-yl]oxy}-3-phenylpropanoic acid Using General Procedure (XVa) and 4,4,5,5-tetramethyl-2-(5-methyl-2-thienyl)-1,3,2-dioxaborolane as the appropriate boronic ester, Example 500 was obtained. HRMS calculated for $C_{34}H_{35}ClN_4O_4S_2$: 662.1788. found 663.1874 (M+H).

Example 501 (2R)-2-{[(5S$_a$)-5-{3-chloro-2-methyl-4-[2-(4-methylpiperazin-1-yl)ethoxy]phenyl}-6-(5-chlorothiophen-2-yl)thieno[2,3-d]pyrimidin-4-yl]oxy}-3-phenylpropanoic acid Using General Procedure (XVa) and (5-chloro-2-thienyl) boronic acid as the appropriate boronic acid, Example 501 was obtained. HRMS calculated for $C_{33}H_{32}Cl_2N_4O_4S_2$: 682.1242. found 683.1308 (M+H).

Example 502 (2R)-2-[((5S$_a$)-5-{3-chloro-2-methyl-4-[2-(4-methylpiperazin-1-yl)ethoxy]phenyl}-6-phenylthieno[2,3-d]pyrimidin-4-yl)oxy]-3-phenylpropanoic acid Using General Procedure (XVa) and 4,4,5,5-tetramethyl-2-phenyl-1,3,2-dioxaborolane as the appropriate boronic ester, Example 502 was obtained. HRMS calculated for $C_{35}H_{35}ClN_4O_4S$: 642.2068. found 643.2135 (M+H).

Example 503 (2R)-2-{[(5S$_a$)-5-{3-chloro-2-methyl-4-[2-(4-methylpiperazin-1-yl)ethoxy]phenyl}-6-(1-methyl-1H-pyrrol-2-yl)thieno[2,3-d]pyrimidin-4-yl]oxy}-3-phenylpropanoic acid Using General Procedure (XVa) and 1-methyl-2-(4,4,5,5-tetramethyl-1,3,2-dioxaborolan-2-yl)-1H-pyrrole as the appropriate boronic ester, Example 503 was obtained. HRMS calculated for $C_{34}H_{36}ClN_5O_4S$: 645.2177. found 646.2222 (M+H).

Example 504 (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-phenylpropanoic acid Using General Procedure (XVa) and 2-(2-furyl)-4,4,5,5-tetramethyl-1,3,2-dioxaborolane as the appropriate boronic ester, Example 504 was obtained. HRMS calculated for $C_{33}H_{33}ClN_4O_5S$: 632.186. found 633.1939 (M+H).

Example 505 (2R)-2-{[(5S$_a$)-5-{3-chloro-2-methyl-4-[2-(4-methylpiperazin-1-yl)ethoxy]phenyl}-6-(thiophen-2-yl)thieno[2,3-d]pyrimidin-4-yl]oxy}-3-phenylpropanoic acid Using General Procedure (XVa) and 2-thienylboronic acid as the appropriate boronic acid, Example 505 was obtained. HRMS calculated for $C_{33}H_{33}ClN_4O_4S_2$: 648.1632. found 649.172 (M+H).

Example 506 (2R)-2-{[(5S$_a$)-5-{3-chloro-2-methyl-4-[2-(4-methylpiperazin-1-yl)ethoxy]phenyl}-6-(1-methyl-1H-pyrazol-3-yl)thieno[2,3-d]pyrimidin-4-yl]oxy}-3-phenylpropanoic acid Using General Procedure (XVa) and 1-methyl-3-(4,4,5,5-tetramethyl-1,3,2-dioxaborolan-2-yl)-1H-pyrazole as the appropriate boronic ester, Example 506 was obtained. HRMS calculated for $C_{33}H_{35}ClN_6O_4S$: 646.2129. found 647.2195 (M+H).

Example 507 (2R)-2-{[(5S$_a$)-5-{3-chloro-2-methyl-4-[2-(4-methylpiperazin-1-yl)ethoxy]phenyl}-6-(pyridin-4-yl)thieno[2,3-d]pyrimidin-4-yl]oxy}-3-phenylpropanoic acid Using General Procedure (XVa) and 4-(4,4,5,5-tetramethyl-1,3,2-dioxaborolan-2-yl)pyridine as the appropriate boronic ester, Example 507 was obtained. HRMS calculated for $C_{34}H_{34}ClN_5O_4S$: 643.202. found 644.2089 (M+H).

Example 508 (2R)-2-{[(5S$_a$)-5-{3-chloro-2-methyl-4-[2-(4-methylpiperazin-1-yl)ethoxy]phenyl}-6-(1-methyl-1H-pyrazol-5-yl)thieno[2,3-d]pyrimidin-4-yl]oxy}-3-phenylpropanoic acid Using General Procedure (XVa) and 1-methyl-5-(4,4,5,5-tetramethyl-1,3,2-dioxaborolan-2-yl)-1H-pyrazole as the appropriate boronic ester, Example 508 was obtained. HRMS calculated for $C_{33}H_{35}ClN_6O_4S$: 646.2129. found 647.222 (M+H).

Example 509 (2R)-2-{[(5S$_a$)-5-{3-chloro-2-methyl-4-[2-(4-methylpiperazin-1-yl)ethoxy]phenyl}-6-(furan-3-yl)thieno[2,3-d]pyrimidin-4-yl]oxy}-3-phenylpropanoic acid Using General Procedure (XVa) and 2-(3-furyl)-4,4,5,5-tetramethyl-1,3,2-dioxaborolane as the appropriate boronic ester Example 509 was obtained. HRMS calculated for $C_{33}H_{33}ClN_4O_5S$: 632.186. found 633.196 (M+H).

Example 510 (2R)-2-{[(5S$_a$)-5-{3-chloro-2-methyl-4-[2-(4-methylpiperazin-1-yl)ethoxy]phenyl}-6-(thiophen-3-yl)thieno[2,3-d]pyrimidin-4-yl]oxy}-3-phenylpropanoic acid Using General Procedure (XVa) and 4,4,5,5-tetramethyl-2-(3-thienyl)-1,3,2-dioxaborolane as the appropriate boronic ester, Example 510 was obtained. HRMS calculated for $C_{33}H_{33}ClN_4O_4S_2$: 648.1632. found 649.1711 (M+H).

Example 511 (2R)-2-{[(5S$_a$)-5-{3-chloro-2-methyl-4-[2-(4-methylpiperazin-1-yl)ethoxy]phenyl}-6-(2-methylthiophen-3-yl)thieno[2,3-d]pyrimidin-4-yl]oxy}-3-phenylpropanoic acid Using General Procedure (XVa) and 4,4,5,5-tetramethyl-2-(2-methyl-3-thienyl)-1,3,2-dioxaborolane as the appropriate boronic ester, Example 511 was obtained. HRMS calculated for $C_{34}H_{35}ClN_4O_4S_2$: 662.1788. found 663.1864 (M+H).

Example 512 (2R)-2-{[(5S$_a$)-5-{3-chloro-2-methyl-4-[2-(4-methylpiperazin-1-yl)ethoxy]phenyl}-6-(1,3-thiazol-5-yl)thieno[2,3-d]pyrimidin-4-yl]oxy}-3-phenylpropanoic acid Using General Procedure (XVa) and 5-(4,4,5,5-tetramethyl-1,3,2-dioxaborolan-2-yl)-1,3-thiazole as the appropriate boronic ester, Example 512 was obtained. HRMS calculated for $C_{32}H_{32}ClN_5O_4S_2$: 649.1584. found 650.1654 (M+H).

Example 513 (2R)-2-{[(5S$_a$)-5-{3-chloro-2-methyl-4-[2-(4-methylpiperazin-1-yl)ethoxy]phenyl}-6-(1-methyl-1H-pyrazol-4-yl)thieno[2,3-d]pyrimidin-4-yl]oxy}-3-phenylpropanoic acid Using General Procedure (XVa) and 1-methyl-4-(4,4,5,5-tetramethyl-1,3,2-dioxaborolan-2-yl)-1H-pyrazole as the appropriate boronic ester, Example 513 was obtained. HRMS calculated for $C_{33}H_{35}ClN_6O_4S$: 646.2129. found 647.2199 (M+H).

Example 514 (2R)-2-{[(5S$_a$)-5-{3-chloro-2-methyl-4-[2-(4-methylpiperazin-1-yl)ethoxy]phenyl}-6-(5-methylthiophen-3-yl)thieno[2,3-d]pyrimidin-4-yl]oxy}-3-phenylpropanoic acid Step A:
531 mg 4-bromo-2-methyl-thiophene (3.0 mmol), 813 mg 2-(5,5-dimethyl-1,3,2-dioxaborinan-2-yl)-5,5-dimethyl-1,3,2-dioxaborinane (3.6 mmol) and 883 mg KOAc (9.0 mmol) were dissolved in 15 mL 1,4-dioxane, then 219 mg Pd(dppf)Cl$_2$ (0.3 mmol) was added. The mixture was heated under nitrogen at 120° C. in a microwave reactor until no further conversion was observed. The volatiles were evaporated under reduced pressure and purified via flash chromatography using heptane and ethyl acetate as eluents to obtain 5,5-dimethyl-2-(5-methyl-3-thienyl)-1,3,2-dioxaborinane.
$^1$H NMR (500 MHz, CDCl$_3$): 7.59 (d, 1H), 7.00 (dd, 1H), 3.73 (s, 4H), 2.49 (d, 3H), 1.02 (s, 6H).
Step B:
Using General Procedure (XVa) and 5,5-dimethyl-2-(5-methyl-3-thienyl)-1,3,2-dioxaborinane as the appropriate boronic ester, Example 514 was obtained. HRMS calculated for $C_{34}H_{35}ClN_4O_4S_2$: 662.1788. found 663.1884 (M+H).

Example 515 (2R)-2-{[(5S$_a$)-5-{3-chloro-2-methyl-4-[2-(4-methylpiperazin-1-yl)ethoxy]phenyl}-6-(2-methyl-1,3-thiazol-4-yl)thieno[2,3-d]pyrimidin-4-yl]oxy}-3-phenylpropanoic acid Using General Procedure (XVa) and 2-methyl-4-(4,4,5,5-tetramethyl-1,3,2-dioxaborolan-2-yl)-1,3-thiazole as the appropriate boronic ester, Example 515 was obtained. HRMS calculated for $C_{33}H_{34}ClN_5O_4S_2$: 663.1741. found 664.1823 (M+H).

Example 516 (2R)-2-{[(5S$_a$)-5-{3-chloro-2-methyl-4-[2-(4-methylpiperazin-1-yl)ethoxy]phenyl}-6-(4-methylthiophen-3-yl)thieno[2,3-d]pyrimidin-4-yl]oxy}-3-phenylpropanoic acid Using General Procedure (XVa) and 4,4,5,5-tetramethyl-2-(4-methyl-3-thienyl)-1,3,2-dioxaborolane as the appropriate boronic ester, Example 516 was obtained. HRMS calculated for $C_{34}H_{35}ClN_4O_4S_2$: 662.1788. found 663.1863 (M+H).

Example 517 (2R)-2-{[(5S$_a$)-5-{3-chloro-2-methyl-4-[2-(4-methylpiperazin-1-yl)ethoxy]phenyl}-6-(3-methylthiophen-2-yl)thieno[2,3-d]pyrimidin-4-yl]oxy}-3-phenylpropanoic acid Using General Procedure (XVa) and 4,4,5,5-tetramethyl-2-(3-methyl-2-thienyl)-1,3,2-dioxaborolane as the appropriate boronic ester, Example 517 was obtained. HRMS calculated for $C_{34}H_{35}ClN_4O_4S_2$: 662.1788. found 663.1882 (M+H).

Example 518 (2R)-2-[(6-bromo-(5S$_a$)-5-{3-chloro-2-methyl-4-[2-(4-methylpiperazin-1-yl)ethoxy]phenyl}thieno[2,3-d]pyrimidin-4-yl)oxy]-3-phenylpropanoic acid Step A:
180 mg methyl (2R)-2-[6-bromo-(5S$_a$)-5-(3-chloro-4-hydroxy-2-methyl-phenyl)thieno[2,3-d]pyrimidin-4-yl]oxy-3-phenyl-propanoate (Preparation 22) (0.335 mmol), 96 mg 2-(4-methylpiperazin-1-yl)ethanol (0.672 mmol) and 177 mg PPh$_3$ (0.672 mmol) were dissolved in 6 mL dry toluene, then 145 mg ditertbutyl azodicarboxylate (0.672 mmol) was added. The mixture was stirred at 50° C. under nitrogen until no further conversion was observed. The volatiles were evaporated under reduced pressure and the residue was purified via flash chromatography using ethyl acetate and methanol as eluents.
Step B:
The product of Step A was dissolved in 5 ml methanol and 50 mg NaOH (1.25 mmol) was added. The mixture was stirred at 50° C. until no further conversion was observed. It was diluted with brine, neutralized with 2 M HCl, and extracted with DCM. The combined organic layers were dried over $Na_2SO_4$, concentrated under reduced pressure, and the residue was purified via preparative reversed phase chromatography using 25 mM aqueous $NH_4HCO_3$ solution and MeCN as eluents to obtain Example 518. HRMS calculated for $C_{29}H_{30}BrClN_4O_4S$: 644.086. found 645.0942 (M+H).

Example 519 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-phenylpropanoic acid Step A:
8.45 g 4-chloro-5,6-diiodo-thieno[2,3-d]pyrimidine (Preparation 1b) (20 mmol), 5.41 g methyl (2R)-2-hydroxy-3-phenyl-propanoate (Preparation 3ag) (30 mmol) and 13.03 g $Cs_2CO_3$ (40 mmol) were placed in a flask. 20 mL DMSO was added and the mixture was stirred at 60° C. until no further conversion was observed. The reaction mixture was diluted with water, the pH was set to 5 with 2 M HCl, and then it was extracted with dichloromethane. The combined organic layers were dried over $Na_2SO_4$, concentrated under reduced pressure, and the residue was purified via flash chromatography using heptane and ethyl acetate as eluents to obtain methyl (2R)-2-(5,6-diiodothieno[2,3-d]pyrimidin-4-yl)oxy-3-phenyl-propanoate. $^1$H NMR (400 MHz, DMSO-$d_6$): 8.49 (s, 1H), 7.42 (m, 2H), 7.30 (m, 2H), 7.25 (m, 1H), 5.78 (dd, 1H), 3.75 (s, 3H), 3.50-3.35 (m, 2H).

Step B:
1.132 g methyl (2R)-2-(5,6-diiodothieno[2,3-d]pyrimidin-4-yl)oxy-3-phenyl-propanoate (2 mmol), 70 mg Pd(PPh$_3$)$_2$Cl (0.1 mmol) and 38 mg CuI (0.2 mmol) were dissolved in 10 mL DIPA, then propyne was bubbled through the reaction mixture, which was stirred at 45° C. until no further conversion was observed. It was concentrated under reduced pressure and purified via flash chromatography using heptane and ethyl acetate as eluents to obtain methyl (2R)-2-(5-iodo-6-prop-1-ynyl-thieno[2,3-d]pyrimidin-4-yl)oxy-3-phenyl-propanoate. MS: (M+H)=479.0.

Step C:
469 mg methyl (2R)-2-(5-iodo-6-prop-1-ynyl-thieno[2,3-d]pyrimidin-4-yl)oxy-3-phenyl-propanoate (0.98 mmol) and 537 mg 2-chloro-3-methyl-4-(4,4,5,5-tetramethyl-1,3,2-dioxaborolan-2-yl)phenol (Preparation 5a) (2.0 mmol) were dissolved in 10 mL 1,4-dioxane, then 815 mg $Cs_2CO_3$ (2.5 mmol) dissolved in 2 mL water was added followed by 71 mg AtaPhos (0.1 mmol) and the mixture was heated under nitrogen at 110° C. in a microwave reactor until no further conversion was observed. After dilution with dichloromethane and brine the pH was set to 5 with 2 M HCl and the aqueous phase was extracted with dichloromethane. The combined organic layers were dried over $Na_2SO_4$, concentrated under reduced pressure. The diastereoisomers were separated via flash chromatography using heptane and ethyl acetate as eluents. The diastereoisomer eluting later was collected as methyl (2R)-2-[(5S$_a$)-5-(2-chloro-4-hydroxy-3-methyl-phenyl)-6-prop-1-ynyl-thieno[2,3-d]pyrimidin-4-yl]oxy-3-phenyl-propanoate. MS: (M+H)=493.0.

Step D:
360 mg methyl (2R)-2-[(5S$_a$)-5-(2-chloro-4-hydroxy-3-methyl-phenyl)-6-prop-1-ynyl-thieno[2,3-d]pyrimidin-4-yl]oxy-3-phenyl-propanoate (0.73 mmol), 211 mg 2-(4-methylpiperazin-1-yl)ethanol (1.46 mmol) and 487 mg triphenyl phosphine (1.46 mmol) were dissolved in 5 mL dry toluene, then 336 mg ditertbutyl azodicarboxylate (1.46 mmol) was added. The mixture was stirred at 50° C. under nitrogen until no further conversion was observed. The volatiles were evaporated under reduced pressure and the crude intermediate was purified via flash chromatography using ethyl acetate and methanol as eluents.

Step E:
The product of Step D was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic layers were dried over $Na_2SO_4$, concentrated under reduced pressure, and the residue was purified via preparative reversed phase chromatography using 25 mM aqueous $NH_4HCO_3$ solution and MeCN as eluents to obtain Example 519. HRMS calculated for $C_{32}H_{33}ClN_4O_4S$: 604.1911. found 605.2 (M+H).

Example 520 (2R)-2-{[(5S$_a$)-5-{3-chloro-2-methyl-4-[2-(4-methylpiperazin-1-yl)ethoxy]phenyl}-6-(cyclopropylethynyl)thieno[2,3-d]pyrimidin-4-yl]oxy}-3-phenylpropanoic acid Step A:
1.132 g methyl (2R)-2-(5,6-diiodothieno[2,3-d]pyrimidin-4-yl)oxy-3-phenyl-propanoate (from Step A of Example 519, 2 mmol), 152 mg ethynylcyclopropane (2.3 mmol), 70 mg Pd(PPh$_3$)$_2$Cl (0.1 mmol) and 38 mg CuI (0.2 mmol) were dissolved in 4 mL DIPA and the mixture was stirred under nitrogen at 40° C. until no further conversion was observed. The reaction was concentrated under reduced pressure and purified via flash chromatography using heptane and ethyl acetate as eluents to obtain methyl (2R)-2-[6-(2-cyclopropylethynyl)-5-iodo-thieno[2,3-d]pyrimidin-4-yl]oxy-3-phenyl-propanoate. MS: (M+H)=505.0.

Step B:
968 mg methyl (2R)-2-[6-(2-cyclopropylethynyl)-5-iodo-thieno[2,3-d]pyrimidin-4-yl]oxy-3-phenyl-propanoate (1.92 mmol) and 670 mg 2-chloro-3-methyl-4-(4,4,5,5-tetramethyl-1,3,2-dioxaborolan-2-yl)phenol (Preparation 5a) (2.5 mmol) were dissolved in 8 mL 2-methyl-tetrahydrofurane and 2.5 mL tetrabutylammonium hydroxyde (1M in water, 2.5 mmol) was added followed by 68 mg AtaPhos (0.096 mmol). The mixture was heated under nitrogen at 110° C. in a microwave reactor until no further conversion was observed.

Then it was diluted with dichloromethane and brine, the pH was set to 5 with 2 M HCl and the aqueous phase was extracted with dichloromethane. The combined organic layers were dried over $Na_2SO_4$, concentrated under reduced pressure. The diastereoisomers were separated via flash chromatography using heptane and ethyl acetate as eluents. The diastereoisomer eluting later was collected as methyl (2R)-2-[(5S$_a$)-5-(2-chloro-4-hydroxy-3-methyl-phenyl)-6-(2-cyclopropylethynyl)thieno[2,3-d]pyrimidin-4-yl]oxy-3-phenyl-propanoate. MS: (M+H)=519.0.

Step C:
156 mg methyl (2R)-2-[(5S$_a$)-5-(2-chloro-4-hydroxy-3-methyl-phenyl)-6-(2-cyclopropylethynyl)thieno[2,3-d]pyrimidin-4-yl]oxy-3-phenyl-propanoate (0.3 mmol), 87 mg 2-(4-methylpiperazin-1-yl)ethanol (0.6 mmol) and 158 mg triphenyl phosphine (0.6 mmol) were dissolved in 3 mL dry toluene, then 138 mg ditertbutyl azodicarboxylate (0.6 mmol) was added. The mixture was stirred at 50° C. under nitrogen until no further conversion was observed. The volatiles were evaporated under reduced pressure and the crude intermediate was purified via flash chromatography using ethyl acetate and methanol as eluents.
Step D:
The product of Step C was dissolved in 5 mL methanol and 200 mg LiOH×H$_2$O (4.76 mmol) was added. The mixture was stirred at room temperature until no further conversion was observed. Then it was diluted with brine, neutralized with 2 M HCl, extracted with DCM, dried over Na$_2$SO$_4$, filtered and concentrated under reduced pressure and purified via preparative reversed phase chromatography using 25 mM aqueous NH$_4$HCO$_3$ solution and MeCN as eluents to obtain Example 520. HRMS calculated for C$_{34}$H$_{35}$ClN$_4$O$_4$S: 630.2068. found 631.2096 (M+H).

Example 521 (2R)-2-[((5S$_a$)-5-{3-chloro-2-methyl-4-[2-(4-methylpiperazin-1-yl)ethoxy]phenyl}-6-cyanothieno[2,3-d]pyrimidin-4-yl)oxy]-3-phenylpropanoic acid Step A:
935 mg [2-chloro-4-(4-chlorothieno[2,3-d]pyrimidin-5-yl)-3-methyl-phenoxy]-triisopropyl-silane (Preparation 23a) (2.0 mmol) was dissolved in 20 mL dry THF then cooled to −78° C. under argon atmosphere. 1.2 mL lithium diisopropylamide (2.4 mmol, 2 M in THF, EtPh, hexanes) was added and the mixture was stirred at −78° C. for 1 hour. Then 471 mg p-tolylsulfonylformonitrile (2.6 mmol) was added and the mixture was allowed to warm up to room temperature. To the reaction mixture saturated aq. NH$_4$Cl was added and then extracted with ethyl acetate. Organic layer was dried over Mg$_2$SO$_4$, filtered and concentrated under reduced pressure. The crude intermediate was purified via flash chromatography using heptane and ethyl acetate as eluents to obtain 4-chloro-5-(3-chloro-2-methyl-4-triisopropylsilyloxy-phenyl)thieno[2,3-d]pyrimidine-6-carbonitrile.
$^1$H NMR (400 MHz, DMSO-d$_6$): 9.16 (s, 1H), 7.26 (d, 1H), 7.03 (d, 1H), 2.10 (s, 3H), 1.42-1.30 (m, 3H), 1.10 (dd, 18H).
Step B:
380 mg 4-chloro-5-(3-chloro-2-methyl-4-triisopropylsilyloxy-phenyl)thieno[2,3-d] pyrimidine-6-carbonitrile (0.77 mmol) was dissolved in 7 mL $^i$PrOH, 166 mg methyl (2R)-2-hydroxy-3-phenyl-propanoate (Preparation 3ag) (0.92 mmol) and 753 mg Cs$_2$CO$_3$ (2.31 mmol) was added and the mixture was stirred at room temperature until no further conversion was observed. It was diluted with water, the pH of the mixture was set to 4 with 2 M HCl, and extracted with DCM. The combined organic layers were dried over Na$_2$SO$_4$, concentrated under reduced pressure, and the residue was purified via flash chromatography using heptane and ethyl acetate as eluents.
Step C:
The product of Step B was dissolved in 10 mL THF, 0.8 mL TBAF (1M in THF) (0.8 mmol) was added and the mixture was stirred until no further conversion was observed. Then it was diluted with ethyl acetate, washed with water and brine. The organic layer was dried over Na$_2$SO$_4$, filtered and concentrated under reduced pressure and purified via flash chromatography using heptane and ethyl acetate as eluents. The diastereoisomer eluting later was collected to obtain methyl (2R)-2-[(5S$_a$)-5-(3-chloro-4-hydroxy-2-methyl-phenyl)-6-cyano-thieno[2,3-d]pyrimidin-4-yl]oxy-3-phenyl-propanoate. MS: (M+H)=480.0.
Step D:
Using General Procedure (XVb) and methyl (2R)-2-[(5S$_a$)-5-(3-chloro-4-hydroxy-2-methyl-phenyl)-6-cyano-thieno[2,3-d]pyrimidin-4-yl]oxy-3-phenyl-propanoate as the appropriate phenol Example 521 was obtained. HRMS calculated for C$_{30}$H$_{30}$ClN$_5$O$_4$S: 591.1707. found 592.1786 (M+H).

Example 522 (2R)-2-[(6-acetyl-(5S$_a$)-5-{3-chloro-2-methyl-4-[2-(4-methylpiperazin-1-yl)ethoxy]phenyl}thieno[2,3-d]pyrimidin-4-yl)oxy]-3-phenyl-propanoic acid Step A:
935 mg [2-chloro-4-(4-chlorothieno[2,3-d]pyrimidin-5-yl)-3-methyl-phenoxy]-triisopropyl-silane (Preparation 23a) (2.0 mmol) was dissolved in 20 mL dry THF then cooled to −78° C. under argon atmosphere. 1.2 mL lithium diisopropylamide (2.4 mmol, 2 M in THF, EtPh, hexanes) was added and the mixture was stirred at −78° C. for 1 hour. Then 265 mg acetic anhydride (2.6 mmol) was added and the mixture was allowed to warm up to room temperature. To the reaction mixture saturated NH$_4$Cl was added and then extracted with ethyl acetate. The combined organic layers were dried over Na$_2$SO$_4$, concentrated under reduced pressure, and the residue purified via flash chromatography, using heptane and EtOAc as eluents to obtain 1-[4-chloro-5-(3-chloro-2-methyl-4-triisopropylsilyloxy-phenyl)thieno[2,3-d]pyrimidin-6-yl]ethanone. $^1$H NMR (400 MHz, CDCl$_3$): 8.94 (s, 1H), 6.98 (d, 1H), 6.95 (d, 1H), 2.17 (s, 1H), 2.03 (s, 1H), 1.44-1.32 (m, 3H), 1.17 (d, 18H).
Step B:
278 mg 1-[4-chloro-5-(3-chloro-2-methyl-4-triisopropylsilyloxy-phenyl)thieno[2,3-d]pyrimidin-6-yl]ethanone (0.55 mmol) was dissolved in 5 mL $^i$PrOH, 118 mg methyl (2R)-2-hydroxy-3-phenyl-propanoate (Preparation 3ag) (0.65 mmol) and 538 mg Cs$_2$CO$_3$ (1.65 mmol) was added and the mixture was stirred at room temperature until no further conversion was observed. It was diluted with water, the pH of the mixture was set to 4 with 2 M HCl, and extracted with dichloromethane. The combined organic layers were dried over Na$_2$SO$_4$, concentrated under reduced pressure, and the residue was purified via flash chromatography using heptane and ethyl acetate as eluents.
Step C:
The product of Step B was dissolved in 10 mL THF, 6 mL TBAF (1M in THF) (0.6 mmol) was added and the mixture was stirred at room temperature until no further conversion was observed. Then it was diluted with ethyl acetate, washed with water and brine. The organic layer was dried over Na$_2$SO$_4$, concentrated under reduced pressure and purified via flash chromatography using heptane and ethyl acetate as eluents. The diastereoisomer eluting later was collected to obtain methyl (2R)-2-[6-acetyl-(5S$_a$)-5-(3-chloro-4-hydroxy-2-methyl-phenyl)thieno[2,3-d]pyrimidin-4-yl]oxy-3-phenyl-propanoate. $^1$H NMR (500 MHz, DMSO-d$_6$): 10.44 (br s, 1H), 8.71 (s, 1H), 7.20 (m, 3H), 7.16 (d, 1H), 7.03 (d, 1H), 6.82 (m, 2H), 5.46 (dd, 1H), 4.75 (m, 1H), 2.87 (dd, 1H), 2.64 (dd, 1H), 2.03 (s, 3H), 1.94 (s, 3H), 1.07 (d, 3H), 0.91 (d, 3H). HRMS: (M+H)=525.1244
Step D:
Using General Procedure (XVb) and methyl (2R)-2-[6-acetyl-(5S$_a$)-5-(3-chloro-4-hydroxy-2-methyl-phenyl)thieno[2,3-d]pyrimidin-4-yl]oxy-3-phenyl-propanoate as the appropriate phenol, Example 522 was obtained. HRMS calculated for C$_{31}$H$_{33}$ClN$_4$O$_5$S: 608.186. found 609.194 (M+H).

General Procedure (XVI)

Step A:

2.5 eq. of the appropriate boronic acid was dissolved in dry dioxane (5 mL/mmol Preparation 25), then 2.5 eq pinacol and dry acidic Amberlyst (100 mg/mmol boronic acid) were added and the mixture was stirred at room temperature overnight, then it was filtered (if the appropriate boronic ester was available, then it was dissolved in dioxane (5 mL/mmol Preparation 25) and this solution was used instead of the filtrate). 1 eq. ethyl (2R)-2-[(5S$_a$)-5-(3-chloro-4-hydroxy-2-methyl-phenyl)-6-iodo-thieno[2,3-d]pyrimidin-4-yl]oxy-3-(2-methoxyphenyl)propanoate (Preparation 25), 0.1 eq. PdCl$_2$×dppf, 2.5 eq. Cs$_2$CO$_3$ and water (2.5 mL/mmol) were added to the filtrate and the mixture was heated under nitrogen at 110° C. in a microwave reactor until no further conversion was observed. Then it was diluted with brine, neutralized with 2 M HCl, and extracted with DCM. The combined organic phases were dried over Na$_2$SO$_4$ and concentrated under reduced pressure. The residue was purified via flash chromatography using heptane and EtOAc as eluents.

Step B:

1 eq. of the product of Step A, 2 eq. of 2-(4-methylpiperazin-1-yl)ethanol and 2 eq. PPh$_3$ were dissolved in dry toluene (0.2 M for the product of Step A), then 2 eq. ditertbutyl azodicarboxylate was added. The mixture was stirred at 50° C. under nitrogen until no further conversion was observed. The volatiles were evaporated under reduced pressure and the residue was purified via flash chromatography using EtOAc and MeOH as eluents.

Step C:

The product of Step B was dissolved in dioxane-water (1:1, 10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$ and concentrated under reduced pressure. The crude product was purified via preparative reversed phase chromatography using 25 mM aqueous NH$_4$HCO$_3$ solution and MeCN as eluents.

Example 523 (2R)-2-{[(5S$_a$)-5-{3-chloro-2-methyl-4-[2-(4-methylpiperazin-1-yl)ethoxy]phenyl}-6-(3,4,5-trifluorophenyl)thieno[2,3-d]pyrimidin-4-yl]oxy}-3-(2-methoxyphenyl)propanoic acid Using General Procedure (XVI) and 4,4,5,5-tetramethyl-2-(3,4,5-trifluorophenyl)-1,3,2-dioxaborolane as the appropriate boronic acid derivative, Example 523 was obtained. HRMS calculated for C$_{36}$H$_{34}$ClF$_3$N$_4$O$_5$S: 726.1891. found 727.1963 (M+H).

Example 524 (2R)-2-{[(5S$_a$)-5-{3-chloro-2-methyl-4-[2-(4-methylpiperazin-1-yl)ethoxy]phenyl}-6-(3,4-difluoro-5-methoxyphenyl)thieno[2,3-d]pyrimidin-4-yl]oxy}-3-(2-methoxyphenyl)propanoic acid Using General Procedure (XVI) and 2-(3,4-difluoro-5-methoxy-phenyl)-4,4,5,5-tetramethyl-1,3,2-dioxaborolane as the appropriate boronic acid derivative, Example 524 was obtained. HRMS calculated for C$_{37}$H$_{37}$ClF$_2$N$_4$O$_6$S: 738.2090. found 739.2158 (M+H).

Example 525 (2R)-2-{[(5S$_a$)-5-{3-chloro-2-methyl-4-[2-(4-methylpiperazin-1-yl)ethoxy]phenyl}-6-(2,3,4,5-tetrafluorophenyl)thieno[2,3-d]pyrimidin-4-yl]oxy}-3-(2-methoxyphenyl)propanoic acid Using General Procedure (XVI) and 4,4,5,5-tetramethyl-2-(2,3,4,5-tetrafluorophenyl)-1,3,2-dioxaborolane as the appropriate boronic acid derivative, Example 525 was obtained. HRMS calculated for C$_{36}$H$_{33}$ClF$_4$N$_4$O$_5$S: 744.1796. found 745.1873 (M+H).

Example 526 (2R)-2-{[6-(3-chloro-5-fluorophenyl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-methoxyphenyl)propanoic acid Using General Procedure (XVI) and 2-(3-chloro-5-fluorophenyl)-4,4,5,5-tetramethyl-1,3,2-dioxaborolane as the appropriate boronic acid derivative, Example 526 was obtained. HRMS calculated for C$_{36}$H$_{35}$Cl$_2$FN$_4$O$_5$S: 724.1689. found 725.1766 (M+H).

Example 527 (2R)-2-{[(5S$_a$)-5-{3-chloro-2-methyl-4-[2-(4-methylpiperazin-1-yl)ethoxy]phenyl}-6-(3,5-difluorophenyl)thieno[2,3-d]pyrimidin-4-yl]oxy}-3-(2-methoxyphenyl)propanoic acid Using General Procedure (XVI) and 2-(3,5-difluorophenyl)-4,4,5,5-tetramethyl-1,3,2-dioxaborolane as the appropriate boronic acid derivative, Example 527 was obtained. HRMS calculated for C$_{36}$H$_{35}$ClF$_2$N$_4$O$_5$S: 708.1985. found 709.2054 (M+H).

Example 528 (2R)-2-{[(5S$_a$)-5-{3-chloro-2-methyl-4-[2-(4-methylpiperazin-1-yl)ethoxy]phenyl}-6-(3-fluoro-5-methoxyphenyl)thieno[2,3-d]pyrimidin-4-yl]oxy}-3-(2-methoxyphenyl)propanoic acid Using General Procedure (XVI) and 2-(3-fluoro-5-methoxy-phenyl)-4,4,5,5-tetramethyl-1,3,2-dioxaborolane as the appropriate boronic acid derivative, Example 528 was obtained. HRMS calculated for C$_{37}$H$_{38}$ClFN$_4$O$_6$S: 720.2185. found 721.2259 (M+H).

Example 529 (2R)-2-{[(5S$_a$)-5-{3-chloro-2-methyl-4-[2-(4-methylpiperazin-1-yl)ethoxy]phenyl}-6-(4-methylfuran-2-yl)thieno[2,3-d]pyrimidin-4-yl]oxy}-3-(2-methoxyphenyl)propanoic acid Using General Procedure (XVI) and 4,4,5,5-tetramethyl-2-(4-methyl-2-furyl)-1,3,2-dioxaborolane as the appropriate boronic acid derivative, Example 529 was obtained. HRMS calculated for C$_{35}$H$_{37}$ClN$_4$O$_6$S: 676.2122. found 677.2239 (M+H).

Example 530 (2R)-2-{[(5S$_a$)-5-{3-chloro-2-methyl-4-[2-(4-methylpiperazin-1-yl)ethoxy]phenyl}-6-(thieno[3,2-b]thiophen-2-yl)thieno[2,3-d]pyrimidin-4-yl]oxy}-3-(2-methoxyphenyl)propanoic acid Step A:

982 mg thieno[3,2-b]thiophene (7.0 mmol) was dissolved in 40 mL dry THF and cooled to −78° C. under argon atmosphere. 11.2 mL ″BuLi (7.0 mmol, 1.6 M in hexanes)

was added and the mixture was stirred at −78° C. for 1 hour. Then 1.6 mL 2-isopropoxy-4,4,5,5-tetramethyl-1,3,2-dioxaborolane (7.7 mmol) was added and the mixture was allowed to warm up to room temperature, then it was quenched with saturated aq. NH$_4$Cl solution, then extracted with THF, dried over Na$_2$SO$_4$, filtered and concentrated and purified via flash chromatography using heptane and EtOAc as eluents to give 4,4,5,5-tetramethyl-2-thieno[3,2-b]thiophen-2-yl-1,3,2-dioxaborolane. MS (EI, 70 eV) m/z (% relative intensity, [ion]): 120 (19), 165 (25), 166 (100), 167 (44), 180 (17), 206 (22), 223 (60), 266 (68, [M$^+$]).

Step B:

Using General Procedure (XVI) and 4,4,5,5-tetramethyl-2-thieno[3,2-b]thiophen-2-yl-1,3,2-dioxaborolane as the appropriate boronic acid derivative, Example 530 was obtained. HRMS calculated for C$_{36}$H$_{35}$ClN$_4$O$_5$S$_3$: 734.1458. found 735.1553 (M+H).

Example 531 (2R)-2-[(5S$_a$)-(5-{3-chloro-2-methyl-4-[2-(4-methylpiperazin-1-yl)ethoxy]phenyl}-6-[4-fluoro-3-(trifluoromethyl)phenyl]thieno[2,3-d]pyrimidin-4-yl)oxy]-3-(2-methoxyphenyl)propanoic acid Using General Procedure (XVI) and 2-[4-fluoro-3-(trifluoromethyl)phenyl]-4,4,5,5-tetramethyl-1,3,2-dioxaborolane as the appropriate boronic acid derivative, Example 531 was obtained. HRMS calculated for C$_{37}$H$_{35}$ClF$_4$N$_4$O$_5$S: 758.1953. found 759.2031 (M+H).

Example 532 (2R)-2-{[6-(3-chloro-4-fluorophenyl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-methoxyphenyl)propanoic acid Using General Procedure (XVI) and 2-(3-chloro-4-fluorophenyl)-4,4,5,5-tetramethyl-1,3,2-dioxaborolane as the appropriate boronic acid derivative, Example 532 was obtained. HRMS calculated for C$_{36}$H$_{35}$Cl$_2$FN$_4$O$_5$S: 724.1689. found 725.1761 (M+H).

Example 533 (2R)-2-{[(5S$_a$)-5-{3-chloro-2-methyl-4-[2-(4-methylpiperazin-1-yl)ethoxy]phenyl}-6-(3,4-difluorophenyl)thieno[2,3-d]pyrimidin-4-yl]oxy}-3-(2-methoxyphenyl)propanoic acid Using General Procedure (XVI) and 2-(3,4-difluorophenyl)-4,4,5,5-tetramethyl-1,3,2-dioxaborolane as the appropriate boronic acid derivative, Example 533 was obtained. HRMS calculated for C$_{36}$H$_{35}$ClF$_2$N$_4$O$_5$S: 708.1985. found 709.2055 (M+H).

Example 534 (2R)-2-{[(5S$_a$)-5-{3-chloro-2-methyl-4-[2-(4-methylpiperazin-1-yl)ethoxy]phenyl}-6-(4-fluoro-3-hydroxyphenyl)thieno[2,3-d]pyrimidin-4-yl]oxy}-3-(2-methoxyphenyl)propanoic acid Using General Procedure (XVI) and 2-fluoro-5-(4,4,5,5-tetramethyl-1,3,2-dioxaborolan-2-yl)phenol as the appropriate boronic acid derivative, Example 534 was obtained. HRMS calculated for C$_{36}$H$_{36}$ClFN$_4$O$_6$S: 706.2028. found 707.2087 (M+H).

Example 535 (2R)-2-[(5S$_a$)-5-{3-chloro-2-methyl-4-[2-(4-methylpiperazin-1-yl)ethoxy]phenyl}-6-[4-fluoro-3-(2,2,2-trifluoroethoxy)phenyl]thieno[2,3-d]pyrimidin-4-yl)oxy]-3-(2-methoxyphenyl)propanoic acid Using General Procedure (XVI) and 2-[4-fluoro-3-(2,2,2-trifluoroethoxy)phenyl]-4,4,5,5-tetramethyl-1,3,2-dioxaborolane as the appropriate boronic acid derivative, Example 535 was obtained. HRMS calculated for C$_{38}$H$_{37}$ClF$_4$N$_4$O$_6$S: 788.2058. found 789.2125 (M+H).

Example 536 (2R)-2-{[6-(3-chloro-2,4-difluorophenyl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-methoxyphenyl)propanoic acid Using General Procedure (XVI) and 2-(3-chloro-2,4-difluoro-phenyl)-4,4,5,5-tetramethyl-1,3,2-dioxaborolane as the appropriate boronic acid derivative, Example 536 was obtained. HRMS calculated for C$_{36}$H$_{34}$Cl$_2$F$_2$N$_4$O$_5$S: 742.1595. found 743.1645 (M+H).

Example 537 (2R)-2-{[(5S$_a$)-5-{3-chloro-2-methyl-4-[2-(4-methylpiperazin-1-yl)ethoxy]phenyl}-6-(2,3,4-trifluorophenyl)thieno[2,3-d]pyrimidin-4-yl]oxy}-3-(2-methoxyphenyl)propanoic acid Using General Procedure (XVI) and 4,4,5,5-tetramethyl-2-(2,3,4-trifluorophenyl)-1,3,2-dioxaborolane as the appropriate boronic acid derivative, Example 537 was obtained. HRMS calculated for C$_{36}$H$_{34}$ClF$_3$N$_4$O$_5$S: 726.1891. found 727.1963 (M+H).

Example 538 (2R)-2-{[(5S$_a$)-5-{3-chloro-2-methyl-4-[2-(4-methylpiperazin-1-yl)ethoxy]phenyl}-6-(4-methylphenyl)thieno[2,3-d]pyrimidin-4-yl]oxy}-3-(2-methoxyphenyl)propanoic acid Using General Procedure (XVI) and 4,4,5,5-tetramethyl-2-(p-tolyl)-1,3,2-dioxaborolane as the appropriate boronic acid derivative, Example 538 was obtained. HRMS calculated for C$_{37}$H$_{39}$ClN$_4$O$_5$S: 686.2330. found 687.2405 (M+H).

Example 539 (2R)-2-{[(5S$_a$)-5-{3-chloro-2-methyl-4-[2-(4-methylpiperazin-1-yl)ethoxy]phenyl}-6-(4-chlorophenyl)thieno[2,3-d]pyrimidin-4-yl]oxy}-3-(2-methoxyphenyl)propanoic acid Using General Procedure (XVI) and 2-(4-chlorophenyl)-4,4,5,5-tetramethyl-1,3,2-dioxaborolane as the appropriate boronic acid derivative, Example 539 was obtained. HRMS calculated for C$_{36}$H$_{36}$Cl$_2$N$_4$O$_5$S: 706.1783. found 707.1865 (M+H).

Example 540 (2R)-2-{[(5S$_a$)-5-{3-chloro-2-methyl-4-[2-(4-methylpiperazin-1-yl)ethoxy]phenyl}-6-(2,4-difluorophenyl)thieno[2,3-d]pyrimidin-4-yl]oxy}-3-(2-methoxyphenyl)propanoic acid Using General Procedure (XVI) and 2-(2,4-difluorophenyl)-4,4,5,5-tetramethyl-1,3,2-dioxaborolane as the appropriate boronic acid derivative, Example 540 was obtained. HRMS calculated for C$_{36}$H$_{35}$ClF$_2$N$_4$O$_5$S: 708.1985. found 709.2055 (M+H).

Example 541 (2R)-2-{[(5S$_a$)-5-{3-chloro-2-methyl-4-[2-(4-methylpiperazin-1-yl)ethoxy]phenyl}-6-(5-methylfuran-2-yl)thieno[2,3-d]pyrimidin-4-yl]oxy}-3-(2-methoxyphenyl)propanoic acid Using General Procedure (XVI) and 4,4,5,5-tetramethyl-2-(5-methyl-2-furyl)-1,3,2-dioxaborolane as the appropriate boronic acid derivative, Example 541 was obtained. HRMS calculated for $C_{35}H_{37}ClN_4O_6S$: 676.2122. found 677.2198 (M+H).

Example 542 (2R)-2-[((5S$_a$)-5-{3-chloro-2-methyl-4-[2-(4-methylpiperazin-1-yl)ethoxy]phenyl}-6-[5-(dimethoxymethyl)furan-2-yl]thieno[2,3-d]pyrimidin-4-yl)oxy]-3-(2-methoxyphenyl)propanoic acid Using Step A and Step B of General Procedure (XVI) and (5-formyl-2-furyl)boronic acid as the appropriate boronic acid derivative ethyl (2R)-2-[(5S$_a$)-5-[3-chloro-2-methyl-4-[2-(4-methylpiperazin-1-yl)ethoxy]phenyl]-6-(5-formyl-2-furyl)thieno[2,3-d]pyrimidin-4-yl] oxy-3-(2-methoxyphenyl)propanoate was obtained. It was dissolved in methanol-water (9:1) containing 5 m/m % NaOH (10 eq.) and the mixture was stirred at 50° C. until no further conversion was observed. Then the mixture was diluted with water and the pH was adjusted to 6 by the addition of 2 M HCl solution. The mixture was extracted with DCM, the combined organic phases dried over $Na_2SO_4$, and concentrated under reduced pressure. The crude product was purified via preparative reversed phase chromatography using 25 mM aqueous $NH_4HCO_3$ solution and MeCN as eluents to obtain Example 542. HRMS calculated for $C_{37}H_{41}ClN_4O_8S$: 736.2334. found 737.2416 (M+H).

Example 543 (2R)-2-{[(5S$_a$)-5-{3-chloro-2-methyl-4-[2-(4-methylpiperazin-1-yl)ethoxy]phenyl}-6-(5-ethylfuran-2-yl)thieno[2,3-d]pyrimidin-4-yl]oxy}-3-(2-methoxyphenyl)propanoic acid Using General Procedure (XVI) and 2-(5-ethyl-2-furyl)-4,4,5,5-tetramethyl-1,3,2-dioxaborolane as the appropriate boronic acid derivative, Example 543 was obtained. HRMS calculated for $C_{36}H_{39}ClN_4O_6S$: 690.2279. found 691.2343 (M+H).

Example 544 (2R)-2-{[(5S$_a$)-5-{3-chloro-2-methyl-4-[2-(4-methylpiperazin-1-yl)ethoxy]phenyl}-6-(5-methoxyfuran-2-yl)thieno[2,3-d]pyrimidin-4-yl]oxy}-3-(2-methoxyphenyl)propanoic acid Using General Procedure (XVI) and 2-(5-methoxy-2-furyl)-4,4,5,5-tetramethyl-1,3,2-dioxaborolane as the appropriate boronic acid derivative, Example 544 was obtained. HRMS calculated for $C_{35}H_{37}ClN_4O_7S$: 692.2071. found 693.2122 (M+H).

Example 545 (2R)-2-{[(5S$_a$)-5-{3-chloro-2-methyl-4-[2-(4-methylpiperazin-1-yl)ethoxy]phenyl}-6-(3-nitrophenyl)thieno[2,3-d]pyrimidin-4-yl]oxy}-3-(2-methoxyphenyl)propanoic acid Using General Procedure (XVI) and 4,4,5,5-tetramethyl-2-(3-nitrophenyl)-1,3,2-dioxaborolane as the appropriate boronic acid derivative, Example 545 was obtained. HRMS calculated for $C_{36}H_{36}ClN_5O_7S$: 717.2024. found 718.2101 (M+H).

Example 546 (2R)-2-{[(5S$_a$)-5-{3-chloro-2-methyl-4-[2-(4-methylpiperazin-1-yl)ethoxy]phenyl}-6-(3-methylphenyl)thieno[2,3-d]pyrimidin-4-yl]oxy}-3-(2-methoxyphenyl)propanoic acid Using General Procedure (XVI) and 4,4,5,5-tetramethyl-2-(m-tolyl)-1,3,2-dioxaborolane as the appropriate boronic acid derivative, Example 546 was obtained. HRMS calculated for $C_{37}H_{39}ClN_4O_5S$: 686.2330. found 687.2401 (M+H).

Example 547 (2R)-2-{[(5S$_a$)-5-{3-chloro-2-methyl-4-[2-(4-methylpiperazin-1-yl)ethoxy]phenyl}-6-(3-ethynylphenyl)thieno[2,3-d]pyrimidin-4-yl]oxy}-3-(2-methoxyphenyl)propanoic acid Using General Procedure (XVI) and trimethyl-[2-[3-(4,4,5,5-tetramethyl-1,3,2-dioxaborolan-2-yl)phenyl]ethynyl]silane as the appropriate boronic acid derivative, Example 547 was obtained. HRMS calculated for $C_{38}H_{37}ClN_4O_5S$: 696.2173. found 697.2234 (M+H).

Example 548 (2R)-2-{[(5S$_a$)-5-{3-chloro-2-methyl-4-[2-(4-methylpiperazin-1-yl)ethoxy]phenyl}-6-(3-cyanophenyl)thieno[2,3-d]pyrimidin-4-yl]oxy}-3-(2-methoxyphenyl)propanoic acid Using General Procedure (XVI) and 3-(4,4,5,5-tetramethyl-1,3,2-dioxaborolan-2-yl)benzonitrile as the appropriate boronic acid derivative, Example 548 was obtained. HRMS calculated for $C_{37}H_{36}ClN_5O_5S$: 697.2126. found 698.2188 (M+H).

Example 549 (2R)-2-[((5S$_a$)-5-{3-chloro-2-methyl-4-[2-(4-methylpiperazin-1-yl)ethoxy]phenyl}-6-[3-(trifluoromethyl)phenyl]thieno[2,3-d]pyrimidin-4-yl)oxy]-3-(2-methoxyphenyl)propanoic acid Using General Procedure (XVI) and 4,4,5,5-tetramethyl-2-[3-(trifluoromethyl)phenyl]-1,3,2-dioxaborolane as the appropriate boronic acid derivative, Example 549 was obtained. HRMS calculated for $C_{37}H_{36}ClF_3N_4O_5S$: 740.2047. found 741.2125 (M+H).

Example 550 (2R)-2-{[(5S$_a$)-5-{3-chloro-2-methyl-4-[2-(4-methylpiperazin-1-yl)ethoxy]phenyl}-6-(3-chlorophenyl)thieno[2,3-d]pyrimidin-4-yl]oxy}-3-(2-methoxyphenyl)propanoic acid Using General Procedure (XVI) and 2-(3-chlorophenyl)-4,4,5,5-tetramethyl-1,3,2-dioxaborolane as the appropriate boronic acid derivative, Example 550 was obtained. HRMS calculated for $C_{36}H_{36}Cl_2N_4O_5S$: 706.1783. found 707.1860 (M+H).

Example 551 (2R)-2-{[(5S$_a$)-5-{3-chloro-2-methyl-4-[2-(4-methylpiperazin-1-yl)ethoxy]phenyl}-6-(3-fluorophenyl)thieno[2,3-d]pyrimidin-4-yl]oxy}-3-(2-methoxyphenyl)propanoic acid Using General Procedure (XVI) and 2-(3-fluorophenyl)-4,4,5,5-tetramethyl-1,3,2-dioxaborolane as the appropriate boronic acid derivative, Example 551 was obtained. HRMS calculated for $C_{36}H_{36}ClFN_4O_5S$: 690.2079. found 691.2152 (M+H).

Example 552 (2R)-2-[((5S$_a$)-5-{3-chloro-2-methyl-4-[2-(4-methylpiperazin-1-yl)ethoxy]phenyl}-6-[3-(dimethylamino)phenyl]thieno[2,3-d]pyrimidin-4-yl)oxy]-3-(2-methoxyphenyl)propanoic acid Using General Procedure (XVI) and N,N-dimethyl-3-(4,4,5,5-tetramethyl-1,3,2-dioxaborolan-2-yl)aniline as the appropriate boronic acid derivative, Example 552 was obtained. HRMS calculated for $C_{38}H_{42}ClN_5O_5S$: 715.2595. found 716.2681 (M+H).

Example 553 (2R)-2-{[(5S$_a$)-5-{3-chloro-2-methyl-4-[2-(4-methylpiperazin-1-yl)ethoxy]phenyl}-6-(3-hydroxyphenyl)thieno[2,3-d]pyrimidin-4-yl]oxy}-3-(2-methoxyphenyl)propanoic acid Using General Procedure (XVI) and 3-(4,4,5,5-tetramethyl-1,3,2-dioxaborolan-2-yl)phenol as the appropriate boronic acid derivative, Example 553 was obtained. HRMS calculated for $C_{36}H_{37}ClN_4O_6S$: 688.2122. found 689.2204 (M+H).

Example 554 (2R)-2-{[(5S$_a$)-5-{3-chloro-2-methyl-4-[2-(4-methylpiperazin-1-yl)ethoxy]phenyl}-6-(3-methoxyphenyl)thieno[2,3-d]pyrimidin-4-yl]oxy}-3-(2-methoxyphenyl)propanoic acid Using General Procedure (XVI) and 2-(3-methoxyphenyl)-4,4,5,5-tetramethyl-1,3,2-dioxaborolane as the appropriate boronic acid derivative, Example 554 was obtained. HRMS calculated for $C_{37}H_{39}ClN_4O_6S$: 702.2279. found 703.2358 (M+H).

Example 555 (2R)-2-[((5S$_a$)-5-{3-chloro-2-methyl-4-[2-(4-methylpiperazin-1-yl)ethoxy]phenyl}-6-[3-(trifluoromethoxy)phenyl]thieno[2,3-d]pyrimidin-4-yl)oxy]-3-(2-methoxyphenyl)propanoic acid Using General Procedure (XVI) and 4,4,5,5-tetramethyl-2-[3-(trifluoromethoxy)phenyl]-1,3,2-dioxaborolane as the appropriate boronic acid derivative, Example 555 was obtained. HRMS calculated for $C_{37}H_{36}ClF_3N_4O_6S$: 756.1996. found 757.2067 (M+H).

Example 556 (2R)-2-[((5S$_a$)-5-{3-chloro-2-methyl-4-[2-(4-methylpiperazin-1-yl)ethoxy]phenyl}-6-[3-(4-fluorophenoxy)phenyl]thieno[2,3-d]pyrimidin-4-yl)oxy]-3-(2-methoxyphenyl)propanoic acid Using General Procedure (XVI) and 2-[3-(4-fluorophenoxy)phenyl]-4,4,5,5-tetramethyl-1,3,2-dioxaborolane as the appropriate boronic acid derivative, Example 556 was obtained. HRMS calculated for $C_{42}H_{40}ClFN_4O_6S$: 782.2341. found 783.2412 (M+H).

Example 557 (2R)-2-{[(5S$_a$)-5-{3-chloro-2-methyl-4-[2-(4-methylpiperazin-1-yl)ethoxy]phenyl}-6-(3-ethoxyphenyl)thieno[2,3-d]pyrimidin-4-yl]oxy}-3-(2-methoxyphenyl)propanoic acid Using General Procedure (XVI) and 2-(3-ethoxyphenyl)-4,4,5,5-tetramethyl-1,3,2-dioxaborolane as the appropriate boronic acid derivative, Example 557 was obtained. HRMS calculated for $C_{38}H_{41}ClN_4O_6S$: 716.2435. found 717.2505 (M+H).

Example 558 (2R)-2-[((5S$_a$)-5-{3-chloro-2-methyl-4-[2-(4-methylpiperazin-1-yl)ethoxy]phenyl}-6-[3-(methylsulfanyl)phenyl]thieno[2,3-d]pyrimidin-4-yl)oxy]-3-(2-methoxyphenyl)propanoic acid Using General Procedure (XVI) and 4,4,5,5-tetramethyl-2-(3-methylsulfanylphenyl)-1,3,2-dioxaborolane as the appropriate boronic acid derivative, Example 558 was obtained. HRMS calculated for $C_{37}H_{39}ClN_4O_5S_2$: 718.2050. found 719.2113 (M+H).

Example 559 (2R)-2-{[6-(3-chloro-2-fluorophenyl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-methoxyphenyl)propanoic acid Using General Procedure (XVI) and 2-(3-chloro-2-fluorophenyl)-4,4,5,5-tetramethyl-1,3,2-dioxaborolane as the appropriate boronic acid derivative, Example 559 was obtained. HRMS calculated for $C_{36}H_{35}Cl_2FN_4O_5S$: 724.1689. found 725.1765 (M+H).

Example 560 (2R)-2-{[(5S$_a$)-5-{3-chloro-2-methyl-4-[2-(4-methylpiperazin-1-yl)ethoxy]phenyl}-6-(2,3-difluorophenyl)thieno[2,3-d]pyrimidin-4-yl]oxy}-3-(2-methoxyphenyl)propanoic acid Using General Procedure (XVI) and 2-(2,3-difluorophenyl)-4,4,5,5-tetramethyl-1,3,2-dioxaborolane as the appropriate boronic acid derivative, Example 560 was obtained. HRMS calculated for $C_{36}H_{35}ClF_2N_4O_5S$: 708.1985. found 709.2052 (M+H).

Example 561 (2R)-2-{[(5S$_a$)-5-{3-chloro-2-methyl-4-[2-(4-methylpiperazin-1-yl)ethoxy]phenyl}-6-(2-fluoro-3-methoxyphenyl)thieno[2,3-d]pyrimidin-4-yl]oxy}-3-(2-methoxyphenyl)propanoic acid Using General Procedure (XVI) and 2-(2-fluoro-3-methoxy-phenyl)-4,4,5,5-tetramethyl-1,3,2-dioxaborolane as the appropriate boronic acid derivative, Example 561 was obtained. HRMS calculated for $C_{37}H_{38}ClFN_4O_6S$: 720.2185. found 721.2281 (M+H).

Example 562 (2R)-2-[((5S$_a$)-5-{3-chloro-2-methyl-4-[2-(4-methylpiperazin-1-yl)ethoxy]phenyl}-6-[2-fluoro-3-(trifluoromethoxy)phenyl]thieno[2,3-d]pyrimidin-4-yl)oxy]-3-(2-methoxyphenyl)propanoic acid Using General Procedure (XVI) and 2-[2-fluoro-3-(trifluoromethoxy)phenyl]-4,4,5,5-tetramethyl-1,3,2-dioxaborolane as the appropriate boronic acid derivative, Example 562 was obtained. HRMS calculated for $C_{37}H_{35}ClF_4N_4O_6S$: 774.1902. found 775.1974 (M+H).

Example 563 (2R)-2-{[6-(1-benzofuran-4-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-methoxyphenyl)propanoic acid Using General Procedure (XVI) and 2-(benzofuran-4-yl)-4,4,5,5-tetramethyl-1,3,2-dioxaborolane as the appropriate boronic acid derivative, Example 563 was obtained. HRMS calculated for $C_{38}H_{37}ClN_4O_6S$: 712.2122. found 713.2193 (M+H).

Example 564 (2R)-2-[((5S$_a$)-5-{3-chloro-2-methyl-4-[2-(4-methylpiperazin-1-yl)ethoxy]phenyl}-6-phenylthieno[2,3-d]pyrimidin-4-yl)oxy]-3-(2-methoxyphenyl)propanoic acid Using General Procedure (XVI) and 4,4,5,5-tetramethyl-2-phenyl-1,3,2-dioxaborolane as the appropriate boronic acid derivative, Example 564 was obtained. HRMS calculated for $C_{36}H_{37}ClN_4O_5S$: 672.2173. found 673.2258 (M+H).

Example 565 (2R)-2-{[(5S$_a$)-5-{3-chloro-2-methyl-4-[2-(4-methylpiperazin-1-yl)ethoxy]phenyl}-6-(2-chlorophenyl)thieno[2,3-d]pyrimidin-4-yl]oxy}-3-(2-methoxyphenyl)propanoic acid Using General Procedure (XVI) and 2-(2-chlorophenyl)-4,4,5,5-tetramethyl-1,3,2-dioxaborolane as the appropriate boronic acid derivative, Example 565 was obtained. HRMS calculated for $C_{36}H_{36}Cl_2N_4O_5S$: 706.1783. found 707.1860 (M+H).

Example 566 (2R)-2-{[(5S$_a$)-5-{3-chloro-2-methyl-4-[2-(4-methylpiperazin-1-yl)ethoxy]phenyl}-6-(2-fluorophenyl)thieno[2,3-d]pyrimidin-4-yl]oxy}-3-(2-methoxyphenyl)propanoic acid Using General Procedure (XVI) and 2-(2-fluorophenyl)-4,4,5,5-tetramethyl-1,3,2-dioxaborolane as the appropriate boronic acid derivative, Example 566 was obtained. HRMS calculated for $C_{36}H_{36}ClFN_4O_5S$: 690.2079. found 691.2169 (M+H).

Example 567 (2R)-2-{[(5S$_a$)-5-{3-chloro-2-methyl-4-[2-(4-methylpiperazin-1-yl)ethoxy]phenyl}-6-(pyridin-3-yl)thieno[2,3-d]pyrimidin-4-yl]oxy}-3-(2-methoxyphenyl)propanoic acid Using General Procedure (XVI) and 3-(4,4,5,5-tetramethyl-1,3,2-dioxaborolan-2-yl)pyridine as the appropriate boronic acid derivative, Example 567 was obtained. HRMS calculated for $C_{35}H_{36}ClN_5O_5S$: 673.2126. found 674.2205 (M+H).

Example 568 (2R)-2-{[(5S$_a$)-5-{3-chloro-2-methyl-4-[2-(4-methylpiperazin-1-yl)ethoxy]phenyl}-6-(thiophen-3-yl)thieno[2,3-d]pyrimidin-4-yl]oxy}-3-(2-methoxyphenyl)propanoic acid Using General Procedure (XVI) and 4,4,5,5-tetramethyl-2-(3-thienyl)-1,3,2-dioxaborolane as the appropriate boronic acid derivative, Example 568 was obtained. HRMS calculated for $C_{34}H_{35}ClN_4O_5S_2$: 678.1737. found 679.1808 (M+H).

Example 569 (2R)-2-{[(5S$_a$)-5-{3-chloro-2-methyl-4-[2-(4-methylpiperazin-1-yl)ethoxy]phenyl}-6-(1,3-oxazol-5-yl)thieno[2,3-d]pyrimidin-4-yl]oxy}-3-(2-methoxyphenyl)propanoic acid Using General Procedure (XVI) and 5-(4,4,5,5-tetramethyl-1,3,2-dioxaborolan-2-yl)-1,3-oxazole as the appropriate boronic acid derivative, Example 569 was obtained. HRMS calculated for $C_{33}H_{34}ClN_5O_6S$: 663.1918. found 664.1997 (M+H).

Example 570 (2R)-2-{[(5S$_a$)-5-{3-chloro-2-methyl-4-[2-(4-methylpiperazin-1-yl)ethoxy]phenyl}-6-(5-chlorothiophen-3-yl)thieno[2,3-d]pyrimidin-4-yl]oxy}-3-(2-methoxyphenyl)propanoic acid Using General Procedure (XVI) and 2-(5-chloro-3-thienyl)-4,4,5,5-tetramethyl-1,3,2-dioxaborolane as the appropriate boronic acid derivative, Example 570 was obtained. HRMS calculated for $C_{34}H_{34}Cl_2N_4O_5S_2$: 712.1348. found 713.1423 (M+H).

Example 571 (2R)-2-{[(5S$_a$)-5-{3-chloro-2-methyl-4-[2-(4-methylpiperazin-1-yl)ethoxy]phenyl}-6-(thieno[3,2-b]thiophen-3-yl)thieno[2,3-d]pyrimidin-4-yl]oxy}-3-(2-methoxyphenyl)propanoic acid Step A:
782 mg 3-bromothieno[3,2-b]thiophene (3.6 mmol), 3.626 g 4,4,5,5-tetramethyl-2-(4,4,5,5-tetramethyl-1,3,2-dioxaborolan-2-yl)-1,3,2-dioxaborolane (14 mmol), 0.783 g PdCl$_2$×dppf (1.07 mmol) and 2.102 g KOAc (21.4 mmol) were dissolved in 4 mL dioxane. The mixture was heated to 60° C. and stirred under argon atmosphere until no further conversion was observed. The reaction mixture was cooled to room temperature and filtered through a pad of celite. The filtrate was concentrated and purified via flash chromatography using heptane and EtOAc as eluents to give 4,4,5,5-tetramethyl-2-thieno[3,2-b]thiophen-3-yl-1,3,2-dioxaborolane. $^1$H NMR (500 MHz, DMSO-d$_6$): 8.11 (d, 1H), 7.67 (dd, 1H), 7.45 (d, 1H), 1.32 (s, 12H). HRMS calculated for $C_{12}H_{15}BO_2S_2$: 266.0607. found: 267.0682 (M+H).
Step B:
Using General Procedure (XVI) and 4,4,5,5-tetramethyl-2-thieno[3,2-b]thiophen-3-yl-1,3,2-dioxaborolane as the appropriate boronic acid derivative, Example 571 was obtained. HRMS calculated for $C_{36}H_{35}ClN_4O_5S_3$: 734.1458. found 735.1531 (M+H).

Example 572 (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-methoxyphenyl)propanoic acid Using Step B and C of General Procedure (XVI) and ethyl (2R)-2-[(5S$_a$)-5-(3-chloro-4-hydroxy-2-methyl-phenyl)-6-prop-1-ynyl-thieno[2,3-d]pyrimidin-4-yl]oxy-3-(2-methoxyphenyl)propanoate (Preparation 61) as the phenol derivative, Example 572 was obtained. HRMS calculated for $C_{33}H_{35}ClN_4O_5S$: 634.2017. found 635.2082 (M+H).

Example 573 (2R)-2-{[6-(but-1-yn-1-yl)-(5S$_a$)-5-{3-chloro-2-methyl-4-[2-(4-methylpiperazin-1-yl) ethoxy]phenyl}thieno[2,3-d]pyrimidin-4-yl]oxy}-3-(2-methoxyphenyl)propanoic acid Step A:
625 mg ethyl (2R)-2-[(5S$_a$)-5-(3-chloro-4-hydroxy-2-methyl-phenyl)-6-iodo-thieno[2,3-d]pyrimidin-4-yl]oxy-3-(2-methoxyphenyl)propanoate (Preparation 25) (1.0 mmol), 35 mg Pd(PPh$_3$)$_2$Cl$_2$ (0.05 mmol) and 19 mg CuI (0.1 mmol) were dissolved in 4 mL DIPA, then but-1-yne was bubbled through the reaction mixture, which was stirred at 50° C. until no further conversion was observed. Then the volatiles were evaporated under reduced pressure and the crude intermediate was purified by flash chromatography using EtOAc and MeOH as eluents to obtain ethyl (2R)-2-[6-but-1-ynyl-(5S$_a$)-5-(3-chloro-4-hydroxy-2-methyl-phenyl) thieno[2,3-d]pyrimidin-4-yl]oxy-3-(2-methoxyphenyl)propanoate.
Step B:
Using Step B and C of General Procedure (XVI) and ethyl (2R)-2-[6-but-1-ynyl-(5S$_a$)-5-(3-chloro-4-hydroxy-2-methyl-phenyl)thieno[2,3-d]pyrimidin-4-yl]oxy-3-(2-methoxyphenyl)propanoate as the phenol derivative, Example 573 was obtained. HRMS calculated for $C_{34}H_{37}ClN_4O_5S$: 648.2173. found 649.2251 (M+H).

Example 574 (2R)-2-{[(5R$_a$)-5-{3-chloro-2-methyl-4-[2-(4-methylpiperazin-1-yl)ethoxy]phenyl}-6-(dimethylcarbamoyl)thieno[2,3-d]pyrimidin-4-yl]oxy}-3-(2-methoxyphenyl)propanoic acid and Example 575 (2R)-2-{[(5S$_a$)-5-{3-chloro-2-methyl-4-[2-(4-methylpiperazin-1-yl)ethoxy]phenyl}-6-(dimethylcarbamoyl)thieno[2,3-d]pyrimidin-4-yl]oxy}-3-(2-methoxyphenyl)propanoic acid Step A:
2.195 g 4-chloro-5-[3-chloro-2-methyl-4-[2-(4-methylpiperazin-1-yl)ethoxy]phenyl] thieno-[2,3-d]pyrimidine (Preparation 12) (5.02 mmol) was dissolved in 50 mL dry THF and then it was cooled to −78° C. under argon atmosphere. 5.2 mL lithium diisopropylamide (10.4 mmol, 2 M in THF, EtPh, hexanes) was added and the mixture was stirred at −78° C. for 1 hour. Then 5.00 g dry-ice was added and the mixture was allowed to warm up to room temperature and it was stirred until no further conversion was observed. The mixture was quenched with saturated aq. NH$_4$Cl and extracted with DCM. The combined organic phases were dried over Na$_2$SO$_4$ and concentrated under reduced pressure. The residue was purified via flash chromatography using DCM and MeOH as eluents to obtain 4-chloro-5-[3-chloro-2-methyl-4-[2-(4-methylpiperazin-1-yl)ethoxy]phenyl]thieno[2,3-d]pyrimidine-6-carboxylic acid.

Step B:
1.444 g 4-chloro-5-[3-chloro-2-methyl-4-[2-(4-methylpiperazin-1-yl)ethoxy]phenyl] thieno[2,3-d]pyrimidine-6-carboxylic acid (3.0 mmol), 444 mg ethyl (2R)-2-hydroxy-3-(2-methoxyphenyl)propanoate (Preparation 3ad) (2.0 mmol) and 987 mg cesium carbonate (9.0 mmol) were stirred in 30 mL dry tertbutanol at 70° C. until no further conversion was observed. The reaction mixture was diluted with brine, neutralized with 2 M HCl, and extracted with DCM. The combined organic phases were dried over Na$_2$SO$_4$ and concentrated under reduced pressure. The crude intermediate was purified via flash chromatography using DCM and MeOH as eluents to obtain 5-{3-chloro-2-methyl-4-[2-(4-methylpiperazin-1-yl)ethoxy]phenyl}-4-{[(2R)-1-ethoxy-3-(2-methoxyphenyl)-1-oxopropan-2-yl]oxy}thieno[2,3-d]pyrimidine-6-carboxylic acid.

Step C:
669 mg 5-{3-chloro-2-methyl-4-[2-(4-methylpiperazin-1-yl)ethoxy]phenyl}-4-{[(2R)-1-ethoxy-3-(2-methoxyphenyl)-1-oxopropan-2-yl]oxy}thieno[2,3-d]pyrimidine-6-carboxylic acid (1.0 mmol), 1 mL dimethylamine (2 mmol, 2 M in THF) and DIPA were dissolved in 5 mL dry DCM, then 520 mg PyBOP (1.0 mmol) was added and the mixture was stirred at room temperature until no further conversion was observed. The volatiles were removed under reduced pressure and the residue was purified via flash chromatography using EtOAc and MeOH as eluents to obtain ethyl (2R)-2-[5-[3-chloro-2-methyl-4-[2-(4-methylpiperazin-1-yl)ethoxy]phenyl]-6-(dimethylcarbamoyl)thieno[2,3-d]pyrimidin-4-yl]oxy-3-(2-methoxyphenyl)propanoate.

Step D:
Ethyl (2R)-2-[5-[3-chloro-2-methyl-4-[2-(4-methylpiperazin-1-yl)ethoxy]phenyl]-6-(dimethylcarbamoyl)thieno[2,3-d]pyrimidin-4-yl]oxy-3-(2-methoxyphenyl)propanoate was hydrolyzed according to Step C of General Procedure (XVI). The diastereoisomer eluting earlier was collected as Example 574. HRMS calculated for $C_{33}H_{38}ClN_5O_6S$: 667.2231. found 668.2287 (M+H). The diastereoisomer eluting later was collected as Example 575. HRMS calculated for $C_{33}H_{38}ClN_5O_6S$: 667.2231. found 668.2280 (M+H).

Example 576 (2R)-2-{[(5S$_a$)-5-{3-chloro-2-methyl-4-[2-(4-methylpiperazin-1-yl)ethoxy]phenyl}-6-(1,1-difluoroethyl)thieno[2,3-d]pyrimidin-4-yl]oxy}-3-(2-methoxyphenyl)propanoic acid Step A:
4.22 g 4-chloro-5,6-diiodo-thieno[2,3-d]pyrimidine (Preparation 1b) (10.0 mmol) was dissolved in 160 mL dry THF, then cooled to −78° C. under argon atmosphere. 5 mL ethylmagnesium chloride (2 M in THF) (10.0 mmol) was added and the mixture was stirred at −78° C. for 10 minutes. Then 1.321 g acetaldehyde (30.0 mmol) was added and the mixture was allowed to warm up to room temperature. Saturated aq. NH$_4$Cl was added and the mixture was extracted with ethyl acetate. The combined organic phases were dried over Na$_2$SO$_4$ and concentrated under reduced pressure. The crude product was purified via flash chromatography using DCM and MeOH as eluents to obtain 1-(4-chloro-5-iodo-thieno[2,3-d]pyrimidin-6-yl)ethanol. $^1$H NMR (400 MHz, DMSO-d$_6$): 8.89 (s, 1H), 6.38 (d, 1H), 5.15 (m, 1H), 1.44 (d, 3H).

Step B:
2.1 g 1-(4-chloro-5-iodo-thieno[2,3-d]pyrimidin-6-yl)ethanol (6.17 mmol) was dissolved in 100 mL dichloromethane, then cooled to 0° C. under argon atmosphere. Then 2.75 g Dess-Martin periodinane (6.47 mmol) was added and stirred until no further conversion was observed. The volatiles were evaporated under reduced pressure and the crude intermediate was purified via flash chromatography using DCM as eluent to obtain 1-(4-chloro-5-iodo-thieno[2,3-d]pyrimidin-6-yl)ethanone. $^1$H NMR (400 MHz, DMSO-d$_6$): 9.04 (s, 1H), 2.80 (s, 3H).

Step C:
1.02 g 1-(4-chloro-5-iodo-thieno[2,3-d]pyrimidin-6-yl)ethanone (3.01 mmol) was dissolved in 25 mL dichloromethane, then 3.22 g DAST (20.0 mmol) was added. The mixture was stirred at 50° C. under argon atmosphere until no further conversion was observed. The volatiles were evaporated under reduced pressure and the crude intermediate was purified via flash chromatography using dichloromethane as eluent to obtain 4-chloro-6-(1,1-difluoroethyl)-5-iodo-thieno[2,3-d]pyrimidine. $^1$H NMR (400 MHz, DMSO-d$_6$): 9.02 (s, 1H), 2.22 (t, 3H).

Step D:
880 mg 4-chloro-6-(1,1-difluoroethyl)-5-iodo-thieno[2,3-d]pyrimidine (2.44 mmol), 821 mg ethyl (2R)-2-hydroxy-3-(2-methoxyphenyl)propanoate (Preparation 3ad) (3.66 mmol) and 1.59 g Cs$_2$CO$_3$ (4.88 mmol) were stirred at 50° C. in 2.5 mL DMSO until no further conversion was observed. The reaction mixture was diluted with brine, then it was extracted with EtOAc. The combined organic phases were dried over Na$_2$SO$_4$ and concentrated under reduced pressure. The residue was purified via flash chromatography using heptane and EtOAc as eluents to obtain ethyl (2R)-2-[6-(1,1-difluoroethyl)-5-iodo-thieno[2,3-d]pyrimidin-4-yl]oxy-3-(2-methoxyphenyl)propanoate. $^1$H NMR (400 MHz, DMSO-d$_6$): 8.70 (s, 1H), 7.44 (dd, 1H), 7.25 (td, 1H), 6.98 (d, 1H), 6.88 (t, 1H), 5.69 (dd, 1H), 4.10 (q, 2H), 3.80 (s, 3H), 3.41 (dd, 1H), 3.26 (dd, 1H), 2.20 (t, 3H), 1.09 (t, 3H).

Step E:

920 mg ethyl (2R)-2-[6-(1,1-difluoroethyl)-5-iodo-thieno[2,3-d]pyrimidin-4-yl]oxy-3-(2-methoxyphenyl)propanoate (1.68 mmol) and 676 mg 2-chloro-3-methyl-4-(4,4,5,5-tetramethyl-1,3,2-dioxaborolan-2-yl)phenol (Preparation 5a) (2.52 mmol) were dissolved in 7 mL 2-Me-THF, then 2.52 mL tetrabutylammonium hydroxide (2.52 mmol, 1 M in water) and 119 mg AtaPhos (0.168 mmol) were added and the mixture was heated under nitrogen at 110° C. in a microwave reactor until no further conversion was observed. Then it was diluted with brine and extracted with dichloromethane. The combined organic phases were dried over $Na_2SO_4$ and concentrated under reduced pressure, and the crude intermediate was purified via flash chromatography using heptane and EtOAc as eluents to obtain ethyl (2R)-2-[5-(3-chloro-4-hydroxy-2-methyl-phenyl)-6-(1,1-difluoroethyl)thieno[2,3-d]pyrimidin-4-yl]oxy-3-(2-methoxyphenyl)propanoate as a mixture of diastereoisomers. $^1$H NMR (400 MHz, DMSO-$d_6$): 10.34 (br s, 1H), 8.68 (s, 1H), 7.20 (td, 1H), 7.04 (d, 1H), 6.96 (d, 1H), 6.93 (d, 1H), 6.81 (t, 1H), 6.55 (dd, 1H), 5.42 (dd, 1H), 3.98 (m, 2H), 3.76 (s, 3H), 2.87 (dd, 1H), 2.46 (dd, 1H), 1.93 (s, 3H), 1.72 (t, 3H), 1.00 (t, 3H).

Step F:

100 mg ethyl (2R)-2-[5-(3-chloro-4-hydroxy-2-methyl-phenyl)-6-(1,1-difluoroethyl)thieno[2,3-d]pyrimidin-4-yl]oxy-3-(2-methoxyphenyl)propanoate (0.178 mmol), 51 mg 2-(4-methylpiperazin-1-yl)ethanol (0.355 mmol) and 534 mg triphenyl phosphine (0.534 mmol) were dissolved in 4 mL dry toluene, then 123 mg ditertbutyl azodicarboxylate (0.534 mmol) was added. The mixture was stirred at 45° C. under nitrogen until no further conversion was observed. The volatiles were evaporated under reduced pressure and the crude intermediate was purified via flash chromatography using EtOAc and methanol as eluents to obtain ethyl (2R)-2-[5-[3-chloro-2-methyl-4-[2-(4-methylpiperazin-1-yl)ethoxy] phenyl]-6-(1,1-difluoroethyl)thieno[2,3-d]pyrimidin-4-yl]oxy-3-(2-methoxyphenyl)propanoate.

Step G:

The intermediate obtained in Step F was dissolved in 3 mL methanol and 100 mg LiOH×$H_2O$ (2.38 mmol) was added. The mixture was stirred at room temperature until no further conversion was observed. Then it was diluted with brine, neutralized with 2 M HCl, and extracted with DCM. The combined organic phases were dried over $Na_2SO_4$ and concentrated under reduced pressure. The crude product was purified via preparative reversed phase chromatography using 25 mM aqueous $NH_4HCO_3$ solution and MeCN as eluents. The diastereoisomer eluting later was collected as Example 576. HRMS calculated for $C_{32}H_{35}ClF_2N_4O_5S$: 660.1985. found 661.2059 (M+H).

Example 577 (2R)-2-{[6-(5-bromofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-methoxyphenyl)propanoic acid 1.326 g (2R)-2-{[(5S$_a$)-5-{3-chloro-2-methyl-4-[2-(4-methylpiperazin-1-yl)ethoxy] phenyl}-6-(furan-2-yl)thieno[2,3-d]pyrimidin-4-yl]oxy}-3-(2-methoxyphenyl)propanoic acid (Example 209) (2 mmol) was dissolved in 20 mL chloroform, then 534 mg NBS (3 mmol) was added. The resulting mixture was stirred at 0° C. until no further conversion was observed. Then the mixture was diluted with water and the pH was adjusted to 6 by the addition of 2 M HCl solution. The mixture was extracted with DCM, the combined organic phases were dried over $Na_2SO_4$ and concentrated under reduced pressure. The crude product was purified via reversed phase chromatography using 25 mM aqueous $NH_4HCO_3$ solution and MeCN as eluents to obtain Example 577. HRMS calculated for $C_{34}H_{34}BrClN_4O_6S$: 740.1071. found 741.1165 (M+H).

Example 578 (2R)-2-{[(5S$_a$)-5-{3-chloro-2-methyl-4-[2-(4-methylpiperazin-1-yl)ethoxy]phenyl}-6-(5-ethynylfuran-2-yl)thieno[2,3-d]pyrimidin-4-yl]oxy}-3-(2-methoxyphenyl)propanoic acid 52 mg (2R)-2-{[6-(5-bromofuran-2-yl)-(5S$_a$)-5-{3-chloro-2-methyl-4-[2-(4-methylpiperazin-1-yl)ethoxy] phenyl}thieno[2,3-d]pyrimidin-4-yl]oxy}-3-(2-methoxyphenyl)propanoic acid (Example 577) (0.07 mmol), 96 mg butyl-dimethyl-[2-(4,4,5,5-tetramethyl-1,3,2-dioxaborolan-2-yl)ethynyl]silane (0.36 mmol), 120 mg $Cs_2CO_3$ (0.36 mmol) and 6 mg $PdCl_2$×dppf (0.008 mmol) were dissolved in a mixture of 0.80 mL dioxane and 0.20 mL water. The reaction mixture was stirred at 70° C. until no further conversion was observed. The reaction was quenched at room temperature with water and the mixture was extracted with DCM. The combined organic phases were dried over $Na_2SO_4$ and concentrated under reduced pressure. The residue was dissolved in 0.50 mL THF, then 50 μL TBAF (1 M in THF) was added and the reaction mixture was stirred at room temperature until no further conversion was observed. Then the mixture was concentrated under reduced pressure and purified via reversed phase chromatography using 5 mM aqueous $NH_4HCO_3$ solution and MeCN as eluents to obtain Example 578. HRMS calculated for $C_{36}H_{35}ClN_4O_6S$: 686.1966. found 687.2039 (M+H).

Example 579 (2R)-2-{[(5S$_a$)-5-{3-chloro-2-methyl-4-[2-(4-methylpiperazin-1-yl)ethoxy]phenyl}-6-(5-cyanofuran-2-yl)thieno[2,3-d]pyrimidin-4-yl]oxy}-3-(2-methoxyphenyl)propanoic acid Step A:

250 mg ethyl (2R)-2-[(5S$_a$)-5-(3-chloro-4-hydroxy-2-methyl-phenyl)-6-iodo-thieno[2,3-d]pyrimidin-4-yl]oxy-3-(2-methoxyphenyl)propanoate (Preparation 25) (0.40 mmol), 315 mg $PPh_3$ (1.20 mmol), 276 mg ditertbutyl azodicarboxylate (1.20 mmol) and 173 mg 2-(4-methylpiperazin-1-yl)ethanol (1.20 mmol) were dissolved in 10 ml dry toluene and the reaction mixture was stirred at 50° C. under nitrogen until no further conversion was observed. The mixture was concentrated under reduced pressure and the crude product was purified via flash chromatography using DCM and MeOH as eluents. The obtained product was hydrolyzed in 3 mL methanol-water (9:1) containing NaOH (5 m/m %) at room temperature. The mixture was diluted with water, the pH was adjusted to 6 by the addition of 2 M HCl solution, and it was extracted with DCM. The combined organic phases were dried over $Na_2SO_4$ and concentrated under reduced pressure. The crude product was purified using reverse phase preparative HPLC resulting (2R)-2-[(5S$_a$)-5-[3-chloro-2-methyl-4-[2-(4-methylpiperazin-1-yl)ethoxy]phenyl]-6-iodo-thieno[2,3-d]pyrimidin-4-yl]oxy-3-(2-methoxyphenyl)propanoic acid.

Step B:

72 mg (2R)-2-[(5S$_a$)-5-[3-chloro-2-methyl-4-[2-(4-methylpiperazin-1-yl)ethoxy]phenyl]-6-iodo-thieno[2,3-d]pyrimidin-4-yl]oxy-3-(2-methoxyphenyl)propanoic acid (0.10 mmol), 66 mg 5-(4,4,5,5-tetramethyl-1,3,2-dioxaborolan-2-yl)furan-2-carbonitrile (0.30 mmol), 18 mg AtaPhos (0.025 mmol) and 98 mg $Cs_2CO_3$ (0.30 mmol) were dissolved in a mixture of 0.75 mL THF and 0.25 mL water and heated under nitrogen at 100° C. for 10 minutes in a microwave reactor. The crude reaction mixture was diluted with water and the pH was adjusted to 6 by the addition of 2N HCl solution. The mixture was extracted with DCM, the combined organic phases were dried over $Na_2SO_4$ and concentrated under reduced pressure. The crude product was purified via reversed phase chromatography using 25 mM aqueous $NH_4HCO_3$ solution and MeCN as eluents to obtain Example 579. HRMS calculated for $C_{35}H_{34}ClN_5O_6S$: 687.1918. found 688.2001 (M+H).

Example 580 (2R)-2-[((5S$_a$)-5-{3-chloro-2-methyl-4-[2-(4-methylpiperazin-1-yl)ethoxy]phenyl}-6-[5-(methoxycarbonoimidoyl)furan-2-yl]thieno[2,3-d]pyrimidin-4-yl)oxy]-3-(2-methoxyphenyl)propanoic acid 222 mg (2R)-2-{[(5S$_a$)-5-{3-chloro-2-methyl-4-[2-(4-methylpiperazin-1-yl)ethoxy] phenyl}-6-(5-cyanofuran-2-yl)thieno[2,3-d]pyrimidin-4-yl]oxy}-3-(2-methoxyphenyl)propanoic acid (Example 579) (0.032 mmol) was hydrolyzed in 3 mL methanol-water (9:1) containing NaOH (5 m/m %) at room temperature. After evaporation of the volatiles under reduced pressure the multicomponent mixture was purified using reversed phase chromatography with 25 mM aqueous $NH_4HCO_3$ solution and MeCN as eluents to give Example 580 as one of the products. HRMS calculated for $C_{36}H_{38}ClN_5O_7S$: 719.2180. found 360.6152 (M+2H).

Example 581 (2R)-2-{[6-(5-carbamoylfuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-(2-methoxyphenyl)propanoic acid Hydrolysis of (2R)-2-{[(5S$_a$)-5-{3-chloro-2-methyl-4-[2-(4-methylpiperazin-1-yl)ethoxy] phenyl}-6-(5-cyanofuran-2-yl)thieno[2,3-d]pyrimidin-4-yl]oxy}-3-(2-methoxyphenyl)propanoic acid (Example 579) was performed as described in Example 580. Example 581 was obtained as one of the products of the multicomponent mixture following separation by reversed phase chromatography with 25 mM aqueous $NH_4HCO_3$ solution and MeCN as eluents. HRMS calculated for $C_{35}H_{36}ClN_5O_7S$: 705.2024. found 706.2105 (M+H).

Example 582 (2R)-2-[((5S$_a$)-5-{3-chloro-2-methyl-4-[2-(4-methylpiperazin-1-yl)ethoxy]phenyl}-6-[5-(dimethylcarbamoyl)furan-2-yl]thieno[2,3-d]pyrimidin-4-yl)oxy]-3-(2-methoxyphenyl)propanoic acid Step A:
984 mg 4-chloro-5-[3-chloro-2-methyl-4-[2-(4-methylpiperazin-1-yl)ethoxy]phenyl] thieno[2,3-d]pyrimidine (Preparation 12) (2.25 mmol) was dissolved in 20 mL dry THF under $N_2$ and cooled to −78° C. 2.25 mL LDA (2 M in THF, 4.5 mmol) was added at −78° C. and the reaction mixture was stirred for 1 h at this temperature, then 9 mL chloro(trimethyl)stannane (1 M in THF, 9 mmol) was added and stirred for 20 min at −78° C., then the reaction mixture was allowed to warm up to room temperature. Saturated aq. $NH_4Cl$ was added and the mixture was extracted with diethyl ether. The combined organic phases were dried over $Na_2SO_4$ and concentrated under reduced pressure. The residue was dissolved in 60 mL EtOAc and following the addition of 40 mL saturated aq. NaF solution it was stirred overnight and filtered. The aqueous phase was extracted with EtOAc and the combined organic phases were dried over $Na_2SO_4$, and evaporated under reduced pressure. The crude product was purified via flash chromatography using DCM and MeOH as eluents to obtain [4-chloro-5-[3-chloro-2-methyl-4-[2-(4-methylpiperazin-1-yl)ethoxy]phenyl] thieno[2,3-d]pyrimidin-6-yl]-trimethyl-stannane. $^1$H NMR (500 MHz, DMSO-d$_6$): 8.90 (s, 1H), 7.13 (d, 1H), 7.11 (d, 1H), 4.22 (m, 2H), 2.77 (t, 2H), 2.57 (br s, 4H), 2.41 (br s, 4H), 2.21 (br s, 3H), 1.97 (s, 3H), 0.14 (s, 9H). HRMS calculated for $C_{23}H_{30}Cl_2N_4OSSn$: 600.0539. found 601.0584 (M+H).

Step B:
1.91 g 5-bromofuran-2-carboxylic acid (10 mmol), 10 mL dimethylamine (2 M in THF, 20 mmol), 5.42 g PyBOP (10.4 mmol) and 3.5 mL DIPA (20 mmol) were dissolved in 20 mL dry DCM and stirred at room temperature under $N_2$ until no further conversion was observed. The DCM was evaporated under reduced pressure and the residue was purified via flash chromatography using heptane and EtOAc as eluents to obtain 5-bromo-N,N-dimethyl-furan-2-carboxamide. MS: (M+H)$^+$=218.2.

Step C:
400 mg [4-chloro-5-[3-chloro-2-methyl-4-[2-(4-methylpiperazin-1-yl)ethoxy]phenyl] thieno[2,3-d]pyrimidin-6-yl]-trimethyl-stannane (product of Step A) (0.6 mmol), 291 mg 5-bromo-N,N-dimethyl-furan-2-carboxamide (product of Step B) (1.3 mmol), 12 mg Pd(PhCN)$_2$Cl$_2$ (0.03 mmol), 13 mg CuI (0.06 mmol) and 20 mg Ph$_3$As (0.06 mmol) were dissolved in 1 mL NMP and stirred at 100° C. under $N_2$ until no further conversion was observed. The mixture was diluted with EtOAc and washed with saturated aq. NaF solution. The aqueous phase was extracted with EtOAc and the combined organic phases were dried over $Na_2SO_4$ and evaporated under reduced pressure. The crude product was purified via flash chromatography using DCM and MeOH as eluents to obtain 5-[4-chloro-5-[3-chloro-2-methyl-4-[2-(4-methylpiperazin-1-yl)ethoxy]phenyl]thieno[2,3-d]pyrimidin-6-yl]-N,N-dimethyl-furan-2-carboxamide. $^1$H NMR (500 MHz, DMSO-d$_6$): 8.97 (s, 1H), 7.26 (d, 1H), 7.20 (d, 1H), 7.04 (d, 1H), 5.80 (d, 1H), 4.24 (t, 2H), 3.13 (br s, 3H), 2.97 (br s, 3H), 2.79 (t, 2H), 2.57 (br s, 4H), 2.35 (br s, 4H), 2.17 (s, 3H), 2.06 (s, 3H). HRMS calculated for $C_{27}H_{29}Cl_2N_5O_3S$: 573.1368. found 574.1463 (M+H).

Step D:
0.255 g 5-[4-chloro-5-[3-chloro-2-methyl-4-[2-(4-methylpiperazin-1-yl)ethoxy]phenyl] thieno[2,3-d]pyrimidin-6-yl]-N,N-dimethyl-furan-2-carboxamide (0.4 mmol), 0.134 g ethyl (2R)-2-hydroxy-3-(2-methoxyphenyl)propanoate (Preparation 3ad) (0.6 mmol) and 0.391 g $Cs_2CO_3$ (1.2 mmol) were placed in a 100 mL flask. 35 mL propan-2-ol was added and the mixture was stirred at 50° C. under $N_2$ until no further conversion was observed. 1 mL water and 0.336 g LiOH×H$_2$O (8 mmol) were added and the mixture was stirred at 50° C. until no further conversion was observed. The reaction was diluted with water; the pH was adjusted between 4-5 using 2 M HCl and extracted with DCM. The combined organic phases were dried over $Na_2SO_4$ and evaporated under reduced pressure. The diastereomers were separated via preparative reversed phase chromatography using 20 mM aqueous $NH_4HCO_3$ solution and MeCN as eluents; the diastereomer eluting later was collected as Example 582. HRMS calculated for $C_{37}H_{40}ClN_5O_7S$: 733.2337. found 734.2450 (M+H).

Example 583 (2R)-2-[((5S$_a$)-5-{3-chloro-2-methyl-4-[2-(4-methylpiperazin-1-yl)ethoxy]phenyl}-6-[5-(methoxycarbonyl)furan-2-yl]thieno[2,3-d]pyrimidin-4-yl)oxy]-3-(2-methoxyphenyl)propanoic acid Hydrolysis of (2R)-2-{[(5S$_a$)-5-{3-chloro-2-methyl-4-[2-(4-methylpiperazin-1-yl)ethoxy] phenyl}-6-(5-cyanofuran-2-yl)thieno[2,3-d]pyrimidin-4-yl]oxy}-3-(2-methoxyphenyl)propanoic acid (Example 579) was performed as described in Example 580. Example 583 was obtained as one of the products of the multicomponent mixture following separation by reversed phase chromatography with 25 mM aqueous NH$_4$HCO$_3$ solution and MeCN as eluents. HRMS calculated for $C_{36}H_{37}ClN_4O_8S$: 720.2021. found 721.2104 (M+H).

Example 584 (2R)-2-{[(5S$_a$)-5-{3-chloro-2-methyl-4-[2-(4-methylpiperazin-1-yl)ethoxy]phenyl}-6-(5-ethenylfuran-2-yl)thieno[2,3-d]pyrimidin-4-yl]oxy}-3-(2-methoxyphenyl)propanoic acid 27 mg (2R)-2-{[6-(5-bromofuran-2-yl)-(5S$_a$)-5-{3-chloro-2-methyl-4-[2-(4-methyl piperazin-1-yl)ethoxy]phenyl}thieno[2,3-d]pyrimidin-4-yl]oxy}-3-(2-methoxyphenyl)propanoic acid (Example 577) (0.036 mmol), 28 mg 4,4,5,5-tetramethyl-2-vinyl-1,3,2-dioxaborolane (0.18 mmol), 23 mg Cs$_2$CO$_3$ (0.072 mmol) and 3 mg AtaPhos (0.004 mmol) were dissolved in a mixture of 0.40 mL dioxane and 0.10 mL water. The reaction mixture was stirred at 70° C. until no further conversion was observed. The reaction mixture was quenched at room temperature with water and the pH was set to 5 using 2 M HCl solution. The mixture was extracted with DCM, and the combined organic phases were dried over Na$_2$SO$_4$ and concentrated under reduced pressure. The crude product was purified via reversed phase chromatography using 25 mM aqueous NH$_4$HCO$_3$ solution and MeCN as eluents to obtain Example 584. HRMS calculated for $C_{36}H_{37}ClN_4O_6S$: 688.2122. found 689.2178 (M+H).

Example 585 (2R)-2-{[(5S$_a$)-5-{3-chloro-2-methyl-4-[2-(4-methylpiperazin-1-yl)ethoxy]phenyl}-6-(5-cyclopropylfuran-2-yl)thieno[2,3-d]pyrimidin-4-yl]oxy}-3-(2-methoxyphenyl)propanoic acid 283 mg (2R)-2-{[6-(5-bromofuran-2-yl)-(5S$_a$)-5-{3-chloro-2-methyl-4-[2-(4-methyl piperazin-1-yl)ethoxy]phenyl}thieno[2,3-d]pyrimidin-4-yl]oxy}-3-(2-methoxyphenyl)propanoic acid (Example 577) (0.38 mmol), 0.70 mL 2-cyclopropyl-4,4,5,5-tetramethyl-1,3,2-dioxaborolane (3.8 mmol), 0.62 g Cs$_2$CO$_3$ (1.9 mmol) and 29 mg PdCl$_2$×dppf (0.04 mmol) were dissolved in a mixture of 4 mL dioxane and 1 mL water. The mixture was heated under nitrogen at 100° C. in a microwave reactor until no further conversion was observed. The reaction was quenched at room temperature with water and the pH was set to 6 using 2 M HCl solution. The mixture was extracted with DCM, the combined organic phases were dried over Na$_2$SO$_4$ and concentrated under reduced pressure. The crude product was purified via reversed phase chromatography using 25 mM aqueous NH$_4$HCO$_3$ solution and MeCN as eluents to obtain Example 585. HRMS calculated for $C_{37}H_{39}ClN_4O_6S$: 702.2279. found 703.2337 (M+H).

Example 586 (2R)-2-{[(5S$_a$)-5-{3-chloro-2-methyl-4-[2-(4-methylpiperazin-1-yl)ethoxy] phenyl}-6-(5-phenylfuran-2-yl)thieno[2,3-d]pyrimidin-4-yl]oxy}-3-(2-methoxyphenyl)propanoic acid 200 mg (2R)-2-{[6-(5-bromofuran-2-yl)-(5S$_a$)-5-{3-chloro-2-methyl-4-[2-(4-methyl piperazin-1-yl)ethoxy] phenyl}thieno[2,3-d]pyrimidin-4-yl]oxy}-3-(2-methoxyphenyl)propanoic acid (Example 577) (0.27 mmol), 275 mg 4,4,5,5-tetramethyl-2-phenyl-1,3,2-dioxaborolane (1.35 mmol), 440 mg Cs$_2$CO$_3$ (1.35 mmol) and 19 mg AtaPhos (0.027 mmol) were dissolved in a mixture of 3 mL dioxane and 0.75 mL water. The reaction mixture was stirred under nitrogen at 70° C. for 1 hour. The reaction was quenched at room temperature with water and the pH was set to 5 using 2 M HCl solution. The mixture was extracted with DCM, the combined organic phases were dried over Na$_2$SO$_4$ and concentrated under reduced pressure. The crude product was purified via reversed phase chromatography using 25 mM aqueous NH$_4$HCO$_3$ solution and MeCN as eluents to obtain Example 586. HRMS calculated for $C_{40}H_{39}ClN_4O_6S$: 738.2279. found 739.2358 (M+H).

Example 587 (2R)-2-[((5S$_a$)-5-{3-chloro-2-methyl-4-[2-(4-methylpiperazin-1-yl)ethoxy]phenyl}-6-[3-(pyridin-4-ylmethoxy)phenyl]thieno[2,3-d]pyrimidin-4-yl)oxy]-3-(2-methoxyphenyl)propanoic acid Step A:

500 mg ethyl (2R)-2-[(5S$_a$)-5-(3-chloro-4-hydroxy-2-methyl-phenyl)-6-iodo-thieno[2,3-d]pyrimidin-4-yl]oxy-3-(2-methoxyphenyl)propanoate (Preparation 25) (0.80 mmol), 630 mg PPh$_3$ (2.40 mmol), 352 mg ditertbutyl azodicarboxylate (2.40 mmol) and 346 mg 2-(4-methylpiperazin-1-yl)ethanol (2.40 mmol) were dissolved in 20 ml dry toluene and the reaction mixture was stirred at 50° C. under nitrogen atmosphere until no further conversion was observed. The mixture was concentrated under reduced pressure and the residue was purified via flash chromatography using DCM and MeOH as eluents to give ethyl (2R)-2-[(5S$_a$)-5-[3-chloro-2-methyl-4-[2-(4-methylpiperazin-1-yl)ethoxy]phenyl]-6-iodo-thieno[2,3-d]pyrimidin-4-yl]oxy-3-(2-methoxyphenyl)propanoate.

Step B:

445 mg ethyl (2R)-2-[(5S$_a$)-5-[3-chloro-2-methyl-4-[2-(4-methylpiperazin-1-yl)ethoxy) phenyl]-6-iodo-thieno[2,3-d]pyrimidin-4-yl]oxy-3-(2-methoxyphenyl)propanoate (0.59 mmol), 264 mg 3-(4,4,5,5-tetramethyl-1,3,2-dioxaborolan-2-yl)phenol (1.20 mmol), 106 mg AtaPhos (0.15 mmol) and 391 mg Cs$_2$CO$_3$ (1.20 mmol) were dissolved in a mixture of 4.5 mL THF and 4.5 mL water. The mixture was heated under nitrogen at 100° C. in a microwave reactor until no further conversion was observed. The crude reaction mixture was diluted with water and the pH was adjusted to 6 by the addition of 2 M HCl solution. The mixture was extracted with DCM, the combined organic phases were dried over Na$_2$SO$_4$ and concentrated under reduced pressure. The residue was purified via flash chromatography using DCM and MeOH as eluents to give ethyl (2R)-2-[(5S$_a$)-5-[3-chloro-2-methyl-4-[2-(4-methylpiperazin-1-yl)ethoxy] phenyl]-6-(3-hydroxyphenyl)thieno[2,3-d]pyrimidin-4-yl]oxy-3-(2-methoxyphenyl)propanoate.

Step C:

72 mg ethyl (2R)-2-[(5S$_a$)-5-[3-chloro-2-methyl-4-[2-(4-methylpiperazin-1-yl)ethoxy] phenyl]-6-(3-hydroxyphenyl)thieno[2,3-d]pyrimidin-4-yl]oxy-3-(2-methoxyphenyl)propanoate (0.10 mmol), 80 mg PPh$_3$ (0.30 mmol), 70 mg ditertbutyl azodicarboxylate (0.30 mmol) and 33 mg 4-pyridylmethanol (0.30 mmol) were dissolved in 3 ml dry toluene and the reaction mixture was stirred under nitrogen at 50° C. until no further conversion was observed. The mixture was concentrated under reduced pressure and the crude product was purified via flash chromatography using DCM and MeOH as eluents. The obtained product was hydrolyzed in 3 mL methanol-water (9:1) containing NaOH (5 m/m %) at room temperature. The mixture was diluted with water and the pH was adjusted to 6 by the addition of 2 M HCl. The mixture was extracted with DCM, the combined organic phases were dried over $Na_2SO_4$ and concentrated under reduced pressure. The crude product was purified via reversed phase chromatography using 25 mM aqueous $NH_4HCO_3$ solution and MeCN as eluents to obtain Example 587. HRMS calculated for $C_{42}H_{42}ClN_5O_6S$: 779.2544. found 390.6339 (M+2H).

Example 588 (2R)-2-[((5S$_a$)-5-{3-chloro-2-methyl-4-[2-(4-methylpiperazin-1-yl)ethoxy]phenyl}-6-{3-[2-(morpholin-4-yl)ethoxy]phenyl}thieno[2,3-d]pyrimidin-4-yl)oxy]-3-(2-methoxyphenyl)propanoic acid Using the same procedures as described for Example 587 and replacing 4-pyridylmethanol with 2-(morpholin-4-yl)ethanol in Step C, Example 588 was obtained. HRMS calculated for $C_{42}H_{48}ClN_5O_7S$: 801.2963. found 401.6554 (M+2H).

Example 589 (2R)-2-[((5S$_a$)-5-{3-chloro-2-methyl-4-[2-(4-methylpiperazin-1-yl)ethoxy]phenyl}-6-[3-(2-methoxyethoxy)phenyl]thieno[2,3-d]pyrimidin-4-yl)oxy]-3-(2-methoxyphenyl)propanoic acid Using the same procedures as described for Example 587 and replacing 4-pyridylmethanol with 2-methoxyethanol in Step C, Example 589 was obtained. HRMS calculated for $C_{39}H_{43}ClN_4O_7S$: 746.2541. found 747.26 (M+H).

Example 590 (2R)-2-{[(5S$_a$)-5-{3-chloro-2-methyl-4-[2-(4-methylpiperazin-1-yl)ethoxy]phenyl}-6-((2S or R)-tetrahydrofuran-2-yl)thieno[2,3-d]pyrimidin-4-yl]oxy}-3-(2-methoxyphenyl)propanoic acid and Example 591 (2R)-2-{[(5S$_a$)-5-{3-chloro-2-methyl-4-[2-(4-methylpiperazin-1-yl)ethoxy]phenyl}-6-((2R or S)-tetrahydrofuran-2-yl)thieno[2,3-d]pyrimidin-4-yl]oxy}-3-(2-methoxyphenyl)propanoic acid Step A:
To a solution of 565 mg Preparation 6e (1.00 mmol) in 90 ml EtOH 1298 mg palladium hydroxide on carbon (Pearlman's catalyst 20 wt. %) was added. The reaction mixture was flushed with nitrogen, and then it was flushed with hydrogen and stirred under hydrogen atmosphere (10 bar) at room temperature for 4 days. The reaction mixture was filtered through a pad of Celite and the filtrate was concentrated under reduced pressure. The residue was purified via preparative reversed phase chromatography using 25 mM aqueous $NH_4HCO_3$ solution and MeCN as eluents to give ethyl (2R)-2-[(5Sa)-5-(3-chloro-4-hydroxy-2-methyl-phenyl)-6-ethyl-furan-2-yl-thieno[2,3-d]pyrimidin-4-yl]oxy-3-(2-methoxyphenyl)propanoate diastereomers. $^1$H NMR (500 MHz, DMSO-d$_6$) of the diastereomer eluted earlier: 10.26 (s, 1H), 8.54 (s, 1H), 7.18 (td, 1H), 7.02 (d, 1H), 6.97 (d, 1H), 6.90 (dd, 1H), 6.75 (t, 1H), 6.32 (dd, 1H), 5.35 (dd, 1H), 4.70 (t, 1H), 4.03-3.96 (m, 3H), 3.76 (s, 3H), 3.73 (m, 1H), 2.95 (m, 1H), 2.45 (dd, 1H), 2.07 (m, 1H), 1.99 (s, 3H), 1.96 (m, 1H), 1.89 (m, 1H), 1.74 (m, 1H), 1.05 (t, 3H).
$^1$H NMR (500 MHz, DMSO-d$_6$) of the diastereomer eluted later: 10.26 (br s, 1H), 8.55 (s, 1H), 7.19 (td, 1H), 7.05 (d, 1H), 6.96 (d, 1H), 6.91 (d, 1H), 6.77 (td, 1H), 6.46 (dd, 1H), 5.36 (dd, 1H), 4.82 (t, 1H), 4.05-3.93 (m, 3H), 3.76 (s, 3H), 3.71 (m, 1H), 2.85 (dd, 1H), 2.57 (m, 1H), 2.04 (m, 1H), 1.95 (m, 1H), 1.94 (s, 3H), 1.88 (m, 1H), 1.66 (m, 1H), 1.00 (t, 3H).
Step B:
Using the Step B and Step C of General Procedure (XVI), starting from the earlier eluted diastereomer in Step A Example 590 was obtained. HRMS calculated for $C_{34}H_{39}ClN_4O_6S$: 666.2279. found 667.2349 (M+H); Starting from the later eluted diastereomer in Step A Example 591 was obtained. HRMS calculated for $C_{34}H_{39}ClN_4O_6S$: 666.2279. found 667.2315 (M+H).

Example 592 (2R)-2-[((5R$_a$)-5-{3-chloro-2-methyl-4-[2-(4-methylpiperazin-1-yl)ethoxy] phenyl}-6-ethylthieno[2,3-d]pyrimidin-4-yl)oxy]-3-(2-methoxyphenyl)propanoic acid Step A:
649 mg 4-chloro-6-ethyl-5-iodo-thieno[2,3-d]pyrimidine (Preparation 1d) (2.0 mmol), 538 mg ethyl (2R)-2-hydroxy-3-(2-methoxyphenyl)propanoate (Preparation 3ad) (2.4 mmol) and 1.955 g cesium carbonate (6.0 mmol) were stirred at 70° C. in 10 mL dry tertbutanol until no further conversion was observed. The mixture was cooled to room temperature, and then 10 mL water, 947 mg 1-[2-[2-chloro-3-methyl-4-(4,4,5,5-tetramethyl-1,3,2-dioxaborolan-2-yl)phenoxy]ethyl]-4-methyl-piperazine (Preparation 5b) (2.4 mmol) and 141 mg AtaPhos (0.2 mmol) were added. The mixture was stirred under nitrogen at 60° C. until no further conversion was observed. Then brine was added and the mixture was extracted with EtOAc. The combined organic phases were dried over MgSO$_4$ and concentrated under reduced pressure. The residue was purified via flash chromatography using EtOAc and MeOH as eluents to obtain ethyl (2R)-2-[5-[3-chloro-2-methyl-4-[2-(4-methylpiperazin-1-yl)ethoxy]phenyl]-6-ethyl-thieno[2,3-d]pyrimidin-4-yl]oxy-3-(2-methoxyphenyl)propanoate.
Step B:
The product of Step A was hydrolyzed according to Step C of General Procedure (XVI); the diastereoisomer eluting earlier was collected as Example 592. HRMS calculated for $C_{32}H_{37}ClN_4O_5S$: 624.2173. found 625.2255 (M+H).

Example 593 (2S)-2-[((5S$_a$)$_5$-{3-chloro-2-methyl-4-[2-(4-methylpiperazin-1-yl)ethoxy] phenyl}-6-ethyl-thieno[2,3-d]pyrimidin-4-yl)oxy]-3-(2-methoxyphenyl)propanoic acid Step A:
649 mg 4-chloro-6-ethyl-5-iodo-thieno[2,3-d]pyrimidine (Preparation 1d) (2.0 mmol), 538 mg ethyl (2S)-2-hydroxy-3-(2-methoxyphenyl)propanoate (Preparation 3bi) (2.4 mmol) and 1.955 g cesium carbonate (6.0 mmol) were stirred at 70° C. in 10 mL dry tertbutanol until no further conversion was observed. The mixture was cooled to room temperature, and then 10 mL water, 947 mg 1-[2-[2-chloro-3-methyl-4-(4,4,5,5-tetramethyl-1,3,2-dioxaborolan-2-yl)

phenoxy]ethyl]-4-methyl-piperazine (Preparation 5b) (2.4 mmol) and 141 mg AtaPhos (0.2 mmol) were added. The mixture was stirred at 60° C. until no further conversion was observed. Then brine was added and the mixture was extracted with EtOAc. The combined organic phases were dried over MgSO$_4$, filtered and concentrated under reduced pressure. The crude intermediate was purified via flash chromatography using EtOAc and MeOH as eluents to obtain ethyl (2S)-2-[5-[3-chloro-2-methyl-4-[2-(4-methyl-piperazin-1-yl)ethoxy]phenyl]-6-ethyl-thieno[2,3-d]pyrimidin-4-yl]oxy-3-(2-methoxyphenyl)propanoate.

Step B:

The product of Step A was hydrolyzed according to Step C of General Procedure (XVI); the diastereoisomer eluting earlier was collected as Example 592. HRMS calculated for C$_{32}$H$_{37}$ClN$_4$O$_5$S: 624.2173. found 625.2239 (M+H).

General Procedure (XVIIa)

Step A:

1 eq. ethyl (2R)-2-[(5S$_a$)-5-[3-chloro-2-methyl-4-[2-(4-methylpiperazin-1-yl)ethoxy] phenyl]-6-(4-fluoro-3-hydroxy-phenyl)thieno[2,3-d]pyrimidin-4-yl]oxy-3-[2-[(2-methoxy pyrimidin-4-yl)methoxy]phenyl]propanoate (Preparation 28a), 2 eq. of the appropriate alcohol and 2 eq. triphenyl phosphine were dissolved in dry toluene (5 mL/mmol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:

The obtained intermediate was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and purified via preparative reversed phase chromatography using 25 mM aqueous NH$_4$HCO$_3$ solution and MeCN as eluents.

Example 594 (2R)-2-[((5S$_a$)-5-{3-chloro-2-methyl-4-[2-(4-methylpiperazin-1-yl)ethoxy]phenyl}-6-[4-fluoro-3-(methoxymethyl)phenyl]thieno[2,3-d]pyrimidin-4-yl)oxy]-3-{2-[(2-methoxypyrimidin-4-yl)methoxy]phenyl}propanoic acid Step A:

0.801 g LiCl (19 mmol) was heated at 250° C. for 10 minutes under N$_2$. Then it was cooled to room temperature and the flask was charged with 0.911 g Mg (38 mmol) and 30 mL dry THF. The Mg was activated with 0.15 mL iBu$_2$AlH (1 M in THF, 0.15 mmol) for 10 minutes, then it was cooled to 0° C. and 3.313 g 4-bromo-1-fluoro-2-(methoxymethyl)benzene (15 mmol) was added. After 30 minutes stirring at 0° C. 4 mL 2-isopropoxy-4,4,5,5-tetramethyl-1,3,2-dioxaborolane (20 mmol) was added and the reaction mixture was stirred for 30 minutes, then filtered through celite, diluted with EtOAc and washed with saturated aq. NH$_4$Cl. The aqueous phase was extracted with EtOAc. The combined organic phases were dried over Na$_2$SO$_4$, concentrated under reduced pressure and the residue was purified via flash chromatography using heptane and EtOAc as eluents to obtain 2-[4-fluoro-3-(methoxymethyl)phenyl]-4,4,5,5-tetramethyl-1,3,2-dioxaborolane. MS (EI, 70 eV) m/z (% relative intensity, [ion]): 59 (21), 85 (20), 134 (24), 135 (100), 136 (28), 150 (30), 165 (24), 166 (43), 167 (95), 192 (20), 251 (44, [M$^+$]).

Step B:

3.94 g 4-chloro-5-[3-chloro-2-methyl-4-[2-(4-methylpiperazin-1-yl)ethoxy]phenyl]-6-iodo-thieno[2,3-d]pyrimidine (Preparation 13) (7 mmol), 2.11 g 2-[4-fluoro-3-(methoxymethyl)phenyl]-4,4,5,5-tetramethyl-1,3,2-dioxaborolane (8.4 mmol), 4.56 g Cs$_2$CO$_3$ (14 mmol), and 0.496 g AtaPhos (0.7 mmol) were placed in a 100 mL flask. 45 mL dioxane and 15 mL water were added, and the mixture was stirred under N$_2$ at 70° C. until no further conversion was observed. Then it was diluted with brine, neutralized with 2 M HCl, and extracted with DCM. The combined organic phases were dried over Na$_2$SO$_4$, concentrated under reduced pressure, and the crude product was purified via flash chromatography using DCM and MeOH as eluents to obtain 4-chloro-5-[3-chloro-2-methyl-4-[2-(4-methylpiperazin-1-yl)ethoxy]phenyl]-6-[4-fluoro-3-(methoxymethyl)phenyl] thieno[2,3-d]pyrimidine. MS: (M+H)=575.2.

Step C:

2.615 g 4-chloro-5-[3-chloro-2-methyl-4-[2-(4-methylpiperazin-1-yl)ethoxy]phenyl]-6-[4-fluoro-3-(methoxymethyl)phenyl]thieno[2,3-d]pyrimidine (4.5 mmol), 1.61 g ethyl (2R)-2-hydroxy-3-(2-tetrahydropyran-2-yloxyphenyl) propanoate (Preparation 3ab-(R)) (5.5 mmol) and 4.40 g Cs$_2$CO$_3$ (13.5 mmol) were placed in a 100 mL flask. 50 mL tert-butanol was added and the mixture was stirred at 80° C. under N$_2$ until no further conversion was observed. The mixture was diluted with water, the pH was set to 7 with 2 M HCl, and then it was extracted with DCM. The combined organic layers were dried over Na$_2$SO$_4$ and concentrated under reduced pressure. The crude product was purified via flash chromatography using EtOAc and MeOH as eluents to obtain ethyl (2R)-2-[5-[3-chloro-2-methyl-4-[2-(4-methylpiperazin-1-yl)ethoxy]phenyl]-6-[4-fluoro-3-(methoxymethyl)phenyl] thieno[2,3-d]pyrimidin-4-yl]oxy-3-(2-tetrahydropyran-2-yloxyphenyl)propanoate as a mixture of diastereoisomers. MS: (M+H)=833.2.

Step D:

2.36 g ethyl (2R)-2-[5-[3-chloro-2-methyl-4-[2-(4-methylpiperazin-1-yl)ethoxy]phenyl]-6-[4-fluoro-3-(methoxymethyl)phenyl]thieno[2,3-d]pyrimidin-4-yl]oxy-3-(2-tetrahydropyran-2-yloxyphenyl)propanoate (28.3 mmol) was dissolved in 15 mL EtOH, then 20 mL 1.25 M HCl in EtOH was added and the mixture was stirred at room temperature until no further conversion was observed. Saturated aq. NaHCO$_3$ solution was added and the reaction mixture was extracted with DCM. The combined organic layers were dried over Na$_2$SO$_4$ and concentrated under reduced pressure. The crude product was purified via flash chromatography using DCM and MeOH as eluents to obtain ethyl (2R)-2-[5-[3-chloro-2-methyl-4-[2-(4-methylpiperazin-1-yl) ethoxy]phenyl]-6-[4-fluoro-3-(methoxymethyl)phenyl] thieno[2,3-d]pyrimidin-4-yl]oxy-3-(2-hydroxyphenyl) propanoate as a mixture of diastereomers. MS: (M+H)= 749.2.

Step E:

0.375 g ethyl (2R)-2-[5-[3-chloro-2-methyl-4-[2-(4-methylpiperazin-1-yl)ethoxy]phenyl]-6-[4-fluoro-3-(methoxymethyl)phenyl]thieno[2,3-d]pyrimidin-4-yl]oxy-3-(2-hydroxyphenyl)propanoate (0.5 mmol), 0.21 g (2-methoxypyrimidin-4-yl)methanol (1.5 mmol) and 0.393 g PPh$_3$ (1.5 mmol) were dissolved in 10 mL dry toluene, then 0.345 g ditertbutyl azodicarboxylate (1.5 mmol) was added. The mixture was stirred at 50° C. under N$_2$ until no further conversion was observed. The volatiles were evaporated under reduced pressure and the crude intermediate was purified via flash chromatography using DCM and methanol as eluents to obtain ethyl (2R)-2-[5-[3-chloro-2-methyl-4-[2-(4-methylpiperazin-1-yl)ethoxy]phenyl]-6-[4-fluoro-3-(methoxymethyl)phenyl]thieno[2,3-d]pyrimidin-4-yl] oxy-3-[2-[(2-methoxypyrimidin-4-yl)methoxy]phenyl] propanoate as a mixture of diastereomers. MS: (M+H)= 871.2.

Step F:

The product of Step E was dissolved in 10 mL dioxane-water (1:1) and 0.21 g LiOH×H$_2$O (5 mmol) was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and purified via preparative reverse phase chromatography using 25 mM aqueous NH$_4$HCO$_3$ solution and MeCN as eluents. The diastereomer eluting later was collected as Example 594. HRMS calculated for C$_{43}$H$_{44}$ClFN$_6$O$_7$S: 842.2665. found 422.1408 (M+2H).

Example 595 (2R)-2-{[(5S$_a$)-5-{3-chloro-2-methyl-4-[2-(4-methylpiperazin-1-yl)ethoxy]phenyl}-6-(4-fluoro-3-hydroxyphenyl)thieno[2,3-d]pyrimidin-4-yl]oxy}-3-{2-[(2-methoxypyrimidin-4-yl)methoxy] phenyl}propanoic acid 316 mg ethyl (2R)-2-[(5S$_a$)-5-[3-chloro-2-methyl-4-[2-(4-methylpiperazin-1-yl)ethoxy]phenyl]-6-(4-fluoro-3-hydroxy-phenyl)thieno[2,3-d]pyrimidin-4-yl]oxy-3-[2-[(2-methoxypyrimidin-4-yl)methoxy]phenyl]propanoate (Preparation 28a) (0.375 mmol) was dissolved in 10 mL dioxane-water 1:1 and 157 mg LiOH×H$_2$O (3.75 mmol) was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and purified via preparative reversed phase chromatography using MeCN and 25 mM aqueous NH$_4$HCO$_3$ solution as eluents to obtain Example 595. HRMS calculated for C$_{41}$H$_{40}$ClFN$_6$O$_7$S: 814.2352. found 408.1254 (M+2H).

Example 596 (2R)-2-[((5S$_a$)-5-{3-chloro-2-methyl-4-[2-(4-methylpiperazin-1-yl)ethoxy]phenyl}-6-{4-fluoro-3-[2-(morpholin-4-yl)ethoxy]phenyl}thieno [2,3-d]pyrimidin-4-yl)oxy]-3-{2-[(2-methoxypyrimidin-4-yl)methoxy]phenyl}propanoic acid Using General Procedure (XVIIa) and 2-(morpholin-4-yl)ethanol as the appropriate alcohol, Example 596 was obtained. HRMS calculated for C$_{47}$H$_{51}$ClFN$_7$O$_8$S: 927.3192. found 464.6657 (M+2H).

Example 597 (2R)-2-[((5S$_a$)-5-{3-chloro-2-methyl-4-[2-(4-methylpiperazin-1-yl)ethoxy]phenyl}-6-[4-fluoro-3-(2-hydroxyethoxy)phenyl]thieno[2,3-d] pyrimidin-4-yl)oxy]-3-{2-[(2-methoxypyrimidin-4-yl)methoxy]phenyl}propanoic acid Using General Procedure (XVIIa) and ethylene glycol as the appropriate alcohol, Example 597 was obtained. HRMS calculated for C$_{43}$H$_{44}$ClFN$_6$O$_8$S: 858.2614. found 430.1402 (M+2H).

Example 598 (2R)-2-[((5S$_a$)-5-{3-chloro-2-methyl-4-[2-(4-methylpiperazin-1-yl)ethoxy]phenyl}-6-[4-fluoro-3-(2-methoxyethoxy)phenyl]thieno[2,3-d] pyrimidin-4-yl)oxy]-3-{2-[(2-methoxypyrimidin-4-yl)methoxy]phenyl}propanoic acid Using General Procedure (XVIIa) and 2-methoxyethanol as the appropriate alcohol, Example 598 was obtained. HRMS calculated for C$_{44}$H$_{46}$ClFN$_6$O$_8$S: 872.277. found 437.1468 (M+2H).

Example 599 (2R)-2-{[(5S$_a$)-5-{3-chloro-2-methyl-4-[2-(4-methylpiperazin-1-yl)ethoxy]phenyl}-6-(3-methoxypropyl)thieno[2,3-d]pyrimidin-4-yl]oxy}-3-{2-[(2-methoxypyrimidin-4-yl)methoxy] phenyl}propanoic acid Step A:

3.754 g 5-bromo-4-chloro-6-iodo-thieno[2,3-d]pyrimidine (Preparation 1a) (10.0 mmol), 1198 mg 3-methoxy-prop-1-yne (17.1 mmol), 702 mg Pd(PPh$_3$)$_2$Cl (1.0 mmol), 288 mg CuI (2.0 mmol) and 2.8 mL TEA (20 mmol) were dissolved in 50 mL THF, and the mixture was stirred under nitrogen at room temperature until no further conversion was observed. It was concentrated under reduced pressure and purified via flash chromatography using heptane and ethyl acetate as eluents to obtain 5-bromo-4-chloro-6-(3-methoxyprop-1-ynyl)thieno[2,3-d]pyrimidine. $^1$H NMR (400 MHz, DMSO-d$_6$): 9.04 (s, 1H), 4.50 (s, 2H), 3.40 (s, 3H).

Step B:

2.07 g 5-bromo-4-chloro-6-(3-methoxyprop-1-ynyl)thieno[2,3-d]pyrimidine (6.517 mmol), 2.11 g ethyl (2R)-2-hydroxy-3-(2-tetrahydropyran-2-yloxyphenyl)propanoate (Preparation 3ab-(R)) (7.17 mmol) and 6.58 g Cs$_2$CO$_3$ (20 mmol) were placed in a flask. 70 mL tert-butanol was added and the mixture was stirred under nitrogen at 65° C. until no further conversion was observed. It was diluted with water and extracted with dichloromethane. The combined organic layers were dried over Na$_2$SO$_4$ and concentrated under reduced pressure to obtain ethyl (2R)-2-[5-bromo-6-(3-methoxyprop-1-ynyl)thieno[2,3-d]pyrimidin-4-yl]oxy-3-(2-tetrahydropyran-2-yloxyphenyl)propanoate. It was used in next step without further purification. MS: (M+H)=575.0.

Step C:

The product of Step B and 2.6 g 2-chloro-3-methyl-4-(4,4,5,5-tetramethyl-1,3,2-dioxaborolan-2-yl)phenol (Preparation 5a) (9.68 mmol) were dissolved in 21 mL THF, then 5.24 g Cs$_2$CO$_3$ (16.08 mmol) dissolved in 7 mL water was added followed by 431 mg AtaPhos (0.61 mmol), and the mixture was stirred under nitrogen at 65° C. until no further conversion was observed. Then it was diluted with dichloromethane and brine. After phase separation the aqueous phase was extracted with dichloromethane. The organic layers were combined and dried over Na$_2$SO$_4$ and concentrated under reduced pressure. The residue was purified via flash chromatography using heptane and ethyl acetate as eluents to obtain ethyl (2R)-2-[5-(3-chloro-4-hydroxy-2-methyl-phenyl)-6-(3-methoxyprop-1-ynyl)thieno[2,3-d]pyrimidin-4-yl]oxy-3-(2-tetrahydropyran-2-yloxyphenyl)propanoate as a mixture of diastereomers. MS: (M+H)=637.2.

Step D:

2.765 g ethyl (2R)-2-[5-(3-chloro-4-hydroxy-2-methyl-phenyl)-6-(3-methoxyprop-1-ynyl)thieno[2,3-d]pyrimidin-4-yl]oxy-3-(2-tetrahydropyran-2-yloxyphenyl)propanoate (4.34 mmol), 1.3 g 2-(4-methylpiperazin-1-yl)ethanol (9.0 mmol) and 2.623 g triphenyl phosphine (10.0 mmol) were dissolved in 40 mL dry toluene, then 2.303 g ditertbutyl azodicarboxylate (10.0 mmol) was added. The mixture was stirred at 50° C. under nitrogen until no further conversion was observed. The volatiles were evaporated under reduced pressure and the residue was purified via flash chromatography using ethyl acetate and methanol as eluents to obtain ethyl (2R)-2-[5-[3-chloro-2-methyl-4-[2-(4-methylpiperazin-1-yl)ethoxy]phenyl]-6-(3-methoxyprop-1-ynyl)thieno[2,3-d]pyrimidin-4-yl]oxy-3-(2-tetrahydropyran-2-yloxyphenyl)propanoate as a mixture of diastereomers. MS: (M+H)=763.2.

Step E:

3.59 g ethyl (2R)-2-[5-[3-chloro-2-methyl-4-[2-(4-methylpiperazin-1-yl)ethoxy]phenyl]-6-(3-methoxyprop-1-ynyl)thieno[2,3-d]pyrimidin-4-yl]oxy-3-(2-tetrahydropyran-2-yloxyphenyl)propanoate (4.3 mmol) and 458 mg Selcat Q6 were dissolved in 50 mL methanol, then 1.87 g tert-butylamine borane (21.5 mmol) was added. The mixture was stirred at room temperature until no further conversion was observed. It was filtered through a plug of celite and the volatiles were evaporated under reduced pressure to obtain ethyl (2R)-2-[5-[3-chloro-2-methyl-4-[2-(4-methylpiperazin-1-yl)ethoxy]phenyl]-6-(3-methoxypropyl)thieno[2,3-d]pyrimidin-4-yl]oxy-3-(2-tetrahydropyran-2-yloxyphenyl)propanoate as a mixture of diastereomers that was used in next step without further purification. MS: (M+H)=767.2.

Step F:

The product of Step E was dissolved in 20 mL EtOH, then 20 mL 1.25 M HCl in EtOH was added and the mixture was stirred at room temperature until no further conversion was observed. Most of the EtOH was evaporated under reduced pressure then water and saturated aq. $NaHCO_3$ solution were added and the mixture was extracted with DCM. The combined organic layers were dried over $Na_2SO_4$ and concentrated under reduced pressure. The crude product was purified via flash chromatography using DCM and MeOH as eluents to obtain ethyl (2R)-2-[5-[3-chloro-2-methyl-4-[2-(4-methylpiperazin-1-yl)ethoxy] phenyl]-6-(3-methoxypropyl)thieno[2,3-d]pyrimidin-4-yl]oxy-3-(2-hydroxyphenyl)propanoate as a mixture of diastereomers. MS: (M+H)= 683.2.

Step G:

479 mg ethyl (2R)-2-[5-[3-chloro-2-methyl-4-[2-(4-methylpiperazin-1-yl)ethoxy]phenyl]-6-(3-methoxypropyl)thieno[2,3-d]pyrimidin-4-yl]oxy-3-(2-hydroxyphenyl)propanoate (0.7 mmol), 280 mg (2-methoxypyrimidin-4-yl) methanol (2.0 mmol) and 525 mg triphenyl phosphine (2.0 mmol) were dissolved in 10 mL dry toluene, then 461 mg ditertbutyl azodicarboxylate (2.0 mmol) was added. The mixture was stirred at 50° C. under nitrogen until no further conversion was observed. The volatiles were evaporated under reduced pressure and the crude intermediate was purified via flash chromatography using ethyl acetate and methanol as eluents.

Step H:

The product of Step G was dissolved in 30 mL dioxane-water (1:1) and 250 mg $LiOH \times H_2O$ (5.95 mmol) was added. The mixture was stirred at room temperature until no further conversion was observed. Then it was diluted with brine, neutralized with 2 M HCl, and extracted with dichloromethane. The combined organic phases were dried over $Na_2SO_4$, concentrated under reduced pressure, and purified via preparative reversed phase chromatography using 25 mM aqueous $NH_4HCO_3$ solution and MeCN as eluents. The diastereoisomer eluting later was collected as Example 599. HRMS calculated for $C_{39}H_{45}ClN_6O_7S$: 776.2759. found 777.2796 (M+H).

General Procedure (XVIIIa)

Step A:

1 eq. ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-iodo-thieno[2,3-d]pyrimidin-4-yl]oxy-propanoate (Preparation 26c), 2 eq. of the appropriate boronic acid derivative and 2.5 eq. $Cs_2CO_3$ were dissolved in THF-water (1:1) (0.1 M for Preparation 26c), then 0.1 eq. $PdCl_2 \times dppf$ was added. The mixture was heated under nitrogen at 100° C. in a microwave reactor until no further conversion was observed. Then it was diluted with brine, extracted with DCM. The combined organic phases were dried over $Na_2SO_4$, concentrated under reduced pressure, and purified via flash chromatography using EtOAc and MeOH as eluents.

Step B:

The product of Step A was dissolved in dioxane-water 1:1 (10 mL/mmol) and 10 eq. $LiOH \times H_2O$ was added. The mixture was stirred at room temperature until no further conversion was observed. Then it was diluted with brine, neutralized with 2 M HCl, and extracted with DCM. The combined organic phases were dried over $Na_2SO_4$, concentrated under reduced pressure and purified via preparative reversed phase chromatography using 25 mM aqueous $NH_4HCO_3$ solution and MeCN as eluents separating the diastereoisomers.

Example 600 (2R)-3-{2-[(1-butyl-1H-pyrazol-5-yl)methoxy]phenyl}-2-{[(5$S_a$)-5-{3-chloro-2-methyl-4-[2-(4-methylpiperazin-1-yl)ethoxy]phenyl}-6-(4-cyanophenyl)thieno[2,3-d]pyrimidin-4-yl]oxy}propanoic acid Using General Procedure (XVIIIa) and (4-cyanophenyl)boronic acid as the appropriate boronic acid derivative, the diastereoisomer eluting later was collected as Example 600. HRMS calculated for $C_{44}H_{46}ClN_7O_5S$: 819.2970. found 410.6565 (M+2H).

Example 601 (2R)-3-{2-[(1-butyl-1H-pyrazol-5-yl)methoxy]phenyl}-2-{[(5$S_a$)-5-{3-chloro-2-methyl-4-[2-(4-methylpiperazin-1-yl)ethoxy]phenyl}-6-(4-ethylphenyl)thieno[2,3-d]pyrimidin-4-yl]oxy}propanoic acid Using General Procedure (XVIIIa) and (4-ethylphenyl)boronic acid as the appropriate boronic acid derivative, the diastereoisomer eluting later was collected as Example 601. HRMS calculated for $C_{45}H_{51}ClN_6O_5S$: 822.3330. found 412.1729 (M+2H).

Example 602 (2R)-3-{2-[(1-butyl-1H-pyrazol-5-yl)methoxy]phenyl}-2-{[(5$S_a$)-5-{3-chloro-2-methyl-4-[2-(4-methylpiperazin-1-yl)ethoxy]phenyl}-6-(4-hydroxyphenyl)thieno[2,3-d]pyrimidin-4-yl]oxy}propanoic acid Using General Procedure (XVIIIa) and (4-hydroxyphenyl)boronic acid as the appropriate boronic acid derivative, the diastereoisomer eluting later was collected as Example 602. HRMS calculated for $C_{43}H_{47}ClN_6O_6S$: 810.2966. found 406.1541 (M+2H).

Example 603 (2R)-3-{2-[(1-butyl-1H-pyrazol-5-yl)methoxy]phenyl}-2-{[(5$S_a$)-5-{3-chloro-2-methyl-4-[2-(4-methylpiperazin-1-yl)ethoxy]phenyl}-6-(4-methoxyphenyl)thieno[2,3-d]pyrimidin-4-yl]oxy}propanoic acid Using General Procedure (XVIIIa) and (4-methoxyphenyl)boronic acid as the appropriate boronic acid derivative, the diastereoisomer eluting later was collected as Example 603. HRMS calculated for $C_{44}H_{49}ClN_6O_6S$: 824.3123. found 413.1648 (M+2H).

Example 604 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(4-ethoxyphenyl)thieno[2,3-d]pyrimidin-4-yl]oxy}propanoic acid Using General Procedure (XVIIIa) and (4-ethoxyphenyl)boronic acid as the appropriate boronic acid derivative, the diastereoisomer eluting later was collected as Example 604. HRMS calculated for $C_{45}H_{51}ClN_6O_6S$: 838.3279. found 420.1700 (M+2H).

Example 605 (2R)-3-{2-[(1-butyl-1H-pyrazol-5-yl)methoxy]phenyl}-2-{[6-(6'-chloro-2,3'-bipyridin-5-yl)-(5S$_a$)-5-{3-chloro-2-methyl-4-[2-(4-methylpiperazin-1-yl)ethoxy]phenyl}thieno[2,3-d]pyrimidin-4-yl]oxy}propanoic acid and

Example 606 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(6-chloropyridin-3-yl)thieno[2,3-d]pyrimidin-4-yl]oxy}propanoic acid Using General Procedure (XVIIIa) and (6-chloro-3-pyridyl)boronic acid as the appropriate boronic acid derivative Example 606 was collected as the secondly eluting diastereoisomer. HRMS calculated for $C_{42}H_{45}Cl_2N_7O_5S$: 829.2580. found 415.6359 (M+2H). Overreaction at the Suzuki coupling was also observed and the later eluting diastereoisomer of this side product was collected as Example 605. HRMS calculated for $C_{47}H_{48}Cl_2N_8O_5S$: 906.2845. found 454.1481 (M+2H).

Example 607 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(6-fluoropyridin-3-yl)thieno[2,3-d]pyrimidin-4-yl]oxy}propanoic acid Using General Procedure (XVIIIa) and (6-fluoro-3-pyridyl)boronic acid as the appropriate boronic acid derivative, the diastereoisomer eluting later was collected as Example 607. HRMS calculated for $C_{42}H_{45}ClFN_7O_5S$: 813.2875. found 407.6496 (M+2H).

Example 608 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(6-methoxypyridin-3-yl)thieno[2,3-d]pyrimidin-4-yl]oxy}propanoic acid Using General Procedure (XVIIIa) and (6-methoxy-3-pyridyl)boronic acid as the appropriate boronic acid derivative, the diastereoisomer eluting later was collected as Example 608. HRMS calculated for $C_{43}H_{48}ClN_7O_6S$: 825.3075. found 413.6608 (M+2H).

Example 609 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(pyridin-3-yl)thieno[2,3-d]pyrimidin-4-yl]oxy}propanoic acid Using General Procedure (XVIIIa) and 3-pyridylboronic acid as the appropriate boronic acid derivative, the diastereoisomer eluting later was collected as Example 609. HRMS calculated for $C_{42}H_{46}ClN_7O_5S$: 795.2970. found 398.6572 (M+2H).

Example 610 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(1-methyl-1H-pyrazol-3-yl)thieno[2,3-d]pyrimidin-4-yl]oxy}propanoic acid Using General Procedure (XVIIIa) and 1-methyl-3-(4,4,5,5-tetramethyl-1,3,2-dioxaborolan-2-yl)pyrazole as the appropriate boronic acid derivative, the diastereoisomer eluting later was collected as Example 610. HRMS calculated for $C_{41}H_{47}ClN_8O_5S$: 798.3079. found 400.1599 (M+2H).

Example 611 (2R)-3-{2-[(1-butyl-1H-pyrazol-5-yl)methoxy]phenyl}-2-[((5S$_a$)-5-{3-chloro-2-methyl-4-[2-(4-methylpiperazin-1-yl)ethoxy]phenyl}-6-ethynylthieno[2,3-d]pyrimidin-4-yl)oxy]propanoic acid Step A:
437 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-iodo-thieno[2,3-d]pyrimidin-4-yl]oxy-propanoate (Preparation 26c) (0.5 mmol), 139 µL ethynyl(trimethyl)silane (1.0 mmol), 35 mg Pd(PPh$_3$)$_2$Cl$_2$ (0.05 mmol) and 19 mg copper(I) iodide (0.1 mmol) were dissolved in 5 mL DIPA, then the mixture was stirred under nitrogen at 60° C. until no further conversion was observed. The reaction mixture was cooled to room temperature and 6001 TBAF (0.6 mmol, 1 M in THF) was added and it was stirred for 30 minutes. Then the volatiles were evaporated under reduced pressure and the crude product was purified by flash chromatography using EtOAc and MeOH as eluents to obtain ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-ethynyl-thieno[2,3-d]pyrimidin-4-yl]oxy-propanoate.
Step B:
The product of Step A was hydrolyzed according to Step B of General Procedure (XVIIIa) and the diastereoisomer eluting later was collected as Example 611. HRMS calculated for $C_{39}H_{43}ClN_6O_5S$: 742.2704. found 743.2789 (M+H).

Example 612 (2R)-3-{2-[(1-butyl-1H-pyrazol-5-yl)methoxy]phenyl}-2-{[6-(but-1-yn-1-yl)-(5S$_a$)-5-{3-chloro-2-methyl-4-[2-(4-methylpiperazin-1-yl)ethoxy]phenyl}thieno[2,3-d]pyrimidin-4-yl]oxy}propanoic acid Step A:
437 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-iodo-thieno[2,3-d]pyrimidin-4-yl] oxy-propanoate (Preparation 26c) (0.5 mmol), 35 mg Pd(PPh$_3$)$_2$Cl$_2$ (0.05 mmol) and 19 mg copper(I) iodide (0.1 mmol) were dissolved in 5 mL DIPA, then but-1-yne was bubbled through the reaction mixture, which was stirred at 60° C. until no further conversion was observed. Then the volatiles were evaporated under reduced pressure and the crude product was purified by flash chromatography using EtOAc and MeOH as eluents to obtain ethyl (2R)-3-[2-[(1-butyl-1H-pyrazol-5-yl)methoxy]phenyl]-2-[6-but-1-ynyl-5-[3-chloro-2-methyl-4-[2-(4-methylpiperazin-1-yl)ethoxy]phenyl]thieno[2,3-d]pyrimidin-4-yl]oxy-propanoate.

Step B:
The obtained intermediate was hydrolyzed according to Step B of General Procedure (XVIIIa) and the diastereoisomer eluting later was collected as Example 612. HRMS calculated for $C_{41}H_{47}ClN_6O_5S$: 770.3017. found 386.1594 (M+2H).

Example 613 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(3-methoxyprop-1-yn-1-yl)thieno[2,3-d]pyrimidin-4-yl]oxy}propanoic acid Step A:
437 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-iodo-thieno[2,3-d]pyrimidin-4-yl]oxy-propanoate (Preparation 26c) (0.5 mmol), 70 mg 3-methoxyprop-1-yne (1.0 mmol), 35 mg Pd(PPh$_3$)$_2$Cl$_2$ (0.05 mmol) and 19 mg CuI (0.1 mmol) were dissolved in 5 mL DIPA and stirred under nitrogen at 60° C. until no further conversion was observed. The volatiles were evaporated under reduced pressure and the crude product was purified by flash chromatography using EtOAc and MeOH as eluents to obtain ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-(3-methoxyprop-1-ynyl)thieno[2,3-d]pyrimidin-4-yl]oxy-propanoate.

Step B:
The product of Step A was hydrolyzed according to Step B of General Procedure (XVIIIa); the diastereoisomer eluting later was collected as Example 613. HRMS calculated for $C_{41}H_{47}ClN_6O_6S$: 786.2966. found 787.3040 (M+H).

Example 614 (2R)-3-{2-[(1-butyl-1H-pyrazol-5-yl)methoxy]phenyl}-2-[((5S$_a$)-5-{3-chloro-2-methyl-4-[2-(4-methylpiperazin-1-yl)ethoxy]phenyl}-6-cyanothieno[2,3-d]pyrimidin-4-yl)oxy]propanoic acid Step A:
437 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-iodo-thieno[2,3-d]pyrimidin-4-yl]oxy-propanoate (Preparation 26c) (0.5 mmol) and 224 mg CuCN (2.5 mmol) were stirred at 100° C. in 5 mL dry DMF until no further conversion was observed. Brine was added and the mixture was extracted with DCM. The combined organic phases were washed with brine, then dried over MgSO$_4$ and concentrated under reduced pressure. The residue was purified via flash chromatography using EtOAc and MeOH as eluents to obtain ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-cyano-thieno[2,3-d]pyrimidin-4-yl]oxy-propanoate.

Step B:
The obtained intermediate was hydrolyzed according to Step B of General Procedure (XVIIIa) and the diastereoisomer eluting later was collected as Example 614. HRMS calculated for $C_{38}H_{42}ClN_7O_5S$: 743.2657. found 372.6390 (M+2H).

Example 615 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(trifluoromethyl) thieno[2,3-d]pyrimidin-4-yl]oxy}propanoic acid Step A:
437 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-iodo-thieno[2,3-d]pyrimidin-4-yl] oxy-propanoate (Preparation 26c) (0.75 mmol), 28.2 mg 1,10-phenanthroline (0.156 mmol), 29.7 mg copper (I) iodide (0.156 mmol), 130 mg potassium fluoride (2.23 mmol), 330 μL trimethyl(trifluoromethyl)silane (2.23 mmol) and 250 μL trimethyl borate (2.23 mmol) were dissolved in 5 mL dry DMSO and the mixture was stirred at room temperature overnight under argon atmosphere. Then brine was added and the mixture was extracted with DCM. The combined organic phases were washed with brine, dried over MgSO$_4$, and concentrated under reduced pressure. The crude product was purified via flash chromatography using EtOAc and MeOH as eluents to obtain ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-(trifluoromethyl)thieno[2,3-d]pyrimidin-4-yl]oxy-propanoate.

Step B:
The product of Step A was hydrolyzed according to Step B of General Procedure (XVIIIa) and the diastereoisomer eluting later was collected as Example 615. HRMS calculated for $C_{38}H_{42}ClF_3N_6O_5S$: 786.2578. found 394.1372 (M+2H).

Example 616 (2R)-3-{2-[(1-butyl-1H-pyrazol-5-yl)methoxy]phenyl}-2-[((5S$_a$)-5-{3-chloro-2-methyl-4-[2-(4-methylpiperazin-1-yl)ethoxy]phenyl}-6-{4-[2-(morpholin-4-yl)ethoxy]phenyl}thieno[2,3-d]pyrimidin-4-yl)oxy]propanoic acid Step A:
420 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-(4-hydroxyphenyl)thieno[2,3-d]pyrimidin-4-yl]oxy-propanoate (see Step A of Example 602) (0.5 mmol), 182 μl 2-(morpholin-4-yl)ethanol (1.5 mmol) and 393 mg triphenylphosphine (3.0 mmol) were dissolved in 10 mL dry toluene, then 261 mg ditertbutyl azodicarboxylate (3.0 mmol) was added. The mixture was stirred at 50° C. under nitrogen until no further conversion was observed. Then the volatiles were evaporated under reduced pressure and the residue was purified via flash chromatography using EtOAc and MeOH as eluents to give ethyl (2R)-3-[2-[(1-butyl-1H-pyrazol-5-yl)methoxy]phenyl]-2-[5-[3-chloro-2-methyl-4-[2-(4-methyl piperazin-1-yl)ethoxy]phenyl]-6-[4-(2-(morpholin-4-yl)ethoxy)phenyl]thieno[2,3-d]pyrimidin-4-yl]oxy-propanoate.

Step B:
The product of Step A was hydrolyzed according to Step B of General Procedure (XVIIIa) and the diastereoisomer eluting later was collected as Example 616. HRMS calculated for $C_{49}H_{58}ClN_7O_7S$: 923.3807. found 462.6977 (M+2H).

Example 617 (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(3-methoxypropyl)thieno[2,3-d]pyrimidin-4-yl]oxy}propanoic acid 350 mg ethyl (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(3-methoxyprop-1-yn-1-yl)thieno[2,3-d]pyrimidin-4-yl]oxy}propanoic acid (Example 613) (0.43 mmol) and 46 mg Selcat Q6 were dissolved in 5 mL methanol, then 187 mg tert-butylamine borane (2.2 mmol) was added and the mixture was stirred at room temperature until no further conversion was observed. The mixture was filtered through celite, then the filtrate was diluted with brine, neutralized with 2 M HCl, and extracted with DCM. The combined organic phases were dried over Na$_2$SO$_4$ and concentrated under reduced pressure. The residue was purified via preparative reversed phase chromatography using 25 mM aqueous NH$_4$HCO$_3$ solution and MeCN as eluents to obtain Example 617. HRMS calculated for C$_{41}$H$_{51}$ClN$_6$O$_6$S: 790.3279. found 791.3329 (M+H).

Example 618 (2R)-2-{[6-(6-aminopyridin-3-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-{2-[(1-butyl-1H-pyrazol-5-yl)methoxy]phenyl}propanoic acid Using General Procedure (XVIIIa) and 5-(4,4,5,5-tetramethyl-1,3,2-dioxaborolan-2-yl)pyridin-2-amine as the appropriate boronic acid derivative; the diastereoisomer eluting later was collected as Example 618. HRMS calculated for C$_{42}$H$_{47}$ClN$_8$O$_5$S: 810.3079. found 811.3129 (M+H).

Example 619 (2R)-3-{2-[(1-butyl-1H-pyrazol-5-yl)methoxy]phenyl}-2-[((5S$_a$)-5-{3-chloro-2-methyl-4-[2-(4-methylpiperazin-1-yl)ethoxy]phenyl}-6-[6-(morpholin-4-yl)pyridin-3-yl]thieno[2,3-d]pyrimidin-4-yl)oxy]propanoic acid Step A:

250 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-(6-fluoro-3-pyridyl)thieno[2,3-d]pyrimidin-4-yl]oxy-propanoate (see Step A of Example 607) (0.29 mmol) and 258 μL morpholine (2.90 mmol) were heated at 150° C. in a microwave reactor until no further conversion was observed. The volatiles were evaporated under reduced pressure and the residue was purified via flash chromatography using EtOAc and MeOH as eluents to give ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-(6-morpholino-3-pyridyl)thieno[2,3-d]pyrimidin-4-yl]oxy-propanoate.

Step B:

The product of Step A was hydrolyzed according to Step B of General Procedure (XVIIIa) and the diastereoisomer eluting later was collected as Example 619. HRMS calculated for C$_{46}$H$_{53}$ClN$_8$O$_6$S: 880.3497. found 441.1825 (M+2H).

Example 620 (2R)-3-{2-[(1-butyl-1H-pyrazol-5-yl)methoxy]phenyl}-2-[((5S$_a$)-5-{3-chloro-2-methyl-4-[2-(4-methylpiperazin-1-yl)ethoxy]phenyl}-6-{6-[(2-methoxyethyl)amino]pyridin-3-yl}thieno[2,3-d]pyrimidin-4-yl)oxy]propanoic acid Step A:

300 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-(6-fluoro-3-pyridyl)thieno[2,3-d]pyrimidin-4-yl]oxy-propanoate (see Step A of Example 607) (0.35 mmol) and 258 μL 2-methoxyethanamine (3.50 mmol) were heated at 150° C. in a microwave reactor until no further conversion was observed. The volatiles were evaporated under reduced pressure and the crude product was purified via flash chromatography using EtOAc and MeOH as eluents to give ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-[6-(2-methoxyethylamino)-3-pyridyl]thieno[2,3-d]pyrimidin-4-yl]oxy-propanoate.

Step B:

The product of Step A was hydrolyzed according to Step B of General Procedure (XVIIIa) and the diastereoisomer eluting later was collected as Example 620. HRMS calculated for C$_{45}$H$_{53}$ClN$_8$O$_6$S: 868.3497. found 435.1839 (M+2H).

Example 621 (2R)-3-{2-[(1-butyl-1H-pyrazol-5-yl)methoxy]phenyl}-2-[((5S$_a$)-5-{3-chloro-2-methyl-4-[2-(4-methylpiperazin-1-yl)ethoxy]phenyl}-6-{6-[2-(morpholin-4-yl)ethoxy]pyridin-3-yl}thieno[2,3-d]pyrimidin-4-yl)oxy]propanoic acid Step A:

260 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-(6-fluoro-3-pyridyl)thieno[2,3-d]pyrimidin-4-yl]oxy-propanoate (Step A of Example 607) (0.31 mmol), 405 mg 2-(morpholin-4-yl)ethanol (3.10 mmol) and 293 mg cesium carbonate (0.93 mmol) were stirred at 60° C. in 10 mL dry tert-butanol until no further conversion was observed. Brine was added and the mixture was extracted with DCM. The combined organic phases were washed with brine, then dried over MgSO$_4$, and concentrated under reduced pressure. The residue was purified via flash chromatography using EtOAc and MeOH as eluents to give ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-[6-(2-morpholinoethoxy)-3-pyridyl]thieno[2,3-d]pyrimidin-4-yl]oxy-propanoate.

Step B:

The product of Step A was hydrolyzed according to Step B of General Procedure (XVIIIa) and the diastereoisomer eluting later was collected as Example 621. HRMS calculated for C$_{48}$H$_{57}$ClN$_8$O$_7$S: 924.3759. found 463.1961 (M+2H).

Example 622 (2R)-3-{2-[(1-butyl-1H-pyrazol-5-yl)methoxy]phenyl}-2-[((5S$_a$)-5-{3-chloro-2-methyl-4-[2-(4-methylpiperazin-1-yl)ethoxy]phenyl}-6-[6-(2-methoxyethoxy)pyridin-3-yl]thieno[2,3-d]pyrimidin-4-yl)oxy]propanoic acid Step A:

200 mg ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-(6-fluoro-3-pyridyl)thieno[2,3-d] pyrimidin-4-yl]oxy-propanoate (see Step A of Example 607) (0.24 mmol), 56 µL 2-methoxyethanol (0.72 mmol) and 232 mg cesium carbonate (0.72 mmol) were stirred at 70° C. in 5 mL dry tert-butanol until no further conversion was observed. Brine was added and the mixture was extracted with DCM. The combined organic phases were washed with brine, then dried over $MgSO_4$, and concentrated under reduced pressure. The residue was purified via flash chromatography using EtOAc and MeOH as eluents to give ethyl (2R)-3-[2-[(1-butyl-1H-pyrazol-5-yl)methoxy]phenyl]-2-[5-[3-chloro-2-methyl-4-[2-(4-methylpiperazin-1-yl)ethoxy]phenyl]-6-[6-(2-methoxyethoxy)-3-pyridyl]thieno[2,3-d]pyrimidin-4-yl]oxy-propanoate.

Step B:

The product of Step A was hydrolyzed according to Step B of General Procedure (XVIIIa) and the diastereoisomer eluting later was collected as Example 622. HRMS calculated for $C_{45}H_{52}ClN_7O_7S$: 869.3337. found 435.6737 (M+2H).

General Procedure (XXa)

The appropriate acid was dissolved in ethanol (20 mL/g) containing 1% cc. sulfuric acid and the mixture was stirred at 70° C. until no further conversion was observed. Water was added to the mixture and it was neutralized with $NaHCO_3$, extracted with DCM, the combined organic phases were dried with $Na_2SO_4$ and concentrated under reduced pressure. The crude ester was purified via preparative reversed phase chromatography using 25 mM aqueous $NH_4HCO_3$ solution and MeCN as eluents.

Example 623 ethyl (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(propan-2-yl)-1H-pyrazol-5-yl]methoxy}phenyl)propanoate Starting from Example 182 using General Procedure (XXa), Example 623 was obtained. HRMS calculated for $C_{42}H_{46}ClFN_6O_6S$: 816.2872. found 409.1516 (M+2H).

Example 624 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(propan-2-yl)-1H-pyrazol-5-yl]methoxy}phenyl)propanoate Starting from Example 71 using General Procedure (XXa), Example 624 was obtained. HRMS calculated for $C_{44}H_{48}ClFN_6O_5S$: 826.3079. found 414.1627 (M+2H).

Example 625 ethyl (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-{2-[(2-methoxypyrimidin-4-yl)methoxy]phenyl}propanoate Starting from Example 176 using General Procedure (XXa), Example 625 was obtained. HRMS calculated for $C_{41}H_{42}ClFN_6O_7S$: 816.2508. found 817.2629 (M+H).

Example 626 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-methoxypyrimidin-4-yl)methoxy]phenyl}propanoate Starting from Example 54 using General Procedure (XXa), Example 626 was obtained. HRMS calculated for $C_{43}H_{44}ClFN_6O_6S$: 826.2716. found 414.1440 (M+2H).

Example 627 ethyl (2R)-2-{[(5S$_a$)-5-{3-chloro-2-methyl-4-[2-(4-methylpiperazin-1-yl)ethoxy]phenyl}-6-(furan-2-yl)thieno[2,3-d]pyrimidin-4-yl]oxy}-3-(2-methoxy phenyl)propanoate Starting from Example 209 using General Procedure (XXa), Example 627 was obtained. HRMS calculated for $C_{36}H_{39}ClN_4O_6S$: 690.2279. found 691.2347 (M+H).

Example 628 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2R)-tetrahydrofuran-2-ylmethoxy]phenyl}propanoate Starting from Example 2 using General Procedure (XXa), Example 628 was obtained. HRMS calculated for $C_{42}H_{46}ClFN_4O_6S$: 788.2811. found 789.2875 (M+H).

Example 629 ethyl (2R)-2-{[(5S$_a$)-5-{3-chloro-2-methyl-4-[2-(morpholin-4-yl)ethoxy]phenyl}-6-(4-fluorophenyl)thieno[2,3-d]pyrimidin-4-yl]oxy}-3-{2-[(2R)-tetrahydrofuran-2-ylmethoxy]phenyl}propanoate Starting from Example 648 using General Procedure (XXa), Example 629 was obtained. HRMS calculated for $C_{41}H_{43}ClFN_3O_7S$: 775.2494. found 776.2560 (M+H).

Example 630 ethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-{2-[(2R)-tetrahydrofuran-2-ylmethoxy]phenyl}propanoate Starting from Example 126 using General Procedure (XXa), Example 630 was obtained. HRMS calculated for $C_{39}H_{41}ClFN_3O_6S$: 733.2389. found 734.2469 (M+H).

Example 631 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(pyrazin-2-ylmethoxy)phenyl]propanoate Starting from Example 91 using General Procedure (XXa), Example 631 was obtained. HRMS calculated for $C_{42}H_{42}ClFN_6O_5S$: 796.2610. found 797.2695 (M+H).

Example 632 ethyl (2R)-2-{[(5S$_a$)-5-{3-chloro-2-methyl-4-[2-(morpholin-4-yl)ethoxy]phenyl}-6-(4-fluorophenyl)thieno[2,3-d]pyrimidin-4-yl]oxy}-3-[2-(pyrazin-2-ylmethoxy)phenyl]propanoate Starting from Example 148 using General Procedure (XXa), Example 632 was obtained. HRMS calculated for $C_{41}H_{39}ClFN_5O_6S$: 783.2294. found 784.2387 (M+H).

Example 633 ethyl (2R)-2-{[(5S$_a$)-5-{3-chloro-2-methyl-4-[2-(4-methylpiperazin-1-yl)ethoxy]phenyl}-6-(thiophen-3-yl)thieno[2,3-d]pyrimidin-4-yl]oxy}-3-(2-methoxyphenyl)propanoate Starting from Example 568 using General Procedure (XXa), Example 633 was obtained. HRMS calculated for $C_{36}H_{39}ClN_4O_5S_2$: 706.2050. found 707.2111 (M+H).

Example 634 ethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-[2-(2,2,2-trifluoroethoxy)phenyl]propanoate Starting from Example 127 using General Procedure (XXa), Example 634 was obtained. HRMS calculated for $C_{36}H_{34}ClF_4N_3O_5S$: 731.1844. found 732.1929 (M+H).

Example 635 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(2,2,2-trifluoroethoxy)phenyl]propanoate Starting from Example 3 using General Procedure (XXa), Example 635 was obtained. HRMS calculated for $C_{39}H_{39}ClF_4N_4O_5S$: 786.2266. found 787.2334 (M+H).

Example 636 ethyl (2R)-2-{[(5S$_a$)-5-(3-chloro-4-hydroxy-2-methylphenyl)-6-(thiophen-3-yl)thieno[2,3-d]pyrimidin-4-yl]oxy}-3-(2-methoxyphenyl)propanoate Starting from Example 715 using General Procedure (XXa), Example 636 was obtained. HRMS calculated for $C_{29}H_{25}ClN_2O_5S_2$: 580.0893. found 581.0953 (M+H).

Example 637 ethyl (2R)-2-{[(5S$_a$)-5-{3-chloro-2-methyl-4-[2-(morpholin-4-yl)ethoxy]phenyl}-6-(4-fluorophenyl)thieno[2,3-d]pyrimidin-4-yl]oxy}-3-[2-(2,2,2-trifluoroethoxy)phenyl]propanoate Starting from Example 657 using General Procedure (XXa), Example 637 was obtained. HRMS calculated for $C_{38}H_{36}ClF_4N_3O_6S$: 773.1949. found 774.2023 (M+H).

Example 638 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2,2,2-trifluoroethoxy)pyrimidin-4-yl]methoxy}phenyl)propanoate Starting from Example 58 using General Procedure (XXa), Example 638 was obtained. HRMS calculated for $C_{44}H_{43}ClF_4N_6O_6S$: 894.2589. found 895.2688 (M+H).

Example 639 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Starting from Example 30 using General Procedure (XXa), Example 639 was obtained. HRMS calculated for $C_{49}H_{48}ClFN_6O_6S$: 902.3029. found 452.1594 (M+2H).

Example 640 2,3-dihydro-1H-inden-5-yl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoate 69 mg (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-methoxyphenyl)propanoic acid (Example 1) (0.10 mmol), 20 mg 2,3-dihydro-1H-inden-5-ol (0.15 mmol), 0.028 mL triethylamine (0.20 mmol) and 78 mg PyBOP (0.15 mmol) were dissolved in 3 mL DCM and the reaction mixture was stirred at room temperature until no further conversion was observed. Water was added and the mixture was extracted with DCM, and the combined organic phases were dried with $Na_2SO_4$ and concentrated under reduced pressure. The crude ester was purified via preparative reversed phase chromatography using 25 mM aqueous $NH_4HCO_3$ solution and MeCN as eluents resulting Example 640. HRMS calculated for $C_{45}H_{44}ClFN_4O_5S$: 806.2705. found 807.2820 (M+H).

Example 641 2,2,2-trifluoroethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoate 69 mg (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-methoxyphenyl)propanoic acid (Example 1) (0.10 mmol), 0.011 mL trifluoroethanol (0.15 mmol), 0.028 mL triethylamine (0.20 mmol) and 78 mg PyBOP (0.15 mmol) were dissolved in 3 mL DCM and the reaction mixture was stirred at room temperature until no further conversion was observed. Water was added and the mixture was extracted with DCM, and the combined organic phases were dried with $Na_2SO_4$ and concentrated under reduced pressure. The crude ester was purified via preparative reversed phase chromatography using 25 mM aqueous $NH_4HCO_3$ solution and MeCN as eluents resulting Example 641. HRMS calculated for $C_{38}H_{37}ClF_4N_4O_5S$: 772.2109. found 773.2188 (M+H).

Example 642 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoate Starting from Example 1 using General Procedure (XXa), Example 642 was obtained. HRMS calculated for $C_{38}H_{40}ClFN_4O_5S$: 718.2392. found 719.2475 (M+H).

Example 643 {[(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoyl]oxy}methyl 2,2-dimethylpropanoate 69 mg (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-methoxyphenyl)propanoic acid (Example 1) (0.10 mmol), 15 mg chloromethyl 2,2-dimethylpropanoate (0.10 mmol), 30 mg sodium iodide (0.20 mmol) and 65 mg $Cs_2CO_3$ (0.20 mmol) were dissolved in 1 mL DMF and the reaction mixture was stirred at room temperature until no further conversion was observed. Water was added and the mixture was extracted with DCM, and the combined organic phases were dried with Na$_2$SO$_4$ and concentrated under reduced pressure. The crude ester was purified via preparative reversed phase chromatography using 25 mM aqueous TFA solution and MeCN as eluents resulting Example 643. HRMS calculated for C$_{42}$H$_{46}$ClFN$_4$O$_7$S: 804.2760. found 805.2822 (M+H).

Example 644 (5-methyl-2-oxo-1,3-dioxol-4-yl) methyl (2R)-2-{[(5S$_a$)-5-{3-chloro-2-methyl-4-[2-(4-methylpiperazin-1-yl)ethoxy]phenyl}-6-(4-fluoro-phenyl)thieno[2,3-d]pyrimidin-4-yl]oxy}-3-(2-methoxyphenyl)propanoate 69 mg (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-(2-methoxyphenyl)propanoic acid (Example 1) (0.10 mmol), 15 mg 4-(chloromethyl)-5-methyl-1,3-dioxol-2-one (0.10 mmol), 30 mg sodium iodide (0.20 mmol) and 65 mg Cs$_2$CO$_3$ (0.20 mmol) were dissolved in 1 mL DMF and the reaction mixture was stirred at room temperature until no further conversion was observed. Water was added and the mixture was extracted with DCM, and the combined organic phases were dried with Na$_2$SO$_4$ and concentrated under reduced pressure. The crude ester was purified via preparative reversed phase chromatography using 25 mM aqueous TFA solution and MeCN as eluents resulting Example 644. HRMS calculated for C$_{41}$H$_{40}$N$_4$O$_8$FSCl: 802.2239. found 803.2298 (M+H).
General Procedure (XXIa)
Step A:
1 eq. phenol derivative, 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using EtOAc and MeOH as eluents.
Step B:
The product of Step A was dissolved in dioxane-water (1:1, 10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure, and purified via preparative reversed phase chromatography using 25 mM aqueous NH$_4$HCO$_3$ solution and MeCN as eluents.
General Procedure (XXIb)
1 eq. ester was dissolved in dioxane-water (1:1, 10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure. If necessary the crude product was purified via preparative reversed phase chromatography using MeCN and 25 mM aqueous NH$_4$HCO$_3$ solution as eluents.

Example 645 (2R)-2-{[(5S$_a$)-5-(4-{2-[4-(4-aminobutyl)piperazin-1-yl]ethoxy}-3-chloro-2-methyl-phenyl)-6-(4-fluorophenyl)thieno[2,3-d]pyrimidin-4-yl]oxy}-3-{2-[(2R)-tetrahydrofuran-2-ylmethoxy]phenyl}propanoic acid Using General Procedure (XXIa), ethyl (2R)-2-[(5S$_a$)-5-(3-chloro-4-hydroxy-2-methyl-phenyl)-6-(4-fluorophenyl) thieno[2,3-d]pyrimidin-4-yl]oxy-3-[2-[[(2R)-tetrahydro-furan-2-yl]methoxy]phenyl]propanoate (Preparation 6r) as the phenol and 2-[4-(4-aminobutyl)piperazin-1-yl]ethanol as the appropriate alcohol, Example 645 was obtained. HRMS calculated for C$_{43}$H$_{49}$ClFN$_5$O$_6$S: 817.3076. found 818.3129 (M+H).

Example 646 (2R)-2-{[(5S$_a$)-5-{3-bromo-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoic acid Step A:
531 mg ethyl (2R)-2-[5-bromo-6-(4-fluorophenyl)thieno[2,3-d]pyrimidin-4-yl]oxy-3-(2-methoxyphenyl)propanoate (Preparation 4n) (1.00 mmol), 598 mg [2-bromo-3-methyl-4-(4,4,5,5-tetramethyl-1,3,2-dioxaborolan-2-yl)phenoxy]-triisopropyl-silane (Preparation 5o) (1.27 mmol), 71 mg AtaPhos (0.10 mmol) and 652 mg Cs$_2$CO$_3$ (2.00 mmol) were dissolved in 8 mL dioxane and 2 mL water. The mixture was heated under nitrogen at 110° C. for 15 minutes in a microwave reactor. Then 1.2 mL TBAF (1.20 mmol in 1 M THF) was added and the mixture was stirred for 5 minutes at room temperature. Then it was diluted with water, acidified to pH 4 with 2 M HCl, and extracted with DCM. The combined organic phases were dried over Na$_2$SO$_4$ and concentrated under reduced pressure. The crude intermediate was purified via flash chromatography using heptane and EtOAc as eluents and the diastereoisomer eluting later was collected as ethyl (2R)-2-[(5S$_a$)-5-(3-bromo-4-hydroxy-2-methyl-phenyl)-6-(4-fluorophenyl)thieno[2,3-d]pyrimidin-4-yl]oxy-3-(2-methoxyphenyl)propanoate.
Step B:
Using the product of Step A as the phenol and 2-(4-methylpiperazin-1-yl)ethanol as the appropriate alcohol in General Procedure (XXIa), Example 646 was obtained. HRMS calculated for C$_{36}$H$_{36}$BrFN$_4$O$_5$S: 734.1574. found 735.1637 (M+H).

Example 647 (2R)-2-{[(5S$_a$)-5-{2,3-dichloro-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoic acid Step A:
266 mg ethyl (2R)-2-[5-bromo-6-(4-fluorophenyl)thieno[2,3-d]pyrimidin-4-yl]oxy-3-(2-methoxyphenyl)propanoate (Preparation 4n) (0.50 mmol), 298 mg 1-[2-[2,3-dichloro-4-(4,4,5,5-tetramethyl-1,3,2-dioxaborolan-2-yl)phenoxy]ethyl]-4-methyl-piperazine (Preparation 5p) (0.70 mmol), 35 mg AtaPhos (0.05 mmol) and 489 mg Cs$_2$CO$_3$ (1.50 mmol) were dissolved in 4 mL dioxane and 1 mL water, and the mixture was heated under nitrogen at 110° C. for 8 minutes in a microwave reactor. Then it was diluted with brine and extracted with DCM. The combined organic phases were dried over Na$_2$SO$_4$, concentrated under reduced pressure, and purified via reversed phase chromatography using 25 mM aqueous NH$_4$HCO$_3$ solution and MeCN as eluents.
Step B:
The product of Step A was hydrolyzed according to General Procedure 21b and the diastereoisomer eluting later was collected as Example 647. HRMS calculated for C$_{35}$H$_{33}$Cl$_2$FN$_4$O$_5$S: 710.1533. found 711.1604 (M+H).

Example 648 (2R)-2-{[(5S$_a$)-5-{3-chloro-2-methyl-4-[2-(morpholin-4-yl)ethoxy]phenyl}-6-(4-fluorophenyl)thieno[2,3-d]pyrimidin-4-yl]oxy}-3-{2-[(2R)-tetrahydrofuran-2-ylmethoxy]phenyl}propanoic acid Using General Procedure (XXIa) with ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[2-[[(2R)-tetrahydrofuran-2-yl]methoxy]phenyl]propanoate (Preparation 6r) as the phenol and 2-(morpholin-4-yl)ethanol as the appropriate alcohol, Example 648 was obtained. HRMS calculated for C$_{39}$H$_{39}$ClFN$_3$O$_7$S: 747.2181. found 748.2237 (M+H).

Example 649 (2R)-2-{[(5S$_a$)-5-{3-chloro-2-methyl-4-[(1-methylpyrrolidin-3-yl)methoxy]phenyl}-6-(4-fluorophenyl)thieno[2,3-d]pyrimidin-4-yl]oxy}-3-{2-[(2R)-tetrahydrofuran-2-ylmethoxy]phenyl}propanoic acid (mixture of diastereoisomers)

Using General Procedure (XXIa) with ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[2-[[(2R)-tetrahydrofuran-2-yl]methoxy]phenyl]propanoate (Preparation 6r) as the phenol and (1-methylpyrrolidin-3-yl)methanol as the appropriate alcohol, Example 649 was obtained. HRMS calculated for C$_{39}$H$_{39}$ClFN$_3$O$_6$S: 731.2232. found 732.2297 (M+H).

Example 650 (2R)-2-{[(5S$_a$)-5-{3-chloro-2-methyl-4-[((3R or S)-1-methylpiperidin-3-yl)oxy] phenyl}-6-(4-fluorophenyl)thieno[2,3-d]pyrimidin-4-yl]oxy}-3-{2-[(2R)-tetrahydrofuran-2-ylmethoxy]phenyl}propanoic acid Using General Procedure (XXIa) with ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[2-[[(2R)-tetrahydrofuran-2-yl]methoxy]phenyl]propanoate (Preparation 6r) as the phenol and 1-methylpiperidin-3-ol as the appropriate alcohol, Example 650 was obtained as a single diastereoisomer (the absolute configuration of the 1-methylpiperidin-3-yl moiety was not determined). HRMS calculated for C$_{39}$H$_{39}$ClFN$_3$O$_6$S: 731.2232. found 732.2319 (M+H).

Example 651 (2R)-2-{[(5R$_a$)-5-{5-chloro-4-methyl-6-[2-(4-methylpiperazin-1-yl)ethoxy]pyridin-3-yl}-6-(4-fluorophenyl)thieno[2,3-d]pyrimidin-4-yl]oxy}-3-{2-[(2-methoxypyrimidin-4-yl)methoxy]phenyl}propanoic acid Using General Procedure (XXIa) with ethyl (2R)-2-[5-[5-chloro-4-methyl-6-[2-(4-methylpiperazin-1-yl)ethoxy]-3-pyridyl]-6-(4-fluorophenyl)thieno[2,3-d]pyrimidin-4-yl]oxy-3-(2-hydroxyphenyl)propanoate (Preparation 8j) as the phenol and (2-methoxypyrimidin-4-yl)methanol as the appropriate alcohol, Example 651 was obtained as the later eluting diastereoisomer. HRMS calculated for C$_{40}$H$_{39}$ClFN$_7$O$_6$S: 799.2355. found 400.6259 (M+2H).

Example 652 (2R)-2-{[(5R$_a$)-5-{5-chloro-4-methyl-6-[2-(4-methylpiperazin-1-yl)ethoxy]pyridin-3-yl}-6-(4-fluorophenyl)thieno[2,3-d]pyrimidin-4-yl]oxy}-3-{2-[(1-ethyl-1H-pyrazol-5-yl)methoxy]phenyl}propanoic acid Using General Procedure (XXIa) with ethyl (2R)-2-[5-[5-chloro-4-methyl-6-[2-(4-methylpiperazin-1-yl)ethoxy]-3-pyridyl]-6-(4-fluorophenyl)thieno[2,3-d]pyrimidin-4-yl]oxy-3-(2-hydroxyphenyl)propanoate (Preparation 8j) as the phenol and (1-ethyl-1H-pyrazol-5-yl)methanol (Preparation 9da) as the appropriate alcohol, Example 652 was obtained as the later eluting diastereoisomer. HRMS calculated for C$_{40}$H$_{41}$ClFN$_7$O$_5$S: 785.2562. found 393.6355 (M+2H).

Example 653 (2R)-2-{[(5S$_a$)-5-{3-chloro-2-methyl-4-[3-(4-methylpiperazin-1-yl)propyl]phenyl}-6-(4-fluorophenyl)thieno[2,3-d]pyrimidin-4-yl]oxy}-3-(2-methoxyphenyl)propanoic acid and Example 654 (2R)-2-{[(5R$_a$)-5-{3-chloro-2-methyl-4-[3-(4-methylpiperazin-1-yl)propyl]phenyl}-6-(4-fluorophenyl)thieno[2,3-d]pyrimidin-4-yl]oxy}-3-(2-methoxyphenyl)propanoic acid Step A:
531 mg ethyl (2R)-2-[5-bromo-6-(4-fluorophenyl)thieno[2,3-d]pyrimidin-4-yl]oxy-3-(2-methoxyphenyl)propanoate (Preparation 4n) (1.00 mmol), 393 mg 1-[3-[2-chloro-3-methyl-4-(4,4,5,5-tetramethyl-1,3,2-dioxaborolan-2-yl)phenyl]propyl]-4-methyl-piperazine (Preparation 5r) (1.00 mmol), 71 mg AtaPhos (0.10 mmol) and 652 mg Cs$_2$CO$_3$ (2.00 mmol) were dissolved in 8 mL dioxane and 2 mL water, and the mixture was heated under nitrogen at 110° C. for 7 minutes in a microwave reactor. Then it was diluted with brine and extracted with DCM. The combined organic phases were dried over Na$_2$SO$_4$, concentrated under reduced pressure, and purified via reversed phase chromatography using 25 mM aqueous NH$_4$HCO$_3$ solution and MeCN as eluents.

Step B:
The product of Step B was hydrolyzed according to General Procedure 21b. The diastereoisomer eluting earlier was collected as Example 654. HRMS calculated for C$_{37}$H$_{38}$ClFN$_4$O$_4$S: 688.2286. found 689.2396 (M+H).
The diastereoisomer eluting later was collected as Example 653. HRMS calculated for C$_{37}$H$_{38}$ClFN$_4$O$_4$S: 688.2286. found 689.2358 (M+H).

Example 655 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(3-methoxypropyl)phenyl]propanoic acid Step A:
1.00 g ethyl (2R)-2-[(5S$_a$)-[3-chloro-2-methyl-4-[2-(4-methylpiperazin-1-yl)ethoxy] phenyl]-6-(4-fluorophenyl)thieno[2,3-d]pyrimidin-4-yl]oxy-3-(2-hydroxyphenyl)propanoate (Preparation 8a) (1.41 mmol) and 594 μL TEA (4.25 mmol) were dissolved in 10 mL dry DCM, then 477 μL trifluoromethylsulfonyl trifluoromethanesulfonate (2.00 mmol) was added and the mixture was stirred at room temperature for 10 minutes. Then it was concentrated under reduced pressure and the residue was dissolved in 10 mL dry DMSO. 156 mg PdCl$_2$×dppf (0.21 mmol), 81 mg copper(I) iodide (0.42 mmol), 1.17 mL 3-methoxyprop-1-yne (14.2 mmol) and 903 mg K$_3$PO$_4$ (3.00 mmol) were added and the mixture was stirred under nitrogen at 80° C. for 8 hours. Then it was diluted with EtOAc and filtered through celite. The filtrate was washed with brine, dried over MgSO$_4$, and concentrated under reduced pressure. The residue was purified via flash chromatography using EtOAc and MeOH as eluents to obtain ethyl (2R)-2-[(5S$_a$)-5-[3-chloro-2-methyl- 4-[2-(4-methylpiperazin-1-yl)ethoxy]phenyl]-6-(4-fluorophenyl)thieno[2,3-d]pyrimidin-4-yl] oxy-3-[2-(3-methoxyprop-1-ynyl)phenyl]propanoate.

Step B:

326 mg ethyl (2R)-2-[(5S$_a$)-5-[3-chloro-2-methyl-4-[2-(4-methylpiperazin-1-yl)ethoxy] phenyl]-6-(4-fluorophenyl)thieno[2,3-d]pyrimidin-4-yl]oxy-3-[2-(3-methoxyprop-1-ynyl)phenyl] propanoate (0.43 mmol) and 46 mg Selcat Q6 were dissolved in 5 mL methanol, then 187 mg tert-butylamine borane (2.2 mmol) was added and the mixture was stirred at room temperature until no further conversion was observed. The mixture was filtered through celite and the filtrate was concentrated under reduced pressure.

Step C:

The product of Step B was hydrolyzed according to General Procedure (XXIb) to give Example 655. HRMS calculated for $C_{39}H_{42}ClFN_4O_5S$: 732.2548. found 733.2614 (M+H).

Example 656 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-(3-methoxyprop-1-yn-1-yl)phenyl]propanoic acid Ethyl (2R)-2-[(5S$_a$)-5-[3-chloro-2-methyl-4-[2-(4-methylpiperazin-1-yl)ethoxy]phenyl]-6-(4-fluorophenyl)thieno[2,3-d]pyrimidin-4-yl]oxy-3-[2-(3-methoxyprop-1-ynyl)phenyl] propanoate (see Step A of Example 655) was hydrolyzed according to General Procedure (XXIb) to give Example 656. HRMS calculated for $C_{39}H_{38}ClFN_4O_5S$: 728.2235. found 729.2301 (M+H).

Example 657 (2R)-2-{[(5S$_a$)-5-{3-chloro-2-methyl-4-[2-(morpholin-4-yl)ethoxy]phenyl}-6-(4-fluorophenyl)thieno[2,3-d]pyrimidin-4-yl]oxy}-3-[2-(2,2,2-trifluoroethoxy)phenyl]propanoic acid Using General Procedure (XXIa) with ethyl (2R)-2-[5-(3-chloro-4-hydroxy-2-methyl-phenyl)-6-(4-fluorophenyl)thieno[2,3-d]pyrimidin-4-yl]oxy-3-[2-(2,2,2-trifluoroethoxy)phenyl] propanoate (Preparation 6s) as the phenol and 2-(morpholin-4-yl)ethanol as the appropriate alcohol, Example 657 was obtained as the secondly eluting diastereoisomer. HRMS calculated for $C_{36}H_{32}ClF_4N_3O_6S$: 745.1636. found 746.1686 (M+H).

Example 658 (2R)-2-{[(5S$_a$)-5-{3-chloro-2-methyl-4-[((2S or R)-1-methylpyrrolidin-2-yl)methoxy]phenyl}-6-(4-fluorophenyl)thieno[2,3-d]pyrimidin-4-yl]oxy}-3-[2-(2,2,2-trifluoroethoxy)phenyl]propanoic acid (single diastereoisomer)

and

Example 659 (2R)-2-{[(5S$_a$)-5-{3-chloro-2-methyl-4-[((2R or S)-1-methylpyrrolidin-2-yl)methoxy]phenyl}-6-(4-fluorophenyl)thieno[2,3-d]pyrimidin-4-yl]oxy}-3-[2-(2,2,2-trifluoroethoxy)phenyl]propanoic acid (single diastereoisomer)

Using General Procedure (XXIa) with ethyl (2R)-2-[5-(3-chloro-4-hydroxy-2-methyl-phenyl)-6-(4-fluorophenyl)thieno[2,3-d]pyrimidin-4-yl]oxy-3-[2-(2,2,2-trifluoroethoxy)phenyl] propanoate (Preparation 6s) as the phenol and 1-methylpiperidin-3-ol as the appropriate alcohol, a rearrangement was observed during the Mitsunobu coupling. Example 658 and Example 659 were isolated as the thirdly and fourthly eluting diastereoisomers differing in the absolute configuration of the 1-methylpyrrolidin-2-yl moiety, which was not determined. Example 658 HRMS calculated for $C_{36}H_{32}ClF_4N_3O_5S$: 729.1687. found 730.1762 (M+H) and 730.1716 (M+H). Example 659 HRMS calculated for $C_{36}H_{32}ClF_4N_3O_5S$: 729.1687. found 730.1716 (M+H).

Example 660 (2R)-2-{[(5S$_a$)-5-(3-chloro-4-methoxy-2-methylphenyl)-6-(4-fluorophenyl)thieno[2,3-d]pyrimidin-4-yl]oxy}-3-(2-{[2-(dimethylamino)pyrimidin-4-yl]methoxy}phenyl)propanoic acid Using General Procedure (XXIa) with ethyl (2R)-2-[(5S$_a$)-5-(3-chloro-4-methoxy-2-methyl-phenyl)-6-(4-fluorophenyl)thieno[2,3-d]pyrimidin-4-yl]oxy-3-(2-hydroxyphenyl)propanoate (Preparation 8l) as the phenol and [2-(dimethylamino)pyrimidin-4-yl]methanol (Preparation 9an) as the appropriate alcohol, Example 660 was obtained. HRMS calculated for $C_{36}H_{31}ClFN_5O_5S$: 699.1718. found 700.1805 (M+H).

Example 661 (2R)-2-{[(5S$_a$)-5-(3-chloro-4-methoxy-2-methylphenyl)-6-(4-fluorophenyl)thieno[2,3-d]pyrimidin-4-yl]oxy}-3-{2-[2-(4-methylpiperazin-1-yl)ethoxy]phenyl}propanoic acid Using General Procedure (XXIa) with ethyl (2R)-2-[(5S$_a$)-5-(3-chloro-4-methoxy-2-methyl-phenyl)-6-(4-fluorophenyl)thieno[2,3-d]pyrimidin-4-yl]oxy-3-(2-hydroxyphenyl)propanoate (Preparation 8l) as the phenol and 2-(4-methylpiperazin-1-yl)ethanol as the appropriate alcohol, Example 661 was obtained. HRMS calculated for $C_{36}H_{36}ClFN_4O_5S$: 690.2079. found 691.2141 (M+H).

Example 662 (2R)-2-{[(5S$_a$)-5-(3-chloro-4-methoxy-2-methylphenyl)-6-(4-fluorophenyl)thieno[2,3-d]pyrimidin-4-yl]oxy}-3-{2-[2-(dimethylamino)ethoxy]phenyl}propanoic acid Using General Procedure (XXIa) with ethyl (2R)-2-[(5S$_a$)-5-(3-chloro-4-methoxy-2-methyl-phenyl)-6-(4-fluorophenyl)thieno[2,3-d]pyrimidin-4-yl]oxy-3-(2-hydroxyphenyl)propanoate (Preparation 8l) as the phenol and 2-(dimethylamino)ethanol as the appropriate alcohol, Example 662 was obtained. HRMS calculated for $C_{33}H_{31}ClFN_3O_5S$: 635.1657. found 636.1770 (M+H).

Example 663 (2R)-2-{[(5S$_a$)-5-(3-chloro-4-methoxy-2-methylphenyl)-6-(4-fluorophenyl)thieno[2,3-d]pyrimidin-4-yl]oxy}-3-[2-({1-[2-(dimethylamino)ethyl]-1H-pyrazol-5-yl}methoxy)phenyl]propanoic acid Using General Procedure (XXIa) with ethyl (2R)-2-[(5S$_a$)-5-(3-chloro-4-methoxy-2-methyl-phenyl)-6-(4-fluorophenyl)thieno[2,3-d]pyrimidin-4-yl]oxy-3-(2-hydroxyphenyl)propanoate (Preparation 8l) as the phenol and {1-[2-(dimethylamino)ethyl]-1H-pyrazol-5-yl}methanol (Preparation 9dj) as the appropriate alcohol, Example 663 was obtained. HRMS calculated for $C_{37}H_{35}ClFN_5O_5S$: 715.2031. found 716.2157 (M+H).

Example 664 (2R)-2-{[(5S$_a$)-5-{3-chloro-5-fluoro-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoic acid and Example 665 (2R)-2-{[(5R$_a$)-5-{3-chloro-5-fluoro-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoic acid Step A:
531 mg ethyl (2R)-2-[5-bromo-6-(4-fluorophenyl)thieno[2,3-d]pyrimidin-4-yl]oxy-3-(2-methoxyphenyl)propanoate (Preparation 4n) (1.00 mmol), 380 mg 2-chloro-6-fluoro-3-methyl-4-(4,4,5,5-tetramethyl-1,3,2-dioxaborolan-2-yl)phenol (Preparation 5m) (1.33 mmol), 71 mg AtaPhos (0.10 mmol) and 652 mg Cs$_2$CO$_3$ (2.00 mmol) were dissolved in 8 mL dioxane and 2 mL water. The mixture was heated under nitrogen at 110° C. for 10 minutes in a microwave reactor. Then it was diluted with brine, neutralized with 2 M HCl, and extracted with DCM. The combined organic phases were dried over Na$_2$SO$_4$ and concentrated under reduced pressure. The residue was purified via flash chromatography, using heptane and EtOAc as eluents to obtain a mixture of diastereoisomers.

Step B:
Using the product of Step A as the phenol and 2-(4-methylpiperazin-1-yl)ethanol as the appropriate alcohol in General Procedure (XXIa) the diastereoisomer eluting earlier was collected as Example 665. HRMS calculated for C$_{36}$H$_{35}$ClF$_2$N$_4$O$_5$S: 708.1985. found 709.2042 (M+H). The diastereoisomer eluting later was collected as Example 664. HRMS calculated for C$_{36}$H$_{35}$ClF$_2$N$_4$O$_5$S: 708.1985. found 709.2037 (M+H).

General Procedure (XXIIa)
Step A:
1 eq. ethyl (2R)-2-[(5S$_a$)-5-(3-chloro-4-hydroxy-2-methyl-phenyl)-6-(2-furyl)thieno[2,3-d]pyrimidin-4-yl]oxy-3-(2-tetrahydropyran-2-yloxyphenyl)propanoate (Preparation 6d), 2 eq. of the appropriate alcohol and 2 eq. triphenyl phosphine were dissolved in dry toluene (5 ml/mmol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:
The product of Step A was dissolved in ethanol (5 mL/mmol), then HCl (1.25 M in ethanol) was added (5 mL/mmol) and the mixture was stirred at room temperature until no further conversion was observed. Most of the ethanol was evaporated under reduced pressure. The reaction mixture was treated carefully with saturated aq. NaHCO$_3$ solution and extracted with DCM. The combined organic phases were dried over Na$_2$SO$_4$ and concentrated under reduced pressure.

Step C:
1 eq. of the product of Step B, 2 eq. of the appropriate alcohol and 2 eq. triphenyl phosphine were dissolved in dry toluene (5 mL/mmol), then 2 eq. ditertbutyl azodicarboxylate was added. The mixture was stirred at 50° C. under nitrogen until no further conversion was observed. The volatiles were evaporated under reduced pressure and the residue was purified via flash chromatography using ethyl acetate and methanol as eluents.

Step D:
The product of Step C was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure, and purified via preparative reversed phase chromatography using 25 mM aqueous NH$_4$HCO$_3$ solution and MeCN as eluents.

Example 666 (2R)-2-{[(5S$_a$)-5-(3-chloro-2-methyl-phenyl)-6-(furan-2-yl)thieno[2,3-d]pyrimidin-4-yl]oxy}-3-{2-[2-(4-methylpiperazin-1-yl)ethoxy]phenyl}propanoic acid Step A:
251 mg 5-bromo-4-chloro-6-iodo-thieno[2,3-d]pyrimidine (Preparation 1a) (0.668 mmol), 270 mg ethyl (2R)-2-hydroxy-3-[2-[2-(4-methylpiperazin-1-yl)ethoxy]phenyl]propanoate (Preparation 3bk) (0.8 mmol) and 871 mg Cs$_2$CO$_3$ (2.67 mmol) were placed in a flask. 7 mL tert-butanol was added and the mixture was stirred at 60° C. until no further conversion was observed. Then it was concentrated under reduced pressure and purified via flash chromatography using ethyl acetate and methanol as eluents to obtain ethyl (2R)-2-(5-bromo-6-iodo-thieno[2,3-d]pyrimidin-4-yl)oxy-3-[2-[2-(4-methylpiperazin-1-yl)ethoxy]phenyl]propanoate.

Step B:
420 mg ethyl (2R)-2-(5-bromo-6-iodo-thieno[2,3-d]pyrimidin-4-yl)oxy-3-[2-[2-(4-methyl piperazin-1-yl)ethoxy]phenyl]propanoate (0.62 mmol), 360 mg 2-(2-furyl)-4,4,5,5-tetramethyl-1,3,2-dioxaborolane (1.86 mmol), 606 mg cesium carbonate (1.86 mmol), and 74 mg Pd(dppf)Cl$_2$ (0.124 mmol) were placed in a flask. 8 mL 1,4-dioxane and 2 mL water were added, and the mixture was stirred at 40° C. under argon until no further conversion was observed. The reaction mixture was concentrated under reduced pressure and purified via preparative reversed phase chromatography using 5 mM aqueous NH$_4$HCO$_3$ solution and MeCN as eluents to obtain ethyl (2R)-2-[5-bromo-6-(2-furyl)thieno[2,3-d]pyrimidin-4-yl]oxy-3-[2-[2-(4-methylpiperazin-1-yl)ethoxy]phenyl]propanoate. MS: (M+H)=615.0.

Step C:
189 mg ethyl (2R)-2-[5-bromo-6-(2-furyl)thieno[2,3-d]pyrimidin-4-yl]oxy-3-[2-[2-(4-methylpiperazin-1-yl)ethoxy]phenyl]propanoate (0.3 mmol) and 146 mg 2-(3-chloro-2-methyl-phenyl)-5,5-dimethyl-1,3,2-dioxaborinane (0.6 mmol) were dissolved in 2.5 mL 1,4-dioxane, then 195 mg Cs$_2$CO$_3$ (0.6 mmol) dissolved in 0.6 mL water was added followed by 21 mg AtaPhos (0.021 mmol), and the mixture was heated under nitrogen at 110° C. in a microwave reactor until no further conversion was observed. Then it was diluted with brine and extracted with dichloromethane. The combined organic phases were dried over Na$_2$SO$_4$, concentrated under reduced pressure, and purified via flash chromatography using dichloromethane and methanol as eluents.

Step D:
The product of Step C was dissolved in 4 mL dioxane-water (1:1) and 126 mg LiOH×H$_2$O (3.0 mmol) was added. The mixture was stirred at room temperature until no further conversion was observed. Then it was diluted with brine, neutralized with 2 M HCl, and extracted with DCM. The combined organic phases were dried over Na$_2$SO$_4$ and concentrated under reduced pressure. The residue was purified via preparative reversed phase chromatography using MeCN and 25 mM aqueous NH$_4$HCO$_3$ solution as eluents. The diastereoisomer eluting later was collected to obtain Example 666. HRMS calculated for C$_{33}$H$_{33}$ClN$_4$O$_5$S: 632.1860. found 633.1962 (M+H).

Example 667 (2S)-2-{[(5R$_a$)-5-(3-chloro-2-methyl-phenyl)-6-(furan-2-yl)thieno[2,3-d] pyrimidin-4-yl]oxy}-3-{2-[2-(4-methylpiperazin-1-yl)ethoxy]phenyl}propanoic acid Step A:
260 mg 5-bromo-4-chloro-6-iodo-thieno[2,3-d]pyrimidine (Preparation 1a) (0.69 mmol), 280 mg ethyl (2S)-2-hydroxy-3-[2-[2-(4-methylpiperazin-1-yl)ethoxy]phenyl]propanoate (Preparation 3bo) (0.83 mmol) and 899 mg Cs$_2$CO$_3$ (2.76 mmol) were placed in a flask. 7 mL tert-butanol was added and the mixture was stirred at 60° C. until no further conversion was observed. Then it was concentrated under reduced pressure and purified via flash chromatography using ethyl acetate and methanol as eluents to obtain ethyl (2S)-2-(5-bromo-6-iodo-thieno[2,3-d]pyrimidin-4-yl)oxy-3-[2-[2-(4-methylpiperazin-1-yl)ethoxy] phenyl]propanoate.
Step B:
420 mg ethyl (2S)-2-(5-bromo-6-iodo-thieno[2,3-d]pyrimidin-4-yl)oxy-3-[2-[2-(4-methylpiperazin-1-yl)ethoxy]phenyl]propanoate (0.62 mmol), 360 mg 2-(2-furyl)-4,4,5,5-tetramethyl-1,3,2-dioxaborolane (1.86 mmol), 606 mg cesium carbonate (1.86 mmol), and 74 mg Pd(dppf)Cl$_2$ (0.124 mmol) were placed in a flask. 8 mL 1,4-dioxane and 2 mL water were added, and the mixture was stirred at 40° C. under argon until no further conversion was observed. The reaction mixture was concentrated under reduced pressure and purified via preparative reversed phase chromatography using 5 mM aqueous NH$_4$HCO$_3$ solution and MeCN as eluents to obtain. ethyl (2S)-2-[5-bromo-6-(2-furyl)thieno[2,3-d]pyrimidin-4-yl]oxy-3-[2-[2-(4-methylpiperazin-1-yl)ethoxy]phenyl]propanoate. MS: (M+H)=615.0.
Step C:
189 mg ethyl (2S)-2-[5-bromo-6-(2-furyl)thieno[2,3-d]pyrimidin-4-yl]oxy-3-[2-[2-(4-methylpiperazin-1-yl)ethoxy]phenyl]propanoate (0.3 mmol) and 146 mg 2-(3-chloro-2-methyl-phenyl)-5,5-dimethyl-1,3,2-dioxaborinane (0.6 mmol) were dissolved in 2.5 mL 1,4-dioxane, then 195 mg Cs$_2$CO$_3$ (0.6 mmol) dissolved in 0.6 mL water was added followed by 21 mg AtaPhos (0.021 mmol), and the mixture was heated under nitrogen at 110° C. in a microwave reactor until no further conversion was observed. Then it was diluted with brine and extracted with dichloromethane. The combined organic phases were dried over Na$_2$SO$_4$, concentrated under reduced pressure, and purified via flash chromatography using dichloromethane and methanol as eluents.
Step D:
The product of Step C was dissolved in 4 mL dioxane-water (1:1) and 126 mg LiOH×H$_2$O (3.0 mmol) was added. The mixture was stirred at room temperature until no further conversion was observed. Then it was diluted with brine, neutralized with 2 M HCl, and extracted with DCM. The combined organic phases were dried over Na$_2$SO$_4$ and concentrated under reduced pressure. The residue was purified via preparative reversed phase chromatography using MeCN and 25 mM aqueous NH$_4$HCO$_3$ solution as eluents. The diastereoisomer eluting later was collected to obtain Example 667. HRMS calculated for C$_{33}$H$_{33}$ClN$_4$O$_5$S: 632.1860. found 633.1959 (M+H).

Example 668 (2R)-2-{[(5S$_a$)-5-{3-chloro-4-[2-(dimethylamino)ethoxy]-2-methylphenyl}-6-(furan-2-yl)thieno[2,3-d]pyrimidin-4-yl]oxy}-3-{2-[(1-methyl-1H-pyrazol-5-yl)methoxy]phenyl}propanoic acid Using General Procedure (XXIIa) with 2-(dimethylamino)ethanol as the appropriate alcohol in Step A and (1-methyl-1H-pyrazol-5-yl)methanol as the appropriate alcohol in Step C, Example 668 was obtained. HRMS calculated for C$_{35}$H$_{34}$ClN$_5$O$_6$S: 687.1918. found 688.1996 (M+H).

Example 669 (2R)-2-{[(5S$_a$)-5-{3-chloro-4-[2-(4-ethylpiperazin-1-yl)ethoxy]-2-methylphenyl}-6-(furan-2-yl)thieno[2,3-d]pyrimidin-4-yl]oxy}-3-[2-(2-methoxyethoxy)phenyl]propanoic acid Using General Procedure (XXIIa) with 2-(4-ethylpiperazin-1-yl)ethanol as the appropriate alcohol in Step A and 2-methoxyethanol as the appropriate alcohol in Step C, Example 669 was obtained. HRMS calculated for C$_{37}$H$_{41}$ClN$_4$O$_7$S: 720.2384. found 721.2455 (M+H).

Example 670 (2R)-2-{[(5S$_a$)-5-{3-chloro-4-[2-(4-ethylpiperazin-1-yl)ethoxy]-2-methylphenyl}-6-(furan-2-yl)thieno[2,3-d]pyrimidin-4-yl]oxy}-3-{2-[(2-methoxypyrimidin-4-yl)methoxy]phenyl}propanoic acid Using General Procedure (XXIIa) with 2-(4-ethylpiperazin-1-yl)ethanol as the appropriate alcohol in Step A and (2-methoxypyrimidin-4-yl)methanol as the appropriate alcohol in Step C, Example 670 was obtained. HRMS calculated for C$_{40}$H$_{41}$ClN$_6$O$_7$S: 784.2446. found 393.1312 (M+2H).

Example 671 (2R)-2-{[(5S$_a$)-5-(3-chloro-2-methyl-4-{2-[4-(propan-2-yl)piperazin-1-yl]ethoxy}phenyl)-6-(furan-2-yl)thieno[2,3-d]pyrimidin-4-yl]oxy}-3-[2-(2-methoxyethoxy)phenyl]propanoic acid Using General Procedure (XXIIa) with 2-(4-isopropylpiperazin-1-yl)ethanol as the appropriate alcohol in Step A and 2-methoxyethanol as the appropriate alcohol in Step C, Example 671 was obtained. HRMS calculated for C$_{38}$H$_{43}$ClN$_4$O$_7$S: 734.2541. found 735.2639 (M+H).

Example 672 (2R)-2-{[(5S$_a$)-5-(3-chloro-2-methyl-4-{2-[4-(propan-2-yl)piperazin-1-yl]ethoxy}phenyl)-6-(furan-2-yl)thieno[2,3-d]pyrimidin-4-yl]oxy}-3-{2-[(2-methoxypyrimidin-4-yl)methoxy]phenyl}propanoic acid Using General Procedure (XXIIa) with 2-(4-isopropylpiperazin-1-yl)ethanol as the appropriate alcohol in Step A and (2-methoxypyrimidin-4-yl)methanol as the appropriate alcohol in Step C, Example 672 was obtained. HRMS calculated for C$_{41}$H$_{43}$ClN$_6$O$_7$S: 798.2602. found 799.2644 (M+H).

Example 673 (2R)-2-[(5S$_a$)-5-[2,3-dimethyl-4-[2-(4-methylpiperazin-1-yl)ethoxy]phenyl]-6-(2-furyl)thieno[2,3-d]pyrimidin-4-yl]oxy-3-[2-(2,2,2-trifluoroethoxy)phenyl]propanoic acid Step A:

574 mg ethyl (2R)-2-[5-bromo-6-(2-furyl)thieno[2,3-d]pyrimidin-4-yl]oxy-3-(2-tetrahydropyran-2-yloxyphenyl)propanoate (Preparation 4d) (1.0 mmol), 562 mg 1-[2-[2,3-dimethyl-4-(4,4,5,5-tetramethyl-1,3,2-dioxaborolan-2-yl)phenoxy]ethyl]-4-methyl-piperazine (Preparation 5s) (1.5 mmol), 71 mg AtaPhos (0.1 mmol) and 652 mg Cs$_2$CO$_3$ (2.0 mmol) were dissolved in a mixture of 5 mL THF and 5 mL water. The reaction was heated under nitrogen at 110° C. in a microwave reactor until no further conversion was observed. Then it was diluted with brine, neutralized with 2 M HCl, and extracted with dichloromethane. The combined organic phases were dried over Na$_2$SO$_4$, concentrated under reduced pressure, and purified via flash chromatography, using ethyl acetate and methanol as eluents.

Step B:

The product of Step A was dissolved in 5 mL ethanol, then 20 mL HCl solution (1.25 M in ethanol) was added and it was stirred at room temperature until no further conversion was observed. Saturated aq. NaHCO$_3$ solution was added carefully and it was extracted with dichloromethane. The combined organic phases were dried over Na$_2$SO$_4$, concentrated under reduced pressure, and purified via flash chromatography using ethyl acetate and methanol as eluents to obtain ethyl (2R)-2-[5-[3-chloro-2-methyl-4-[2-(4-methyl-piperazin-1-yl)ethoxy]phenyl]-6-(2-furyl)thieno[2,3-d]pyrimidin-4-yl]oxy-3-(2-hydroxyphenyl)propanoate as mixture of diastereoisomers. MS: (M+H)=641.4.

Step C:

The product of Step B was dissolved in 5 mL DMF, 276 mg K$_2$CO$_3$ (2.00 mmol) and 232 mg 2,2,2-trifluoroethyl trifluoromethanesulfonate (1.00 mmol) were added and the mixture was stirred at room temperature until no further conversion was observed. It was diluted with brine and extracted with DCM. The combined organic phases were dried over Na$_2$SO$_4$, concentrated under reduced pressure, and purified via flash chromatography using ethyl acetate and methanol as eluents.

Step D:

The product of Step C was dissolved in 12 mL dioxane-water (1:1) and 300 mg LiOH×H$_2$O (7.14 mmol) was added. The mixture was stirred at room temperature until no further conversion was observed. Then it was diluted with brine, neutralized with 2 M HCl, and extracted with DCM. The combined organic phases were dried over Na$_2$SO$_4$ and concentrated under reduced pressure. The residue was purified via preparative reversed phase chromatography using MeCN and 25 mM aqueous NH$_4$HCO$_3$ solution as eluents. The diastereoisomer eluting later was collected as Example 673. HRMS calculated for C$_{36}$H$_{37}$F$_3$N$_4$O$_6$S: 710.2386. found 711.2442 (M+H).

Example 674 (2R)-2-{[(5S$_a$)-5-(3-chloro-4-hydroxy-2-methylphenyl)-6-(furan-2-yl)thieno[2,3-d]pyrimidin-4-yl]oxy}-3-[2-(pyridin-2-ylmethoxy)phenyl]propanoic acid Step A:

488 mg 5-bromo-4-chloro-6-(2-furyl)thieno[2,3-d]pyrimidine (Preparation 2c) (1.3 mmol), 471 mg ethyl (2R)-2-hydroxy-3-[2-(2-pyridylmethoxy)phenyl]propanoate (Preparation 3bn) (1.56 mmol) and 1.27 g Cs$_2$CO$_3$ (3.9 mmol) were placed in a flask. 20 mL tert-butanol was added and the mixture was stirred at 70° C. until no further conversion was observed. The solvent was evaporated under reduced pressure, the residue was diluted with water, the pH was set to 8 with 2 M HCl, and then it was extracted with DCM. The combined organic layers were dried over Na$_2$SO$_4$, concentrated under reduced pressure, and purified via flash chromatography using heptane and ethyl acetate as eluents.

Step B:

The product of Step A and 83.27 mg 2-chloro-3-methyl-4-(4,4,5,5-tetramethyl-1,3,2-dioxaborolan-2-yl)phenol (Preparation 5a) (0.31 mmol) were dissolved in 2 mL THF, then 252 mg Cs$_2$CO$_3$ (0.78 mmol) dissolved in 2 mL water was added followed by 18 mg AtaPhos (0.03 mmol), and the mixture was heated under nitrogen at 100° C. in a microwave reactor until no further conversion was observed. It was diluted with ethyl acetate and brine, the organic layer was dried over Na$_2$SO$_4$ and concentrated under reduced pressure. The residue was purified via flash chromatography using heptane and ethyl acetate as eluents. MS: (M+H)=641.4.

Step C:

The product of Step B was dissolved in 4 mL dioxane-water (1:1) and 59 mg LiOH×H$_2$O (1.4 mmol) was added. The mixture was stirred at room temperature until no further conversion was observed. Then it was diluted with brine, neutralized with 2 M HCl, and extracted with DCM. The combined organic phases were dried over Na$_2$SO$_4$ and concentrated under reduced pressure. The residue was purified via preparative reversed phase chromatography using MeCN and 25 mM aqueous NH$_4$HCO$_3$ solution as eluents. The diastereoisomer eluting later was collected as Example 674. HRMS calculated for C$_{32}$H$_{24}$ClN$_3$O$_6$S: 613.1074. found 614.1152 (M+H).

General Procedure (XXIIIa)

To 1 eq. of the appropriate ester in MeOH (24 mL/mmol) 28 eq. LiOH×H$_2$O (5.96 mmol) was added and the mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and purified via preparative reversed phase chromatography using 0.1% aqueous TFA solution and MeCN as eluents

Example 675 (2R)-3-(1,3-benzodioxol-4-yl)-2-{[(5S$_a$)-5-(3-chloro-4-hydroxy-2-methylphenyl)-6-ethylthieno[2,3-d]pyrimidin-4-yl]oxy}propanoic acid Ethyl (2R)-3-(1,3-benzodioxol-4-yl)-2-[(5S$_a$)-5-(3-chloro-4-hydroxy-2-methyl-phenyl)-6-ethyl-thieno[2,3-d]pyrimidin-4-yl]oxy-propanoate (Preparation 17b) in General Procedure (XXIIIa) gave Example 675. HRMS calculated for C$_{25}$H$_{21}$ClN$_2$O$_6$S: 512.0809. found 513.0869 (M+H).

Example 676 (2S)-3-(1,3-benzodioxol-4-yl)-2-{[(5S$_a$)-5-(3-chloro-4-hydroxy-2-methylphenyl)-6-ethylthieno[2,3-d]pyrimidin-4-yl]oxy}propanoic acid Ethyl (2S)-3-(1,3-benzodioxol-4-yl)-2-[(5S$_a$)-5-(3-chloro-4-hydroxy-2-methyl-phenyl)-6-ethyl-thieno[2,3-d]pyrimidin-4-yl]oxy-propanoate (Preparation 17i) in General Procedure (XXIIIa) gave Example 676. HRMS calculated for $C_{25}H_{21}ClN_2O_6S$: 512.0809. found 513.0877 (M+H).

Example 677 (2S)-3-(1,3-benzodioxol-4-yl)-2-{[(5R$_a$)-5-(3-chloro-4-hydroxy-2-methylphenyl)-6-ethylthieno[2,3-d]pyrimidin-4-yl]oxy}propanoic acid Ethyl (2S)-3-(1,3-benzodioxol-4-yl)-2-[(5R$_a$)-5-(3-chloro-4-hydroxy-2-methyl-phenyl)-6-ethyl-thieno[2,3-d]pyrimidin-4-yl]oxy-propanoate (Preparation 17j) in General Procedure (XXIIIa) gave Example 677. HRMS calculated for $C_{25}H_{21}ClN_2O_6S$: 512.0809. found 513.089 (M+H).

Example 678 (2R)-3-(1,3-benzodioxol-4-yl)-2-{[(5R$_a$)-5-(3-chloro-4-hydroxy-2-methylphenyl)-6-ethylthieno[2,3-d]pyrimidin-4-yl]oxy}propanoic acid Ethyl (2R)-3-(1,3-benzodioxol-4-yl)-2-[(5R$_a$)-5-(3-chloro-4-hydroxy-2-methyl-phenyl)-6-ethyl-thieno[2,3-d]pyrimidin-4-yl]oxy-propanoate (Preparation 17a) in General Procedure (XXIIIa) gave Example 678. HRMS calculated for $C_{25}H_{21}ClN_2O_6S$: 512.0809. found 513.0868 (M+H).

Example 679 (2S)-2-{[(5R$_a$)-5-(3-chloro-4-hydroxy-2-methylphenyl)-6-ethylthieno[2,3-d]pyrimidin-4-yl]oxy}-3-(2-methoxyphenyl)propanoic acid and Example 680 (2S)-2-{[(5S$_a$)-5-(3-chloro-4-hydroxy-2-methylphenyl)-6-ethylthieno[2,3-d] pyrimidin-4-yl]oxy}-3-(2-methoxyphenyl)propanoic acid Step A:
0.61 g ethyl (2S)-2-(6-ethyl-5-iodo-thieno[2,3-d]pyrimidin-4-yl)oxy-3-(2-methoxyphenyl)propanoate (Preparation 4r) (1.19 mmol), 0.480 g 2-chloro-3-methyl-4-(4,4,5,5-tetramethyl-1,3,2-dioxaborolan-2-yl)phenol (Preparation 5a) (1.79 mmol), 0.218 g Pd$_2$(dba)$_3$ (0.24 mmol), 0.171 g "BuPAd$_2$ (0.48 mmol), 1.79 mL Bu$_4$NOH solution (1.79 mmol, 1 M in water) and 7 mL 2-Me-THF were heated with stirring at 110° C. under argon for 10 mins in a microwave reactor. The pH of the mixture was set to 6 with 2 M HCl, and then it was extracted with MTBE. The combined organic phases were dried over Na$_2$SO$_4$, concentrated under reduced pressure, and purified via flash chromatography using heptane and EtOAc as eluents, yielding ethyl (2S)-2-[5-(3-chloro-4-hydroxy-2-methyl-phenyl)-6-ethyl-thieno[2,3-d]pyrimidin-4-yl]oxy-3-(2-methoxyphenyl)propanoate as a mixture of diastereomers. MS: (M+H)$^+$=527.2.
Step B:
To 0.529 g of the product of Step A (1.0 mmol) dissolved in 6 mL THF-water (1:1) 0.250 g LiOH×H$_2$O (5.96 mmol) was added and the mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and purified via preparative reverse phase chromatography using 0.1% aqueous TFA solution and MeCN as eluents to obtain Example 680 as the product eluting earlier [HRMS calculated for $C_{25}H_{23}ClN_2O_5S$: 498.1016. found 499.1079 (M+H)], and Example 679 as the product eluting later [HRMS calculated for $C_{25}H_{23}ClN_2O_5S$: 498.1016. found 499.1097 (M+H)].

Example 681 (2R)-2-{[(5S$_a$)-5-(3-chloro-4-hydroxy-2-methylphenyl)-6-ethylthieno[2,3-d]pyrimidin-4-yl]oxy}-3-(2-methoxyphenyl)propanoic acid and Example 682 (2R)-2-{[(5R$_a$)-5-(3-chloro-4-hydroxy-2-methylphenyl)-6-ethylthieno[2,3-d]pyrimidin-4-yl]oxy}-3-(2-methoxyphenyl)propanoic acid Step A:
0.50 g ethyl (2R)-2-(6-ethyl-5-iodo-thieno[2,3-d]pyrimidin-4-yl)oxy-3-(2-methoxyphenyl)propanoate (Preparation 4q) (0.98 mmol), 0.393 g 2-chloro-3-methyl-4-(4,4,5,5-tetramethyl-1,3,2-dioxaborolan-2-yl)phenol (Preparation 5a) (1.46 mmol), 0.179 g Pd$_2$(dba)$_3$ (0.2 mmol), 0.140 g "BuPAd$_2$ (0.39 mmol), 1.46 mL Bu$_4$NOH solution (1.46 mmol, 1 M in water) and 5 mL 2-Me-THF were heated under nitrogen with stirring at 110° C. for 10 mins in a microwave reactor. The pH of the mixture was set to 6 with 2 M HCl, and then it was extracted with MTBE. The combined organic phases were dried over Na$_2$SO$_4$, concentrated under reduced pressure and purified via flash chromatography using heptane and EtOAc as eluents to yield ethyl (2R)-2-[5-(3-chloro-4-hydroxy-2-methyl-phenyl)-6-ethyl-thieno[2,3-d]pyrimidin-4-yl]oxy-3-(2-methoxyphenyl)propanoate as a mixture of diastereomers. MS: (M+H)$^+$=527.2.
Step B:
To 0.454 g of the product of Step A (0.86 mmol) dissolved in 6 mL THF-water (1:1) 0.250 g LiOH×H$_2$O (5.96 mmol) was added and the mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure, and purified via preparative reverse phase chromatography using 0.1% aqueous TFA solution and MeCN as eluents to obtain Example 682 as the product eluting earlier [HRMS calculated for $C_{25}H_{23}ClN_2O_5S$: 498.1016. found 499.1091 (M+H)$^+$], and Example 681 as the product eluting later [HRMS calculated for $C_{25}H_{23}ClN_2O_5S$: 498.1016. found 499.1074 (M+H)$^+$].

Example 683 (2S)-2-[(5R$_a$)-(5-{3-chloro-2-methyl-4-[2-(4-methylpiperazin-1-yl)ethoxy]phenyl}-6-ethylthieno[2,3-d]pyrimidin-4-yl)oxy]-3-(2-methoxyphenyl)propanoic acid Step A:
0.2 g (2S)-2-{[(5R$_a$)-5-(3-chloro-4-hydroxy-2-methylphenyl)-6-ethylthieno[2,3-d] pyrimidin-4-yl]oxy}-3-(2-methoxyphenyl)propanoic acid (Example 679) (0.4 mmol) was dissolved in 2 mL dry methanol and 20 μL concentrated sulfuric acid was added and it was stirred at room temperature until no further conversion was observed. Then the mixture was concentrated, the residue was dissolved in EtOAc and it was washed with saturated aq. NaHCO$_3$ solution. The organic layer was dried over Na$_2$SO$_4$ and concentrated under reduced pressure to give methyl (2S)-2-{[(5R$_a$)-5-(3-chloro-4-hydroxy-2-methylphenyl)-6-ethylthieno[2,3-d]pyrimidin-4-yl]oxy}-3-(2-methoxyphenyl)propanoate, which was used without further purification.
Step B:
The mixture of 0.232 g of the product of Step A (0.45 mmol), 0.13 g 2-(4-methylpiperazin-1-yl)ethanol (0.9 mmol), 0.208 g ditertbutyl azodicarboxylate (0.9 mmol) and 0.301 g resin bound triphenylphosphine (3 mmol/g, 0.9 mmol) was stirred in 3 mL dry toluene at 50° C. until no further conversion was observed. Then the mixture was filtered through a pad of Celite, the pad was washed with EtOAc and the filtrate was concentrated under reduced pressure. The residue was dissolved in 4 mL methanol and 0.108 g LiOH×H$_2$O (2.57 mmol) was added and the mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and purified via preparative reverse phase chromatography using 40 mM aqueous NH$_4$OAc solution (pH set to 4 with AcOH) and MeCN as eluents to obtain Example 683. HRMS calculated for C$_{32}$H$_{37}$ClN$_4$O$_5$S: 624.2173. found 625.2253 (M+H)$^+$.

General Procedure (XXIVa)

Step A:

1 eq. phenol derivative, 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the residue was purified via flash chromatography using EtOAc and MeOH as eluents.

Step B:

The obtained intermediate was dissolved in dioxane-water (1:1, 10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure, and purified via preparative reversed phase chromatography using 25 mM aqueous NH$_4$HCO$_3$ solution and MeCN as eluents.

Example 684 (2R)-2-{[(5S$_a$)-5-{3-chloro-2-methyl-4-[2-(piperazin-1-yl)ethoxy]phenyl}-6-(prop-1-yn-1-yl)thieno[2,3-d]pyrimidin-4-yl]oxy}-3-(2-methoxyphenyl)propanoic acid Using General Procedure (XXIVa), ethyl (2R)-2-[(5S$_a$)-5-(3-chloro-4-hydroxy-2-methyl-phenyl)-6-prop-1-ynyl-thieno[2,3-d]pyrimidin-4-yl]oxy-3-(2-methoxyphenyl)propanoate (Preparation 6l) as the phenol and 2-piperazin-1-ylethanol as the appropriate alcohol, Example 684 was obtained. HRMS calculated for C$_{32}$H$_{33}$ClN$_4$O$_5$S: 620.1860. found 621.1944 (M+H).

Example 685 (2R)-2-{[(5S$_a$)-5-{3-chloro-2-methyl-4-[2-(morpholin-4-yl)ethoxy]phenyl}-6-(prop-1-yn-1-yl)thieno[2,3-d]pyrimidin-4-yl]oxy}-3-(2-methoxyphenyl)propanoic acid Using General Procedure (XXIVa), ethyl (2R)-2-[(5S$_a$)-5-(3-chloro-4-hydroxy-2-methyl-phenyl)-6-prop-1-ynyl-thieno[2,3-d]pyrimidin-4-yl]oxy-3-(2-methoxyphenyl)propanoate (Preparation 6l) as the phenol and 2-(morpholin-4-yl)ethanol as the appropriate alcohol, Example 685 was obtained. HRMS calculated for C$_{32}$H$_{32}$ClN$_3$O$_6$S: 621.1700. found 622.1776 (M+H).

Example 686 (2R)-2-{[(5R$_a$)-5-{3-fluoro-2-methyl-4-[2-(4-methylpiperazin-1-yl)ethoxy]phenyl}-6-(prop-1-yn-1-yl)thieno[2,3-d]pyrimidin-4-yl]oxy}-3-(2-methoxyphenyl)propanoic acid and Example 687 (2R)-2-{[(5S$_a$)-5-{3-fluoro-2-methyl-4-[2-(4-methylpiperazin-1-yl)ethoxy]phenyl}-6-(prop-1-yn-1-yl)thieno[2,3-d]pyrimidin-4-yl]oxy}-3-(2-methoxyphenyl)propanoic acid Step A:

522 mg ethyl (2R)-2-(5-iodo-6-prop-1-ynyl-thieno[2,3-d]pyrimidin-4-yl)oxy-3-(2-methoxyphenyl)propanoate (Preparation 4k) (1.00 mmol), 378 mg 2-fluoro-3-methyl-4-(4,4,5,5-tetramethyl-1,3,2-dioxaborolan-2-yl)phenol (Preparation 5g) (1.50 mmol), 73 mg PdCl$_2$×dppf (0.10 mmol) and 489 mg Cs$_2$CO$_3$ (1.50 mmol) were dissolved in 8 mL dioxane and 2 mL water. The mixture was heated under nitrogen at 110° C. for 10 minutes in a microwave reactor. The reaction was diluted with brine, neutralized with 2 M HCl, and extracted with DCM. The combined organic phases were dried over Na$_2$SO$_4$, concentrated under reduced pressure and purified via flash chromatography, using heptane and EtOAc as eluents to give a mixture of diastereoisomers.

Step B:

Using General Procedure (XXIVa) with the product of Step A as the phenol and 2-(4-methylpiperazin-1-yl)ethanol as the appropriate alcohol Example 686 and Example 687 were obtained. The diastereoisomer eluting earlier was collected as Example 686. HRMS calculated for C$_{33}$H$_{35}$FN$_4$O$_5$S: 618.2312. found 619.2398 (M+H). The diastereoisomer eluting later was collected as Example 687. HRMS calculated for C$_{33}$H$_{35}$FN$_4$O$_5$S: 618.2312. found 619.2396 (M+H).

Example 688 (2R)-2-{[(5R$_a$)-5-{3-chloro-2-methyl-4-[2-(morpholin-4-yl)ethoxy]phenyl}-6-(5-fluoro-furan-2-yl)thieno[2,3-d]pyrimidin-4-yl]oxy}-3-[2-(2,2,2-trifluoroethoxy)phenyl] propanoic acid Step A:

667 mg of ethyl (2R)-2-[(5R$_a$)-5-(3-chloro-4-hydroxy-2-methyl-phenyl)-6-(5-fluoro-2-furyl)thieno[2,3-d]pyrimidin-4-yl]oxy-3-(2-tetrahydropyran-2-yloxyphenyl)propanoate (Preparation 6q) (1.00 mmol), 262 mg 2-(morpholin-4-yl) ethanol (2.00 mmol), and 525 mg PPh$_3$ (2.00 mmol) were dissolved in 5 mL dry toluene, then 461 mg ditertbutyl azodicarboxylate (2.00 mmol) was added. The mixture was stirred at 50° C. under nitrogen until no further conversion was observed. The volatiles were evaporated under reduced pressure and the residue was purified via flash chromatography using EtOAc and methanol as eluents to give ethyl (2R)-2-[(5R$_a$)-5-[3-chloro-2-methyl-4-(2-morpholinoethoxy)phenyl]-6-(5-fluoro-2-furyl)thieno[2,3-d]pyrimidin-4-yl]oxy-3-(2-tetrahydropyran-2-yloxyphenyl)propanoate.

Step B:

The product of Step A was dissolved in 35 mL HCl (1.25 M in EtOH) and the mixture was stirred at 60° C. for 2 h. Saturated aq. NaHCO$_3$ solution was added to the reaction mixture, and it was extracted with DCM. The combined organic phases were dried over Na$_2$SO$_4$, concentrated under reduced pressure and purified via flash chromatography using DCM and methanol as eluents to give ethyl (2R)-2-[(5R$_a$)-5-[3-chloro-2-methyl-4-(2-(morpholin-4-yl)ethoxy)

phenyl]-6-(5-fluoro-2-furyl)thieno[2,3-d]pyrimidin-4-yl]oxy-3-(2-hydroxyphenyl)propanoate.

Step C:

The product of Step B (232 mg, 0.34 mmol) was dissolved in 2 ml DMF, 138 mg $K_2CO_3$ (1.0 mmol) and 77 mg 2,2,2-trifluoroethyl trifluoromethanesulfonate (1.0 mmol) were added. The mixture was stirred at room temperature under nitrogen for 7 hours. Then it was diluted with brine, neutralized with 2 M HCl, and extracted with DCM. The combined organic phases were dried over $Na_2SO_4$ and concentrated under reduced pressure. The obtained ester was dissolved in 5 mL dioxane-water (1:1) and 142 mg LiOH×$H_2O$ (3.40 mmol) was added. The mixture was stirred at room temperature for 1 hour, then it was diluted with brine, neutralized with 2 M HCl, and extracted with DCM. The combined organic phases were dried over $Na_2SO_4$, concentrated under reduced pressure and purified via preparative reversed phase chromatography using 5 mM aqueous $NH_4HCO_3$ solution and MeCN as eluents to give Example 688. HRMS calculated for $C_{34}H_{30}ClF_4N_3O_7S$: 735.1429. found 736.1469 (M+H).

Example 689 (2R)-2-{[(5$S_a$)-5-{3-chloro-2-methyl-4-[2-(morpholin-4-yl)ethoxy]phenyl}-6-(5-fluoro-furan-2-yl)thieno[2,3-d]pyrimidin-4-yl]oxy}-3-[2-(2,2,2-trifluoroethoxy)phenyl]propanoic acid Starting from ethyl (2R)-2-[(5$S_a$)-5-(3-chloro-4-hydroxy-2-methyl-phenyl)-6-(5-fluoro-2-furyl)thieno[2,3-d]pyrimidin-4-yl]oxy-3-(2-tetrahydropyran-2-yloxyphenyl)propanoate (Preparation 6c) and using the same steps as described for Example 688 gave Example 689. HRMS calculated for $C_{34}H_{30}ClF_4N_3O_7S$: 735.1429. found 736.1501 (M+H).

Example 690 (2R)-2-{[(5$S_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[4-fluoro-2-(methoxymethoxy)phenyl]propanoic acid Step A:

2.816 g 4-Chloro-5-[3-chloro-2-methyl-4-[2-(4-methylpiperazin-1-yl)ethoxy]phenyl]-6-iodo-thieno[2,3-d]pyrimidine (Preparation 13) (5.00 mmol), 1.634 g ethyl (2R)-3-[4-fluoro-2-(methoxymethoxy)phenyl]-2-hydroxy-propanoate (Preparation 3bf) (6.00 mmol) and 4.88 g $Cs_2CO_3$ (15.0 mmol) were placed in a 50 mL flask. 15 mL tert-butanol was added and the mixture was stirred at 35° C. under $N_2$ for 16 hours. The reaction mixture was diluted with water, the pH was set to 7 with 2 M HCl, and it was extracted with DCM. The combined organic phases were dried over $Na_2SO_4$, concentrated under reduced pressure and purified via flash chromatography using EtOAc and methanol as eluents to obtain ethyl (2R)-2-[5-[3-chloro-2-methyl-4-[2-(4-methylpiperazin-1-yl)ethoxy]phenyl]-6-iodo-thieno[2,3-d]pyrimidin-4-yl]oxy-3-[4-fluoro-2-(methoxymethoxy)phenyl]propanoate as a mixture of diastereoisomers.

Step B:

1.075 g of the product of Step A (1.35 mmol), 0.856 g 2-(5-fluoro-2-furyl)-4,4,5,5-tetramethyl-1,3,2-dioxaborolane (4.04 mmol), 0.880 g cesium carbonate (2.70 mmol), and 99 mg [1,1'-bis(diphenylphoshino)ferrocene]dichloropalladium(II) (0.135 mmol) were dissolved in 12 mL dioxane and 3 mL water, and the mixture was heated under argon at 110° C. for 15 min in a microwave reactor. The reaction mixture was diluted with EtOAc and washed with brine. The organic layer was dried over $Na_2SO_4$ and concentrated. The residue was purified via flash chromatography using EtOAc and methanol as eluents to obtain ethyl (2R)-2-[5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-[4-fluoro-2-(methoxymethoxy)phenyl] propanoate. HRMS calculated for $C_{37}H_{39}ClF_2N_4O_7S$: 756.2196044. found 757.2255 (M+H).

Step C:

To the solution of 350 mg of the product of Step A (0.462 mmol) in 10 ml methanol 200 mg LiOH×$H_2O$ (4.77 mmol) was added. The mixture was stirred at room temperature until no further conversion was observed. Then it was diluted with brine, neutralized with 2 M HCl, and extracted with EtOAc. The combined organic phases were dried over $Na_2SO_4$, concentrated under reduced pressure. The residue was purified via preparative reversed phase chromatography using 25 mM aqueous $NH_4HCO_3$ solution and MeCN as eluents. The diastereomer eluting later was collected as Example 690. HRMS calculated for $C_{35}H_{35}ClF_2N_4O_7S$: 728.1883. found 729.1955 (M+H).

Example 691 (2R)-2-{[(5$S_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-[4-fluoro-2-(pyrazin-2-ylmethoxy)phenyl] propanoic acid Step A:

35 mL HCl (1.25 M in EtOH) was added to 396 mg ethyl (2R)-2-[5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-[4-fluoro-2-(methoxymethoxy)phenyl]propanoate (0.522 mmol, product of Step B of Example 690) and the mixture was stirred at room temperature for 48 h. Saturated aq. $NaHCO_3$ solution was added to the reaction mixture, and it was extracted with EtOAc. The combined organic layers were dried over $Na_2SO_4$ and concentrated. The residue was purified via flash chromatography using DCM and methanol as eluents to give ethyl (2R)-2-[5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-(4-fluoro-2-hydroxyphenyl)propanoate. HRMS calculated for $C_{35}H_{35}ClF_2N_4O_6S$: 712.1933897. found 713.2005 (M+H).

Step B:

200 mg of the product of Step A (0.281 mmol), 61.8 mg pyrazin-2-ylmethanol (0.562 mmol) and 147 mg $PPh_3$ (0.562 mmol) were dissolved in 2 mL dry toluene, then 129 mg ditertbutyl azodicarboxylate (0.562 mmol) was added. The mixture was stirred at 50° C. under nitrogen until no further conversion was observed. The volatiles were evaporated under reduced pressure and the crude intermediate was purified via flash chromatography using EtOAc and MeOH as eluents.

Step C:

The product of Step B was dissolved in 4 mL dioxane-water (1:1) and 109 mg LiOH×$H_2O$ (2.60 mmol) was added. The mixture was stirred at room temperature until no further conversion was observed. Then it was diluted with brine, neutralized with 2 M HCl, and extracted with EtOAc. The combined organic phases were dried over $Na_2SO_4$ and concentrated under reduced pressure. The residue was purified via preparative reversed phase chromatography using 25 mM aqueous $NH_4HCO_3$ solution and MeCN as eluents. The diastereomer eluting later was collected as Example 691. HRMS calculated for $C_{38}H_{35}ClF_2N_6O_6S$: 776.1995. found 777.209 (M+H).

Example 692 (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(4-fluoro-2-methoxyphenyl)propanoic acid Step A:
200 mg ethyl (2R)-2-[5-[3-chloro-2-methyl-4-[2-(4-methylpiperazin-1-yl)ethoxy]phenyl]-6-(5-fluoro-2-furyl)thieno[2,3-d]pyrimidin-4-yl]oxy-3-(4-fluoro-2-hydroxyphenyl)propanoate (Step A of Example 691, 0.281 mmol), 22.7 µl methanol (0.562 mmol) and 147 mg PPh$_3$ (0.562 mmol) were dissolved in 2 mL dry toluene, then 129 mg ditertbutyl azodicarboxylate (0.562 mmol) was added. The mixture was stirred at 50° C. under nitrogen until no further conversion was observed. The volatiles were evaporated under reduced pressure and the crude intermediate was purified via flash chromatography using EtOAc and MeOH as eluents.
Step B:
The product of Step A was dissolved in 4 mL dioxane-water (1:1) and 109 mg LiOH×H$_2$O (2.60 mmol) was added. The mixture was stirred at room temperature until no further conversion was observed. Then it was diluted with brine, neutralized with 2 M HCl, and extracted with EtOAc. The combined organic phases were dried over Na$_2$SO$_4$ and concentrated under reduced pressure. The residue was purified via preparative reversed phase chromatography using 25 mM aqueous NH$_4$HCO$_3$ solution and MeCN as eluents. The diastereomer eluting later was collected as Example 692. HRMS calculated for $C_{34}H_{33}ClF_2N_4O_6S$: 698.1777. found 699.1846 (M+H).

Example 693 (2R)-2-{[(5S$_a$)-5-{3-chloro-2-methyl-4-[2-(4-methylpiperazin-1-yl)ethoxy]phenyl}-6-(6-fluoropyridin-3-yl)thieno[2,3-d]pyrimidin-4-yl]oxy}-3-(2-{[1-(2,2,2-trifluoroethyl)-1H-pyrazol-5-yl]methoxy}phenyl)propanoic acid Step A:
2.88 g ethyl (2R)-2-[5-[3-chloro-2-methyl-4-[2-(4-methylpiperazin-1-yl)ethoxy]phenyl]-6-iodo-thieno[2,3-d]pyrimidin-4-yl]oxy-3-(2-hydroxyphenyl)propanoate (Preparation 26b) (4 mmol), 1.80 g [1-(2,2,2-trifluoroethyl)-1H-pyrazol-5-yl]methanol (Preparation 9du) (10 mmol) and 2.62 g PPh$_3$ were dissolved in dry toluene (0.2 M for Preparation 26b), then 2.30 g ditertbutyl azodicarboxylate was added. The mixture was stirred at 50° C. under argon atmosphere. After reaching appropriate conversion the volatiles were evaporated under reduced pressure and the crude ester was purified via flash chromatography using EtOAc and MeOH as eluents to obtain ethyl (2R)-2-[5-[3-chloro-2-methyl-4-[2-(4-methylpiperazin-1-yl)ethoxy]phenyl]-6-iodo-thieno[2,3-d]pyrimidin-4-yl]oxy-3-[2-[[1-(2,2,2-trifluoroethyl)-1H-pyrazol-5-yl]methoxy]phenyl]propanoate.
Step B:
1.35 g of the product of Step A (1.5 mmol), 254 mg (6-fluoro-3-pyridyl)boronic acid (1.8 mmol), 110 mg Pd(dppf)Cl$_2$ (0.15 mmol) and 1.59 g cesium carbonate (4.5 mmol) were dissolved in 10 mL THF-water (1:1). The mixture was heated under nitrogen at 100° C. in a microwave reactor until no further conversion was observed. Then it was diluted with brine and extracted with DCM. The combined organic phases were dried over Na$_2$SO$_4$, filtered and concentrated under reduced pressure. The crude product was purified via flash chromatography using EtOAc and MeOH as eluents to obtain ethyl (2R)-2-[5-[3-chloro-2-methyl-4-[2-(4-methylpiperazin-1-yl)ethoxy]phenyl]-6-(6-fluoro-3-pyridyl)thieno[2,3-d] pyrimidin-4-yl]oxy-3-[2-[[2-(2,2,2-trifluoroethyl)pyrazol-3-yl]methoxy]phenyl] propanoate.
Step C:
250 mg of the product of Step B (0.29 mmol) was dissolved in 3 mL dioxane-water (1:1, 10 mL/mmol) and 122 mg LiOH×H$_2$O (2.9 mmol, 10 eq.) was added. The mixture was stirred at room temperature until no further conversion was observed. Then it was diluted with brine, neutralized with 2 M HCl, and extracted with DCM. The combined organic phases were dried over Na$_2$SO$_4$ and concentrated. The residue was purified via preparative reversed phase chromatography using 25 mM aqueous NH$_4$HCO$_3$ solution and MeCN as eluents. The diastereoisomer eluting later was collected as Example 693. HRMS calculated for $C_{40}H_{38}ClF_4N_7O_5S$: 839.2280. found 840.2366 (M+H).

Example 694 (2R)-2-[((5S$_a$)-5-{3-chloro-2-methyl-4-[2-(4-methylpiperazin-1-yl)ethoxy]phenyl}-6-[6-(2-methoxyethoxy)pyridin-3-yl]thieno[2,3-d]pyrimidin-4-yl)oxy]-3-(2-{[1-(2,2,2-trifluoroethyl)-1H-pyrazol-5-yl]methoxy}phenyl)propanoic acid Step A:
416 mg ethyl (2R)-2-[5-[3-chloro-2-methyl-4-[2-(4-methylpiperazin-1-yl)ethoxy]phenyl]-6-(6-fluoro-3-pyridyl)thieno[2,3-d]pyrimidin-4-yl]oxy-3-[2-[[1-(2,2,2-trifluoroethyl)-1H-pyrazol-5-yl]methoxy]phenyl]propanoate (product of Step B of Example 693) (0.48 mmol), 112 µL 2-methoxyethanol (1.44 mmol) and 464 mg cesium carbonate (1.44 mmol) were stirred at 70° C. in 5 mL dry tert-butanol until no further conversion was observed. Brine was added and the mixture was extracted with DCM. The combined organic phases were washed with brine, then dried over MgSO$_4$ and concentrated under reduced pressure. The residue was purified via flash chromatography using EtOAc and MeOH as eluents to obtain ethyl (2R)-2-[5-[3-chloro-2-methyl-4-[2-(4-methylpiperazin-1-yl)ethoxy]phenyl]-6-[6-(2-methoxyethoxy)-3-pyridyl]thieno[2,3-d]pyrimidin-4-yl]oxy-3-[2-[[1-(2,2,2-trifluoroethyl)-1H-pyrazol-5-yl]methoxy]phenyl]propanoate.
Step B:
The product of Step A was hydrolyzed according to Step C of Example 693; the diastereoisomer eluting later was collected as Example 694. HRMS calculated for $C_{43}H_{45}ClF_3N_7O_7S$: 895.2742. found 896.2801 (M+H).

Example 695 (2R)-2-[((5S$_a$)-5-{3-chloro-2-methyl-4-[2-(4-methylpiperazin-1-yl)ethoxy]phenyl}-6-[6-(2,2,2-trifluoroethoxy)pyridin-3-yl]thieno[2,3-d]pyrimidin-4-yl)oxy]-3-(2-{[1-(2,2,2-trifluoroethyl)-1H-pyrazol-5-yl]methoxy}phenyl)propanoic acid Step A:
434 mg ethyl (2R)-2-[5-[3-chloro-2-methyl-4-[2-(4-methylpiperazin-1-yl)ethoxy]phenyl]-6-(6-fluoro-3-pyridyl)thieno[2,3-d]pyrimidin-4-yl]oxy-3-[2-[[1-(2,2,2-trifluoroethyl)-1H-pyrazol-5-yl]methoxy]phenyl]propanoate (product of Step B of Example 693) (0.50 mmol), 510 µL 2,2,2-trifluoroethanol (7.0 mmol) and 489 mg cesium carbonate (1.5 mmol) were stirred at 70° C. in 5 mL dry $^t$BuOH until no further conversion was observed. Brine was added and the mixture was extracted with DCM. The organic phase was washed with brine, then dried over MgSO$_4$ and concentrated under reduced pressure. The residue was purified via flash chromatography using EtOAc and MeOH as eluents to obtain ethyl (2R)-2-[5-[3-chloro-2-methyl-4-[2-(4-methylpiperazin-1-yl)ethoxy]phenyl]-6-[6-(2,2,2-trifluoroethoxy)-3-pyridyl]thieno[2,3-d]pyrimidin-4-yl]oxy-3-[2-[[1-(2,2,2-trifluoroethyl)-1H-pyrazol-5-yl]methoxy]phenyl]propanoate.

Step B:

The product of Step A was hydrolyzed according to Step C of Example 693; the diastereoisomer eluting later was collected as Example 695. HRMS calculated for C$_{42}$H$_{40}$ClF$_6$N$_7$O$_6$S: 919.2353. found 920.2414 (M+H).

Example 696 (2R)-2-{[(5S$_a$)-5-{3-chloro-2-methyl-4-[2-(4-methylpiperazin-1-yl)ethoxy]phenyl}-6-(6-methoxypyridin-3-yl)thieno[2,3-d]pyrimidin-4-yl]oxy}-3-(2-{[1-(2,2,2-trifluoroethyl)-1H-pyrazol-5-yl]methoxy}phenyl)propanoic acid Step A:

450 mg (2R)-2-[5-[3-chloro-2-methyl-4-[2-(4-methylpiperazin-1-yl)ethoxy]phenyl]-6-iodo-thieno[2,3-d]pyrimidin-4-yl]oxy-3-[2-[[1-(2,2,2-trifluoroethyl)-1H-pyrazol-5-yl]methoxy]phenyl]propanoate (product of Step A of Example 693) (0.5 mmol), 92 mg (6-methoxy-3-pyridyl)boronic acid (0.6 mmol), 37 mg Pd(dppf)Cl$_2$ (0.05 mmol) and 530 mg cesium carbonate (1.5 mmol) were dissolved in 5 mL THF-water (1:1) and the mixture was heated under nitrogen at 100° C. in a microwave reactor until no further conversion was observed. Then it was diluted with brine and extracted with DCM. The combined organic phases were dried over Na$_2$SO$_4$ and concentrated under reduced pressure. The crude product was purified via flash chromatography using EtOAc and MeOH as eluents to obtain ethyl (2R)-2-[5-[3-chloro-2-methyl-4-[2-(4-methylpiperazin-1-yl)ethoxy]phenyl]-6-(6-methoxy-3-pyridyl)thieno[2,3-d]pyrimidin-4-yl]oxy-3-[2-[[1-(2,2,2-trifluoroethyl)-1H-pyrazol-5-yl]methoxy]phenyl]propanoate Step B:

The product of Step A was hydrolyzed according to Step C of Example 693; the diastereoisomer eluting later was collected as Example 696. HRMS calculated for C$_{41}$H$_{41}$ClF$_3$N$_7$O$_6$S: 851.2480. found 852.2514 (M+H).

General Procedure (XXVIIa)

Step A:

1 eq. ethyl (2R)-2-[5-(3-chloro-4-methoxy-2-methyl-phenyl)-6-(4-fluoro-3-hydroxy-phenyl)thieno[2,3-d]pyrimidin-4-yl]oxy-3-[2-[(2-methoxypyrimidin-4-yl)methoxy]phenyl]propanoate (Preparation 28b), 2 eq. of the appropriate alcohol and 2 eq. PPh$_3$ were dissolved in dry toluene (0.2 M for the phenol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using DCM and MeOH as eluents.

Step B:

The product of Step A was dissolved in dioxane-water (1:1, 10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic layers were dried over Na$_2$SO$_4$ and concentrated under reduced pressure. The residue was purified via preparative reversed phase chromatography using 25 mM aqueous NH$_4$HCO$_3$ solution and MeCN as eluents. The diastereoisomers were separated at this stage.

Example 697 (2R)-2-{[(5R$_a$)-5-(3-chloro-4-methoxy-2-methylphenyl)-6-{4-fluoro-3-[2-(4-methylpiperazin-1-yl)ethoxy]phenyl}thieno[2,3-d]pyrimidin-4-yl]oxy}-3-{2-[(2-methoxypyrimidin-4-yl)methoxy]phenyl}propanoic acid Using General Procedure (XXVIIa) starting from 2-(4-methylpiperazin-1-yl)ethanol as the appropriate alcohol, Example 697 was obtained as the diastereomer eluting earlier. HRMS calculated for C$_{42}$H$_{42}$ClFN$_6$O$_7$S: 828.2508. found 415.1324 (M+2H).

Example 698 (2R)-2-{[(5S$_a$)-5-(3-chloro-4-methoxy-2-methylphenyl)-6-{4-fluoro-3-[2-(4-methylpiperazin-1-yl)ethoxy]phenyl}thieno[2,3-d]pyrimidin-4-yl]oxy}-3-{2-[(2-methoxypyrimidin-4-yl)methoxy]phenyl}propanoic acid Using General Procedure (XXVIIa) starting from 2-(4-methylpiperazin-1-yl)ethanol as the appropriate alcohol, Example 698 was obtained as the diastereomer eluting later. HRMS calculated for C$_{42}$H$_{42}$ClFN$_6$O$_7$S: 828.2508. found 415.1343 (M+2H).

Example 699 (2R)-2-{[(5R$_a$)-5-(3-chloro-4-methoxy-2-methylphenyl)-6-{4-fluoro-3-[2-(morpholin-4-yl)ethoxy]phenyl}thieno[2,3-d]pyrimidin-4-yl]oxy}-3-{2-[(2-methoxypyrimidin-4-yl)methoxy]phenyl}propanoic acid Using General Procedure (XXVIIa) starting from 2-(morpholin-4-yl)ethanol as the appropriate alcohol, Example 699 was obtained as the diastereomer eluting earlier. HRMS calculated for C$_{41}$H$_{39}$ClFN$_5$O$_8$S: 815.2192. found 408.6163 (M+2H).

Example 700 (2R)-2-{[(5S$_a$)-5-(3-chloro-4-methoxy-2-methylphenyl)-6-{4-fluoro-3-[2-(morpholin-4-yl)ethoxy]phenyl}thieno[2,3-d]pyrimidin-4-yl]oxy}-3-{2-[(2-methoxypyrimidin-4-yl)methoxy]phenyl}propanoic acid Using General Procedure (XXVIIa) starting from 2-(morpholin-4-yl)ethanol as the appropriate alcohol, Example 700 was obtained as the diastereomer eluting later. HRMS calculated for C$_{41}$H$_{39}$ClFN$_5$O$_8$S: 815.2192. found 408.6173 (M+2H).

Example 701 (2R)-2-{[(5R$_a$)-5-(3-chloro-4-methoxy-2-methylphenyl)-6-{3-[2-(dimethylamino)ethoxy]-4-fluorophenyl}thieno[2,3-d]pyrimidin-4-yl]oxy}-3-{2-[(2-methoxypyrimidin-4-yl)methoxy]phenyl}propanoic acid Using General Procedure (XXVIIa) starting from 2-(dimethylamino)ethanol as the appropriate alcohol, Example 701 was obtained as the diastereomer eluting earlier. HRMS calculated for C$_{39}$H$_{37}$ClFN$_5$O$_7$S: 773.2086. found 387.6122 (M+2H).

Example 702 (2R)-2-{[(5S$_a$)-5-(3-chloro-4-methoxy-2-methylphenyl)-6-{3-[2-(dimethylamino)ethoxy]-4-fluorophenyl}thieno[2,3-d]pyrimidin-4-yl]oxy}-3-{2-[(2-methoxypyrimidin-4-yl)methoxy]phenyl}propanoic acid Using General Procedure (XXVIIa) starting from 2-(dimethylamino)ethanol as the appropriate alcohol, Example 702 was obtained as the diastereomer eluting later. HRMS calculated for $C_{39}H_{37}ClFN_5O_7S$: 773.2086. found 387.6114 (M+2H).

General Procedure (XXXIa)

Step A:

1 eq. ethyl (2R)-2-[(5S$_a$)-5-[3-chloro-2-methyl-4-[2-(4-methylpiperazin-1-yl)ethoxy] phenyl]-6-(2,3-difluorophenyl)thieno[2,3-d]pyrimidin-4-yl]oxy-3-(2-hydroxyphenyl) propanoate (Preparation 8m), 3 eq. of the appropriate alcohol and 3 eq. triphenyl phosphine were dissolved in dry toluene (20 mL/mmol), then 3 eq. ditertbutyl azodicarboxylate was added. The mixture was stirred at 50° C. under $N_2$ until no further conversion was observed. The volatiles were evaporated under reduced pressure and the residue was purified via flash chromatography using DCM and methanol as eluents.

Step B:

The product of Step A was dissolved in dioxane-water (1:1, 10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and purified via preparative reverse phase chromatography using 25 mM aqueous NH$_4$HCO$_3$ solution and MeCN as eluents.

Example 703 (2R)-2-{[(5S$_a$)-5-{3-chloro-2-methyl-4-[2-(4-methylpiperazin-1-yl)ethoxy]phenyl}-6-(2,3-difluorophenyl)thieno[2,3-d]pyrimidin-4-yl]oxy}-3-{2-[(2-methoxypyrimidin-4-yl)methoxy] phenyl}propanoic acid Using General Procedure (XXXIa) and (2-methoxypyrimidin-4-yl)methanol as the appropriate alcohol, Example 703 was obtained. HRMS calculated for $C_{41}H_{39}ClF_2N_6O_6S$: 816.2308. found 817.2434 (M+H).

Example 704 (2R)-2-{[(5S$_a$)-5-{3-chloro-2-methyl-4-[2-(4-methylpiperazin-1-yl)ethoxy]phenyl}-6-(2,3-difluorophenyl)thieno[2,3-d]pyrimidin-4-yl]oxy}-3-{2-[(1-ethyl-1H-pyrazol-5-yl)methoxy] phenyl}propanoic acid Using General Procedure (XXXIa) and (1-ethyl-1H-pyrazol-5-yl)methanol (Preparation 9da) as the appropriate alcohol, Example 704 was obtained. HRMS calculated for $C_{41}H_{41}ClF_2N_6O_5S$: 802.2516. found 803.2607 (M+H).

Example 705 (2R)-2-{[(5S$_a$)-5-{3-chloro-2-methyl-4-[2-(4-methylpiperazin-1-yl)ethoxy]phenyl}-6-(2,3-difluorophenyl)thieno[2,3-d]pyrimidin-4-yl]oxy}-3-(2-{[2-(trifluoromethyl)pyrimidin-4-yl] methoxy}phenyl)propanoic acid Using General Procedure (XXXIa) and [2-(trifluoromethyl)pyrimidin-4-yl]methanol (Preparation 9bj) as the appropriate alcohol, Example 705 was obtained. HRMS calculated for $C_{41}H_{36}ClF_5N_6O_5S$: 854.2077. found 855.2121 (M+H).

General Procedure (XXXIIa)

Step A:

1 eq. ethyl (2R)-2-[(5S$_a$)-5-[3-chloro-2-methyl-4-[2-(4-methylpiperazin-1-yl)ethoxy] phenyl]-6-(3,4-difluorophenyl)thieno[2,3-d]pyrimidin-4-yl]oxy-3-(2-hydroxyphenyl) propanoate (Preparation 8k), 2 eq. of the appropriate alcohol and 2 eq. triphenyl phosphine were dissolved in abs. toluene (5 ml/mmol), then 2 eq. ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents.

Step B:

The product of Step A was dissolved in dioxane-water (1:1, 10 mL/mmol) and 10 eq. LiOH×H$_2$O was added. The mixture was stirred at room temperature until no further conversion was observed. Then it was diluted with brine, neutralized with 2 M HCl, and extracted with DCM. The combined organic phases were dried over Na$_2$SO$_4$, concentrated under reduced pressure and purified via preparative reversed phase chromatography using 25 mM aqueous NH$_4$HCO$_3$ solution and MeCN as eluents.

Example 706 (2R)-2-{[(5S$_a$)-5-{3-chloro-2-methyl-4-[2-(4-methylpiperazin-1-yl)ethoxy]phenyl}-6-(3,4-difluorophenyl)thieno[2,3-d]pyrimidin-4-yl]oxy}-3-{2-[(2-methoxypyrimidin-4-yl)methoxy] phenyl}propanoic acid Using General Procedure (XXXIIa) and (2-methoxypyrimidin-4-yl)methanol as the appropriate alcohol, Example 706 was obtained. HRMS calculated for $C_{41}H_{39}ClF_2N_6O_6S$: 816.2308. found 817.2389 (M+H).

Example 707 (2R)-2-{[(5S$_a$)-5-{3-chloro-2-methyl-4-[2-(4-methylpiperazin-1-yl)ethoxy]phenyl}-6-(3,4-difluorophenyl)thieno[2,3-d]pyrimidin-4-yl]oxy}-3-(2-{[2-(trifluoromethyl)pyrimidin-4-yl] methoxy}phenyl)propanoic acid Using General Procedure (XXXIIa) and [2-(trifluoromethyl)pyrimidin-4-yl]methanol (Preparation 9bj) as the appropriate alcohol, Example 707 was obtained. HRMS calculated for $C_{41}H_{36}ClF_5N_6O_5S$: 854.2077. found 855.2146 (M+H).

Example 708 (2R)-2-{[(5S$_a$)-5-{3-chloro-2-methyl-4-[2-(4-methylpiperazin-1-yl)ethoxy]phenyl}-6-(3,4-difluorophenyl)thieno[2,3-d]pyrimidin-4-yl]oxy}-3-{2-[(1-ethyl-1H-pyrazol-5-yl)methoxy] phenyl}propanoic acid Using General Procedure (XXXIIa) and (1-ethyl-1H-pyrazol-5-yl)methanol (Preparation 9da) as the appropriate alcohol, Example 708 was obtained. HRMS calculated for $C_{41}H_{41}ClF_2N_6O_5S$: 802.2516. found 803.2561 (M+H).

Example 709 (2R)-2-{[(5S$_a$)-5-{3-chloro-2-methyl-4-[2-(4-methylpiperazin-1-yl)ethoxy]phenyl}-6-(3-fluorophenyl)thieno[2,3-d]pyrimidin-4-yl]oxy}-3-[2-(propan-2-yloxy)phenyl]propanoic acid Step A:

3.75 g 5-bromo-4-chloro-6-iodo-thieno[2,3-d]pyrimidine (Preparation 1a) (10 mmol), 2.44 g 2-(3-fluoro-phenyl)-4,4,5,5-tetramethyl-1,3,2-dioxaborolane (11 mmol), 8.15 g Cs$_2$CO$_3$ (25 mmol), and 366 mg Pd(dppf)Cl$_2$ (0.5 mmol) were placed in a 250 mL flask. 40 mL THF and 40 mL water were added, and then stirred overnight at 70° C. under N$_2$. To the reaction mixture brine was added, the pH was set to 6 with 2 M HCl and it was extracted with DCM. The combined organic layers were dried over Na$_2$SO$_4$ and concentrated under reduced pressure. The crude product was purified via flash chromatography using heptane and EtOAc as eluents to obtain 5-bromo-4-chloro-6-(3-fluorophenyl)thieno[2,3-d]pyrimidine. $^1$H NMR (500 MHz, DMSO-$d_6$): 9.04 (s, 1H), 7.66-7.60 (m, 2H), 7.56 (d, 1H), 7.44 (td, 1H).

HRMS calculated for $C_{12}H_5ClFBrN_2S$: 341.9029. found 342.9093 (M+H).

Step B:

2.62 g of the product of Step A (7.6 mmol), 3.78 g ethyl (2R)-2-hydroxy-3-[2-[(4-methoxyphenyl)methoxy]phenyl]propanoate (Preparation 3ae) (11.5 mmol) and 7.46 g $Cs_2CO_3$ (22.9 mmol) were placed in a 250 mL flask. 150 mL tert-butanol was added and the mixture was stirred at 60° C. under $N_2$ until no further conversion was observed. Water was added to the mixture and it was extracted with DCM. The combined organic layers were dried over $Na_2SO_4$, concentrated, and purified via flash chromatography using heptane and EtOAc as eluents to obtain ethyl (2R)-2-[5-bromo-6-(3-fluorophenyl)thieno[2,3-d]pyrimidin-4-yl]oxy-3-[2-[(4-methoxyphenyl)methoxy]phenyl]propanoate. $^1$H NMR (500 MHz, DMSO-$d_6$): 8.67 (s, 1H), 7.62-7.54 (m, 3H), 7.40 (m, 4H), 7.22 (td, 1H), 7.08 (d, 1H), 6.90 (d, 2H), 6.88 (td, 1H), 5.71 (dd, 1H), 5.10 (d, 1H), 5.06 (d, 1H), 4.11 (m, 2H), 3.74 (s, 3H), 3.45 (dd, 1H), 3.21 (dd, 1H), 1.10 (t, 3H).

HRMS calculated for $C_{31}H_{26}BrFN_2O_5S$: 636.0730. found 637.0815 (M+H).

Step C:

0.152 g of the product of Step B (0.24 mmol), 0.160 g 2-chloro-3-methyl-4-(4,4,5,5-tetramethyl-1,3,2-dioxaborolan-2-yl)phenol (Preparation 5a) (0.60 mmol), and 0.017 g Ataphos (0.024 mmol) were dissolved in 1.7 mL 2-Me-THF, and 0.6 mL tetrabutylammonium hydroxide (1M in $H_2O$, 0.6 mmol) was added. The mixture was heated under nitrogen at 110° C. for 10 min in a microwave reactor. The reaction was diluted with water, the pH was adjusted to 4 by the addition of 2 M HCl, and it was extracted with DCM. The combined organic phases were dried over $Na_2SO_4$ and concentrated under reduced pressure. The mixture of diastereomers was separated via flash chromatography using heptane and EtOAc as eluents. The diastereomer eluting later was collected as ethyl (2R)-2-[(5$S_a$)-5-(3-chloro-4-hydroxy-2-methyl-phenyl)-6-(3-fluorophenyl)thieno[2,3-d]pyrimidin-4-yl]oxy-3-[2-[(4-methoxyphenyl)methoxy]phenyl]propanoate. $^1$H NMR (500 MHz, DMSO-$d_6$): 10.28 (s, 1H), 8.62 (s, 1H), 7.41-7.39 (m, 3H), 7.20-7.12 (m, 4H), 7.01-6.96 (m, 3H), 6.90 (d, 2H), 6.71 (td, 1H), 6.33 (dd, 1H), 5.43 (dd, 1H), 5.05 (d, 1H), 5.01 (d, 1H), 4.03 (q, 2H), 3.73 (s, 3H), 3.04 (dd, 1H), 2.46 (dd, 1H), 1.79 (s, 3H), 1.04 (t, 3H).

HRMS calculated for $C_{38}H_{32}ClFN_2O_6S$: 698.1654. found 699.1754 (M+H).

Step D:

0.966 g of the product of Step C (1.4 mmol), 0.60 g 2-(4-methylpiperazin-1-yl)ethanol (4.1 mmol) were dissolved in 20 mL dry toluene, then 1.38 g $PPh_3$ polymer (3 mmol/g, 4.1 mmol) and 0.95 g di-tert-butyl azodicarboxylate (4.1 mmol) was added. The mixture was stirred at 50° C. under $N_2$ until no further conversion was observed. The polymer was filtered off, toluene was evaporated under reduced pressure and the residue was purified via flash chromatography using EtOAc and MeOH as eluents to obtain ethyl (2R)-2-[(5$S_a$)-5-[3-chloro-2-methyl-4-[2-(4-methylpiperazin-1-yl)ethoxy]phenyl]-6-(3-fluorophenyl)thieno[2,3-d]pyrimidin-4-yl]oxy-3-[2-[(4-methoxyphenyl)methoxy]phenyl]propanoate. $^1$H NMR (500 MHz, DMSO-$d_6$): 8.64 (s, 1H), 7.41-7.38 (m, 3H), 7.29 (d, 1H), 7.20-7.12 (m, 4H), 7.03-7.01 (m, 2H), 6.90 (d, 2H), 6.70 (t, 1H), 6.31 (dd, 1H), 5.42 (dd, 1H), 5.04 (d, 1H), 5.00 (d, 1H), 4.19 (m, 2H), 4.02 (q, 2H), 3.73 (s, 3H), 2.99 (dd, 1H), 2.70 (t, 2H), 2.50 (dd, 1H), 2.46 (br s, 4H), 2.22 (br s, 4H), 2.08 (s, 3H), 1.82 (s, 3H), 1.02 (t, 3H).

HRMS calculated for $C_{45}H_{46}ClFN_4O_6S$: 824.2811. found 825.2899 (M+H).

Step E:

0.20 g of the product of Step D (0.24 mmol) was dissolved in 0.5 mL DCM and cooled to 0° C. 4 mL HBr (33% solution in acetic acid) was added and the mixture was stirred for 10 min. Water was added and the pH was adjusted to 4 by the addition of saturated aq. $NaHCO_3$ solution. The mixture was extracted with DCM, the combined organic phases were dried over $Na_2SO_4$ and concentrated under reduced pressure. The crude product was dissolved in 20 mL EtOH and 0.2 mL cc. $H_2SO_4$ was added. The reaction mixture was stirred at 50° C. until no further conversion was observed. Brine was added and the mixture was extracted with DCM. The combined organic phases were dried over $Na_2SO_4$ and concentrated under reduced pressure. The crude product was purified via flash chromatography using EtOAc and MeOH as eluents to obtain ethyl (2R)-2-[(5$S_a$)-5-[3-chloro-2-methyl-4-[2-(4-methylpiperazin-1-yl)ethoxy]phenyl]-6-(3-fluorophenyl)thieno[2,3-d]pyrimidin-4-yl]oxy-3-(2-hydroxyphenyl)propanoate. HRMS calculated for $C_{37}H_{46}FN_4O_6S$: 704.2235. found 705.2307 (M+H).

Step F:

95 mg of the product of Step E (0.13 mmol), 94 mg $PPh_3$ (0.39 mmol), 96 mg ditertbutyl azodicarboxylate (0.39 mmol) and 32 µL propan-2-ol (0.39 mmol) were dissolved in 2 ml dry toluene and the reaction mixture was stirred at 50° C. under $N_2$ until no further conversion was observed. The mixture was concentrated under reduced pressure. The residue was dissolved in 5 mL MeOH, 252 mg LiOH×$H_2O$ (6.0 mmol) was added and it was stirred at room temperature until no further conversion was observed. The methanol was evaporated under reduced pressure, water was added to the residue, the pH was adjusted to 4 by the addition of 2 M HCl solution, and it was extracted with DCM. The combined organic phases were dried over $Na_2SO_4$ and concentrated under reduced pressure. The crude product was purified via preparative reverse phase chromatography using 25 mM aqueous $NH_4HCO_3$ solution and MeCN as eluents to obtain Example 709. HRMS calculated for $C_{38}H_{40}ClFN_4O_5S$: 718.2392. found 719.2469 (M+H).

Example 710 (2R)-2-{[(5$S_a$)-5-{3-chloro-2-methyl-4-[2-(4-methylpiperazin-1-yl)ethoxy] phenyl}-6-(3-fluorophenyl)thieno[2,3-d]pyrimidin-4-yl]oxy}-3-{2-[(4-methoxybenzyl)oxy] phenyl}propanoic acid 100 mg of the product of Step D in Example 709 (0.12 mmol) was dissolved in 5 mL MeOH. 252 mg LiOH×$H_2O$ (6 mmol) was added and the mixture was stirred at room temperature until no further conversion was observed. The methanol was evaporated under reduced pressure, water was added, and the pH was adjusted to 4 by the addition of 2 M HCl. The precipitated crude product was filtered, dried and purified via preparative reverse phase chromatography using 25 mM aqueous $NH_4HCO_3$ solution and MeCN as eluents to obtain Example 710. HRMS calculated for $C_{43}H_{42}ClFN_4O_6S$: 796.2498. found 797.2565 (M+H).

Example 711 (2R)-2-{[(5$S_a$)-5-{3-chloro-2-methyl-4-[2-(4-methylpiperazin-1-yl)ethoxy]phenyl}-6-(3-fluorophenyl)thieno[2,3-d]pyrimidin-4-yl]oxy}-3-(2-hydroxyphenyl)propanoic acid 100 mg of the product of Step E in Example 709 (0.14 mmol) was dissolved in 5 mL MeOH, 252 mg LiOH×$H_2O$ (6 mmol) was added and the mixture was stirred at room temperature until no further conversion was observed. The methanol was evaporated under reduced pressure, water was added, and the pH was adjusted to 4 by the addition of 2 M HCl. The precipitated crude product was filtered, dried and purified via preparative reverse phase chromatography using 25 mM aqueous $NH_4HCO_3$ solution and MeCN as eluents to obtain Example 711. HRMS calculated for $C_{35}H_{34}ClFN_4O_5S$: 676.1922. found 677.2005 (M+H).

Example 712 (2R)-2-{[(5$S_a$)-5-{3-chloro-2-methyl-4-[2-(morpholin-4-yl)ethoxy]phenyl}-6-(1-methyl-1H-pyrazol-4-yl)thieno[2,3-d]pyrimidin-4-yl]oxy}-3-phenylpropanoic acid Step A:

266 mg methyl (2R)-2-[6-bromo-(5$S_a$)-5-(3-chloro-4-hydroxy-2-methyl-phenyl)thieno[2,3-d]pyrimidin-4-yl]oxy-3-phenyl-propanoate (Preparation 22) (0.50 mmol), 312 mg 1-methyl-4-(4,4,5,5-tetramethyl-1,3,2-dioxaborolan-2-yl) pyrazole (1.50 mmol), 488 mg $Cs_2CO_3$ (1.50 mmol), and 54 mg $Pd(dppf)Cl_2$ (0.075 mmol) were dissolved in a mixture of 8 mL 2-Me-THF and 1 mL water and the mixture was heated under nitrogen at 100° C. for 30 minutes in a microwave reactor. The reaction was diluted with water, the pH was adjusted between 3-4 by the addition of 2 M HCl, and the mixture was extracted with DCM. The combined organic phases were dried over $Na_2SO_4$ and concentrated under reduced pressure. The residue was purified via flash chromatography using DCM and MeOH as eluents to give methyl (2R)-2-[(5$S_a$)-5-(3-chloro-4-hydroxy-2-methyl-phenyl)-6-(1-methylpyrazol-4-yl)thieno[2,3-d]pyrimidin-4-yl] oxy-3-phenyl-propanoate. HRMS calculated for $C_{27}H_{23}ClN_4O_4S$: 534.1129. found 535.1210 (M+H).

Step B:

99 mg methyl (2R)-2-[(5$S_a$)-5-(3-chloro-4-hydroxy-2-methyl-phenyl)-6-(1-methylpyrazol-4-yl)thieno[2,3-d]pyrimidin-4-yl]oxy-3-phenyl-propanoate (0.185 mmol), 97 mg $PPh_3$ (0.37 mmol), 85 mg ditertbutyl azodicarboxylate (0.37 mmol) and 53 mg 2-(morpholin-4-yl)ethanol (0.37 mmol) were dissolved in 3 ml dry toluene and the reaction mixture was stirred at 50° C. under nitrogen atmosphere for 2 hours. The mixture was concentrated under reduced pressure and the residue was purified via flash chromatography using DCM and MeOH as eluents.

Step C:

The product of Step B was hydrolyzed at room temperature in 5 mL methanol-water (9:1) containing NaOH (5 m/m %). After completion the mixture was diluted with water, the pH was adjusted to 6 by the addition of 2 M HCl, and the mixture was extracted with DCM. The combined organic phases were dried over $Na_2SO_4$ and concentrated under reduced pressure. The crude product was purified using reverse phase preparative HPLC resulting Example 712. HRMS calculated for $C_{32}H_{32}ClN_5O_5S$: 633.1813. found 634.1894 (M+H).

Example 713 (2R)-2-{[(5$S_a$)-5-(3-chloro-4-methoxy-2-methylphenyl)-6-{3-[2-(4-methylpiperazin-1-yl)ethoxy]phenyl}thieno[2,3-d]pyrimidin-4-yl]oxy}-3-(2-methoxyphenyl)propanoic acid Step A:

250 mg ethyl (2R)-2-[(5$S_a$)-5-(3-chloro-4-hydroxy-2-methyl-phenyl)-6-iodo-thieno[2,3-d]pyrimidin-4-yl]oxy-3-(2-methoxyphenyl)propanoate (Preparation 25) (0.40 mmol), 315 mg $PPh_3$ (1.20 mmol) and 276 mg ditertbutyl azodicarboxylate (1.20 mmol) were dissolved in 3 mL methanol. The mixture was stirred at 50° C. under nitrogen atmosphere for 30 minutes. The mixture was concentrated under reduced pressure and the crude product was purified via flash chromatography using heptane and EtOAc as eluents to give ethyl (2R)-2-[(5$S_a$)-5-(3-chloro-4-methoxy-2-methyl-phenyl)-6-iodo-thieno[2,3-d] pyrimidin-4-yl]oxy-3-(2-methoxyphenyl)propanoate. HRMS calculated for $C_{26}H_{24}ClIN_2O_5S$: 638.0139. found 639.0222 (M+H).

Step B:

291 mg of the product of Step A (0.40 mmol), 352 mg 3-(4,4,5,5-tetramethyl-1,3,2-dioxaborolan-2-yl)phenol (1.60 mmol), 652 mg $Cs_2CO_3$ (2.00 mmol) and 19 mg $Pd(dppf)Cl_2$ (0.04 mmol) were dissolved in a mixture of 2.4 mL dioxane and 1.2 mL water, and the mixture was heated under nitrogen at 110° C. for 10 minutes in a microwave reactor. The reaction was diluted with water, the pH was adjusted between 3-4 by the addition of 2 M HCl, and the mixture was extracted with DCM. The combined organic phases were dried over $Na_2SO_4$ and concentrated under reduced pressure. The residue was purified via flash chromatography using heptane and EtOAc as eluents to give ethyl (2R)-2-[(5$S_a$)-5-(3-chloro-4-methoxy-2-methyl-phenyl)-6-(3-hydroxyphenyl)thieno[2,3-d] pyrimidin-4-yl]oxy-3-(2-methoxyphenyl)propanoate. HRMS calculated for $C_{32}H_{29}ClN_2O_6S$: 604.1435. found 605.1518 (M+H).

Step C:

146 mg of the product of Step B (0.24 mmol), 197 mg $PPh_3$ (0.75 mmol), 152 mg ditertbutyl azodicarboxylate (0.75 mmol) and 108 mg 2-(4-methylpiperazin-1-yl)ethanol (0.75 mmol) were dissolved in 4 ml dry toluene and the reaction mixture was stirred at 50° C. under nitrogen for 30 minutes. The mixture was concentrated under reduced pressure and the obtained crude product was hydrolyzed at room temperature in 5 mL methanol-water (9:1) containing NaOH (5 m/m %). After completion the mixture was diluted with water, the pH was adjusted to 6 by the addition of 2 M HCl, and the mixture was extracted with DCM. The combined organic phases were dried over $Na_2SO_4$ and concentrated under reduced pressure. The crude product was purified using reverse phase preparative HPLC resulting Example 713. HRMS calculated for $C_{37}H_{39}ClN_4O_6S$: 702.2279. found 703.2362 (M+H).

Example 714 (2R)-2-{[6-(5-chlorofuran-2-yl)-(5$S_a$)-5-{3-chloro-2-methyl-4-[2-(4-methylpiperazin-1-yl) ethoxy]phenyl}thieno[2,3-d]pyrimidin-4-yl]oxy}-3-(5-chloro-2-methoxyphenyl)propanoic acid A mixture of 200 mg (2R)-2-[(5$S_a$)-5-[3-chloro-2-methyl-4-[2-(4-methylpiperazin-1-yl)ethoxy]phenyl]-6-(2-furyl) thieno[2,3-d]pyrimidin-4-yl]oxy-3-(2-methoxyphenyl)propanoic acid (Example 209) (0.30 mmol) and 300 mg NCS (2.25 mmol) in 5 mL chloroform was stirred overnight under nitrogen at room temperature. The mixture was diluted with water and extracted with DCM. The combined organic phases were dried over $Na_2SO_4$ and concentrated under reduced pressure. The crude product was purified using reverse phase preparative HPLC to give Example 714. HRMS calculated for $C_{34}H_{33}Cl_3N_4O_6S$: 730.1186. found 731.1251 (M+H).

Example 715 (2R)-2-{[(5S$_a$)-5-(3-chloro-4-hydroxy-2-methylphenyl)-6-(thiophen-3-yl)thieno[2,3-d]pyrimidin-4-yl]oxy}-3-(2-methoxyphenyl)propanoic acid Step A:

462 mg ethyl (2R)-2-[(5S$_a$)-5-(3-chloro-4-hydroxy-2-methyl-phenyl)-6-iodo-thieno[2,3-d]pyrimidin-4-yl]oxy-3-(2-methoxyphenyl)propanoate (Preparation 25) (0.8 mmol), 336 mg 4,4,5,5-tetramethyl-2-(3-thienyl)-1,3,2-dioxaborolane (1.6 mmol), 58 mg Pd(dppf)Cl$_2$ (0.08 mmol), and 521 mg cesium carbonate (1.6 mmol) was dissolved in 8 mL dioxane and 2 mL water and it was heated under nitrogen at 110° C. for 7 min in a microwave reactor. Water was added to the reaction, the pH was adjusted between 4-5 with 2 M HCl, and it was extracted with DCM. The combined organic phases were dried over Na2SO4, concentrated under reduced pressure, and purified via flash chromatography using heptane and ethyl acetate as eluents.

Step B:

140 mg of the product of Step A (0.24 mmol) was dissolved in 10 mL MeOH, 202 mg LiOH×H$_2$O (4.80 mmol) was added and it was stirred at room temperature until no further conversion was observed. Then it was diluted with brine, neutralized with 2 M HCl, and extracted with DCM. The combined organic phases were dried over Na$_2$SO$_4$, concentrated under reduced pressure, and purified via preparative reversed phase chromatography using 40 mM aqueous NH$_4$OAc solution (pH set to 4 with AcOH) and MeCN as eluents to obtain Example 715. HRMS calculated for C$_{27}$H$_{21}$ClN$_2$O$_5$S$_2$: 552.0580. found 553.0647 (M+H).

Example 716 (2R)-2-{[(5R$_a$)-5-{3-chloro-2-methyl-4-[3-(4-methylpiperazin-1-yl)prop-1-yn-1-yl]phenyl}-6-(2,3-difluorophenyl)thieno[2,3-d]pyrimidin-4-yl]oxy}-3-(2-methoxyphenyl)propanoic acid and

Example 717 (2R)-2-{[(5S$_a$)-5-{3-chloro-2-methyl-4-[3-(4-methylpiperazin-1-yl)prop-1-yn-1-yl]phenyl}-6-(2,3-difluorophenyl)thieno[2,3-d]pyrimidin-4-yl]oxy}-3-(2-methoxyphenyl)propanoic acid Step A:

297 mg 4-chloro-5-iodo-thieno[2,3-d]pyrimidine (Preparation 1c) (1.00 mmol), 398 mg 2-(4-bromo-3-chloro-2-methyl-phenyl)-4,4,5,5-tetramethyl-1,3,2-dioxaborolane (Preparation 5t) (1.20 mmol), 73 mg PdCl$_2$×dppf (0.10 mmol) and 978 mg Cs$_2$CO$_3$ (3.00 mmol) were dissolved in 10 mL dioxane and 2.5 mL water, and heated under nitrogen at 60° C. for 90 minutes in a microwave reactor. The reaction mixture was concentrated under reduced pressure and purified via flash chromatography, using heptane and EtOAc as eluents to obtain 5-(4-bromo-3-chloro-2-methyl-phenyl)-4-chloro-thieno[2,3-d]pyrimidine.

Step B:

192 mg of the product of Step A (0.51 mmol) was dissolved in 5 mL dry THF under N$_2$ and was cooled to −78° C. with dry ice-acetone. 308 µL LDA (0.62 mmol in 2 M THF, EtPh) was added and it was stirred for 1 hour, then 163 mg iodine (0.64 mmol) was added and the mixture was allowed to warm up to room temperature. It was diluted with Et$_2$O, washed with saturated Na$_2$S$_2$O$_3$ solution, dried over Na$_2$SO$_4$, filtered and concentrated under reduced pressure and purified via flash chromatography using heptane and EtOAc as eluents to obtain 5-(4-bromo-3-chloro-2-methyl-phenyl)-4-chloro-6-iodo-thieno[2,3-d] pyrimidine.

Step C:

50 mg of the product of Step B (0.1 mmol) was dissolved in 2 mL dioxane, then 72 mg 2-(2,3-difluorophenyl)-4,4,5,5-tetramethyl-1,3,2-dioxaborolane (0.30 mmol), 7.3 mg Pd(dppf)Cl$_2$ (0.01 mmol), 98 mg Cs$_2$CO$_3$ (0.30 mmol) and 0.5 mL water were added. The mixture was heated under nitrogen to 60° C. for 30 minutes in a microwave reactor. Then it was concentrated under reduced pressure and purified via flash chromatography, using heptane and EtOAc as eluents to obtain 5-(4-bromo-3-chloro-2-methyl-phenyl)-4-chloro-6-(2,3-difluorophenyl)thieno[2,3-d]pyrimidine.

Step D:

165 mg of the product of Step C was dissolved in 2 mL isopropanol. 112 mg ethyl (2R)-2-hydroxy-3-(2-methoxyphenyl)propanoate (Preparation 3ad) (0.50 mmol) and 326 mg Cs$_2$CO$_3$ (1.00 mmol) were added and the mixture was stirred at 50° C. for 2 hours. Then it was diluted with water, neutralized with 2 M HCl, and extracted with DCM. The combined organic phases were dried over Na$_2$SO$_4$ and concentrated under reduced pressure. Then it was dissolved in 5 mL MeOH, 141 mg LiOH×H$_2$O (3.35 mmol) was added and it was stirred at room temperature for 1 hour. Then it was diluted with brine, neutralized with 2 M HCl, and extracted with DCM. The combined organic phases were dried over Na$_2$SO$_4$, concentrated under reduced pressure and purified via preparative reversed phase chromatography using 40 mM aqueous NH$_4$OAc solution (pH set to 4 with AcOH) and MeCN as eluents to obtain (2R)-2-[5-(4-bromo-3-chloro-2-methyl-phenyl)-6-(2,3-difluorophenyl)thieno[2,3-d]pyrimidin-4-yl]oxy-3-(2-methoxyphenyl)propanoic acid as a mixture of diastereomers.

Step E:

To 77 mg of the product of Step D (0.12 mmol), 82 mg 1-methyl-4-prop-2-ynyl-piperazine (0.60 mmol), 2.7 mg Pd(OAc)$_2$ (0.012 mmol), 8.5 mg BuPAd$_2$ (0.024 mmol), and 2.3 mg copper(I) iodide (0.012 mmol) 1 mL DIPA was added and the mixture was heated under nitrogen to 120° C. for 40 minutes in a microwave reactor. The reaction mixture was concentrated under reduced pressure and purified via preparative reversed phase chromatography using 40 mM aqueous NH$_4$OAc solution (pH was set to 4 with AcOH) and MeCN as eluents to obtain Example 716 and Example 717. The diastereoisomer eluting earlier was collected as Example 716. HRMS calculated for C$_{37}$H$_{33}$ClF$_2$N$_4$O$_4$S: 702.1879. found 703.1963 (M+H). The diastereoisomer eluting later was collected as Example 717. HRMS calculated for C$_{37}$H$_{33}$ClF$_2$N$_4$O$_4$S: 702.1879. found 703.1947 (M+H).

Example 718 (2R)-2-{[6-(5-chlorofuran-2-yl)-(5S$_a$)-5-{3-chloro-2-methyl-4-[2-(4-methylpiperazin-1-yl)ethoxy]phenyl}thieno[2,3-d]pyrimidin-4-yl]oxy}-3-(4-fluoro-2-methoxyphenyl)propanoic acid Step A:

700 mg 5-bromo-4-chloro-6-(5-chloro-2-furyl)thieno[2,3-d]pyrimidine (Preparation 2d) (2.0 mmol), 581 mg ethyl (2R)-3-(4-fluoro-2-methoxy-phenyl)-2-hydroxy-propanoate (Preparation 3 as) (2.4 mmol) and 1.955 g cesium carbonate (6.0 mmol) were stirred at 70° C. in 10 mL dry tertbutanol until no further conversion was observed. The mixture was cooled to room temperature, and then 10 mL water, 947 mg 1-[2-[2-chloro-3-methyl-4-(4,4,5,5-tetramethyl-1,3,2-dioxaborolan-2-yl)phenoxy]ethyl]-4-methyl-piperazine (Preparation 5b) (2.4 mmol) and 141 mg AtaPhos (0.2 mmol) were added. The mixture was stirred under nitrogen at 60° C. until no further conversion was observed. Then brine was added and the mixture was extracted with EtOAc. The combined organic phases were dried over MgSO$_4$ and concentrated under reduced pressure. The crude intermediate was purified via flash chromatography using EtOAc and MeOH as eluents to obtain ethyl (2R)-2-[6-(5-chloro-2-furyl)-5-[3-chloro-2-methyl-4-[2-(4-methylpiperazin-1-yl)ethoxy]phenyl] thieno[2,3-d]pyrimidin-4-yl]oxy-3-(4-fluoro-2-methoxy-phenyl)propanoate.
Step B:

560 mg of the product of Step A (0.75 mmol) was dissolved in 20 mL dioxane-water (1:1) and 632 mg LiOH×H$_2$O (15.1 mmol) was added. The mixture was stirred at room temperature until no further conversion was observed. Then it was diluted with brine, neutralized with 2 M HCl, and extracted with DCM. The combined organic phases were dried over Na$_2$SO$_4$, filtered and concentrated. The residue was purified via preparative reversed phase chromatography using 25 mM aqueous NH$_4$HCO$_3$ solution and MeCN as eluents; the diastereoisomer eluting later was collected as Example 718. HRMS calculated for C$_{34}$H$_{33}$Cl$_2$FN$_4$O$_6$S: 714.1482. found 715.1553 (M+H).

Example 719 (2R)-2-{[(5R$_a$)-5-(3-chloro-2-methyl-phenyl)-6-(prop-1-en-2-yl)thieno[2,3-d] pyrimidin-4-yl]oxy}-3-phenylpropanoic acid and Example 720 (2R)-2-{[(5S$_a$)-5-(3-chloro-2-methyl-phenyl)-6-(prop-1-en-2-yl)thieno[2,3-d] pyrimidin-4-yl]oxy}-3-phenylpropanoic acid Step A:

The mixture of 0.421 g 4-Chloro-5-(3-chloro-2-methyl-phenyl)-6-iodo-thieno[2,3-d]pyrimidine (Preparation 24b) (1.0 mmol), 0.207 mL 2-isopropenyl-4,4,5,5-tetramethyl-1,3,2-dioxaborolane (1.1 mmol), 0.303 g Ag$_2$CO$_3$ (1.1 mmol), 0.173 g Pd(PPh$_3$)$_4$ (0.15 mmol), and 5 mL 2-MeTHF was heated under nitrogen at 100° C. for 15 min in a microwave reactor. The reaction was diluted with 50 mL DCM and it was filtered through a pad of celite. The celite was washed with DCM and the filtrate was evaporated under reduced pressure. The residue was purified via flash chromatography using heptane and EtOAc as eluents to give 4-chloro-5-(3-chloro-2-methyl-phenyl)-6-isopropenyl-thieno[2,3-d]pyrimidine. $^1$H NMR (500 MHz, DMSO-d$_6$): 8.95 (s, 1H), 7.56 (dd, 1H), 7.31 (t, 1H), 7.25 (dd, 1H), 5.33 (m, 1H), 5.22 (m, 1H), 2.08 (s, 3H), 1.77 (m 1H).
Step B:

The mixture of 0.12 g product of Step A (0.36 mmol), 0.193 g methyl (2R)-2-hydroxy-3-phenyl-propanoate (Preparation 3ag) (1.07 mmol), 0.466 g Cs$_2$CO$_3$ (1.43 mmol), and 4 mL dry DMSO was heated at 80° C. until no further conversion was observed. The mixture was cooled to room temperature, it was diluted with DCM and brine, neutralized with 2 M HCl, and it was extracted with DCM. The combined organic layers were dried over Na$_2$SO$_4$ and evaporated under reduced pressure. The obtained crude material was dissolved in 10 mL MeOH-THF (1:1), 227 mg LiOH×H$_2$O (5.5 mmol) was added and the mixture was stirred at 45° C. until no further conversion was observed. Then it was diluted with brine, neutralized with 2 M HCl, and extracted with DCM. The combined organic phases were dried over Na$_2$SO$_4$ and concentrated under reduced pressure. The residue was purified via preparative reverse phase chromatography using 0.1% aqueous TFA solution and MeCN as eluents to obtain Example 719, as the diastereomer eluting earlier [HRMS calculated for C$_{25}$H$_{21}$ClN$_2$O$_3$S: 464.0961. found 465.1054 (M+H)], and Example 720, as the diastereomer eluting later [HRMS calculated for C$_{25}$H$_{21}$ClN$_2$O$_3$S: 464.0961. found 465.1028 (M+H)].

Example 721 (2R)-2-{[(5S$_a$)-5-(3-chloro-2-methyl-phenyl)-6-ethenylthieno[2,3-d] pyrimidin-4-yl]oxy}-3-phenylpropanoic acid Step A:

The mixture of 550 mg 4-chloro-5-(3-chloro-2-methyl-phenyl)-6-iodo-thieno[2,3-d]pyrimidine (Preparation 24b) (1.3 mmol), 0.245 mL 4,4,5,5-tetramethyl-2-vinyl-1,3,2-dioxaborolane (1.43 mmol), 0.397 g Ag$_2$CO$_3$ (1.43 mmol), 0.227 g Pd(PPh$_3$)$_4$ (0.195 mmol), and 6 mL 2-MeTHF was heated under nitrogen at 100° C. for 15 min in a microwave reactor. The mixture was diluted with 50 mL DCM and it was filtered through a pad of celite. The celite was washed with DCM and the filtrate was evaporated under reduced pressure. The residue was purified via flash chromatography using heptane and EtOAc as eluents to give 4-chloro-5-(3-chloro-2-methyl-phenyl)-6-vinyl-thieno[2,3-d]pyrimidine. $^1$H NMR (500 MHz, DMSO-d$_6$): 8.94 (s, 1H), 7.59 (dm, 1H), 7.35 (t, 1H), 7.24 (dm, 1H), 6.44 (dd, 1H), 5.90 (d, 1H), 5.54 (d, 1H), 2.04 (s, 3H).
Step B:

The mixture of 150 mg product of Step A (0.47 mmol), 0.252 g methyl (2R)-2-hydroxy-3-phenyl-propanoate (Preparation 3ag) (1.4 mmol), 0.456 g Cs$_2$CO$_3$ (1.40 mmol), and 5 mL dry DMSO was heated at 80° C. until no further conversion was observed. The mixture was cooled to room temperature, it was diluted with DCM and brine, neutralized with 2 M HCl, and the phases were separated. The aqueous layer was extracted with DCM, the combined organic layers were dried over Na$_2$SO$_4$, and evaporated under reduced pressure. The crude product was dissolved in 10 mL MeOH-THF (1:1), 0.196 g LiOH×H$_2$O (4.67 mmol) was added and the mixture was stirred at 45° C. until no further conversion was observed. Then it was diluted with brine, neutralized with 2 M HCl, and extracted with DCM. The combined organic phases were dried over Na$_2$SO$_4$ and concentrated under reduced pressure. The residue was purified via preparative reverse phase chromatography using 0.1% aqueous TFA solution and MeCN as eluents to obtain Example 721 as the diastereomer eluting later. HRMS calculated for C$_{24}$H$_{19}$ClN$_2$O$_3$S: 450.0805. found 451.0893 (M+H).
General Procedure (XXb)

The appropriate acid was dissolved in the appropriate alcohol (20 mL/g) containing 1% cc. sulfuric acid and the mixture was stirred at 70° C. until no further conversion was observed. Water was added to the mixture and it was neutralized with NaHCO$_3$, extracted with DCM, the combined organic phases were dried over Na$_2$SO$_4$ and concentrated under reduced pressure. The crude ester was purified via preparative reversed phase chromatography using 25 mM aqueous NH$_4$HCO$_3$ solution and MeCN as eluents.
General Procedure (XXc)

1 eq. from the appropriate acid was dissolved in DMF (10 mL/mmol), then 1.1 eq. from the appropriate alkyl halide, 2 eq. NaI and 2 eq. Cs$_2$CO$_3$ were added. The mixture was stirred at room temperature under N$_2$ atmosphere until no further conversion was observed. Then it was diluted with water and extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XXXIIIa)

1 eq. ethyl (2R)-2-[5-[3-chloro-2-methyl-4-[2-(4-methyl-piperazin-1-yl)ethoxy]phenyl]-6-iodo-thieno[2,3-d]pyrimidin-4-yl]oxy-3-[2-[[2-(2-methoxyphenyl)pyrimidin-4-yl]methoxy]phenyl]propanoate (Preparation 30), 1.5 eq. boronic acid, 2 eq. cesium carbonate, 0.05 eq. Pd(OAc)$_2$, and 0.05 eq. $^t$BuX-Phos were placed in a flask. 8 mL/mmol THF and 2 mL/mmol water were added, and then the mixture was stirred at 70° C. under argon atmosphere until no further conversion was observed. Volatiles were evaporated under reduced pressure. The residue was purified via flash chromatography using DCM and MeOH as eluents to obtain the appropriate intermediate as a mixture of diastereomers. The obtained intermediate was dissolved in dioxane-water 1:1 (10 mL/mmol) and 10 eq. LiOH×H$_2$O was added. The mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure. Diastereomers were separated by preparative reversed phase chromatography using 25 mM aqueous NH$_4$HCO$_3$ solution and MeCN as eluents.

General Procedure (XXXIIIb):

1 eq. ethyl (2R)-2-[5-[3-chloro-2-methyl-4-[2-(4-methyl-piperazin-1-yl)ethoxy]phenyl]-6-(4-hydroxyphenyl)thieno[2,3-d]pyrimidin-4-yl]oxy-3-[2-[[2-(2-methoxyphenyl)pyrimidin-4-yl]methoxy]phenyl]propanoate (Preparation 31), 2 eq. of the appropriate alcohol and 2 eq. PPh$_3$ were dissolved in dry toluene (4 mL/mmol), then 2 eq. ditertbutyl azodicarboxylate was added. The mixture was stirred at 50° C. under N$_2$ until no further conversion was observed. Volatiles were evaporated under reduced pressure. The residue was purified via flash chromatography using EtOAc and MeOH as eluents. The obtained intermediate was dissolved in dioxane-water 1:1 (25 ml/mmol) and 10 eq. LiOH×H$_2$O was added. The mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XXXIIIc)

1 eq. ethyl (2R)-2-[5-[3-chloro-2-methyl-4-[2-(4-methyl-piperazin-1-yl)ethoxy]phenyl]-6-iodo-thieno[2,3-d]pyrimidin-4-yl]oxy-3-[2-[[2-(2-methoxyphenyl)pyrimidin-4-yl]methoxy]phenyl]propanoate (Preparation 30), 3 eq. of the appropriate alkyne, 0.1 eq. CuI, 0.05 eq bis(triphenylphosphine) palladium(II) dichloride and DIPA (4 mL/0.1 mmol) were stirred under N$_2$ at room temperature until no further conversion was observed. The volatiles were removed in vacuo, the residue was purified via flash chromatography. Product was dissolved in dioxane:H$_2$O=1:1 (25 ml/mmol), and 10 eq. LiOH×H$_2$O was added. The mixture was stirred until no further conversion was observed. Then it was diluted with brine, acidified with 2M HCl and extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XXXIV)

1 eq. ethyl (2R)-2-[5-bromo-6-(4-fluorophenyl)thieno[2,3-d]pyrimidin-4-yl]oxy-3-[2-[[2-(2-methoxyphenyl)pyrimidin-4-yl]methoxy]phenyl]propanoate (Preparation 4v), 1.2 eq. of the appropriate boronic acid derivative, 3 eq. cesium carbonate and 0.1 eq. AtaPhos were placed in a flask. 2.5 mL dioxane and 2.5 mL water were added, and the mixture was stirred at 70° C. under argon atmosphere until no further conversion was observed. The mixture was diluted with water and extracted with EtOAc. The combined organic layers were dried over Na$_2$SO$_4$, filtered and concentrated under reduced pressure. The crude product was purified via flash chromatography using EtOAc and MeOH as eluents. The obtained intermediate was dissolved in dioxane:water 1:1 (8 ml/mmol), 5 eq. NaOH was added, and the mixture was stirred at room temperature until no further conversion was observed. Then it was diluted with brine, acidified with 2 M HCl and extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XXXV)

1 eq. ethyl (2R)-2-[(5S$_a$)-5-(3-chloro-4-hydroxy-2-methyl-phenyl)-6-(4-fluorophenyl)thieno[2,3-d]pyrimidin-4-yl]oxy-3-[2-[[2-(2-fluorophenyl)pyrimidin-4-yl]methoxy]phenyl] propanoate (Preparation 6u), 3 eq. of the appropriate alcohol, and 3 eq. PPh$_3$ were dissolved in dry toluene (20 mL/mmol), then 3 eq. ditertbutyl azodicarboxylate was added. The mixture was stirred at 50° C. under N$_2$ until no further conversion was observed. The toluene was evaporated under reduced pressure and the residue was purified via flash chromatography using DCM and MeOH as eluents. To this intermediate 10 eq. LiOH×H$_2$O, and dioxane:H$_2$O 1:1 (15 mL/mmol) were added and the mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XXXVI)

1 eq. ethyl (2R)-2-[(5Sa)-5-[3-chloro-2-methyl-4-[2-(4-methylpiperazin-1-yl)ethoxy] phenyl]-6-(4-fluorophenyl) thieno[2,3-d]pyrimidin-4-yl]oxy-3-[2-[(2-chloropyrimidin-4-yl)methoxy]phenyl]propanoate (0.24 mmol Preparation 29), 2 eq. of the appropriate boronic acid derivative, 0.04 eq. bis(triphenylphosphine)palladium(II) dichloride, 2M Na$_2$CO$_3$ solution (2.5 mL/mmol) and dioxane (2.5 mL/mmol) were stirred under N$_2$ atmosphere at 90° C. until no further conversion was observed. Then LiOH×H$_2$O (416 mg/mmol) was added and the mixture was stirred until no further conversion was observed. Then it was diluted with brine, acidified with 2M HCl and extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XXXVII)

1 eq. paraformaldehyde and 3 eq. NaI were dissolved in DCM (10 ml/mmol paraformaldehyde) and 2.5 eq. from the appropriate alkanoyl-chloride was added (dissolved in 1 ml/mmol DCM). The mixture was stirred at room temperature until no further conversion was observed. Mixture was then filtered and concentrated in vacuo.

General Procedure (XXXVIII)

1 eq. from the appropriate phenol derivative, 3 eq. of the appropriate alcohol, and 3 eq. PPh$_3$ were dissolved in dry toluene (20 ml/mmol), then 3 eq. ditertbutyl azodicarboxylate was added. The mixture was stirred at 50° C. under N$_2$ until no further conversion was observed. The toluene was evaporated under reduced pressure and the residue was purified via flash chromatography using DCM and MeOH as eluents. To this intermediate 10 eq. LiOH×H$_2$O, and dioxane:H$_2$O 1:1 (15 ml/mmol) were added and the mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

General Procedure (XXXIX)

1 eq. Preparation 38, 3 eq. of the appropriate alcohol, and 3 eq. PPh$_3$ were dissolved in dry toluene (20 ml/mmol), then 3 eq. ditertbutyl azodicarboxylate was added. The mixture was stirred at 50° C. under N$_2$ until no further conversion was observed. The toluene was evaporated under reduced pressure and the residue was purified via flash chromatography using DCM and MeOH as eluents. To this intermediate 10 eq. LiOH×H$_2$O, and dioxane:H$_2$O 1:1 (15 ml/mmol) were added and the mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents.

Example 722 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-hydroxyphenyl)pyrimidin-4-yl]methoxy}phenyl)propanoic acid 220 mg (0.25 mmol) Example 30 was dissolved in 5 ml DCM and treated with BBr$_3$ (0.625 ml, 1M in DCM) at 40° C. until no further conversion was observed. The mixture was diluted with water, pH was adjusted to 7 with saturated NaHCO$_3$ solution and extracted with DCM. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents to obtain Example 722. HRMS calculated for C$_{46}$H$_{42}$ClFN$_6$O$_6$S: 860.2559. found 431.1340 (M+2H).

Example 723 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(propan-2-yloxy)phenyl]pyrimidin-4-yl}methoxy)phenyl]propanoic acid Using General Procedure (Ib) and 2-isopropoxyphenylboronic acid as the appropriate boronic acid derivative, Example 723 was obtained. HRMS calculated for C$_{49}$H$_{48}$ClFN$_6$O$_6$S: 902.3029. found 452.1607 (M+2H).

Example 724 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(2-methoxyethoxy)phenyl]pyrimidin-4-yl}methoxy)phenyl]propanoic acid Using General Procedure (Ib) and 2-(2-methoxyethoxy)phenylboronic acid as the appropriate boronic acid derivative, Example 724 was obtained. HRMS calculated for C$_{49}$H$_{48}$ClFN$_6$O$_7$S: 918.2978. found 460.1564 (M+2H).

Example 725 (2R)-3-[2-({2-[2-(benzyloxy)phenyl]pyrimidin-4-yl}methoxy)phenyl]-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid Using General Procedure (Ib) and 2-benzyloxyphenylboronic acid as the appropriate boronic acid derivative, Example 725 was obtained. HRMS calculated for C$_{53}$H$_{48}$ClFN$_6$O$_6$S: 950.3029. found 476.1587 (M+2H).

Example 726 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-ethylphenyl)pyrimidin-4-yl]methoxy}phenyl)propanoic acid Using General Procedure (Ib) and 2-ethylphenylboronic acid as the appropriate boronic acid derivative, Example 726 was obtained. HRMS calculated for C$_{48}$H$_{46}$ClFN$_6$O$_5$S: 872.2923. found 437.1541 (M+2H).

Example 727 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(trifluoromethyl)phenyl]pyrimidin-4-yl}methoxy)phenyl]propanoic acid Using General Procedure (Ib) and 2-(trifluoromethyl)phenylboronic acid as the appropriate boronic acid derivative, Example 727 was obtained. HRMS calculated for C$_{47}$H$_{41}$ClF$_4$N$_6$O$_5$S: 912.2484. found 913.2554 (M+H).

Example 728 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(hydroxymethyl)phenyl]pyrimidin-4-yl}methoxy)phenyl]propanoic acid Using General Procedure (Ib) and 2-(hydroxymethyl)phenylboronic acid as the appropriate boronic acid derivative, Example 728 was obtained. HRMS calculated for C$_{47}$H$_{44}$ClFN$_6$O$_6$S: 874.2716. found 875.2804 (M+H).

Example 729 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[4-methoxy-2-(trifluoromethyl)phenyl]pyrimidin-4-yl}methoxy)phenyl]propanoic acid Using General Procedure (Ia) and [2-[4-methoxy-2-(trifluoromethyl)phenyl]pyrimidin-4-yl]methanol (Preparation 9ej) as the appropriate alcohol, Example 729 was obtained. HRMS calculated for C$_{48}$H$_{43}$ClF$_4$N$_6$O$_6$S: 942.2589. found 943.2636 (M+H).

Example 730 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3-methoxypyridin-4-yl)pyrimidin-4-yl]methoxy}phenyl)propanoic acid Using General Procedure (XXXVI) and 3-methoxypyridine-4-boronic acid as the appropriate boronic acid derivative, Example 730 was obtained. HRMS calculated for $C_{46}H_{43}ClFN_7O_6S$: 875.2668. found 438.6420 (M+2H).

Example 731 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2,5-dimethylpyridin-4-yl)pyrimidin-4-yl]methoxy}phenyl)propanoic acid Using General Procedure (XXXVI) and 2,5-dimethyl-4-(4,4,5,5-tetramethyl-1,3,2-dioxaborolan-2-yl)pyridine as the appropriate boronic acid derivative, Example 731 was obtained. HRMS calculated for $C_{47}H_{45}ClFN_7O_5S$: 873.2875. found 437.6516 (M+2H).

Example 732 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(5,6-dimethylpyridin-3-yl)pyrimidin-4-yl]methoxy}phenyl)propanoic acid Using General Procedure (XXXVI) and 2,3-dimethyl-5-(4,4,5,5-tetramethyl-1,3,2-dioxaborolan-2-yl)pyridine as the appropriate boronic acid derivative, Example 732 was obtained. HRMS calculated for $C_{47}H_{45}ClFN_7O_5S$: 873.2875. found 473.6524 (M+2H).

Example 733 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2,4-dimethoxyphenyl)pyrimidin-4-yl]methoxy}phenyl)propanoic acid Using General Procedure (Ib) and 2,4-dimethoxyphenylboronic acid as the appropriate boronic acid derivative, Example 733 was obtained. HRMS calculated for $C_{48}H_{46}ClFN_6O_7S$: 904.2821. found 453.1494 (M+2H).

Example 734 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(5-methoxy-2-methylpyridin-4-yl)pyrimidin-4-yl]methoxy}phenyl)propanoic acid Using General Procedure (XXXVI) and 5-methoxy-2-methyl-4-(4,4,5,5-tetramethyl-1,3,2-dioxaborolan-2-yl)pyridine as the appropriate boronic acid derivative, Example 734 was obtained. HRMS calculated for $C_{47}H_{45}ClFN_7O_6S$: 889.2825. found 445.6481 (M+2H).

Example 735 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxypyridin-4-yl)pyrimidin-4-yl]methoxy}phenyl)propanoic acid Using General Procedure (XXXVI) and 2-methoxypyridine-4-boronic acid as the appropriate boronic acid derivative, Example 735 was obtained. HRMS calculated for $C_{46}H_{43}ClFN_7O_6S$: 875.2668. found 438.6420 (M+2H).

Example 736 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(pyridin-4-ylmethyl)-1H-pyrazol-5-yl]methoxy}phenyl)propanoic acid Using General Procedure (Ia) and [1-(4-pyridylmethyl)pyrazol-5-yl]methanol (Preparation 9ek) as the appropriate alcohol, Example 736 was obtained. HRMS calculated for $C_{45}H_{43}ClFN_7O_5S$: 847.2719. found 424.6432 (M+2H).

Example 737 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2-methoxyphenyl)-1H-pyrazol-3-yl]methoxy}phenyl)propanoic acid Using General Procedure (Ia) and [1-(2-methoxyphenyl)pyrazol-3-yl]methanol (Preparation 9el) as the appropriate alcohol, Example 737 was obtained. HRMS calculated for $C_{46}H_{44}ClFN_6O_6S$: 862.2716. found 863.2783 (M+H).

Example 738 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2-methoxyphenyl)-1H-pyrazol-5-yl]methoxy}phenyl)propanoic acid Using General Procedure (Ia) and [1-(2-methoxyphenyl)pyrazol-5-yl]methanol (Preparation 9em) as the appropriate alcohol, Example 738 was obtained. HRMS calculated for $C_{46}H_{44}ClFN_6O_6S$: 862.2716. found 863.2807 (M+H).

Example 739 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2-methoxybenzyl)-1H-pyrazol-5-yl]methoxy}phenyl)propanoic acid Using General Procedure (Ia) and [[1-[(2-methoxyphenyl)methyl]pyrazol-5-yl]methanol (Preparation 9en) as the appropriate alcohol, Example 739 was obtained. HRMS calculated for $C_{47}H_{46}ClFN_6O_6S$: 876.2872. found 439.1519 (M+2H).

Example 740 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[1-(2-methoxybenzyl)-1H-pyrazol-3-yl]methoxy}phenyl)propanoic acid Using General Procedure (Ia) and [1-[(2-methoxyphenyl)methyl]pyrazol-3-yl]methanol (Preparation 9eo) as the appropriate alcohol, Example 740 was obtained. HRMS calculated for $C_{47}H_{46}ClFN_6O_6S$: 876.2872. found 439.1490 (M+2H).

Example 741 (2R)-2-{[(5S$_a$)-5-{3-chloro-2-ethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIV) and 1-[2-[2-chloro-3-ethyl-4-(4,4,5,5-tetramethyl-1,3,2-dioxaborolan-2-yl)phenoxy]ethyl]-4-methyl-piperazine (Preparation 5u) as the appropriate boronic acid derivative, Example 741 was obtained as the diastereomer eluting later. HRMS calculated for $C_{48}H_{46}ClFN_6O_6S$: 888.2872. found 445.1515 (M+2H).

Example 742 (2R)-2-{[(5S$_a$)-5-{2-bromo-3-chloro-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIV) and 1-[2-[3-bromo-2-chloro-4-(4,4,5,5-tetramethyl-1,3,2-dioxaborolan-2-yl)

phenoxy]ethyl]-4-methyl-piperazine (Preparation 5v) as the appropriate boronic acid derivative, Example 742 was obtained as the diastereomer eluting later. HRMS calculated for $C_{46}H_{41}BrClFN_6O_6S$: 938.1664. found 470.0914 (M+2H).

Example 743 (2R)-2-{[(5S$_a$)-5-{2,3-dichloro-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid Using General Procedure (XXXIV) and 1-[2-[2,3-dichloro-4-(4,4,5,5-tetramethyl-1,3,2-dioxaborolan-2-yl)phenoxy]ethyl]-4-methyl-piperazine (Preparation 5w) as the appropriate boronic acid derivative, Example 743 was obtained as the diastereomer eluting later. HRMS calculated for $C_{46}H_{41}Cl_2FN_6O_6S$: 894.2169. found 448.1157 (M+2H).

Example 744 (2R)-2-{[(5S$_a$)-5-{3-chloro-2-methyl-4-[2-(piperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid 657 mg (0.95 mmol) ethyl (2R)-2-[(5S$_a$)-[3-chloro-2-methyl-4-[2-(piperazin-1-yl)ethoxy] phenyl]-6-(4-fluorophenyl)thieno[2,3-d]pyrimidin-4-yl]oxy-3-(2-hydroxyphenyl) propanoate (Preparation 8o), 411 mg (1.9 mmol) 2[2-(2-methoxyphenyl)pyrimidin-4-yl] methanol (Preparation 9bp) and 498 mg (1.9 mmol) triphenyl phosphine were dissolved in 25 ml abs. toluene, then 437 mg (1.9 mmol) ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents. The obtained intermediate was dissolved in 10 ml dioxane-water 1:1 and 420 mg (10 mmol) LiOH×H$_2$O was added. The mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents to obtain Example 744. HRMS calculated for $C_{46}H_{42}N_6O_6FSCl$: 860.2559. found 431.1368 (M+2H).

Example 745 (2R)-2-{[(5S$_a$)-5-{3-chloro-4-[2-(4-ethylpiperazin-1-yl)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoic acid 470 mg (0.55 mmol) ethyl (2R)-2-[(5S$_a$)-[3-chloro-2-methyl-4-[2-(4-ethylpiperazin-1-yl)ethoxy]phenyl]-6-(4-fluorophenyl)thieno[2,3-d]pyrimidin-4-yl]oxy-3-[2-[(2-methylsulfanylpyrimidin-4-yl)methoxy]phenyl]propanoate (Preparation 10d), 231 mg (1.65 mmol) 2-fluorophenylboronic acid and 315 mg (1.65 mmol) copper(I) thiophenecarboxylate were dissolved in 10 ml dry THF, then 95 mg (0.0825 mmol) Pd(PPh$_3$)$_4$ was added. The mixture was stirred at 70° C. under nitrogen until no further conversion was observed. Then it was concentrated under reduced pressure and the crude intermediate was purified via flash chromatography using dichloromethane and methanol as eluents. The obtained intermediate was dissolved in 5 ml dioxane-water 1:1 and 231 mg (5.5 mmol) LiOH×H$_2$O was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 5 mM aqueous NH$_4$HCO$_3$ solution and MeCN as eluents to obtain Example 745. HRMS calculated for $C_{47}H_{43}ClF_2N_6O_5S$: 876.2672. found 439.1426 (M+2H).

Example 746 (2R)-2-{[(5S$_a$)-5-{3-chloro-4-[2-(diethylamino)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl) propanoic acid Using General Procedure (XXXV) and N,N-diethylethanolamine as the appropriate alcohol, Example 746 was obtained. HRMS calculated for $C_{45}H_{40}ClF_2N_5O_5S$: 835.2407. found 836.2482 (M+H).

Example 747 (2R)-2-{[(5S$_a$)-5-(3-chloro-4-{2-[ethyl(methyl)amino]ethoxy}-2-methylphenyl)-6-(4-fluorophenyl)thieno[2,3-d]pyrimidin-4-yl]oxy}-3-(2-{[2-(2-fluorophenyl)pyrimidin-4-yl]methoxy}phenyl)propanoic acid Using General Procedure (XXXV) and 2-(N-methyl-ethylamino)ethanol as the appropriate alcohol, Example 747 was obtained. HRMS calculated for $C_{44}H_{38}ClF_2N_5O_5S$: 821.225. found 822.2324 (M+H).

Example 748 (2R)-2-{[(5S$_a$)-5-(3-chloro-4-{2-[cyclopropyl(methyl)amino]ethoxy}-2-methylphenyl)-6-(4-fluorophenyl)thieno[2,3-d]pyrimidin-4-yl]oxy}-3-(2-{[2-(2-fluorophenyl)pyrimidin-4-yl]methoxy}phenyl)propanoic acid Using General Procedure (XXXV) and 2-(cyclopropyl (methyl)amino)ethanol as the appropriate alcohol, Example 748 was obtained. HRMS calculated for $C_{45}H_{38}ClF_2N_5O_5S$: 833.225. found 834.2344 (M+H).

Example 749 (2R)-2-{[(5S$_a$)-5-{3-chloro-2-methyl-4-[2-(piperazin-1-yl)ethoxy]phenyl}-6-(4-fluorophenyl)thieno[2,3-d]pyrimidin-4-yl]oxy}-3-(2-{[2-(2-hydroxyphenyl)pyrimidin-4-yl]methoxy}phenyl) propanoic acid 244 mg (0.283 mmol) Example 30 was dissolved in 6 ml DCM and treated with 0.71 ml BBr$_3$ (1M in DCM) at 40° C. until no further conversion was observed. The mixture was diluted with water, the pH was adjusted to 7 with saturated NaHCO$_3$ solution and extracted with DCM. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents to obtain Example 749. HRMS calculated for $C_{45}H_{40}ClFN_6O_6S$: 846.2403. found 424.1281 (M+2H).

Example 750 (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}propanoic acid Using General Procedure (IIa) and (1-tert-butyl-1H-pyrazol-5-yl)methanol (Preparation 9dt) as the appropriate alcohol, Example 750 was obtained. HRMS calculated for $C_{40}H_{41}ClFN_5O_5S$: 757.2501. found 379.6326 (M+2H).

Example 751 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2,5-dimethylpyridin-4-yl)pyrimidin-4-yl]methoxy}phenyl)propanoic acid Using General Procedure (IIb) and 2,5-dimethylpyridine-4-boronic acid pinacol ester as the appropriate boronic acid derivative, Example 751 was obtained. HRMS calculated for $C_{44}H_{40}ClFN_6O_5S$: 818.2454. found 410.1319 (M+2H).

Example 752 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[1-(propan-2-yl)-1H-pyrazol-5-yl]methoxy}phenyl)propanoic acid Using General Procedure IIa and [1-(propan-2-yl)-1H-pyrazol-5-yl]methanol as the appropriate alcohol, Example 752 was obtained. HRMS calculated for $C_{39}H_{39}ClFN_5O_5S$: 743.2344. found 744.2422 (M+H).

Example 753 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-[2-({2-[2-(2-methoxyethoxy)phenyl]pyrimidin-4-yl}methoxy)phenyl]propanoic acid Using General Procedure (IIb) and 2-(2-methoxyethoxy)phenylboronic acid as the appropriate boronic acid derivative, Example 753 was obtained. HRMS calculated for $C_{46}H_{43}ClFN_5O_7S$: 863.2556. found 864.2656 (M+H).

Example 754 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[1-(2-ethoxyethyl)-1H-pyrazol-5-yl]methoxy}phenyl)propanoic acid Using General Procedure (IIa) and [1-(2-ethoxyethyl)pyrazol-5-yl]methanol (Preparation 9ep) as the appropriate alcohol, Example 754 was obtained. HRMS calculated for $C_{40}H_{41}ClFN_5O_6S$: 773.245. found 774.2551 (M+H).

Example 755 (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(2,3-difluorophenyl)thieno[2,3-d]pyrimidin-4-yl]oxy}propanoic acid 212 mg (0.317 mmol) ethyl (2R)-2-[(5S$_a$)-5-[3-chloro-2-methyl-4-[2-dimethylaminoethoxy]phenyl]-6-(2,3-difluorophenyl)thieno[2,3-d]pyrimidin-4-yl]oxy-3-(2-hydroxyphenyl)propanoate (Preparation 8n), 147 mg (0.95 mmol) (1-tert-butyl-1H-pyrazol-5-yl)methanol (Preparation 9dt) and 249 mg (0.95 mmol) triphenyl phosphine were dissolved in 10 ml abs. toluene, then 222 mg (0.96 mmol) ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents. The obtained intermediate was dissolved in 7 ml dioxane and 7 ml water and 133 mg (3.17 mmol) LiOH×H$_2$O was added. The mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents to obtain Example 755. HRMS calculated for $C_{40}H_{40}ClF_2N_5O_5S$: 775.2407. found 776.2498 (M+H).

Example 756 Ethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (IIa) Step A and [2-(2-methoxyphenyl)pyrimidin-4-yl]methanol (Preparation 9bp) as the appropriate alcohol, Example 756 was obtained. HRMS calculated for $C_{46}H_{43}ClFN_5O_6S$: 847.2607. found 424.6386 (M+2H).

Example 757 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoic acid Using General Procedure (IIb) and 2-fluorophenylboronic acid as the appropriate boronic acid derivative, Example 757 was obtained. HRMS calculated for $C_{43}H_{36}ClF_2N_5O_5S$: 807.2094. found 808.2171 (M+H).

Example 758 (2R)-2-{[(5R$_a$)-5-{3-chloro-2-methyl-4-[2-(4-methylpiperazin-1-yl)ethoxy]phenyl}-6-(4-phenoxyphenyl)thieno[2,3-d]pyrimidin-4-yl]oxy}-3-(2-{[2-(2-methoxyphenyl)pyrimidin-4-yl]methoxy}phenyl)propanoic acid and Example 759 (2R)-2-{[(5S$_a$)-5-{3-chloro-2-methyl-4-[2-(4-methylpiperazin-1-yl)ethoxy]phenyl}-6-(4-phenoxyphenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIIIa) and 4-phenoxyphenylboronic acid as the appropriate boronic acid derivative, the diastereomer eluting earlier was isolated as Example 758 [HRMS calculated $C_{53}H_{49}ClN_6O_7S$: 948.3072. found 475.1602 (M+2H)] and the diastereomer eluting later as Example 759 [HRMS calculated $C_{53}H_{49}ClN_6O_7S$: 948.3072. found 475.1602 (M+2H)].

Example 760 (2R)-2-{[(5S$_a$)-5-{3-chloro-2-methyl-4-[2-(4-methylpiperazin-1-yl)ethoxy]phenyl}-6-(4-methoxyphenyl)thieno[2,3-d]pyrimidin-4-yl]oxy}-3-(2-{[2-(2-methoxyphenyl)pyrimidin-4-yl]methoxy}phenyl)propanoic acid and Example 761 (2R)-2-{[(5R$_a$)-5-{3-chloro-2-methyl-4-[2-(4-methylpiperazin-1-yl)ethoxy]phenyl}-6-(4-methoxyphenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIIIa) and 4-methoxyphenylboronic acid as the appropriate boronic acid derivative, the diastereomer eluting earlier was isolated as Example 760 [HRMS calculated $C_{48}H_{47}ClN_6O_7S$: 886.2915. found 444.1536 (M+2H)] and the diastereomer eluting later as Example 761 [HRMS calculated $C_{48}H_{47}ClN_6O_7S$: 886.2915. found 444.1525 (M+2H)].

Example 762 (2R)-2-[(6-[4-(benzyloxy)phenyl]-(5S$_a$)-5-{3-chloro-2-methyl-4-[2-(4-methylpiperazin-1-yl)ethoxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIa) and 4-benzyloxyphenylboronic acid as the appropriate boronic acid derivative, the diastereomer eluting later was isolated as Example 762. HRMS calculated $C_{54}H_{51}ClN_6O_7S$: 962.3228. found 482.1698 (M+2H).

Example 763 (2R)-2-[((5R$_a$)-5-{3-chloro-2-methyl-4-[2-(4-methylpiperazin-1-yl)ethoxy]phenyl}-6-{4-[2-(morpholin-4-yl)ethoxy]phenyl}thieno[2,3-d]pyrimidin-4-yl)oxy]-3-(2-{[2-(2-methoxyphenyl)pyrimidin-4-yl]methoxy}phenyl)propanoic acid and Example 764 (2R)-2-[((5S$_a$)-5-{3-chloro-2-methyl-4-[2-(4-methylpiperazin-1-yl)ethoxy]phenyl}-6-{4-[2-(morpholin-4-yl)ethoxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and N-(2-hydroxyethyl)morpholine as the appropriate alcohol, the diastereomer eluting earlier was isolated as Example 763 [HRMS calculated $C_{53}H_{56}ClN_7O_8S$: 985.3600. found 493.6883 (M+2H)] and the diastereomer eluting later as Example 764 [HRMS calculated $C_{53}H_{56}ClN_7O_8S$: 985.3600. found 493.6876 (M+2H)].

Example 765 (2R)-2-[((5R$_a$)-5-{3-chloro-2-methyl-4-[2-(4-methylpiperazin-1-yl)ethoxy]phenyl}-6-{4-(2-phenylethoxy)phenyl]thieno[2,3-d]pyrimidin-4-yl)oxy]-3-(2-{[2-(2-methoxyphenyl)pyrimidin-4-yl]methoxy}phenyl)propanoic acid and Example 766 (2R)-2-[((5S$_a$)-5-{3-chloro-2-methyl-4-[2-(4-methylpiperazin-1-yl)ethoxy]phenyl}-6-{4-(2-phenylethoxy)phenyl]thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 2-phenylethanol as the appropriate alcohol, the diastereomer eluting earlier was isolated as Example 765 [HRMS calculated $C_{55}H_{53}ClN_6O_7S$: 976.3385. found 489.1787 (M+2H] and the diastereomer eluting later as Example 766 [HRMS calculated $C_{55}H_{53}ClN_6O_7S$: 976.3385. found 489.1743 (M+2H)].

Example 767 (2R)-2-[((5S$_a$)-5-{3-chloro-2-methyl-4-[2-(4-methylpiperazin-1-yl)ethoxy]phenyl}-6-{4-[(2-methylbenzyl)oxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 2-methylbenzyl alcohol as the appropriate alcohol, Example 767 was obtained as the diastereomer eluting later. HRMS calculated $C_{55}H_{53}ClN_6O_7S$: 976.3385. found 489.1774 (M+2H).

Example 768 (2R)-2-[((5S$_a$)-5-{3-chloro-2-methyl-4-[2-(4-methylpiperazin-1-yl)ethoxy]phenyl}-6-{4-[(4-methylbenzyl)oxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 4-methylbenzyl alcohol as the appropriate alcohol, Example 768 was obtained as the diastereomer eluting later. HRMS calculated $C_{55}H_{53}ClN_6O_7S$: 976.3385. found 489.1775 (M+2H).

Example 769 (2R)-2-[((5S$_a$)-5-{3-chloro-2-methyl-4-[2-(4-methylpiperazin-1-yl)ethoxy]phenyl}-6-[4-(pyridin-2-ylmethoxy)phenyl]thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 2-pyridinemethanol as the appropriate alcohol, Example 769 was obtained as the diastereomer eluting later. HRMS calculated $C_{53}H_{50}ClN_7O_7S$: 963.3181. found 482.6681 (M+2H).

Example 770 (2R)-2-[((5S$_a$)-5-{3-chloro-2-methyl-4-[2-(4-methylpiperazin-1-yl)ethoxy]phenyl}-6-{4-[(4-methoxybenzyl)oxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 4-methoxybenzylalcohol as the appropriate alcohol, Example 770 was obtained as the diastereomer eluting later. HRMS calculated $C_{55}H_{53}ClN_6O_8S$: 992.3334. found 497.1725 (M+2H).

Example 771 (2R)-2-[((5S$_a$)-5-{3-chloro-2-methyl-4-[2-(4-methylpiperazin-1-yl)ethoxy] phenyl}-6-{4-[(1-methyl-1H-pyrazol-5-yl)methoxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and (1-methyl-1H-pyrazol-5-yl)methanol as the appropriate alcohol, Example 771 was obtained as the diastereomer eluting later. HRMS calculated $C_{52}H_{51}ClN_8O_7S$: 966.329. found 484.1700 (M+2H).

Example 772 (2R)-2-[((5S$_a$)-5-{3-chloro-2-methyl-4-[2-(4-methylpiperazin-1-yl)ethoxy]phenyl}-6-[4-(pyridin-3-ylmethoxy)phenyl]thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 3-pyridinemethanol as the appropriate alcohol, Example 772 was obtained as the diastereomer eluting later. HRMS calculated $C_{53}H_{50}ClN_7O_7S$: 963.3181. found 482.6673 (M+2H).

Example 773 (2R)-2-[((5S$_a$)-5-{3-chloro-2-methyl-4-[2-(4-methylpiperazin-1-yl)ethoxy]phenyl}-6-{4-[(3-methylbenzyl)oxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 3-methylbenzyl alcohol as the appropriate alcohol, Example 773 was obtained as the diastereomer eluting later. HRMS calculated $C_{55}H_{53}ClN_6O_7S$: 976.3385. found 489.1780 (M+2H).

Example 774 (2R)-2-[((5S$_a$)-5-{3-chloro-2-methyl-4-[2-(4-methylpiperazin-1-yl)ethoxy]phenyl}-6-[4-(pyridin-4-ylmethoxy)phenyl]thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 4-pyridinemethanol as the appropriate alcohol Example 774 was obtained as the diastereomer eluting later. HRMS calculated $C_{53}H_{50}ClN_7O_7S$: 963.3181. found 482.6644 (M+2H).

Example 775 (2R)-2-[(6-{4-[(4-chlorobenzyl)oxy]phenyl}-(5S$_a$)-5-{3-chloro-2-methyl-4-[2-(4-methylpiperazin-1-yl)ethoxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 4-chlorobenzyl alcohol as the appropriate alcohol, Example 775 was obtained as the diastereomer eluting later. HRMS calculated $C_{54}H_{50}Cl_2N_6O_7S$: 996.2839. found 499.1510 (M+2H).

Example 776 (2R)-2-[((5S$_a$)-5-{3-chloro-2-methyl-4-[2-(4-methylpiperazin-1-yl)ethoxy] phenyl}-6-{4-[(1-methyl-1H-pyrazol-3-yl)methoxy]phenyl}thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and (1-methyl-1H-pyrazol-3-yl)methanol as the appropriate alcohol, Example 776 was obtained as the diastereomer eluting later. HRMS calculated $C_{52}H_{51}ClN_8O_7S$: 966.329. found 484.1727 (M+2H).

Example 777 (2R)-2-[((5S$_a$)-5-{3-chloro-2-methyl-4-[2-(4-methylpiperazin-1-yl)ethoxy]phenyl}-6-[4-(thiophen-2-ylmethoxy)phenyl]thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 2-thiophenemethanol as the appropriate alcohol, Example 777 was obtained as the diastereomer eluting later. HRMS calculated $C_{52}H_{49}ClN_6O_7S_2$: 968.2793. found 485.1469 (M+2H).

Example 778 (2R)-2-[((5S$_a$)-5-{3-chloro-2-methyl-4-[2-(4-methylpiperazin-1-yl)ethoxy]phenyl}-6-[4-(thiophen-3-ylmethoxy)phenyl]thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIb) and 3-thiophenemethanol as the appropriate alcohol, Example 778 was obtained as the diastereomer eluting later. HRMS calculated $C_{52}H_{49}ClN_6O_7S_2$: 968.2793. found 485.1450 (M+2H).

Example 779 (2R)-2-[((5S$_a$)-5-{3-chloro-2-methyl-4-[2-(4-methylpiperazin-1-yl)ethoxy] phenyl}-6-{4-[(1-methyl-1H-pyrazol-3-yl)methoxy]phenyl}thieno[2,3-d]pyrimidin-4-yl)oxy]-3-(2-{[1-(2,2,2-trifluoroethyl)-1H-pyrazol-5-yl]methoxy}phenyl)propanoic acid 216 mg (0.25 mmol) Preparation 32, 84 mg (0.75 mmol) (1-methyl-1H-pyrazol-3-yl)methanol and 197 mg (0.75 mmol) PPh$_3$ were dissolved in 5 ml toluene, then 173 mg (0.75 mmol) ditertbutyl azodicarboxylate was added. The mixture was stirred at 50° C. under N$_2$ until no further conversion was observed. The toluene was evaporated under reduced pressure and the residue was purified via flash chromatography using DCM and MeOH. To this intermediate 105 mg LiOH×H$_2$O (2.5 mmol), 5 ml dioxane and 5 ml H$_2$O were added and the mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents Example 779 was obtained as the diastereomer eluting later. HRMS calculated for $C_{46}H_{46}ClF_3N_8O_6S$: 930.2902. found 466.1531 (M+2H).

Example 780 (2R)-2-[((5S$_a$)-5-{3-chloro-2-methyl-4-[2-(4-methylpiperazin-1-yl)ethoxy] phenyl}-6-{4-[(1-methyl-1H-pyrazol-3-yl)methoxy]phenyl}thieno[2,3-d]pyrimidin-4-yl)oxy]-3-[2-(2,2,2-trifluoroethoxy)phenyl]propanoic acid 215 mg (0.27 mmol) Preparation 33, 92 mg (0.82 mmol) (1-methyl-1H-pyrazol-3-yl)methanol and 215 mg (0.82 mmol) PPh$_3$ were dissolved in 5 ml toluene, then 189 mg (0.82 mmol) ditertbutyl azodicarboxylate was added. The mixture was stirred at 50° C. under N$_2$ until no further conversion was observed. The toluene was evaporated under reduced pressure and the residue was purified via flash chromatography using DCM and MeOH. To this intermediate 113 mg LiOH×H$_2$O (2.7 mmol), 5 ml dioxane and 5 ml H$_2$O were added and the mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents to obtain Example 780. HRMS calculated for $C_{42}H_{42}ClF_3N_6O_6S$: 850.2527. found 426.1333 (M+2H).

Example 781 (2R)-2-{[(5S$_a$)-5-{3-chloro-2-methyl-4-[2-(4-methylpiperazin-1-yl)ethoxy]phenyl}-6-(4-phenylbut-1-yn-1-yl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIIIc) and 4-phenyl-1-butyne as the appropriate alkyne, Example 781 was obtained as the diastereomer eluting later. HRMS calculated for $C_{51}H_{49}ClN_6O_6S$: 908.3123. found 455.1646 (M+2H).

Example 782 (2R)-2-{[(5S$_a$)-5-{3-chloro-2-methyl-4-[2-(4-methylpiperazin-1-yl)ethoxy]phenyl}-6-(3-phenoxyprop-1-yn-1-yl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIIIc) and phenyl propargyl ether as the appropriate alkyne, Example 782 was obtained as the diastereomer eluting later. HRMS calculated for $C_{50}H_{47}N_6O_7SCl$: 910.2915. found 456.1537 (M+2H).

Example 783 (2R)-2-{[(5S$_a$)-5-{3-chloro-2-methyl-4-[2-(4-methylpiperazin-1-yl)ethoxy]phenyl}-6-(5-phenylpent-1-yn-1-yl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIIIc) and 5-phenyl-1-pentyne as the appropriate alkyne, Example 783 was obtained as the diastereomer eluting later. HRMS calculated for $C_{52}H_{51}ClN_6O_6S$: 922.3279. found 462.1712 (M+2H).

Example 784 (2R)-2-{[(5S$_a$)-5-{3-chloro-2-methyl-4-[2-(4-methylpiperazin-1-yl)ethoxy]phenyl}-6-(3-methoxyprop-1-yn-1-yl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIIIc) and methyl propargyl ether as the appropriate alkyne, Example 784 was obtained as the diastereomer eluting later. HRMS calculated for $C_{45}H_{45}ClN_6O_7S$: 848.2759. found 425.1431 (M+2H).

Example 785 (2R)-2-[((5S$_a$)-5-{3-chloro-2-methyl-4-[2-(4-methylpiperazin-1-yl)ethoxy]phenyl}-6-[4-(morpholin-4-yl)but-1-yn-1-yl]thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIc) and 4-(3-butyn-1-yl)-morpholine as the appropriate alkyne, Example 785 was obtained as the diastereomer eluting later. HRMS calculated for $C_{49}H_{52}ClN_7O_7S$: 917.3337. found 459.6732 (M+2H).

Example 786 (2R)-2-[((5S$_a$)-5-{3-chloro-2-methyl-4-[2-(4-methylpiperazin-1-yl)ethoxy]phenyl}-6-[3-(morpholin-4-yl)prop-1-yn-1-yl]thieno[2,3-d]pyrimidin-4-yl)oxy]-3-(2-{[2-(2-methoxyphenyl)pyrimidin-4-yl]methoxy}phenyl)propanoic acid Using General Procedure (XXXIIIc) and 4-(prop-2-yn-1-yl)morpholine as the appropriate alkyne, Example 786 was obtained as the diastereomer eluting later. HRMS calculated for $C_{48}H_{50}ClN_7O_7S$: 903.3181. found 452.6657 (M+2H).

Example 787 methyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXb) with Example 30 as the appropriate acid and MeOH as the appropriate alcohol, Example 787 was obtained. HRMS calculated for $C_{48}H_{46}ClFN_6O_6S$: 888.2872. found 889.2942 (M+H).

Example 788 propan-2-yl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXb) with Example 30 as the appropriate acid and 2-propanol as the appropriate alcohol, Example 788 was obtained. HRMS calculated for $C_{50}H_{50}ClFN_6O_6S$: 916.3185. found 459.1679 (M+2H).

Example 789 2-methoxyethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXb) with Example 30 as the appropriate acid and 2-methoxyethanol as the appropriate alcohol, Example 789 was obtained. HRMS calculated for $C_{50}H_{50}ClFN_6O_7S$: 932.3134. found 467.1658 (M+2H).

Example 790 ethyl (2R)-2-{[(5S$_a$)-5-{3-chloro-4-[2-(4-ethylpiperazin-1-yl)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXa) with Example 745 as the appropriate acid, Example 790 was obtained. HRMS calculated for $C_{49}H_{47}ClF_2N_6O_5S$: 904.2985. found 905.3029 (M+H).

Example 791 ethyl (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoate Using General Procedure (XXa) and Example 70 as the appropriate acid, Example 791 was obtained. HRMS calculated for $C_{45}H_{50}ClFN_6O_5S$: 840.3236. found 841.3319 (M+H).

Example 792 ethyl (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}propanoate 260 mg (0.4 mmol) ethyl (2R)-2-[(5S$_a$)-5-[3-chloro-2-methyl-4-[2-(4-methylpiperazin-1-yl)ethoxy]phenyl]-6-prop-1-ynyl-thieno[2,3-d]pyrimidin-4-yl]oxy-3-(2-hydroxyphenyl)propanoate (Preparation 8i), 185 mg (1.2 mmol) (1-tert-butyl-1H-pyrazol-5-yl)methanol (Preparation 9dt) and 276 mg (1.2 mmol) triphenyl phosphine were dissolved in 7 ml abs. toluene then 315 mg (1.2 mmol) ditertbutyl azodicarboxylate was added. The mixture was stirred at 50° C. under nitrogen until no further conversion was observed. Volatiles were evaporated under reduced pressure and the crude intermediate was purified via flash chromatography using DCM and methanol as eluents to obtain Example 792. HRMS calculated for $C_{42}H_{49}ClN_6O_5S$: 756.2861. found 393.1677 (M+2H).

Example 793 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-hydroxyphenyl)pyrimidin-4-yl]methoxy}phenyl)propanoate Using General Procedure (XXa) with Example 722 as the appropriate acid, Example 793 was obtained. HRMS calculated for $C_{48}H_{46}ClFN_6O_6S$: 888.2872. found 889.2902.

Example 794 ethyl (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}propanoate Using General Procedure (XXa) with Example 750 as the appropriate acid, Example 794 was obtained. HRMS calculated for $C_{42}H_{45}ClFN_5O_5S$: 785.2814. found 393.6469 (M+2H).

Example 795 ethyl (2R)-2-{[(5S$_a$)-5-{3-chloro-2-methyl-4-[2-(piperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate 657 mg (0.95 mmol) ethyl (2R)-2-[(5S$_a$)-[3-chloro-2-methyl-4-[2-(piperazin-1-yl)ethoxy] phenyl]-6-(4-fluorophenyl)thieno[2,3-d]pyrimidin-4-yl]oxy-3-(2-hydroxyphenyl) propanoate (Preparation 8o), 411 mg (1.9 mmol) 2-[2-(2-methoxyphenyl)pyrimidin-4-yl] methanol (Preparation 9bp) and 498 mg (1.9 mmol) triphenyl phosphine were dissolved in 25 ml abs. toluene, then 437 mg (1.9 mmol) ditertbutyl azodicarboxylate was added. The mixture was stirred at 50° C. under nitrogen until no further conversion was observed. The volatiles were evaporated under reduced pressure and the crude intermediate was purified via flash chromatography using ethyl acetate and methanol as eluents to obtain Example 795. HRMS calculated for $C_{48}H_{46}ClFN_6O_6S$: 888.2872. found 445.1502 (M+2H).

Example 796 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(2-methoxyethoxy)phenyl]pyrimidin-4-yl}methoxy)phenyl]propanoate Using General Procedure (XXa) with Example 724 as the appropriate acid, Example 796 was obtained. HRMS calculated for $C_{51}H_{52}ClFN_6O_7S$: 946.3291. found 474.1723 (M+2H).

Example 797 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXa) with Example 114 as the appropriate acid, Example 797 was obtained. HRMS calculated for $C_{48}H_{45}ClF_2N_6O_5S$: 890.2829. found 446.1503 (M+2H).

Example 798 ethyl (2R)-2-{[(5S$_a$)-5-{3-chloro-2-methyl-4-[2-(piperazin-1-yl)ethoxy]phenyl}-6-(4-fluorophenyl)thieno[2,3-d]pyrimidin-4-yl]oxy}-3-(2-{[2-(2-hydroxyphenyl)pyrimidin-4-yl]methoxy}phenyl)propanoate Using General Procedure (XXa) with Example 749 as the appropriate acid, Example 798 was obtained. HRMS calculated for $C_{47}H_{44}ClFN_6O_6S$: 874.2716. found 875.2812 (M+H).

Example 799 2-methoxyethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXc) with Example 757 as the appropriate acid and 2-bromoethyl methyl ether as the appropriate alkyl halide, Example 799 was obtained. HRMS calculated for $C_{46}H_{42}ClF_2N_5O_6S$: 865.2512. found 866.2581 (M+H).

Example 800 2-methoxyethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-[2-({2-[2-(2-methoxyethoxy)phenyl]pyrimidin-4-yl}methoxy)phenyl]propanoate Using General Procedure (XXb) with Example 753 as the appropriate acid and 2-methoxyethanol as the appropriate alcohol, Example 800 was obtained. HRMS calculated for $C_{49}H_{49}ClFN_5O_8S$: 921.2974. found 461.6576 (M+2H).

Example 801 ethyl (2R)-2-{[(5S$_a$)-5-(3-chloro-4-{2-[ethyl(methyl)amino]ethoxy}-2-methylphenyl)-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXa) with Example 747 as the appropriate acid, Example 801 was obtained. HRMS calculated for $C_{46}H_{42}ClF_2N_5O_5S$: 849.2563. found 850.2645 (M+H).

Example 802 2-methoxyethyl (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}propanoate Using General Procedure (XXc) with Example 750 as the appropriate acid and 2-bromoethyl methyl ether as the appropriate alkyl halide, Example 802 was obtained. HRMS calculated for $C_{43}H_{47}ClFN_5O_6S$: 815.2919. found 816.3029 (M+H).

Example 803 2-methoxyethyl (2R)-2-{[(5S$_a$)-5-(3-chloro-4-{2-[ethyl(methyl)amino]ethoxy}-2-methylphenyl)-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXc) with Example 747 as the appropriate acid and 2-bromoethyl methyl ether as the appropriate alkyl halide, Example 803 was obtained. HRMS calculated for $C_{47}H_{44}ClF_2N_5O_6S$: 879.2669. found 880.2722 (M+H).

Example 804 ethyl (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(2,3-difluorophenyl)thieno[2,3-d]pyrimidin-4-yl]oxy}propanoate Using General Procedure (XXa) with Example 755 as the appropriate acid, Example 804 was obtained. HRMS calculated for $C_{42}H_{44}ClF_2N_5O_5S$: 803.272. found 804.2792 (M+H).

Example 805 2-methoxyethyl (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methyl-phenyl}-6-(2,3-difluorophenyl)thieno[2,3-d]pyrimidin-4-yl]oxy}propanoate Using General Procedure (XXc) with Example 755 as the appropriate acid and 2-bromoethyl methyl ether as the appropriate alkyl halide, Example 805 was obtained. HRMS calculated for $C_{43}H_{46}ClF_2N_5O_6S$: 833.2825. found 834.2926 (M+H).

Example 806 ethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-[2-({2-[2-(2-methoxyethoxy)phenyl]pyrimidin-4-yl}methoxy)phenyl]propanoate Using General Procedure (XXa) with Example 753 as the appropriate acid, Example 806 was obtained. HRMS calculated for $C_{48}H_{47}ClFN_5O_7S$: 891.2869. found 446.6493 (M+2H).

Example 807 ethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXa) with Example 757 as the appropriate acid, Example 807 was obtained. HRMS calculated for $C_{45}H_{40}ClF_2N_5O_5S$(.HCl): 835.2407. found 836.2449 (M+H).

Example 808 2,2,2-trifluoroethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate 250 mg (0.286 mmol) Example 30 was dissolved in 10 ml DCM, then 41 µL (0.572 mmol) 2,2,2-trifluoroethanol, 223 mg (0.429 mmol) PyBOP and 80 µl (0.572 mmol) triethylamine were added. The mixture was stirred at room temperature under $N_2$ atmosphere until no further conversion was observed. Then it was diluted with water and extracted with dichloromethane. The combined organic phases were dried over $Na_2SO_4$, filtered and concentrated under reduced pressure and purified via preparative reversed phase chromatography using 25 mM aqueous $NH_4HCO_3$ solution and MeCN as eluents to obtain Example 808. HRMS calculated for $C_{49}H_{45}ClF_4N_6O_6S$: 956.2746. found 957.2821 (M+H).

Example 809 2,3-dihydro-1H-inden-5-yl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate 438 mg (0.5 mmol) Example 30, 134 mg (1 mmol) 5-indanol, and 140 µl (1 mmol) triethylamine were dissolved in 10 ml DCM, then 520 mg (1 mmol) PyBOP was added at 0° C. The mixture was stirred at room temperature under $N_2$ atmosphere until no further conversion was observed. Then it was diluted with water and extracted with dichloromethane. The combined organic phases were dried over $Na_2SO_4$, filtered and concentrated under reduced pressure and purified via preparative reversed phase chromatography using 25 mM aqueous $NH_4HCO_3$ solution and MeCN as eluents to obtain Example 809. HRMS calculated for $C_{56}H_{52}ClFN_6O_6S$: 990.3342. found 496.1739 (M+2H).

Example 810 {[(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxy phenyl)pyrimidin-4-yl]methoxy}phenyl)propanoyl]oxy}methyl 2,2-dimethylpropanoate Using General Procedure (XXc) with Example 30 as the appropriate acid and chloromethyl pivalate as the appropriate alkyl halide, Example 810 was obtained. HRMS calculated for $C_{53}H_{54}ClFN_6O_8S$: 988.3396. found 495.175 (M+2H).

Example 811 (5-methyl-2-oxo-1,3-dioxol-4-yl)methyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d] pyrimidin-4-yl]oxy}-3-(2-{[2-(2-methoxyphenyl)pyrimidin-4-yl]methoxy}phenyl)propanoate Using General Procedure (XXc) with Example 30 as the appropriate acid and 4-chloromethyl-5-methyl-1,3-dioxol-2-one as the appropriate alkyl halide, Example 811 was obtained. HRMS calculated for $C_{52}H_{48}ClFN_6O_9S$: 986.2876. found 494.1504 (M+2H).

Example 812 2-(dimethylamino)-2-oxoethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) with Example 30 as the appropriate acid and 2-chloro-N,N-dimethylacetamide as the appropriate alkyl halide, Example 812 was obtained. HRMS calculated for $C_{51}H_{51}ClFN_7O_7S$: 959.3243. found 480.6699 (M+2H).

Example 813 2-(dimethylamino)ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate 500 mg (0.571 mmol) Example 30 was dissolved in 3 ml DCM, then 102 mg (1.142 mmol) N,N-dimethylethanolamine, 594 mg (1.142 mmol) PYBOP and 160 µl (1.142 mmol) triethylamine were added. The mixture was stirred at room temperature under $N_2$ atmosphere until no further conversion was observed. Then it was diluted with water, treated with $NaHCO_3$ and extracted with dichloromethane. The combined organic phases were dried over $Na_2SO_4$, filtered and concentrated under reduced pressure and purified via preparative reversed phase chromatography using 25 mM aqueous $NH_4HCO_3$ solution and MeCN as eluents to obtain Example 813. HRMS calculated for $C_{51}H_{53}ClFN_7O_6S$: 945.3451. found 473.6805 (M+2H).

Example 814 2-(2-methoxyethoxy)ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) with Example 30 as the appropriate acid and 1-bromo-2-(2-methoxyethoxy)ethane as the appropriate alkyl halide, Example 814 was obtained. HRMS calculated for $C_{52}H_{54}ClFN_6O_8S$: 976.3396. found 489.1763 (M+2H).

Example 815 octyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) and Example 30 as the appropriate acid and 1-bromooctane as the appropriate alkyl-halide, Example 815 was obtained. HRMS calculated for $C_{55}H_{60}N_6O_6FSCl$: 986.3968. found: 987.4025 (M+H).

Example 816 2-(dimethylamino)-2-oxoethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXc) with Example 114 as the appropriate acid and 2-chloro-N,N-dimethylacetamide as the appropriate alkyl halide, Example 816 was obtained. HRMS calculated for $C_{50}H_{48}ClF_2N_7O_6$: 947.3043. found 948.3137 (M+H).

Example 817 2-(dimethylamino)-2-oxoethyl (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}propanoate Using General Procedure (XXc) and Example 750 as the appropriate acid and 2-chloro-N,N-dimethylacetamide as the appropriate alkyl halide, Example 817 was obtained. HRMS calculated for $C_{44}H_{48}ClFN_6O_6S$: 842.3029. found 422.1599 (M+2H).

Example 818 2-(dimethylamino)-2-oxoethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXc) with Example 757 as the appropriate acid and 2-chloro-N,N-dimethylacetamide as the appropriate alkyl halide, Example 818 was obtained. HRMS calculated for $C_{47}H_{43}ClF_2N_6O_6S$: 892.2621. found 893.2671 (M+H).

Example 819 2-(dimethylamino)-2-oxoethyl (2R)-2-{[(5S$_a$)-5-{3-chloro-4-[2-(dimethyl amino)ethoxy]-2-methylphenyl}-6-(4-fluorophenyl)thieno[2,3-d]pyrimidin-4-yl]oxy}-3-[2-({2-[2-(2-methoxyethoxy)phenyl]pyrimidin-4-yl}methoxy)phenyl]propanoate Using General Procedure (XXc) with Example 753 as the appropriate acid and 2-chloro-N,N-dimethylacetamide as the appropriate alkyl halide, Example 819 was obtained. HRMS calculated for $C_{50}H_{50}ClFN_6O_8S$: 948.3083. found 475.1624 (M+2H).

Example 820 (5-methyl-2-oxo-1,3-dioxol-4-yl)methyl (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}propanoate Using General Procedure (XXc) with Example 750 as the appropriate acid and 4-chloromethyl-5-methyl-1,3-dioxol-2-one as the appropriate alkyl halide, Example 820 was obtained. HRMS calculated for $C_{45}H_{45}ClFN_5O_8S$: 869.2661. found 870.2700 (M+H).

Example 821 {[(2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}propanoyl]oxy}methyl 2,2-dimethylpropanoate Using General Procedure (XXc) with Example 750 as the appropriate acid and chloromethyl pivalate as the appropriate alkyl halide, Example 821 was obtained. HRMS calculated for $C_{46}H_{51}ClFN_5O_7S$: 871.3182. found 872.3248 (M+H).

Example 822 2-(dimethylamino)-2-oxoethyl (2R)-2-{[(5S$_a$)-5-(3-chloro-4-{2-[ethyl(methyl)amino]ethoxy}-2-methylphenyl)-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXc) with Example 747 as the appropriate acid and 2-chloro-N,N-dimethylacetamide as the appropriate alkyl halide, Example 822 was obtained. HRMS calculated for $C_{48}H_{45}ClF_2N_6O_6S$: 906.2778. found 907.2874 (M+H).

Example 823 (5-methyl-2-oxo-1,3-dioxol-4-yl)methyl (2R)-2-{[(5S$_a$)-5-(3-chloro-4-{2-[ethyl(methyl)amino]ethoxy}-2-methylphenyl)-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXc) with Example 747 as the appropriate acid and 4-chloromethyl-5-methyl-1,3-dioxol-2-one as the appropriate alkyl halide, Example 823 was obtained. HRMS calculated for $C_{49}H_{42}ClF_2N_5O_8S$: 933.2411. found 934.2522 (M+H).

Example 824 (5-methyl-2-oxo-1,3-dioxol-4-yl)methyl (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(2,3-difluorophenyl)thieno[2,3-d]pyrimidin-4-yl]oxy}propanoate Using General Procedure (XXc) with Example 755 as the appropriate acid and 4-chloromethyl-5-methyl-1,3-dioxol-2-one as the appropriate alkyl halide, Example 824 was obtained. HRMS calculated for $C_{45}H_{44}ClF_2N_5O_8S$: 887.2567. found 888.2638 (M+H).

Example 825 2-(dimethylamino)-2-oxoethyl (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(2,3-difluorophenyl)thieno[2,3-d]pyrimidin-4-yl]oxy}propanoate Using General Procedure (XXc) with Example 755 as the appropriate acid and 2-chloro-N,N-dimethylacetamide as the appropriate alkyl halide, Example 825 was obtained. HRMS calculated for $C_{44}H_{47}ClF_2N_6O_6S$: 860.2935. found 861.2966 (M+H).

Example 826 (2R)-2-{[(5R$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid 1 eq. ethyl (2R)-2-[(5R$_a$)-5-[3-chloro-2-methyl-4-[2-(4-methylpiperazin-1-yl)ethoxy] phenyl]-6-(4-fluorophenyl)thieno[2,3-d]pyrimidin-4-yl]oxy-3-[2-[(2-methylsulfanyl pyrimidin-4-yl)methoxy]phenyl]propanoate (Preparation 10e), 3.0 eq. [2-(2-methoxy phenyl)pyrimidin-4-yl]methanol (Preparation 9bp) and 3.0 eq. copper(I) thiophenecarboxylate were dissolved in dry THF (0.1 M for Preparation 10e), then 0.15 eq. Pd(PPh$_3$)$_4$ was added. The mixture was stirred at 70° C. under nitrogen until no further conversion was observed. Then it was concentrated under reduced pressure and the crude intermediate was purified via flash chromatography using dichloromethane and methanol as eluents. The obtained intermediate was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 5 mM aqueous NH$_4$HCO$_3$ solution and MeCN as eluents to obtain Example 826. HRMS calculated for $C_{47}H_{44}ClFN_6O_6S$: 874.2716. found 438.1443 (M+2H).

Example 827 (2S)-2-{[(5R$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid and Example 828 (2S)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid 1 eq. ethyl (2S)-2-[(5-[3-chloro-2-methyl-4-[2-(4-methyl-piperazin-1-yl)ethoxy]phenyl]-6-(4-fluorophenyl)thieno[2,3-d]pyrimidin-4-yl]oxy-3-[2-[(2-methylsulfanylpyrimidin-4-yl)methoxy]phenyl]propanoate (Preparation 10f), 3.0 eq. [2-(2-methoxyphenyl)pyrimidin-4-yl]methanol (Preparation 9bp) and 3.0 eq. copper(I) thiophenecarboxylate were dissolved in dry THF (0.1 M for Preparation 10f), then 0.15 eq. Pd(PPh$_3$)$_4$ was added. The mixture was stirred at 70° C. under nitrogen until no further conversion was observed. Then it was concentrated under reduced pressure and the crude intermediate was purified via flash chromatography using dichloromethane and methanol as eluents. The obtained intermediate was dissolved in dioxane-water 1:1 (10 mL/mmol) and 10 eq LiOH×H$_2$O was added. The mixture was stirred at room temperature until no further conversion was observed. Then it was diluted with brine, neutralized with 2 M HCl, extracted with DCM. The combined organic phases were dried over Na$_2$SO$_4$, filtered and concentrated under reduced pressure and purified via preparative reversed phase chromatography using 5 mM aqueous NH$_4$HCO$_3$ solution and MeCN as eluents. The diastereomer eluated later was isolated as Example 827. HRMS calculated for $C_{47}H_{44}ClFN_6O_6S$: 874.2716. found 438.1437 (M+2H).

The diastereomer eluated earlier was isolated as Example 828. HRMS calculated for $C_{47}H_{44}ClFN_6O_6S$: 874.2716. found 438.1422 (M+2H).

Example 829 ethyl (2S)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Starting from Example 827 and using General Procedure (XXa), Example 829 was obtained. HRMS calculated for $C_{49}H_{48}ClFN_6O_6S$: 902.3029. found 452.1575 (M+2H).

Example 830 ethyl (2R)-2-{[(5R$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Starting from Example 826 and using General Procedure (XXa), Example 830 was obtained. HRMS calculated for $C_{49}H_{48}ClFN_6O_6S$: 902.3029. found 452.1574 (M+2H).

Example 831 ethyl (2S)-2-{[(5R$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Starting from Example 828 and using General Procedure (XXa), Example 831 was obtained. HRMS calculated for $C_{49}H_{48}ClFN_6O_6S$: 902.3029. found 903.3066 (M+H).

Example 832 (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-[2-({2-[2-(hydroxymethyl)phenyl]pyrimidin-4-yl}methoxy)phenyl]propanoic acid 1 eq. Example 857 and 10 eq. LiOH×H$_2$O were dissolved in H$_2$O: dioxane (10 ml/mmol) and stirred at room temperature until no further conversion was observed. Mixture was then acidified with 1M HCl solution and extracted with EtOAc. Organic phases were dried over Na$_2$SO$_4$ and concentrated in vacuo. Crude product was purified using preparative reversed phase chromatography using 25 mM aqueous NH$_4$HCO$_3$ solution and MeCN as eluents to obtain Example 832. HRMS calculated for $C_{44}H_{39}ClFN_5O_6S$: 819.2294. found: 820.2373 (M+H).

Example 833 (2R)-2-{[(5S$_a$)-5-{3-chloro-2-methyl-4-[2-(6-methyl-2,6-diazaspiro[3.3]hept-2-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid 319 mg (0.41 mmol) Preparation 6v, 256 mg (1.64 mg) Preparation 34, and 323 mg (1.23 mmol) PPh$_3$ were dissolved in 4 ml dry toluene, then 283 mg (1.23 mmol) ditertbutyl azodicarboxylate was added. The mixture was stirred at 50° C. under N$_2$ until no further conversion was observed. The toluene was evaporated under reduced pressure and the residue was purified via flash chromatography using DCM and MeOH as eluents. To this intermediate 10 eq. LiOH×H$_2$O, and dioxane:H$_2$O 1:1 (15 ml/mmol) were added and the mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents to obtain Example 833 as the earlier eluated diastereomer. HRMS calculated for C$_{48}$H$_{44}$ClFN$_6$O$_6$S: 886.2715. found: 444.1449 (M+H).

Example 834 (2R)-2-[((5S$_a$)-5-{3-chloro-2-methyl-4-[2-(4-methylpiperazin-1-yl)ethoxy]phenyl}-6-iodothieno[2,3-d]pyrimidin-4-yl)oxy]-3-(2-{[2-(2-methoxyphenyl)pyrimidin-4-yl]methoxy}phenyl)propanoic acid 1 eq. Preparation 30 and 10 eq. LiOH×H$_2$O were dissolved in H$_2$O: dioxane (10 ml/mmol) and stirred at room temperature until no further conversion was observed. Mixture was then acidified with 1M HCl solution and extracted with EtOAc. Organic phases were dried over Na$_2$SO$_4$ and concentrated in vacuo. Crude product was purified using preparative reversed phase chromatography using 25 mM aqueous NH$_4$HCO$_3$ solution and MeCN as eluents to obtain Example 834 as the later eluated diastereomer. HRMS calculated for C$_{41}$H$_{40}$ClIN$_6$O$_6$S: 906.1463. found: 454.0789 (M+2H).

Example 835 (2R)-2-{[(5S$_a$)-5-{3-chloro-2-methyl-4-[2-(4-methylpiperazin-1-yl)ethoxy]phenyl}-6-(2-fluorophenyl)thieno[2,3-d]pyrimidin-4-yl]oxy}-3-(2-{[2-(2-methoxyphenyl)pyrimidin-4-yl]methoxy}phenyl)propanoic acid 90.7 mg Example 834 (0.1 mmol), 26.6 mg 2-(2-fluorophenyl)-4,4,5,5-tetramethyl-1,3,2-dioxaborolane (0.12 mmol), 97.7 mg cesium carbonate (0.3 mmol), 1.12 mg Pd(OAc)$_2$ (5 mol %) and 4.25 mg $^t$BuX-Phos (10 mol %) were placed in a 4 mL vial. 0.5 mL dioxane and 0.5 mL water were added, and then stirred for 40 min at 70° C. under argon atmosphere. Then it was diluted with brine, neutralized with 2 M HCl, extracted with dichloromethane, the combined organic phases were dried over Mg$_2$SO$_4$, filtered and concentrated under reduced pressure and purified via preparative reversed phase chromatography using 25 mM aqueous NH$_4$HCO$_3$ solution and MeCN as eluents to obtain Example 835. HRMS calculated for C$_{47}$H$_{44}$N$_6$O$_6$FSCl: 874.2715. found: 438.1430 (M+2H).

Example 836 (2R)-2-{[(5S$_a$)-5-{3-chloro-2-methyl-4-[2-(4-methylpiperazin-1-yl)ethoxy]phenyl}-6-(3-fluorophenyl)thieno[2,3-d]pyrimidin-4-yl]oxy}-3-(2-{[2-(2-methoxyphenyl)pyrimidin-4-yl]methoxy}phenyl)propanoic acid 90.7 mg Example 834 (0.1 mmol), 26.6 mg 2-(3-fluorophenyl)-4,4,5,5-tetramethyl-1,3,2-dioxaborolane (0.12 mmol), 97.7 mg cesium carbonate (0.3 mmol), 1.12 mg Pd(OAc)$_2$ (5 mol %) and 4.25 mg $^t$BuX-Phos (10 mol %) were placed in a 4 mL vial. 0.5 mL dioxane and 0.5 mL water were added, and then stirred for 40 min at 70° C. under argon atmosphere. Then it was diluted with brine, neutralized with 2 M HCl, extracted with dichloromethane, the combined organic phases were dried over Mg$_2$SO$_4$, filtered and concentrated under reduced pressure and purified via preparative reversed phase chromatography using 25 mM aqueous NH$_4$HCO$_3$ solution and MeCN as eluents to obtain Example 836. HRMS calculated for C$_{47}$H$_{44}$N$_6$O$_6$FSCl: 874.2715. found: 438.1443 (M+2H).

Example 837 (2R)-2-{[5-{3-chloro-2-methoxy-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIX) and methanol as the appropriate alcohol, Example 837 was obtained. HRMS calculated for C$_{47}$H$_{44}$N$_6$O$_7$FSCl: 890.2665. found: 446.1408 and 446.1416 for the two diastereoisomers.

Example 838 (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[($^2$H$_3$)methyloxy]phenyl}pyrimidin-4-yl)methoxy]phenyl}propanoic acid 1 eq. Example 839 and 10 eq. LiOH×H$_2$O were dissolved in H$_2$O: dioxane (10 ml/mmol) and stirred at room temperature until no further conversion was observed. Mixture was then acidified with 1M HCl solution and extracted with EtOAc. Organic phases were dried over Na$_2$SO$_4$ and concentrated in vacuo. Crude product was purified using preparative reversed phase chromatography using 25 mM aqueous NH$_4$HCO$_3$ solution and MeCN as eluents to obtain Example 838. HRMS calculated for C$_{47}$H$_{41}$ClD$_3$FN$_6$O$_6$S: 877.2904. found: 878.2997 (M+H).

Example 839 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-{2-[(2-{2-[($^2$H$_3$)methyloxy]phenyl}pyrimidin-4-yl)methoxy]phenyl}propanoate Using General Procedure (Ib-Step A) and Preparation 9er as the appropriate alcohol, Example 839 was obtained. HRMS calculated for C$_{49}$H$_{45}$ClD$_3$FN$_6$O$_6$S: 905.3217. found: 906.3288 (M+H).

Example 840 (2R)-2-{[(5S$_a$)-5-(3-chloro-4-methoxy-2-methylphenyl)-6-(4-fluorophenyl)thieno[2,3-d]pyrimidin-4-yl]oxy}-3-(2-methoxyphenyl)propanoic acid 1 eq. Example 842 and 10 eq. LiOH×H$_2$O were dissolved in H$_2$O: dioxane (10 ml/mmol) and stirred at room temperature until no further conversion was observed. Mixture was then acidified with 1M HCl solution and extracted with EtOAc. Organic phases were dried over $Na_2SO_4$ and concentrated in vacuo. Crude product was purified using preparative reversed phase chromatography using 25 mM aqueous $NH_4HCO_3$ solution and MeCN as eluents to obtain Example 840. HRMS calculated for $C_{30}H_{24}ClFN_2O_5S$: 578.1078. found: 579.1140 (M+H).

Example 841 (2R)-2-{[(5S$_a$)-5-(3-chloro-4-methoxy-2-methylphenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid 1 eq. Example 843 and 10 eq. LiOH×H$_2$O were dissolved in H$_2$O: dioxane (10 ml/mmol) and stirred at room temperature until no further conversion was observed. Mixture was then acidified with 1M HCl solution and extracted with EtOAc. Organic phases were dried over $Na_2SO_4$ and concentrated in vacuo. Crude product was purified using preparative reversed phase chromatography using 25 mM aqueous $NH_4HCO_3$ solution and MeCN as eluents to obtain Example 841. HRMS calculated for $C_{41}H_{32}ClFN_4O_6S$: 762.1715. found: 763.1787 (M+H).

Example 842 ethyl (2R)-2-{[(5S$_a$)-5-(3-chloro-4-methoxy-2-methylphenyl)-6-(4-fluorophenyl)thieno[2,3-d]pyrimidin-4-yl]oxy}-3-(2-methoxyphenyl)propanoate 1.40 g (2.36 mmol) Preparation 8l, 1.55 g (5.90 mmol) PPh$_3$, 250 µl MeOH and 20 ml toluene were cooled to 0° C. and 1.36 g (5.90 mmol) di-tert-butyl azodicarboxylate was added. Mixture was stirred at 60° C. for 2 hs. Mixture was then concentrated and purified via flash chromatography using heptane-EtOAc-MeOH as eluents to obtain Example 842. HRMS calculated for $C_{32}H_{28}ClFN_2O_5S$: 606.1392. found: 607.1479 (M+H).

Example 843 ethyl (2R)-2-{[(5S$_a$)-5-(3-chloro-4-methoxy-2-methylphenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoate 1.40 g (2.36 mmol) Preparation 8l, 1.55 g (5.90 mmol) PPh$_3$, 1.27 g (5.90 mmol) Preparation 9bp and 20 ml toluene were cooled to 0° C. and 1.36 g (5.90 mmol) di-tert-butyl azodicarboxylate was added. Mixture was stirred at 60° C. for 2hs. Mixture was then concentrated and purified via flash chromatography using heptane-EtOAc-MeOH as eluents to obtain Example 843. HRMS calculated for $C_{43}H_{36}ClFN_4O_6S$: 790.2028. found: 791.2123 (M+H).

Example 844 2-(dimethylamino)-2-oxoethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoate Using General Procedure (XXc) and Example 1 as the appropriate acid and 2-chloro-N,N-dimethylacetamide as the appropriate alkyl-halide, Example 844 was obtained. HRMS calculated for $C_{40}H_{43}N_5O_6FCl$: 775.2607. found: 776.2689 (M+H).

Example 845 2-(dimethylamino)-2-oxoethyl (2R)-2-{[(5S$_a$)-5-(3-chloro-4-methoxy-2-methylphenyl)-6-(4-fluorophenyl)thieno[2,3-d]pyrimidin-4-yl]oxy}-3-(2-methoxyphenyl)propanoate Using General Procedure (XXc) and Example 840 as the appropriate acid and 2-chloro-N,N-dimethylacetamide as the appropriate alkyl-halide, Example 845 was obtained. HRMS calculated for $C_{34}H_{31}ClFN_3O_6S$: 663.1606. found: 664.1709 (M+H).

Example 846 {[(2R)-2-{[(5S$_a$)-5-(3-chloro-4-methoxy-2-methylphenyl)-6-(4-fluorophenyl)thieno[2,3-d]pyrimidin-4-yl]oxy}-3-(2-methoxyphenyl)propanoyl]oxy}methyl 2,2-dimethylpropanoate Using General Procedure (XXc) and Example 840 as the appropriate acid and chloromethyl pivalate as the appropriate alkyl-halide, Example 846 was obtained. HRMS calculated for $C_{36}H_{34}ClFN_2O_7S$: 692.1759. found: 693.1793 (M+H).

Example 847 octyl (2R)-2-{[(5S$_a$)-5-(3-chloro-4-methoxy-2-methylphenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) and Example 841 as the appropriate acid and 1-bromo-octane as the appropriate alkyl-halide, Example 847 was obtained. HRMS calculated for $C_{49}H_{48}ClFN_4O_6S$: 874.2967. found: 875.3002 (M+H).

Example 848 2-(dimethylamino)-2-oxoethyl (2R)-2-{[(5S$_a$)-5-(3-chloro-4-methoxy-2-methylphenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) and Example 841 as the appropriate acid and 2-chloro-N,N-dimethylacetamide as the appropriate alkyl-halide, Example 848 was obtained. HRMS calculated for $C_{45}H_{39}ClFN_5O_7S$: 847.2243. found: 848.2276 (M+H).

Example 849 {[(2R)-2-{[(5S$_a$)-5-(3-chloro-4-methoxy-2-methylphenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoyl]oxy}methyl 2,2-dimethylpropanoate Using General Procedure (XXc) and Example 841 as the appropriate acid and chloromethyl pivalate as the appropriate alkyl-halide, Example 849 was obtained. HRMS calculated for $C_{47}H_{42}ClFN_4O_8S$: 876.2396. found: 877.2450 (M+H).

Example 850 octyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-methoxyphenyl)propanoate Using General Procedure (XXc) and Example 1 as the appropriate acid and 1-bromo-octane as the appropriate alkyl-halide, Example 850 was obtained. HRMS calculated for $C_{44}H_{52}ClFN_4O_5S$: 802.3331. found: 803.3381 (M+H).

Example 851 octyl (2R)-2-{[(5S$_a$)-5-(3-chloro-4-methoxy-2-methylphenyl)-6-(4-fluorophenyl)thieno[2,3-d]pyrimidin-4-yl]oxy}-3-(2-methoxyphenyl)propanoate Using General Procedure (XXc) and Example 840 as the appropriate acid and 1-bromo-octane as the appropriate alkyl-halide, Example 851 was obtained. HRMS calculated for $C_{38}H_{40}ClFN_2O_5S$: 690.2330. found: 691.2373 (M+H).

Example 852 (5-methyl-2-oxo-1,3-dioxol-4-yl)methyl (2R)-2-{[(5S$_a$)-5-(3-chloro-4-methoxy-2-methylphenyl)-6-(4-fluorophenyl)thieno[2,3-d]pyrimidin-4-yl]oxy}-3-(2-methoxyphenyl)propanoate Using General Procedure (XXc) and Example 840 as the appropriate acid and 4-chloromethyl-5-methyl-1,3-dioxol-2-one as the appropriate alkyl-halide, Example 852 was obtained. HRMS calculated for $C_{35}H_{28}ClFN_2O_8S$: 690.1239. found: 691.1323 (M+H).

Example 853 (5-methyl-2-oxo-1,3-dioxol-4-yl)methyl (2R)-2-{[(5S$_a$)-5-(3-chloro-4-methoxy-2-methylphenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) and Example 841 as the appropriate acid and 4-chloromethyl-5-methyl-1,3-dioxol-2-one as the appropriate alkyl-halide, Example 853 was obtained. HRMS calculated for $C_{46}H_{36}ClFN_4O_9S$: 874.1876. found: 875.1976 (M+H).

Example 854 {[(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoyl]oxy}methyl 2,2-dimethylpropanoate Using General Procedure (XXc) and Example 114 as the appropriate acid and chloromethyl pivalate as the appropriate alkyl-halide, Example 854 was obtained. HRMS calculated for $C_{52}H_{51}ClF_2N_6O_7S$: 976.3196. found: 977.3262 (M+H).

Example 855 (5-methyl-2-oxo-1,3-dioxol-4-yl)methyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXc) and Example 114 as the appropriate acid and 4-chloromethyl-5-methyl-1,3-dioxol-2-one as the appropriate alkyl-halide, Example 855 was obtained. HRMS calculated for $C_{51}H_{45}ClF_2N_6O_8S$: 974.2676. found: 488.1406 (M+2H).

Example 856 ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-[2-({2-[2-(hydroxymethyl)phenyl]pyrimidin-4-yl}methoxy)phenyl]propanoate Using General Procedure (Ib) and 2-(hydroxymethyl)phenylboronic acid as the appropriate boronic acid Example 856 was obtained. HRMS calculated for $C_{49}H_{48}ClFN_6O_6S$: 902.3029. found: 903.3076 (M+H).

Example 857 ethyl (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-[2-({2-[2-(hydroxymethyl)phenyl]pyrimidin-4-yl}methoxy)phenyl]propanoate Using General Procedure (IIb) and 2-(hydroxymethyl)phenylboronic acid as the appropriate boronic acid Example 857 was obtained. HRMS calculated for $C_{46}H_{43}CFN_5O_6S$: 847.2607. found: 848.2649 (M+H).

Example 858 1-(acetyloxy)ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) and Example 30 as the appropriate acid and 1-iodoethyl acetate (Preparation 35a) as the appropriate alkyl-halide, Example 858 was obtained. HRMS calculated for $C_{51}H_{50}ClFN_6O_8S$: 960.3083. found: 481.1627 and 481.1617 for the two diastereomers (M+2H).

Example 859 1-{[(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoyl]oxy}ethyl 2,2-dimethylpropanoate Using General Procedure (XXc) and Example 30 as the appropriate acid and 1-iodoethyl 2,2-dimethylpropanoate (Preparation 35b) as the appropriate alkyl-halide, Example 859 was obtained. HRMS calculated for $C_{54}H_{56}ClFN_6O_8S$: 1002.3553. found: 502.1852 (M+2H).

Example 860 1-(propanoyloxy)ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) and Example 30 as the appropriate acid and 1-iodoethyl propanoate (Preparation 35c) as the appropriate alkyl-halide, Example 860 was obtained. HRMS calculated for $C_{52}H_{52}ClFN_6O_8S$: 974.324. found: 488.1701 and 488.1717 for the two diastereomers (M+2H).

Example 861 1-[(2-methylpropanoyl)oxy]ethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) and Example 30 as the appropriate acid and 1-iodoethyl 2-methylpropanoate (Preparation 35d) as the appropriate alkyl-halide, Example 861 was obtained. HRMS calculated for $C_{53}H_{54}ClFN_6O_8S$: 988.3397. found: 495.1767 and 495.1793 for the two diastereomers (M+2H).

Example 862 (5-methyl-2-oxo-1,3-dioxol-4-yl) methyl (2R)-2-{[(5S$_a$)-5-{3-chloro-4-[2-(dimethyl-amino)ethoxy]-2-methylphenyl}-6-(4-fluorophenyl)thieno[2,3-d]pyrimidin-4-yl]oxy}-3-[2-({2-[2-(2-methoxyethoxy)phenyl]pyrimidin-4-yl}methoxy)phenyl]propanoate Using General Procedure (XXc) and Example 753 as the appropriate acid and 4-chloromethyl-5-methyl-1,3-dioxol-2-one as the appropriate alkyl-halide, Example 862 was obtained. HRMS calculated for $C_{51}H_{47}ClFN_5O_{10}S$: 975.2716. found: 488.6412 (M+2H).

Example 863 (5-methyl-2-oxo-1,3-dioxol-4-yl) methyl (2R)-2-{[(5S$_a$)-5-{3-chloro-4-[2-(dimethyl-amino)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoate Using General Procedure (XXc) and Example 757 as the appropriate acid and 4-chloromethyl-5-methyl-1,3-dioxol-2-one as the appropriate alkyl-halide, Example 863 was obtained. HRMS calculated for $C_{48}H_{40}ClF_2N_5O_8S$: 919.2254. found: 920.2332 (M+H).

Example 864 1-[(methoxyacetyl)oxy]ethyl (2R)-2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate Using General Procedure (XXc) and Example 30 as the appropriate acid and Preparation 35e as the appropriate alkyl-halide, Example 864 was obtained. HRMS calculated for $C_{52}H_{52}ClFN_6O_9S$: 990.3189. found: 496.1674 and 496.1678 for the two diastereoisomers (M+2H).

Example 865 (2R)-2-{[5-{3-chloro-2-ethoxy-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIX) and ethanol as the appropriate alcohol, Example 865 was obtained. HRMS calculated for $C_{48}H_{46}ClFN_6O_7S$: 904.2821. found: 453.1487 and 453.1491 for the two diastereoisomers.

Example 866 (2R)-2-{[5-{3-chloro-4-[2-(4-methyl-piperazin-1-yl)ethoxy]-2-(propan-2-yloxy)phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXIX) and isopropanol as the appropriate alcohol, Example 866 was obtained. HRMS calculated for $C_{49}H_{48}ClFN_6O_7S$: 918.2978. found: 460.1568 and 460.1573 for the two diastereomers.

Example 867 (2R)-2-{[5-{3-chloro-2-hydroxy-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid 1 eq. Preparation 38, 10 eq. LiOH×H$_2$O, and dioxane:H$_2$O 1:1 (15 ml/mmol) were added and the mixture was stirred at room temperature until no further conversion was observed. Then it was diluted with brine, neutralized with 2 M HCl, extracted with dichloromethane. The combined organic phases were dried over Na$_2$SO$_4$, filtered and concentrated under reduced pressure and purified via preparative reversed phase chromatography using 25 mM aqueous NH$_4$HCO$_3$ solution and MeCN as eluents to obtain Example 867. HRMS calculated for $C_{46}H_{42}ClFN_6O_7S$: 876.2509. found: 439.1343 (M+2H).

Example 868 (2R)-2-{[5-{3-chloro-2-cyano-4-[2-(4-methylpiperazin-1-yl)ethoxy]phenyl}-6-(4-fluoro-phenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXVIII) and Preparation 36 as the appropriate phenol derivative and 2-(4-methylpiper-azin-1-yl)ethanol as the appropriate alcohol, diastereoisomer eluting earlier was collected as Example 868. HRMS calculated for $C_{47}H_{41}ClFN_7O_6S$: 885.2512. found 443.6351 (M+2H).

Example 869 (2R)-2-{[5-{3-chloro-2-cyano-4-[2-(4-methylpiperazin-1-yl)ethoxy]phenyl}-6-(4-fluoro-phenyl)thieno[2,3-d]pyrimidin-4-yl]oxy}-3-(2-{[2-(2-methoxyphenyl)pyrimidin-4-yl]methoxy}phenyl)propanoic acid Using General Procedure (XXXVIII) and Preparation 36 as the appropriate phenol derivative and 2-(4-methylpiper-azin-1-yl)ethanol as the appropriate alcohol, the diastereoisomer eluting later was collected as Example 869. HRMS calculated for $C_{47}H_{41}ClFN_7O_6S$: 885.2512. found 443.6339 (M+2H).

Example 870 (2R)-2-{[5-{3-chloro-2-(methoxymethoxy)-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid 1 eq. Preparation 37 and 10 eq. LiOH×H$_2$O were dissolved in H$_2$O: dioxane (10 ml/mmol) and stirred at room temperature until no further conversion was observed. Mixture was then acidified with 1M HCl solution and extracted with EtOAc. Organic phases were dried over Na$_2$SO$_4$ and concentrated in vacuo. Crude product was purified using preparative reversed phase chromatography using 25 mM aqueous NH$_4$HCO$_3$ solution and MeCN as eluents to obtain Example 870. HRMS calculated for $C_{48}H_{46}ClFN_6O_8S$: 920.2770. found: 461.1445 and 461.1460 for the two diastereomers.

Example 871 (2R)-2-{[(5S$_a$)-5-(3-chloro-2-methyl-4-{2-[4-($^2$H$_3$)methylpiperazin-1-yl]ethoxy}phenyl)-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid Step A:
To the solution of 144 mg (0.162 mmol) of Example 795 and 66 mg (0.202 mmol, 1.25 eq) Cs$_2$CO$_3$ in 1 mL DMF 162 μL (0.162 mmol, 1.0 eq) 1 M solution of ($^2$H$_3$)iodomethane in DMF was added and it was stirred at room temperature for 16 h. Reaction mixture was filtered and purified on prep HPLC using water (5 mM NH$_4$HCO$_3$) and acetonitrile as eluents to give ethyl (2R)-2-[(5S$_a$)-5-[3-chloro-2-methyl-4-[2-[4-($^2$H$_3$)methyl-piperazin-1-yl]ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate as white crystals.

Step B:

To the solution of 76 mg (1.0 eq, 0.08384 mmol) ethyl (2R)-2-[(5S$_a$)-5-[3-chloro-2-methyl-4-[2-[4-($^2$H$_3$)methyl-piperazin-1-yl]ethoxy]phenyl]-6-(4-fluorophenyl)thieno[2,3-d]pyrimidin-4-yl]oxy-3-[2-[[2-(2-methoxyphenyl)pyrimidin-4-yl]methoxy]phenyl]propanoate in 2 mL dioxan and 1.25 mL water, 35.2 mg (10.0 eq, 0.838 mmol) LiOH×H$_2$O was added and the reaction mixture was stirred at room temperature until full conversion. The pH of the reaction mixture was adjusted to 6 using 1N HCl, then it was filtered and purified on reversed phase preparative HPLC using water (5 mM NH$_4$HCO$_3$) and acetonitrile as eluents to give Example 871.

HRMS calculated for C$_{47}$H$_{41}$ClD$_3$FN$_6$O$_6$S: 877.2904. found 439.6534 (M+2H).

Pharmacological Study

Example A: Inhibition of Mcl-1 by the Fluorescence Polarisation Technique

The relative binding potency of each compound was determined via Fluorescence Polarisation (FP). The method utilised a Fluorescein labelled ligand (Fluorescein-βAla-Ahx-A-REIGAQLRRMADDLNAQY-OH; mw 2,765) which binds to the Mcl-1 protein (such that Mcl-1 corresponds to the UniProtKB® primary accession number: Q07820) leading to an increased anisotropy measured in milli-polarisation (mP) units using a reader. The addition of a compound which binds competitively to the same site as the ligand will result in a greater proportion of unbound ligand in the system indicated by a decrease in mP units.

Method 1:

An 11 point serial dilution of each compound was prepared in DMSO and 2 µl transferred into flat bottomed, low binding, 384-well plate (final DMSO concentration 5%). 38 µl of buffer (10 mM 4-(2-hydroxyethyl)-1-piperazineethanesulfonic acid [HEPES], 150 mM NaCl, 0.05% Tween 20, pH 7.4), containing the Fluorescein labelled ligand (final concentration 1 nM) and Mcl-1 protein (final concentration 5 nM) was then added.

Assay plates were incubated ~2 hours at room temperature before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' (10 µM Example 38) controls. 11-point dose response curves were plotted with XL-Fit software using a 4-Parameter Logistic Model (Sigmoidal Dose-Response Model) and the inhibitory concentrations that gave a 50% reduction in mP (IC50) were determined. Results obtained using Method 1 are presented in Table 1 below; IC$_{50}$ of Mcl-1 inhibition obtained using Method 1 are not underlined.

Method 2:

An 11 point serial dilution of each compound was prepared in DMSO and 2 µl transferred into flat bottomed, low binding, 384-well plate (final DMSO concentration 5%). 38 µl of buffer (20 mM Na$_2$PO$_4$, 1 mM EDTA, 50 mM NaCl$_2$, pH 7.4), containing the Fluorescein labelled ligand (final concentration 10 nM) and Mcl-1 protein (final concentration 10 nM) was then added.

Assay plates were incubated ~2 hours at room temperature before FP was measured on a Biomek Synergy2 reader (Ex. 528 nm, Em. 640 nm, Cut off 510 nm) and mP units calculated. The binding of increasing doses of test compound was expressed as a percentage reduction in mP compared to a window established between '5% DMSO only' and '100% inhibition' controls (50 µM unlabelled ligand). 11-point dose response curves were plotted with XL-Fit software using a 4-Parameter Logistic Model (Sigmoidal Dose-Response Model) and the inhibitory concentrations that gave a 50% reduction in mP (IC50) were determined. Results obtained using Method 2 are presented in Table 1 below; IC$_{50}$ of Mcl-1 inhibition obtained using Method 2 are underlined.

The results show that the compounds of the invention inhibit interaction between the Mcl-1 protein and the fluorescent peptide described hereinbefore.

Example B: In Vitro Cytotoxicity

The cytotoxicity studies were carried out on the H929 multiple myeloma tumour line.

The cells are distributed onto microplates and exposed to the test compounds for 48 hours.

The cell viability is then quantified by a colorimetric assay, the Microculture Tetrazolium Assay (Cancer Res., 1987, 47, 939-942).

The results are expressed in IC$_{50}$ (the concentration of compound that inhibits cell viability by 50%) and are presented in Table 1 below.

The results show that the compounds of the invention are cytotoxic.

TABLE 1

IC$_{50}$ of Mcl-1 inhibition (fluorescence polarisation test) and of cytotoxicity for H929 cells
Note: IC$_{50}$ of Mcl-1 inhibition obtained using Method 2 are underlined.

| | IC$_{50}$ (M) Mcl-1 FP | IC$_{50}$ (µM) MTT H929 |
|---|---|---|
| Example 1 | 8.0E−08 | 0.16 |
| Example 2 | 1.2E−08 | 0.136 |
| Example 3 | 8.9E−09 | 0.114 |
| Example 4 | 1.6E−08 | 0.192 |
| Example 5 | 6.2E−09 | 0.418 |
| Example 6 | 4.9E−09 | 0.332 |
| Example 7 | 8.6E−09 | 0.066 |
| Example 8 | 1.6E−08 | 0.145 |
| Example 9 | 9.3E−09 | 0.363 |
| Example 10 | 9.7E−09 | 0.275 |
| Example 11 | 4.4E−08 | 0.13 |
| Example 12 | 1.6E−08 | 0.076 |
| Example 13 | 2.2E−08 | 0.146 |
| Example 14 | 1.3E−08 | 0.168 |
| Example 15 | 3.7E−08 | 0.494 |
| Example 16 | 5.9E−09 | 0.095 |
| Example 17 | 1.2E−08 | 0.062 |
| Example 18 | 8.3E−09 | 0.076 |
| Example 19 | 4.4E−09 | 0.064 |
| Example 20 | 6.4E−09 | 0.08 |
| Example 21 | 1.6E−08 | 0.162 |
| Example 22 | 8.3E−09 | 0.092 |
| Example 23 | 2.4E−08 | 0.054 |
| Example 24 | 8.1E−09 | 0.012 |
| Example 25 | 5.6E−09 | 0.074 |
| Example 26 | 1.1E−08 | 0.028 |
| Example 27 | 6.6E−09 | 0.045 |
| Example 28 | 4.5E−09 | 0.021 |

TABLE 1-continued

IC$_{50}$ of Mcl-1 inhibition (fluorescence polarisation test) and of cytotoxicity for H929 cells
Note: IC$_{50}$ of Mcl-1 inhibition obtained using Method 2 are underlined.

| | IC$_{50}$ (M) Mcl-1 FP | IC$_{50}$ (μM) MTT H929 |
|---|---|---|
| Example 29 | 3.3E−09 | 0.007 |
| Example 30 | 2.8E−09 | 0.003 |
| Example 31 | 5.6E−09 | 0.012 |
| Example 32 | 4.8E−09 | 0.006 |
| Example 33 | 7.8E−09 | 0.017 |
| Example 34 | 3.3E−09 | 0.004 |
| Example 35 | 4.8E−09 | 0.027 |
| Example 36 | 1.1E−08 | 0.015 |
| Example 37 | 6.0E−09 | 0.014 |
| Example 38 | 1.9E−09 | 0.016 |
| Example 39 | 4.8E−09 | 0.015 |
| Example 40 | 5.6E−09 | 0.008 |
| Example 41 | 2.9E−09 | 0.007 |
| Example 42 | 3.2E−09 | 0.012 |
| Example 43 | 9.8E−09 | 0.465 |
| Example 44 | 4.8E−09 | 0.006 |
| Example 45 | 6.7E−09 | 0.009 |
| Example 46 | 7.3E−09 | 0.024 |
| Example 47 | 7.8E−09 | 0.005 |
| Example 48 | 1.1E−08 | 0.122 |
| Example 49 | 2.5E−09 | 0.012 |
| Example 50 | 7.6E−09 | 0.076 |
| Example 51 | 3.5E−09 | 0.038 |
| Example 52 | 5.6E−09 | 0.014 |
| Example 53 | 3.4E−09 | 0.015 |
| Example 54 | 5.7E−09 | 0.024 |
| Example 55 | 5.8E−09 | 0.007 |
| Example 56 | 4.4E−09 | 0.022 |
| Example 57 | 5.0E−09 | 0.008 |
| Example 58 | 4.0E−09 | 0.01 |
| Example 59 | 4.0E−09 | 0.021 |
| Example 60 | 2.4E−09 | 0.17 |
| Example 61 | 6.7E−09 | 0.01 |
| Example 62 | 3.9E−09 | 0.008 |
| Example 63 | 4.5E−09 | 0.009 |
| Example 64 | 4.4E−09 | 0.018 |
| Example 65 | 1.0E−08 | 0.043 |
| Example 66 | 4.6E−09 | 0.037 |
| Example 67 | 3.4E−09 | 0.03 |
| Example 68 | 9.1E−09 | 0.035 |
| Example 69 | 9.7E−08 | 0.114 |
| Example 70 | 1.6E−09 | 0.018 |
| Example 71 | 9.4E−09 | 0.032 |
| Example 72 | 9.3E−09 | 0.04 |
| Example 73 | 8.3E−09 | 0.122 |
| Example 74 | 1.6E−08 | 0.365 |
| Example 75 | 4.0E−09 | 0.11 |
| Example 76 | 1.6E−08 | 0.044 |
| Example 77 | 5.9E−09 | 0.042 |
| Example 78 | 6.6E−09 | 0.033 |
| Example 79 | 1.3E−08 | 0.168 |
| Example 80 | 4.5E−09 | 0.035 |
| Example 81 | 7.6E−09 | 0.034 |
| Example 82 | 5.1E−09 | 0.078 |
| Example 83 | 5.1E−09 | 0.016 |
| Example 84 | 3.8E−09 | 0.018 |
| Example 85 | 3.6E−09 | 0.063 |
| Example 86 | 2.9E−09 | 0.063 |
| Example 87 | 7.0E−09 | 0.274 |
| Example 88 | 4.2E−09 | 0.062 |
| Example 89 | 6.5E−09 | 0.027 |
| Example 90 | 3.2E−09 | 0.058 |
| Example 91 | 7.3E−09 | 0.042 |
| Example 92 | 1.2E−08 | ND |
| Example 93 | 1.4E−08 | 0.087 |
| Example 94 | 1.9E−09 | 0.085 |
| Example 95 | 4.2E−09 | 0.022 |
| Example 96 | 3.8E−09 | 0.034 |
| Example 97 | 3.3E−09 | 0.075 |
| Example 98 | 3.3E−07 | 0.118 |
| Example 99 | 2.0E−08 | ND |
| Example 100 | 1.2E−08 | ND |
| Example 101 | 8.0E−09 | 0.398 |
| Example 102 | 9.5E−09 | ND |
| Example 103 | 2.4E−08 | 0.214 |
| Example 104 | 7.5E−09 | 0.386 |
| Example 105 | 1.2E−08 | 0.251 |
| Example 106 | 1.2E−08 | 0.195 |
| Example 107 | 5.3E−09 | 0.007 |
| Example 108 | 3.5E−09 | 0.007 |
| Example 109 | 8.4E−09 | 0.108 |
| Example 110 | 4.3E−09 | 0.022 |
| Example 111 | 3.3E−09 | 0.008 |
| Example 112 | 5.6E−09 | 0.011 |
| Example 113 | 2.6E−09 | 0.005 |
| Example 114 | 2.1E−09 | 0.005 |
| Example 115 | 2.6E−09 | 0.003 |
| Example 116 | 2.9E−09 | 0.007 |
| Example 117 | 6.1E−09 | 0.008 |
| Example 118 | 5.5E−09 | 0.006 |
| Example 119 | 4.8E−09 | 0.02 |
| Example 120 | 3.8E−09 | 0.003 |
| Example 121 | 5.6E−09 | 0.015 |
| Example 122 | 3.8E−09 | 0.01 |
| Example 123 | 4.3E−09 | 0.002 |
| Example 124 | 4.3E−09 | 0.024 |
| Example 125 | 7.3E−09 | 0.354 |
| Example 126 | 1.4E−08 | 0.7 |
| Example 127 | 2.0E−08 | 0.558 |
| Example 128 | 4.0E−09 | 0.018 |
| Example 129 | 2.2E−09 | 0.069 |
| Example 130 | 3.4E−09 | 0.065 |
| Example 131 | 7.9E−09 | 0.039 |
| Example 132 | 4.8E−09 | 0.102 |
| Example 133 | 3.4E−09 | 0.099 |
| Example 134 | 1.3E−08 | 0.193 |
| Example 135 | 8.6E−09 | 0.005 |
| Example 136 | 7.7E−09 | 0.015 |
| Example 137 | 5.5E−09 | 0.007 |
| Example 138 | 8.9E−09 | 0.013 |
| Example 139 | 8.5E−08 | 0.636 |
| Example 140 | 2.2E−09 | 0.205 |
| Example 141 | 3.1E−08 | 0.27 |
| Example 142 | 4.2E−08 | 1.67 |
| Example 143 | 2.6E−08 | 1.61 |
| Example 144 | 1.6E−08 | 1.6 |
| Example 145 | 1.1E−08 | 0.293 |
| Example 146 | 3.5E−08 | 1.16 |
| Example 147 | 2.4E−08 | 0.787 |
| Example 148 | 3.1E−08 | ND |
| Example 149 | 1.2E−08 | 0.092 |
| Example 150 | 9.3E−09 | 0.027 |
| Example 151 | 3.6E−09 | 0.309 |
| Example 152 | 9.9E−09 | 0.19 |
| Example 153 | 5.0E−09 | 0.146 |
| Example 154 | 6.6E−09 | 0.1 |
| Example 155 | 7.6E−09 | 0.189 |
| Example 156 | 7.0E−09 | 0.092 |
| Example 157 | 7.0E−09 | 0.286 |
| Example 158 | 4.6E−09 | 0.033 |
| Example 159 | 9.8E−09 | 0.246 |
| Example 160 | 5.0E−09 | 0.021 |
| Example 161 | 3.9E−09 | 0.081 |
| Example 162 | 9.9E−09 | 0.027 |
| Example 163 | 1.2E−08 | 0.047 |
| Example 164 | 8.2E−09 | 0.046 |
| Example 165 | 1.6E−06 | ND |
| Example 166 | 6.0E−09 | 0.036 |
| Example 167 | 4.6E−09 | 0.01 |
| Example 168 | 2.8E−09 | 0.025 |
| Example 169 | 9.0E−09 | 0.009 |
| Example 170 | 5.3E−09 | 0.006 |
| Example 171 | 4.1E−09 | 0.003 |
| Example 172 | 3.0E−09 | 0.004 |
| Example 173 | 3.1E−09 | 0.004 |
| Example 174 | 2.3E−09 | 0.005 |

TABLE 1-continued

IC$_{50}$ of Mcl-1 inhibition (fluorescence polarisation test) and of cytotoxicity for H929 cells
Note: IC$_{50}$ of Mcl-1 inhibition obtained using Method 2 are underlined.

| | IC$_{50}$ (M) Mcl-1 FP | IC$_{50}$ (μM) MTT H929 |
|---|---|---|
| Example 175 | 3.9E−09 | 0.003 |
| Example 176 | 3.1E−09 | 0.016 |
| Example 177 | 2.8E−09 | 0.005 |
| Example 178 | 6.3E−09 | 0.002 |
| Example 179 | 5.0E−09 | 0.03 |
| Example 180 | 8.9E−09 | 0.042 |
| Example 181 | 4.8E−09 | 0.008 |
| Example 182 | 4.4E−09 | 0.013 |
| Example 183 | 5.7E−09 | 0.012 |
| Example 184 | 6.0E−09 | 0.022 |
| Example 185 | 4.8E−09 | 0.012 |
| Example 186 | 4.3E−09 | 0.013 |
| Example 187 | 2.8E−09 | 0.02 |
| Example 188 | 6.4E−09 | 0.005 |
| Example 189 | 5.5E−09 | 0.034 |
| Example 190 | 7.5E−09 | 0.037 |
| Example 191 | 6.5E−09 | 0.063 |
| Example 192 | 7.7E−09 | 0.848 |
| Example 193 | 5.4E−09 | 0.116 |
| Example 194 | 8.0E−09 | 0.058 |
| Example 195 | 5.5E−09 | 0.311 |
| Example 196 | 5.6E−09 | 0.076 |
| Example 197 | 5.4E−09 | 0.07 |
| Example 198 | 7.7E−09 | 0.002 |
| Example 199 | 6.6E−09 | 0.28 |
| Example 200 | 6.1E−09 | 0.106 |
| Example 201 | 5.8E−09 | 0.027 |
| Example 202 | 3.5E−09 | 0.009 |
| Example 203 | 9.1E−09 | 0.005 |
| Example 204 | 4.9E−09 | 0.034 |
| Example 205 | 3.8E−09 | 0.028 |
| Example 206 | 8.0E−09 | 0.135 |
| Example 207 | 6.5E−09 | 0.186 |
| Example 208 | 5.5E−09 | 0.571 |
| Example 209 | 9.8E−09 | 0.115 |
| Example 210 | 1.0E−08 | 0.406 |
| Example 211 | 5.2E−09 | 0.063 |
| Example 212 | 1.6E−08 | 0.616 |
| Example 213 | 1.8E−08 | ND |
| Example 214 | 9.3E−09 | 0.897 |
| Example 215 | 8.0E−09 | 0.203 |
| Example 216 | 8.5E−09 | 0.217 |
| Example 217 | 5.3E−09 | 1.48 |
| Example 218 | 6.5E−09 | 0.805 |
| Example 219 | 9.9E−09 | 0.191 |
| Example 220 | 9.0E−09 | 0.277 |
| Example 221 | 6.3E−09 | 0.059 |
| Example 222 | 7.4E−09 | 0.314 |
| Example 223 | 1.4E−08 | 0.346 |
| Example 224 | 3.7E−09 | 0.049 |
| Example 225 | 8.4E−09 | 0.105 |
| Example 226 | 2.4E−08 | 0.311 |
| Example 227 | 2.0E−08 | 0.192 |
| Example 228 | 2.2E−08 | 0.166 |
| Example 229 | 4.5E−09 | 0.134 |
| Example 230 | 1.2E−08 | 0.312 |
| Example 231 | 1.0E−08 | 0.116 |
| Example 232 | 9.0E−09 | 0.046 |
| Example 233 | 3.4E−09 | 0.099 |
| Example 234 | 1.1E−08 | 0.135 |
| Example 235 | 5.1E−09 | 0.098 |
| Example 236 | 7.4E−09 | 0.137 |
| Example 237 | 1.5E−08 | 0.186 |
| Example 238 | 5.9E−09 | 0.077 |
| Example 239 | 1.1E−08 | 0.55 |
| Example 240 | 7.2E−09 | 0.225 |
| Example 241 | 5.5E−09 | 0.074 |
| Example 242 | 7.3E−09 | 0.09 |
| Example 243 | 5.6E−09 | 0.211 |
| Example 244 | 8.6E−09 | 0.205 |
| Example 245 | 5.8E−09 | 0.099 |
| Example 246 | 9.1E−09 | 0.324 |
| Example 247 | 8.0E−09 | 0.022 |
| Example 248 | 6.9E−09 | 0.015 |
| Example 249 | 4.0E−09 | 0.023 |
| Example 250 | 3.6E−09 | 0.499 |
| Example 251 | 6.3E−09 | 0.035 |
| Example 252 | 4.2E−09 | 0.009 |
| Example 253 | 3.1E−09 | 0.041 |
| Example 254 | 3.3E−09 | 0.044 |
| Example 255 | 7.5E−09 | 0.018 |
| Example 256 | 4.8E−09 | 0.006 |
| Example 257 | 5.0E−09 | 0.019 |
| Example 258 | 6.6E−09 | 0.069 |
| Example 259 | 5.2E−09 | 0.07 |
| Example 260 | 6.7E−09 | 0.033 |
| Example 261 | 1.7E−09 | 0.018 |
| Example 262 | 3.9E−09 | 0.023 |
| Example 263 | 2.0E−09 | 0.126 |
| Example 264 | 9.1E−09 | 0.034 |
| Example 265 | 3.5E−09 | 0.016 |
| Example 266 | 5.7E−09 | 0.093 |
| Example 267 | 8.8E−09 | 1.6 |
| Example 268 | 8.2E−09 | 0.086 |
| Example 269 | 1.1E−08 | 0.069 |
| Example 270 | 1.2E−08 | 0.068 |
| Example 271 | 1.6E−08 | 0.197 |
| Example 272 | 2.2E−08 | 0.822 |
| Example 273 | 9.2E−09 | 0.905 |
| Example 274 | 7.7E−09 | 0.131 |
| Example 275 | 4.5E−09 | 0.051 |
| Example 276 | 6.2E−09 | ND |
| Example 277 | 4.8E−09 | 0.07 |
| Example 278 | 6.7E−09 | 0.202 |
| Example 279 | 8.0E−09 | 0.406 |
| Example 280 | 4.0E−09 | 0.071 |
| Example 281 | 7.9E−09 | 0.081 |
| Example 282 | 4.0E−09 | 0.601 |
| Example 283 | 2.6E−08 | 0.25 |
| Example 284 | 4.8E−08 | 1.79 |
| Example 285 | 1.7E−08 | 0.588 |
| Example 286 | 7.6E−09 | 0.508 |
| Example 287 | 8.3E−09 | 0.667 |
| Example 288 | 1.2E−08 | 0.086 |
| Example 289 | 1.4E−08 | 0.18 |
| Example 290 | 5.8E−09 | 0.097 |
| Example 291 | 3.8E−08 | 1.3 |
| Example 292 | 9.3E−09 | 0.192 |
| Example 293 | 8.9E−07 | ND |
| Example 294 | 1.6E−08 | 0.886 |
| Example 295 | 4.7E−09 | 0.021 |
| Example 296 | 9.3E−09 | ND |
| Example 297 | 6.6E−09 | ND |
| Example 298 | 1.2E−08 | 1.14 |
| Example 299 | 1.6E−08 | 1.03 |
| Example 300 | 3.7E−08 | ND |
| Example 301 | 1.2E−08 | 0.108 |
| Example 302 | 1.4E−08 | 1.59 |
| Example 303 | 9.3E−09 | 0.998 |
| Example 304 | 1.1E−08 | 1.7 |
| Example 305 | 6.9E−08 | 1.64 |
| Example 306 | 1.4E−08 | 1.12 |
| Example 307 | 8.3E−09 | 0.998 |
| Example 308 | 5.9E−09 | 1.5 |
| Example 309 | 1.0E−08 | 1.48 |
| Example 310 | 1.4E−08 | 0.26 |
| Example 311 | 1.5E−08 | 1.59 |
| Example 312 | 8.9E−09 | 1 |
| Example 313 | 1.0E−08 | 0.886 |
| Example 314 | 6.9E−09 | 1.82 |
| Example 315 | 2.2E−08 | ND |
| Example 316 | 7.7E−09 | 1.46 |
| Example 317 | 1.8E−08 | 0.852 |
| Example 318 | 3.0E−08 | ND |
| Example 319 | 1.5E−08 | 0.834 |
| Example 320 | 6.5E−09 | 0.471 |

TABLE 1-continued

IC$_{50}$ of Mcl-1 inhibition (fluorescence polarisation test) and of cytotoxicity for H929 cells
Note: IC$_{50}$ of Mcl-1 inhibition obtained using Method 2 are underlined.

| | IC$_{50}$ (M) Mcl-1 FP | IC$_{50}$ (μM) MTT H929 |
|---|---|---|
| Example 321 | 6.0E−09 | ND |
| Example 322 | 4.3E−09 | 0.113 |
| Example 323 | 8.8E−09 | ND |
| Example 324 | 1.5E−08 | 0.254 |
| Example 325 | 5.2E−08 | ND |
| Example 326 | 7.9E−09 | ND |
| Example 327 | 1.5E−08 | ND |
| Example 328 | 5.0E−09 | 3.03 |
| Example 329 | 6.0E−08 | 3.31 |
| Example 330 | 8.3E−09 | 1.17 |
| Example 331 | 6.0E−09 | 0.394 |
| Example 332 | 1.3E−08 | ND |
| Example 333 | 7.9E−07 | ND |
| Example 334 | 1.4E−08 | 0.968 |
| Example 335 | 1.2E−08 | 0.217 |
| Example 336 | 43.2% @ 10 uM | ND |
| Example 337 | 3.8E−08 | 1.87 |
| Example 338 | 3.0E−08 | 1.04 |
| Example 339 | 18.85% @ 10 uM | ND |
| Example 340 | 6.7E−07 | ND |
| Example 341 | 3.5E−08 | 0.706 |
| Example 342 | <u>3.5E−07</u> | ND |
| Example 343 | <u>2.5E−07</u> | ND |
| Example 344 | 1.6E−08 | 0.22 |
| Example 345 | 8.6E−09 | 0.322 |
| Example 346 | 1.7E−08 | 0.063 |
| Example 347 | 1.4E−08 | 0.25 |
| Example 348 | 2.1E−08 | 0.346 |
| Example 349 | 2.7E−08 | 2.46 |
| Example 350 | 2.8E−08 | ND |
| Example 351 | 1.5E−08 | 0.526 |
| Example 352 | 1.4E−08 | 0.91 |
| Example 353 | 2.8E−08 | ND |
| Example 354 | 1.1E−08 | 0.544 |
| Example 355 | 3.0E−08 | ND |
| Example 356 | 1.1E−08 | ND |
| Example 357 | 5.5E−07 | 3.39 |
| Example 358 | 9.5E−09 | 1.61 |
| Example 359 | 6.6E−09 | 0.336 |
| Example 360 | 2.0E−07 | ND |
| Example 361 | 7.1E−07 | ND |
| Example 362 | 2.6E−08 | 1 |
| Example 363 | 7.7E−09 | 0.071 |
| Example 364 | 5.1E−09 | 0.052 |
| Example 365 | 5.9E−09 | 0.026 |
| Example 366 | 8.6E−09 | 0.346 |
| Example 367 | 3.2E−09 | 0.015 |
| Example 368 | 1.4E−08 | 0.005 |
| Example 369 | 5.1E−09 | 0.009 |
| Example 370 | 8.7E−09 | 0.018 |
| Example 371 | 5.6E−09 | 0.027 |
| Example 372 | 9.7E−09 | 0.018 |
| Example 373 | 4.6E−09 | 0.012 |
| Example 374 | 9.2E−09 | 0.038 |
| Example 375 | 5.6E−09 | 0.081 |
| Example 376 | 2.0E−08 | 0.076 |
| Example 377 | 3.8E−09 | 0.047 |
| Example 378 | <u>3.2E−09</u> | 0.202 |
| Example 379 | 1.3E−08 | 0.174 |
| Example 380 | 1.1E−08 | 0.162 |
| Example 381 | 1.3E−08 | 0.119 |
| Example 382 | 7.1E−09 | 0.033 |
| Example 383 | 5.6E−09 | 0.03 |
| Example 384 | 3.8E−09 | 0.053 |
| Example 385 | 3.5E−09 | 0.048 |
| Example 386 | 1.0E−08 | 0.075 |
| Example 387 | 4.0E−09 | 0.202 |
| Example 388 | <u>2.3E−08</u> | ND |
| Example 389 | <u>1.2E−06</u> | ND |
| Example 390 | 4.0E−08 | 20 |
| Example 391 | 3.7E−08 | 22.1 |
| Example 392 | 3.0E−08 | 17.1 |
| Example 393 | 4.1E−08 | 16.6 |
| Example 394 | <u>3.4E−08</u> | ND |
| Example 395 | <u>1.6E−08</u> | ND |
| Example 396 | 9.9E−08 | 16.1 |
| Example 397 | <u>8.0E−09</u> | 15.7 |
| Example 398 | 1.5E−06 | 23.8 |
| Example 399 | <u>1.4E−08</u> | ND |
| Example 400 | 8.4E−08 | 14.4 |
| Example 401 | 4.9E−08 | 22.3 |
| Example 402 | 6.6E−08 | 10.4 |
| Example 403 | <u>1.4E−08</u> | ND |
| Example 404 | 5.7E−08 | 21.6 |
| Example 405 | <u>7.4E−09</u> | ND |
| Example 406 | 3.5E−08 | 21.9 |
| Example 407 | 1.1E−07 | 7.33 |
| Example 408 | 26.25% @ 10 uM | 15.9 |
| Example 409 | <u>2.0E−07</u> | ND |
| Example 410 | <u>2.2E−06</u> | ND |
| Example 411 | 3.4E−08 | 19 |
| Example 412 | 5.1E−08 | 28.7 |
| Example 413 | <u>1.3E−08</u> | 15.8 |
| Example 414 | 21.35% @ 10 uM | 27.2 |
| Example 415 | 5.0E−08 | 6.41 |
| Example 416 | 7.0E−07 | ND |
| Example 417 | <u>1.5E−07</u> | ND |
| Example 418 | 5.6E−08 | 13.3 |
| Example 419 | 3.4E−08 | 21.5 |
| Example 420 | 4.0E−08 | 15.6 |
| Example 421 | 38.1% @ 10 uM | ND |
| Example 422 | <u>1.4E−08</u> | 14.4 |
| Example 423 | 5.3E−08 | ND |
| Example 424 | 9.6E−08 | ND |
| Example 425 | <u>9.6E−09</u> | ND |
| Example 426 | <u>4.6E−09</u> | ND |
| Example 427 | <u>4.7E−09</u> | ND |
| Example 428 | <u>7.5E−09</u> | ND |
| Example 429 | <u>5.3E−08</u> | ND |
| Example 430 | 1.4E−07 | 15.5 |
| Example 431 | 3.2E−08 | ND |
| Example 432 | 6.8E−08 | 13.6 |
| Example 433 | ND | ND |
| Example 434 | 1.7E−07 | 11.3 |
| Example 435 | 3.2E−07 | 11.1 |
| Example 436 | <u>2.9E−08</u> | 15.1 |
| Example 437 | 4.5E−08 | 20.3 |
| Example 438 | <u>8.5E−08</u> | ND |
| Example 439 | <u>2.5E−07</u> | ND |
| Example 440 | <u>3.0E−07</u> | ND |
| Example 441 | <u>2.7E−08</u> | ND |
| Example 442 | 1.1E−07 | 20.4 |
| Example 443 | <u>1.8E−08</u> | ND |
| Example 444 | <u>1.2E−08</u> | ND |
| Example 445 | 1.3E−07 | 21 |
| Example 446 | 1.1E−07 | 25.7 |
| Example 447 | <u>6.8E−08</u> | ND |
| Example 448 | <u>4.4E−07</u> | ND |
| Example 449 | <u>2.8E−08</u> | ND |
| Example 450 | <u>2.6E−08</u> | ND |
| Example 451 | <u>5.8E−07</u> | ND |
| Example 452 | <u>3.0E−07</u> | ND |
| Example 453 | 2.6E−08 | 3 |
| Example 454 | 1.2E−08 | ND |
| Example 455 | 6.2E−09 | 0.339 |
| Example 456 | 8.0E−09 | 0.513 |
| Example 457 | 3.4E−08 | ND |
| Example 458 | 3.2E−08 | 2.73 |
| Example 459 | 3.7E−06 | ND |
| Example 460 | 1.3E−07 | 6.82 |
| Example 461 | 8.5E−08 | 4.86 |
| Example 462 | 3.7E−05 | ND |
| Example 463 | 4.6E−08 | 5.11 |
| Example 464 | <u>3.9E−07</u> | ND |
| Example 465 | <u>2.5E−08</u> | 2.06 |
| Example 466 | 3.9E−08 | 3.35 |

TABLE 1-continued

IC$_{50}$ of Mcl-1 inhibition (fluorescence polarisation test) and of cytotoxicity for H929 cells
Note: IC$_{50}$ of Mcl-1 inhibition obtained using Method 2 are underlined.

| | IC$_{50}$ (M) Mcl-1 FP | IC$_{50}$ (μM) MTT H929 |
|---|---|---|
| Example 467 | 1.1E−08 | 0.502 |
| Example 468 | 8.6E−09 | 2.02 |
| Example 469 | 1.5E−08 | 3.06 |
| Example 470 | <u>4.8E−07</u> | ND |
| Example 471 | <u>6.3E−09</u> | ND |
| Example 472 | 13.05% @ 10 uM | ND |
| Example 473 | 5.0E−08 | ND |
| Example 474 | <u>5.5E−07</u> | ND |
| Example 475 | <u>6.8E−09</u> | 1.12 |
| Example 476 | 2.0E−08 | 1.03 |
| Example 477 | <u>5.6E−08</u> | 2.57 |
| Example 478 | 5.3E−07 | ND |
| Example 479 | 1.1E−08 | ND |
| Example 480 | 2.8E−08 | ND |
| Example 481 | 5.4E−09 | 0.643 |
| Example 482 | 7.4E−09 | 0.004 |
| Example 483 | 5.2E−09 | 0.003 |
| Example 484 | 3.4E−09 | 0.014 |
| Example 485 | 4.3E−09 | 0.012 |
| Example 486 | 1.9E−09 | 0.146 |
| Example 487 | 6.5E−09 | 0.004 |
| Example 488 | 5.4E−09 | 0.014 |
| Example 489 | 1.2E−09 | 0.026 |
| Example 490 | 3.0E−09 | 0.018 |
| Example 491 | 28.3% @ 10 uM | ND |
| Example 492 | 9.0E−08 | 2.19 |
| Example 493 | <u>5.0E−09</u> | ND |
| Example 494 | 4.4E−08 | 2.56 |
| Example 495 | 3.6E−08 | 1.19 |
| Example 496 | 2.0E−07 | 3.39 |
| Example 497 | 9.1E−07 | 5.95 |
| Example 498 | 7.4E−08 | ND |
| Example 499 | 1.0E−07 | 1.5 |
| Example 500 | 8.0E−08 | 2.25 |
| Example 501 | 2.8E−07 | 2.84 |
| Example 502 | 1.9E−08 | 0.766 |
| Example 503 | 5.0E−07 | 7.02 |
| Example 504 | 2.9E−08 | 0.324 |
| Example 505 | 5.8E−08 | 0.954 |
| Example 506 | 7.5E−08 | 8.29 |
| Example 507 | 2.2E−07 | ND |
| Example 508 | 3.7E−07 | ND |
| Example 509 | 6.2E−08 | 1.46 |
| Example 510 | 3.9E−08 | 0.639 |
| Example 511 | 4.8E−07 | ND |
| Example 512 | 1.3E−07 | 7.42 |
| Example 513 | 3.7E−07 | ND |
| Example 514 | 9.6E−08 | 1.7 |
| Example 515 | 8.4E−08 | 2.95 |
| Example 516 | 1.3E−07 | 5.07 |
| Example 517 | 5.1E−08 | 6.09 |
| Example 518 | 3.5E−08 | 9.18 |
| Example 519 | 2.3E−08 | 0.523 |
| Example 520 | 4.1E−08 | 1.13 |
| Example 521 | 2.4E−07 | ND |
| Example 522 | 7.5E−08 | ND |
| Example 523 | <u>1.8E−09</u> | 0.532 |
| Example 524 | 3.1E−08 | 0.417 |
| Example 525 | <u>3.3E−09</u> | 0.755 |
| Example 526 | <u>4.1E−09</u> | 0.835 |
| Example 527 | 7.1E−08 | 0.272 |
| Example 528 | 1.6E−08 | 0.334 |
| Example 529 | 1.3E−08 | 0.308 |
| Example 530 | 1.2E−07 | 1.59 |
| Example 531 | <u>3.5E−09</u> | 1.22 |
| Example 532 | 5.9E−08 | 0.323 |
| Example 533 | 2.8E−08 | 0.201 |
| Example 534 | 1.6E−08 | 0.413 |
| Example 535 | 1.3E−07 | 1.84 |
| Example 536 | 7.7E−08 | 0.797 |
| Example 537 | 4.3E−08 | 0.208 |
| Example 538 | 4.7E−08 | 0.672 |
| Example 539 | 7.2E−08 | 0.731 |
| Example 540 | <u>3.2E−09</u> | 0.311 |
| Example 541 | 2.9E−08 | 0.329 |
| Example 542 | 4.3E−07 | ND |
| Example 543 | 4.2E−08 | 0.766 |
| Example 544 | 1.4E−08 | 0.274 |
| Example 545 | 3.9E−08 | 1.1 |
| Example 546 | 1.7E−08 | 0.416 |
| Example 547 | 3.3E−08 | 0.475 |
| Example 548 | 1.8E−08 | 0.497 |
| Example 549 | 1.3E−07 | 1.5 |
| Example 550 | 4.8E−08 | 0.203 |
| Example 551 | 2.8E−08 | 0.201 |
| Example 552 | 4.1E−08 | 0.784 |
| Example 553 | 1.1E−08 | 0.585 |
| Example 554 | 2.4E−08 | 0.177 |
| Example 555 | 3.9E−07 | ND |
| Example 556 | <u>1.2E−08</u> | ND |
| Example 557 | <u>4.5E−09</u> | 0.475 |
| Example 558 | 5.9E−08 | 0.742 |
| Example 559 | <u>5.2E−09</u> | 0.293 |
| Example 560 | 1.1E−08 | 0.128 |
| Example 561 | 2.7E−08 | 0.61 |
| Example 562 | 5.1E−07 | ND |
| Example 563 | 7.4E−08 | 1.16 |
| Example 564 | <u>8.5E−10</u> | 0.202 |
| Example 565 | 4.8E−07 | 1.96 |
| Example 566 | 3.0E−08 | 0.233 |
| Example 567 | 2.1E−08 | 1.04 |
| Example 568 | 2.5E−08 | 0.22 |
| Example 569 | 3.9E−08 | 1.73 |
| Example 570 | 2.0E−08 | 0.324 |
| Example 571 | 4.4E−08 | 0.559 |
| Example 572 | 1.9E−08 | 0.394 |
| Example 573 | 1.1E−08 | 0.366 |
| Example 574 | 24.3% @ 10 uM | ND |
| Example 575 | 46.8% @ 10 uM | ND |
| Example 576 | 6.2E−08 | 1.51 |
| Example 577 | 7.6E−09 | 0.119 |
| Example 578 | 3.8E−08 | 0.347 |
| Example 579 | 8.5E−09 | 0.463 |
| Example 580 | 3.7E−08 | ND |
| Example 581 | 4.2E−07 | ND |
| Example 582 | 8.4E−08 | ND |
| Example 583 | 1.1E−07 | ND |
| Example 584 | 2.9E−08 | 0.902 |
| Example 585 | 8.5E−08 | 2.92 |
| Example 586 | 1.4E−06 | ND |
| Example 587 | 2.6E−08 | 0.539 |
| Example 588 | 8.0E−09 | 0.256 |
| Example 589 | 8.7E−09 | 0.233 |
| Example 590 | 8.4E−08 | ND |
| Example 591 | 6.5E−08 | 1.67 |
| Example 592 | <u>2.4E−06</u> | ND |
| Example 593 | <u>1.9E−06</u> | ND |
| Example 594 | 6.1E−09 | 0.13 |
| Example 595 | 6.2E−09 | 0.114 |
| Example 596 | 2.7E−09 | 0.12 |
| Example 597 | 6.2E−09 | 0.449 |
| Example 598 | 7.8E−09 | 0.097 |
| Example 599 | 1.1E−08 | ND |
| Example 600 | 4.1E−09 | 0.031 |
| Example 601 | 1.2E−08 | 0.133 |
| Example 602 | 3.7E−09 | 0.156 |
| Example 603 | 5.0E−09 | 0.036 |
| Example 604 | 5.7E−09 | 0.064 |
| Example 605 | 8.2E−09 | 0.254 |
| Example 606 | 4.0E−09 | 0.064 |
| Example 607 | 3.5E−09 | 0.04 |
| Example 608 | 4.2E−09 | 0.021 |
| Example 609 | 3.5E−09 | 0.063 |
| Example 610 | 3.5E−09 | 0.091 |
| Example 611 | 3.9E−09 | 0.23 |
| Example 612 | 3.5E−09 | 0.02 |

TABLE 1-continued

IC$_{50}$ of Mcl-1 inhibition (fluorescence polarisation test) and of cytotoxicity for H929 cells
Note: IC$_{50}$ of Mcl-1 inhibition obtained using Method 2 are underlined.

| | IC$_{50}$ (M) Mcl-1 FP | IC$_{50}$ (µM) MTT H929 |
|---|---|---|
| Example 613 | 3.5E−09 | 0.158 |
| Example 614 | 8.4E−09 | ND |
| Example 615 | 8.0E−10 | 0.292 |
| Example 616 | 4.0E−09 | 0.07 |
| Example 617 | 5.4E−09 | 0.277 |
| Example 618 | 5.6E−09 | ND |
| Example 619 | 7.0E−09 | 0.336 |
| Example 620 | 5.9E−09 | 0.532 |
| Example 621 | 5.3E−09 | 0.095 |
| Example 622 | 1.1E−08 | 0.109 |
| Example 623 | 67.8% @ 10 uM | ND |
| Example 624 | 26.95% @ 10 uM | ND |
| Example 625 | 74.85% @ 10 uM | 0.62 |
| Example 626 | 39.45% @ 10 uM | ND |
| Example 627 | <u>4.9E−07</u> | ND |
| Example 628 | 33.2% @ 10 uM | ND |
| Example 629 | 14.95% @ 10 uM | ND |
| Example 630 | 27.95% @ 10 uM | ND |
| Example 631 | 56% @ 10 uM | ND |
| Example 632 | 41.8% @ 10 uM | ND |
| Example 633 | <u>40.2 % @ 10 uM</u> | ND |
| Example 634 | 10.7% @ 10 uM | ND |
| Example 635 | 50.75% @ 10 uM | ND |
| Example 636 | <u>71.7 % @ 1000 uM</u> | ND |
| Example 637 | 5.9% @ 10 uM | ND |
| Example 638 | 34.5% @ 10 uM | ND |
| Example 639 | 66.25% @ 10 uM | ND |
| Example 640 | 42.4% @ 10 uM | ND |
| Example 641 | 9.6E−07 | ND |
| Example 642 | 11% @ 10 uM | ND |
| Example 643 | 6.6E−07 | 0.303 |
| Example 644 | 3.7E−07 | 0.248 |
| Example 645 | 2.2E−08 | ND |
| Example 646 | 2.1E−08 | 0.298 |
| Example 647 | 2.3E−08 | 0.498 |
| Example 648 | 1.4E−08 | ND |
| Example 649 | 2.3E−08 | 0.341 |
| Example 650 | 5.1E−08 | ND |
| Example 651 | 6.8E−09 | 0.282 |
| Example 652 | 4.7E−09 | 0.059 |
| Example 653 | 1.6E−08 | ND |
| Example 654 | 4.0E−08 | 2.08 |
| Example 655 | 2.6E−08 | ND |
| Example 656 | 6.1E−08 | 0.523 |
| Example 657 | 2.1E−08 | ND |
| Example 658 | 1.8E−08 | 1.71 |
| Example 659 | 2.2E−08 | ND |
| Example 660 | 5.1E−08 | ND |
| Example 661 | 1.0E−07 | ND |
| Example 662 | 2.7E−07 | ND |
| Example 663 | 2.5E−07 | ND |
| Example 664 | 3.86E−08 | 2.08 |
| Example 665 | 3.9E−06 | ND |
| Example 666 | 7.7E−08 | ND |
| Example 667 | 2.1E−06 | ND |
| Example 668 | 1.1E−08 | 0.13 |
| Example 669 | 4.9E−09 | 0.108 |
| Example 670 | 3.2E−09 | 0.027 |
| Example 671 | 6.9E−09 | 0.107 |
| Example 672 | 4.3E−09 | 0.019 |
| Example 673 | 1.1E−08 | 0.576 |
| Example 674 | 2.1E−08 | ND |
| Example 675 | <u>2.2E−08</u> | ND |
| Example 676 | <u>3.6E−05</u> | ND |
| Example 677 | <u>2.2E−06</u> | ND |
| Example 678 | <u>1.8E−06</u> | ND |
| Example 679 | <u>8.9E−07</u> | ND |
| Example 680 | <u>2.8E−05</u> | ND |
| Example 681 | <u>6.7E−09</u> | ND |
| Example 682 | <u>5.1E−07</u> | ND |
| Example 683 | <u>3.3E−06</u> | ND |
| Example 684 | 1.9E−08 | 2.23 |
| Example 685 | 1.2E−08 | ND |
| Example 686 | 1.0E−06 | ND |
| Example 687 | 2.9E−08 | 3.66 |
| Example 688 | 3.3E−07 | ND |
| Example 689 | 8.5E−09 | 0.657 |
| Example 690 | 2.3E−08 | 0.178 |
| Example 691 | 9.6E−09 | 0.037 |
| Example 692 | 1.0E−08 | 0.079 |
| Example 693 | 9.3E−10 | 0.101 |
| Example 694 | 6.4E−09 | 0.183 |
| Example 695 | 1.6E−08 | 0.268 |
| Example 696 | 9.6E−09 | 0.05 |
| Example 697 | 45.55% @ 1 uM | ND |
| Example 698 | 7.3E−09 | ND |
| Example 699 | 28.5% @ 1 uM | ND |
| Example 700 | 1.2E−08 | ND |
| Example 701 | 40.75% @ 1 uM | ND |
| Example 702 | 9.4E−09 | ND |
| Example 703 | 9.3E−09 | 0.03 |
| Example 704 | 9.9E−09 | 0.025 |
| Example 705 | 1.7E−08 | 0.02 |
| Example 706 | 3.6E−09 | 0.04 |
| Example 707 | 1.4E−08 | 0.042 |
| Example 708 | 9.6E−09 | 0.055 |
| Example 709 | 3.2E−08 | 0.518 |
| Example 710 | <u>2.4E−09</u> | 0.384 |
| Example 711 | <u>3.7E−09</u> | 0.591 |
| Example 712 | 4.1E−07 | ND |
| Example 713 | 1.6E−08 | ND |
| Example 714 | 3.4E−08 | 0.188 |
| Example 715 | <u>1.6E−09</u> | ND |
| Example 716 | 1.5E−08 | ND |
| Example 717 | 2.7E−08 | 0.865 |
| Example 718 | 1.2E−08 | 0.082 |
| Example 719 | <u>2.7E−06</u> | ND |
| Example 720 | <u>4.4E−08</u> | ND |
| Example 721 | <u>7.6E−08</u> | ND |
| Example 722 | 1.4E−09 | 0.023 |
| Example 723 | 1.18E−09 | 0.004 |
| Example 724 | 9.48E−10 | 0.002 |
| Example 725 | 1.46E−09 | 0.01 |
| Example 726 | 1.18E−09 | 0.011 |
| Example 727 | 1.32E−09 | 0.013 |
| Example 728 | 1.18E−09 | 0.003 |
| Example 729 | 1.24E−09 | 0.009 |
| Example 730 | 9.48E−10 | 0.005 |
| Example 731 | 9.48E−10 | 0.005 |
| Example 732 | 1.27E−09 | 0.013 |
| Example 733 | 9.48E−10 | 0.005 |
| Example 734 | 9.48E−10 | 0.006 |
| Example 735 | 9.48E−10 | 0.007 |
| Example 736 | 2.58E−09 | ND |
| Example 737 | 1.43E−08 | ND |
| Example 738 | 3.78E−09 | 0.103 |
| Example 739 | 2.32E−09 | 0.093 |
| Example 740 | 5.04E−09 | ND |
| Example 741 | 9.48E−10 | 0.002 |
| Example 742 | 9.48E−10 | 0.002 |
| Example 743 | 9.48E−10 | 0.005 |
| Example 744 | 9.48E−10 | 0.042 |
| Example 745 | 9.48E−10 | 0.003 |
| Example 746 | 3.5E−09 | 0.111 |
| Example 747 | 3.6E−09 | 0.0263 |
| Example 748 | 1.21E−08 | ND |
| Example 749 | 8.24E−09 | ND |
| Example 750 | 1.33E−09 | 0.035 |
| Example 751 | 9.48E−10 | 0.008 |
| Example 752 | 5.5E−09 | 0.084 |
| Example 753 | 3.0E−09 | 0.005 |
| Example 754 | 4.7E−09 | 0.089 |
| Example 755 | 4.65E−09 | 0.032 |
| Example 756 | 6.89E−07 | ND |
| Example 757 | 3.95E−09 | 0.013 |
| Example 758 | 3.53E−07 | ND |

TABLE 1-continued

IC$_{50}$ of Mcl-1 inhibition (fluorescence polarisation test) and of cytotoxicity for H929 cells
Note: IC$_{50}$ of Mcl-1 inhibition obtained using Method 2 are underlined.

|  | IC$_{50}$ (M) Mcl-1 FP | IC$_{50}$ (µM) MTT H929 |
|---|---|---|
| Example 759 | 9.06E−09 | 0.054 |
| Example 760 | 1.18E−09 | 0.004 |
| Example 761 | 1.07E−07 | 0.148 |
| Example 762 | 1.88E−09 | 0.014 |
| Example 763 | 9.05E−08 | ND |
| Example 764 | 1.35E−09 | 0.019 |
| Example 765 | 6.58E−07 | ND |
| Example 766 | 3.66E−09 | 0.037 |
| Example 767 | 1.73E−09 | 0.050 |
| Example 768 | 1.04E−09 | 0.039 |
| Example 769 | 9.48E−10 | 0.010 |
| Example 770 | 1.01E−09 | 0.010 |
| Example 771 | 1.04E−09 | 0.019 |
| Example 772 | 9.48E−10 | 0.010 |
| Example 773 | 1.25E−09 | 0.017 |
| Example 774 | 9.48E−10 | 0.009 |
| Example 775 | 3.55E−09 | 0.039 |
| Example 776 | 9.48E−10 | 0.007 |
| Example 777 | 1.12E−09 | 0.008 |
| Example 778 | 1.09E−09 | 0.013 |
| Example 779 | 1.86E−09 | 0.056 |
| Example 780 | 7.26E−09 | ND |
| Example 781 | 9.48E−10 | 0.033 |
| Example 782 | 1.68E−09 | 0.057 |
| Example 783 | 1.06E−09 | 0.037 |
| Example 784 | 9.48E−10 | 0.023 |
| Example 785 | 3.85E−09 | ND |
| Example 786 | 4.95E−09 | ND |
| Example 787 | 4.71E−07 | 0.245 |
| Example 788 | 6.74E−07 | 0.494 |
| Example 789 | 3.82E−07 | 0.206 |
| Example 790 | 1.91E−06 | ND |
| Example 791 | 2.26E−06 | ND |
| Example 792 | 6.44E−06 | ND |
| Example 793 | 5.37E−06 | ND |
| Example 794 | 5.35E−06 | ND |
| Example 795 | 8.5E−07 | ND |
| Example 796 | 5.16E−07 | ND |
| Example 797 | 2.75E−06 | ND |
| Example 798 | 5.15E−06 | ND |
| Example 799 | 59.6% @ 10 uM | ND |
| Example 800 | 1.39E−06 | ND |
| Example 801 | 4.37E−06 | ND |
| Example 802 | 2.88E−06 | ND |
| Example 803 | 3.14E−06 | ND |
| Example 804 | 4.68E−05 | ND |
| Example 805 | 53.5% @ 10 uM | ND |
| Example 806 | 1.63E−06 | ND |
| Example 807 | 52.45% @ 10 uM | ND |
| Example 808 | 1.72E−07 | 0.010 |
| Example 809 | 6.91E−07 | 0.047 |
| Example 810 | 4.2E−07 | 0.001 |
| Example 811 | 8.55E−09 | 0.002 |
| Example 812 | 6.51E−07 | 0.103 |
| Example 813 | 5.47E−09 | 0.011 |
| Example 814 | 6.39E−07 | 0.314 |
| Example 815 | 19.95% @ 10 uM | ND |
| Example 816 | 1.72E−07 | ND |
| Example 817 | 4.75E−07 | ND |
| Example 818 | 1.12E−06 | ND |
| Example 819 | 1.57E−07 | ND |
| Example 820 | 1.29E−08 | ND |
| Example 821 | 3.61E−07 | ND |
| Example 822 | 2.4E−06 | ND |
| Example 823 | 1.98E−08 | ND |
| Example 824 | 3.82E−08 | ND |
| Example 825 | 5.82E−07 | ND |
| Example 826 | 7.35E−08 | ND |
| Example 827 | ND | ND |
| Example 828 | 2.4E−07 | ND |
| Example 829 | ND | ND |
| Example 830 | −11.9% @ 10 uM | ND |
| Example 831 | ND | ND |
| Example 832 | 3.15E−09 | 0.004 |
| Example 833 | 3.35E−09 | ND |
| Example 834 | ND | ND |
| Example 835 | 2.9E−09 | 0.002 |
| Example 836 | 2.8E−09 | 0.002 |
| Example 837 | 2.35E−09 | 0.003 |
| Example 838 | 3.15E−09 | 0.002 |
| Example 839 | 6.91E−07 | ND |
| Example 840 | 1.28E−07 | ND |
| Example 841 | 4.8E−09 | ND |
| Example 842 | 7.65% @ 10 uM | ND |
| Example 843 | 23.05% @ 10 uM | ND |
| Example 844 | 1.67E−06 | ND |
| Example 845 | 7.85% @ 10 uM | ND |
| Example 846 | 25.1% @ 10 uM | ND |
| Example 847 | 3.55% @ 10 uM | ND |
| Example 848 | 46.7% @ 10 uM | ND |
| Example 849 | 61.35% @ 10 uM | ND |
| Example 850 | 29.4% @ 10 uM | ND |
| Example 851 | 7.85% @ 10 uM | ND |
| Example 852 | ND | ND |
| Example 853 | ND | ND |
| Example 854 | 1.72E−07 | ND |
| Example 855 | ND | ND |
| Example 856 | 9.79E−07 | ND |
| Example 857 | 77.85% @ 10 uM | ND |
| Example 858 | 2.11E−07 | ND |
| Example 859 | 1.13E−06 | ND |
| Example 860 | 2.04E−07 | ND |
| Example 861 | 5.77E−07 | ND |
| Example 862 | ND | ND |
| Example 863 | ND | ND |
| Example 864 | 2.7E−08 | ND |
| Example 865 | ND | ND |
| Example 866 | ND | ND |
| Example 867 | ND | ND |
| Example 868 | ND | ND |
| Example 869 | ND | ND |
| Example 870 | ND | ND |
| Example 871 | ND | ND |

ND: not determined

For partial inhibitors, the percentage fluorescence polarisation inhibition for a given concentration of the test compound is indicated. Accordingly, 45.1% @10 µM means that 45.1% fluorescence polarisation inhibition is observed for a concentration of test compound equal to 10 µM.

Example C: Quantification of the Cleaved Form of PARP In Vivo

The ability of the compounds of the invention to induce apoptosis, by measuring cleaved PARP levels, is evaluated in a xenograft model of AMO-1 multiple myeloma cells. $1.10^7$ AMO-1 cells are grafted sub-cutaneously into immunosuppressed mice (SCID strain). 12 to 14 days after the graft, the animals are treated by intraveinous or oral routes with the various compounds. After treatment, the tumour masses are recovered and lysed, and the cleaved form of PARP is quantified in the tumour lysates.

The quantification is carried out using the "Meso Scale Discovery (MSD) ELISA platform" test, which specifically assays the cleaved form of PARP. It is expressed in the form of an activation factor corresponding to the ratio between the quantity of cleaved PARP in the treated mice divided by the quantity of cleaved PARP in the control mice.

The results (presented in Table 2 below) show that the compounds of the invention are capable of inducing apoptosis in AMO-1 tumour cells in vivo.

TABLE 2

Quantification of the cleaved form of PARP in vivo

| | PARP fold |
|---|---|
| Example 30 | 285.3 |
| Example 31 | 138.6 |
| Example 32 | 216.7 |
| Example 41 | 288.1 |
| Example 44 | 180.4 |
| Example 45 | 194.3 |
| Example 47 | 101.1 |
| Example 49 | 180.5 |
| Example 52 | 211.4 |
| Example 53 | 178.7 |
| Example 55 | 188.4 |
| Example 57 | 198.3 |
| Example 58 | 181.9 |
| Example 62 | 391.6 |
| Example 63 | 177.8 |
| Example 70 | 184.1 |
| Example 71 | 128.3 |
| Example 77 | 178.2 |
| Example 83 | 187.6 |
| Example 91 | 105.5 |
| Example 95 | 156.8 |
| Example 113 | 189.8 |
| Example 114 | 158.2 |
| Example 115 | 136 |
| Example 117 | 188.7 |
| Example 118 | 159.8 |
| Example 120 | 206.8 |
| Example 123 | 243.8 |
| Example 135 | 293.3 |
| Example 138 | 333.9 |
| Example 158 | 125.1 |
| Example 167 | 230.1 |
| Example 168 | 179.2 |
| Example 170 | 144 |
| Example 171 | 207.4 |
| Example 172 | 175.3 |
| Example 174 | 170.3 |
| Example 175 | 155.4 |
| Example 176 | 133.4 |
| Example 177 | 233.8 |
| Example 180 | 238.8 |
| Example 181 | 152.6 |
| Example 182 | 242.5 |
| Example 185 | 308.8 |
| Example 188 | 121.6 |
| Example 198 | 280 |
| Example 202 | 153.8 |
| Example 209 | 120.7 |
| Example 256 | 125.1 |
| Example 290 | 121 |
| Example 483 | 411 |
| Example 485 | 110.8 |
| Example 487 | 141.4 |
| Example 488 | 175.5 |
| Example 489 | 233.2 |
| Example 490 | 275.4 |
| Example 623 | 441.5 |
| Example 638 | 136.7 |
| Example 639 | 195.7 |
| Example 722 | 296.6 |
| Example 723 | 191.2 |
| Example 724 | 188.9 |
| Example 726 | 112.5 |
| Example 729 | 221 |
| Example 731 | 175.5 |
| Example 734 | 126.49 |
| Example 741 | 244 |
| Example 742 | 267.2 |
| Example 743 | 147.3 |
| Example 750 | 181.6 |

TABLE 2-continued

Quantification of the cleaved form of PARP in vivo

| | PARP fold |
|---|---|
| Example 756 | 117 |
| Example 757 | 135.6 |
| Example 762 | 136.9 |
| Example 774 | 104.8 |
| Example 781 | 113.3 |
| Example 787 | 131.5 |
| Example 788 | 144.8 |
| Example 789 | 135.2 |
| Example 790 | 282.9 |
| Example 794 | 125.6 |
| Example 808 | 155 |
| Example 810 | 122.4 |
| Example 811 | 117.6 |
| Example 812 | 136 |
| Example 814 | 118.5 |

Example D: Anti-Tumour Activity In Vivo

The anti-tumour activity of the compounds of the invention is evaluated in a xenograft model of AMO-1 multiple myeloma cells.

$1 \times 10^7$ AMO-1 cells are grafted sub-cutaneously into immunosuppressed mice (SCID strain).

6 to 8 days after the graft, when the tumour mass has reached about 150 mm³, the mice are treated with the various compounds in a daily schedule (5-day treatment). The tumour mass is measured twice weekly from the start of treatment.

The compounds of the invention have anti-tumour activities (tumour regression) in the AMO-1 multiple myeloma model with ΔT/C (qualification parameter of the activity of a product, which is defined as the ratio tumour volume of the treated group/tumour volume of the untreated control group) ranging from −26 to −100%. The results obtained show that the compounds of the invention induce significant tumour regression during the treatment period.

Example E: Pharmaceutical Composition: Tablets

| 1000 tablets containing a dose of 5 mg of a compound selected from Examples 1 to 871 | 5 g |
|---|---|
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:
1. A compound of formula (I):

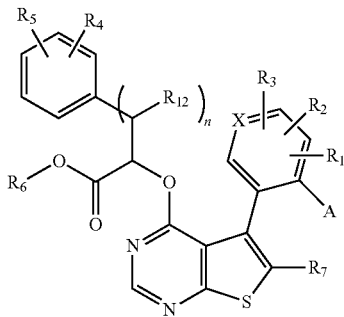

wherein:
A represents linear or branched $(C_1-C_6)$alkyl, linear or branched $(C_2-C_6)$alkenyl, linear or branched $(C_2-C_6)$alkynyl, linear or branched $(C_1-C_6)$alkoxy, —S—$(C_1-C_6)$alkyl, linear or branched $(C_1-C_6)$polyhaloalkyl, hydroxy, cyano, —NR$_{10}$R$_{10}$', -Cy$_6$, or halogen;

R$_1$, R$_2$, R$_3$, R$_4$ and R$_5$ independently of one another represent hydrogen, halogen, linear or branched $(C_1-C_6)$alkyl, linear or branched $(C_2-C_6)$alkenyl, linear or branched $(C_2-C_6)$alkynyl, linear or branched $(C_1-C_6)$polyhaloalkyl, hydroxy, linear or branched $(C_1-C_6)$alkoxy, —S—$(C_1-C_6)$alkyl, cyano, nitro, -alkyl$(C_0-C_6)$—NR$_8$R$_8$', —O-Cy$_1$, -alkyl$(C_0-C_6)$-Cy$_1$, -alkenyl$(C_2-C_6)$-Cy$_1$, -alkynyl$(C_2-C_6)$-Cy$_1$, —O-alkyl$(C_1-C_6)$—R$_9$, —C(O)—OR$_8$, —O—C(O)—R$_8$, —C(O)—NR$_8$R$_8$', —NR$_8$—C(O)—R$_8$', —NR$_8$—C(O)—OR$_8$', -alkyl$(C_1-C_6)$—NR$_8$—C(O)—R$_8$', —SO$_2$—NR$_8$R$_8$', or —SO$_2$-alkyl$(C_1-C_6)$, or the substituents of one of the pairs (R$_1$, R$_2$), (R$_2$, R$_3$), (R$_1$, R$_3$), (R$_4$, R$_5$) when grafted onto two adjacent carbon atoms, together with the carbon atoms carrying them, form an aromatic or non-aromatic ring having from 5 to 7 ring members, which ring may have from 1 to 3 heteroatoms selected from oxygen, sulphur and nitrogen, and which ring may be optionally substituted by a group selected from linear or branched $(C_1-C_6)$alkyl, —NR$_{10}$R$_{10}$', -alkyl$(C_0-C_6)$-Cy$_1$, and oxo;

X represents a carbon or a nitrogen atom;

R$_6$ represents hydrogen, linear or branched $(C_1-C_8)$ alkyl, aryl, heteroaryl, arylalkyl$(C_1-C_6)$, heteroarylalkyl$(C_1-C_6)$;

R$_7$ represents linear or branched $(C_1-C_6)$alkyl, linear or branched $(C_2-C_6)$alkenyl, linear or branched $(C_2-C_6)$alkynyl, -Cy$_3$, -alkyl$(C_1-C_6)$-Cy$_3$, -alkenyl$(C_2-C_6)$-Cy$_3$, -alkynyl$(C_2-C_6)$-Cy$_3$, -Cy$_3$-Cy$_4$, -alkynyl$(C_2-C_6)$—O-Cy$_3$, -Cy$_3$-alkyl$(C_0-C_6)$—O-alkyl$(C_0-C_6)$-Cy$_4$, halogen, cyano, —C(O)—R$_{11}$, or —C(O)—NR$_{11}$R$_{11}$';

R$_8$ and R$_8$' independently of one another represent hydrogen, linear or branched $(C_1-C_6)$alkyl, or -alkyl$(C_0-C_6)$-Cy$_1$,
or (R$_8$, R$_8$'), together with the nitrogen atom carrying them, form an aromatic or non-aromatic ring having from 5 to 7 ring members, which ring may have, in addition to the nitrogen atom, from 1 to 3 heteroatoms selected from oxygen, sulphur and nitrogen, wherein the nitrogen in question may be substituted by hydrogen, or linear or branched $(C_1-C_6)$alkyl and wherein one or more of the carbon atoms of the possible substituents, may be deuterated;

R$_9$ represents -Cy$_1$, -Cy$_1$-alkyl$(C_0-C_6)$-Cy$_2$, -Cy$_1$-alkyl$(C_0-C_6)$—O-alkyl$(C_0-C_6)$-Cy$_2$, -Cy$_1$-alkyl$(C_0-C_6)$—NR$_8$-alkyl$(C_0-C_6)$-Cy$_2$, -Cy$_1$-Cy$_2$-O-alkyl$(C_0-C_6)$-Cy$_5$, —NR$_8$R$_8$', —C(O)—NR$_8$R$_8$', —OR$_8$, —NR$_8$—C(O)—R$_8$', —O-alkyl$(C_1-C_6)$—OR$_8$, —SO$_2$—R$_8$, —C(O)—OR$_8$, or —NH—C(O)—NH—R$_8$;

R$_{10}$, R$_{10}$', R$_{11}$ and R$_{11}$' independently of one another represent hydrogen or optionally substituted linear or branched $(C_1-C_6)$alkyl;

R$_{12}$ represents hydrogen or hydroxy;

Cy$_1$, Cy$_2$, Cy$_3$, Cy$_4$, Cy$_5$ and Cy$_6$ independently of one another, represent cycloalkyl, heterocycloalkyl, aryl or heteroaryl;

n is an integer equal to 0 or 1;

it being understood that:
"aryl" means a phenyl, naphthyl, biphenyl, indanyl, or indenyl;
"heteroaryl" means any mono- or bi-cyclic group having from 5 to 10 ring members, having at least one aromatic moiety and having from 1 to 3 heteroatoms selected from oxygen, sulphur and nitrogen;
"cycloalkyl" means any mono- or bi-cyclic non-aromatic carbocyclic group containing from 3 to 10 ring members,
"heterocycloalkyl" means any mono- or bi-cyclic non-aromatic carbocyclic group having from 3 to 10 ring members, and having from 1 to 3 heteroatoms selected from oxygen, sulphur and nitrogen, which may include fused, bridged or spiro ring systems;
wherein the aryl, heteroaryl, cycloalkyl and heterocycloalkyl groups so defined and the alkyl, alkenyl, alkynyl, alkoxy groups, may be optionally substituted by from 1 to 4 groups selected from:
linear or branched $(C_1-C_6)$alkyl, optionally substituted by a group selected from:
linear or branched $(C_1-C_6)$alkoxy, optionally substituted by linear or branched $(C_1-C_6)$alkoxy,
linear or branched $(C_1-C_6)$polyhaloalkyl,
hydroxy,
halogen,
oxo,
—NR'R",
—O—C(O)—R', and
—CO—NR'R";
linear or branched $(C_2-C_6)$alkenyl;
linear or branched $(C_2-C_6)$alkynyl, optionally substituted by linear or branched $(C_1-C_6)$alkoxy;
linear or branched $(C_1-C_6)$alkoxy, optionally substituted by a group selected from:
linear or branched $(C_1-C_6)$alkoxy,
linear or branched $(C_1-C_6)$polyhaloalkyl,
linear or branched $(C_2-C_6)$alkynyl,
—NR'R", and
hydroxy;
$(C_1-C_6)$alkyl-S— optionally substituted by linear or branched $(C_1-C_6)$alkoxy;
hydroxy;
oxo (or N-oxide where appropriate);
nitro;
cyano;
—C(O)—OR';
—O—C(O)—R';
—CO—NR'R";

—NR'R";

—(C=NR')—OR";

linear or branched (C$_1$-C$_6$)polyhaloalkyl;

trifluoromethoxy; and halogen;

wherein R' and R" independently of one another represent a hydrogen atom or a linear or branched (C$_1$-C$_6$)alkyl group, optionally substituted by linear or branched (C$_1$-C$_6$)alkoxy; and wherein one or more of the carbon atoms of the preceding possible substituents, may be deuterated, or an enantiomer, a diastereoisomer, an atropoisomer, or an addition salt thereof with a pharmaceutically acceptable acid or base.

2. The compound according to claim 1, wherein at least one of the groups selected from R$_1$, R$_2$, and R$_3$ does not represent hydrogen.

3. The compound according to claim 1, wherein n is an integer equal to 1.

4. The compound according to claim 1, wherein A represents linear or branched (C$_1$-C$_6$)alkyl or halogen.

5. The compound according to claim 1, wherein X represents a carbon atom.

6. The compound according to claim 1, wherein R$_{12}$ represents hydrogen.

7. The compound according to claim 1, wherein:

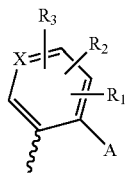

represents

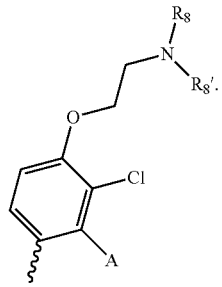

8. The compound according to claim 1, wherein:

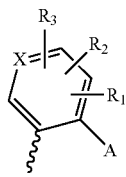

represents

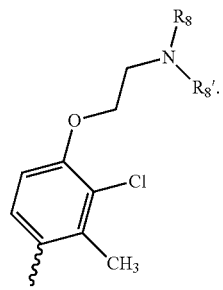

9. The compound according to claim 1, wherein R$_4$ represents optionally substituted linear or branched (C$_1$-C$_6$) alkoxy or —O-alkyl(C$_1$-C$_6$)—R$_9$.

10. The compound according to claim 1, wherein R$_5$ represents hydrogen.

11. The compound according to claim 1, wherein:

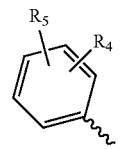

represents

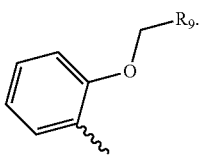

12. The compound according to claim 1, wherein R$_6$ represents hydrogen, optionally substituted linear or branched (C$_1$-C$_8$)alkyl, or heteroarylalkyl(C$_1$-C$_6$).

13. The compound according to claim 1, wherein R$_7$ represents linear or branched (C$_1$-C$_6$)alkyl, linear or branched (C$_2$-C$_6$)alkenyl, linear or branched (C$_2$-C$_6$)alkynyl, aryl, or heteroaryl.

14. The compound according to claim 1, wherein R$_8$ and R$_8$' independently of one another represent linear or branched (C$_1$-C$_6$)alkyl, or (R$_8$, R$_8$'), together with the nitrogen atom carrying them, form a non-aromatic ring having from 5 to 7 ring members, which ring may have, in addition to the nitrogen atom, from 1 to 3 heteroatoms selected from oxygen, sulphur and nitrogen, wherein the nitrogen in question may be substituted by hydrogen atom or linear or branched (C$_1$-C$_6$)alkyl.

15. The compound according to claim 1, wherein R$_9$ represents -Cy$_1$, -Cy$_1$-alkyl(C$_0$-C$_6$)-Cy$_2$, or -Cy$_1$-alkyl(C$_0$-C$_6$)—O-alkyl(C$_0$-C$_6$)-Cy$_2$.

16. The compound according to claim 15, wherein Cy$_1$ represents heteroaryl.

17. The compound according to claim 15, wherein Cy$_2$ represents phenyl, pyridinyl, pyrazolyl, morpholinyl, furanyl, or cyclopropyl.

18. The compound according to claim 15, wherein R$_9$ represents -Cy$_1$-Cy$_2$ wherein Cy$_1$ represents pyrimidinyl and Cy$_2$ represents phenyl, pyridinyl, pyrazolyl, morpholinyl, furanyl, or cyclopropyl.

19. The compound according to claim 1, which is selected from:

(2R)-2-{[(5S$_a$)-5-{3-chloro-2-methyl-4-[2-(4-methylpiperazin-1-yl)ethoxy] phenyl}-6-(furan-2-yl)thieno[2,3-d]pyrimidin-4-yl]oxy}-3-(2-methoxyphenyl) propanoic acid, (2R)-2-{[(5S$_a$)-5-{3-chloro-2-methyl-4-[2-(4-methylpiperazin-1-yl)ethoxy] phenyl}-6-(furan-2-yl)thieno[2,3-d]pyrimidin-4-yl]oxy}-3-[2-(2-methoxyethoxy) phenyl]propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-[2-(2,2,2-trifluoroethoxy)phenyl]propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-[2-(pyrazin-2-yl methoxy)phenyl]propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-{2-[(1-methyl-1H-pyrazol-5-yl)methoxy]phenyl}propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[1-(propan-2-yl)-1H-pyrazol-5-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[1-(propan-2-yl)-1H-pyrazol-5-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy)}-3-(2-{[2-(trifluoromethyl)pyridin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-{2-[(2-ethoxy pyrimidin-4-yl)methoxy]phenyl}propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(propan-2-yloxy)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(pyridin-2-yl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-methoxy ethyl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(furan-2-yl)thieno[2,3-d]pyrimidin-4-yl]oxy}-3-(2-{[2-(cyclopropyl methoxy)pyrimidin-4-yl]methoxy}phenyl)propanoic acid, (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}propanoic acid, (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}propanoic acid, (2R)-3-{2-[(1-tert-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}propanoic acid, ethyl (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[1-(propan-2-yl)-1H-pyrazol-5-yl]methoxy}phenyl)propanoate, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-{2-[(2-cyclopropylpyrimidin-4-yl)methoxy]phenyl}propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(furan-2-yl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-{2-[(2-propyl pyrimidin-4-yl)methoxy]phenyl}propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[1-(2,2,2-trifluoroethyl)-1H-pyrazol-5-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl) propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[2-(thiophen-2-yl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(morpholin-4-yl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[2-(pyridin-4-yl)pyrimidin-4-yl]methoxy)phenyl}propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-{2-[(2-ethoxy pyrimidin-4-yl)methoxy]phenyl}propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-methoxy ethoxy)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[2-(2-methoxyethyl)pyrimidin-4-yl]methoxy}phenyl) propanoic acid, (2R)-2-{[(5S$_a$)-5 (3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(1H-pyrazol-1-yl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-{2-[(2-methoxy pyridin-4-yl)methoxy]phenyl}propanoic acid, (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-methyl pyridin-4-yl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-methoxy phenyl)pyrimidin-4-yl]methoxy}phenyl)propanoic acid, (2R)-3-{2-[(1-butyl-1H-1,2,3-triazol-5-yl)methoxy]phenyl}-2-{[(5S<sub>a</sub>)-5-{3-chloro-2-methyl-4-[2-(4-methyl-piperazin-1-yl)ethoxy]phenyl}-6-(4-fluorophenyl)thieno[2,3-d]pyrimidin-4-yl]oxy}propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(4-methyl pyridin-3-yl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[2-(morpholin-4-yl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2,2,2-trifluoroethoxy)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-[2-({2-[(2-methoxy ethyl)amino]pyrimidin-4-yl}methoxy)phenyl]propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-methyl phenyl)pyrimidin-4-yl]methoxy}phenyl)propanoic acid, (2R)-2-{[(5S<sub>a</sub>)-5-{3-chloro-2-methyl-4-[2-(4-methylpiperazin 1-yl)ethoxy] phenyl}-6-(prop-1-yn-1-yl)thieno[2,3-d]pyrimidin-4-yl]oxy}-3-(2-{[1-(2,2,2-trifluoroethyl)-1H-pyrazol-5-yl]methoxy}phenyl)propanoic acid, (2R)-2-{[(S<sub>a</sub>)-5-{3-chloro-4-[2-(dimethylamino)ethoxy]-2-methylphenyl}-6-(5-fluorofuran-2-yl)thieno[2,3-d]pyrimidin-4-yl]oxy}-3-(2-{[2-(morpholin-4-yl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(prop-1-yn-1-yl)thieno[2,3-d]pyrimidin-4-yl]oxy}-3-(2-{[2-(morpholin-4-yl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-ethoxy phenyl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(3-methyl pyridin-4-yl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(3,3,3-trifluoropropoxy)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(prop-1-yn-1-yl)thieno[2,3-d]pyrimidin-4-yl]oxy}-3-(2-{[2-(3-methyl pyridin-4-yl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(methoxy methyl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-(2-{[2-(3-methyl-pyridin-4-yl)pyrimidin-4-yl]methoxy}phenyl)propanoic acid, (2R)-2-{[(5S<sub>a</sub>)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(4-methylpyridin-3-yl)pyrimidin-4-yl]methoxy}phenyl)propanoic acid, (2R)-2-{[(5S<sub>a</sub>)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(prop-1-yn-1-yl)thieno[2,3-d]pyrimidin-4-yl]oxy}-3-(2-{[2-(2,2,2-trifluoroethoxy)pyrimidin-4-yl]methoxy}phenyl)propanoic acid, ethyl (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2,2,2-trifluoroethoxy)pyrimidin-4-yl]methoxy}phenyl) propanoate, ethyl (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-methoxy phenyl)pyrimidin-4-yl]methoxy}phenyl) propanoate, 2,2,2-trifluoroethyl (2R)-2-{[(5S<sub>a</sub>)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate, propan-2-yl (2R)-2-{[(5S<sub>a</sub>)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoate, 2-methoxyethyl (2R)-2-{([(5S<sub>a</sub>)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{([2-(2-methoxyphenyl)pyrimidin-4-yl]methoxy}phenyl) propanoate, ethyl (2R)-2-{[(5S<sub>a</sub>)-5-{3-chloro-4-[2-(dimethylamino) ethoxy]-2-methylphenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(pyridin-3-yl)pyrimidin-4-yl]methoxy}phenyl)propanoic acid, (2R)-2-{[(5S<sub>a</sub>)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(ethoxy methyl)pyrimidin-4-yl]methoxy}phenyl)propanoic acid, (2R)-3-{2-[(1-tert-butyl-1H-pyrazol-5-yl)methoxy]phenyl}-2-{[(5S<sub>a</sub>)-5-{3-chloro-2-methyl-4-[2-(4-methyl-piperazin-1-yl)ethoxy]phenyl}-6-(4-fluorophenyl)thieno[2,3-d]pyrimidin-4-yl]oxy}propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-fluoro phenyl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(5-fluorofuran-2-yl)thieno[2,3-d]pyrimidin-4-yl]oxy}-3-{2-[(2-methoxy pyrimidin-4-yl)methoxy]phenyl}propanoic acid, (2R)-3-{2-[(1-tert-butyl-1H-pyrazol-5-yl)methoxy]phenyl}-2-{[(5S$_a$)-5-{3-chloro-2-methyl-4-[2-(4-methyl-piperazin-1-yl)ethoxy]phenyl}-6-(prop-1-yn-1-yl)thieno[2,3-d]pyrimidin-4-yl]oxy}propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-hydroxy phenyl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-[2-({2-[2-(propan-2-yloxy)phenyl]pyrimidin-4-yl}methoxy)phenyl]propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-[2-({2-[2-(2-methoxyethoxy)phenyl]pyrimidin-4-yl}methoxy)phenyl]propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2-ethyl phenyl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-[2-({2-[4-methoxy-2-(trifluoromethyl)phenyl]pyrimidin-4-yl}methoxy)phenyl]propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(2,5-dimethylpyridin-4-yl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-fluorophenyl)thieno[2,3-d]pyrimidin-4-yl]oxy}-3-(2-{[2-(5-methoxy-2-methylpyridin-4-yl)pyrimidin-4-yl]methoxy}phenyl)propanoic acid, (2R)-2-{[(5S$_a$)-5-{3-chloro-2-ethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, (2R)-2-{[(5S$_a$)-5-{2-bromo-3-chloro-4-[2-(4-methylpiperazin-1-yl)ethoxy] phenyl}-6-(4-fluorophenyl)thieno[2,3-d]pyrimidin-4-yl]oxy}-3-(2-{[2-(2-methoxy phenyl)pyrimidin-4-yl]methoxy}phenyl)propanoic acid, (2R)-2-{[(5S$_a$)-5-{2,3-dichloro-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, (2R)-3-{2-[(1-tert-butyl-1H-pyrazol-5-yl)methoxy]phenyl}-2-{[(5S$_a$)-5-{3-chloro-4-[2-(dimethylamino)ethoxy]-2-methylphenyl}-6-(4-fluorophenyl)thieno[2,3-d] pyrimidin-4-yl]oxy}propanoic acid, (2R)-2-{[(5S$_a$)-5-{3-Chloro-4-[2-(dimethylamino)ethoxy]-2-methylphenyl}-6-(4-fluorophenyl)thieno[2,3-d]pyrimidin-4-yl]oxy}-3-(2-{[2-(2-fluorophenyl)pyrimidin-4-yl]methoxy}phenyl)propanoic acid, (2R)-2-[(6-[4-(benzyloxy)phenyl]-(5S$_a$)-5-{3-chloro-methyl-4-[2-(4-methyl piperazin-1-yl)ethoxy] phenyl}thieno[2,3-d]pyrimidin-4-yl)oxy]-3-(2-{[2-(2-methoxyphenyl)pyrimidin-4-yl]methoxy}phenyl)propanoic acid, (2R)-2-[((5S$_a$)-5-{3-chloro-2-methyl-4-[2-(4-methylpiperazin-1-yl)ethoxy] phenyl}-6-[4-(pyridin-4-yl-methoxy)phenyl]thieno[2,3-d]pyrimidin-4-yl)oxy]-3-(2-{[2-(2-methoxyphenyl)pyrimidin-4-yl]methoxy}phenyl)propanoic acid, (2R)-2-{[(5S$_a$)-5-{3-chloro-2-methyl-4-[2-(4-methylpiperazin-1-yl)ethoxy] phenyl}-6-(4-phenylbut-1-yn-1-yl)thieno[2,3-d]pyrimidin-4-yl]oxy}-3-(2-{[2-(2-methoxyphenyl)pyrimidin-4-yl]methoxy}phenyl)propanoic acid, methyl (2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate, ethyl (2R)-2-{[(5S$_a$)-5-{3-chloro-4-[2-(4-ethylpiperazin-1-yl)ethoxy]-2-methyl phenyl}-6-(4-fluorophenyl)thieno[2,3-d]pyrimidin-4-yl]oxy}-3-(2-{[2-(2-fluoro phenyl)pyrimidin-4-yl]methoxy}phenyl)propanoate, ethyl (2R)-3-{2-[(1-tert-butyl-1H-pyrazol-5-yl)methoxy]phenyl}-2-{[5(5S$_a$)-{3-chloro-4-[2-(dimethylamino)ethoxy]-2-methylphenyl}-6-(4-fluorophenyl) thieno[2,3-d]pyrimidin-4-yl]oxy}propanoate, {[(2R)-2-{[(5S$_a$)-5-{3-chloro-2-methyl-4-[2-(4-methyl-piperazin-1-yl)ethoxy] phenyl}-6-(4-fluorophenyl)thieno[2,3-d]pyrimidin-4-yl]oxy}-3-(2-{[2-(2-methoxy phenyl)pyrimidin-4-yl]methoxy}phenyl)propanoyl]oxy}methyl 2,2-dimethyl propanoate, (5-methyl-2-oxo-1,3-dioxol-4-yl)methyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoate, 2-(dimethylamino)-2-oxoethyl (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoate, and 2-(2-methoxyethoxy)ethyl (2R)-2-{[(5S$_a$)-5-{3-chloro-2-methyl-4-[2-(4-methyl piperazin-1-yl)ethoxy]phenyl}-6-(4-fluorophenyl)thieno[2,3-d]pyrimidin-4-yl] oxy}-3-(2-{[2-(2-methoxyphenyl)pyrimidin-4-yl]methoxy}phenyl)propanoate.

20. A pharmaceutical composition comprising a compound according to claim 1 in combination with one or more pharmaceutically acceptable excipients.

21. A method in a subject in need thereof, comprising administration of an effective amount of the compound according to claim 1, alone or in combination with one or more pharmaceutically acceptable excipients.

22. A combination of a compound according to claim 1 with an anti-cancer agent selected from genotoxic agents, mitotic poisons, anti-metabolites, proteasome inhibitors, kinase inhibitors, and antibodies.

23. A pharmaceutical composition comprising a combination according to claim 22 in combination with one or more pharmaceutically acceptable excipients.

24. A method of treating myelomas in a subject in need thereof, comprising administration of an effective amount of a combination according to claim 22.

25. A method of treating myelomas in a subject in need thereof, comprising administration of an effective amount of a compound according to claim 1 in combination with radiotherapy.

26. The compound according to claim 1, which is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(3,3,3-trifluoropropoxy)pyrimidin-4-yl]methoxy}phenyl)propanoic acid.

27. The compound according to claim 1, which is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{([1-(propan-2-yl)-1H-pyrazol-5-yl]methoxy}phenyl)propanoic acid.

28. The compound according to claim 1, which is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(trifluoromethyl)pyridin-4-yl]methoxy}phenyl) propanoic acid.

29. The compound according to claim 1, which is ethyl (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(propan-2-yl)-1H-pyrazol-5-yl]methoxy}phenyl)propanoate.

30. The compound according to claim 1, which is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid.

31. The compound according to claim 1, which (2R)-3-{2-[(1-butyl-1H-pyrazol-5-yl)methoxy]phenyl}-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}propanoic acid.

32. The compound according to claim 1, which (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[1-(2,2,2-trifluoroethyl)-1H-pyrazol-5-yl]methoxy}phenyl)propanoic acid.

33. The compound according to claim 1, which is (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(4-methylpyridin-3-yl)pyrimidin-4-yl]methoxy}phenyl)propanoic acid.

34. The compound according to claim 1, which is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[2-(3-methylpyridin-4-yl)pyrimidin-4-yl]methoxy}phenyl)propanoic acid.

35. The compound according to claim 1, which is (2R)-2-{[(5S$_a$)-5-{3-chloro-2-methyl-4-[2-(4-methylpiperazin-1-yl)ethoxy]phenyl}-6-(prop-1-yn-1-yl)thieno[2,3-d]pyrimidin-4-yl]oxy}-3-(2-{[2-(3-methylpyridin-4-yl)pyrimidin-4-yl]methoxy}phenyl)propanoic acid.

36. The compound according to claim 1, which is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

37. The compound according to claim 1, which is (2R)-2-{[(5S$_a$)-5-{3-chloro-4-[2-(dimethylamino)ethoxy]-2-methylphenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

38. The compound according to claim 1, which is (2R)-2-{[(5S$_a$)-5-{3-chloro-2-ethyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

39. The compound according to claim 1, which is (2R)-2-{[(5S$_a$)-5-{2-bromo-3-chloro-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

40. The compound according to claim 1, which is (2R)-2-{[(5S$_a$)-5-{2,3-dichloro-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

\* \* \* \* \*

UNITED STATES PATENT AND TRADEMARK OFFICE
CERTIFICATE OF CORRECTION

PATENT NO. : 9,670,227 B2
APPLICATION NO. : 14/576683
DATED : June 6, 2017
INVENTOR(S) : András Kotschy et al.

It is certified that error appears in the above-identified patent and that said Letters Patent is hereby corrected as shown below:

Column 384, Line 51: "A method in a subject" should be --A method of treating myelomas, in a subject--.

Signed and Sealed this
Eighth Day of May, 2018

Andrei Iancu
*Director of the United States Patent and Trademark Office*